United States Patent
Mastracchio et al.

(10) Patent No.: US 9,650,358 B2
(45) Date of Patent: May 16, 2017

(54) PYRIDINE CDK9 KINASE INHIBITORS

(71) Applicant: AbbVie Inc., North Chicago, IL (US)

(72) Inventors: Anthony Mastracchio, Waukegan, IL (US); Milan Bruncko, Green Oaks, IL (US); Chunqiu Lai, Libertyville, IL (US); Julie M. Miyashiro, Morton Grove, IL (US); Zhi-Fu Tao, Vernon Hills, IL (US); Keith W. Woods, Lincolnshire, IL (US); Thomas D. Penning, Elmhurst, IL (US); Andrew J. Souers, Libertyville, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/207,854

(22) Filed: Mar. 13, 2014

(65) Prior Publication Data

US 2014/0275011 A1  Sep. 18, 2014

Related U.S. Application Data

(60) Provisional application No. 61/780,307, filed on Mar. 13, 2013.

(51) Int. Cl.

| | |
|---|---|
| *C07D 401/04* | (2006.01) |
| *C07D 401/14* | (2006.01) |
| *C07D 405/14* | (2006.01) |
| *C07D 409/14* | (2006.01) |
| *C07D 417/14* | (2006.01) |
| *C07D 453/02* | (2006.01) |
| *C07D 471/04* | (2006.01) |
| *A61K 31/4545* | (2006.01) |
| *A61K 31/4439* | (2006.01) |
| *A61K 31/5377* | (2006.01) |
| *A61K 31/444* | (2006.01) |
| *A61K 31/506* | (2006.01) |
| *A61K 31/439* | (2006.01) |

(52) U.S. Cl.
CPC .......... *C07D 401/04* (2013.01); *A61K 31/439* (2013.01); *A61K 31/444* (2013.01); *A61K 31/4439* (2013.01); *A61K 31/4545* (2013.01); *A61K 31/506* (2013.01); *A61K 31/5377* (2013.01); *C07D 401/14* (2013.01); *C07D 405/14* (2013.01); *C07D 409/14* (2013.01); *C07D 417/14* (2013.01); *C07D 453/02* (2013.01); *C07D 471/04* (2013.01)

(58) Field of Classification Search
CPC .. C07D 401/04; C07D 401/14; C07D 405/14; C07D 409/14; C07D 417/14; C07D 453/02; C07D 471/04

See application file for complete search history.

(56) References Cited

U.S. PATENT DOCUMENTS

| 7,511,013 | B2 | 3/2009 | Molino et al. |
|---|---|---|---|
| 7,514,068 | B2 | 4/2009 | Tung |
| 7,521,421 | B2 | 4/2009 | Naicker et al. |
| 7,528,131 | B2 | 5/2009 | Persichetti et al. |
| 7,531,685 | B2 | 5/2009 | Czarnik |
| 7,534,814 | B2 | 5/2009 | Ascher et al. |
| 7,538,189 | B2 | 5/2009 | Naicker et al. |
| 2009/0082471 | A1 | 3/2009 | Czarnik |
| 2009/0088416 | A1 | 4/2009 | Czarnik |
| 2009/0093422 | A1 | 4/2009 | Tung et al. |
| 2009/0105147 | A1 | 4/2009 | Masse |
| 2009/0105307 | A1 | 4/2009 | Galley et al. |
| 2009/0105338 | A1 | 4/2009 | Czarnik |
| 2009/0111840 | A1 | 4/2009 | Herold et al. |
| 2009/0118238 | A1 | 5/2009 | Czarnik |
| 2009/0131363 | A1 | 5/2009 | Harbeson |
| 2009/0131485 | A1 | 5/2009 | Liu et al. |

(Continued)

FOREIGN PATENT DOCUMENTS

| WO | 9507271 A1 | 3/1995 |
|---|---|---|
| WO | 9710223 A1 | 3/1997 |

(Continued)

OTHER PUBLICATIONS

Berge, S. M. et al., "Pharmaceutical Salts," Journal of Pharmaceutical Sciences, 1977, vol. 66 (1), pp. 1-19.
Beylot, M. et al., "In Vivo Studies of Intrahepatic Metabolic Pathways," Diabetes Metabolism, 1997, vol. 23 (3), pp. 251-257.
Blagojevic N., et al., In "Dosimetry & Treatment Planning for Neutron Capture Therapy", Zamenhof R, et al., Edition, 1994, Advanced Medical Publishing, pp. 125-134.
Blake, M. I. et al., "Studies With Deuterated Drugs," Journal of Pharmaceutical Sciences, 1975, vol. 64 (3), pp. 367-391.
Brickner, S.J. et al., "Synthesis and Antibacterial Activity of U-100592 and U-100766, Two Oxazolidinone Antibacterial Agents for the Potential Treatment of Multidrug-Resistant Gram-Positive Bacterial Infections," Journal of Medicinal Chemistry, 1996, vol. 39 (3), pp. 673-679.
Coley W., et al., "Novel HIV-1 Therapeutics Through Targeting Altered Host Cell Pathways.," Expert Opinion on Biological Therapy, 2009, vol. 9 (11), pp. 1369-1382.
Czajka, D. M. et al., "Effect of Deuterium Oxide on the Reproductive Potential of Mice," Annals of the New York Academy of Sciences, 1960, vol. 84, pp. 770-779.

(Continued)

*Primary Examiner* — Rebecca Anderson
(74) *Attorney, Agent, or Firm* — Changxia Sun

(57) ABSTRACT

Disclosed are compound of Formula (Ia),

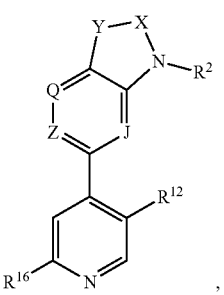

wherein $R^2$, $R^{12}$, $R^{16}$, J, Q, X, Y and Z are as defined in the specification, and pharmaceutically acceptable salts thereof. The compounds may be used as agents in the treatment of diseases, including cancer. Also provided are pharmaceutical compositions comprising one or more compounds of Formula (Ia).

18 Claims, No Drawings

(56) References Cited

U.S. PATENT DOCUMENTS

| | | | |
|---|---|---|---|
| 2009/0137457 A1 | 5/2009 | Harbeson | |
| 2015/0344457 A1* | 12/2015 | Duncan | C07D 401/14 514/210.18 |

FOREIGN PATENT DOCUMENTS

| | | |
|---|---|---|
| WO | 03/000695 | 1/2003 |
| WO | 2005099353 A2 | 10/2005 |
| WO | 2006008754 A1 | 1/2006 |
| WO | 2006/017443 | 2/2006 |
| WO | 2008049856 A2 | 5/2008 |
| WO | 2008079918 | 7/2008 |
| WO | 2008/128072 | 10/2008 |
| WO | 2008145688 | 12/2008 |
| WO | 2009047359 A1 | 4/2009 |
| WO | 2010003133 | 1/2010 |
| WO | 2010/020675 | 2/2010 |
| WO | 2013/157021 | 10/2013 |

OTHER PUBLICATIONS

Czajka, D. M. et al., "Physiological Effects of Deuterium on Dogs," American Journal of Physiology, 1961, vol. 201 (2), pp. 357-362.

Foster, A. B. et al., "Deuterium Isotope Effects in the Metabolism of Drugs and Xenobiotics: Implications for Drug Design," Advances in Drug Research, 1985, vol. 14, pp. 2-36.

"IUPAC 1974 Recommendations for Section E, Fundamental Stereochemistry," Pure and Applied Chemistry, 1976, vol. 45, pp. 10-13.

Kato, S. et al., "Synthesis of Deuterated Mosapride Citrate," Journal of Labelled Compounds and Radiopharmaceuticals, 1995, vol. 36 (10), pp. 927-932.

Krystof V., et al., "Pharmacological Targeting of CDK9 in Cardiac Hypertrophy.," Medicinal Research Reviews, 2010, vol. 30 (4), pp. 646-666.

Kushner D.J., et al., "Pharmacological Uses and Perspectives of Heavy Water and Deuterated Compounds.," Canadian Journal of Physiology and Pharmacology, 1999, vol. 77 (2), pp. 79-88.

Lizondo, J. et al., "Linezolid: Oxazolidinone antibacterial," Drugs of the Future, 1996, vol. 21 (11), pp. 1116-1123.

Mallesham, B. et al., "Highly Efficient CuI-Catalyzed Coupling of Aryl Bromides With Oxazolidinones Using Buchwald's Protocol: A Short Route to Linezolid and Toloxatone," Organic Letters, 2003, vol. 5 (7), pp. 963-965.

Malumbres M., et al., "Cell Cycle, CDKs and Cancer: a Changing Paradigm.," Nature Reviews Cancer, 2009, vol. 9 (3), pp. 153-166.

Miyaura N., et al., "Palladium-Catalyzed Cross-Coupling Reactions of Organoboron Compounds," Chemical Reviews, 1995, vol. 95 (7), pp. 2457-2483.

Prescott, Ed., Methods in Cell Biology, vol. XIV, Academic Press, New York, 1976, pp. 33.

Sutton, V.R. et al., "Bcl-2 Prevents Apoptosis Induced by Perforin and Granzyme B, But Not That Mediated by Whole Cytotoxic Lymphocytes," Journal of Immunology, 1997, vol. 158 (12), pp. 5783-5790.

Suzuki A, "Recent Advances in the Cross-Coupling Reactions of Organoboron Derivatives with Organic Electrophiles," Journal of Organometallic Chemistry, 1999, vol. 576, pp. 147-168.

Thomson, J.F., "Physiological Effects of D20 in Mammals," Annals of the New York Academy of Sciences, 1960, vol. 84, pp. 736-744.

Wang S., et al., "Cyclin-dependent kinase 9: a key Transcriptional Regulator and Potential Drug Target in Oncology, Virology and Cardiology.," Trends in Pharmacological Sciences, 2009, vol. 29 (6), pp. 302-312.

The International Search Report and Written Opinion for PCT/US2014/025740 mailed May 27, 2014.

The International Search Report and Written Opinion for PCT/US2014/025670 mailed May 22, 2014.

* cited by examiner

PYRIDINE CDK9 KINASE INHIBITORS

BACKGROUND OF THE INVENTION

Cyclin-dependent kinases (CDKs) are serine/threonine protein kinases whose activity depends on binding and activation by cyclin partners. These heterodimeric complexes can phosphorylate various substrates involved in the control of transcription and cell-cycle progression in response to different stimuli. CDK8 and CDK9 have key roles in the control of transcription by RNA polymerase II. CDK9 responds specifically to several cytokines, including tumor necrosis factor and interleukin-6, indicating that it might have special roles in the regulation of a variety of physiological processes, especially immune responses, inflammation, cell activation, and differentiation.

Deregulated CDK activity is a hallmark of human cancer, and a variety of genetic and epigenetic events, such as over expression of cyclins, diminished levels of CDK inhibiting proteins or gain-of function mutations in CDK, have been described to cause increased activity of these enzymes and provide a selective growth advantage in tumor cells. CDK9 inhibition causes rapid depletion of short-lived mRNA transcripts and their associated protein products. Many genes encoding proteins involved in cell growth, proliferation, and tumor development (Myc, Cyclin D1, and Mcl-1) are characterized by short-lived mRNAs and proteins and hence the consequences of CDK9 inhibition include anti-proliferative and pro-apoptotic effects through loss of function at many cellular pathways. Tumor types that are dependent on labile pro-survival proteins (e.g., Mcl-1), which includes multiple myeloma, CLL, breast, melanoma and pancreatic cancers as well as the MYC-driven tumors (multiple cancer types) would be susceptible to CDK9 inhibition. CDK9 inhibitors might also be effective in combination with standard of care in tumors in which NF-κB is constitutively active and contributing to chemo resistance. This includes hematologic malignancies as well as solid tumors (breast, colorectal, prostate, melanoma and pancreatic). Thus, CDK9 inhibition targets multiple cancer-relevant pathways by inhibition of a single protein and thereby renders CDK9 as an attractive target for anti-cancer therapy. (Nature Reviews Cancer: 2009, 9, 153-166).

CDK9 inhibitors can also find therapeutic application in cardiology and virology as many viruses depend on the infected host for transcription of their genome. (Cyclin-dependent kinase 9: a key transcriptional regulator and potential drug target in oncology, virology and cardiology. Trends in Pharmacol. Sci. 2009, 29. 302-312; Pharmacological targeting of CDK9 in cardiac hypertrophy. Med Res. Rev. 2010 30:646-66; Novel HIV-1 therapeutics through targeting altered host cell pathways. Expert Opin Biol Ther. 2009 9:1369-82).

CDK9 inhibitors have also been reported as potential therapeutics for the treatment of chronic, inflammatory and neuropathic pain (WO2008/049856; WO2009/047359).

In view of the above, there is a need in the art for small molecule therapeutics that can inhibit the activity of CDK9. The present invention fulfills at least this need.

SUMMARY OF THE INVENTION

In one aspect, the present invention provides compounds of Formula (Ia), or a pharmaceutically acceptable salt thereof,

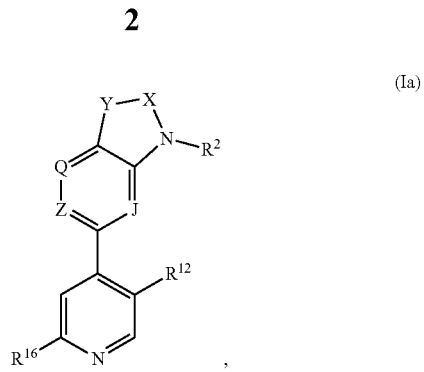

(Ia)

wherein
$R^{12}$ is halo or H;
J is N or CH;
Q is N or $CR^1$;
Z is N or $CR^1$;
wherein the bond between X and Y may be a single or a double bond; and
if a double bond is present, then Y is $CR^3$ and X is CH, Y is CH and X is CH, Y is N and X is CH, Y is N and X is $CR^3$, Y is $CR^3$ and X is N, Y is N and X is N, or Y is CH and X is N; and
if a single bond is present, then Y is $CH_2$ and X is $CH_2$ or C(O), or Y is NH or $N(C_1$-$C_3$ alkyl) and X is C(O);
$R^3$ is selected from the group consisting of $R^{3A}$, C(O)$R^{3A}$, and CN;
$R^{3A}$ is selected from the group consisting of $C_1$-$C_6$ alkyl, $C_2$-$C_6$ alkenyl, $C_2$-$C_6$ alkynyl, aryl, cycloalkyl, cycloalkenyl, heteroaryl, heterocycloalkyl, and heterocycloalkenyl; wherein the $R^{3A}$ $C_1$-$C_6$ alkyl, $C_2$-$C_6$ alkenyl, and $C_2$-$C_6$ alkynyl are optionally substituted with one or more substituents independently selected from the group consisting of $R^{3B}$, $OR^{3B}$, and halo; wherein the $R^{3A}$ aryl, cycloalkyl, cycloalkenyl, heteroaryl, heterocycloalkyl, and heterocycloalkenyl are optionally substituted with one or more halo;
$R^{3B}$ is selected from the group consisting of $C_1$-$C_6$ alkyl, $C_2$-$C_6$ alkenyl, $C_2$-$C_6$ alkynyl, and aryl, wherein the $R^{3B}$ aryl is optionally substituted with one or more substituents independently selected from the group consisting of F, Cl, Br, and I;
$R^1$ is selected from the group consisting of H, CN, Cl, Br, I, F, $R^{1A}$; and $OR^{1A}$;
$R^{1A}$ is selected from the group consisting of $C_1$-$C_6$ alkyl, $C_2$-$C_6$ alkenyl, and $C_2$-$C_6$ alkynyl;
$R^2$ is selected from the group consisting of H, $C_1$-$C_6$ alkyl, $C_2$-$C_6$ alkenyl, and $C_2$-$C_6$ alkynyl; wherein the $R^2$ $C_1$-$C_6$ alkyl, $C_2$-$C_6$ alkenyl, and $C_2$-$C_6$ alkynyl are optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $SO_2NHC(O)R^4$, $SO_2NR^4C(O)R^4$, $NHS(O)_2R^4$, $NR^4S(O)_2R^4$, $NHC(O)OR^4$, $NR^4C(O)OR^4$, $SO_2NHC(O)OR^4$, $SO_2NR^4C(O)OR^4$, $NHSO_2NHC(O)OR^4$, $NHSO_2NR^4C(O)OR^4$, $NR^4SO_2NR^4C(O)OR^4$, $NR^4SO_2NHC(O)OR^4$, NHC(O)$NH_2$, NHC(O)$NHR^4$, NHC(O)N($R^4)_2$, $NR^4C(O)NHR^4$, $NR^4C(O)N(R^4)_2$, OC(O)$NH_2$, OC(O)$NHR^4$, OC(O)N($R^4)_2$, OC(O)NHSO$_2R^4$, OC(O)NR$^4$SO$_2R^4$, C(O)$NH_2$, C(O)$NHR^4$, C(O)N($R^4)_2$, C(O)NHOH, C(O)NHOR$^4$, C(O)NHSO$_2R^4$, C(O)NR$^4$SO$_2R^4$, SO$_2NH_2$, SO$_2NHR^4$, SO$_2N(R^4)_2$, OSO$_2NH_2$, OSO$_2NHR^4$, OSO$_2N(R^4)_2$, C(O)NHCN, C(O)NR$^4$CN, S(O)NR$^4$, S(O)NSO$_2R^4$, C(O)H, C(O)OH, (O), OH, CN, $NO_2$, F, Cl, Br and I;

$R^4$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^4$ $C_1$-$C_6$ alkyl, $C_2$-$C_6$ alkenyl, and $C_2$-$C_6$ alkynyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $OH$, $CN$, $NO_2$, F, Cl, Br and I; wherein each $R^4$ aryl, cycloalkyl, cycloalkenyl, heteroaryl, heterocycloalkyl, and heterocycloalkenyl is optionally substituted with one or more substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, (O), $OH$, $CN$, $NO_2$, F, Br and I;

$R^5$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl;

$R^6$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^6$ $C_1$-$C_6$ alkyl, $C_2$-$C_6$ alkenyl, and $C_2$-$C_6$ alkynyl is optionally substituted with one or more substituents independently selected from the group consisting of halo and $R^{6A}$;

$R^{6A}$, at each occurrence, is independently selected from the group consisting of aryl, heteroaryl, heterocycloalkyl, heterocycloalkenyl, cycloalkyl, and cycloalkenyl; wherein each $R^{6A}$ aryl, heteroaryl, heterocycloalkyl, heterocycloalkenyl, cycloalkyl, and cycloalkenyl is optionally substituted with $C_1$-$C_6$ alkyl;

$R^{16}$ is selected from the group consisting of $NH_2$, $NHR^7$, $NHC(O)R^7$, $NHS(O)_2R^7$, $NHC(O)OR^7$, $NHC(O)NH_2$, $NHC(O)NHR^7$, and $NHC(O)N(R^7)_2$;

$R^7$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^7$ $C_1$-$C_6$ alkyl, $C_2$-$C_6$ alkenyl, and $C_2$-$C_6$ alkynyl is optionally substituted with one or more substituents independently selected from the group consisting of $R^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHSO_2NH_2$, $NR^8SO_2NH_2$, $NHSO_2NHR^8$, $NR^8SO_2NHR^8$, $NHSO_2N(R^8)_2$, $NR^8SO_2N(R^8)_2$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $C(O)NHC(O)NH_2$, $C(O)NR^8C(O)NH_2$, $C(O)NHC(O)NHR^8$, $C(O)NR^8C(O)NHR^8$, $C(O)NHC(O)N(R^8)_2$, $C(O)NR^8C(O)N(R^8)_2$, $SO_2NH_2$, $SO_2NHR^8$, $SO_2N(R^8)_2$, $C(O)H$, $C(O)OH$, $OH$, $CN$, $NO_2$, F, Cl, Br and I; wherein each $R^7$ aryl, cycloalkyl, cycloalkenyl, heteroaryl, heterocycloalkyl, and heterocycloalkenyl is optionally substituted with one or more substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $SO_2NHC(O)OH$, $SO_2NR^9C(O)OH$, $SO_2NHC(O)OR^9$, $SO_2NR^9C(O)OR^9$, $C(O)H$, $C(O)OH$, (O), $OH$, $CN$, $NO_2$, F, Cl, Br and I;

$R^8$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^8$ $C_1$-$C_6$ alkyl, $C_2$-$C_6$ alkenyl, and $C_2$-$C_6$ alkynyl is optionally substituted with one or more substituents independently selected from the group consisting of $NHR^{10}$, and aryl; wherein each $R^8$ aryl, heteroaryl, heterocycloalkyl, heterocycloalkenyl, cycloalkyl, and cycloalkenyl is optionally substituted with one or more substituents independently selected from the group consisting of $R^{11}$, $OR^{11}$, halo, $NH_2$, $OH$, and (O);

$R^9$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{13}$, $OR^{13}$, $SR^{13}$, $S(O)R^{13}$, $SO_2R^{13}$, $C(O)R^{13}$, $CO(O)R^{13}$, $OC(O)R^{13}$, $OC(O)OR^{13}$, $NH_2$, $NHR^{13}$, $N(R^{13})_2$, $NHC(O)R^{13}$, $NR^{13}C(O)R^{13}$, $NHS(O)_2R^{13}$, $NR^{13}S(O)_2R^{13}$, $NHC(O)OR^{13}$, $NR^{13}C(O)OR^{13}$, $NHC(O)NH_2$, $NHC(O)NHR^{13}$, $NHC(O)N(R^{13})_2$, $NR^{13}C(O)NHR^{13}$, $NR^{13}C(O)N(R^{13})_2$, $C(O)NH_2$, $C(O)NHR^{13}$, $C(O)N(R^{13})_2$, $C(O)NHOH$, $C(O)NHOR^{13}$, $C(O)NHSO_2R^{13}$, $C(O)NR^{13}SO_2R^{13}$, $SO_2NH_2$, $SO_2NHR^{13}$, $SO_2N(R^{13})_2$, $C(O)H$, $C(O)OH$, $OH$, $CN$, $NO_2$, F, Cl, Br and I; wherein each $R^9$ aryl, cycloalkyl, cycloalkenyl, heteroaryl, heterocycloalkyl, and heterocycloalkenyl is optionally substituted with one or more substituents independently selected from the group consisting of $R^{14}$, $OR^{14}$, $SR^{14}$, $S(O)R^{14}$, $SO_2R^{14}$, $C(O)R^{14}$, $CO(O)R^{14}$, $OC(O)R^{14}$, $OC(O)OR^{14}$, $NH_2$, $NHR^{14}$, $N(R^{14})_2$, $NHC(O)R^{14}$, $NR^{14}C(O)R^{14}$, $NHS(O)_2R^{14}$, $NR^{14}S(O)_2R^{14}$, $NHC(O)OR^{14}$, $NR^{14}C(O)OR^{14}$, $NHC(O)NH_2$, $NHC(O)NHR^{14}$, $NHC(O)N(R^{14})_2$, $NR^{14}C(O)NHR^{14}$, $NR^{14}C(O)N(R^{14})_2$, $C(O)NH_2$, $C(O)NHR^{14}$, $C(O)N(R^{14})_2$, $C(O)NHOH$, $C(O)NHOR^{14}$, $C(O)NHSO_2R^{14}$, $C(O)NR^{14}SO_2R^{14}$, $SO_2NH_2$, $SO_2NHR^{14}$, $SO_2N(R^{14})_2$, $C(O)H$, $C(O)OH$, (O), $OH$, $CN$, $NO_2$, F, Cl, Br and I;

$R^{10}$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl;

$R^{11}$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^{11}$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, $OH$, $CN$, $NO_2$, F, Cl, Br and I; wherein each $R^{11}$ aryl, cycloalkyl, cycloalkenyl, heteroaryl, heterocycloalkyl, and heterocycloalkenyl is optionally substituted with one or more substituents independently selected from the group consisting of $C_1$-$C_6$ alkyl, $O$—$C_1$-$C_6$ alkyl, $NH_2$, $C(O)NH_2$, $C(O)H$, $C(O)OH$, $OH$, $CN$, $NO_2$, F, Cl, Br and I;

$R^{13}$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^{13}$ $C_1$-$C_6$ alkyl, $C_2$-$C_6$ alkenyl, and $C_2$-$C_6$ alkynyl is optionally substituted with one or more substituents independently selected from the group consisting of aryl, $NH_2$, $C(O)NH_2$, $SO_2NH_2$, $C(O)H$, $C(O)OH$, OH, CN, $NO_2$, F, Cl, Br and I; wherein each $R^{13}$ aryl, cycloalkyl, cycloalkenyl, heteroaryl, heterocycloalkyl, and heterocycloalkenyl is optionally substituted with one or more substituents independently selected from the group consisting of $C_1$-$C_6$ alkyl, O—$C_1$-$C_6$ alkyl, $C_1$-$C_6$ alkyl-O—$C_1$-$C_6$ alkyl, $NH_2$, $C(O)NH_2$, $C(O)H$, $C(O)OH$, OH, CN, $NO_2$, F, Cl, Br and I; and $R^{14}$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^{14}$ $C_1$-$C_6$ alkyl, $C_2$-$C_6$ alkenyl, and $C_2$-$C_6$ alkynyl is optionally substituted with one or more substituents independently selected from the group consisting of aryl, $NH_2$, $C(O)NH_2$, $SO_2NH_2$, $C(O)H$, $C(O)OH$, OH, CN, $NO_2$, F, Cl, Br and I; wherein each $R^{14}$ aryl, cycloalkyl, cycloalkenyl, heteroaryl, heterocycloalkyl, and heterocycloalkenyl is optionally substituted with one or more substituents independently selected from the group consisting of $C_1$-$C_6$ alkyl, O—$C_1$-$C_6$ alkyl, $C_1$-$C_6$ alkyl-O—$C_1$-$C_6$ alkyl, $NH_2$, $C(O)NH_2$, $C(O)H$, $C(O)OH$, OH, $NO_2$, F, Cl, Br and I.

In another embodiment of Formula (Ia), $R^{12}$ is halo. In another embodiment of Formula (Ia), $R^{12}$ is Cl. In another embodiment of Formula (Ia), $R^{12}$ is Cl; and $R^{16}$ is selected from the group consisting of $NHR^7$ and $NHC(O)R^7$. In another embodiment of Formula (Ia), $R^{12}$ is Cl; $R^{16}$ is selected from the group consisting of $NHR^7$ and $NHC(O)R^7$; J is CH; Q is $CR^1$; Z is $CR^1$; wherein the bond between X and Y is a single bond; Y is $CH_2$ and X is $CH_2$; and $R^1$ is H. In another embodiment of Formula (Ia), $R^{12}$ is Cl; $R^{16}$ is selected from the group consisting of $NHR^7$ and $NHC(O)R^7$; J is CH; Q is $CR^1$; Z is $CR^1$; wherein the bond between X and Y is a double bond; Y is N and X is CH; and $R^1$ is H. In another embodiment of Formula (Ia), $R^{12}$ is Cl; $R^{16}$ is selected from the group consisting of $NHR^7$ and $NHC(O)R^7$; J is CH; Q is $CR^1$; Z is $CR^1$; wherein the bond between X and Y is a single bond; Y is $CH_2$ and X is $CH_2$; $R^1$ is H; and $R^2$ is $C_1$-$C_6$ alkyl; wherein the $R^2$ $C_1$-$C_6$ alkyl is optionally substituted with one or more substituents independently selected from the group consisting of $R^4$, $SO_2R^4$, $C(O)R^4$, $N(R^4)_2$, $C(O)N(R^4)_2$, $SO_2NH_2$, and OH. In another embodiment of Formula (Ia), $R^{12}$ is Cl; $R^{16}$ is selected from the group consisting of $NHR^7$ and $NHC(O)R^7$; J is CH; Q is $CR^1$; Z is $CR^1$; wherein the bond between X and Y is a double bond; Y is N and X is CH; $R^1$ is H; and $R^2$ is $C_1$-$C_6$ alkyl; wherein the $R^2$ $C_1$-$C_6$ alkyl is optionally substituted with one or more substituents independently selected from the group consisting of $R^4$, $SO_2R^4$, $C(O)R^4$, $N(R^4)_2$, $C(O)N(R^4)_2$, $SO_2NH_2$, and OH. In another embodiment of Formula (Ia), $R^{12}$ is Cl; $R^{16}$ is selected from the group consisting of $NHR^7$ and $NHC(O)R^7$; J is CH; Q is $CR^1$; Z is $CR^1$; wherein the bond between X and Y is a single bond; Y is $CH_2$ and X is $CH_2$; $R^1$ is H; $R^2$ is $C_1$-$C_6$ alkyl; wherein the $R^2$ $C_1$-$C_6$ alkyl is optionally substituted with one or more substituents independently selected from the group consisting of $R^4$, $SO_2R^4$, $C(O)R^4$, $N(R^4)_2$, $C(O)N(R^4)_2$, $SO_2NH_2$, and OH; and $R^4$, at each occurrence, is independently selected from the group consisting of $C_1$-$C_6$ alkyl, aryl, heteroaryl, heterocycloalkyl, and cycloalkyl; wherein each $R^4$ $C_1$-$C_6$ alkyl is optionally substituted with one or more OH; wherein each $R^4$ aryl, cycloalkyl, heteroaryl, and heterocycloalkyl is optionally substituted with one or more substituents independently selected from the group consisting of $R^6$, $SO_2R^6$, $CO(O)R^6$, $NHS(O)_2R^6$, $SO_2NH_2$, $C(O)OH$, OH, CN, and F. In another embodiment of Formula (Ia), $R^{12}$ is Cl; $R^{16}$ is selected from the group consisting of $NHR^7$ and $NHC(O)R^7$; J is CH; Q is $CR^1$; Z is $CR^1$; wherein the bond between X and Y is a double bond; Y is N and X is CH; $R^1$ is H; $R^2$ is $C_1$-$C_6$ alkyl; wherein the $R^2$ $C_1$-$C_6$ alkyl is optionally substituted with one or more substituents independently selected from the group consisting of $R^4$, $SO_2R^4$, $C(O)R^4$, $N(R^4)_2$, $C(O)N(R^4)_2$, $SO_2NH_2$, and OH; and $R^4$, at each occurrence, is independently selected from the group consisting of $C_1$-$C_6$ alkyl, aryl, heteroaryl, heterocycloalkyl, and cycloalkyl; wherein each $R^4$ $C_1$-$C_6$ alkyl is optionally substituted with one or more OH; wherein each $R^4$ aryl, cycloalkyl, heteroaryl, and heterocycloalkyl is optionally substituted with one or more substituents independently selected from the group consisting of $R^6$, $SO_2R^6$, $CO(O)R^6$, $NHS(O)_2R^6$, $SO_2NH_2$, $C(O)OH$, OH, CN, and F. In another embodiment of Formula (Ia), $R^{12}$ is Cl; $R^{16}$ is selected from the group consisting of $NHR^7$ and $NHC(O)R^7$; J is CH; Q is $CR^1$; Z is $CR^1$; wherein the bond between X and Y is a single bond; Y is $CH_2$ and X is $CH_2$; $R^1$ is H; $R^2$ is $C_1$-$C_6$ alkyl; wherein the $R^2$ $C_1$-$C_6$ alkyl is optionally substituted with one or more substituents independently selected from the group consisting of $R^4$, $SO_2R^4$, $C(O)R^4$, $N(R^4)_2$, $C(O)N(R^4)_2$, $SO_2NH_2$, and OH; and wherein $R^4$, at each occurrence, is independently $C_1$-$C_6$ alkyl; wherein each $R^4$ $C_1$-$C_6$ alkyl is optionally substituted with one or more OH. In another embodiment of Formula (Ia), $R^{12}$ is Cl; $R^{16}$ is selected from the group consisting of $NHR^7$ and $NHC(O)R^7$; J is CH; Q is $CR^1$; Z is $CR^1$; wherein the bond between X and Y is a double bond; Y is N and X is CH; $R^1$ is H; $R^2$ is $C_1$-$C_6$ alkyl; wherein the $R^2$ $C_1$-$C_6$ alkyl is optionally substituted with one or more substituents independently selected from the group consisting of $R^4$, $SO_2R^4$, $C(O)R^4$, $N(R^4)_2$, $C(O)N(R^4)_2$, $SO_2NH_2$, and OH; and wherein $R^4$, at each occurrence, is independently $C_1$-$C_6$ alkyl; wherein each $R^4$ $C_1$-$C_6$ alkyl is optionally substituted with one or more OH. In another embodiment of Formula (Ia), $R^{12}$ is Cl; $R^{16}$ is selected from the group consisting of $NHR^7$ and $NHC(O)R^7$; J is CH; Q is $CR^1$; Z is $CR^1$; wherein the bond between X and Y is a single bond; Y is $CH_2$ and X is $CH_2$; $R^1$ is H; $R^2$ is $C_1$-$C_6$ alkyl; wherein the $R^2$ $C_1$-$C_6$ alkyl is optionally substituted with one or more substituents independently selected from the group consisting of $R^4$, $SO_2R^4$, $C(O)R^4$, $N(R^4)_2$, $C(O)N(R^4)_2$, $SO_2NH_2$, and OH; and wherein $R^4$, at each occurrence, is independently selected from the group consisting of aryl, heteroaryl, heterocycloalkyl, and cycloalkyl; wherein each $R^4$ aryl, cycloalkyl, heteroaryl, and heterocycloalkyl is optionally substituted with one or more substituents independently selected from the group consisting of $R^6$, $SO_2R^6$, $CO(O)R^6$, $NHS(O)_2R^6$, $SO_2NH_2$, $C(O)OH$, OH, CN, and F. In another embodiment of Formula (Ia), $R^{12}$ is Cl; $R^{16}$ is selected from the group consisting of $NHR^7$ and $NHC(O)R^7$; J is CH; Q is $CR^1$; Z is $CR^1$; wherein the bond between X and Y is a double bond; Y is N and X is CH; $R^1$ is H; $R^2$ is $C_1$-$C_6$ alkyl; wherein the $R^2$ $C_1$-$C_6$ alkyl is optionally substituted with one or more substituents independently selected from the group consisting of $R^4$, $SO_2R^4$, $C(O)R^4$, $N(R^4)_2$, $C(O)N(R^4)_2$, $SO_2NH_2$, and OH; and wherein $R^4$, at each occurrence, is independently selected from the group consisting of aryl, heteroaryl, heterocycloalkyl, and cycloalkyl; wherein each $R^4$ aryl, cycloalkyl, heteroaryl, and heterocycloalkyl is optionally substituted with one or more substituents independently selected from the group consisting of $R^6$, $SO_2R^6$, $CO(O)R^6$, $NHS(O)_2R^6$, $SO_2NH_2$, $C(O)OH$, $OH$, $CN$, and $F$.

Still another embodiment pertains to compounds of Formula (Ia), selected from the group consisting of (3R)—N-{5-chloro-4-[1-(3-fluorobenzyl)-2,3-dihydro-1H-indol-6-yl]pyridin-2-yl}piperidine-3-carboxamide;

(3R)—N-[5-chloro-4-(2,3-dihydro-1H-indol-6-yl)pyridin-2-yl]piperidine-3-carboxamide;

(3R)—N-[5-chloro-4-(1-methyl-1H-benzimidazol-6-yl)pyridin-2-yl]piperidine-3-carboxamide;

(3R)—N-{5-chloro-4-[1-(tetrahydro-2H-pyran-4-ylmethyl)-2,3-dihydro-1H-indol-6-yl]pyridin-2-yl}piperidine-3-carboxamide;

(3R)—N-{5-chloro-4-[1-(3-fluorobenzyl)-1H-benzimidazol-5-yl]pyridin-2-yl}piperidine-3-carboxamide;

(3R)—N-{5-chloro-4-[1-(3-fluorobenzyl)-1H-benzimidazol-6-yl]pyridin-2-yl}piperidine-3-carboxamide;

(3R)—N-{5-chloro-4-[1-(3-fluorobenzyl)-1H-indol-6-yl]pyridin-2-yl}piperidine-3-carboxamide;

trans-N-{5-chloro-4-[1-(3-fluorobenzyl)-1H-benzimidazol-6-yl]pyridin-2-yl}cyclohexane-1,4-diamine;

trans-N-{5-chloro-4-[1-(3-fluorobenzyl)-2,3-dihydro-1H-indol-6-yl]pyridin-2-yl}cyclohexane-1,4-diamine;

trans-4-({5-chloro-4-[1-(3-fluorobenzyl)-2,3-dihydro-1H-indol-6-yl]pyridin-2-yl}amino)cyclohexanol;

trans-4-({5-chloro-4-[1-(3-fluorobenzyl)-1H-benzimidazol-6-yl]pyridin-2-yl}amino)cyclohexanol;

trans-N-[5-chloro-4-(1-methyl-1H-benzimidazol-6-yl)pyridin-2-yl]cyclohexane-1,4-diamine;

(3R)—N-{5-chloro-4-[1-(tetrahydro-2H-pyran-4-ylmethyl)-1H-benzimidazol-6-yl]pyridin-2-yl}piperidine-3-carboxamide;

(3R)—N-(5-chloro-4-{1-[2-(morpholin-4-yl)ethyl]-1H-benzimidazol-6-yl}pyridin-2-yl)piperidine-3-carboxamide;

(3R)—N-{5-chloro-4-[1-(3-hydroxy-3-methylbutyl)-1H-benzimidazol-6-yl]pyridin-2-yl}piperidine-3-carboxamide;

(3R)—N-{5-chloro-4-[1-(4-fluorobenzyl)-1H-benzimidazol-6-yl]pyridin-2-yl}piperidine-3-carboxamide;

(3R)—N-{5-chloro-4-[1-(3,4-difluorobenzyl)-1H-benzimidazol-6-yl]pyridin-2-yl}piperidine-3-carboxamide;

(3R)—N-(5-chloro-4-{1-[2-(3-fluorophenyl)ethyl]-1H-benzimidazol-6-yl}pyridin-2-yl)piperidine-3-carboxamide;

(3R)—N-{5-chloro-4-[1-(2-sulfamoylethyl)-1H-benzimidazol-6-yl]pyridin-2-yl}piperidine-3-carboxamide;

(3R)—N-(5-chloro-4-{1-[(1,1-dioxidotetrahydrothiophen-3-yl)methyl]-1H-benzimidazol-6-yl}pyridin-2-yl)piperidine-3-carboxamide;

(3R)—N-{5-chloro-4-[1-(2-fluorobenzyl)-1H-benzimidazol-6-yl]pyridin-2-yl}piperidine-3-carboxamide;

(3R)—N-{5-chloro-4-[1-(pyridin-3-ylmethyl)-1H-benzimidazol-6-yl]pyridin-2-yl}piperidine-3-carboxamide;

(3R)—N-(5-chloro-4-{1-[(1,1-dioxidotetrahydro-2H-thiopyran-4-yl)methyl]-1H-benzimidazol-6-yl}pyridin-2-yl)piperidine-3-carboxamide;

(3R)—N-(5-chloro-4-{1-[(5-methyl-4H-1,2,4-triazol-3-yl)methyl]-1H-benzimidazol-6-yl}pyridin-2-yl)piperidine-3-carboxamide;

(3R)—N-{5-chloro-4-[1-(1,3-thiazol-4-ylmethyl)-1H-benzimidazol-5-yl]pyridin-2-yl}piperidine-3-carboxamide-(3R)—N-{5-chloro-4-[1-(1,3-thiazol-4-ylmethyl)-1H-benzimidazol-6-yl]pyridin-2-yl}piperidine-3-carboxamide (1:1);

5-chloro-N-cyclopentyl-4-[1-(3-fluorobenzyl)-1H-benzimidazol-6-yl]pyridin-2-amine;

1-[trans-4-({5-chloro-4-[1-(3-fluorobenzyl)-1H-benzimidazol-6-yl]pyridin-2-yl}amino)cyclohexyl]-3-methylurea;

N-[trans-4-({5-chloro-4-[1-(3-fluorobenzyl)-1H-benzimidazol-6-yl]pyridin-2-yl}amino)cyclohexyl]methanesulfonamide;

(3R)—N-[4-(1-benzyl-3-cyano-1H-indol-6-yl)-5-chloropyridin-2-yl]piperidine-3-carboxamide;

N'-{5-chloro-4-[1-(3-fluorobenzyl)-1H-benzimidazol-6-yl]pyridin-2-yl}-N-methyl-N-(pyridin-2-yl)propane-1,3-diamine;

1-({5-chloro-4-[1-(3-fluorobenzyl)-1H-benzimidazol-6-yl]pyridin-2-yl}amino)-3-(dimethylamino)propan-2-ol;

5-chloro-4-[1-(3-fluorobenzyl)-1H-benzimidazol-6-yl]-N-[(5-methyl-4H-1,2,4-triazol-3-yl)methyl]pyridin-2-amine;

(3R)—N-{5-chloro-4-[1-(3-fluorobenzyl)-1H-pyrrolo[3,2-b]pyridin-6-yl]pyridin-2-yl}piperidine-3-carboxamide;

N-{5-chloro-4-[1-(3-fluorobenzyl)-1H-benzimidazol-6-yl]pyridin-2-yl}-N'-(pyridin-3-yl)ethane-1,2-diamine;

N-[(5-amino-4H-1,2,4-triazol-3-yl)methyl]-5-chloro-4-[1-(3-fluorobenzyl)-1H-benzimidazol-6-yl]pyridin-2-amine;

N-benzyl-N'-{5-chloro-4-[1-(3-fluorobenzyl)-1H-benzimidazol-6-yl]pyridin-2-yl}-N-methylpropane-1,3-diamine;

5-chloro-4-[1-(3-fluorobenzyl)-1H-benzimidazol-6-yl]-N-(pyrimidin-2-ylmethyl)pyridin-2-amine;

5-chloro-4-[1-(3-fluorobenzyl)-1H-benzimidazol-6-yl]-N-[1-(pyridin-4-yl)propan-2-yl]pyridin-2-amine;

5-chloro-4-[1-(3-fluorobenzyl)-1H-benzimidazol-6-yl]-N-[1-(1-methyl-1H-pyrazol-4-yl)piperidin-3-yl]pyridin-2-amine;

5-[({5-chloro-4-[1-(3-fluorobenzyl)-1H-benzimidazol-6-yl]pyridin-2-yl}amino)methyl]pyrimidin-2-amine;

5-chloro-N-[2-(1-ethylpiperidin-4-yl)ethyl]-4-[1-(3-fluorobenzyl)-1H-benzimidazol-6-yl]pyridin-2-amine;

5-chloro-4-[1-(3-fluorobenzyl)-1H-benzimidazol-6-yl]-N-[2-(5-methyl-4H-1,2,4-triazol-3-yl)ethyl]pyridin-2-amine;

N-{5-chloro-4-[1-(3-fluorobenzyl)-1H-benzimidazol-6-yl]pyridin-2-yl}-N'-(pyridin-4-yl)ethane-1,2-diamine;

5-chloro-4-[1-(3-fluorobenzyl)-1H-benzimidazol-6-yl]-N-[2-(1-methylpiperidin-4-yl)ethyl]pyridin-2-amine;

5-chloro-4-[1-(3-fluorobenzyl)-1H-benzimidazol-6-yl]-N-[2-(pyridin-4-yl)propyl]pyridin-2-amine;

$N^1$-{5-chloro-4-[1-(3-fluorobenzyl)-1H-benzimidazol-6-yl]pyridin-2-yl}-$N^2,N^2$,2-trimethylpropane-1,2-diamine;

N-{5-chloro-4-[1-(3-fluorobenzyl)-1H-benzimidazol-6-yl]pyridin-2-yl}-N'-phenylpropane-1,3-diamine;

$N^3$-{5-chloro-4-[1-(3-fluorobenzyl)-1H-benzimidazol-6-yl]pyridin-2-yl}butane-1,3-diamine;

5-chloro-4-[1-(3-fluorobenzyl)-1H-benzimidazol-6-yl]pyridin-2-amine;

5-chloro-4-[1-(3-fluorobenzyl)-1H-benzimidazol-6-yl]-N-(1H-imidazol-4-ylmethyl)pyridin-2-amine;

5-chloro-4-[1-(3-fluorobenzyl)-1H-benzimidazol-6-yl]-N-(pyrazin-2-ylmethyl)pyridin-2-amine;

5-chloro-4-[1-(3-fluorobenzyl)-1H-benzimidazol-6-yl]-N-[1-(pyrazin-2-yl)propan-2-yl]pyridin-2-amine;

5-chloro-4-[1-(3-fluorobenzyl)-1H-benzimidazol-6-yl]-N-(1-methylpyrrolidin-3-yl)pyridin-2-amine;

5-chloro-4-[1-(3-fluorobenzyl)-1H-benzimidazol-6-yl]-N-[2-(pyridin-3-yl)ethyl]pyridin-2-amine;

N'-{5-chloro-4-[1-(3-fluorobenzyl)-1H-benzimidazol-6-yl]pyridin-2-yl}-N,N-dimethylbutane-1,4-diamine;

5-chloro-4-[1-(3-fluorobenzyl)-1H-benzimidazol-6-yl]-N-[(1-methylpiperidin-4-yl)methyl]pyridin-2-amine;

N-benzyl-N'-{5-chloro-4-[1-(3-fluorobenzyl)-1H-benzimidazol-6-yl]pyridin-2-yl}-N-methylethane-1,2-diamine;

5-chloro-4-[1-(3-fluorobenzyl)-1H-benzimidazol-6-yl]-N-[2-(pyridin-2-yl)ethyl]pyridin-2-amine;

4-({5-chloro-4-[1-(3-fluorobenzyl)-1H-benzimidazol-6-yl]pyridin-2-yl}amino)-2-methylbutan-2-ol;

N'-{5-chloro-4-[1-(3-fluorobenzyl)-1H-benzimidazol-6-yl]pyridin-2-yl}-N-methyl-N-phenylpropane-1,3-diamine;

5-chloro-4-[1-(3-fluorobenzyl)-1H-benzimidazol-6-yl]-N-(1-methylpiperidin-4-yl)pyridin-2-amine;

5-chloro-4-[1-(3-fluorobenzyl)-1H-benzimidazol-6-yl]-N-[2-(pyridin-4-yl)ethyl]pyridin-2-amine;

5-chloro-4-[1-(3-fluorobenzyl)-1H-benzimidazol-6-yl]-N-(pyrimidin-5-ylmethyl)pyridin-2-amine;

$N^2$-{5-chloro-4-[1-(3-fluorobenzyl)-1H-benzimidazol-6-yl]pyridin-2-yl}-2-methylpropane-1,2-diamine;

5-chloro-N-(2-cyclohexylethyl)-4-[1-(3-fluorobenzyl)-1H-benzimidazol-6-yl]pyridin-2-amine;

N-{5-chloro-4-[1-(3-fluorobenzyl)-1H-benzimidazol-6-yl]pyridin-2-yl}-N'-phenylethane-1,2-diamine;

N'-{5-chloro-4-[1-(3-fluorobenzyl)-1H-benzimidazol-6-yl]pyridin-2-yl}-N,N,2,2-tetramethylpropane-1,3-diamine;

2-({5-chloro-4-[1-(3-fluorobenzyl)-1H-benzimidazol-6-yl]pyridin-2-yl}amino)ethanol;

N-benzyl-5-chloro-4-[1-(3-fluorobenzyl)-1H-benzimidazol-6-yl]pyridin-2-amine;

N'-{5-chloro-4-[1-(3-fluorobenzyl)-1H-benzimidazol-6-yl]pyridin-2-yl}-N,N-dimethylpropane-1,3-diamine;

3-({5-chloro-4-[1-(3-fluorobenzyl)-1H-benzimidazol-6-yl]pyridin-2-yl}amino)propan-1-ol;

N-{5-chloro-4-[1-(3-fluorobenzyl)-1H-benzimidazol-6-yl]pyridin-2-yl}propane-1,3-diamine;

4-[({5-chloro-4-[1-(3-fluorobenzyl)-1H-benzimidazol-6-yl]pyridin-2-yl}amino)methyl]phenol;

N-{5-chloro-4-[1-(3-fluorobenzyl)-1H-benzimidazol-6-yl]pyridin-2-yl}butane-1,4-diamine;

N-[2-(4-aminophenyl)ethyl]-5-chloro-4-[1-(3-fluorobenzyl)-1H-benzimidazol-6-yl]pyridin-2-amine;

N-{5-chloro-4-[1-(3-fluorobenzyl)-1H-benzimidazol-6-yl]pyridin-2-yl}-2,2-dimethylpropane-1,3-diamine;

N-{5-chloro-4-[1-(3-fluorobenzyl)-1H-benzimidazol-6-yl]pyridin-2-yl}ethane-1,2-diamine;

N-[4-(aminomethyl)benzyl]-5-chloro-4-[1-(3-fluorobenzyl)-1H-benzimidazol-6-yl]pyridin-2-amine;

1-({5-chloro-4-[1-(3-fluorobenzyl)-1H-benzimidazol-6-yl]pyridin-2-yl}amino)-2-methylpropan-2-ol;

1-amino-3-{5-chloro-4-[1-(3-fluorobenzyl)-1H-benzimidazol-6-yl]pyridin-2-yl}amino)propan-2-ol;

N-{5-chloro-4-[1-(3-fluorobenzyl)-1H-benzimidazol-6-yl]pyridin-2-yl}-N'-(pyridin-2-yl)ethane-1,2-diamine;

(3R)—N-{5-chloro-4-[1-(3-fluorobenzyl)-1H-benzimidazol-6-yl]pyridin-2-yl}-1-azabicyclo[2.2.2]octan-3-amine;

(3S)—N-{5-chloro-4-[1-(3-fluorobenzyl)-1H-benzimidazol-6-yl]pyridin-2-yl}-1-azabicyclo[2.2.2]octan-3-amine;

2-benzyl-N-{5-chloro-4-[1-(3-fluorobenzyl)-1H-benzimidazol-6-yl]pyridin-2-yl}octahydro-1H-isoindol-4-amine;

2-benzyl-N-{5-chloro-4-[1-(3-fluorobenzyl)-1H-benzimidazol-6-yl]pyridin-2-yl}octahydrocyclopenta[c]pyrrol-4-amine;

N-{5-chloro-4-[1-(3-fluorobenzyl)-1H-benzimidazol-6-yl]pyridin-2-yl}-9-(cyclopropylmethyl)-9-azabicyclo[3.3.1]nonan-3-amine;

benzyl 4-({5-chloro-4-[1-(3-fluorobenzyl)-1H-benzimidazol-6-yl]pyridin-2-yl}amino)-4-(4-fluorophenyl)piperidine-1-carboxylate;

tert-butyl {5-chloro-4-[1-(3-fluorobenzyl)-1H-benzimidazol-6-yl]pyridin-2-yl}carbamate;

(3R)—N-(5-chloro-4-{1-[(5-methyl-1,3,4-thiadiazol-2-yl)methyl]-1H-benzimidazol-6-yl}pyridin-2-yl)piperidine-3-carboxamide;

(3R)—N-(5-chloro-4-{1-[2-(pyridin-3-yl)ethyl]-1H-benzimidazol-6-yl}pyridin-2-yl)piperidine-3-carboxamide;

N-{5-chloro-4-[1-(3-fluorobenzyl)-1H-benzimidazol-6-yl]pyridin-2-yl}-N'-methylpropane-1,3-diamine;

N-[(trans-4-aminocyclohexyl)methyl]-5-chloro-4-[1-(3-fluorobenzyl)-1H-benzimidazol-6-yl]pyridin-2-amine;

N-{5-chloro-4-[1-(3-fluorobenzyl)-1H-benzimidazol-6-yl]pyridin-2-yl}-N'-methylbutane-1,4-diamine;

N-benzyl-N'-{5-chloro-4-[1-(3-fluorobenzyl)-1H-benzimidazol-6-yl]pyridin-2-yl}ethane-1,2-diamine;

5-chloro-4-[1-(3-fluorobenzyl)-1H-benzimidazol-6-yl]-N-[2-(piperidin-4-yl)ethyl]pyridin-2-amine;

5-chloro-4-[1-(3-fluorobenzyl)-1H-benzimidazol-6-yl]-N-[2-(piperidin-3-yl)ethyl]pyridin-2-amine;

$N^2$-{5-chloro-4-[1-(3-fluorobenzyl)-1H-benzimidazol-6-yl]pyridin-2-yl}-1-phenylethane-1,2-diamine;

5-chloro-4-[1-(3-fluorobenzyl)-1H-benzimidazol-6-yl]-N-(piperidin-3-yl)pyridin-2-amine;

N-[(2R)-azetidin-2-ylmethyl]-5-chloro-4-[1-(3-fluorobenzyl)-1H-benzimidazol-6-yl]pyridin-2-amine;

N-[2-(azetidin-2-yl)ethyl]-5-chloro-4-[1-(3-fluorobenzyl)-1H-benzimidazol-6-yl]pyridin-2-amine;

(4aS,8R,8aS)—N-{5-chloro-4-[1-(3-fluorobenzyl)-1H-benzimidazol-6-yl]pyridin-2-yl}decahydroisoquinolin-8-amine;

5-chloro-4-[1-(3-fluorobenzyl)-1H-benzimidazol-6-yl]-N-[2-(pyrrolidin-2-yl)ethyl]pyridin-2-amine;

N-{5-chloro-4-[1-(3-fluorobenzyl)-1H-benzimidazol-6-yl]pyridin-2-yl}-6-azaspiro[3.5]nonan-2-amine;

N-{5-chloro-4-[1-(3-fluorobenzyl)-1H-benzimidazol-6-yl]pyridin-2-yl}-7-azaspiro[3.5]nonan-2-amine;

N-{5-chloro-4-[1-(3-fluorobenzyl)-1H-benzimidazol-6-yl]pyridin-2-yl}-7-azaspiro[3.5]nonan-1-amine;

5-chloro-4-[1-(3-fluorobenzyl)-1H-benzimidazol-6-yl]-N-{[(2R,4S)-4-fluoropyrrolidin-2-yl]methyl}pyridin-2-amine;

5-chloro-4-[1-(3-fluorobenzyl)-1H-benzimidazol-6-yl]-N-[(4-fluoropyrrolidin-3-yl)methyl]pyridin-2-amine;

N-{5-chloro-4-[1-(3-fluorobenzyl)-1H-benzimidazol-6-yl]pyridin-2-yl}-6-azaspiro[3.4]octan-2-amine;

(3R)—N-{5-chloro-4-[1-(3-fluorobenzyl)-1H-benzotriazol-6-yl]pyridin-2-yl}piperidine-3-carboxamide;

(3R)—N-(5-chloro-4-{1-[2-(methylsulfonyl)ethyl]-1H-benzimidazol-6-yl}pyridin-2-yl)piperidine-3-carboxamide;

(3R)—N-(5-chloro-4-{1-[2-(methylsulfonyl)ethyl]-1H-benzotriazol-6-yl}pyridin-2-yl)piperidine-3-carboxamide;

(3R)—N-{5-chloro-4-[1-(4-fluorobenzyl)-1H-benzotriazol-6-yl]pyridin-2-yl}piperidine-3-carboxamide;

(3R)—N-{5-chloro-4-[1-(3,4-difluorobenzyl)-1H-benzotriazol-6-yl]pyridin-2-yl}piperidine-3-carboxamide;

(3R)—N-(5-chloro-4-{1-[2-(3-fluorophenyl)ethyl]-1H-benzotriazol-6-yl}pyridin-2-yl)piperidine-3-carboxamide;

(3R)—N-{5-chloro-4-[1-(2-sulfamoylethyl)-1H-benzotriazol-6-yl]pyridin-2-yl}piperidine-3-carboxamide;

5-chloro-4-[1-(3-fluorobenzyl)-1H-benzimidazol-6-yl]-N-{2-[4-(4-methylphenyl)piperidin-4-yl]ethyl}pyridin-2-amine;

5-chloro-4-[1-(3-fluorobenzyl)-1H-benzimidazol-6-yl]-N-{2-[4-(4-methoxyphenyl)piperidin-4-yl]ethyl}pyridin-2-amine;

5-chloro-4-[1-(3-fluorobenzyl)-1H-benzimidazol-6-yl]-N-[(4-fluoropiperidin-4-yl)methyl]pyridin-2-amine;

5-chloro-4-[1-(3-fluorobenzyl)-1H-benzimidazol-6-yl]-N-{2-[3-(4-methoxyphenyl)pyrrolidin-3-yl]ethyl}pyridin-2-amine;
N-{5-chloro-4-[1-(3-fluorobenzyl)-1H-benzimidazol-6-yl]pyridin-2-yl}-6-azaspiro[3.4]octan-1-amine;
(1S,4R)—N-{5-chloro-4-[1-(3-fluorobenzyl)-1H-benzimidazol-6-yl]pyridin-2-yl}-6-azaspiro[3.5]nonan-1-amine;
N-{5-chloro-4-[1-(3-fluorobenzyl)-1H-benzimidazol-6-yl]pyridin-2-yl}-5-thia-2-azaspiro[3.4]octan-8-amine 5,5-dioxide;
N-{5-chloro-4-[1-(3-fluorobenzyl)-1H-benzimidazol-6-yl]pyridin-2-yl}-9-azabicyclo[3.3.1]nonan-3-amine;
(3S)—N-{5-chloro-4-[1-(3-fluorobenzyl)-1H-benzimidazol-6-yl]pyridin-2-yl}azepan-3-amine;
(3R)—N-{5-chloro-4-[1-(3-fluorobenzyl)-1H-benzimidazol-6-yl]pyridin-2-yl}azepan-3-amine;
(1R,4R)—N-{5-chloro-4-[1-(3-fluorobenzyl)-1H-benzimidazol-6-yl]pyridin-2-yl}-6-azaspiro[3.5]nonan-1-amine;
N-{[3-(aminomethyl)cyclohexyl]methyl}-5-chloro-4-[1-(3-fluorobenzyl)-1H-benzimidazol-6-yl]pyridin-2-amine;
N-{5-chloro-4-[1-(3-fluorobenzyl)-1H-benzimidazol-6-yl]pyridin-2-yl}-2-(piperidin-4-yl)acetamide;
4-({5-chloro-4-[1-(3-fluorobenzyl)-1H-benzimidazol-6-yl]pyridin-2-yl}amino)benzenesulfonamide;
(3R)—N-(5-chloro-4-{1-[(5-fluoropyridin-3-yl)methyl]-1H-benzimidazol-6-yl}pyridin-2-yl)piperidine-3-carboxamide;
(3R)—N-(5-chloro-4-{1-[(4-cyanotetrahydro-2H-pyran-4-yl)methyl]-1H-benzimidazol-6-yl}pyridin-2-yl)piperidine-3-carboxamide;
(3R)—N-{5-chloro-4-[1-(3-fluorobenzyl)-1H-pyrrolo[3,2-c]pyridin-6-yl]pyridin-2-yl}piperidine-3-carboxamide;
(3R)—N-{5-chloro-4-[1-(3-fluorobenzyl)-1H-pyrrolo[2,3-b]pyridin-6-yl]pyridin-2-yl}piperidine-3-carboxamide;
(3R)—N-{5-chloro-4-[5-fluoro-1-(3-fluorobenzyl)-1H-benzimidazol-6-yl]pyridin-2-yl}piperidine-3-carboxamide;
(3R)—N-{5-chloro-4-[1-(3-fluorobenzyl)-1H-indazol-6-yl]pyridin-2-yl}piperidine-3-carboxamide;
(3R)—N-[4-(1-{2-[bis(2-hydroxyethyl)amino]ethyl}-1H-benzotriazol-6-yl)-5-chloropyridin-2-yl]piperidine-3-carboxamide;
(3R)—N-[5-chloro-4-(2-oxo-2,3-dihydro-1H-indol-6-yl)pyridin-2-yl]piperidine-3-carboxamide;
(3R)—N-(5-chloro-4-{1-[3-(dimethylamino)propyl]-1H-benzimidazol-6-yl}pyridin-2-yl)piperidine-3-carboxamide;
(3R)—N-(5-chloro-4-{1-[3-(dimethylamino)propyl]-1H-benzotriazol-6-yl}pyridin-2-yl)piperidine-3-carboxamide;
(3R)—N-(5-chloro-4-{1-[2-(morpholin-4-yl)ethyl]-1H-benzotriazol-6-yl}pyridin-2-yl)piperidine-3-carboxamide;
(3R)—N-{5-chloro-4-[1-(3-fluorobenzyl)-2-methyl-1H-benzimidazol-6-yl]pyridin-2-yl}piperidine-3-carboxamide;
(3R)—N-{5-chloro-4-[3-(tetrahydro-2H-pyran-4-ylmethyl)-3H-imidazo[4,5-b]pyridin-5-yl]pyridin-2-yl}piperidine-3-carboxamide;
(3R)—N-(5-chloro-4-{1-[(1R)-1-(3-fluorophenyl)ethyl]-1H-benzimidazol-6-yl}pyridin-2-yl)piperidine-3-carboxamide;
(3R)—N-(5-chloro-4-{1-[(1R)-1-(3-fluorophenyl)ethyl]-1H-benzotriazol-6-yl}pyridin-2-yl)piperidine-3-carboxamide;
(3R)—N-{5-chloro-4-[1-(3-fluorobenzyl)-2-oxo-2,3-dihydro-1H-benzimidazol-5-yl]pyridin-2-yl}piperidine-3-carboxamide;
(3R)—N-{5-chloro-4-[5-chloro-1-(tetrahydro-2H-pyran-4-ylmethyl)-1H-benzimidazol-6-yl]pyridin-2-yl}piperidine-3-carboxamide;
N-(5-chloro-4-{1-[(5-methylpyrazin-2-yl)methyl]-2,3-dihydro-1H-indol-6-yl}pyridin-2-yl)piperidine-3-carboxamide;
N-[5-chloro-4-(1-{4-[(methylsulfonyl)amino]benzyl}-2,3-dihydro-1H-indol-6-yl)pyridin-2-yl]piperidine-3-carboxamide;
N-(5-chloro-{1-[4-fluoro-3-(methylsulfonyl)benzyl]-2,3-dihydro-1H-indol-6-yl}pyridin-2-yl)piperidine-3-carboxamide;
N-(5-chloro-4-{1-[(2-methylpyrimidin-5-yl)methyl]-2,3-dihydro-1H-indol-6-yl}pyridin-2-yl)piperidine-3-carboxamide;
N-(5-chloro-4-{1-[3-(methylsulfonyl)benzyl]-2,3-dihydro-1H-indol-6-yl}pyridin-2-yl)piperidine-3-carboxamide;
N-(5-chloro-4-{1-[(6-methylpyridin-3-yl)methyl]-2,3-dihydro-1H-indol-6-yl}pyridin-2-yl)piperidine-3-carboxamide;
N-{5-chloro-4-[1-(pyrrolidin-3-ylmethyl)-2,3-dihydro-1H-indol-6-yl]pyridin-2-yl}piperidine-3-carboxamide;
4-[(6-{5-chloro-2-[(piperidin-3-ylcarbonyl)amino]pyridin-4-yl}-2,3-dihydro-1H-indol-1-yl)methyl]benzoic acid;
N-(5-chloro-4-{1-[4-(methylsulfonyl)benzyl]-2,3-dihydro-1H-indol-6-yl}pyridin-2-yl)piperidine-3-carboxamide;
methyl 4-[(6-{5-chloro-2-[(piperidin-3-ylcarbonyl)amino]pyridin-4-yl}-2,3-dihydro-1H-indol-1-yl)methyl]benzoate;
N-{5-chloro-4-[1-(pyrimidin-5-ylmethyl)-2,3-dihydro-1H-indol-6-yl]pyridin-2-yl}piperidine-3-carboxamide;
N-[5-chloro-4-(1-{[6-(trifluoromethyl)pyridin-2-yl]methyl}-2,3-dihydro-1H-indol-6-yl)pyridin-2-yl]piperidine-3-carboxamide;
N-{5-chloro-4-[1-(quinolin-6-ylmethyl)-2,3-dihydro-1H-indol-6-yl]pyridin-2-yl}piperidine-3-carboxamide;
N-{4-[1-(1H-benzimidazol-2-ylmethyl)-2,3-dihydro-1H-indol-6-yl]-5-chloropyridin-2-yl}piperidine-3-carboxamide;
N-{5-chloro-4-[1-(2,3-dihydro-1,4-benzodioxin-5-ylmethyl)-2,3-dihydro-1H-indol-6-yl]pyridin-2-yl}piperidine-3-carboxamide;
N-(5-chloro-4-{1-[(1-methyl-1H-benzimidazol-2-yl)methyl]-2,3-dihydro-1H-indol-6-yl}pyridin-2-yl)piperidine-3-carboxamide;
N-(5-chloro-4-{1-[(1-methyl-1H-benzotriazol-5-yl)methyl]-2,3-dihydro-1H-indol-6-yl}pyridin-2-yl)piperidine-3-carboxamide;
N-{4-[1-(1,3-benzodioxol-4-ylmethyl)-2,3-dihydro-1H-indol-6-yl]-5-chloropyridin-2-yl}piperidine-3-carboxamide;
N-{5-chloro-4-[1-(4-methylbenzyl)-2,3-dihydro-1H-indol-6-yl]pyridin-2-yl}piperidine-3-carboxamide;
N-{5-chloro-4-[1-(quinoxalin-6-ylmethyl)-2,3-dihydro-1H-indol-6-yl]pyridin-2-yl}piperidine-3-carboxamide;
N-{5-chloro-4-[1-(pyrazin-2-ylmethyl)-2,3-dihydro-1H-indol-6-yl]pyridin-2-yl}piperidine-3-carboxamide;
N-{5-chloro-4-[1-(2,3-dihydro[1,4]dioxino[2,3-b]pyridin-7-ylmethyl)-2,3-dihydro-1H-indol-6-yl]pyridin-2-yl}piperidine-3-carboxamide;
N-[5-chloro-4-(1-{[6-(methylsulfonyl)pyridin-3-yl]methyl}-2,3-dihydro-1H-indol-6-yl)pyridin-2-yl]piperidine-3-carboxamide;
N-{5-chloro-4-[1-(4-sulfamoylbenzyl)-2,3-dihydro-1H-indol-6-yl]pyridin-2-yl}piperidine-3-carboxamide;

N-(5-chloro-4-{1-[3-fluoro-4-(methylsulfonyl)benzyl]-2,3-dihydro-1H-indol-6-yl}pyridin-2-yl)piperidine-3-carboxamide;
N-(5-chloro-4-{1-[4-(2H-tetrazol-5-yl)benzyl]-2,3-dihydro-1H-indol-6-yl}pyridin-2-yl)piperidine-3-carboxamide;
N-{5-chloro-4-[1-(pyrrolidin-2-ylmethyl)-2,3-dihydro-1H-indol-6-yl]pyridin-2-yl}piperidine-3-carboxamide;
N-(5-chloro-4-{1-[(1-methylpiperidin-4-yl)methyl]-2,3-dihydro-1H-indol-6-yl}pyridin-2-yl)piperidine-3-carboxamide;
N-{5-chloro-4-[1-(3-fluorobenzyl)-1H-imidazo[4,5-b]pyridin-6-yl]pyridin-2-yl}piperidine-3-carboxamide;
(3R)—N-[5-chloro-4-(1-{[3-(morpholin-4-yl)oxetan-3-yl]methyl}-1H-benzimidazol-6-yl)pyridin-2-yl]piperidine-3-carboxamide;
(3R)—N-[5-chloro-4-(1-{[3-(pyrrolidin-1-yl)oxetan-3-yl]methyl}-1H-benzimidazol-6-yl)pyridin-2-yl]piperidine-3-carboxamide;
N-{5-chloro-4-[1-(tetrahydro-2H-pyran-4-ylmethyl)-1H-benzimidazol-6-yl]pyridin-2-yl}-7-azaspiro[3.5]nonan-2-amine;
N-{5-chloro-4-[1-(tetrahydro-2H-pyran-4-ylmethyl)-1H-benzimidazol-6-yl]pyridin-2-yl}-7-(methylsulfonyl)-7-azaspiro[3.5]nonan-2-amine;
(2E)-N-{5-chloro-4-[1-(3-fluorobenzyl)-1H-benzimidazol-6-yl]pyridin-2-yl}-3-(pyridin-4-yl)prop-2-enamide;
(1R,2S)—N-{5-chloro-4-[1-(3-fluorobenzyl)-1H-benzimidazol-6-yl]pyridin-2-yl}-N'-cyclopentylcyclobutane-1,2-dicarboxamide;
N-{5-chloro-4-[1-(3-fluorobenzyl)-1H-benzimidazol-6-yl]pyridin-2-yl}-2-(2-oxopyridin-1(2H)-yl)propanamide;
N-{5-chloro-4-[1-(3-fluorobenzyl)-1H-benzimidazol-6-yl]pyridin-2-yl}-2-(methylsulfonyl)acetamide;
N-{5-chloro-4-[1-(3-fluorobenzyl)-1H-benzimidazol-6-yl]pyridin-2-yl}-1-(3-chlorophenyl)-5-oxopyrrolidine-3-carboxamide;
1-benzyl-N-{5-chloro-4-[1-(3-fluorobenzyl)-1H-benzimidazol-6-yl]pyridin-2-yl}-5-oxopyrrolidine-3-carboxamide;
N-{5-chloro-4-[1-(3-fluorobenzyl)-1H-benzimidazol-6-yl]pyridin-2-yl}-2,3-dihydro[1,4]dioxino[2,3-b]pyridine-7-carboxamide;
(3R)—N-{5-chloro-4-[1-(3-fluorobenzyl)-1H-benzimidazol-6-yl]pyridin-2-yl}-3-(pyridin-3-yl)-1H-pyrrolo[1,2-c][1,3]thiazole-7-carboxamide;
N-{5-chloro-4-[1-(3-fluorobenzyl)-1H-benzimidazol-6-yl]pyridin-2-yl}-3-oxocyclobutanecarboxamide;
N-{5-chloro-4-[1-(3-fluorobenzyl)-1H-benzimidazol-6-yl]pyridin-2-yl}-6-oxospiro[3.3]heptane-2-carboxamide;
benzyl (1R,5S,6r)-6-({5-chloro-4-[1-(3-fluorobenzyl)-1H-benzimidazol-6-yl]pyridin-2-yl}carbamoyl)-3-azabicyclo[3.1.0]hexane-3-carboxylate;
N-{5-chloro-4-[1-(3-fluorobenzyl)-1H-benzimidazol-6-yl]pyridin-2-yl}-1-methylazetidine-3-carboxamide;
N-{5-chloro-4-[1-(3-fluorobenzyl)-1H-benzimidazol-6-yl]pyridin-2-yl}-3-methyloxetane-3-carboxamide;
N-{5-chloro-4-[1-(3-fluorobenzyl)-1H-benzimidazol-6-yl]pyridin-2-yl}-4-hydroxy-4-(trifluoromethyl)cyclohexanecarboxamide;
N-{5-chloro-4-[1-(3-fluorobenzyl)-1H-benzimidazol-6-yl]pyridin-2-yl}-1-(2,2-dimethylpropanoyl)-2,3-dihydro-1H-pyrido[2,3-b][1,4]oxazine-6-carboxamide;
N-{5-chloro-4-[3-(3-fluorobenzyl)-1H-benzimidazol-6-yl]pyridin-2-yl}-2-(methylsulfonyl)-5-thia-2-azaspiro[3.4]octane-8-carboxamide 5,5-dioxide;
$N^8$-{5-chloro-4-[1-(3-fluorobenzyl)-1H-benzimidazol-6-yl]pyridin-2-yl}-$N^2$-ethyl-5-thia-2-azaspiro[3.4]octane-2,8-dicarboxamide 5,5-dioxide;
$N^8$-{5-chloro-4-[1-(3-fluorobenzyl)-1H-benzimidazol-6-yl]pyridin-2-yl}-$N^2$-phenyl-5-thia-2-azaspiro[3.4]octane-2,8-dicarboxamide 5,5-dioxide;
N-{5-chloro-4-[1-(3-fluorobenzyl)-1H-benzimidazol-6-yl]pyridin-2-yl}-7-(cyclohexylcarbonyl)-1-thia-7-azaspiro[4.4]nonane-4-carboxamide 1,1-dioxide;
N-{5-chloro-4-[1-(3-fluorobenzyl)-1H-benzimidazol-6-yl]pyridin-2-yl}-7-(2-methylpropanoyl)-1-thia-7-azaspiro[4.4]nonane-4-carboxamide 1,1-dioxide;
N-{5-chloro-4-[1-(3-fluorobenzyl)-1H-benzimidazol-6-yl]pyridin-2-yl}-7-(phenylsulfonyl)-1-thia-7-azaspiro[4.4]nonane-4-carboxamide 1,1-dioxide;
7-benzoyl-N-{5-chloro-4-[1-(3-fluorobenzyl)-1H-benzimidazol-6-yl]pyridin-2-yl}-1-thia-7-azaspiro[4.4]nonane-4-carboxamide 1,1-dioxide;
N-{5-chloro-4-[1-(3-fluorobenzyl)-1H-benzimidazol-6-yl]pyridin-2-yl}-7-ethyl-1-thia-7-azaspiro[4.4]nonane-4-carboxamide 1,1-dioxide;
N-{5-chloro-4-[1-(3-fluorobenzyl)-1H-benzimidazol-6-yl]pyridin-2-yl}-2-oxohexahydro-2H-cyclopenta[d][1,3]oxazole-5-carboxamide;
N-{5-chloro-4-[1-(3-fluorobenzyl)-1H-benzimidazol-6-yl]pyridin-2-yl}-7-(methylsulfonyl)-1-thia-7-azaspiro[4.4]nonane-4-carboxamide 1,1-dioxide;
(2E)-N-carbamoyl-N'-{5-chloro-4-[1-(3-fluorobenzyl)-1H-benzimidazol-6-yl]pyridin-2-yl}but-2-enediamide;
N-{5-chloro-4-[1-(3-fluorobenzyl)-1H-benzimidazol-6-yl]pyridin-2-yl}cyclopropane-1,1-dicarboxamide;
N-{5-chloro-4-[1-(3-fluorobenzyl)-1H-benzimidazol-6-yl]pyridin-2-yl}-1H-pyrazole-4-carboxamide;
trans-N-{5-chloro-4-[1-(tetrahydro-2H-pyran-4-ylmethyl)-1H-benzimidazol-6-yl]pyridin-2-yl}cyclohexane-1,4-diamine;
N-{5-chloro-4-[1-(tetrahydro-2H-pyran-4-ylmethyl)-1H-benzimidazol-6-yl]pyridin-2-yl}piperidine-4-carboxamide;
N-{5-chloro-4-[1-(tetrahydro-2H-pyran-4-ylmethyl)-1H-benzimidazol-6-yl]pyridin-2-yl}-2-oxohexahydro-2H-cyclopenta[d][1,3]oxazole-5-carboxamide;
(2s,4r)-N-{5-chloro-4-[1-(3-fluorobenzyl)-1H-benzimidazol-6-yl]pyridin-2-yl}-6-azaspiro[3.4]octan-2-amine;
(2r,4s)-N-{5-chloro-4-[1-(3-fluorobenzyl)-1H-benzimidazol-6-yl]pyridin-2-yl}-6-azaspiro[3.4]octan-2-amine;
(2s,4r)-N-{5-chloro-4-[1-(3-fluorobenzyl)-1H-benzimidazol-6-yl]pyridin-2-yl}-6-azaspiro[3.5]nonan-2-amine;
(2r,4s)-N-{5-chloro-4-[1-(3-fluorobenzyl)-1H-benzimidazol-6-yl]pyridin-2-yl}-6-azaspiro[3.5]nonan-2-amine;
(3S)—N-{5-chloro-4-[1-(tetrahydro-2H-pyran-4-ylmethyl)-1H-benzimidazol-6-yl]pyridin-2-yl}piperidine-3-carboxamide;
(3R)—N-{5-chloro-4-[1-(3-fluorobenzyl)-1H-imidazo[4,5-b]pyrazin-6-yl]pyridin-2-yl}piperidine-3-carboxamide;
N-(5-chloro-4-{1-[2-(dimethylamino)-2-oxoethyl]-2,3-dihydro-1H-indol-6-yl}pyridin-2-yl)piperidine-3-carboxamide;
N-(5-chloro-4-{1-[2-(morpholin-4-yl)-2-oxoethyl]-2,3-dihydro-1H-indol-6-yl}pyridin-2-yl)piperidine-3-carboxamide;
N-(5-chloro-4-{1-[2-oxo-2-(pyrrolidin-1-yl)ethyl]-2,3-dihydro-1H-indol-6-yl}pyridin-2-yl)piperidine-3-carboxamide;
(3R)—N-{5-chloro-4-[3-cyano-1-(tetrahydro-2H-pyran-4-ylmethyl)-1H-pyrrolo[3,2-b]pyridin-6-yl]pyridin-2-yl}piperidine-3-carboxamide;

4-[(6-{5-chloro-2-[(2-hydroxyethyl)amino]pyridin-4-yl}-1H-benzimidazol-1-yl)methyl]tetrahydro-2H-pyran-4-carbonitrile;

2-[(5-chloro-4-{1-[(5-fluoropyridin-3-yl)methyl]-1H-benzimidazol-6-yl}pyridin-2-yl)amino]ethanol;

trans-N-{5-chloro-4-[1-(3-fluorobenzyl)-1H-benzimidazol-6-yl]pyridin-2-yl}-N'-(pyridin-2-ylmethyl)cyclohexane-1,4-diamine;

trans-N-{5-chloro-4-[1-(3-fluorobenzyl)-1H-benzimidazol-6-yl]pyridin-2-yl}-N'-(pyridin-3-ylmethyl)cyclohexane-1,4-diamine;

trans-N-{5-chloro-4-[1-(3-fluorobenzyl)-1H-benzimidazol-6-yl]pyridin-2-yl}-N'-(pyridin-4-ylmethyl)cyclohexane-1,4-diamine;

trans-N-(1,3-benzodioxol-5-ylmethyl)-N'-{5-chloro-4-[1-(3-fluorobenzyl)-1H-benzimidazol-6-yl]pyridin-2-yl}cyclohexane-1,4-diamine;

trans-N-{5-chloro-4-[1-(3-fluorobenzyl)-1H-benzimidazol-6-yl]pyridin-2-yl}-N'-(1,3-thiazol-2-ylmethyl)cyclohexane-1,4-diamine;

trans-N-{5-chloro-4-[1-(3-fluorobenzyl)-1H-benzimidazol-6-yl]pyridin-2-yl}-N'-{[1-(methoxymethyl)-2,3-dihydro-1H-1,2,3-triazol-4-yl]methyl}cyclohexane-1,4-diamine;

trans-N-{5-chloro-4-[1-(3-fluorobenzyl)-1H-benzimidazol-6-yl]pyridin-2-yl}-N'-[2-(morpholin-4-yl)ethyl]cyclohexane-1,4-diamine;

trans-N-{5-chloro-4-[1-(3-fluorobenzyl)-1H-benzimidazol-6-yl]pyridin-2-yl}-N'-[2-methyl-2-(morpholin-4-yl)propyl]cyclohexane-1,4-diamine;

trans-N-{5-chloro-4-[1-(3-fluorobenzyl)-1H-benzimidazol-6-yl]pyridin-2-yl}-N'-(tetrahydrofuran-2-ylmethyl)cyclohexane-1,4-diamine;

trans-N-{5-chloro-4-[1-(3-fluorobenzyl)-1H-benzimidazol-6-yl]pyridin-2-yl}-N'-[(2,5-dimethoxytetrahydrofuran-3-yl)methyl]cyclohexane-1,4-diamine;

trans-N-{5-chloro-4-[1-(3-fluorobenzyl)-1H-benzimidazol-6-yl]pyridin-2-yl}-N'-(cyclopropylmethyl)cyclohexane-1,4-diamine;

3-{[trans-4-({5-chloro-4-[1-(3-fluorobenzyl)-1H-benzimidazol-6-yl]pyridin-2-yl}amino)cyclohexyl]amino}propane-1,2-diol;

trans-N-{5-chloro-4-[1-(3-fluorobenzyl)-1H-benzimidazol-6-yl]pyridin-2-yl}-N'-(1-methoxypropan-2-yl)cyclohexane-1,4-diamine;

trans-N-{5-chloro-4-[1-(3-fluorobenzyl)-1H-benzimidazol-6-yl]pyridin-2-yl}-N'-(1,3-dimethoxypropan-2-yl)cyclohexane-1,4-diamine;

trans-N-{5-chloro-4-[1-(3-fluorobenzyl)-1H-benzimidazol-6-yl]pyridin-2-yl}-N'-(2-phenoxyethyl)cyclohexane-1,4-diamine;

trans-N-[3-(benzyloxy)propyl]-N'-{5-chloro-4-[1-(3-fluorobenzyl)-1H-benzimidazol-6-yl]pyridin-2-yl}cyclohexane-1,4-diamine;

trans-N-{5-chloro-4-[1-(3-fluorobenzyl)-1H-benzimidazol-6-yl]pyridin-2-yl}-N'-[2,2-dimethyl-3-(phenylsulfinyl)propyl]cyclohexane-1,4-diamine;

trans-N-{5-chloro-4-[1-(3-fluorobenzyl)-1H-benzimidazol-6-yl]pyridin-2-yl}-N'-(2-methoxypropyl)cyclohexane-1,4-diamine;

trans-N-{5-chloro-4-[1-(3-fluorobenzyl)-1H-benzimidazol-6-yl]pyridin-2-yl}-N'-[2-(cyclohexyloxy)propyl]cyclohexane-1,4-diamine;

trans-N-{5-chloro-4-[1-(3-fluorobenzyl)-1H-benzimidazol-6-yl]pyridin-2-yl}-N'-[(5,5-dimethyltetrahydrofuran-2-yl)methyl]cyclohexane-1,4-diamine;

trans-N-{5-chloro-4-[1-(3-fluorobenzyl)-1H-benzimidazol-6-yl]pyridin-2-yl}-N'-(3-methoxypropyl)cyclohexane-1,4-diamine;

2-{[trans-4-({5-chloro-4-[1-(3-fluorobenzyl)-1H-benzimidazol-6-yl]pyridin-2-yl}amino)cyclohexyl]amino}propan-1-ol;

(3R)—N-{5-chloro-4-[1-(3-fluorobenzyl)-1H-[1,2,3]triazolo[4,5-b]pyrazin-6-yl]pyridin-2-yl}piperidine-3-carboxamide;

(3R)—N-{5-chloro-4-[1-(tetrahydro-2H-pyran-4-ylmethyl)-1H-benzotriazol-6-yl]pyridin-2-yl}piperidine-3-carboxamide;

N-{5-chloro-4-[1-(3-fluorobenzyl)-1H-pyrrolo[3,2-b]pyridin-6-yl]pyridin-2-yl}-6-azaspiro[3.4]octan-2-amine;

N-{5-chloro-4-[1-(3-fluorobenzyl)-1H-benzimidazol-6-yl]pyridin-2-yl}cyclohexane-1,3-diamine;

(3R)—N-{5-chloro-4-[1-(3-fluorobenzyl)-2-(trifluoromethyl)-1H-benzimidazol-6-yl]pyridin-2-yl}piperidine-3-carboxamide;

(3R)—N-{5-chloro-4-[2-(trifluoromethyl)-1H-benzimidazol-6-yl]pyridin-2-yl}piperidine-3-carboxamide;

(3R)—N-{5-chloro-4-[1-(3-fluorobenzyl)-3-(methoxymethyl)-1H-pyrrolo[3,2-b]pyridin-6-yl]pyridin-2-yl}piperidine-3-carboxamide;

(3R)—N-{5-chloro-4-[3-(methoxymethyl)-1-(tetrahydro-2H-pyran-4-ylmethyl)-1H-pyrrolo[3,2-b]pyridin-6-yl]pyridin-2-yl}piperidine-3-carboxamide;

N-{5-chloro-4-[1-(tetrahydro-2H-pyran-4-ylmethyl)-1H-benzimidazol-6-yl]pyridin-2-yl}pyridine-4-carboxamide;

N-{5-chloro-4-[1-(tetrahydro-2H-pyran-4-ylmethyl)-1H-benzimidazol-6-yl]pyridin-2-yl}pyridine-3-carboxamide;

N-{5-chloro-4-[1-(tetrahydro-2H-pyran-4-ylmethyl)-1H-benzimidazol-6-yl]pyridin-2-yl}-1-methyl-1H-imidazole-4-carboxamide;

N-{5-chloro-4-[1-(tetrahydro-2H-pyran-4-ylmethyl)-1H-benzimidazol-6-yl]pyridin-2-yl}-1H-imidazole-4-carboxamide;

N-{5-chloro-4-[1-(tetrahydro-2H-pyran-4-ylmethyl)-1H-benzimidazol-6-yl]pyridin-2-yl}-1,3-thiazole-4-carboxamide;

N-{5-chloro-4-[1-(tetrahydro-2H-pyran-4-ylmethyl)-1H-benzimidazol-6-yl]pyridin-2-yl}-1H-1,2,4-triazole-3-carboxamide;

N-{5-chloro-4-[1-(tetrahydro-2H-pyran-4-ylmethyl)-1H-benzimidazol-6-yl]pyridin-2-yl}pyrimidine-5-carboxamide;

N-{5-chloro-4-[1-(tetrahydro-2H-pyran-4-ylmethyl)-1H-benzimidazol-6-yl]pyridin-2-yl}pyrazine-2-carboxamide;

N-{5-chloro-4-[1-(tetrahydro-2H-pyran-4-ylmethyl)-1H-benzimidazol-6-yl]pyridin-2-yl}-1H-pyrazole-3-carboxamide;

N-{5-chloro-4-[1-(tetrahydro-2H-pyran-4-ylmethyl)-1H-benzimidazol-6-yl]pyridin-2-yl}-1H-1,2,3-triazole-4-carboxamide;

N-{5-chloro-4-[1-(tetrahydro-2H-pyran-4-ylmethyl)-1H-benzimidazol-6-yl]pyridin-2-yl}azetidine-3-carboxamide;

N-{5-chloro-4-[1-(tetrahydro-2H-pyran-4-ylmethyl)-1H-benzimidazol-6-yl]pyridin-2-yl}-1H-pyrazole-4-carboxamide;

(3aR,6aS)—N-{5-chloro-4-[1-(tetrahydro-2H-pyran-4-ylmethyl)-1H-benzimidazol-6-yl]pyridin-2-yl}octahydrocyclopenta[c]pyrrole-5-carboxamide;

N-{5-chloro-4-[1-(tetrahydro-2H-pyran-4-ylmethyl)-1H-benzimidazol-6-yl]pyridin-2-yl}-2-azaspiro[3.3]heptane-6-carboxamide;

N-{5-chloro-4-[1-(tetrahydro-2H-pyran-4-ylmethyl)-1H-benzimidazol-6-yl]pyridin-2-yl}-3-azabicyclo[3.1.0]hexane-6-carboxamide;

N-{5-chloro-4-[1-(tetrahydro-2H-pyran-4-ylmethyl)-1H-benzimidazol-6-yl]pyridin-2-yl}-3-oxocyclobutanecarboxamide;

(3R)—N-{5-chloro-4-[2-(3-fluorophenyl)-1-methyl-1H-benzimidazol-6-yl]pyridin-2-yl}piperidine-3-carboxamide;

(3R)—N-{5-chloro-4-[2-(3-fluorobenzyl)-1-methyl-1H-benzimidazol-6-yl]pyridin-2-yl}piperidine-3-carboxamide;

N-{5-chloro-4-[1-(tetrahydro-2H-pyran-4-ylmethyl)-1H-benzimidazol-6-yl]pyridin-2-yl}-1,2,5,6-tetrahydropyridine-3-carboxamide;

N-{5-chloro-4-[1-(3-fluorobenzyl)-1H-benzimidazol-6-yl]pyridin-2-yl}-2-(tetrahydro-2H-pyran-4-ylsulfonyl)propanamide;

N-{5-chloro-4-[1-(3-fluorobenzyl)-1H-benzimidazol-6-yl]pyridin-2-yl}-5,6,7,8-tetrahydro[1,2,4]triazolo[4,3-a]pyridine-6-carboxamide;

N-{5-chloro-4-[1-(3-fluorobenzyl)-1H-benzimidazol-6-yl]pyridin-2-yl}-5,6,7,8-tetrahydroimidazo[1,2-a]pyridine-6-carboxamide;

N-{5-chloro-4-[1-(3-fluorobenzyl)-1H-benzimidazol-6-yl]pyridin-2-yl}-3,4-dihydro-2H-pyrano[2,3-b]pyridine-6-carboxamide;

N-{5-chloro-4-[1-(3-fluorobenzyl)-1H-benzimidazol-6-yl]pyridin-2-yl}-2-sulfamoylacetamide;

N-{5-chloro-4-[1-(3-fluorobenzyl)-1H-benzimidazol-6-yl]pyridin-2-yl}-2-[(4-methylpiperazin-1-yl)sulfonyl]acetamide;

N-{5-chloro-4-[1-(3-fluorobenzyl)-1H-benzimidazol-6-yl]pyridin-2-yl}-5-oxo-D-prolinamide;

N-{5-chloro-4-[1-(3-fluorobenzyl)-1H-benzimidazol-6-yl]pyridin-2-yl}-$N^2$-(dimethylsulfamoyl)glycinamide;

N-{5-chloro-4-[1-(tetrahydro-2H-pyran-4-ylmethyl)-1H-benzimidazol-6-yl]pyridin-2-yl}-2-(tetrahydro-2H-pyran-4-ylsulfonyl)propanamide;

N-{5-chloro-4-[1-(tetrahydro-2H-pyran-4-ylmethyl)-1H-benzimidazol-6-yl]pyridin-2-yl}-5,6,7,8-tetrahydro[1,2,4]triazolo[4,3-a]pyridine-6-carboxamide;

N-{5-chloro-4-[1-(tetrahydro-2H-pyran-4-ylmethyl)-1H-benzimidazol-6-yl]pyridin-2-yl}-5,6,7,8-tetrahydroimidazo[1,2-a]pyridine-6-carboxamide;

N-{5-chloro-4-[1-(tetrahydro-2H-pyran-4-ylmethyl)-1H-benzimidazol-6-yl]pyridin-2-yl}-3,4-dihydro-2H-pyrano[2,3-b]pyridine-6-carboxamide;

N-{5-chloro-4-[1-(tetrahydro-2H-pyran-4-ylmethyl)-1H-benzimidazol-6-yl]pyridin-2-yl}-2-sulfamoylacetamide;

N-{5-chloro-4-[1-(tetrahydro-2H-pyran-4-ylmethyl)-1H-benzimidazol-6-yl]pyridin-2-yl}-$N^2$-(ethylsulfonyl)glycinamide;

N-{5-chloro-4-[1-(tetrahydro-2H-pyran-4-ylmethyl)-1H-benzimidazol-6-yl]pyridin-2-yl}-5-oxo-D-prolinamide;

N-{5-chloro-4-[1-(tetrahydro-2H-pyran-4-ylmethyl)-1H-benzimidazol-6-yl]pyridin-2-yl}-$N^2$-(dimethylsulfamoyl)glycinamide;

N-{5-chloro-4-[1-(tetrahydro-2H-pyran-4-ylmethyl)-1H-benzimidazol-6-yl]pyridin-2-yl}-2-[(4-methylpiperazin-1-yl)sulfonyl]acetamide;

(3R)—N-(5-chloro-4-{1-[4-(methylsulfonyl)benzyl]-1H-benzotriazol-6-yl}pyridin-2-yl)piperidine-3-carboxamide;

cis-3-amino-N-{5-chloro-4-[1-(tetrahydro-2H-pyran-4-ylmethyl)-1H-benzimidazol-6-yl]pyridin-2-yl}cyclobutanecarboxamide;

trans-3-amino-N-{5-chloro-4-[1-(tetrahydro-2H-pyran-4-ylmethyl)-1H-benzimidazol-6-yl]pyridin-2-yl}cyclobutanecarboxamide;

(1R,5S,6r)-N-{5-chloro-4-[1-(tetrahydro-2H-pyran-4-ylmethyl)-1H-benzimidazol-6-yl]pyridin-2-yl}-3-azabicyclo[3.1.0]hexane-6-carboxamide;

(2R)—N-{5-chloro-4-[1-(tetrahydro-2H-pyran-4-ylmethyl)-1H-benzimidazol-6-yl]pyridin-2-yl}azetidine-2-carboxamide;

6-amino-N-{5-chloro-4-[1-(tetrahydro-2H-pyran-4-ylmethyl)-1H-benzimidazol-6-yl]pyridin-2-yl}spiro[3.3]heptane-2-carboxamide;

N-{5-chloro-4-[1-(tetrahydro-2H-pyran-4-ylmethyl)-1H-benzimidazol-6-yl]pyridin-2-yl}-2-(furan-2-yl)-2-(piperazin-1-yl)acetamide;

1-amino-N-{5-chloro-4-[1-(tetrahydro-2H-pyran-4-ylmethyl)-1H-benzimidazol-6-yl]pyridin-2-yl}cyclopentanecarboxamide;

N-{5-chloro-4-[1-(tetrahydro-2H-pyran-4-ylmethyl)-1H-benzimidazol-6-yl]pyridin-2-yl}-5-thia-2-azaspiro[3.4]octane-8-carboxamide 5,5-dioxide;

(2S,3R)—N-{5-chloro-4-[1-(tetrahydro-2H-pyran-4-ylmethyl)-1H-benzimidazol-6-yl]pyridin-2-yl}-3-ethylazetidine-2-carboxamide;

N-{5-chloro-4-[1-(tetrahydro-2H-pyran-4-ylmethyl)-1H-benzimidazol-6-yl]pyridin-2-yl}-4-(4-fluorophenyl)piperidine-4-carboxamide;

N-{5-chloro-4-[1-(tetrahydro-2H-pyran-4-ylmethyl)-1H-benzimidazol-6-yl]pyridin-2-yl}-1-thia-7-azaspiro[4.4]nonane-4-carboxamide 1,1-dioxide;

(3R)—N-(5-chloro-4-{1-[2-(3-fluorophenyl)-2-oxoethyl]-1H-pyrrolo[3,2-b]pyridin-6-yl}pyridin-2-yl)piperidine-3-carboxamide;

N-(5-chloro-4-{1-[(5-fluoropyridin-3-yl)methyl]-1H-pyrrolo[3,2-b]pyridin-6-yl}pyridin-2-yl)-3-oxo cyclobutanecarboxamide;

(3R)—N-(5-chloro-4-{1-[(1-methyl-1H-benzotriazol-6-yl)methyl]-1H-pyrrolo[3,2-b]pyridin-6-yl}pyridin-2-yl)piperidine-3-carboxamide;

(3R)—N-(5-chloro-4-{1-[2-oxo-2-(tetrahydro-2H-pyran-4-yl)ethyl]-1H-pyrrolo[3,2-b]pyridin-6-yl}pyridin-2-yl)piperidine-3-carboxamide;

(3R)—N-(5-chloro-4-{1-[2-hydroxy-2-(tetrahydro-2H-pyran-4-yl)ethyl]-1H-pyrrolo[3,2-b]pyridin-6-yl}pyridin-2-yl)piperidine-3-carboxamide;

(3R)—N-(5-chloro-4-{1-[(trans-4-hydroxy-4-methylcyclohexyl)methyl]-1H-benzotriazol-6-yl}pyridin-2-yl)piperidine-3-carboxamide;

(3R)—N-(5-chloro-4-{5-fluoro-1-[(1R)-1-(3-fluorophenyl)ethyl]-1H-benzotriazol-6-yl}pyridin-2-yl)piperidine-3-carboxamide;

methyl 4-{[6-(5-chloro-2-{[(3R)-piperidin-3-ylcarbonyl]amino}pyridin-4-yl)-1H-benzimidazol-1-yl]methyl}benzoate;

methyl 4-{[6-(5-chloro-2-{[(3R)-piperidin-3-ylcarbonyl]amino}pyridin-4-yl)-1H-benzotriazol-1-yl]methyl}benzoate;

(3R)—N-(5-chloro-4-{1-[3-(3-fluorophenyl)propyl]-1H-benzimidazol-6-yl}pyridin-2-yl)piperidine-3-carboxamide;

(3R)—N-(5-chloro-4-{1-[3-(3-fluorophenyl)propyl]-1H-benzotriazol-6-yl}pyridin-2-yl)piperidine-3-carboxamide;

4-{[6-(5-chloro-2-{[(3R)-piperidin-3-ylcarbonyl]amino}pyridin-4-yl)-1H-benzotriazol-1-yl]methyl}benzoic acid;

4-{[6-(2-amino-5-chloropyridin-4-yl)-1H-benzotriazol-1-yl]methyl}benzoic acid;

(3R)—N-{4-[1-(tetrahydro-2H-pyran-4-ylmethyl)-1H-benzimidazol-6-yl]pyridin-2-yl}piperidine-3-carboxamide;

(3R)—N-(5-chloro-4-{1-[(5-fluoropyridin-3-yl)methyl]-1H-pyrrolo[3,2-b]pyridin-6-yl}pyridin-2-yl)piperidine-3-carboxamide;

(3R)—N-(5-chloro-4-{1-[1-(pyridin-3-yl)ethyl]-1H-benzotriazol-6-yl}pyridin-2-yl)piperidine-3-carboxamide;

(3R)—N-{5-chloro-4-[1-(3-fluorobenzyl)-5-methoxy-1H-benzimidazol-6-yl]pyridin-2-yl}piperidine-3-carboxamide;

4-{[6-(5-chloro-2-{[(3R)-piperidin-3-ylcarbonyl]amino}pyridin-4-yl)-1H-benzimidazol-1-yl]methyl}benzoic acid;

(3R)—N-{5-chloro-4-[1-(3-fluorobenzyl)-5-methoxy-1H-benzotriazol-6-yl]pyridin-2-yl}piperidine-3-carboxamide;

(1R,4R,6R)—N-{5-chloro-4-[1-(tetrahydro-2H-pyran-4-ylmethyl)-1H-benzimidazol-6-yl]pyridin-2-yl}-2-azabicyclo[2.2.1]heptane-6-carboxamide;

(1R,4R,6S)—N-{5-chloro-4-[1-(tetrahydro-2H-pyran-4-ylmethyl)-1H-benzimidazol-6-yl]pyridin-2-yl}-2-azabicyclo[2.2.1]heptane-6-carboxamide;

(3R)—N-{5-chloro-4-[1-(thiophen-2-ylmethyl)-1H-benzimidazol-6-yl]pyridin-2-yl}piperidine-3-carboxamide;

(3R)—N-{5-chloro-4-[1-(thiophen-2-ylmethyl)-1H-benzotriazol-6-yl]pyridin-2-yl}piperidine-3-carboxamide;

(3R)—N-(5-chloro-4-{1-[2-(dimethylamino)-2-(3-fluorophenyl)ethyl]-1H-benzotriazol-6-yl}pyridin-2-yl)piperidine-3-carboxamide;

(3R)—N-[5-chloro-4-(1-{3-[(4-methylpiperazin-1-yl)methyl]benzyl}-1H-benzotriazol-6-yl)pyridin-2-yl]piperidine-3-carboxamide;

5-chloro-4-[1-(3-fluorobenzyl)-1H-benzimidazol-6-yl]-N-{3-[(methylsulfonyl)methyl]phenyl}pyridin-2-amine;

(3R)—N-{5-chloro-4-[1-fluoro-1-(tetrahydro-2H-pyran-4-ylmethyl)-1H-benzimidazol-6-yl]pyridin-2-yl}piperidine-3-carboxamide;

ethyl {[(3R)-3-({5-chloro-4-[1-(tetrahydro-2H-pyran-4-ylmethyl)-1H-benzimidazol-6-yl]pyridin-2-yl}carbamoyl)piperidin-1-yl]sulfonyl}carbamate;

methyl (cis)-3-({5-chloro-4-[1-(tetrahydro-2H-pyran-4-ylmethyl)-1H-benzimidazol-6-yl]pyridin-2-yl}carbamoyl)cyclohexanecarboxylate;

(cis)-3-({5-chloro-4-[1-(tetrahydro-2H-pyran-4-ylmethyl)-1H-benzimidazol-6-yl]pyridin-2-yl}carbamoyl)cyclohexanecarboxylic acid;

(cis)-N-{5-chloro-4-[1-(tetrahydro-2H-pyran-4-ylmethyl)-1H-benzimidazol-6-yl]pyridin-2-yl}-3-[(3-hydroxyazetidin-1-yl)carbonyl]cyclohexanecarboxamide;

(cis)-N'-{5-chloro-4-[1-(tetrahydro-2H-pyran-4-ylmethyl)-1H-benzimidazol-6-yl]pyridin-2-yl}-N-(2-hydroxyethyl)-N-methylcyclohexane-1,3-dicarboxamide;

(cis)-N-{5-chloro-4-[1-(tetrahydro-2H-pyran-4-ylmethyl)-1H-benzimidazol-6-yl]pyridin-2-yl}-3-{[(2S)-2-(hydroxymethyl)pyrrolidin-1-yl]carbonyl}cyclohexanecarboxamide;

(3R)—N-[4-(1-methyl-1H-benzimidazol-6-yl)pyridin-2-yl]piperidine-3-carboxamide;

tert-butyl (3aR,6aS)-5-({5-chloro-4-[1-(tetrahydro-2H-pyran-4-ylmethyl)-1H-benzimidazol-6-yl]pyridin-2-yl}carbamoyl)hexahydrocyclopenta[c]pyrrole-2(1H)-carboxylate;

(3aR,6aS)—$N^5$-{5-chloro-4-[1-(tetrahydro-2H-pyran-4-ylmethyl)-1H-benzimidazol-6-yl]pyridin-2-yl}-$N^2$-methylhexahydrocyclopenta[c]pyrrole-2,5(1H)-dicarboxamide;

cis-4-({5-chloro-4-[1-(3-fluorobenzyl)-1H-benzimidazol-6-yl]pyridin-2-yl}amino)cyclohexanecarboxylic acid; and pharmaceutically acceptable salts thereof.

In another aspect, the present invention provides pharmaceutical compositions comprising a pharmaceutically acceptable excipient and a therapeutically effective amount of a compound of formula (Ia), or a pharmaceutically acceptable salt thereof.

In another aspect, the present invention provides methods of treating cancer in a patient, comprising administering to a patient suffering from a cancer a therapeutically effective amount of a compound of formula (I), or a pharmaceutically acceptable salt thereof. In certain embodiments, the cancer is selected from the group consisting of acoustic neuroma, acute leukemia, acute lymphoblastic leukemia, acute myelogenous leukemia, acute t-cell leukemia, basal cell carcinoma, bile duct carcinoma, bladder cancer, brain cancer, breast cancer, bronchogenic carcinoma, Burkitt's lymphoma, cervical cancer, chondrosarcoma, chordoma, choriocarcinoma, chronic leukemia, chronic lymphocytic leukemia, chronic myelocytic leukemia, chronic myelogenous leukemia, colon cancer, colorectal cancer, craniopharyngioma, cystadenocarcinoma, dysplasias, metaplasias, embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer, lymphangioendothelio-sarcoma, lymphangiosarcoma, lymphoblastic leukemia, lymphoma, malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors, stomach cancer, squamous cell carcinoma, synovioma, sweat gland carcinoma, testicular cancer, thyroid cancer, Waldenström's macroglobulinemia, testicular tumors, uterine cancer, and Wilms' tumor. In certain embodiments, the methods further comprise administering a therapeutically effective amount of at least one additional therapeutic agent.

DETAILED DESCRIPTION OF THE INVENTION

Abbreviations and Definitions

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. In this application, the use of "or" means "and/or" unless stated otherwise. Furthermore, the use of the term "including", as well as other forms, such as "includes" and "included", is not limiting. With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below. For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

It is meant to be understood that proper valences are maintained for all combinations herein, that monovalent moieties having more than one atom are attached through their left ends, and that divalent moieties are drawn from left to right.

As used in the specification and the appended claims, unless specified to the contrary, the following terms have the meaning indicated:

The term "alkyl" (alone or in combination with another term(s)) means a straight- or branched-chain saturated radical of an alkane typically containing from 1 to about 10 carbon atoms; or in another embodiment, from 1 to about 8 carbon atoms; in another embodiment, from 1 to about 6 carbon atoms; and in another embodiment, from 1 to about 4 carbon atoms. Examples of alkyls include methyl, ethyl, n-propyl, isopropyl, n-butyl, isobutyl, sec-butyl, tert-butyl, pentyl, iso-amyl, hexyl, pentan-3-y), 2,2-dimethylpropan-2-yl), heptan-4-yl, and 2,6-dimethylheptan-4-yl, and the like. The term "$C_1$-$C_6$ alkyl" refers to an alkyl substituent containing from 1 to 6 carbon atoms and "$C_1$-$C_3$ alkyl" refers to an alkyl substituent containing from 1 to 3 carbon atoms.

The term "O—$C_1$-$C_6$ alkyl" refers to an oxygen atom attached to an alkyl substituent containing from 1 to 6 carbon atoms.

The term "$C_1$-$C_6$ alkyl-O—$C_1$-$C_6$ alkyl" refers to an alkyl substituent containing from 1 to 6 carbon atoms attached to an oxygen atom attached to an alkyl substituent containing from 1 to 6 carbon atoms.

The term "alkenyl" (alone or in combination with another term(s)) means a straight- or branched-chain radical of an alkene containing one or more double bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethenyl (vinyl), 2-propenyl, 3-propenyl, 1,4-pentadienyl, 1,4-butadienyl, 1-butenyl, 2-butenyl, and 3-butenyl and the like. The term "$C_2$-$C_6$ alkenyl" means an alkenyl group containing 2-6 carbon atoms.

The term "alkynyl" (alone or in combination with another term(s)) means a straight- or branched-chain radical of an alkyne containing one or more triple bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethynyl, 2-propynyl, 3-propynyl, 2-butynyl, and 3-butynyl and the like. The term "$C_2$-$C_6$ alkynyl" means an alkynyl group of 2 to 6 carbon atoms.

The term "cycloalkyl" (alone or in combination with another term(s)) means a saturated cyclic hydrocarbyl substituent containing from 3 or more carbon ring atoms ("ring atoms" are the atoms bound together to form the ring or rings of a cyclic substituent). A cycloalkyl may be a single carbon ring, which typically contains from 3 to 8 carbon ring atoms and more typically from 3 to 6 ring atoms. Examples of single-ring cycloalkyls include cyclopropyl, cyclobutyl, cyclopentyl, and cyclohexyl. A cycloalkyl may alternatively be polycyclic (contain more than one ring). Examples of polycyclic cycloalkyls include bridged, fused, and spirocyclic cycloalkyls.

The term "$C_3$-$C_7$ cycloalkyl" (alone or in combination with another term(s)) means a saturated cyclic radical of a monocyclic cycloalkane containing from 3 to 7 carbon ring atoms. Examples of monocyclic cycloalkyl groups include, but are not limited to, cyclopropyl (cyclopropanyl), cyclobutyl (cyclobutanyl), cyclopentyl (cyclopentanyl), cyclopentenyl, cyclohexyl (cyclohexanyl), and cycloheptyl.

The term "cycloalkenyl" (alone or in combination with another term(s)) means a partially unsaturated cyclic hydrocarbyl substituent containing from 4 or more carbon ring atoms ("ring atoms" are the atoms bound together to form the ring or rings of a cyclic substituent). A cycloalkenyl may be a single carbon ring, which typically contains from 4 to 8 carbon ring atoms and more typically from 4 to 6 ring atoms. Examples of single-ring cycloalkenyls include cyclobutenyl, cyclopentenyl, and cyclohexenyl. A cycloalkenyl may alternatively be polycyclic (contain more than one ring). Examples of polycyclic cycloalkenyls include bridged, fused, and spirocyclic cycloalkenyls.

The term "$C_5$-$C_7$ cycloalkenyl" (alone or in combination with another term(s)) means a partially unsaturated monocylic cycloalkane radical containing from 5 to 7 carbon ring atoms. Examples of single-ring cycloalkenyls include cyclopentenyl, cyclohexenyl, and cycloheptenyl.

The term "heterocycloalkyl" (alone or in combination with another term(s)) means a non-aromatic saturated monocyclic or polycyclic heterocycloalkane radical having carbon atoms and 1 or more heteroatoms independently selected from S, N or O, wherein when two O atoms or one O atom and one S atom are present, the two O atoms or one O atom and one S atom are not bonded to each other, respectively. A heterocycloalkyl may be a single carbon ring, which typically contains from 3 to 8 ring atoms and more typically from 3 to 6 ring atoms. Examples of single-ring heterocycloalkyls include oxetanyl, azetidinyl, thietanyl, tetrahydrofuranyl, dihydrofuranyl, tetrahydrothienyl, dihydrothienyl, imidazolidinyl, oxazolidinyl, imidazolinyl, isoxazolidinyl, pyrrolidinyl, 2-pyrrolinyl, 3-pyrrolinyl, tetrahydropyranyl, dihydropyranyl, dioxanyl, 1,3-dioxolanyl, 1,4-dithianyl, hexahydropyrimidine, morpholinyl, piperazinyl, piperidinyl, 2H-pyranyl, 4H-pyranyl, pyrazolidinyl, pyrazolinyl, 1,2,3,6-tetrahydropyridinyl, tetrahydrothiopyranyl, thiomorpholinyl, thioxanyl, trithianyl, azepanyl, 2,3,4,5-tetrahydro-1H-azepinyl, oxepanyl, 2,3,4,5-tetrahydro-1H-oxepinyl, thiepanyl, and 2,3,4,5-tetrahydro-1H-thiepinyl, azocanyl, thiocanyl, oxocanyl, tetrahydro-2H-thiopyranyl 1,1-dioxide and 3,4,5,6-tetrahydro-2H-oxocinyl. A heterocycloalkyl may alternatively be polycyclic (contain more than one ring). Examples of polycyclic heterocycloalkyls include bridged, fused, and spirocyclic heterocycloalkyls in which at least one ring is a heterocycloalkyl and the others are heterocycloalkyl, or cycloalkyl rings.

The term "heterocycloalkenyl" (alone or in combination with another term(s)) means a non-aromatic partially unsaturated monocyclic or polycyclic heterocycloalkene radical having carbon atoms and 1 or more heteroatoms independently selected from S, N or O, wherein when two O atoms or one O atom and one S atom are present, the two O atoms or one O atom and one S atom are not bonded to each other, respectively. A heterocycloalkenyl may be a single carbon ring, which typically contains from 3 to 8 ring atoms and more typically from 3 to 6 ring atoms. Examples of single-ring heterocycloalkenyls include 1,2,3,6-tetrahydropyridinyl, and 4,5-dihydro-1H-imidazolyl. A heterocycloalkenyl may alternatively be polycyclic (contain more than one ring). Examples of polycyclic heterocycloalkenyls include bridged, fused, and spirocyclic heterocycloalkenyls in which at least one ring is a heterocycloalkenyl and the others are heterocycloalkenyl, heterocycloalkyl, cycloalkenyl or cycloalkyl rings. Alternatively, a polycyclic heterocycloalkenyl may consist of one or more heterocycloalkyl rings and one or more cycloalkenyl rings. Examples of polycyclic heterocycloalkenyls include 8-azabicyclo[3.2.1]oct-2-enyl, and 1,2,3,3a,4,6a-hexahydrocyclopenta[c]pyrrolyl.

The term "5 to 7-membered heterocycloalkyl" (alone or in combination with another term(s)) means a non-aromatic monocyclic radical having carbon atoms and 1 to 3 heteroatoms independently selected from S, N or O, wherein when two O atoms or one O atom and one S atom are present, the two O atoms or one O atom and one S atom are not bonded to each other, respectively.

The term "4-membered monocyclic heterocycloalkyl" (alone or in combination with another term(s)) means a 4-membered, monocyclic radical having 3 carbon atoms and 1 heteroatom selected from the group consisting of: 1 O; 1 S; and 1 N. Illustrative examples of 4-membered monocyclic heterocycloalkyls include oxetanyl, azetidinyl, and thietanyl.

The term "5-membered monocyclic heterocycloalkyl" (alone or in combination with another term(s)) means a 5-membered, monocyclic radical having from 1 to 4 carbon atoms and from 1 to 3 heteroatoms selected from the group consisting of: 1 O; 1 S; 1 N; 2 N; 3 N; 1 S and 1 N; 1 S, and 2 N; 1 O and 1 N; and 1 O and 2 N. Illustrative examples of 5-membered monocyclic heterocycloalkyls include tetrahydrofuranyl, dihydrofuranyl, tetrahydrothienyl, dihydrothienyl, imidazolidinyl, oxazolidinyl, imidazolinyl, isoxazolidinyl, pyrrolidinyl, 2-pyrrolinyl, and 3-pyrrolinyl.

The term "6-membered monocyclic heterocycloalkyl" (alone or in combination with another term(s)) means a 6-membered, monocyclic radical having from 3 to 5 carbon atoms and from 1 to 3 heteroatoms selected from the group consisting of: 1 O; 2 O; 3 O; 1 S; 2 S; 3 S; 1 N; 2 N; 3 N; 1 S, 1 O, and 1 N; 1 S and 1 N; 1 S and 2 N; 1 S and 1 O; 1 S and 2 O; 1 O and 1 N; and 1 O and 2 N. Illustrative examples of 6-membered monocyclic heterocycloalkyls include tetrahydropyranyl, dihydropyranyl, dioxanyl, 1,3-dioxolanyl, 1,4-dithianyl, hexahydropyrimidine, morpholinyl, piperazinyl, piperidinyl, 2H-pyranyl, 4H-pyranyl, pyrazolidinyl, pyrazolinyl, 1,2,3,6-tetrahydropyridinyl, tetrahydrothiopyranyl, thiomorpholinyl, thioxanyl, and trithianyl.

The term "7-membered monocyclic heterocycloalkyl" (alone or in combination with another term(s)) means a 7-membered, monocyclic radical having from 5 or 6 carbon atoms and from 1 to 3 heteroatoms selected from the group consisting of: 1 O; 2 O; 1 S; 2 S; 1 N; 2 N; 1 S, 1 O, and 1 N; 1 S and 1 N; 1 S and 2 N; 1 S and 1 O; 1 S and 2 O; 1 O and 1 N; and 1 O and 2 N. Illustrative examples of 7-membered monocyclic heterocycloalkyls include azepa-nyl, 2,3,4,5-tetrahydro-1H-azepinyl, oxepanyl, 2,3,4,5-tetrahydro-1H-oxepinyl, thiepanyl, and 2,3,4,5-tetrahydro-1H-thiepinyl.

The term "8-membered monocyclic heterocycloalkyl" (alone or in combination with another term(s)) means a 8-membered, monocyclic radical having from 5 to 7 carbon atoms and from 1 to 3 heteroatoms selected from the group consisting of: 1 O; 2 O; 3 P; 1 S; 2 S; 3 S; 1 N; 2 N; 3 N; 1 S, 1 O, and 1 N; 1 S and 1 N; 1 S and 2 N; 1 S and 1 O; 1 S and 2 O; 1 O and 1 N; and 1 O and 2 N. Illustrative examples of 8-membered monocyclic heterocycloalkyls include azocanyl, thiocanyl, oxocanyl, 3,4,5,6-tetrahydro-2H-oxocinyl, etc.

The nitrogen and sulfur heteroatoms in the heterocycloalkyl rings may optionally be oxidized (e.g. 1,1-dioxido-tetrahydrothienyl, 1,2-dioxido-1,2-thiazolidinyl, 1,1-dioxidothiomorpholinyl)) and the nitrogen atoms may optionally be quarternized. Unless otherwise indicated, the foregoing heterocycloalkyls can be C-attached or N-attached where such is possible and which results in the creation of a stable structure. For example, piperidinyl can be piperidin-1-yl (N-attached) or piperidin-4-yl (C-attached).

The term "aryl" (alone or in combination with another term(s)) means an aromatic hydrocarbon radical. Furthermore, the term "aryl" includes polycyclic aryl groups, such as bicyclic, e.g., naphthyl. Typical aryl groups include phenyl, and naphthyl. The term aryl also includes a "9- to 12-membered bicyclic aryl," which is a ring structure formed by the fusion of a benzene ring to: (1) a cycloalkyl or cycloalkenyl (e.g., indanyl; 1,2,3,4-tetrahydro-naphthalenyl; 6,7,8,9-tetrahydro-5H-benzocycloheptenyl, etc.); (2) another benzene ring (e.g., naphthalenyl); wherein the fusion junctions are at adjacent carbons on the benzene ring; or (3) a heterocycloalkyl or heterocycloalkenyl (e.g., benzo[d][1,3]dioxolyl, isoindolinyl).

The term "heteroaryl" (alone or in combination with another term(s)) means a monocyclic 5 or 6 membered heteroaryl or a bicyclic heteroaryl.

The term "5-membered heteroaryl" (alone or in combination with another term(s)) means a 5-membered, monocyclic, aromatic ring radical having from 1 to 4 carbon atoms and from 1 to 4 heteroatoms selected from the group consisting of: 1 O; 1 S; 1 N; 2 N; 3 N; 4 N; 1 S and 1 N; 1 S and 2 N; 1 O and 1 N; and 1 O and 2 N. Illustrative examples of 5-membered heteroaryls include, but are not limited to, furanyl, 2-furanyl, 3-furanyl, imidazolyl, isoxazolyl, isothiazolyl, oxadiazolyl, oxazolyl, pyrazolyl, pyrrolyl, 2- or 3-pyrrolyl, thienyl, 2-thienyl, 3-thienyl, tetrazolyl, thiazolyl, thiadiazolyl, and triazolyl.

The term "6-membered heteroaryl" (alone or in combination with another term(s)) means a 6-membered, monocyclic, aromatic ring radical having from 3 to 5 carbon atoms and from 1 to 3 heteroatoms selected from the group consisting of: 1 N; 2 N; and 3 N. Illustrative examples of 6-membered heteroaryls include, but are not limited to, pyridinyl, 2-, 3-, or 4-pyridinyl, pyrimidinyl, 2-, 4-, or 5-pyrimidinyl, pyrazinyl, pyridazinyl, 3- or 4-pyridazinyl, 2-pyrazinyl, and triazinyl.

The term "bicyclic heteroaryl" (alone or in combination with another term(s)) means a ring structure formed by the fusion of 5- or 6-membered heteroaryl to: (1) an independently selected 5-membered heteroaryl; (2) an independently selected 6-membered heteroaryl (e.g., naphthyridinyl, pteridinyl, phthalazinyl, purinyl, etc.); (3) a cycloalkyl or cycloalkenyl; (4) a heterocycloalkyl or heterocycloalkenyl; or (5) a benzene ring (e.g., benzimidazolyl, benzofuranyl, benzofurazanyl, 2H-1-benzopyranyl, benzothiadiazine, benzothiazinyl, benzothiazolyl, benzothiophenyl, benzoxazolyl, cinnolinyl, furopyridinyl, indolinyl, indolizinyl, indolyl, or 2-, 3-, 4-, 5-, 6-, or 7-indolyl, 3H-indolyl, quinazolinyl, quinoxalinyl, isoindolyl, and isoquinolinyl), wherein the fusion junctions are at adjacent ring atoms. The fusion junctions may be at nitrogen (e.g., indolizine) or carbon atoms in the 5- or 6-membered heteroaryl.

The term "hydrogen" (alone or in combination with another term(s)) means a hydrogen radical, and may be depicted as —H.

The term "hydroxy" (alone or in combination with another term(s)) means —OH.

The term "carboxy" (alone or in combination with another term(s)) means —C(O)—OH.

The term "amino" (alone or in combination with another term(s)) means —NH$_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical. If a substituent is described as being optionally substituted with one or more non-hydrogen radicals, that substituent may be either (1) not substituted; or (2) substituted by up to the maximum number of substitutable positions on the substituent. Thus, for example, if a substituent is described as a heteroaryl optionally substituted with one or more non-hydrogen radicals, then any heteroaryl with 3 substitutable positions would be optionally substituted by one, two or three non-hydrogen radicals. To illustrate, tetrazolyl (which has only one substitutable position) would be optionally substituted with up to one non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

A prefix attached to a multi-component substituent only applies to the first component. To illustrate, the term "alkylcycloalkyl" contains two components: alkyl and cycloalkyl. Thus, the $C_1$-$C_6$-prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkyloxyalkyl indicates that only the alkyloxy component of the alkyloxyalkyl substituent is substituted with one or more halogen radicals. If halogen substitution may alternatively or additionally occur on the alkyl component, the substituent would instead be described as "halogen-substituted alkyloxyalkyl" rather than "haloalkyloxyalkyl." And finally, if the halogen substitution may only occur on the alkyl component, the substituent would instead be described as "alkyloxyhaloalkyl."

The terms "treat," "treating," and "treatment" refer to a method of alleviating or abrogating a disease and/or its attendant symptoms.

The terms "prevent," "preventing," and "prevention" refer to a method of preventing the onset of a disease and/or its attendant symptoms or barring a subject from acquiring a disease. As used herein, "prevent," "preventing," and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

Compounds

Geometric isomers may exist in the present compounds. Compounds of this invention may contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z"

isomers. Substituents around a cycloalkyl or heterocycloalkyl may also be designated as being of cis or trans configuration.

Compounds of this invention may contain asymmetrically substituted carbon atoms in the R or S configuration, in which the terms "R" and "S" are as defined by the IUPAC 1974 Recommendations for Section E, Fundamental Stereochemistry, Pure Appl. Chem. (1976) 45, 13-10. Compounds having asymmetrically substituted carbon atoms with equal amounts of R and S configurations are racemic at those carbon atoms. Atoms with an excess of one configuration over the other are assigned the configuration present in the higher amount, preferably an excess of about 85%-90%, more preferably an excess of about 95%-99%, and still more preferably an excess greater than about 99%. Accordingly, this invention includes racemic mixtures, relative and absolute stereoisomers, and mixtures of relative and absolute stereoisomers.

Isotope Enriched or Labeled Compounds

Compounds of the invention can exist in isotope-labeled or -enriched form containing one or more atoms having an atomic mass or mass number different from the atomic mass or mass number most abundantly found in nature. Isotopes can be radioactive or non-radioactive isotopes. Isotopes of atoms such as hydrogen, carbon, phosphorous, sulfur, fluorine, chlorine, and iodine include, but are not limited to $^2H$, $^3H$, $^{13}C$, $^{14}C$, $^{15}N$, $^{18}O$, $^{32}P$, $^{35}S$, $^{18}F$, $^{36}Cl$ and $^{125}I$. Compounds that contain other isotopes of these and/or other atoms are within the scope of this invention.

In another embodiment, the isotope-labeled compounds contain deuterium ($^2H$), tritium ($^3H$) or $^{14}C$ isotopes. Isotope-labeled compounds of this invention can be prepared by the general methods well known to persons having ordinary skill in the art. Such isotope-labeled compounds can be conveniently prepared by carrying out the procedures disclosed in the Examples disclosed herein and Schemes by substituting a readily available isotope-labeled reagent for a non-labeled reagent. In some instances, compounds may be treated with isotope-labeled reagents to exchange a normal atom with its isotope, for example, hydrogen for deuterium can be exchanged by the action of a deuteric acid such as $D_2SO_4/D_2O$. In addition to the above, relevant procedures and intermediates are disclosed, for instance, in Lizondo, J et al., *Drugs Fut*, 21(11), 1116 (1996); Brickner, S J et al., *J Med Chem*, 39(3), 673 (1996); Mallesham, B et al., *Org Lett*, 5(7), 963 (2003); PCT publications WO1997010223, WO2005099353, WO1995007471, WO2006008754; U.S. Pat. Nos. 7,538,189; 7,534,814; 7,531,685; 7,528,131; 7,521,421; 7,514,068; 7,511,013; and US Patent Application Publication Nos. 20090137457; 20090131485; 20090131363; 20090118238; 20090111840; 20090105338; 20090105307; 20090105147; 20090093422; 20090088416; and 20090082471, the methods are hereby incorporated by reference.

The isotope-labeled compounds of the invention may be used as standards to determine the effectiveness of CDK9 inhibitors in binding assays. Isotope containing compounds have been used in pharmaceutical research to investigate the in vivo metabolic fate of the compounds by evaluation of the mechanism of action and metabolic pathway of the nonisotope-labeled parent compound (Blake et al. *J. Pharm. Sci.* 64, 3, 367-391 (1975)). Such metabolic studies are important in the design of safe, effective therapeutic drugs, either because the in vivo active compound administered to the patient or because the metabolites produced from the parent compound prove to be toxic or carcinogenic (Foster et al., Advances in Drug Research Vol. 14, pp. 2-36, Academic press, London, 1985; Kato et al., J. *Labelled Comp. Radiopharmaceut.*, 36(10):927-932 (1995); Kushner et al., *Can. J. Physiol. Pharmacol.*, 77, 79-88 (1999).

In addition, non-radio active isotope containing drugs, such as deuterated drugs called "heavy drugs," can be used for the treatment of diseases and conditions related to CDK9 activity. Increasing the amount of an isotope present in a compound above its natural abundance is called enrichment. Examples of the amount of enrichment include from about 0.5, 1, 2, 3, 4, 5, 6, 7, 8, 9, 10, 12, 16, 21, 25, 29, 33, 37, 42, 46, 50, 54, 58, 63, 67, 71, 75, 79, 84, 88, 92, 96, to about 100 mol %. Replacement of up to about 15% of normal atom with a heavy isotope has been effected and maintained for a period of days to weeks in mammals, including rodents and dogs, with minimal observed adverse effects (Czajka D M and Finkel A J, Ann. N.Y. Acad. Sci. 1960 84: 770; Thomson J F, Ann. New York Acad. Sci. 1960 84: 736; Czakja D M et al., Am. J. Physiol. 1961 201: 357). Acute replacement of as high as 15%-23% in human fluids with deuterium was found not to cause toxicity (Blagojevic N et al. in "Dosimetry & Treatment Planning for Neutron Capture Therapy", Zamenhof R, Solares G and Harling O Eds. 1994. Advanced Medical Publishing, Madison Wis. pp. 125-134; Diabetes Metab. 23: 251 (1997)).

Stable isotope labeling of a drug can alter its physicochemical properties such as pKa and lipid solubility. These effects and alterations can affect the pharmacodynamic response of the drug molecule if the isotopic substitution affects a region involved in a ligand-receptor interaction. While some of the physical properties of a stable isotope-labeled molecule are different from those of the unlabeled one, the chemical and biological properties are the same, with one important exception: because of the increased mass of the heavy isotope, any bond involving the heavy isotope and another atom will be stronger than the same bond between the light isotope and that atom. Accordingly, the incorporation of an isotope at a site of metabolism or enzymatic transformation will slow said reactions potentially altering the pharmacokinetic profile or efficacy relative to the non-isotopic compound.

Compounds

Suitable groups for $R^2$, $R^{12}$, $R^{16}$, J, Q, X, Y, and Z in compounds of Formula (I) and (Ia) and $R^2$ and $R^{16}$ in compounds of Formula (IIa) and (IIIa) are independently selected. The described embodiments of the present invention may be combined. Such combination is contemplated and within the scope of the present invention. For example, it is contemplated that embodiments for any of $R^2$, $R^{12}$, $R^{16}$, J, Q, X, Y, and Z in compounds of Formula (Ia) can be combined with embodiments defined for any other of $R^2$, $R^{12}$, $R^{16}$, J, Q, X, Y, and Z in compounds of Formula (Ia).

Embodiments of Formula (I)

In one aspect, the present invention relates to compounds of Formula (I) or a pharmaceutically acceptable salt thereof,

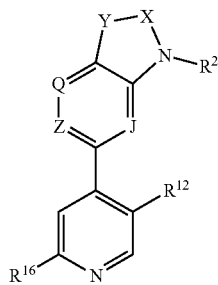

(I)

wherein:
R$^{12}$ is halo or H;
J is N or CH;
Q is N or CH;
Z is N, CH, C—Cl, or C—F;
the bond between X and Y may be a single or a double bond,
  wherein if a double bond is present, then Y is CR$^3$ and X is CH, Y is N and X is CH, C$_1$-C$_3$ haloalkyl or C$_1$-C$_3$ alkyl, Y is CR$^3$ and X is N, or Y is N and X is N, wherein R$^3$ is selected from the group consisting of: —CN, C$_1$-C$_3$ alkyl, C$_1$-C$_3$ haloalkyl and H,
  wherein if a single bond is present, then Y is CH$_2$ and X is CH$_2$ or —C(O)—, or Y is NH or N(C$_1$-C$_3$ alkyl) and X is C(O)—;
R$^2$ at each position is H, C$_1$-C$_3$ alkyl, R$^{30}$, or L-R$^{22}$;
R$^{30}$ is C$_1$-C$_5$ alkylene-OH, C$_1$-C$_3$ alkylene-SO$_2$—NH$_2$, —SO$_2$NR$^{27}$R$^{28}$, C$_1$-C$_3$ alkylene-SO$_2$—C$_1$-C$_3$ alkyl, C$_1$-C$_3$ alkylene-N(C$_1$-C$_3$ alkylene-OH)(C$_1$-C$_3$ alkylene-OH), or C$_1$-C$_3$ alkylene-N(C$_1$-C$_3$ alkyl)(C$_1$-C$_3$ alkyl), wherein R$^{27}$ and R$^{28}$ are independently selected from H and C$_1$-C$_3$ alkyl;
L is absent or is a C$_1$-C$_3$ alkylene;
R$^{22}$ is phenyl, a 5 to 7 membered heterocycloalkyl, or a five to ten membered heteroaryl, each of which may substituted with one to three substituents selected from the group consisting of: halo, C$_1$-C$_3$ alkyl, SO$_2$—C$_1$-C$_3$alkyl, NHSO$_2$—C$_1$-C$_3$alkyl, COOR$^{28}$, COOH, wherein R$^{28}$ is a C$_1$-C$_4$ alkyl;
R$^{16}$ is selected from the group consisting of: NH$_2$, a five to 12 membered heterocycloalkyl, NH—U—R$^{20}$, NH—R$^{24}$, and NH—R$^{30}$,
  wherein U is selected from the group consisting of: C(O), C(O)—C$_1$-C$_3$ alkylene, C(O)—C$_2$-C$_3$ alkenylene, C$_1$-C$_3$ alkylene, C$_1$-C$_3$ alkylene-N(R$^{29}$)—, C$_1$-C$_3$ alkylene-N(R$^{29}$)—C$_1$-C$_3$ alkylene and C$_1$-C$_2$ alkylene-CH(NR$^{29}$)—, wherein R$^{29}$ is H or C$_1$-C$_3$ alkyl;
  wherein R$^{20}$ is selected from the group consisting of: C$_3$-C$_7$ cycloalkyl, phenyl, heteroaryl, or a 4 to 12 membered heterocycloalkyl, each of which may be independently substituted with one to three substituents selected from the group consisting of: halo, oxo, OH, NH$_2$, C$_1$-C$_3$ alkyl, C$_1$-C$_3$ haloalkyl, C$_1$-C$_3$ alkyl-NH$_2$, —O—C$_1$-C$_3$ alkyl, C(O)NH—C$_5$-C$_7$ cycloalkyl, phenyl optionally independently substituted with one to three halo groups, a 5 to 7 membered heteroaryl, C(O)O—CH$_2$-phenyl, C(O)—C$_1$-C$_4$ alkyl, SO$_2$—C$_1$-C$_3$ alkyl, C(O)—NH—C$_1$-C$_4$ alkyl, C(O)—NH-phenyl, C(O)—C$_5$-C$_7$ cycloalkyl, SO$_2$-phenyl, C(O)-phenyl, C(O)—NH$_2$,
  wherein R$^{24}$ is a C$_5$-C$_7$ cycloalkyl, which may be substituted with NH$_2$, OH, N(H)C(O)NH$_2$, N(H)C(O)NH(C$_1$-C$_3$ alkyl), or N(H)SO$_2$—(C$_1$-C$_3$ alkyl); a 5 to 9 membered heterocycloalkyl which may be substituted with one or two groups independently selected from C$_1$-C$_3$ alkyl, C$_1$-C$_3$ alkylene-C$_3$-C$_5$ cycloalkyl, SO$_2$—(C$_1$-C$_3$ alkyl), phenyl, phenyl substituted with one to three halo groups, and C(O)O—C$_1$-C$_3$alkyl-phenyl; heteroaryl, which may be substituted with one to three groups independently selected from C$_1$-C$_3$ alkyl and halo; phenyl which may be substituted with one to three substituents independently selected from SO$_2$NH$_2$, —SO$_2$NH(C$_1$-C$_3$alkyl), —SO$_2$N(C$_1$-C$_3$alkyl)(C$_1$-C$_3$alkyl), C$_1$-C$_3$ alkyl, and halo,
  wherein R$^{30}$ is selected from the group consisting of: C$_1$-C$_5$ alkylene-OH; C$_1$-C$_5$ alkylene-N(R$^{26}$)(R$^{28}$), wherein the C$_1$-C$_5$ alkylene may be substituted with one or two hydroxyls, wherein R$^{26}$ and R$^{28}$ are independently selected from H or C$_1$-C$_3$alkyl; C(O)—C$_1$-C$_4$ alkyl, C(O)—C$_1$-C$_4$ alkylene-SO$_2$—C$_1$-C$_3$ alkyl, and C(O)—C$_2$-C$_4$ alkenylene-C(O)—NHC(O)NH$_2$.

In certain embodiments, Q is CH, J is CH, and Z is CH or C—F. In certain embodiments, Q is CH, J is CH, and Z is N. In certain embodiments, Q is N, J is CH, and Z is CH or C—F. In certain embodiments, only one of J, Q or Z is N. In certain embodiments, J is CH and Z is CH. In certain embodiments, R$^{12}$ is chloro. In certain embodiments, R$^2$ is L-R$^{22}$. In certain embodiments, R$^2$ is phenyl, morpholinyl, piperidinyl, 1,1-dioxidotetrahydrothiophen-2-yl, 1,1-dioxidotetrahydro-2H-thiopyran-3-yl, pyrrolidinyl, thiazolyl, triazolyl, 1,3,4-thiadolzolyl, pyrazinyl, pyrimidinyl, tetrazolyl, pyridinyl, quinolinyl, 1,4-benzodioxinyl, benzotriazolyl, 1,3-benzodioxolyl, quinoxalinyl, or 2,3-dihydro-[1,4]dioxino[2,3-b]pyridinyl, each of which may substituted with one to three substituents selected from the group consisting of: halo, C$_1$-C$_3$ alkyl, SO$_2$—C$_1$-C$_3$alkyl, NHSO$_2$—C$_1$-C$_3$alkyl, COOR$^{28}$, COOH, wherein R$^{28}$ is a C$_1$-C$_4$ alkyl. In certain embodiments, L is a C$_1$-C$_3$ alkylene and R$^{22}$ is phenyl or pyridinyl substituted with one to three fluoro groups. In certain embodiments, L is a C$_{1-2}$alkylene and R$^{22}$ is 4-tetrahydropyranyl or 3-fluorophenyl. In certain embodiments, R$^{16}$ is NH—U—R$^{20}$. In certain embodiments, U is C(O) and R$^{20}$ is a 5 to 7 membered heterocycloalkyl. R$^{20}$ is piperidinyl-3-yl. In certain embodiments, R$^{16}$ is NH—R$^{24}$. In certain embodiments, R$^{24}$ is a C$_5$-C$_7$ cycloalkyl, which may be substituted with one of the following groups: OH, NH$_2$, N(H)C(O)NH$_2$, N(H)C(O)NH(C$_1$-C$_3$ alkyl), or N(H)SO$_2$—(C$_1$-C$_3$ alkyl). In certain embodiments, R$^{24}$ is a 5 to 9 membered heterocycloalkyl which may be substituted with one or two groups independently selected from C$_1$-C$_3$ alkyl, C$_1$-C$_3$ alkylene-C$_3$-C$_5$ cycloalkyl, SO$_2$—(C$_1$-C$_3$ alkyl), phenyl, phenyl substituted with one to three halo groups, and C(O)O—C$_1$-C$_3$alkyl-phenyl. In certain embodiments, the bond between X and Y is a double bond. In certain embodiments, Y is N and X is CH.

In certain embodiments are compounds of formula I(a) where R$^2$, R$^{12}$, and R$^{16}$ may be substituted as set out above, and Z is CH, C—Cl, or C—F:

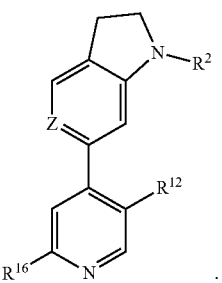

I(a)

In certain embodiments are compounds of formula I(b) where $R^2$, $R^{12}$, and $R^{16}$ may be substituted as set out above, and Z is CH, C—Cl, or C—F:

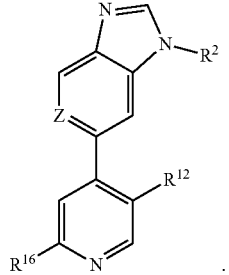

I(b)

In certain embodiments are compounds of formula I(c) where $R^2$, $R^3$, $R^{12}$, and $R^{16}$ may be substituted as set out above, and Z is CH, C—Cl, or C—F:

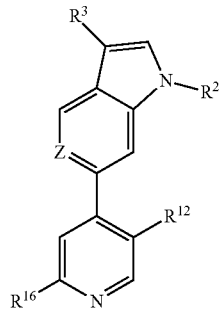

I(c)

In certain embodiments are compounds of formula I(d) where $R^2$, $R^{12}$, and $R^{16}$ may be substituted as set out above, and Z is CH, C—Cl, or C—F:

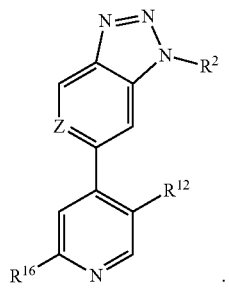

I(d)

In certain embodiments are compounds of formula I(e) where $R^2$, $R^{12}$, and $R^{16}$ may be substituted as set out above, and Z is CH, C—Cl, or C—F:

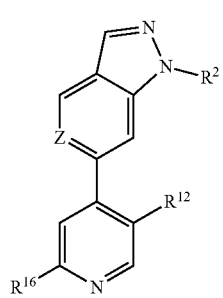

I(e)

In certain embodiments are compounds of formula I(f) where $R^2$, $R^{12}$, and $R^{16}$ may be substituted as set out above, and Z is CH, C—Cl, or C—F:

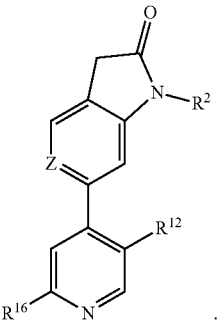

I(f)

In certain embodiments are compounds of formula I(g) where $R^2$, $R^{12}$, and $R^{16}$ may be substituted as set out above:

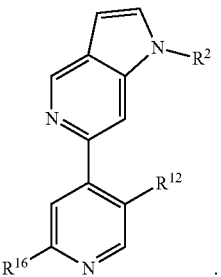

I(g)

In certain embodiments are compounds of formula I(h) where $R^2$, $R^{12}$, and $R^{16}$ may be substituted as set out above:

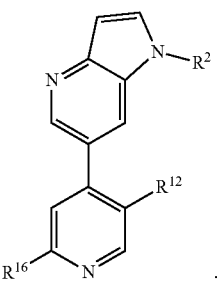

I(h)

In certain embodiments, a compound of formula I is selected from the group consisting of:

(3R)—N-{5-chloro-4-[1-(3-fluorobenzyl)-2,3-dihydro-1H-indol-6-yl]pyridin-2-yl}piperidine-3-carboxamide;

(3R)—N-[5-chloro-4-(2,3-dihydro-1H-indol-6-yl)pyridin-2-yl]piperidine-3-carboxamide;

(3R)—N-[5-chloro-4-(1-methyl-1H-benzimidazol-6-yl)pyridin-2-yl]piperidine-3-carboxamide;

(3R)—N-{5-chloro-4-[1-(tetrahydro-2H-pyran-4-ylmethyl)-2,3-dihydro-1H-indol-6-yl]pyridin-2-yl}piperidine-3-carboxamide;

(3R)—N-{5-chloro-4-[1-(3-fluorobenzyl)-1H-benzimidazol-5-yl]pyridin-2-yl}piperidine-3-carboxamide;
(3R)—N-{5-chloro-4-[1-(3-fluorobenzyl)-1H-benzimidazol-6-yl]pyridin-2-yl}piperidine-3-carboxamide;
(3R)—N-{5-chloro-4-[1-(3-fluorobenzyl)-1H-indol-6-yl]pyridin-2-yl}piperidine-3-carboxamide;
trans-N-{5-chloro-4-[1-(3-fluorobenzyl)-1H-benzimidazol-6-yl]pyridin-2-yl}cyclohexane-1,4-diamine;
trans-N-{5-chloro-4-[1-(3-fluorobenzyl)-2,3-dihydro-1H-indol-6-yl]pyridin-2-yl}cyclohexane-1,4-diamine;
trans-4-({5-chloro-4-[1-(3-fluorobenzyl)-2,3-dihydro-1H-indol-6-yl]pyridin-2-yl}amino)cyclohexanol;
trans-4-({5-chloro-4-[1-(3-fluorobenzyl)-1H-benzimidazol-6-yl]pyridin-2-yl}amino)cyclohexanol;
trans-N-[5-chloro-4-(1-methyl-1H-benzimidazol-6-yl)pyridin-2-yl]cyclohexane-1,4-diamine;
(3R)—N-{5-chloro-4-[1-(tetrahydro-2H-pyran-4-ylmethyl)-1H-benzimidazol-6-yl]pyridin-2-yl}piperidine-3-carboxamide;
(3R)—N-(5-chloro-4-{1-[2-(morpholin-4-yl)ethyl]-1H-benzimidazol-6-yl}pyridin-2-yl)piperidine-3-carboxamide;
(3R)—N-{5-chloro-4-[1-(3-hydroxy-3-methylbutyl)-1H-benzimidazol-6-yl]pyridin-2-yl}piperidine-3-carboxamide;
(3R)—N-{5-chloro-4-[1-(4-fluorobenzyl)-1H-benzimidazol-6-yl]pyridin-2-yl}piperidine-3-carboxamide;
(3R)—N-{5-chloro-4-[1-(3,4-difluorobenzyl)-1H-benzimidazol-6-yl]pyridin-2-yl}piperidine-3-carboxamide;
(3R)—N-(5-chloro-4-{1-[2-(3-fluorophenyl)ethyl]-1H-benzimidazol-6-yl}pyridin-2-yl)piperidine-3-carboxamide;
(3R)—N-{5-chloro-4-[1-(2-sulfamoylethyl)-1H-benzimidazol-6-yl]pyridin-2-yl}piperidine-3-carboxamide;
(3R)—N-(5-chloro-4-{1-[(1,1-dioxidotetrahydrothiophen-3-yl)methyl]-1H-benzimidazol-6-yl}pyridin-2-yl)piperidine-3-carboxamide;
(3R)—N-{5-chloro-4-[1-(2-fluorobenzyl)-1H-benzimidazol-6-yl]pyridin-2-yl}piperidine-3-carboxamide;
(3R)—N-{5-chloro-4-[1-(pyridin-3-ylmethyl)-1H-benzimidazol-6-yl]pyridin-2-yl}piperidine-3-carboxamide;
(3R)—N-(5-chloro-4-{1-[(1,1-dioxidotetrahydro-2H-thiopyran-4-yl)methyl]-1H-benzimidazol-6-yl}pyridin-2-yl)piperidine-3-carboxamide;
(3R)—N-(5-chloro-4-{1-[(5-methyl-4H-1,2,4-triazol-3-yl)methyl]-1H-benzimidazol-6-yl}pyridin-2-yl)piperidine-3-carboxamide;
(3R)—N-{5-chloro-4-[1-(1,3-thiazol-4-ylmethyl)-1H-benzimidazol-5-yl]pyridin-2-yl}piperidine-3-carboxamide-(3R)—N-{5-chloro-4-[1-(1,3-thiazol-4-ylmethyl)-1H-benzimidazol-6-yl]pyridin-2-yl}piperidine-3-carboxamide (1:1);
5-chloro-N-cyclopentyl-4-[1-(3-fluorobenzyl)-1H-benzimidazol-6-yl]pyridin-2-amine;
1-[trans-4-({5-chloro-4-[1-(3-fluorobenzyl)-1H-benzimidazol-6-yl]pyridin-2-yl}amino)cyclohexyl]-3-methylurea;
N-[trans-4-({5-chloro-4-[1-(3-fluorobenzyl)-1H-benzimidazol-6-yl]pyridin-2-yl}amino)cyclohexyl]methanesulfonamide;
(3R)—N-[4-(1-benzyl-3-cyano-1H-indol-6-yl)-5-chloropyridin-2-yl]piperidine-3-carboxamide;
N'-{5-chloro-4-[1-(3-fluorobenzyl)-1H-benzimidazol-6-yl]pyridin-2-yl}-N-methyl-N-(pyridin-2-yl)propane-1,3-diamine;
1-({5-chloro-4-[1-(3-fluorobenzyl)-1H-benzimidazol-6-yl]pyridin-2-yl}amino)-3-(dimethylamino)propan-2-ol;
5-chloro-4-[1-(3-fluorobenzyl)-1H-benzimidazol-6-yl]-N-[(5-methyl-4H-1,2,4-triazol-3-yl)methyl]pyridin-2-amine;
(3R)—N-{5-chloro-4-[1-(3-fluorobenzyl)-1H-pyrrolo[3,2-b]pyridin-6-yl]pyridin-2-yl}piperidine-3-carboxamide;
N-{5-chloro-4-[1-(3-fluorobenzyl)-1H-benzimidazol-6-yl]pyridin-2-yl}-N'-(pyridin-3-yl)ethane-1,2-diamine;
N-[(5-amino-4H-1,2,4-triazol-3-yl)methyl]-5-chloro-4-[1-(3-fluorobenzyl)-1H-benzimidazol-6-yl]pyridin-2-amine;
N-benzyl-N'-{5-chloro-4-[1-(3-fluorobenzyl)-1H-benzimidazol-6-yl]pyridin-2-yl}-N-methylpropane-1,3-diamine;
5-chloro-4-[1-(3-fluorobenzyl)-1H-benzimidazol-6-yl]-N-(pyrimidin-2-ylmethyl)pyridin-2-amine;
5-chloro-4-[1-(3-fluorobenzyl)-1H-benzimidazol-6-yl]-N-[1-(pyridin-4-yl)propan-2-yl]pyridin-2-amine;
5-chloro-4-[1-(3-fluorobenzyl)-1H-benzimidazol-6-yl]-N-[1-(1-methyl-1H-pyrazol-4-yl)piperidin-3-yl]pyridin-2-amine;
5-[({5-chloro-4-[1-(3-fluorobenzyl)-1H-benzimidazol-6-yl]pyridin-2-yl}amino)methyl]pyrimidin-2-amine;
5-chloro-N-[2-(1-ethylpiperidin-4-yl)ethyl]-4-[1-(3-fluorobenzyl)-1H-benzimidazol-6-yl]pyridin-2-amine;
5-chloro-4-[1-(3-fluorobenzyl)-1H-benzimidazol-6-yl]-N-[2-(5-methyl-4H-1,2,4-triazol-3-yl)ethyl]pyridin-2-amine;
N-{5-chloro-4-[1-(3-fluorobenzyl)-1H-benzimidazol-6-yl]pyridin-2-yl}-N'-(pyridin-4-yl)ethane-1,2-diamine;
5-chloro-4-[1-(3-fluorobenzyl)-1H-benzimidazol-6-yl]-N-[2-(1-methylpiperidin-4-yl)ethyl]pyridin-2-amine;
5-chloro-4-[1-(3-fluorobenzyl)-1H-benzimidazol-6-yl]-N-[2-(pyridin-4-yl)propyl]pyridin-2-amine;
$N^1$-{5-chloro-4-[1-(3-fluorobenzyl)-1H-benzimidazol-6-yl]pyridin-2-yl}-$N^2,N^2$,2-trimethylpropane-1,2-diamine;
N-{5-chloro-4-[1-(3-fluorobenzyl)-1H-benzimidazol-6-yl]pyridin-2-yl}-N'-phenylpropane-1,3-diamine;
$N^3$-{5-chloro-4-[1-(3-fluorobenzyl)-1H-benzimidazol-6-yl]pyridin-2-yl}butane-1,3-diamine;
5-chloro-4-[1-(3-fluorobenzyl)-1H-benzimidazol-6-yl]pyridin-2-amine;
5-chloro-4-[1-(3-fluorobenzyl)-1H-benzimidazol-6-yl]-N-(1H-imidazol-4-ylmethyl)pyridin-2-amine;
5-chloro-4-[1-(3-fluorobenzyl)-1H-benzimidazol-6-yl]-N-(pyrazin-2-ylmethyl)pyridin-2-amine;
5-chloro-4-[1-(3-fluorobenzyl)-1H-benzimidazol-6-yl]-N-[1-(pyrazin-2-yl)propan-2-yl]pyridin-2-amine;
5-chloro-4-[1-(3-fluorobenzyl)-1H-benzimidazol-6-yl]-N-(1-methylpyrrolidin-3-yl)pyridin-2-amine;
5-chloro-4-[1-(3-fluorobenzyl)-1H-benzimidazol-6-yl]-N-[2-(pyridin-3-yl)ethyl]pyridin-2-amine;
N'-{5-chloro-4-[1-(3-fluorobenzyl)-1H-benzimidazol-6-yl]pyridin-2-yl}-N,N-dimethylbutane-1,4-diamine;
5-chloro-4-[1-(3-fluorobenzyl)-1H-benzimidazol-6-yl]-N-[(1-methylpiperidin-4-yl)methyl]pyridin-2-amine;
N-benzyl-N'-{5-chloro-4-[1-(3-fluorobenzyl)-1H-benzimidazol-6-yl]pyridin-2-yl}-N-methylethane-1,2-diamine;
5-chloro-4-[1-(3-fluorobenzyl)-1H-benzimidazol-6-yl]-N-[2-(pyridin-2-yl)ethyl]pyridin-2-amine;
4-({5-chloro-4-[1-(3-fluorobenzyl)-1H-benzimidazol-6-yl]pyridin-2-yl}amino)-2-methylbutan-2-ol;
N'-{5-chloro-4-[1-(3-fluorobenzyl)-1H-benzimidazol-6-yl]pyridin-2-yl}-N-methyl-N-phenylpropane-1,3-diamine;
5-chloro-4-[1-(3-fluorobenzyl)-1H-benzimidazol-6-yl]-N-(1-methylpiperidin-4-yl)pyridin-2-amine;
5-chloro-4-[1-(3-fluorobenzyl)-1H-benzimidazol-6-yl]-N-[2-(pyridin-4-yl)ethyl]pyridin-2-amine;
5-chloro-4-[1-(3-fluorobenzyl)-1H-benzimidazol-6-yl]-N-(pyrimidin-5-ylmethyl)pyridin-2-amine;

N²-{5-chloro-4-[1-(3-fluorobenzyl)-1H-benzimidazol-6-yl]pyridin-2-yl}-2-methylpropane-1,2-diamine;
5-chloro-N-(2-cyclohexylethyl)-4-[1-(3-fluorobenzyl)-1H-benzimidazol-6-yl]pyridin-2-amine;
N-{5-chloro-4-[1-(3-fluorobenzyl)-1H-benzimidazol-6-yl]pyridin-2-yl}-N'-phenylethane-1,2-diamine;
N'-{5-chloro-4-[1-(3-fluorobenzyl)-1H-benzimidazol-6-yl]pyridin-2-yl}-N,N,2,2-tetramethylpropane-1,3-diamine;
2-({5-chloro-4-[1-(3-fluorobenzyl)-1H-benzimidazol-6-yl]pyridin-2-yl}amino)ethanol;
N-benzyl-5-chloro-4-[1-(3-fluorobenzyl)-1H-benzimidazol-6-yl]pyridin-2-amine;
N'-{5-chloro-4-[1-(3-fluorobenzyl)-1H-benzimidazol-6-yl]pyridin-2-yl}-N,N-dimethylpropane-1,3-diamine;
3-({5-chloro-4-[1-(3-fluorobenzyl)-1H-benzimidazol-6-yl]pyridin-2-yl}amino)propan-1-ol;
N-{5-chloro-4-[1-(3-fluorobenzyl)-1H-benzimidazol-6-yl]pyridin-2-yl}propane-1,3-diamine;
4-[({5-chloro-4-[1-(3-fluorobenzyl)-1H-benzimidazol-6-yl]pyridin-2-yl}amino)methyl]phenol;
N-{5-chloro-4-[1-(3-fluorobenzyl)-1H-benzimidazol-6-yl]pyridin-2-yl}butane-1,4-diamine;
N-[2-(4-aminophenyl)ethyl]-5-chloro-4-[1-(3-fluorobenzyl)-1H-benzimidazol-6-yl]pyridin-2-amine;
N-{5-chloro-4-[1-(3-fluorobenzyl)-1H-benzimidazol-6-yl]pyridin-2-yl}-2,2-dimethylpropane-1,3-diamine;
N-{5-chloro-4-[1-(3-fluorobenzyl)-1H-benzimidazol-6-yl]pyridin-2-yl}ethane-1,2-diamine;
N-[4-(aminomethyl)benzyl]-5-chloro-4-[1-(3-fluorobenzyl)-1H-benzimidazol-6-yl]pyridin-2-amine;
1-({5-chloro-4-[1-(3-fluorobenzyl)-1H-benzimidazol-6-yl]pyridin-2-yl}amino)-2-methylpropan-2-ol;
1-amino-3-{5-chloro-4-[1-(3-fluorobenzyl)-1H-benzimidazol-6-yl]pyridin-2-yl}amino)propan-2-ol;
N-{5-chloro-4-[1-(3-fluorobenzyl)-1H-benzimidazol-6-yl]pyridin-2-yl}-N'-(pyridin-2-yl)ethane-1,2-diamine;
(3R)—N-{5-chloro-4-[1-(3-fluorobenzyl)-1H-benzimidazol-6-yl]pyridin-2-yl}-1-azabicyclo[2.2.2]octan-3-amine;
(3S)—N-{5-chloro-4-[1-(3-fluorobenzyl)-1H-benzimidazol-6-yl]pyridin-2-yl}-1-azabicyclo[2.2.2]octan-3-amine;
2-benzyl-N-{5-chloro-4-[1-(3-fluorobenzyl)-1H-benzimidazol-6-yl]pyridin-2-yl}octahydro-1H-isoindol-4-amine;
2-benzyl-N-{5-chloro-4-[1-(3-fluorobenzyl)-1H-benzimidazol-6-yl]pyridin-2-yl}octahydrocyclopenta[c]pyrrol-4-amine;
N-{5-chloro-4-[1-(3-fluorobenzyl)-1H-benzimidazol-6-yl]pyridin-2-yl}-9-(cyclopropylmethyl)-9-azabicyclo[3.3.1]nonan-3-amine;
benzyl 4-({5-chloro-4-[1-(3-fluorobenzyl)-1H-benzimidazol-6-yl]pyridin-2-yl}amino)-4-(4-fluorophenyl)piperidine-1-carboxylate;
tert-butyl {5-chloro-4-[1-(3-fluorobenzyl)-1H-benzimidazol-6-yl]pyridin-2-yl}carbamate;
(3R)—N-(5-chloro-4-{1-[(5-methyl-1,3,4-thiadiazol-2-yl)methyl]-1H-benzimidazol-6-yl}pyridin-2-yl)piperidine-3-carboxamide;
(3R)—N-(5-chloro-4-{1-[2-(pyridin-3-yl)ethyl]-1H-benzimidazol-6-yl}pyridin-2-yl)piperidine-3-carboxamide;
N-{5-chloro-4-[1-(3-fluorobenzyl)-1H-benzimidazol-6-yl]pyridin-2-yl}-N'-methylpropane-1,3-diamine;
N-[(trans-4-aminocyclohexyl)methyl]-5-chloro-4-[1-(3-fluorobenzyl)-1H-benzimidazol-6-yl]pyridin-2-amine;
N-{5-chloro-4-[1-(3-fluorobenzyl)-1H-benzimidazol-6-yl]pyridin-2-yl}-N'-methylbutane-1,4-diamine;
N-benzyl-N'-{5-chloro-4-[1-(3-fluorobenzyl)-1H-benzimidazol-6-yl]pyridin-2-yl}ethane-1,2-diamine;
5-chloro-4-[1-(3-fluorobenzyl)-1H-benzimidazol-6-yl]-N-[2-(piperidin-4-yl)ethyl]pyridin-2-amine;
5-chloro-4-[1-(3-fluorobenzyl)-1H-benzimidazol-6-yl]-N-[2-(piperidin-3-yl)ethyl]pyridin-2-amine;
N²-{5-chloro-4-[1-(3-fluorobenzyl)-1H-benzimidazol-6-yl]pyridin-2-yl}-1-phenylethane-1,2-diamine;
5-chloro-4-[1-(3-fluorobenzyl)-1H-benzimidazol-6-yl]-N-(piperidin-3-yl)pyridin-2-amine;
N-[(2R)-azetidin-2-ylmethyl]-5-chloro-4-[1-(3-fluorobenzyl)-1H-benzimidazol-6-yl]pyridin-2-amine;
N-[2-(azetidin-2-yl)ethyl]-5-chloro-4-[1-(3-fluorobenzyl)-1H-benzimidazol-6-yl]pyridin-2-amine;
(4aS,8R,8aS)—N-{5-chloro-4-[1-(3-fluorobenzyl)-1H-benzimidazol-6-yl]pyridin-2-yl}decahydroisoquinolin-8-amine;
5-chloro-4-[1-(3-fluorobenzyl)-1H-benzimidazol-6-yl]-N-[2-(pyrrolidin-2-yl)ethyl]pyridin-2-amine;
11-{5-chloro-4-[1-(3-fluorobenzyl)-1H-benzimidazol-6-yl]pyridin-2-yl}-1,8-dioxa-4,11-diazaspiro[5.6]dodecane;
N-{5-chloro-4-[1-(3-fluorobenzyl)-1H-benzimidazol-6-yl]pyridin-2-yl}-6-azaspiro[3.5]nonan-2-amine;
N-{5-chloro-4-[1-(3-fluorobenzyl)-1H-benzimidazol-6-yl]pyridin-2-yl}-7-azaspiro[3.5]nonan-2-amine;
N-{5-chloro-4-[1-(3-fluorobenzyl)-1H-benzimidazol-6-yl]pyridin-2-yl}-7-azaspiro[3.5]nonan-1-amine;
5-chloro-4-[1-(3-fluorobenzyl)-1H-benzimidazol-6-yl]-N-{[(2R,4S)-4-fluoropyrrolidin-2-yl]methyl}pyridin-2-amine;
5-chloro-4-[1-(3-fluorobenzyl)-1H-benzimidazol-6-yl]-N-[(4-fluoropyrrolidin-3-yl)methyl]pyridin-2-amine;
N-{5-chloro-4-[1-(3-fluorobenzyl)-1H-benzimidazol-6-yl]pyridin-2-yl}-6-azaspiro[3.4]octan-2-amine;
(3R)—N-{5-chloro-4-[1-(3-fluorobenzyl)-1H-benzotriazol-6-yl]pyridin-2-yl}piperidine-3-carboxamide;
(3R)—N-(5-chloro-4-{1-[2-(methylsulfonyl)ethyl]-1H-benzimidazol-6-yl}pyridin-2-yl)piperidine-3-carboxamide;
(3R)—N-(5-chloro-4-{1-[2-(methylsulfonyl)ethyl]-1H-benzotriazol-6-yl}pyridin-2-yl)piperidine-3-carboxamide;
(3R)—N-{5-chloro-4-[1-(4-fluorobenzyl)-1H-benzotriazol-6-yl]pyridin-2-yl}piperidine-3-carboxamide;
(3R)—N-{5-chloro-4-[1-(3,4-difluorobenzyl)-1H-benzotriazol-6-yl]pyridin-2-yl}piperidine-3-carboxamide;
(3R)—N-(5-chloro-4-{1-[2-(2-fluorophenyl)ethyl]-1H-benzotriazol-6-yl}pyridin-2-yl)piperidine-3-carboxamide;
(3R)—N-{5-chloro-4-[1-(2-sulfamoylethyl)-1H-benzotriazol-6-yl]pyridin-2-yl}piperidine-3-carboxamide;
5-chloro-4-[1-(3-fluorobenzyl)-1H-benzimidazol-6-yl]-N-{2-[4-(4-methylphenyl)piperidin-4-yl]ethyl}pyridin-2-amine;
5-chloro-4-[1-(3-fluorobenzyl)-1H-benzimidazol-6-yl]-N-{2-[4-(4-methoxyphenyl)piperidin-4-yl]ethyl}pyridin-2-amine;
5-chloro-4-[1-(3-fluorobenzyl)-1H-benzimidazol-6-yl]-N-[(4-fluoropiperidin-4-yl)methyl]pyridin-2-amine;
5-chloro-4-[1-(3-fluorobenzyl)-1H-benzimidazol-6-yl]-N-{2-[3-(4-methoxyphenyl)pyrrolidin-3-yl]ethyl}pyridin-2-amine;
N-{5-chloro-4-[1-(3-fluorobenzyl)-1H-benzimidazol-6-yl]pyridin-2-yl}-6-azaspiro[3.4]octan-1-amine;
(1S,4R)—N-{5-chloro-4-[1-(3-fluorobenzyl)-1H-benzimidazol-6-yl]pyridin-2-yl}-6-azaspiro[3.5]nonan-1-amine;
N-{5-chloro-4-[1-(3-fluorobenzyl)-1H-benzimidazol-6-yl]pyridin-2-yl}-5-thia-2-azaspiro[3.4]octan-8-amine 5,5-dioxide;
N-{5-chloro-4-[1-(3-fluorobenzyl)-1H-benzimidazol-6-yl]pyridin-2-yl}-9-azabicyclo[3.3.1]nonan-3-amine;

(3S)—N-{5-chloro-4-[1-(3-fluorobenzyl)-1H-benzimidazol-6-yl]pyridin-2-yl}azepan-3-amine;
(3R)—N-{5-chloro-4-[1-(3-fluorobenzyl)-1H-benzimidazol-6-yl]pyridin-2-yl}azepan-3-amine;
(1R,4R)—N-{5-chloro-4-[1-(3-fluorobenzyl)-1H-benzimidazol-6-yl]pyridin-2-yl}-6-azaspiro[3.5]nonan-1-amine;
N-{[3-(aminomethyl)cyclohexyl]methyl}-5-chloro-4-[1-(3-fluorobenzyl)-1H-benzimidazol-6-yl]pyridin-2-amine;
N-{5-chloro-4-[1-(3-fluorobenzyl)-1H-benzimidazol-6-yl]pyridin-2-yl}-2-(piperidin-4-yl)acetamide;
4-({5-chloro-4-[1-(3-fluorobenzyl)-1H-benzimidazol-6-yl]pyridin-2-yl}amino)benzenesulfonamide;
(3R)—N-(5-chloro-4-{1-[(5-fluoropyridin-3-yl)methyl]-1H-benzimidazol-6-yl}pyridin-2-yl)piperidine-3-carboxamide;
(3R)—N-(5-chloro-4-{1-[(4-cyanotetrahydro-2H-pyran-4-yl)methyl]-1H-benzimidazol-6-yl}pyridin-2-yl)piperidine-3-carboxamide;
(3R)—N-{5-chloro-4-[1-(3-fluorobenzyl)-1H-pyrrolo[3,2-c]pyridin-6-yl]pyridin-2-yl}piperidine-3-carboxamide;
(3R)—N-{5-chloro-4-[1-(3-fluorobenzyl)-1H-pyrrolo[2,3-b]pyridin-6-yl]pyridin-2-yl}piperidine-3-carboxamide;
(3R)—N-{5-chloro-4-[5-fluoro-1-(3-fluorobenzyl)-1H-benzimidazol-6-yl]pyridin-2-yl}piperidine-3-carboxamide;
(3R)—N-{5-chloro-4-[1-(3-fluorobenzyl)-1H-indazol-6-yl]pyridin-2-yl}piperidine-3-carboxamide;
(3R)—N-[4-(1-{2-[bis(2-hydroxyethyl)amino]ethyl}-1H-benzotriazol-6-yl)-5-chloropyridin-2-yl]piperidine-3-carboxamide;
(3R)—N-[5-chloro-4-(2-oxo-2,3-dihydro-1H-indol-6-yl)pyridin-2-yl]piperidine-3-carboxamide;
(3R)—N-(5-chloro-4-{1-[3-(dimethylamino)propyl]-1H-benzimidazol-6-yl}pyridin-2-yl)piperidine-3-carboxamide;
(3R)—N-(5-chloro-4-{1-[3-(dimethylamino)propyl]-1H-benzotriazol-6-yl}pyridin-2-yl)piperidine-3-carboxamide;
(3R)—N-(5-chloro-4-{1-[2-(morpholin-4-yl)ethyl]-1H-benzotriazol-6-yl}pyridin-2-yl)piperidine-3-carboxamide;
(3R)—N-{5-chloro-4-[1-(3-fluorobenzyl)-2-methyl-1H-benzimidazol-6-yl]pyridin-2-yl}piperidine-3-carboxamide;
(3R)—N-{5-chloro-4-[3-(tetrahydro-2H-pyran-4-ylmethyl)-3H-imidazo[4,5-b]pyridin-5-yl]pyridin-2-yl}piperidine-3-carboxamide;
(3R)—N-(5-chloro-4-{1-[(1R)-1-(3-fluorophenyl)ethyl]-1H-benzimidazol-6-yl}pyridin-2-yl)piperidine-3-carboxamide;
(3R)—N-(5-chloro-4-{1-[(1R)-1-(3-fluorophenyl)ethyl]-1H-benzotriazol-6-yl}pyridin-2-yl)piperidine-3-carboxamide;
(3R)—N-{5-chloro-4-[3-(3-fluorobenzyl)-2-oxo-2,3-dihydro-1H-benzimidazol-5-yl]pyridin-2-yl}piperidine-3-carboxamide;
(3R)—N-{5-chloro-4-[5-chloro-1-(tetrahydro-2H-pyran-4-ylmethyl)-1H-benzimidazol-6-yl]pyridin-2-yl}piperidine-3-carboxamide;
N-(5-chloro-4-{1-[(5-methylpyrazin-2-yl)methyl]-2,3-dihydro-1H-indol-6-yl}pyridin-2-yl)piperidine-3-carboxamide;
N-[5-chloro-4-(1-{4-[(methylsulfonyl)amino]benzyl}-2,3-dihydro-1H-indol-6-yl)pyridin-2-yl]piperidine-3-carboxamide;
N-(5-chloro-4-{1-[4-fluoro-3-(methylsulfonyl)benzyl]-2,3-dihydro-1H-indol-6-yl}pyridin-2-yl)piperidine-3-carboxamide;
N-(5-chloro-4-{1-[(2-methylpyrimidin-5-yl)methyl]-2,3-dihydro-1H-indol-6-yl}pyridin-2-yl)piperidine-3-carboxamide;
N-(5-chloro-4-{1-[3-(methylsulfonyl)benzyl]-2,3-dihydro-1H-indol-6-yl}pyridin-2-yl)piperidine-3-carboxamide;
N-(5-chloro-4-{1-[(6-methylpyridin-3-yl)methyl]-2,3-dihydro-1H-indol-6-yl}pyridin-2-yl)piperidine-3-carboxamide;
N-{5-chloro-4-[1-(pyrrolidin-3-ylmethyl)-2,3-dihydro-1H-indol-6-yl]pyridin-2-yl}piperidine-3-carboxamide;
4-[(6-{5-chloro-2-[(piperidin-3-ylcarbonyl)amino]pyridin-4-yl}-2,3-dihydro-1H-indol-1-yl)methyl]benzoic acid;
N-(5-chloro-4-{1-[4-(methylsulfonyl)benzyl]-2,3-dihydro-1H-indol-6-yl}pyridin-2-yl)piperidine-3-carboxamide;
methyl 4-[(6-{5-chloro-2-[(piperidin-3-ylcarbonyl)amino]pyridin-4-yl}-2,3-dihydro-1H-indol-1-yl)methyl]benzoate;
N-{5-chloro-4-[1-(pyrimidin-5-ylmethyl)-2,3-dihydro-1H-indol-6-yl]pyridin-2-yl}piperidine-3-carboxamide;
N-[5-chloro-4-(1-{[6-(trifluoromethyl)pyridin-2-yl]methyl}-2,3-dihydro-1H-indol-6-yl)pyridin-2-yl]piperidine-3-carboxamide;
N-{5-chloro-4-[1-(quinolin-6-ylmethyl)-2,3-dihydro-1H-indol-6-yl]pyridin-2-yl}piperidine-3-carboxamide;
N-{4-[1-(1H-benzimidazol-2-ylmethyl)-2,3-dihydro-1H-indol-6-yl]-5-chloropyridin-2-yl}piperidine-3-carboxamide;
N-{5-chloro-4-[1-(2,3-dihydro-1,4-benzodioxin-5-ylmethyl)-2,3-dihydro-1H-indol-6-yl]pyridin-2-yl}piperidine-3-carboxamide;
N-(5-chloro-4-{1-[(1-methyl-1H-benzimidazol-2-yl)methyl]-2,3-dihydro-1H-indol-6-yl}pyridin-2-yl)piperidine-3-carboxamide;
N-(5-chloro-4-{1-[(1-methyl-1H-benzotriazol-5-yl)methyl]-2,3-dihydro-1H-indol-6-yl}pyridin-2-yl)piperidine-3-carboxamide;
N-{4-[1-(1,3-benzodioxol-4-ylmethyl)-2,3-dihydro-1H-indol-6-yl]-5-chloropyridin-2-yl}piperidine-3-carboxamide;
N-{5-chloro-4-[1-(4-methylbenzyl)-2,3-dihydro-1H-indol-6-yl]pyridin-2-yl}piperidine-3-carboxamide;
N-{5-chloro-4-[1-(quinoxalin-6-ylmethyl)-2,3-dihydro-1H-indol-6-yl]pyridin-2-yl}piperidine-3-carboxamide;
N-{5-chloro-4-[1-(pyrazin-2-ylmethyl)-2,3-dihydro-1H-indol-6-yl]pyridin-2-yl}piperidine-3-carboxamide;
N-{5-chloro-4-[1-(2,3-dihydro[1,4]dioxino[2,3-b]pyridin-7-ylmethyl)-2,3-dihydro-1H-indol-6-yl]pyridin-2-yl}piperidine-3-carboxamide;
N-[5-chloro-4-(1-{[6-(methylsulfonyl)pyridin-3-yl]methyl}-2,3-dihydro-1H-indol-6-yl)pyridin-2-yl]piperidine-3-carboxamide;
N-{5-chloro-4-[1-(4-sulfamoylbenzyl)-2,3-dihydro-1H-indol-6-yl]pyridin-2-yl}piperidine-3-carboxamide;
N-(5-chloro-4-{1-[3-fluoro-4-(methylsulfonyl)benzyl]-2,3-dihydro-1H-indol-6-yl}pyridin-2-yl)piperidine-3-carboxamide;
N-(5-chloro-4-{1-[4-(2H-tetrazol-5-yl)benzyl]-2,3-dihydro-1H-indol-6-yl}pyridin-2-yl)piperidine-3-carboxamide;
N-{5-chloro-4-[1-(pyrrolidin-2-ylmethyl)-2,3-dihydro-1H-indol-6-yl]pyridin-2-yl}piperidine-3-carboxamide;
N-(5-chloro-4-{1-[(1-methylpiperidin-4-yl)methyl]-2,3-dihydro-1H-indol-6-yl}pyridin-2-yl)piperidine-3-carboxamide;
N-{5-chloro-4-[1-(3-fluorobenzyl)-1H-imidazo[4,5-b]pyridin-6-yl]pyridin-2-yl}piperidine-3-carboxamide;

(3R)—N-[5-chloro-4-(1-{[3-(morpholin-4-yl)oxetan-3-yl]methyl}-1H-benzimidazol-6-yl)pyridin-2-yl]piperidine-3-carboxamide;
(3R)—N-[5-chloro-4-(1-{[3-(pyrrolidin-1-yl)oxetan-3-yl]methyl}-1H-benzimidazol-6-yl)pyridin-2-yl]piperidine-3-carboxamide;
N-{5-chloro-4-[1-(tetrahydro-2H-pyran-4-ylmethyl)-1H-benzimidazol-6-yl]pyridin-2-yl}-7-azaspiro[3.5]nonan-2-amine;
N-{5-chloro-4-[1-(tetrahydro-2H-pyran-4-ylmethyl)-1H-benzimidazol-6-yl]pyridin-2-yl}-7-(methylsulfonyl)-7-azaspiro[3.5]nonan-2-amine;
(2E)-N-{5-chloro-4-[1-(3-fluorobenzyl)-1H-benzimidazol-6-yl]pyridin-2-yl}-3-(pyridin-4-yl)prop-2-enamide;
(1R,2S)—N-{5-chloro-4-[1-(3-fluorobenzyl)-1H-benzimidazol-6-yl]pyridin-2-yl}-N'-cyclopentylcyclobutane-1,2-dicarboxamide;
N-{5-chloro-4-[1-(3-fluorobenzyl)-1H-benzimidazol-6-yl]pyridin-2-yl}-2-(2-oxopyridin-1(2H)-yl)propanamide;
N-{5-chloro-4-[1-(3-fluorobenzyl)-1H-benzimidazol-6-yl]pyridin-2-yl}-2-(methylsulfonyl)acetamide;
N-{5-chloro-4-[1-(3-fluorobenzyl)-1H-benzimidazol-6-yl]pyridin-2-yl}-1-(3-chlorophenyl)-5-oxopyrrolidine-3-carboxamide;
1-benzyl-N-{5-chloro-4-[1-(3-fluorobenzyl)-1H-benzimidazol-6-yl]pyridin-2-yl}-5-oxopyrrolidine-3-carboxamide;
N-{5-chloro-4-[1-(3-fluorobenzyl)-1H-benzimidazol-6-yl]pyridin-2-yl}-2,3-dihydro[1,4]dioxino[2,3-b]pyridine-7-carboxamide;
(3R)—N-{5-chloro-4-[1-(3-fluorobenzyl)-1H-benzimidazol-6-yl]pyridin-2-yl}-3-(pyridin-3-yl)-1H-pyrrolo[1,2-c][1,3]thiazole-7-carboxamide;
N-{5-chloro-4-[1-(3-fluorobenzyl)-1H-benzimidazol-6-yl]pyridin-2-yl}-3-oxo cyclobutanecarboxamide;
N-{5-chloro-4-[1-(3-fluorobenzyl)-1H-benzimidazol-6-yl]pyridin-2-yl}-6-oxospiro[3.3]heptane-2-carboxamide;
benzyl (1R,5S,6r)-6-({5-chloro-4-[1-(3-fluorobenzyl)-1H-benzimidazol-6-yl]pyridin-2-yl}carbamoyl)-3-azabicyclo[3.1.0]hexane-3-carboxylate;
N-{5-chloro-4-[1-(3-fluorobenzyl)-1H-benzimidazol-6-yl]pyridin-2-yl}-1-methylazetidine-3-carboxamide;
N-{5-chloro-4-[1-(3-fluorobenzyl)-1H-benzimidazol-6-yl]pyridin-2-yl}-3-methyloxetane-3-carboxamide;
N-{5-chloro-4-[1-(3-fluorobenzyl)-1H-benzimidazol-6-yl]pyridin-2-yl}-4-hydroxy-4-(trifluoromethyl)cyclohexanecarboxamide;
N-{5-chloro-4-[1-(3-fluorobenzyl)-1H-benzimidazol-6-yl]pyridin-2-yl}-1-(2,2-dimethylpropanoyl)-2,3-dihydro-1H-pyrido[2,3-b][1,4]oxazine-6-carboxamide;
N-{5-chloro-4-[1-(3-fluorobenzyl)-1H-benzimidazol-6-yl]pyridin-2-yl}-2-(methylsulfonyl)-5-thia-2-azaspiro[3.4]octane-8-carboxamide 5,5-dioxide;
$N^8$-{5-chloro-4-[1-(3-fluorobenzyl)-1H-benzimidazol-6-yl]pyridin-2-yl}-$N^2$-ethyl-5-thia-2-azaspiro[3.4]octane-2,8-dicarboxamide 5,5-dioxide;
$N^8$-{5-chloro-4-[1-(3-fluorobenzyl)-1H-benzimidazol-6-yl]pyridin-2-yl}-$N^2$-phenyl-5-thia-2-azaspiro[3.4]octane-2,8-dicarboxamide 5,5-dioxide;
N-{5-chloro-4-[1-(3-fluorobenzyl)-1H-benzimidazol-6-yl]pyridin-2-yl}-7-(cyclohexylcarbonyl)-1-thia-7-azaspiro[4.4]nonane-4-carboxamide 1,1-dioxide;
N-{5-chloro-4-[1-(3-fluorobenzyl)-1H-benzimidazol-6-yl]pyridin-2-yl}-7-(2-methylpropanoyl)-1-thia-7-azaspiro[4.4]nonane-4-carboxamide 1,1-dioxide;
N-{5-chloro-4-[1-(3-fluorobenzyl)-1H-benzimidazol-6-yl]pyridin-2-yl}-7-(phenylsulfonyl)-1-thia-7-azaspiro[4.4]nonane-4-carboxamide 1,1-dioxide;
7-benzoyl-N-{5-chloro-4-[1-(3-fluorobenzyl)-1H-benzimidazol-6-yl]pyridin-2-yl}-1-thia-7-azaspiro[4.4]nonane-4-carboxamide 1,1-dioxide;
N-{5-chloro-4-[1-(3-fluorobenzyl)-1H-benzimidazol-6-yl]pyridin-2-yl}-7-ethyl-1-thia-7-azaspiro[4.4]nonane-4-carboxamide 1,1-dioxide;
N-{5-chloro-4-[1-(3-fluorobenzyl)-1H-benzimidazol-6-yl]pyridin-2-yl}-2-oxohexahydro-2H-cyclopenta[d][1,3]oxazole-5-carboxamide;
N-{5-chloro-4-[1-(3-fluorobenzyl)-1H-benzimidazol-6-yl]pyridin-2-yl}-7-(methylsulfonyl)-1-thia-7-azaspiro[4.4]nonane-4-carboxamide 1,1-dioxide;
(2E)-N-carbamoyl-N'-{5-chloro-4-[1-(3-fluorobenzyl)-1H-benzimidazol-6-yl]pyridin-2-yl}but-2-enediamide;
N-{5-chloro-4-[1-(3-fluorobenzyl)-1H-benzimidazol-6-yl]pyridin-2-yl}cyclopropane-1,1-dicarboxamide;
N-{5-chloro-4-[1-(3-fluorobenzyl)-1H-benzimidazol-6-yl]pyridin-2-yl}-1H-pyrazole-4-carboxamide; and
trans-N-{5-chloro-4-[1-(tetrahydro-2H-pyran-4-ylmethyl)-1H-benzimidazol-6-yl]pyridin-2-yl}cyclohexane-1,4-diamine; and pharmaceutically acceptable salts thereof.

Embodiments of Formula (Ia)

In one aspect, the present invention provides compounds of Formula (Ia) or a pharmaceutically acceptable salt thereof,

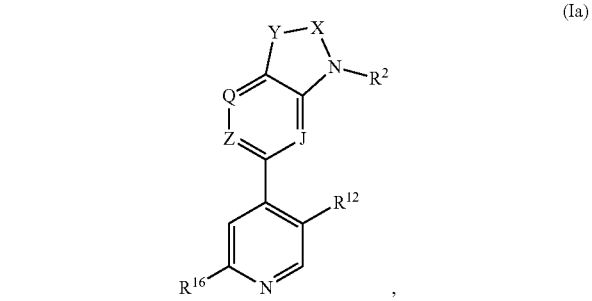

wherein
$R^{12}$ is halo or H;
J is N or CH;
Q is N or $CR^1$;
Z is N or $CR^1$;
wherein the bond between X and Y may be a single or a double bond; and
if a double bond is present, then Y is $CR^3$ and X is CH, Y is CH and X is CH, Y is N and X is CH, Y is N and X is $CR^3$, Y is $CR^3$ and X is N, Y is N and X is N, or Y is CH and X is N; and
if a single bond is present, then Y is $CH_2$ and X is $CH_2$ or C(O), or Y is NH or $N(C_1-C_3$ alkyl) and X is C(O);
$R^3$ is selected from the group consisting of $R^{3A}$, $C(O)R^{3A}$, and CN;
$R^{3A}$ is selected from the group consisting of $C_1-C_6$ alkyl, $C_2-C_6$ alkenyl, $C_2-C_6$ alkynyl, aryl, cycloalkyl, cycloalkenyl, heteroaryl, heterocycloalkyl, and heterocycloalkenyl; wherein the $R^{3A}$ $C_1-C_6$ alkyl, $C_2-C_6$ alkenyl, and $C_2-C_6$ alkynyl are optionally substituted with one or more substituents independently selected from the group consisting of $R^{3B}$, $OR^{3B}$, and halo; wherein the $R^{3A}$ aryl, cycloalkyl, cycloalkenyl, heteroaryl, heterocycloalkyl, and heterocycloalkenyl are optionally substituted with one or more halo;

$R^{3B}$ is selected from the group consisting of $C_1$-$C_6$ alkyl, $C_2$-$C_6$ alkenyl, $C_2$-$C_6$ alkynyl, and aryl, wherein the $R^{3B}$ aryl is optionally substituted with one or more substituents independently selected from the group consisting of F, Cl, Br, and I;

$R^1$ is selected from the group consisting of H, CN, Cl, Br, I, F, $R^{1A}$; and $OR^{1A}$;

$R^{1A}$ is selected from the group consisting of $C_1$-$C_6$ alkyl, $C_2$-$C_6$ alkenyl, and $C_2$-$C_6$ alkynyl;

$R^2$ is selected from the group consisting of H, $C_1$-$C_6$ alkyl, $C_2$-$C_6$ alkenyl, and $C_2$-$C_6$ alkynyl; wherein the $R^2$ $C_1$-$C_6$ alkyl, $C_2$-$C_6$ alkenyl, and $C_2$-$C_6$ alkynyl are optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $SO_2NHC(O)R^4$, $SO_2NR^4C(O)R^4$, $NHS(O)_2R^4$, $NR^4S(O)_2R^4$, $NHC(O)OR^4$, $NR^4C(O)OR^4$, $SO_2NHC(O)OR^4$, $SO_2NR^4C(O)OR^4$, $NHSO_2NHC(O)OR^4$, $NHSO_2NR^4C(O)OR^4$, $NR^4SO_2NR^4C(O)OR^4$, $NR^4SO_2NHC(O)OR^4$, $NHC(O)NH_2$, $NHC(O)NHR^4$, $NHC(O)N(R^4)_2$, $NR^4C(O)NHR^4$, $NR^4C(O)N(R^4)_2$, $OC(O)NH_2$, $OC(O)NHR^4$, $OC(O)N(R^4)_2$, $OC(O)NHSO_2R^4$, $OC(O)NR^4SO_2R^4$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $OSO_2NH_2$, $OSO_2NHR^4$, $OSO_2N(R^4)_2$, $C(O)NHCN$, $C(O)NR^4CN$, $S(O)NR^4$, $S(O)NSO_2R^4$, $C(O)H$, $C(O)OH$, (O), OH, CN, $NO_2$, F, Cl, Br and I;

$R^4$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^4$ $C_1$-$C_6$ alkyl, $C_2$-$C_6$ alkenyl, and $C_2$-$C_6$ alkynyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, OH, CN, $NO_2$, F, Cl, Br and I; wherein each $R^4$ aryl, cycloalkyl, cycloalkenyl, heteroaryl, heterocycloalkyl, and heterocycloalkenyl is optionally substituted with one or more substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, (O), OH, CN, $NO_2$, F, Br and I;

$R^5$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl;

$R^6$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^6$ $C_1$-$C_6$ alkyl, $C_2$-$C_6$ alkenyl, and $C_2$-$C_6$ alkynyl is optionally substituted with one or more substituents independently selected from the group consisting of halo and $R^{6A}$;

$R^{6A}$, at each occurrence, is independently selected from the group consisting of aryl, heteroaryl, heterocycloalkyl, heterocycloalkenyl, cycloalkyl, and cycloalkenyl; wherein each $R^{6A}$ aryl, heteroaryl, heterocycloalkyl, heterocycloalkenyl, cycloalkyl, and cycloalkenyl is optionally substituted with $C_1$-$C_6$ alkyl;

$R^{16}$ is selected from the group consisting of $NH_2$, $NHR^7$, $NHC(O)R^7$, $NHS(O)_2R^7$, $NHC(O)OR^7$, $NHC(O)NH_2$, $NHC(O)NHR^7$, and $NHC(O)N(R^7)_2$;

$R^7$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^7$ $C_1$-$C_6$ alkyl, $C_2$-$C_6$ alkenyl, and $C_2$-$C_6$ alkynyl is optionally substituted with one or more substituents independently selected from the group consisting of $R^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHSO_2NH_2$, $NR^8SO_2NH_2$, $NHSO_2NHR^8$, $NR^8SO_2NHR^8$, $NHSO_2N(R^8)_2$, $NR^8SO_2N(R^8)_2$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $C(O)NHC(O)NH_2$, $C(O)NR^8C(O)NH_2$, $C(O)NHC(O)NHR^8$, $C(O)NR^8C(O)NHR^8$, $C(O)NHC(O)N(R^8)_2$, $C(O)NR^8C(O)N(R^8)_2$, $SO_2NH_2$, $SO_2NHR^8$, $SO_2N(R^8)_2$, $C(O)H$, $C(O)OH$, OH, CN, $NO_2$, F, Cl, Br and I; wherein each $R^7$ aryl, cycloalkyl, cycloalkenyl, heteroaryl, heterocycloalkyl, and heterocycloalkenyl is optionally substituted with one or more substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $SO_2NHC(O)OH$, $SO_2NR^9C(O)OH$, $SO_2NHC(O)OR^9$, $SO_2NR^9C(O)OR^9$, $C(O)H$, $C(O)OH$, (O), OH, CN, $NO_2$, F, Cl, Br and I;

$R^8$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^8$ $C_1$-$C_6$ alkyl, $C_2$-$C_6$ alkenyl, and $C_2$-$C_6$ alkynyl is optionally substituted with one or more substituents independently selected from the group consisting of $NHR^{10}$, and aryl; wherein each $R^8$ aryl, heteroaryl, heterocycloalkyl, heterocycloalkenyl, cycloalkyl, and cycloalkenyl is optionally substituted with one or more substituents independently selected from the group consisting of $R^{11}$, $OR^{11}$, halo, $NH_2$, OH, and (O);

$R^9$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{13}$, $OR^{13}$, $SR^{13}$, $S(O)R^{13}$, $SO_2R^{13}$, $C(O)R^{13}$, $CO(O)R^{13}$, $OC(O)R^{13}$, $OC(O)OR^{13}$, $NH_2$, $NHR^{13}$, $N(R^{13})_2$, $NHC(O)R^{13}$, $NR^{13}C(O)R^{13}$, $NHS(O)_2R^{13}$, $NR^{13}S(O)_2R^{13}$, $NHC(O)OR^{13}$, $NR^{13}C(O)OR^{13}$, $NHC(O)NH_2$, $NHC(O)NHR^{13}$, $NHC(O)N(R^{13})_2$, $NR^{13}C(O)NHR^{13}$, $NR^{13}C(O)N(R^{13})_2$, $C(O)NH_2$, $C(O)NHR^{13}$, $C(O)N(R^{13})_2$, $C(O)NHOH$, $C(O)NHOR^{13}$, $C(O)NR^{13}SO_2R^{13}$, $SO_2NH_2$, $SO_2NHR^{13}$, $SO_2N(R^{13})_2$, $C(O)H$, $C(O)OH$, OH, CN, $NO_2$, F, Cl, Br and I; wherein each $R^9$ aryl, cycloalkyl, cycloalkenyl, heteroaryl, heterocycloalkyl, and heterocycloalkenyl is optionally substituted with one or more substituents independently selected from the group consisting of $R^{14}$, $OR^{14}$, $SR^{14}$, $S(O)R^{14}$, $SO_2R^{14}$, $C(O)R^{14}$, $CO(O)R^{14}$, $OC(O)R^{14}$, $OC(O)OR^{14}$, $NH_2$, $NHR^{14}$, $N(R^{14})_2$, $NHC(O)R^{14}$, $NR^{14}C(O)R^{14}$, $NHS(O)_2R^{14}$, $NR^{14}S(O)_2R^{14}$, $NHC(O)OR^{14}$, $NR^{14}C(O)OR^{14}$, $NHC(O)NH_2$, $NHC(O)NHR^{14}$, $NHC(O)N(R^{14})_2$, $NR^{14}C(O)NHR^{14}$, $NR^{14}C(O)N(R^{14})_2$, $C(O)NH_2$, $C(O)NHR^{14}$, $C(O)N(R^{14})_2$, $C(O)NHOH$, $C(O)NHOR^{14}$, $C(O)NHSO_2R^{14}$, $C(O)NR^{14}SO_2R^{14}$, $SO_2NH_2$, $SO_2NHR^{14}$, $SO_2N(R^{14})_2$, $C(O)H$, $C(O)OH$, $(O)$, $OH$, $CN$, $NO_2$, $F$, $Cl$, $Br$ and $I$;

$R^{10}$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl;

$R^{11}$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^{11}$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, $OH$, $CN$, $NO_2$, $F$, $Cl$, $Br$ and $I$; wherein each $R^{11}$ aryl, cycloalkyl, cycloalkenyl, heteroaryl, heterocycloalkyl, and heterocycloalkenyl is optionally substituted with one or more substituents independently selected from the group consisting of $C_1$-$C_6$ alkyl, $O$—$C_1$-$C_6$ alkyl, $NH_2$, $C(O)NH_2$, $C(O)H$, $C(O)OH$, $OH$, $CN$, $NO_2$, $F$, $Cl$, $Br$ and $I$;

$R^{13}$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^{13}$ $C_1$-$C_6$ alkyl, $C_2$-$C_6$ alkenyl, and $C_2$-$C_6$ alkynyl is optionally substituted with one or more substituents independently selected from the group consisting of aryl, $NH_2$, $C(O)NH_2$, $SO_2NH_2$, $C(O)H$, $C(O)OH$, $OH$, $CN$, $NO_2$, $F$, $Cl$, $Br$ and $I$; wherein each $R^{13}$ aryl, cycloalkyl, cycloalkenyl, heteroaryl, heterocycloalkyl, and heterocycloalkenyl is optionally substituted with one or more substituents independently selected from the group consisting of $C_1$-$C_6$ alkyl, $O$—$C_1$-$C_6$ alkyl, $C_1$-$C_6$ alkyl-$O$—$C_1$-$C_6$ alkyl, $NH_2$, $C(O)NH_2$, $C(O)H$, $C(O)OH$, $OH$, $CN$, $NO_2$, $F$, $Cl$, $Br$ and $I$; and $R^{14}$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^{14}$ $C_1$-$C_6$ alkyl, $C_2$-$C_6$ alkenyl, and $C_2$-$C_6$ alkynyl is optionally substituted with one or more substituents independently selected from the group consisting of aryl, $NH_2$, $C(O)NH_2$, $SO_2NH_2$, $C(O)H$, $C(O)OH$, $OH$, $CN$, $NO_2$, $F$, $Cl$, $Br$ and $I$; wherein each $R^{14}$ aryl, cycloalkyl, cycloalkenyl, heteroaryl, heterocycloalkyl, and heterocycloalkenyl is optionally substituted with one or more substituents independently selected from the group consisting of $C_1$-$C_6$ alkyl, $O$—$C_1$-$C_6$ alkyl, $C_1$-$C_6$ alkyl-$O$—$C_1$-$C_6$ alkyl, $NH_2$, $C(O)NH_2$, $C(O)H$, $C(O)OH$, $OH$, $NO_2$, $F$, $Cl$, $Br$ and $I$.

In one embodiment of Formula (Ia), $R^{12}$ is halo or H. In another embodiment of Formula (Ia), $R^{12}$ is halo. In another embodiment of Formula (Ia), $R^{12}$ is H. In another embodiment of Formula (Ia), $R^{12}$ is Cl.

In one embodiment of Formula (Ia), J is N or CH. In another embodiment of Formula (Ia), J is N. In another embodiment of Formula (Ia), J is CH.

In one embodiment of Formula (Ia), Q is N or $CR^1$. In another embodiment of Formula (Ia), Q is N. In another embodiment of Formula (Ia), Q is $CR^1$. In another embodiment of Formula (Ia), Q is $CR^1$; $R^1$ is selected from the group consisting of H, CN, Cl, Br, I, F, $R^{14}$; and $OR^{14}$; and $R^{14}$ is selected from the group consisting of $C_1$-$C_6$ alkyl, $C_2$-$C_6$ alkenyl, and $C_2$-$C_6$ alkynyl. In another embodiment of Formula (Ia), Q is $CR^1$; and $R^1$ is H. In another embodiment of Formula (Ia), Q is $CR^1$; $R^1$ is selected from the group consisting of H, Cl, F, and $OR^{14}$; and $R^{14}$ is $C_1$-$C_6$ alkyl.

In one embodiment of Formula (Ia), Z is N or $CR^1$. In another embodiment of Formula (Ia), Z is N. In another embodiment of Formula (Ia), Z is $CR^1$. In another embodiment of Formula (Ia), Z is $CR^1$; $R^1$ is selected from the group consisting of H, CN, Cl, Br, I, F, $R^{14}$; and $OR^{14}$; and $R^{14}$ is selected from the group consisting of $C_1$-$C_6$ alkyl, $C_2$-$C_6$ alkenyl, and $C_2$-$C_6$ alkynyl. In another embodiment of Formula (Ia), Z is $CR^1$; and $R^1$ is H. In another embodiment of Formula (Ia), Z is $CR^1$; $R^1$ is selected from the group consisting of H, Cl, F, and $OR^{14}$; and $R^{14}$ is $C_1$-$C_6$ alkyl.

In one embodiment of Formula (Ia), the bond between X and Y may be a single or a double bond. In another embodiment of Formula (Ia), the bond between X and Y is a single bond. In another embodiment of Formula (Ia), the bond between X and Y is a double bond.

In one embodiment of Formula (Ia), the bond between X and Y is a double bond; and Y is $CR^3$ and X is CH, Y is CH and X is CH, Y is N and X is CH, Y is N and X is $CR^3$, Y is $CR^3$ and X is N, Y is N and X is N, or Y is CH and X is N. In one embodiment of Formula (Ia), the bond between X and Y is a double bond; and Y is $CR^3$ and X is CH. In one embodiment of Formula (Ia), the bond between X and Y is a double bond; and Y is CH and X is CH. In one embodiment of Formula (Ia), the bond between X and Y is a double bond; and Y is N and X is CH. In one embodiment of Formula (Ia), the bond between X and Y is a double bond; and Y is N and X is $CR^3$. In another embodiment of Formula (Ia), the bond between X and Y is a double bond; and Y is $CR^3$ and X is N. In another embodiment of Formula (Ia), the bond between X and Y is a double bond; and Y is N and X is N. In another embodiment of Formula (Ia), the bond between X and Y is a double bond; and Y is CH and X is N.

In one embodiment of Formula (Ia), the bond between X and Y is a single bond; and Y is $CH_2$ and X is $CH_2$ or $C(O)$, or Y is NH or $N(C_1$-$C_3$ alkyl) and X is $C(O)$. In another embodiment of Formula (Ia), the bond between X and Y is a single bond; and Y is $CH_2$ and X is $CH_2$. In another embodiment of Formula (Ia), the bond between X and Y is a single bond; and Y is $CH_2$ and X is $C(O)$. In another embodiment of Formula (Ia), the bond between X and Y is a single bond; and Y is NH and X is $C(O)$. In another embodiment of Formula (Ia), the bond between X and Y is a single bond; and Y is $N(C_1$-$C_3$ alkyl) and X is $C(O)$.

In one embodiment of Formula (Ia), J is CH; Q is CH; Z is CH; wherein the bond between X and Y is a single bond; and Y is $CH_2$ and X is $CH_2$. In another embodiment of Formula (Ia), J is CH; Q is CH; Z is CH; wherein the bond between X and Y is a double bond; and Y is N and X is CH. In another embodiment of Formula (Ia), J is CH; Q is CH; Z is CH; wherein the bond between X and Y is a double bond; and Y is CH and X is CH. In another embodiment of Formula (Ia), J is CH; Q is N; Z is CH; wherein the bond between X and Y is a double bond; and Y is CH and X is CH. In another embodiment of Formula (Ia), J is CH; Q is CH; Z is CH; wherein the bond between X and Y is a double bond; and Y is N and X is N. In another embodiment of Formula (Ia), J is CH; Q is CH; Z is N; wherein the bond between X and Y is a double bond; and Y is CH and X is CH. In another embodiment of Formula (Ia), J is N; Q is CH; Z is CH; wherein the bond between X and Y is a double bond;

and Y is CH and X is CH. In another embodiment of Formula (Ia), J is CH; Q is CH; Z is CH; wherein the bond between X and Y is a double bond; and Y is CH and X is N. In another embodiment of Formula (Ia), J is N; Q is CH; Z is CH; wherein the bond between X and Y is a double bond; and Y is N and X is CH. In another embodiment of Formula (Ia), J is CH; Q is N; Z is CH; wherein the bond between X and Y is a double bond; and Y is N and X is CH. In another embodiment of Formula (Ia), J is CH; Q is CH; Z is CH; wherein the bond between X and Y is a double bond; and Y is CH and X is CH. In another embodiment of Formula (Ia), J is N; Q is N; Z is CH; wherein the bond between X and Y is a double bond; and Y is N and X is CH. In another embodiment of Formula (Ia), J is N; Q is N; Z is CH; wherein the bond between X and Y is a double bond; and Y is N and X is N.

In one embodiment of Formula (Ia), $R^2$ is selected from the group consisting of H, $C_1$-$C_6$ alkyl, $C_2$-$C_6$ alkenyl, and $C_2$-$C_6$ alkynyl; wherein the $R^2$ $C_1$-$C_6$ alkyl, $C_2$-$C_6$ alkenyl, and $C_2$-$C_6$ alkynyl are optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $SO_2NHC(O)R^4$, $SO_2NR^4C(O)R^4$, $NHS(O)_2R^4$, $NR^4S(O)_2R^4$, $NHC(O)OR^4$, $NR^4C(O)OR^4$, $SO_2NHC(O)OR^4$, $SO_2NR^4C(O)OR^4$, $NHSO_2NHC(O)OR^4$, $NHSO_2NR^4C(O)OR^4$, $NR^4SO_2NR^4C(O)OR^4$, $NR^4SO_2NHC(O)OR^4$, $NHC(O)NH_2$, $NHC(O)NHR^4$, $NHC(O)N(R^4)_2$, $NR^4C(O)NHR^4$, $NR^4C(O)N(R^4)_2$, $OC(O)NH_2$, $OC(O)NHR^4$, $OC(O)N(R^4)_2$, $OC(O)NHSO_2R^4$, $OC(O)NR^4SO_2R^4$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $OSO_2NH_2$, $OSO_2NHR^4$, $OSO_2N(R^4)_2$, $C(O)NHCN$, $C(O)NR^4CN$, $S(O)NR^4$, $S(O)NSO_2R^4$, $C(O)H$, $C(O)OH$, $(O)$, $OH$, $CN$, $NO_2$, $F$, $Cl$, $Br$ and $I$. In another embodiment of Formula (Ia), $R^2$ is selected from the group consisting of H and $C_1$-$C_6$ alkyl; wherein the $R^2$ $C_1$-$C_6$ alkyl is optionally substituted with one or more substituents independently selected from the group consisting of $R^4$, $SO_2R^4$, $C(O)R^4$, $N(R^4)_2$, $C(O)N(R^4)_2$, $SO_2NH_2$, and OH. In another embodiment of Formula (Ia), $R^2$ is H. In another embodiment of Formula (Ia), $R^2$ is $C_1$-$C_6$ alkyl; wherein the $R^2$ $C_1$-$C_6$ alkyl is optionally substituted with one or more substituents independently selected from the group consisting of $R^4$, $SO_2R^4$, $C(O)R^4$, $N(R^4)_2$, $C(O)N(R^4)_2$, $SO_2NH_2$, and OH.

In one embodiment of Formula (Ia), $R^4$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^4$ $C_1$-$C_6$ alkyl, $C_2$-$C_6$ alkenyl, and $C_2$-$C_6$ alkynyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $OH$, $CN$, $NO_2$, F, Cl, Br and I; wherein each $R^4$ aryl, cycloalkyl, cycloalkenyl, heteroaryl, heterocycloalkyl, and heterocycloalkenyl is optionally substituted with one or more substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $(O)$, $OH$, $CN$, $NO_2$, F, Br and I. In another embodiment of Formula (Ia), $R^4$, at each occurrence, is independently selected from the group consisting of $C_1$-$C_6$ alkyl, aryl, heteroaryl, heterocycloalkyl, and cycloalkyl; wherein each $R^4$ $C_1$-$C_6$ alkyl is optionally substituted with one or more OH; wherein each $R^4$ aryl, cycloalkyl, heteroaryl, and heterocycloalkyl is optionally substituted with one or more substituents independently selected from the group consisting of $R^6$, $SO_2R^6$, $CO(O)R^6$, $NHS(O)_2R^6$, $SO_2NH_2$, $C(O)OH$, OH, CN, and F. In another embodiment of Formula (Ia), $R^4$, at each occurrence, is independently $C_1$-$C_6$ alkyl; wherein each $R^4$ $C_1$-$C_6$ alkyl is optionally substituted with one or more OH. In another embodiment of Formula (Ia), $R^4$, at each occurrence, is independently selected from the group consisting of aryl, heteroaryl, heterocycloalkyl, and cycloalkyl; wherein each $R^4$ aryl, cycloalkyl, heteroaryl, and heterocycloalkyl is optionally substituted with one or more substituents independently selected from the group consisting of $R^6$, $SO_2R^6$, $CO(O)R^6$, $NHS(O)_2R^6$, $SO_2NH_2$, $C(O)OH$, OH, CN, and F.

In one embodiment of Formula (Ia), $R^6$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^6$ $C_1$-$C_6$ alkyl, $C_2$-$C_6$ alkenyl, and $C_2$-$C_6$ alkynyl is optionally substituted with one or more substituents independently selected from the group consisting of halo and $R^{6A}$; and $R^{6A}$, at each occurrence, is independently selected from the group consisting of aryl, heteroaryl, heterocycloalkyl, heterocycloalkenyl, cycloalkyl, and cycloalkenyl; wherein each $R^{6A}$ aryl, heteroaryl, heterocycloalkyl, heterocycloalkenyl, cycloalkyl, and cycloalkenyl is optionally substituted with $C_1$-$C_6$ alkyl. In another embodiment of Formula (Ia), $R^6$, at each occurrence, is independently selected from the group consisting of $C_1$-$C_6$ alkyl, heteroaryl, and heterocycloalkyl; wherein each $R^6$ $C_1$-$C_6$ alkyl is optionally substituted with one or more substituents independently selected from the group consisting of halo and $R^{6A}$; and $R^{6A}$, at each occurrence, is independently heterocycloalkyl; wherein each $R^{6A}$ heterocycloalkyl is optionally substituted with $C_1$-$C_6$ alkyl.

In one embodiment of Formula (Ia), $R^{16}$ is selected from the group consisting of $NH_2$, $NHR^7$, $NHC(O)R^7$, $NHS(O)_2R^7$, $NHC(O)OR^7$, $NHC(O)NH_2$, $NHC(O)NHR^7$, and $NHC(O)N(R^7)_2$. In another embodiment of Formula (Ia), $R^{16}$ is selected from the group consisting of $NH_2$, $NHR^7$, $NHC(O)R^7$, and $NHC(O)OR^7$. In another embodiment of Formula (Ia), $R^{16}$ is selected from the group consisting of $NHR^7$ and $NHC(O)R^7$. In another embodiment of Formula (Ia), $R^{16}$ is $NH_2$. In another embodiment of Formula (Ia), $R^{16}$ is $NHR^7$. In another embodiment of Formula (Ia), $R^{16}$ is $NHC(O)R^7$. In another embodiment of Formula (Ia), $R^{16}$ is $NHC(O)OR^7$.

In one embodiment of Formula (Ia), $R^7$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^7$ $C_1$-$C_6$ alkyl, $C_2$-$C_6$ alkenyl, and $C_2$-$C_6$ alkynyl is optionally substituted with one or more substituents independently selected from the group consisting of $R^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHSO_2NH_2$, $NR^8SO_2NH_2$, $NHSO_2NHR^8$, $NR^8SO_2NHR^8$, $NHSO_2N(R^8)_2$, $NR^8SO_2N$ (R$^8$)$_2$, NHC(O)OR$^8$, NR$^8$C(O)OR$^8$, NHC(O)NH$_2$, NHC(O)NHR$^8$, NHC(O)N(R$^8$)$_2$, NR$^8$C(O)NHR$^8$, NR$^8$C(O)N(R$^8$)$_2$, C(O)NH$_2$, C(O)NHR$^8$, C(O)N(R$^8$)$_2$, C(O)NHOH, C(O)NHOR$^8$, C(O)NHSO$_2$R$^8$, C(O)NR$^8$SO$_2$R$^8$, C(O)NHC(O)NH$_2$, C(O)NR$^8$C(O)NH$_2$, C(O)NHC(O)NHR$^8$, C(O)NR$^8$C(O)NHR$^8$, C(O)NHC(O)N(R$^8$)$_2$, C(O)NR$^8$C(O)N(R$^8$)$_2$, SO$_2$NH$_2$, SO$_2$NHR$^8$, SO$_2$N(R$^8$)$_2$, C(O)H, C(O)OH, OH, CN, NO$_2$, F, Cl, Br and I; wherein each R$^7$ aryl, cycloalkyl, cycloalkenyl, heteroaryl, heterocycloalkyl, and heterocycloalkenyl is optionally substituted with one or more substituents independently selected from the group consisting of R$^9$, OR$^9$, SR$^9$, S(O)R$^9$, SO$_2$R$^9$, C(O)R$^9$, CO(O)R$^9$, OC(O)R$^9$, OC(O)OR$^9$, NH$_2$, NHR$^9$, N(R$^9$)$_2$, NHC(O)R$^9$, NR$^9$C(O)R$^9$, NHS(O)$_2$R$^9$, NR$^9$S(O)$_2$R$^9$, NHC(O)OR$^9$, NR$^9$C(O)OR$^9$, NHC(O)NH$_2$, NHC(O)NHR$^9$, NHC(O)N(R$^9$)$_2$, NR$^9$C(O)NHR$^9$, NR$^9$C(O)N(R$^9$)$_2$, C(O)NH$_2$, C(O)NHR$^9$, C(O)N(R$^9$)$_2$, C(O)NHOH, C(O)NHOR$^9$, C(O)NHSO$_2$R$^9$, C(O)NR$^9$SO$_2$R$^9$, SO$_2$NH$_2$, SO$_2$NHR$^9$, SO$_2$N(R$^9$)$_2$, SO$_2$NHC(O)OH, SO$_2$NR$^9$C(O)OH, SO$_2$NHC(O)OR$^9$, SO$_2$NR$^9$C(O)OR$^9$, C(O)H, C(O)OH, (O), OH, CN, NO$_2$, F, Cl, Br and I. In another embodiment of Formula (Ia), R$^7$, at each occurrence, is independently selected from the group consisting of C$_1$-C$_6$ alkyl, C$_2$-C$_6$ alkenyl, aryl, heteroaryl, heterocycloalkyl, heterocycloalkenyl, and cycloalkyl; wherein each R$^7$ C$_1$-C$_6$ alkyl and C$_2$-C$_6$ alkenyl is optionally substituted with one or more substituents independently selected from the group consisting of R$^8$, SO$_2$R$^8$, NH$_2$, NHR$^8$, N(R$^8$)$_2$, NHS(O)$_2$R$^8$, NHSO$_2$N(R$^8$)$_2$, C(O)NHC(O)NH$_2$, SO$_2$NH$_2$, and OH; wherein each R$^7$ aryl, cycloalkyl, heteroaryl, heterocycloalkenyl, and heterocycloalkyl is optionally substituted with one or more substituents independently selected from the group consisting of R$^9$, SO$_2$R$^9$, C(O)R$^9$, CO(O)R$^9$, NH$_2$, NHR$^9$, NHS(O)$_2$R$^9$, NHC(O)NHR$^9$, C(O)NH$_2$, C(O)NHR$^9$, C(O)N(R$^9$)$_2$, SO$_2$NH$_2$, SO$_2$NHC(O)OR$^9$, C(O)OH, (O), and OH.

In one embodiment of Formula (Ia), R$^8$, at each occurrence, is independently selected from the group consisting of C$_1$-C$_6$ alkyl, C$_2$-C$_6$ alkenyl, C$_2$-C$_6$ alkynyl, aryl, heteroaryl, heterocycloalkyl, heterocycloalkenyl, cycloalkyl, and cycloalkenyl; wherein each R$^8$ C$_1$-C$_6$ alkyl, C$_2$-C$_6$ alkenyl, and C$_2$-C$_6$ alkynyl is optionally substituted with one or more substituents independently selected from the group consisting of NHR$^{10}$, and aryl; wherein each R$^8$ aryl, heteroaryl, heterocycloalkyl, heterocycloalkenyl, cycloalkyl, and cycloalkenyl is optionally substituted with one or more substituents independently selected from the group consisting of R$^{11}$, OR$^{11}$, halo, NH$_2$, OH, and (O). In another embodiment of Formula (Ia), R$^8$, at each occurrence, is independently selected from the group consisting of C$_1$-C$_6$ alkyl, aryl, heteroaryl, heterocycloalkyl, heterocycloalkenyl, and cycloalkyl; wherein each R$^8$ C$_1$-C$_6$ alkyl is optionally substituted with one or more aryl; wherein each R$^8$ aryl, heteroaryl, heterocycloalkyl, and cycloalkyl is optionally substituted with one or more substituents independently selected from the group consisting of R$^{11}$, halo, NH$_2$, and OH.

In one embodiment of Formula (Ia), R$^9$, at each occurrence, is independently selected from the group consisting of C$_1$-C$_6$ alkyl, C$_2$-C$_6$ alkenyl, C$_2$-C$_6$ alkynyl, aryl, heteroaryl, heterocycloalkyl, heterocycloalkenyl, cycloalkyl, and cycloalkenyl; wherein each R$^9$ C$_1$-C$_6$ alkyl, C$_2$-C$_6$ alkenyl, and C$_2$-C$_6$ alkynyl is optionally substituted with one or more substituents independently selected from the group consisting of R$^{13}$, OR$^{13}$, SR$^{13}$, S(O)R$^{13}$, SO$_2$R$^{13}$, C(O)R$^{13}$, CO(O)R$^{13}$, OC(O)R$^{13}$, OC(O)OR$^{13}$, NH$_2$, NHR$^{13}$, N(R$^{13}$)$_2$, NHC(O)R$^{13}$, NR$^{13}$C(O)R$^{13}$, NHS(O)$_2$R$^{13}$, NR$^{13}$S(O)$_2$R$^{13}$, NHC(O)OR$^{13}$, NR$^{13}$C(O)OR$^{13}$, NHC(O)NH$_2$, NHC(O)NHR$^{13}$, NHC(O)N(R$^{13}$)$_2$, NR$^{13}$C(O)NHR$^{13}$, NR$^{13}$C(O)N(R$^{13}$)$_2$, C(O)NH$_2$, C(O)NHR$^{13}$, C(O)N(R$^{13}$)$_2$, C(O)NHOH, C(O)NHOR$^{13}$, C(O)NHSO$_2$R$^{13}$, C(O)NR$^{13}$SO$_2$R$^{13}$, SO$_2$NH$_2$, SO$_2$NHR$^{13}$, SO$_2$N(R$^{13}$)$_2$, C(O)H, C(O)OH, OH, CN, NO$_2$, F, Cl, Br and I; wherein each R$^9$ aryl, cycloalkyl, cycloalkenyl, heteroaryl, heterocycloalkyl, and heterocycloalkenyl is optionally substituted with one or more substituents independently selected from the group consisting of R$^{14}$, OR$^{14}$, SR$^{14}$, S(O)R$^{14}$, SO$_2$R$^{14}$, C(O)R$^{14}$, CO(O)R$^{14}$, OC(O)R$^{14}$, OC(O)OR$^{14}$, NH$_2$, NHR$^{14}$, N(R$^{14}$)$_2$, NHC(O)R$^{14}$, NR$^{14}$C(O)R$^{14}$, NHS(O)$_2$R$^{14}$, NR$^{14}$S(O)$_2$R$^{14}$, NHC(O)OR$^{14}$, NR$^{14}$C(O)OR$^{14}$, NHC(O)NH$_2$, NHC(O)NHR$^{14}$, NHC(O)N(R$^{14}$)$_2$, NR$^{14}$C(O)NHR$^{14}$, NR$^{14}$C(O)N(R$^{14}$)$_2$, C(O)NH$_2$, C(O)NHR$^{14}$, C(O)N(R$^{14}$)$_2$, C(O)NHOH, C(O)NHOR$^{14}$, C(O)NHSO$_2$R$^{14}$, C(O)NR$^{14}$SO$_2$R$^{14}$, SO$_2$NH$_2$, SO$_2$NHR$^{14}$, SO$_2$N(R$^{14}$)$_2$, C(O)H, C(O)OH, (O), OH, CN, NO$_2$, F, Cl, Br and I. In another embodiment of Formula (Ia), R$^9$, at each occurrence, is independently selected from the group consisting of C$_1$-C$_6$ alkyl, aryl, heteroaryl, heterocycloalkyl, and cycloalkyl; wherein each R$^9$ C$_1$-C$_6$ alkyl is optionally substituted with one or more substituents independently selected from the group consisting of R$^{13}$, OR$^{13}$, S(O)R$^{13}$, SO$_2$R$^{13}$, OH, and F; wherein each R$^9$ aryl, heteroaryl, heterocycloalkyl, and cycloalkyl is optionally substituted with one or more substituents independently selected from the group consisting of R$^{14}$, OH, and F.

In one embodiment of Formula (Ia), R$^{11}$, at each occurrence, is independently selected from the group consisting of C$_1$-C$_6$ alkyl, C$_2$-C$_6$ alkenyl, C$_2$-C$_6$ alkynyl, aryl, heteroaryl, heterocycloalkyl, heterocycloalkenyl, cycloalkyl, and cycloalkenyl; wherein each R$^{11}$ C$_1$-C$_6$ alkyl, C$_2$-C$_6$ alkenyl, and C$_2$-C$_6$ alkynyl is optionally substituted with one or more substituents independently selected from the group consisting of NH$_2$, C(O)NH$_2$, SO$_2$NH$_2$, C(O)H, C(O)OH, OH, CN, NO$_2$, F, Cl, Br and I; wherein each R$^{11}$ aryl, cycloalkyl, cycloalkenyl, heteroaryl, heterocycloalkyl, and heterocycloalkenyl is optionally substituted with one or more substituents independently selected from the group consisting of C$_1$-C$_6$ alkyl, O—C$_1$-C$_6$ alkyl, NH$_2$, C(O)NH$_2$, C(O)H, C(O)OH, OH, CN, NO$_2$, F, Cl, Br and I. In another embodiment of Formula (Ia), R$^{11}$, at each occurrence, is independently selected from the group consisting of C$_1$-C$_6$ alkyl and aryl; wherein each R$^{11}$ C$_1$-C$_6$ alkyl is optionally substituted with one or more NH$_2$; wherein each R$^{11}$ aryl is optionally substituted with one or more substituents independently selected from the group consisting of C$_1$-C$_6$ alkyl, and O—C$_1$-C$_6$ alkyl.

In one embodiment of Formula (Ia), R$^{13}$, at each occurrence, is independently selected from the group consisting of C$_1$-C$_6$ alkyl, C$_2$-C$_6$ alkenyl, C$_2$-C$_6$ alkynyl, aryl, heteroaryl, heterocycloalkyl, heterocycloalkenyl, cycloalkyl, and cycloalkenyl; wherein each R$^{13}$ C$_1$-C$_6$ alkyl, C$_2$-C$_6$ alkenyl, and C$_2$-C$_6$ alkynyl is optionally substituted with one or more substituents independently selected from the group consisting of aryl, NH$_2$, C(O)NH$_2$, SO$_2$NH$_2$, C(O)H, C(O)OH, OH, CN, NO$_2$, F, Cl, Br and I; wherein each R$^{13}$ aryl, cycloalkyl, cycloalkenyl, heteroaryl, heterocycloalkyl, and heterocycloalkenyl is optionally substituted with one or more substituents independently selected from the group consisting of C$_1$-C$_6$ alkyl, O—C$_1$-C$_6$ alkyl, C$_1$-C$_6$ alkyl-O—C$_1$-C$_6$ alkyl, NH$_2$, C(O)NH$_2$, C(O)H, C(O)OH, OH, CN, NO$_2$, F, Cl, Br and I. In another embodiment of Formula (Ia), R$^{13}$, at each occurrence, is independently selected from the group consisting of C$_1$-C$_6$ alkyl, aryl, heteroaryl, heterocycloalkyl, and cycloalkyl; wherein each R$^{13}$ C$_1$-C$_6$ alkyl is optionally substituted with one or more substituents independently aryl; wherein each R$^{13}$ aryl, cycloalkyl, heteroaryl, and heterocycloalkyl is optionally substituted with one or more substituents independently selected from the group consisting of $C_1$-$C_6$ alkyl and O—$C_1$-$C_6$ alkyl, and $C_1$-$C_6$ alkyl-O—$C_1$-$C_6$ alkyl.

In one embodiment of Formula (Ia), $R^{14}$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^{14}$ $C_1$-$C_6$ alkyl, $C_2$-$C_6$ alkenyl, and $C_2$-$C_6$ alkynyl is optionally substituted with one or more substituents independently selected from the group consisting of aryl, $NH_2$, $C(O)NH_2$, $SO_2NH_2$, $C(O)H$, $C(O)OH$, OH, CN, $NO_2$, F, Cl, Br and I; wherein each $R^{14}$ aryl, cycloalkyl, cycloalkenyl, heteroaryl, heterocycloalkyl, and heterocycloalkenyl is optionally substituted with one or more substituents independently selected from the group consisting of $C_1$-$C_6$ alkyl, O—$C_1$-$C_6$ alkyl, $C_1$-$C_6$ alkyl-O—$C_1$-$C_6$ alkyl, $NH_2$, $C(O)NH_2$, $C(O)H$, $C(O)OH$, OH, $NO_2$, F, Cl, Br and I. In another embodiment of Formula (Ia), $R^{14}$, at each occurrence, is $C_1$-$C_6$ alkyl; wherein each $R^{14}$ $C_1$-$C_6$ alkyl is optionally substituted with one or more OH.

In another embodiment of Formula (Ia), $R^{12}$ is halo or H;

J is N or CH;

Q is N or $CR^1$;

Z is N or $CR^1$;

wherein the bond between X and Y may be a single or a double bond; and if a double bond is present, then Y is $CR^3$ and X is CH, Y is CH and X is CH, Y is N and X is CH, Y is N and X is $CR^3$, Y is N and X is N, or Y is CH and X is N; and if a single bond is present, then Y is $CH_2$ and X is $CH_2$ or C(O), or Y is NH and X is C(O);

$R^3$ is selected from the group consisting of $R^{3A}$, $C(O)R^{3A}$, and CN;

$R^{3A}$ is selected from the group consisting of $C_1$-$C_6$ alkyl and aryl; wherein the $R^{3A}$ $C_1$-$C_6$ alkyl, is optionally substituted with one or more substituents independently selected from the group consisting of $R^{3B}$, $OR^{3B}$, and halo; wherein the $R^{3A}$ aryl is optionally substituted with one or more halo;

$R^{3B}$ is selected from the group consisting of $C_1$-$C_6$ alkyl and aryl, wherein the $R^{3B}$ aryl is optionally substituted with one or more F;

$R^1$ is selected from the group consisting of H, Cl, F, and $OR^{14}$;

$R^{14}$ is $C_1$-$C_6$ alkyl;

$R^2$ is selected from the group consisting of H and $C_1$-$C_6$ alkyl; wherein the $R^2$ $C_1$-$C_6$ alkyl is optionally substituted with one or more substituents independently selected from the group consisting of $R^4$, $SO_2R^4$, $C(O)R^4$, $N(R^4)_2$, $C(O)N(R^4)_2$, $SO_2NH_2$, and OH;

$R^4$, at each occurrence, is independently selected from the group consisting of $C_1$-$C_6$ alkyl, aryl, heteroaryl, heterocycloalkyl, and cycloalkyl; wherein each $R^4$ $C_1$-$C_6$ alkyl is optionally substituted with one or more OH; wherein each $R^4$ aryl, cycloalkyl, heteroaryl, and heterocycloalkyl is optionally substituted with one or more substituents independently selected from the group consisting of $R^6$, $SO_2R^6$, $CO(O)R^6$, $NHS(O)_2R^6$, $SO_2NH_2$, $C(O)OH$, OH, CN, and F;

$R^6$, at each occurrence, is independently selected from the group consisting of $C_1$-$C_6$ alkyl, heteroaryl, and heterocycloalkyl; wherein each $R^6$ $C_1$-$C_6$ alkyl is optionally substituted with one or more substituents independently selected from the group consisting of halo and $R^{6A}$;

$R^{6A}$, at each occurrence, is independently heterocycloalkyl; wherein each $R^{6A}$ heterocycloalkyl is optionally substituted with $C_1$-$C_6$ alkyl;

$R^{16}$ is selected from the group consisting of $NH_2$, $NHR^7$, $NHC(O)R^7$, and $NHC(O)OR^7$;

$R^7$, at each occurrence, is independently selected from the group consisting of $C_1$-$C_6$ alkyl, $C_2$-$C_6$ alkenyl, aryl, heteroaryl, heterocycloalkyl, heterocycloalkenyl, and cycloalkyl; wherein each $R^7 C_1$-$C_6$ alkyl, and $C_2$-$C_6$ alkenyl is optionally substituted with one or more substituents independently selected from the group consisting of $R^8$, $SO_2R^8$, $NH_2$, $NHR^8$, $N(R^8)_2$, $NHS(O)_2R^8$, $NHSO_2N(R^8)_2$, $C(O)NHC(O)NH_2$, $SO_2NH_2$, and OH; wherein each $R^7$ aryl, cycloalkyl, heteroaryl, and heterocycloalkyl is optionally substituted with one or more substituents independently selected from the group consisting of $R^9$, $SO_2R^9$, $C(O)R^9$, $CO(O)R^9$, $NH_2$, $NHR^9$, $NHS(O)_2R^9$, $NHC(O)NHR^9$, $C(O)NH_2$, $C(O)NHR^9$, $C(O)N(R^9)_2$, $SO_2NH_2$, $SO_2NHC(O)OR^9$, $C(O)OH$, (O), and OH;

$R^8$, at each occurrence, is independently selected from the group consisting of $C_1$-$C_6$ alkyl, aryl, heteroaryl, heterocycloalkyl, heterocycloalkenyl, and cycloalkyl; wherein each $R^8$ $C_1$-$C_6$ alkyl is optionally substituted with one or more aryl; wherein each $R^8$ aryl, heteroaryl, heterocycloalkyl, heterocycloalkenyl, and cycloalkyl is optionally substituted with one or more substituents independently selected from the group consisting of $R^{11}$, halo, $NH_2$, and OH;

$R^9$, at each occurrence, is independently selected from the group consisting of $C_1$-$C_6$ alkyl, aryl, heteroaryl, heterocycloalkyl, and cycloalkyl; wherein each $R^9$ $C_1$-$C_6$ alkyl is optionally substituted with one or more substituents independently selected from the group consisting of $R^{13}$, $OR^{13}$, $S(O)R^{13}$, $SO_2R^{13}$, OH, and F; wherein each $R^9$ aryl, heteroaryl, heterocycloalkyl, and cycloalkyl is optionally substituted with one or more substituents independently selected from the group consisting of $R^{14}$, OH, and F;

$R^{11}$, at each occurrence, is independently selected from the group consisting of $C_1$-$C_6$ alkyl and aryl; wherein each $R^{11}$ $C_1$-$C_6$ alkyl is optionally substituted with one or more $NH_2$; wherein each $R^{11}$ aryl is optionally substituted with one or more substituents independently selected from the group consisting of $C_1$-$C_6$ alkyl, and O—$C_1$-$C_6$ alkyl;

$R^{13}$, at each occurrence, is independently selected from the group consisting of $C_1$-$C_6$ alkyl, aryl, heteroaryl, heterocycloalkyl, and cycloalkyl; wherein each $R^{13}$ $C_1$-$C_6$ alkyl is optionally substituted with one or more aryl; wherein each $R^{13}$ aryl, heteroaryl, heterocycloalkyl, and cycloalkyl is optionally substituted with one or more substituents independently selected from the group consisting of $C_1$-$C_6$ alkyl, O—$C_1$-$C_6$ alkyl, and $C_1$-$C_6$ alkyl-O—$C_1$-$C_6$ alkyl; and $R^{14}$, at each occurrence, is independently $C_1$-$C_6$ alkyl; wherein each $R^{14}$ $C_1$-$C_6$ alkyl is optionally substituted with one or more OH.

Still another embodiment pertains to compounds of Formula (Ia), selected from the group consisting of (3R)—N-{5-chloro-4-[1-(3-fluorobenzyl)-2,3-dihydro-1H-indol-6-yl]pyridin-2-yl}piperidine-3-carboxamide;

(3R)—N-[5-chloro-4-(2,3-dihydro-1H-indol-6-yl)pyridin-2-yl]piperidine-3-carboxamide;

(3R)—N-[5-chloro-4-(1-methyl-1H-benzimidazol-6-yl) pyridin-2-yl]piperidine-3-carboxamide;

(3R)—N-{5-chloro-4-[1-(tetrahydro-2H-pyran-4-ylmethyl)-2,3-dihydro-1H-indol-6-yl]pyridin-2-yl}piperidine-3-carboxamide;

(3R)—N-{5-chloro-4-[1-(3-fluorobenzyl)-1H-benzimidazol-5-yl]pyridin-2-yl}piperidine-3-carboxamide;

(3R)—N-{5-chloro-4-[1-(3-fluorobenzyl)-1H-benzimidazol-6-yl]pyridin-2-yl}piperidine-3-carboxamide;

(3R)—N-{5-chloro-4-[1-(3-fluorobenzyl)-1H-indol-6-yl] pyridin-2-yl}piperidine-3-carboxamide;

trans-N-{5-chloro-4-[1-(3-fluorobenzyl)-1H-benzimidazol-6-yl]pyridin-2-yl}cyclohexane-1,4-diamine;
trans-N-{5-chloro-4-[1-(3-fluorobenzyl)-2,3-dihydro-1H-indol-6-yl]pyridin-2-yl}cyclohexane-1,4-diamine;
trans-4-({5-chloro-4-[1-(3-fluorobenzyl)-2,3-dihydro-1H-indol-6-yl]pyridin-2-yl}amino)cyclohexanol;
trans-4-({5-chloro-4-[1-(3-fluorobenzyl)-1H-benzimidazol-6-yl]pyridin-2-yl}amino)cyclohexanol;
trans-N-[5-chloro-4-(1-methyl-1H-benzimidazol-6-yl)pyridin-2-yl]cyclohexane-1,4-diamine;
(3R)—N-{5-chloro-4-[1-(tetrahydro-2H-pyran-4-ylmethyl)-1H-benzimidazol-6-yl]pyridin-2-yl}piperidine-3-carboxamide;
(3R)—N-(5-chloro-4-{1-[2-(morpholin-4-yl)ethyl]-1H-benzimidazol-6-yl}pyridin-2-yl)piperidine-3-carboxamide;
(3R)—N-{5-chloro-4-[1-(3-hydroxy-3-methylbutyl)-1H-benzimidazol-6-yl]pyridin-2-yl}piperidine-3-carboxamide;
(3R)—N-{5-chloro-4-[1-(4-fluorobenzyl)-1H-benzimidazol-6-yl]pyridin-2-yl}piperidine-3-carboxamide;
(3R)—N-{5-chloro-4-[1-(3,4-difluorobenzyl)-1H-benzimidazol-6-yl]pyridin-2-yl}piperidine-3-carboxamide;
(3R)—N-(5-chloro-4-{1-[2-(3-fluorophenyl)ethyl]-1H-benzimidazol-6-yl}pyridin-2-yl)piperidine-3-carboxamide;
(3R)—N-{5-chloro-4-[1-(2-sulfamoylethyl)-1H-benzimidazol-6-yl]pyridin-2-yl}piperidine-3-carboxamide;
(3R)—N-(5-chloro-4-{1-[(1,1-dioxidotetrahydrothiophen-3-yl)methyl]-1H-benzimidazol-6-yl}pyridin-2-yl)piperidine-3-carboxamide;
(3R)—N-{5-chloro-4-[1-(2-fluorobenzyl)-1H-benzimidazol-6-yl]pyridin-2-yl}piperidine-3-carboxamide;
(3R)—N-{5-chloro-4-[1-(pyridin-3-ylmethyl)-1H-benzimidazol-6-yl]pyridin-2-yl}piperidine-3-carboxamide;
(3R)—N-(5-chloro-4-{1-[(1,1-dioxidotetrahydro-2H-thiopyran-4-yl)methyl]-1H-benzimidazol-6-yl}pyridin-2-yl)piperidine-3-carboxamide;
(3R)—N-(5-chloro-4-{1-[(5-methyl-4H-1,2,4-triazol-3-yl)methyl]-1H-benzimidazol-6-yl}pyridin-2-yl)piperidine-3-carboxamide;
(3R)—N-{5-chloro-4-[1-(1,3-thiazol-4-ylmethyl)-1H-benzimidazol-5-yl]pyridin-2-yl}piperidine-3-carboxamide-(3R)—N-{5-chloro-4-[1-(1,3-thiazol-4-ylmethyl)-1H-benzimidazol-6-yl]pyridin-2-yl}piperidine-3-carboxamide (1:1);
5-chloro-N-cyclopentyl-4-[1-(3-fluorobenzyl)-1H-benzimidazol-6-yl]pyridin-2-amine;
1-[trans-4-({5-chloro-4-[1-(3-fluorobenzyl)-1H-benzimidazol-6-yl]pyridin-2-yl}amino)cyclohexyl]-3-methylurea;
N-[trans-4-({5-chloro-4-[1-(3-fluorobenzyl)-1H-benzimidazol-6-yl]pyridin-2-yl}amino)cyclohexyl]methanesulfonamide;
(3R)—N-[4-(1-benzyl-3-cyano-1H-indol-6-yl)-5-chloropyridin-2-yl]piperidine-3-carboxamide;
N'-{5-chloro-4-[1-(3-fluorobenzyl)-1H-benzimidazol-6-yl]pyridin-2-yl}-N-methyl-N-(pyridin-2-yl)propane-1,3-diamine;
1-({5-chloro-4-[1-(3-fluorobenzyl)-1H-benzimidazol-6-yl]pyridin-2-yl}amino)-3-(dimethylamino)propan-2-ol;
5-chloro-4-[1-(3-fluorobenzyl)-1H-benzimidazol-6-yl]-N-[(5-methyl-4H-1,2,4-triazol-3-yl)methyl]pyridin-2-amine;
(3R)—N-{5-chloro-4-[1-(3-fluorobenzyl)-1H-pyrrolo[3,2-b]pyridin-6-yl]pyridin-2-yl}piperidine-3-carboxamide;
N-{5-chloro-4-[1-(3-fluorobenzyl)-1H-benzimidazol-6-yl]pyridin-2-yl}-N'-(pyridin-3-yl)ethane-1,2-diamine;
N-[(5-amino-4H-1,2,4-triazol-3-yl)methyl]-5-chloro-4-[1-(3-fluorobenzyl)-1H-benzimidazol-6-yl]pyridin-2-amine;
N-benzyl-N'-{5-chloro-4-[1-(3-fluorobenzyl)-1H-benzimidazol-6-yl]pyridin-2-yl}-N-methylpropane-1,3-diamine;
5-chloro-4-[1-(3-fluorobenzyl)-1H-benzimidazol-6-yl]-N-(pyrimidin-2-ylmethyl)pyridin-2-amine;
5-chloro-4-[1-(3-fluorobenzyl)-1H-benzimidazol-6-yl]-N-[1-(pyridin-4-yl)propan-2-yl]pyridin-2-amine;
5-chloro-4-[1-(3-fluorobenzyl)-1H-benzimidazol-6-yl]-N-[1-(1-methyl-1H-pyrazol-4-yl)piperidin-3-yl]pyridin-2-amine;
5-[({5-chloro-4-[1-(3-fluorobenzyl)-1H-benzimidazol-6-yl]pyridin-2-yl}amino)methyl]pyrimidin-2-amine;
5-chloro-N-[2-(1-ethylpiperidin-4-yl)ethyl]-4-[1-(3-fluorobenzyl)-1H-benzimidazol-6-yl]pyridin-2-amine;
5-chloro-4-[1-(3-fluorobenzyl)-1H-benzimidazol-6-yl]-N-[2-(5-methyl-4H-1,2,4-triazol-3-yl)ethyl]pyridin-2-amine;
N-{5-chloro-4-[1-(3-fluorobenzyl)-1H-benzimidazol-6-yl]pyridin-2-yl}-N'-(pyridin-4-yl)ethane-1,2-diamine;
5-chloro-4-[1-(3-fluorobenzyl)-1H-benzimidazol-6-yl]-N-[2-(1-methylpiperidin-4-yl)ethyl]pyridin-2-amine;
5-chloro-4-[1-(3-fluorobenzyl)-1H-benzimidazol-6-yl]-N-[2-(pyridin-4-yl)propyl]pyridin-2-amine;
$N^1$-{5-chloro-4-[1-(3-fluorobenzyl)-1H-benzimidazol-6-yl]pyridin-2-yl}-$N^2,N^2$,2-trimethylpropane-1,2-diamine;
N-{5-chloro-4-[1-(3-fluorobenzyl)-1H-benzimidazol-6-yl]pyridin-2-yl}-N'-phenylpropane-1,3-diamine;
$N^3$-{5-chloro-4-[1-(3-fluorobenzyl)-1H-benzimidazol-6-yl]pyridin-2-yl}butane-1,3-diamine;
5-chloro-4-[1-(3-fluorobenzyl)-1H-benzimidazol-6-yl]pyridin-2-amine;
5-chloro-4-[1-(3-fluorobenzyl)-1H-benzimidazol-6-yl]-N-(1H-imidazol-4-ylmethyl)pyridin-2-amine;
5-chloro-4-[1-(3-fluorobenzyl)-1H-benzimidazol-6-yl]-N-(pyrazin-2-ylmethyl)pyridin-2-amine;
5-chloro-4-[1-(3-fluorobenzyl)-1H-benzimidazol-6-yl]-N-[1-(pyrazin-2-yl)propan-2-yl]pyridin-2-amine;
5-chloro-4-[1-(3-fluorobenzyl)-1H-benzimidazol-6-yl]-N-(1-methylpyrrolidin-3-yl)pyridin-2-amine;
5-chloro-4-[1-(3-fluorobenzyl)-1H-benzimidazol-6-yl]-N-[2-(pyridin-3-yl)ethyl]pyridin-2-amine;
N'-{5-chloro-4-[1-(3-fluorobenzyl)-1H-benzimidazol-6-yl]pyridin-2-yl}-N,N-dimethylbutane-1,4-diamine;
5-chloro-4-[1-(3-fluorobenzyl)-1H-benzimidazol-6-yl]-N-[(1-methylpiperidin-4-yl)methyl]pyridin-2-amine;
N-benzyl-N'-{5-chloro-4-[1-(3-fluorobenzyl)-1H-benzimidazol-6-yl]pyridin-2-yl}-N-methylethane-1,2-diamine;
5-chloro-4-[1-(3-fluorobenzyl)-1H-benzimidazol-6-yl]-N-[2-(pyridin-2-yl)ethyl]pyridin-2-amine;
4-({5-chloro-4-[1-(3-fluorobenzyl)-1H-benzimidazol-6-yl]pyridin-2-yl}amino)-2-methylbutan-2-ol;
N'-{5-chloro-4-[1-(3-fluorobenzyl)-1H-benzimidazol-6-yl]pyridin-2-yl}-N-methyl-N-phenylpropane-1,3-diamine;
5-chloro-4-[1-(3-fluorobenzyl)-1H-benzimidazol-6-yl]-N-(1-methylpiperidin-4-yl)pyridin-2-amine;
5-chloro-4-[1-(3-fluorobenzyl)-1H-benzimidazol-6-yl]-N-[2-(pyridin-4-yl)ethyl]pyridin-2-amine;
5-chloro-4-[1-(3-fluorobenzyl)-1H-benzimidazol-6-yl]-N-(pyrimidin-5-ylmethyl)pyridin-2-amine;
$N^2$-{5-chloro-4-[1-(3-fluorobenzyl)-1H-benzimidazol-6-yl]pyridin-2-yl}-2-methylpropane-1,2-diamine;
5-chloro-N-(2-cyclohexylethyl)-4-[1-(3-fluorobenzyl)-1H-benzimidazol-6-yl]pyridin-2-amine;
N-{5-chloro-4-[1-(3-fluorobenzyl)-1H-benzimidazol-6-yl]pyridin-2-yl}-N'-phenylethane-1,2-diamine;

N'-{5-chloro-4-[1-(3-fluorobenzyl)-1H-benzimidazol-6-yl]
  pyridin-2-yl}-N,N,2,2-tetramethylpropane-1,3-diamine;
2-({5-chloro-4-[1-(3-fluorobenzyl)-1H-benzimidazol-6-yl]
  pyridin-2-yl}amino)ethanol;
N-benzyl-5-chloro-4-[1-(3-fluorobenzyl)-1H-benzimidazol-
  6-yl]pyridin-2-amine;
N'-{5-chloro-4-[1-(3-fluorobenzyl)-1H-benzimidazol-6-yl]
  pyridin-2-yl}-N,N-dimethylpropane-1,3-diamine;
3-({5-chloro-4-[1-(3-fluorobenzyl)-1H-benzimidazol-6-yl]
  pyridin-2-yl}amino)propan-1-ol;
N-{5-chloro-4-[1-(3-fluorobenzyl)-1H-benzimidazol-6-yl]
  pyridin-2-yl}propane-1,3-diamine;
4-[({5-chloro-4-[1-(3-fluorobenzyl)-1H-benzimidazol-6-yl]
  pyridin-2-yl}amino)methyl]phenol;
N-{5-chloro-4-[1-(3-fluorobenzyl)-1H-benzimidazol-6-yl]
  pyridin-2-yl}butane-1,4-diamine;
N-[2-(4-aminophenyl)ethyl]-5-chloro-4-[1-(3-fluoroben-
  zyl)-1H-benzimidazol-6-yl]pyridin-2-amine;
N-{5-chloro-4-[1-(3-fluorobenzyl)-1H-benzimidazol-6-yl]
  pyridin-2-yl}-2,2-dimethylpropane-1,3-diamine;
N-{5-chloro-4-[1-(3-fluorobenzyl)-1H-benzimidazol-6-yl]
  pyridin-2-yl}ethane-1,2-diamine;
N-[4-(aminomethyl)benzyl]-5-chloro-4-[1-(3-fluoroben-
  zyl)-1H-benzimidazol-6-yl]pyridin-2-amine;
1-({5-chloro-4-[1-(3-fluorobenzyl)-1H-benzimidazol-6-yl]
  pyridin-2-yl}amino)-2-methylpropan-2-ol;
1-amino-3-{5-chloro-4-[1-(3-fluorobenzyl)-1H-benzimida-
  zol-6-yl]pyridin-2-yl}amino)propan-2-ol;
N-{5-chloro-4-[1-(3-fluorobenzyl)-1H-benzimidazol-6-yl]
  pyridin-2-yl}-N'-(pyridin-2-yl)ethane-1,2-diamine;
(3R)—N-{5-chloro-4-[1-(3-fluorobenzyl)-1H-benzimida-
  zol-6-yl]pyridin-2-yl}-1-azabicyclo[2.2.2]octan-3-amine;
(3S)—N-{5-chloro-4-[1-(3-fluorobenzyl)-1H-benzimida-
  zol-6-yl]pyridin-2-yl}-1-azabicyclo[2.2.2]octan-3-amine;
2-benzyl-N-{5-chloro-4-[1-(3-fluorobenzyl)-1H-benzimi-
  dazol-6-yl]pyridin-2-yl}octahydro-1H-isoindol-4-amine;
2-benzyl-N-{5-chloro-4-[1-(3-fluorobenzyl)-1H-benzimi-
  dazol-6-yl]pyridin-2-yl}octahydrocyclopenta[c]pyrrol-4-
  amine;
N-{5-chloro-4-[1-(3-fluorobenzyl)-1H-benzimidazol-6-yl]
  pyridin-2-yl}-9-(cyclopropylmethyl)-9-azabicyclo[3.3.1]
  nonan-3-amine;
benzyl 4-({5-chloro-4-[1-(3-fluorobenzyl)-1H-benzimida-
  zol-6-yl]pyridin-2-yl}amino)-4-(4-fluorophenyl)piperi-
  dine-1-carboxylate;
tert-butyl {5-chloro-4-[1-(3-fluorobenzyl)-1H-benzimida-
  zol-6-yl]pyridin-2-yl}carbamate;
(3R)—N-(5-chloro-4-{1-[(5-methyl-1,3,4-thiadiazol-2-yl)
  methyl]-1H-benzimidazol-6-yl}pyridin-2-yl)piperidine-
  3-carboxamide;
(3R)—N-(5-chloro-4-{1-[2-(pyridin-3-yl)ethyl]-1H-benz-
  imidazol-6-yl}pyridin-2-yl)piperidine-3-carboxamide;
N-{5-chloro-4-[1-(3-fluorobenzyl)-1H-benzimidazol-6-yl]
  pyridin-2-yl}-N'-methylpropane-1,3-diamine;
N-[(trans-4-aminocyclohexyl)methyl]-5-chloro-4-[1-(3-
  fluorobenzyl)-1H-benzimidazol-6-yl]pyridin-2-amine;
N-{5-chloro-4-[1-(3-fluorobenzyl)-1H-benzimidazol-6-yl]
  pyridin-2-yl}-N'-methylbutane-1,4-diamine;
N-benzyl-N'-{5-chloro-4-[1-(3-fluorobenzyl)-1H-benzimi-
  dazol-6-yl]pyridin-2-yl}ethane-1,2-diamine;
5-chloro-4-[1-(3-fluorobenzyl)-1H-benzimidazol-6-yl]-N-
  [2-(piperidin-4-yl)ethyl]pyridin-2-amine;
5-chloro-4-[1-(3-fluorobenzyl)-1H-benzimidazol-6-yl]-N-
  [2-(piperidin-3-yl)ethyl]pyridin-2-amine;
N²-{5-chloro-4-[1-(3-fluorobenzyl)-1H-benzimidazol-6-yl]
  pyridin-2-yl}-1-phenylethane-1,2-diamine;
5-chloro-4-[1-(3-fluorobenzyl)-1H-benzimidazol-6-yl]-N-
  (piperidin-3-yl)pyridin-2-amine;
N-[(2R)-azetidin-2-ylmethyl]-5-chloro-4-[1-(3-fluoroben-
  zyl)-1H-benzimidazol-6-yl]pyridin-2-amine;
N-[2-(azetidin-2-yl)ethyl]-5-chloro-4-[1-(3-fluorobenzyl)-
  1H-benzimidazol-6-yl]pyridin-2-amine;
(4aS,8R,8aS)—N-{5-chloro-4-[1-(3-fluorobenzyl)-1H-ben-
  zimidazol-6-yl]pyridin-2-yl}decahydroisoquinolin-8-
  amine;
5-chloro-4-[1-(3-fluorobenzyl)-1H-benzimidazol-6-yl]-N-
  [2-(pyrrolidin-2-yl)ethyl]pyridin-2-amine;
N-{5-chloro-4-[1-(3-fluorobenzyl)-1H-benzimidazol-6-yl]
  pyridin-2-yl}-6-azaspiro[3.5]nonan-2-amine;
N-{5-chloro-4-[1-(3-fluorobenzyl)-1H-benzimidazol-6-yl]
  pyridin-2-yl}-7-azaspiro[3.5]nonan-2-amine;
N-{5-chloro-4-[1-(3-fluorobenzyl)-1H-benzimidazol-6-yl]
  pyridin-2-yl}-7-azaspiro[3.5]nonan-1-amine;
5-chloro-4-[1-(3-fluorobenzyl)-1H-benzimidazol-6-yl]-
  N-{[(2R,4S)-4-fluoropyrrolidin-2-yl]methyl}pyridin-2-
  amine;
5-chloro-4-[1-(3-fluorobenzyl)-1H-benzimidazol-6-yl]-N-
  [(4-fluoropyrrolidin-3-yl)methyl]pyridin-2-amine;
N-{5-chloro-4-[1-(3-fluorobenzyl)-1H-benzimidazol-6-yl]
  pyridin-2-yl}-6-azaspiro[3.4]octan-2-amine;
(3R)—N-{5-chloro-4-[1-(3-fluorobenzyl)-1H-benzotriazol-
  6-yl]pyridin-2-yl}piperidine-3-carboxamide;
(3R)—N-(5-chloro-4-{1-[2-(methylsulfonyl)ethyl]-1H-ben-
  zimidazol-6-yl}pyridin-2-yl)piperidine-3-carboxamide;
(3R)—N-(5-chloro-4-{1-[2-(methylsulfonyl)ethyl]-1H-ben-
  zotriazol-6-yl}pyridin-2-yl)piperidine-3-carboxamide;
(3R)—N-{5-chloro-4-[1-(4-fluorobenzyl)-1H-benzotriazol-
  6-yl]pyridin-2-yl}piperidine-3-carboxamide;
(3R)—N-{5-chloro-4-[1-(3,4-difluorobenzyl)-1H-benzotri-
  azol-6-yl]pyridin-2-yl}piperidine-3-carboxamide;
(3R)—N-(5-chloro-4-{1-[2-(3-fluorophenyl)ethyl]-1H-ben-
  zotriazol-6-yl}pyridin-2-yl)piperidine-3-carboxamide;
(3R)—N-{5-chloro-4-[1-(2-sulfamoylethyl)-1H-benzotri-
  azol-6-yl]pyridin-2-yl}piperidine-3-carboxamide;
5-chloro-4-[1-(3-fluorobenzyl)-1H-benzimidazol-6-yl]-N-
  {2-[4-(4-methylphenyl)piperidin-4-yl]ethyl}pyridin-2-
  amine;
5-chloro-4-[1-(3-fluorobenzyl)-1H-benzimidazol-6-yl]-N-
  {2-[4-(4-methoxyphenyl)piperidin-4-yl]ethyl}pyridin-2-
  amine;
5-chloro-4-[1-(3-fluorobenzyl)-1H-benzimidazol-6-yl]-N-
  [(4-fluoropiperidin-4-yl)methyl]pyridin-2-amine;
5-chloro-4-[1-(3-fluorobenzyl)-1H-benzimidazol-6-yl]-N-
  {2-[3-(4-methoxyphenyl)pyrrolidin-3-yl]ethyl}pyridin-
  2-amine;
N-{5-chloro-4-[1-(3-fluorobenzyl)-1H-benzimidazol-6-yl]
  pyridin-2-yl}-6-azaspiro[3.4]octan-1-amine;
(1S,4R)—N-{5-chloro-4-[1-(3-fluorobenzyl)-1H-benzimi-
  dazol-6-yl]pyridin-2-yl}-6-azaspiro[3.5]nonan-1-amine;
N-{5-chloro-4-[1-(3-fluorobenzyl)-1H-benzimidazol-6-yl]
  pyridin-2-yl}-5-thia-2-azaspiro[3.4]octan-8-amine 5,5-
  dioxide;
N-{5-chloro-4-[1-(3-fluorobenzyl)-1H-benzimidazol-6-yl]
  pyridin-2-yl}-9-azabicyclo[3.3.1]nonan-3-amine;
(3S)—N-{5-chloro-4-[1-(3-fluorobenzyl)-1H-benzimida-
  zol-6-yl]pyridin-2-yl}azepan-3-amine;
(3R)—N-{5-chloro-4-[1-(3-fluorobenzyl)-1H-benzimida-
  zol-6-yl]pyridin-2-yl}azepan-3-amine;
(1R,4R)—N-{5-chloro-4-[1-(3-fluorobenzyl)-1H-benzimi-
  dazol-6-yl]pyridin-2-yl}-6-azaspiro[3.5]nonan-1-amine;
N-{[3-(aminomethyl)cyclohexyl]methyl}-5-chloro-4-[1-(3-
  fluorobenzyl)-1H-benzimidazol-6-yl]pyridin-2-amine;

N-{5-chloro-4-[1-(3-fluorobenzyl)-1H-benzimidazol-6-yl]pyridin-2-yl}-2-(piperidin-4-yl)acetamide;

4-({5-chloro-4-[1-(3-fluorobenzyl)-1H-benzimidazol-6-yl]pyridin-2-yl}amino)benzenesulfonamide;

(3R)—N-(5-chloro-4-{1-[(5-fluoropyridin-3-yl)methyl]-1H-benzimidazol-6-yl}pyridin-2-yl)piperidine-3-carboxamide;

(3R)—N-(5-chloro-4-{1-[(4-cyanotetrahydro-2H-pyran-4-yl)methyl]-1H-benzimidazol-6-yl}pyridin-2-yl)piperidine-3-carboxamide;

(3R)—N-{5-chloro-4-[1-(3-fluorobenzyl)-1H-pyrrolo[3,2-c]pyridin-6-yl]pyridin-2-yl}piperidine-3-carboxamide;

(3R)—N-{5-chloro-4-[1-(3-fluorobenzyl)-1H-pyrrolo[2,3-b]pyridin-6-yl]pyridin-2-yl}piperidine-3-carboxamide;

(3R)—N-{5-chloro-4-[5-fluoro-1-(3-fluorobenzyl)-1H-benzimidazol-6-yl]pyridin-2-yl}piperidine-3-carboxamide;

(3R)—N-{5-chloro-4-[1-(3-fluorobenzyl)-1H-indazol-6-yl]pyridin-2-yl}piperidine-3-carboxamide;

(3R)—N-[4-(1-{2-bis(2-hydroxyethyl)amino]ethyl}-1H-benzotriazol-6-yl)-5-chloropyridin-2-yl]piperidine-3-carboxamide;

(3R)—N-[5-chloro-4-(2-oxo-2,3-dihydro-1H-indol-6-yl)pyridin-2-yl]piperidine-3-carboxamide;

(3R)—N-(5-chloro-4-{1-[3-(dimethylamino)propyl]-1H-benzimidazol-6-yl}pyridin-2-yl)piperidine-3-carboxamide;

(3R)—N-(5-chloro-4-{1-[3-(dimethylamino)propyl]-1H-benzotriazol-6-yl}pyridin-2-yl)piperidine-3-carboxamide;

(3R)—N-(5-chloro-4-{1-[2-(morpholin-4-yl)ethyl]-1H-benzotriazol-6-yl}pyridin-2-yl)piperidine-3-carboxamide;

(3R)—N-{5-chloro-4-[1-(3-fluorobenzyl)-2-methyl-1H-benzimidazol-6-yl]pyridin-2-yl}piperidine-3-carboxamide;

(3R)—N-{5-chloro-4-[3-(tetrahydro-2H-pyran-4-ylmethyl)-3H-imidazo[4,5-b]pyridin-5-yl]pyridin-2-yl}piperidine-3-carboxamide;

(3R)—N-(5-chloro-4-{1-[(1R)-1-(3-fluorophenyl)ethyl]-1H-benzimidazol-6-yl}pyridin-2-yl)piperidine-3-carboxamide;

(3R)—N-(5-chloro-4-{1-[(1R)-1-(3-fluorophenyl)ethyl]-1H-benzotriazol-6-yl}pyridin-2-yl)piperidine-3-carboxamide;

(3R)—N-{5-chloro-4-[3-(3-fluorobenzyl)-2-oxo-2,3-dihydro-1H-benzimidazol-5-yl]pyridin-2-yl}piperidine-3-carboxamide;

(3R)—N-{5-chloro-4-[5-chloro-1-(tetrahydro-2H-pyran-4-ylmethyl)-1H-benzimidazol-6-yl]pyridin-2-yl}piperidine-3-carboxamide;

N-(5-chloro-4-{1-[(5-methylpyrazin-2-yl)methyl]-2,3-dihydro-1H-indol-6-yl}pyridin-2-yl)piperidine-3-carboxamide;

N-[5-chloro-4-(1-{4-[(methylsulfonyl)amino]benzyl}-2,3-dihydro-1H-indol-6-yl)pyridin-2-yl]piperidine-3-carboxamide;

N-(5-chloro-4-{1-[4-fluoro-3-(methylsulfonyl)benzyl]-2,3-dihydro-1H-indol-6-yl}pyridin-2-yl)piperidine-3-carboxamide;

N-(5-chloro-4-{1-[(2-methylpyrimidin-5-yl)methyl]-2,3-dihydro-1H-indol-6-yl}pyridin-2-yl)piperidine-3-carboxamide;

N-(5-chloro-4-{1-[3-(methylsulfonyl)benzyl]-2,3-dihydro-1H-indol-6-yl}pyridin-2-yl)piperidine-3-carboxamide;

N-(5-chloro-4-{1-[(6-methylpyridin-3-yl)methyl]-2,3-dihydro-1H-indol-6-yl}pyridin-2-yl)piperidine-3-carboxamide;

N-{5-chloro-4-[1-(pyrrolidin-3-ylmethyl)-2,3-dihydro-1H-indol-6-yl]pyridin-2-yl}piperidine-3-carboxamide;

4-[(6-{5-chloro-2-[(piperidin-3-ylcarbonyl)amino]pyridin-4-yl}-2,3-dihydro-1H-indol-1-yl)methyl]benzoic acid;

N-(5-chloro-4-{1-[4-(methylsulfonyl)benzyl]-2,3-dihydro-1H-indol-6-yl}pyridin-2-yl)piperidine-3-carboxamide;

methyl 4-[(6-{5-chloro-2-[(piperidin-3-ylcarbonyl)amino]pyridin-4-yl}-2,3-dihydro-1H-indol-1-yl)methyl]benzoate;

N-{5-chloro-4-[1-(pyrimidin-5-ylmethyl)-2,3-dihydro-1H-indol-6-yl]pyridin-2-yl}piperidine-3-carboxamide;

N-[5-chloro-4-(1-{[6-(trifluoromethyl)pyridin-2-yl]methyl}-2,3-dihydro-1H-indol-6-yl)pyridin-2-yl]piperidine-3-carboxamide;

N-{5-chloro-4-[1-(quinolin-6-ylmethyl)-2,3-dihydro-1H-indol-6-yl]pyridin-2-yl}piperidine-3-carboxamide;

N-{4-[1-(1H-benzimidazol-2-ylmethyl)-2,3-dihydro-1H-indol-6-yl]-5-chloropyridin-2-yl}piperidine-3-carboxamide;

N-{5-chloro-4-[1-(2,3-dihydro-1,4-benzodioxin-5-ylmethyl)-2,3-dihydro-1H-indol-6-yl]pyridin-2-yl}piperidine-3-carboxamide;

N-(5-chloro-4-{1-[(1-methyl-1H-benzimidazol-2-yl)methyl]-2,3-dihydro-1H-indol-6-yl}pyridin-2-yl)piperidine-3-carboxamide;

N-(5-chloro-4-{1-[(1-methyl-1H-benzotriazol-5-yl)methyl]-2,3-dihydro-1H-indol-6-yl}pyridin-2-yl)piperidine-3-carboxamide;

N-{4-[1-(1,3-benzodioxol-4-ylmethyl)-2,3-dihydro-1H-indol-6-yl]-5-chloropyridin-2-yl}piperidine-3-carboxamide;

N-{5-chloro-4-[1-(4-methylbenzyl)-2,3-dihydro-1H-indol-6-yl]pyridin-2-yl}piperidine-3-carboxamide;

N-{5-chloro-4-[1-(quinoxalin-6-ylmethyl)-2,3-dihydro-1H-indol-6-yl]pyridin-2-yl}piperidine-3-carboxamide;

N-{5-chloro-4-[1-(pyrazin-2-ylmethyl)-2,3-dihydro-1H-indol-6-yl]pyridin-2-yl}piperidine-3-carboxamide;

N-{5-chloro-4-[1-(2,3-dihydro[1,4]dioxino[2,3-b]pyridin-7-ylmethyl)-2,3-dihydro-1H-indol-6-yl]pyridin-2-yl}piperidine-3-carboxamide;

N-[5-chloro-4-(1-{[6-(methylsulfonyl)pyridin-3-yl]methyl}-2,3-dihydro-1H-indol-6-yl)pyridin-2-yl]piperidine-3-carboxamide;

N-{5-chloro-4-[1-(4-sulfamoylbenzyl)-2,3-dihydro-1H-indol-6-yl]pyridin-2-yl}piperidine-3-carboxamide;

N-(5-chloro-4-{1-[3-fluoro-4-(methylsulfonyl)benzyl]-2,3-dihydro-1H-indol-6-yl}pyridin-2-yl)piperidine-3-carboxamide;

N-(5-chloro-4-{1-[4-(2H-tetrazol-5-yl)benzyl]-2,3-dihydro-1H-indol-6-yl}pyridin-2-yl)piperidine-3-carboxamide;

N-{5-chloro-4-[1-(pyrrolidin-2-ylmethyl)-2,3-dihydro-1H-indol-6-yl]pyridin-2-yl}piperidine-3-carboxamide;

N-(5-chloro-4-{1-[(1-methylpiperidin-4-yl)methyl]-2,3-dihydro-1H-indol-6-yl}pyridin-2-yl)piperidine-3-carboxamide;

N-{5-chloro-4-[1-(3-fluorobenzyl)-1H-imidazo[4,5-b]pyridin-6-yl]pyridin-2-yl}piperidine-3-carboxamide;

(3R)—N-[5-chloro-4-(1-{[3-(morpholin-4-yl)oxetan-3-yl]methyl}-1H-benzimidazol-6-yl)pyridin-2-yl]piperidine-3-carboxamide;

(3R)—N-[5-chloro-4-(1-{[3-(pyrrolidin-1-yl)oxetan-3-yl]methyl}-1H-benzimidazol-6-yl)pyridin-2-yl]piperidine-3-carboxamide;

N-{5-chloro-4-[1-(tetrahydro-2H-pyran-4-ylmethyl)-1H-benzimidazol-6-yl]pyridin-2-yl}-7-azaspiro[3.5]nonan-2-amine;

N-{5-chloro-4-[1-(tetrahydro-2H-pyran-4-ylmethyl)-1H-benzimidazol-6-yl]pyridin-2-yl}-7-(methylsulfonyl)-7-azaspiro[3.5]nonan-2-amine;

(2E)-N-{5-chloro-4-[1-(3-fluorobenzyl)-1H-benzimidazol-6-yl]pyridin-2-yl}-3-(pyridin-4-yl)prop-2-enamide;

(1R,2S)—N-{5-chloro-4-[1-(3-fluorobenzyl)-1H-benzimidazol-6-yl]pyridin-2-yl}-N'-cyclopentylcyclobutane-1,2-dicarboxamide;

N-{5-chloro-4-[1-(3-fluorobenzyl)-1H-benzimidazol-6-yl]pyridin-2-yl}-2-(2-oxopyridin-1(2H)-yl)propanamide;

N-{5-chloro-4-[1-(3-fluorobenzyl)-1H-benzimidazol-6-yl]pyridin-2-yl}-2-(methylsulfonyl)acetamide;

N-{5-chloro-4-[1-(3-fluorobenzyl)-1H-benzimidazol-6-yl]pyridin-2-yl}-1-(3-chlorophenyl)-5-oxopyrrolidine-3-carboxamide;

1-benzyl-N-{5-chloro-4-[1-(3-fluorobenzyl)-1H-benzimidazol-6-yl]pyridin-2-yl}-5-oxopyrrolidine-3-carboxamide;

N-{5-chloro-4-[1-(3-fluorobenzyl)-1H-benzimidazol-6-yl]pyridin-2-yl}-2,3-dihydro[1,4]dioxino[2,3-b]pyridine-7-carboxamide;

(3R)—N-{5-chloro-4-[1-(3-fluorobenzyl)-1H-benzimidazol-6-yl]pyridin-2-yl}-3-(pyridin-3-yl)-1H-pyrrolo[1,2-c][1,3]thiazole-7-carboxamide;

N-{5-chloro-4-[1-(3-fluorobenzyl)-1H-benzimidazol-6-yl]pyridin-2-yl}-3-oxocyclobutanecarboxamide;

N-{5-chloro-4-[1-(3-fluorobenzyl)-1H-benzimidazol-6-yl]pyridin-2-yl}-6-oxospiro[3.3]heptane-2-carboxamide;

benzyl (1R,5S,6r)-6-({5-chloro-4-[1-(3-fluorobenzyl)-1H-benzimidazol-6-yl]pyridin-2-yl}carbamoyl)-3-azabicyclo[3.1.0]hexane-3-carboxylate;

N-{5-chloro-4-[1-(3-fluorobenzyl)-1H-benzimidazol-6-yl]pyridin-2-yl}-1-methylazetidine-3-carboxamide;

N-{5-chloro-4-[1-(3-fluorobenzyl)-1H-benzimidazol-6-yl]pyridin-2-yl}-3-methyloxetane-3-carboxamide;

N-{5-chloro-4-[1-(3-fluorobenzyl)-1H-benzimidazol-6-yl]pyridin-2-yl}-4-hydroxy-4-(trifluoromethyl)cyclohexanecarboxamide;

N-{5-chloro-4-[1-(3-fluorobenzyl)-1H-benzimidazol-6-yl]pyridin-2-yl}-1-(2,2-dimethylpropanoyl)-2,3-dihydro-1H-pyrido[2,3-b][1,4]oxazine-6-carboxamide;

N-{5-chloro-4-[1-(3-fluorobenzyl)-1H-benzimidazol-6-yl]pyridin-2-yl}-2-(methylsulfonyl)-5-thia-2-azaspiro[3.4]octane-8-carboxamide 5,5-dioxide;

$N^8$-{5-chloro-4-[1-(3-fluorobenzyl)-1H-benzimidazol-6-yl]pyridin-2-yl}-$N^2$-ethyl-5-thia-2-azaspiro[3.4]octane-2,8-dicarboxamide 5,5-dioxide;

$N^8$-{5-chloro-4-[1-(3-fluorobenzyl)-1H-benzimidazol-6-yl]pyridin-2-yl}-$N^2$-phenyl-5-thia-2-azaspiro[3.4]octane-2,8-dicarboxamide 5,5-dioxide;

N-{5-chloro-4-[1-(3-fluorobenzyl)-1H-benzimidazol-6-yl]pyridin-2-yl}-7-(cyclohexylcarbonyl)-1-thia-7-azaspiro[4.4]nonane-4-carboxamide 1,1-dioxide;

N-{5-chloro-4-[1-(3-fluorobenzyl)-1H-benzimidazol-6-yl]pyridin-2-yl}-7-(2-methylpropanoyl)-1-thia-7-azaspiro[4.4]nonane-4-carboxamide 1,1-dioxide;

N-{5-chloro-4-[1-(3-fluorobenzyl)-1H-benzimidazol-6-yl]pyridin-2-yl}-7-(phenylsulfonyl)-1-thia-7-azaspiro[4.4]nonane-4-carboxamide 1,1-dioxide;

7-benzoyl-N-{5-chloro-4-[1-(3-fluorobenzyl)-1H-benzimidazol-6-yl]pyridin-2-yl}-1-thia-7-azaspiro[4.4]nonane-4-carboxamide 1,1-dioxide;

N-{5-chloro-4-[1-(3-fluorobenzyl)-1H-benzimidazol-6-yl]pyridin-2-yl}-7-ethyl-1-thia-7-azaspiro[4.4]nonane-4-carboxamide 1,1-dioxide;

N-{5-chloro-4-[1-(3-fluorobenzyl)-1H-benzimidazol-6-yl]pyridin-2-yl}-2-oxohexahydro-2H-cyclopenta[d][1,3]oxazole-5-carboxamide;

N-{5-chloro-4-[1-(3-fluorobenzyl)-1H-benzimidazol-6-yl]pyridin-2-yl}-7-(methylsulfonyl)-1-thia-7-azaspiro[4.4]nonane-4-carboxamide 1,1-dioxide;

(2E)-N-carbamoyl-N'-{5-chloro-4-[1-(3-fluorobenzyl)-1H-benzimidazol-6-yl]pyridin-2-yl}but-2-enediamide;

N-{5-chloro-4-[1-(3-fluorobenzyl)-1H-benzimidazol-6-yl]pyridin-2-yl}cyclopropane-1,1-dicarboxamide;

N-{5-chloro-4-[1-(3-fluorobenzyl)-1H-benzimidazol-6-yl]pyridin-2-yl}-1H-pyrazole-4-carboxamide;

trans-N-{5-chloro-4-[1-(tetrahydro-2H-pyran-4-ylmethyl)-1H-benzimidazol-6-yl]pyridin-2-yl}cyclohexane-1,4-diamine;

N-{5-chloro-4-[1-(tetrahydro-2H-pyran-4-ylmethyl)-1H-benzimidazol-6-yl]pyridin-2-yl}piperidine-4-carboxamide;

N-{5-chloro-4-[1-(tetrahydro-2H-pyran-4-ylmethyl)-1H-benzimidazol-6-yl]pyridin-2-yl}-2-oxohexahydro-2H-cyclopenta[d][1,3]oxazole-5-carboxamide;

(2s,4r)-N-{5-chloro-4-[1-(3-fluorobenzyl)-1H-benzimidazol-6-yl]pyridin-2-yl}-6-azaspiro[3.4]octan-2-amine;

(2r,4s)-N-{5-chloro-4-[1-(3-fluorobenzyl)-1H-benzimidazol-6-yl]pyridin-2-yl}-6-azaspiro[3.4]octan-2-amine;

(2s,4r)-N-{5-chloro-4-[1-(3-fluorobenzyl)-1H-benzimidazol-6-yl]pyridin-2-yl}-6-azaspiro[3.5]nonan-2-amine;

(2r,4s)-N-{5-chloro-4-[1-(3-fluorobenzyl)-1H-benzimidazol-6-yl]pyridin-2-yl}-6-azaspiro[3.5]nonan-2-amine;

(3S)—N-{5-chloro-4-[1-(tetrahydro-2H-pyran-4-ylmethyl)-1H-benzimidazol-6-yl]pyridin-2-yl}piperidine-3-carboxamide;

(3R)—N-{5-chloro-4-[1-(3-fluorobenzyl)-1H-imidazo[4,5-b]pyrazin-6-yl]pyridin-2-yl}piperidine-3-carboxamide;

N-(5-chloro-4-{1-[2-(dimethylamino)-2-oxoethyl]-2,3-dihydro-1H-indol-6-yl}pyridin-2-yl)piperidine-3-carboxamide;

N-(5-chloro-4-{1-[2-(morpholin-4-yl)-2-oxoethyl]-2,3-dihydro-1H-indol-6-yl}pyridin-2-yl)piperidine-3-carboxamide;

N-(5-chloro-4-{1-[2-oxo-2-(pyrrolidin-1-yl)ethyl]-2,3-dihydro-1H-indol-6-yl}pyridin-2-yl)piperidine-3-carboxamide;

(3R)—N-{5-chloro-4-[3-cyano-1-(tetrahydro-2H-pyran-4-ylmethyl)-1H-pyrrolo[3,2-b]pyridin-6-yl]pyridin-2-yl}piperidine-3-carboxamide;

4-[(6-{5-chloro-2-[(2-hydroxyethyl)amino]pyridin-4-yl}-1H-benzimidazol-1-yl)methyl]tetrahydro-2H-pyran-4-carbonitrile;

2-[(5-chloro-4-{1-[(5-fluoropyridin-3-yl)methyl]-1H-benzimidazol-6-yl}pyridin-2-yl)amino]ethanol;

trans-N-{5-chloro-4-[1-(3-fluorobenzyl)-1H-benzimidazol-6-yl]pyridin-2-yl}-N'-(pyridin-2-ylmethyl)cyclohexane-1,4-diamine;

trans-N-{5-chloro-4-[1-(3-fluorobenzyl)-1H-benzimidazol-6-yl]pyridin-2-yl}-N'-(pyridin-3-ylmethyl)cyclohexane-1,4-diamine;

trans-N-{5-chloro-4-[1-(3-fluorobenzyl)-1H-benzimidazol-6-yl]pyridin-2-yl}-N'-(pyridin-4-ylmethyl)cyclohexane-1,4-diamine;

trans-N-(1,3-benzodioxol-5-ylmethyl)-N'-{5-chloro-4-[1-(3-fluorobenzyl)-1H-benzimidazol-6-yl]pyridin-2-yl}cyclohexane-1,4-diamine;

trans-N-{5-chloro-4-[1-(3-fluorobenzyl)-1H-benzimidazol-6-yl]pyridin-2-yl}-N'-(1,3-thiazol-2-ylmethyl)cyclohexane-1,4-diamine;

trans-N-{5-chloro-4-[1-(3-fluorobenzyl)-1H-benzimidazol-6-yl]pyridin-2-yl}-N'-{[1-(methoxymethyl)-2,3-dihydro-1H-1,2,3-triazol-4-yl]methyl}cyclohexane-1,4-diamine;

trans-N-{5-chloro-4-[1-(3-fluorobenzyl)-1H-benzimidazol-6-yl]pyridin-2-yl}-N'-[2-(morpholin-4-yl)ethyl]cyclohexane-1,4-diamine;

trans-N-{5-chloro-4-[1-(3-fluorobenzyl)-1H-benzimidazol-6-yl]pyridin-2-yl}-N'-[2-methyl-2-(morpholin-4-yl)propyl]cyclohexane-1,4-diamine;

trans-N-{5-chloro-4-[1-(3-fluorobenzyl)-1H-benzimidazol-6-yl]pyridin-2-yl}-N'-(tetrahydrofuran-2-ylmethyl)cyclohexane-1,4-diamine;

trans-N-{5-chloro-4-[1-(3-fluorobenzyl)-1H-benzimidazol-6-yl]pyridin-2-yl}-N'-[(2,5-dimethoxytetrahydrofuran-3-yl)methyl]cyclohexane-1,4-diamine;

trans-N-{5-chloro-4-[1-(3-fluorobenzyl)-1H-benzimidazol-6-yl]pyridin-2-yl}-N'-(cyclopropylmethyl)cyclohexane-1,4-diamine;

3-{[trans-4-({5-chloro-4-[1-(3-fluorobenzyl)-1H-benzimidazol-6-yl]pyridin-2-yl}amino)cyclohexyl]amino}propane-1,2-diol;

trans-N-{5-chloro-4-[1-(3-fluorobenzyl)-1H-benzimidazol-6-yl]pyridin-2-yl}-N'-(1-methoxypropan-2-yl)cyclohexane-1,4-diamine;

trans-N-{5-chloro-4-[1-(3-fluorobenzyl)-1H-benzimidazol-6-yl]pyridin-2-yl}-N'-(1,3-dimethoxypropan-2-yl)cyclohexane-1,4-diamine;

trans-N-{5-chloro-4-[1-(3-fluorobenzyl)-1H-benzimidazol-6-yl]pyridin-2-yl}-N'-(2-phenoxyethyl)cyclohexane-1,4-diamine;

trans-N-[3-(benzyloxy)propyl]-N'-{5-chloro-4-[1-(3-fluorobenzyl)-1H-benzimidazol-6-yl]pyridin-2-yl}cyclohexane-1,4-diamine;

trans-N-{5-chloro-4-[1-(3-fluorobenzyl)-1H-benzimidazol-6-yl]pyridin-2-yl}-N'-[2,2-dimethyl-3-(phenylsulfinyl)propyl]cyclohexane-1,4-diamine;

trans-N-{5-chloro-4-[1-(3-fluorobenzyl)-1H-benzimidazol-6-yl]pyridin-2-yl}-N'-(2-methoxypropyl)cyclohexane-1,4-diamine;

trans-N-{5-chloro-4-[1-(3-fluorobenzyl)-1H-benzimidazol-6-yl]pyridin-2-yl}-N'-[2-(cyclohexyloxy)propyl]cyclohexane-1,4-diamine;

trans-N-{5-chloro-4-[1-(3-fluorobenzyl)-1H-benzimidazol-6-yl]pyridin-2-yl}-N'-[(5,5-dimethyltetrahydrofuran-2-yl)methyl]cyclohexane-1,4-diamine;

trans-N-{5-chloro-4-[1-(3-fluorobenzyl)-1H-benzimidazol-6-yl]pyridin-2-yl}-N'-(3-methoxypropyl)cyclohexane-1,4-diamine;

2-{[trans-4-({5-chloro-4-[1-(3-fluorobenzyl)-1H-benzimidazol-6-yl]pyridin-2-yl}amino)cyclohexyl]amino}propan-1-ol;

(3R)—N-{5-chloro-4-[1-(3-fluorobenzyl)-1H-[1,2,3]triazolo[4,5-b]pyrazin-6-yl]pyridin-2-yl}piperidine-3-carboxamide;

(3R)—N-{5-chloro-4-[1-(tetrahydro-2H-pyran-4-ylmethyl)-1H-benzotriazol-6-yl]pyridin-2-yl}piperidine-3-carboxamide;

N-{5-chloro-4-[1-(3-fluorobenzyl)-1H-pyrrolo[3,2-b]pyridin-6-yl]pyridin-2-yl}-6-azaspiro[3.4]octan-2-amine;

N-{5-chloro-4-[1-(3-fluorobenzyl)-1H-benzimidazol-6-yl]pyridin-2-yl}cyclohexane-1,3-diamine;

(3R)—N-{5-chloro-4-[1-(3-fluorobenzyl)-2-(trifluoromethyl)-1H-benzimidazol-6-yl]pyridin-2-yl}piperidine-3-carboxamide;

(3R)—N-{5-chloro-4-[2-(trifluoromethyl)-1H-benzimidazol-6-yl]pyridin-2-yl}piperidine-3-carboxamide;

(3R)—N-{5-chloro-4-[1-(3-fluorobenzyl)-3-(methoxymethyl)-1H-pyrrolo[3,2-b]pyridin-6-yl]pyridin-2-yl}piperidine-3-carboxamide;

(3R)—N-{5-chloro-4-[3-(methoxymethyl)-1-(tetrahydro-2H-pyran-4-ylmethyl)-1H-pyrrolo[3,2-b]pyridin-6-yl]pyridin-2-yl}piperidine-3-carboxamide;

N-{5-chloro-4-[1-(tetrahydro-2H-pyran-4-ylmethyl)-1H-benzimidazol-6-yl]pyridin-2-yl}pyridine-4-carboxamide;

N-{5-chloro-4-[1-(tetrahydro-2H-pyran-4-ylmethyl)-1H-benzimidazol-6-yl]pyridin-2-yl}pyridine-3-carboxamide;

N-{5-chloro-4-[1-(tetrahydro-2H-pyran-4-ylmethyl)-1H-benzimidazol-6-yl]pyridin-2-yl}-1-methyl-1H-imidazole-4-carboxamide;

N-{5-chloro-4-[1-(tetrahydro-2H-pyran-4-ylmethyl)-1H-benzimidazol-6-yl]pyridin-2-yl}-1H-imidazole-4-carboxamide;

N-{5-chloro-4-[1-(tetrahydro-2H-pyran-4-ylmethyl)-1H-benzimidazol-6-yl]pyridin-2-yl}-1,3-thiazole-4-carboxamide;

N-{5-chloro-4-[1-(tetrahydro-2H-pyran-4-ylmethyl)-1H-benzimidazol-6-yl]pyridin-2-yl}-1H-1,2,4-triazole-3-carboxamide;

N-{5-chloro-4-[1-(tetrahydro-2H-pyran-4-ylmethyl)-1H-benzimidazol-6-yl]pyridin-2-yl}pyrimidine-5-carboxamide;

N-{5-chloro-4-[1-(tetrahydro-2H-pyran-4-ylmethyl)-1H-benzimidazol-6-yl]pyridin-2-yl}pyrazine-2-carboxamide;

N-{5-chloro-4-[1-(tetrahydro-2H-pyran-4-ylmethyl)-1H-benzimidazol-6-yl]pyridin-2-yl}-1H-pyrazole-3-carboxamide;

N-{5-chloro-4-[1-(tetrahydro-2H-pyran-4-ylmethyl)-1H-benzimidazol-6-yl]pyridin-2-yl}-1H-1,2,3-triazole-4-carboxamide;

N-{5-chloro-4-[1-(tetrahydro-2H-pyran-4-ylmethyl)-1H-benzimidazol-6-yl]pyridin-2-yl}azetidine-3-carboxamide;

N-{5-chloro-4-[1-(tetrahydro-2H-pyran-4-ylmethyl)-1H-benzimidazol-6-yl]pyridin-2-yl}-1H-pyrazole-4-carboxamide;

(3aR,6aS)—N-{5-chloro-4-[1-(tetrahydro-2H-pyran-4-ylmethyl)-1H-benzimidazol-6-yl]pyridin-2-yl}octahydrocyclopenta[c]pyrrole-5-carboxamide;

N-{5-chloro-4-[1-(tetrahydro-2H-pyran-4-ylmethyl)-1H-benzimidazol-6-yl]pyridin-2-yl}-2-azaspiro[3.3]heptane-6-carboxamide;

N-{5-chloro-4-[1-(tetrahydro-2H-pyran-4-ylmethyl)-1H-benzimidazol-6-yl]pyridin-2-yl}-3-azabicyclo[3.1.0]hexane-6-carboxamide;

N-{5-chloro-4-[1-(tetrahydro-2H-pyran-4-ylmethyl)-1H-benzimidazol-6-yl]pyridin-2-yl}-3-oxocyclobutanecarboxamide;

(3R)—N-{5-chloro-4-[2-(3-fluorophenyl)-1-methyl-1H-benzimidazol-6-yl]pyridin-2-yl}piperidine-3-carboxamide;

(3R)—N-{5-chloro-4-[2-(3-fluorobenzyl)-1-methyl-1H-benzimidazol-6-yl]pyridin-2-yl}piperidine-3-carboxamide;

N-{5-chloro-4-[1-(tetrahydro-2H-pyran-4-ylmethyl)-1H-benzimidazol-6-yl]pyridin-2-yl}-1,2,5,6-tetrahydropyridine-3-carboxamide;

N-{5-chloro-4-[1-(3-fluorobenzyl)-1H-benzimidazol-6-yl]pyridin-2-yl}-2-(tetrahydro-2H-pyran-4-ylsulfonyl)propanamide;

N-{5-chloro-4-[1-(3-fluorobenzyl)-1H-benzimidazol-6-yl]pyridin-2-yl}-5,6,7,8-tetrahydro[1,2,4]triazolo[4,3-a]pyridine-6-carboxamide;

N-{5-chloro-4-[1-(3-fluorobenzyl)-1H-benzimidazol-6-yl]pyridin-2-yl}-5,6,7,8-tetrahydroimidazo[1,2-a]pyridine-6-carboxamide;

N-{5-chloro-4-[1-(3-fluorobenzyl)-1H-benzimidazol-6-yl]pyridin-2-yl}-3,4-dihydro-2H-pyrano[2,3-b]pyridine-6-carboxamide;

N-{5-chloro-4-[1-(3-fluorobenzyl)-1H-benzimidazol-6-yl]pyridin-2-yl}-2-sulfamoylacetamide;

N-{5-chloro-4-[1-(3-fluorobenzyl)-1H-benzimidazol-6-yl]pyridin-2-yl}-2-[(4-methylpiperazin-1-yl)sulfonyl]acetamide;

N-{5-chloro-4-[1-(3-fluorobenzyl)-1H-benzimidazol-6-yl]pyridin-2-yl}-5-oxo-D-prolinamide;

N-{5-chloro-4-[1-(3-fluorobenzyl)-1H-benzimidazol-6-yl]pyridin-2-yl}-$N^2$-(dimethylsulfamoyl)glycinamide;

N-{5-chloro-4-[1-(tetrahydro-2H-pyran-4-ylmethyl)-1H-benzimidazol-6-yl]pyridin-2-yl}-2-(tetrahydro-2H-pyran-4-ylsulfonyl)propanamide;

N-{5-chloro-4-[1-(tetrahydro-2H-pyran-4-ylmethyl)-1H-benzimidazol-6-yl]pyridin-2-yl}-5,6,7,8-tetrahydro[1,2,4]triazolo[4,3-a]pyridine-6-carboxamide;

N-{5-chloro-4-[1-(tetrahydro-2H-pyran-4-ylmethyl)-1H-benzimidazol-6-yl]pyridin-2-yl}-5,6,7,8-tetrahydroimidazo[1,2-a]pyridine-6-carboxamide;

N-{5-chloro-4-[1-(tetrahydro-2H-pyran-4-ylmethyl)-1H-benzimidazol-6-yl]pyridin-2-yl}-3,4-dihydro-2H-pyrano[2,3-b]pyridine-6-carboxamide;

N-{5-chloro-4-[1-(tetrahydro-2H-pyran-4-ylmethyl)-1H-benzimidazol-6-yl]pyridin-2-yl}-2-sulfamoylacetamide;

N-{5-chloro-4-[1-(tetrahydro-2H-pyran-4-ylmethyl)-1H-benzimidazol-6-yl]pyridin-2-yl}-$N^2$-(ethylsulfonyl)glycinamide;

N-{5-chloro-4-[1-(tetrahydro-2H-pyran-4-ylmethyl)-1H-benzimidazol-6-yl]pyridin-2-yl}-5-oxo-D-prolinamide;

N-{5-chloro-4-[1-(tetrahydro-2H-pyran-4-ylmethyl)-1H-benzimidazol-6-yl]pyridin-2-yl}-$N^2$-(dimethylsulfamoyl)glycinamide;

N-{5-chloro-4-[1-(tetrahydro-2H-pyran-4-ylmethyl)-1H-benzimidazol-6-yl]pyridin-2-yl}-2-[(4-methylpiperazin-1-yl)sulfonyl]acetamide;

(3R)—N-(5-chloro-4-{1-[4-(methylsulfonyl)benzyl]-1H-benzotriazol-6-yl}pyridin-2-yl)piperidine-3-carboxamide;

cis-3-amino-N-{5-chloro-4-[1-(tetrahydro-2H-pyran-4-ylmethyl)-1H-benzimidazol-6-yl]pyridin-2-yl}cyclobutanecarboxamide;

trans-3-amino-N-{5-chloro-4-[1-(tetrahydro-2H-pyran-4-ylmethyl)-1H-benzimidazol-6-yl]pyridin-2-yl}cyclobutanecarboxamide;

(1R,5S,6r)-N-{5-chloro-4-[1-(tetrahydro-2H-pyran-4-ylmethyl)-1H-benzimidazol-6-yl]pyridin-2-yl}-3-azabicyclo[3.1.0]hexane-6-carboxamide;

(2R)—N-{5-chloro-4-[1-(tetrahydro-2H-pyran-4-ylmethyl)-1H-benzimidazol-6-yl]pyridin-2-yl}azetidine-2-carboxamide;

6-amino-N-{5-chloro-4-[1-(tetrahydro-2H-pyran-4-ylmethyl)-1H-benzimidazol-6-yl]pyridin-2-yl}spiro[3.3]heptane-2-carboxamide;

N-{5-chloro-4-[1-(tetrahydro-2H-pyran-4-ylmethyl)-1H-benzimidazol-6-yl]pyridin-2-yl}-2-(furan-2-yl)-2-(piperazin-1-yl)acetamide;

1-amino-N-{5-chloro-4-[1-(tetrahydro-2H-pyran-4-ylmethyl)-1H-benzimidazol-6-yl]pyridin-2-yl}cyclopentanecarboxamide;

N-{5-chloro-4-[1-(tetrahydro-2H-pyran-4-ylmethyl)-1H-benzimidazol-6-yl]pyridin-2-yl}-5-thia-2-azaspiro[3.4]octane-8-carboxamide 5,5-dioxide;

(2S,3R)—N-{5-chloro-4-[1-(tetrahydro-2H-pyran-4-ylmethyl)-1H-benzimidazol-6-yl]pyridin-2-yl}-3-ethylazetidine-2-carboxamide;

N-{5-chloro-4-[1-(tetrahydro-2H-pyran-4-ylmethyl)-1H-benzimidazol-6-yl]pyridin-2-yl}-4-(4-fluorophenyl)piperidine-4-carboxamide;

N-{5-chloro-4-[1-(tetrahydro-2H-pyran-4-ylmethyl)-1H-benzimidazol-6-yl]pyridin-2-yl}-1-thia-7-azaspiro[4.4]nonane-4-carboxamide 1,1-dioxide;

(3R)—N-(5-chloro-4-{1-[2-(3-fluorophenyl)-2-oxoethyl]-1H-pyrrolo[3,2-b]pyridin-6-yl}pyridin-2-yl)piperidine-3-carboxamide;

N-(5-chloro-4-{1-[(5-fluoropyridin-3-yl)methyl]-1H-pyrrolo[3,2-b]pyridin-6-yl}pyridin-2-yl)-3-oxocyclobutanecarboxamide;

(3R)—N-(5-chloro-4-{1-[(1-methyl-1H-benzotriazol-6-yl)methyl]-1H-pyrrolo[3,2-b]pyridin-6-yl}pyridin-2-yl)piperidine-3-carboxamide;

(3R)—N-(5-chloro-4-{1-[2-oxo-2-(tetrahydro-2H-pyran-4-yl)ethyl]-1H-pyrrolo[3,2-b]pyridin-6-yl}pyridin-2-yl)piperidine-3-carboxamide;

(3R)—N-(5-chloro-4-{1-[2-hydroxy-2-(tetrahydro-2H-pyran-4-yl)ethyl]-1H-pyrrolo[3,2-b]pyridin-6-yl}pyridin-2-yl)piperidine-3-carboxamide;

(3R)—N-(5-chloro-4-{1-[(trans-4-hydroxy-4-methylcyclohexyl)methyl]-1H-benzotriazol-6-yl}pyridin-2-yl)piperidine-3-carboxamide;

(3R)—N-(5-chloro-4-{5-fluoro-1-[(1R)-1-(3-fluorophenyl)ethyl]-1H-benzotriazol-6-yl}pyridin-2-yl)piperidine-3-carboxamide;

methyl 4-{[6-(5-chloro-2-{[(3R)-piperidin-3-ylcarbonyl]amino}pyridin-4-yl)-1H-benzimidazol-1-yl]methyl}benzoate;

methyl 4-{[6-(5-chloro-2-{[(3R)-piperidin-3-ylcarbonyl]amino}pyridin-4-yl)-1H-benzotriazol-1-yl]methyl}benzoate;

(3R)—N-(5-chloro-4-{1-[3-(3-fluorophenyl)propyl]-1H-benzimidazol-6-yl}pyridin-2-yl)piperidine-3-carboxamide;

(3R)—N-(5-chloro-4-{1-[3-(3-fluorophenyl)propyl]-1H-benzotriazol-6-yl}pyridin-2-yl)piperidine-3-carboxamide;

4-{[6-(5-chloro-2-{[(3R)-piperidin-3-ylcarbonyl]amino}pyridin-4-yl)-1H-benzotriazol-1-yl]methyl}benzoic acid;

4-{[6-(2-amino-5-chloropyridin-4-yl)-1H-benzotriazol-1-yl]methyl}benzoic acid;

(3R)—N-{4-[1-(tetrahydro-2H-pyran-4-ylmethyl)-1H-benzimidazol-6-yl]pyridin-2-yl}piperidine-3-carboxamide;

(3R)—N-(5-chloro-4-{1-[(5-fluoropyridin-3-yl)methyl]-1H-pyrrolo[3,2-b]pyridin-6-yl}pyridin-2-yl)piperidine-3-carboxamide;

(3R)—N-(5-chloro-4-{1-[1-(pyridin-3-yl)ethyl]-1H-benzotriazol-6-yl}pyridin-2-yl)piperidine-3-carboxamide;

(3R)—N-{5-chloro-4-[1-(3-fluorobenzyl)-5-methoxy-1H-benzimidazol-6-yl]pyridin-2-yl}piperidine-3-carboxamide;

4-{[6-(5-chloro-2-{[(3R)-piperidin-3-ylcarbonyl]amino}pyridin-4-yl)-1H-benzimidazol-1-yl]methyl}benzoic acid;

(3R)—N-{5-chloro-4-[1-(3-fluorobenzyl)-5-methoxy-1H-benzotriazol-6-yl]pyridin-2-yl}piperidine-3-carboxamide;

(1R,4R,6R)—N-{5-chloro-4-[1-(tetrahydro-2H-pyran-4-ylmethyl)-1H-benzimidazol-6-yl]pyridin-2-yl}-2-azabicyclo[2.2.1]heptane-6-carboxamide;

(1R,4R,6S)—N-{5-chloro-4-[1-(tetrahydro-2H-pyran-4-yl-methyl)-1H-benzimidazol-6-yl]pyridin-2-yl}-2-azabicyclo[2.2.1]heptane-6-carboxamide;
(3R)—N-{5-chloro-4-[1-(thiophen-2-ylmethyl)-1H-benzimidazol-6-yl]pyridin-2-yl}piperidine-3-carboxamide;
(3R)—N-{5-chloro-4-[1-(thiophen-2-ylmethyl)-1H-benzotriazol-6-yl]pyridin-2-yl}piperidine-3-carboxamide;
(3R)—N-(5-chloro-4-{1-[2-(dimethylamino)-2-(3-fluorophenyl)ethyl]-1H-benzotriazol-6-yl}pyridin-2-yl)piperidine-3-carboxamide;
(3R)—N-[5-chloro-4-(1-{3-[(4-methylpiperazin-1-yl)methyl]benzyl}-1H-benzotriazol-6-yl)pyridin-2-yl]piperidine-3-carboxamide;
5-chloro-4-[1-(3-fluorobenzyl)-1H-benzimidazol-6-yl]-N-{3-[(methylsulfonyl)methyl]phenyl}pyridin-2-amine;
(3R)—N-{5-chloro-4-[4-fluoro-1-(tetrahydro-2H-pyran-4-ylmethyl)-1H-benzimidazol-6-yl]pyridin-2-yl}piperidine-3-carboxamide;
ethyl {[(3R)-3-({5-chloro-4-[1-(tetrahydro-2H-pyran-4-ylmethyl)-1H-benzimidazol-6-yl]pyridin-2-yl}carbamoyl)piperidin-1-yl]sulfonyl}carbamate;
methyl (cis)-3-({5-chloro-4-[1-(tetrahydro-2H-pyran-4-ylmethyl)-1H-benzimidazol-6-yl]pyridin-2-yl}carbamoyl)cyclohexanecarboxylate;
(cis)-3-({5-chloro-4-[1-(tetrahydro-2H-pyran-4-ylmethyl)-1H-benzimidazol-6-yl]pyridin-2-yl}carbamoyl)cyclohexanecarboxylic acid;
(cis)-N-{5-chloro-4-[1-(tetrahydro-2H-pyran-4-ylmethyl)-1H-benzimidazol-6-yl]pyridin-2-yl}-3-[(3-hydroxyazetidin-1-yl)carbonyl]cyclohexanecarboxamide;
(cis)-N'-{5-chloro-4-[1-(tetrahydro-2H-pyran-4-ylmethyl)-1H-benzimidazol-6-yl]pyridin-2-yl}-N-(2-hydroxyethyl)-N-methylcyclohexane-1,3-dicarboxamide;
(cis)-N-{5-chloro-4-[1-(tetrahydro-2H-pyran-4-ylmethyl)-1H-benzimidazol-6-yl]pyridin-2-yl}-3-{[(2S)-2-(hydroxymethyl)pyrrolidin-1-yl]carbonyl}cyclohexanecarboxamide;
(3R)—N-[4-(1-methyl-1H-benzimidazol-6-yl)pyridin-2-yl]piperidine-3-carboxamide;
tert-butyl (3aR,6aS)-5-({5-chloro-4-[1-(tetrahydro-2H-pyran-4-ylmethyl)-1H-benzimidazol-6-yl]pyridin-2-yl}carbamoyl)hexahydrocyclopenta[c]pyrrole-2(1H)-carboxylate;
(3aR,6aS)—$N^5$-{5-chloro-4-[1-(tetrahydro-2H-pyran-4-ylmethyl)-1H-benzimidazol-6-yl]pyridin-2-yl}-$N^2$-methylhexahydrocyclopenta[c]pyrrole-2,5(1H)-dicarboxamide;
cis-4-({5-chloro-4-[1-(3-fluorobenzyl)-1H-benzimidazol-6-yl]pyridin-2-yl}amino)cyclohexanecarboxylic acid; and pharmaceutically acceptable salts thereof.

Embodiments of Formula (IIa)

In one aspect, the present invention provides compounds of Formula (IIa) or a pharmaceutically acceptable salt thereof,

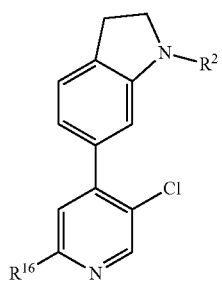

(IIa)

wherein
$R^2$ is selected from the group consisting of H, $C_1$-$C_6$ alkyl, $C_2$-$C_6$ alkenyl, and $C_2$-$C_6$ alkynyl; wherein the $R^2$ $C_1$-$C_6$ alkyl, $C_2$-$C_6$ alkenyl, and $C_2$-$C_6$ alkynyl are optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $SO_2NHC(O)R^4$, $SO_2NR^4C(O)R^4$, $NHS(O)_2R^4$, $NR^4S(O)_2R^4$, $NHC(O)OR^4$, $NR^4C(O)OR^4$, $SO_2NHC(O)OR^4$, $SO_2NR^4C(O)OR^4$, $NHSO_2NHC(O)OR^4$, $NHSO_2NR^4C(O)OR^4$, $NR^4SO_2NR^4C(O)OR^4$, $NR^4SO_2NHC(O)OR^4$, $NHC(O)NH_2$, $NHC(O)NHR^4$, $NHC(O)N(R^4)_2$, $NR^4C(O)NHR^4$, $NR^4C(O)N(R^4)_2$, $OC(O)NH_2$, $OC(O)NHR^4$, $OC(O)N(R^4)_2$, $OC(O)NHSO_2R^4$, $OC(O)NR^4SO_2R^4$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $OSO_2NH_2$, $OSO_2NHR^4$, $OSO_2N(R^4)_2$, $C(O)NHCN$, $C(O)NR^4CN$, $S(O)NR^4$, $S(O)NSO_2R^4$, $C(O)H$, $C(O)OH$, $(O)$, $OH$, $CN$, $NO_2$, F, Cl, Br and I;

$R^4$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^4$ $C_1$-$C_6$ alkyl, $C_2$-$C_6$ alkenyl, and $C_2$-$C_6$ alkynyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, OH, CN, $NO_2$, F, Cl, Br and I; wherein each $R^4$ aryl, cycloalkyl, cycloalkenyl, heteroaryl, heterocycloalkyl, and heterocycloalkenyl is optionally substituted with one or more substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $(O)$, OH, CN, $NO_2$, F, Br and I;

$R^5$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl;

$R^6$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^6$ $C_1$-$C_6$ alkyl, $C_2$-$C_6$ alkenyl, and $C_2$-$C_6$ alkynyl is optionally substituted with one or more substituents independently selected from the group consisting of halo and $R^{6A}$;

$R^{6A}$, at each occurrence, is independently selected from the group consisting of aryl, heteroaryl, heterocycloalkyl, heterocycloalkenyl, cycloalkyl, and cycloalkenyl; wherein each $R^{6A}$ aryl, heteroaryl, heterocycloalkyl, heterocycloalkenyl, cycloalkyl, and cycloalkenyl is optionally substituted with $C_1$-$C_6$ alkyl;

$R^{16}$ is selected from the group consisting of $NH_2$, $NHR^7$, $NHC(O)R^7$, $NHS(O)_2R^7$, $NHC(O)OR^7$, $NHC(O)NH_2$, $NHC(O)NHR^7$, and $NHC(O)N(R^7)_2$;

$R^7$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^7$ $C_1$-$C_6$ alkyl, $C_2$-$C_6$ alkenyl, and $C_2$-$C_6$ alkynyl is optionally substituted with one or more substituents independently selected from the group consisting of $R^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHSO_2NH_2$, $NR^8SO_2NH_2$, $NHSO_2NHR^8$, $NR^8SO_2NHR^8$, $NHSO_2N(R^8)_2$, $NR^8SO_2N(R^8)_2$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $C(O)NHC(O)NH_2$, $C(O)NR^8C(O)NH_2$, $C(O)NHC(O)NHR^8$, $C(O)NR^8C(O)NHR^8$, $C(O)NHC(O)N(R^8)_2$, $C(O)NR^8C(O)N(R^8)_2$, $SO_2NH_2$, $SO_2NHR^8$, $SO_2N(R^8)_2$, $C(O)H$, $C(O)OH$, $OH$, $CN$, $NO_2$, F, Cl, Br and I; wherein each $R^7$ aryl, cycloalkyl, cycloalkenyl, heteroaryl, heterocycloalkyl, and heterocycloalkenyl is optionally substituted with one or more substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $SO_2NHC(O)OH$, $SO_2NR^9C(O)OH$, $SO_2NHC(O)OR^9$, $SO_2NR^9C(O)OR^9$, $C(O)H$, $C(O)OH$, $(O)$, $OH$, $CN$, $NO_2$, F, Cl, Br and I;

$R^8$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^8$ $C_1$-$C_6$ alkyl, $C_2$-$C_6$ alkenyl, and $C_2$-$C_6$ alkynyl is optionally substituted with one or more substituents independently selected from the group consisting of $NHR^{10}$, and aryl; wherein each $R^8$ aryl, heteroaryl, heterocycloalkyl, heterocycloalkenyl, cycloalkyl, and cycloalkenyl is optionally substituted with one or more substituents independently selected from the group consisting of $R^{11}$, $OR^{11}$, halo, $NH_2$, $OH$, and $(O)$;

$R^9$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{13}$, $OR^{13}$, $SR^{13}$, $S(O)R^{13}$, $SO_2R^{13}$, $C(O)R^{13}$, $CO(O)R^{13}$, $OC(O)R^{13}$, $OC(O)OR^{13}$, $NH_2$, $NHR^{13}$, $N(R^{13})_2$, $NHC(O)R^{13}$, $NR^{13}C(O)R^{13}$, $NHS(O)_2R^{13}$, $NR^{13}S(O)_2R^{13}$, $NHC(O)OR^{13}$, $NR^{13}C(O)OR^{13}$, $NHC(O)NH_2$, $NHC(O)NHR^{13}$, $NHC(O)N(R^{13})_2$, $NR^{13}C(O)NHR^{13}$, $NR^{13}C(O)N(R^{13})_2$, $C(O)NH_2$, $C(O)NHR^{13}$, $C(O)N(R^{13})_2$, $C(O)NHOH$, $C(O)NHOR^{13}$, $C(O)NHSO_2R^{13}$, $C(O)NR^{13}SO_2R^{13}$, $SO_2NH_2$, $SO_2NHR^{13}$, $SO_2N(R^{13})_2$, $C(O)H$, $C(O)OH$, $OH$, $CN$, $NO_2$, F, Cl, Br and I; wherein each $R^9$ aryl, cycloalkyl, cycloalkenyl, heteroaryl, heterocycloalkyl, and heterocycloalkenyl is optionally substituted with one or more substituents independently selected from the group consisting of $R^{14}$, $OR^{14}$, $SR^{14}$, $S(O)R^{14}$, $SO_2R^{14}$, $C(O)R^{14}$, $CO(O)R^{14}$, $OC(O)R^{14}$, $OC(O)OR^{14}$, $NH_2$, $NHR^{14}$, $N(R^{14})_2$, $NHC(O)R^{14}$, $NR^{14}C(O)R^{14}$, $NHS(O)_2R^{14}$, $NR^{14}S(O)_2R^{14}$, $NHC(O)OR^{14}$, $NR^{14}C(O)OR^{14}$, $NHC(O)NH_2$, $NHC(O)NHR^{14}$, $NHC(O)N(R^{14})_2$, $NR^{14}C(O)NHR^{14}$, $NR^{14}C(O)N(R^{14})_2$, $C(O)NH_2$, $C(O)NHR^{14}$, $C(O)N(R^{14})_2$, $C(O)NHOH$, $C(O)NHOR^{14}$, $C(O)NHSO_2R^{14}$, $C(O)NR^{14}SO_2R^{14}$, $SO_2NH_2$, $SO_2NHR^{14}$, $SO_2N(R^{14})_2$, $C(O)H$, $C(O)OH$, $(O)$, $OH$, $CN$, $NO_2$, F, Cl, Br and I;

$R^{10}$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl;

$R^{11}$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^{11}$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, $OH$, $CN$, $NO_2$, F, Cl, Br and I; wherein each $R^{11}$ aryl, cycloalkyl, cycloalkenyl, heteroaryl, heterocycloalkyl, and heterocycloalkenyl is optionally substituted with one or more substituents independently selected from the group consisting of $C_1$-$C_6$ alkyl, $O$—$C_1$-$C_6$ alkyl, $NH_2$, $C(O)NH_2$, $C(O)H$, $C(O)OH$, $OH$, $CN$, $NO_2$, F, Cl, Br and I;

$R^{13}$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^{13}$ $C_1$-$C_6$ alkyl, $C_2$-$C_6$ alkenyl, and $C_2$-$C_6$ alkynyl is optionally substituted with one or more substituents independently selected from the group consisting of aryl, $NH_2$, $C(O)NH_2$, $SO_2NH_2$, $C(O)H$, $C(O)OH$, $OH$, $CN$, $NO_2$, F, Cl, Br and I; wherein each $R^{13}$ aryl, cycloalkyl, cycloalkenyl, heteroaryl, heterocycloalkyl, and heterocycloalkenyl is optionally substituted with one or more substituents independently selected from the group consisting of $C_1$-$C_6$ alkyl, $O$—$C_1$-$C_6$ alkyl, $C_1$-$C_6$ alkyl-$O$—$C_1$-$C_6$ alkyl, $NH_2$, $C(O)NH_2$, $C(O)H$, $C(O)OH$, $OH$, $CN$, $NO_2$, F, Cl, Br and I; and $R^{14}$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^{14}$ $C_1$-$C_6$ alkyl, $C_2$-$C_6$ alkenyl, and $C_2$-$C_6$ alkynyl is optionally substituted with one or more substituents independently selected from the group consisting of aryl, $NH_2$, $C(O)NH_2$, $SO_2NH_2$, $C(O)H$, $C(O)OH$, $OH$, $CN$, $NO_2$, F, Cl, Br and I; wherein each $R^{14}$ aryl, cycloalkyl, cycloalkenyl, heteroaryl, heterocycloalkyl, and heterocycloalkenyl is optionally substituted with one or more substituents independently selected from the group consisting of $C_1$-$C_6$ alkyl, $O$—$C_1$-$C_6$ alkyl, $C_1$-$C_6$ alkyl-$O$—$C_1$-$C_6$ alkyl, $NH_2$, $C(O)NH_2$, $C(O)H$, $C(O)OH$, $OH$, $NO_2$, F, Cl, Br and I.

In one embodiment of Formula (IIa), $R^2$ is selected from the group consisting of H, $C_1$-$C_6$ alkyl, $C_2$-$C_6$ alkenyl, and $C_2$-$C_6$ alkynyl; wherein the $R^2$ $C_1$-$C_6$ alkyl, $C_2$-$C_6$ alkenyl, and $C_2$-$C_6$ alkynyl are optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $SO_2NHC(O)R^4$, $SO_2NR^4C(O)R^4$, $NHS(O)_2R^4$, $NR^4S(O)_2R^4$, $NHC(O)OR^4$, $NR^4C(O)OR^4$, $SO_2NHC(O)OR^4$, $SO_2NR^4C(O)OR^4$, $NHSO_2NHC(O)OR^4$, $NHSO_2NR^4C(O)OR^4$, $NR^4SO_2NR^4C(O)OR^4$, $NR^4SO_2NHC(O)OR^4$, $NHC(O)NH_2$, $NHC(O)NHR^4$, $NHC(O)N(R^4)_2$, $NR^4C(O)NHR^4$, $NR^4C(O)N(R^4)_2$, $OC(O)NH_2$, $OC(O)NHR^4$, $OC(O)N(R^4)_2$, $OC(O)NHSO_2R^4$, $OC(O)NR^4SO_2R^4$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $OSO_2NH_2$, $OSO_2NHR^4$, $OSO_2N(R^4)_2$, $C(O)NHCN$, $C(O)NR^4CN$, $S(O)NR^4$, $S(O)NSO_2R^4$, $C(O)H$, $C(O)OH$, $(O)$, $OH$, $CN$, $NO_2$, F, Cl, Br and I. In another embodiment of Formula (IIa), $R^2$ is selected from the group consisting of H and $C_1$-$C_6$ alkyl; wherein the $R^2$ $C_1$-$C_6$ alkyl is optionally substituted with one or more substituents independently selected from the group consisting of $R^4$, $SO_2R^4$, $C(O)R^4$, $N(R^4)_2$, $C(O)N(R^4)_2$, $SO_2NH_2$, and OH. In another embodiment of Formula (IIa), $R^2$ is H. In another embodiment of Formula (IIa), $R^2$ is $C_1$-$C_6$ alkyl; wherein the $R^2$ $C_1$-$C_6$ alkyl is optionally substituted with one or more substituents independently selected from the group consisting of $R^4$, $SO_2R^4$, $C(O)R^4$, $N(R^4)_2$, $C(O)N(R^4)_2$, $SO_2NH_2$, and OH.

In one embodiment of Formula (IIa), $R^4$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^4$ $C_1$-$C_6$ alkyl, $C_2$-$C_6$ alkenyl, and $C_2$-$C_6$ alkynyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $NHSO_2R^5$, $C(O)NR^5SO_2R^5$, $SO_2NH_2$, $SO_2NHR^5$, $SO_2N(R^5)_2$, $C(O)H$, $C(O)OH$, OH, CN, $NO_2$, F, Cl, Br and I; wherein each $R^4$ aryl, cycloalkyl, cycloalkenyl, heteroaryl, heterocycloalkyl, and heterocycloalkenyl is optionally substituted with one or more substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, (O), OH, CN, $NO_2$, F, Br and I. In another embodiment of Formula (IIa), $R^4$, at each occurrence, is independently selected from the group consisting of $C_1$-$C_6$ alkyl, aryl, heteroaryl, heterocycloalkyl, and cycloalkyl; wherein each $R^4$ $C_1$-$C_6$ alkyl is optionally substituted with one or more OH; wherein each $R^4$ aryl, cycloalkyl, heteroaryl, and heterocycloalkyl is optionally substituted with one or more substituents independently selected from the group consisting of $R^6$, $SO_2R^6$, $CO(O)R^6$, $NHS(O)_2R^6$, $SO_2NH_2$, $C(O)OH$, OH, CN, and F. In another embodiment of Formula (IIa), $R^4$, at each occurrence, is independently $C_1$-$C_6$ alkyl; wherein each $R^4$ $C_1$-$C_6$ alkyl is optionally substituted with one or more OH. In another embodiment of Formula (IIa), $R^4$, at each occurrence, is independently selected from the group consisting of aryl, heteroaryl, heterocycloalkyl, and cycloalkyl; wherein each $R^4$ aryl, cycloalkyl, heteroaryl, and heterocycloalkyl is optionally substituted with one or more substituents independently selected from the group consisting of $R^6$, $SO_2R^6$, $CO(O)R^6$, $NHS(O)_2R^6$, $SO_2NH_2$, $C(O)OH$, OH, CN, and F.

In one embodiment of Formula (IIa), $R^6$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^6$ $C_1$-$C_6$ alkyl, $C_2$-$C_6$ alkenyl, and $C_2$-$C_6$ alkynyl is optionally substituted with one or more substituents independently selected from the group consisting of halo and $R^{6A}$; and $R^{6A}$, at each occurrence, is independently selected from the group consisting of aryl, heteroaryl, heterocycloalkyl, heterocycloalkenyl, cycloalkyl, and cycloalkenyl; wherein each $R^{6A}$ aryl, heteroaryl, heterocycloalkyl, heterocycloalkenyl, cycloalkyl, and cycloalkenyl is optionally substituted with $C_1$-$C_6$ alkyl. In another embodiment of Formula (IIa), $R^6$, at each occurrence, is independently selected from the group consisting of $C_1$-$C_6$ alkyl, heteroaryl, and heterocycloalkyl; wherein each $R^6$ $C_1$-$C_6$ alkyl is optionally substituted with one or more substituents independently selected from the group consisting of halo and $R^{6A}$; and $R^{6A}$, at each occurrence, is independently heterocycloalkyl; wherein each $R^{6A}$ heterocycloalkyl is optionally substituted with $C_1$-$C_6$ alkyl.

In one embodiment of Formula (IIa), $R^{16}$ is selected from the group consisting of $NH_2$, $NHR^7$, $NHC(O)R^7$, $NHS(O)_2R^7$, $NHC(O)OR^7$, $NHC(O)NH_2$, $NHC(O)NHR^7$, and $NHC(O)N(R^7)_2$. In another embodiment of Formula (IIa), $R^{16}$ is selected from the group consisting of $NH_2$, $NHR^7$, $NHC(O)R^7$, and $NHC(O)OR^7$. In another embodiment of Formula (IIa), $R^{16}$ is $NH_2$. In another embodiment of Formula (IIa), $R^{16}$ is $NHR^7$. In another embodiment of Formula (IIa), $R^{16}$ is $NHC(O)R^7$. In another embodiment of Formula (IIa), $R^{16}$ is $NHC(O)OR^7$.

In one embodiment of Formula (IIa), $R^7$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^7$ $C_1$-$C_6$ alkyl, $C_2$-$C_6$ alkenyl, and $C_2$-$C_6$ alkynyl is optionally substituted with one or more substituents independently selected from the group consisting of $R^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHSO_2NH_2$, $NR^8SO_2NH_2$, $NHSO_2NHR^8$, $NR^8SO_2NHR^8$, $NHSO_2N(R^8)_2$, $NR^8SO_2N(R^8)_2$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $C(O)NHC(O)NH_2$, $C(O)NHC(O)NHR^8$, $C(O)NR^8C(O)NHR^8$, $C(O)NHC(O)N(R^8)_2$, $C(O)NR^8C(O)N(R^8)_2$, $SO_2NH_2$, $SO_2NHR^8$, $SO_2N(R^8)_2$, $C(O)H$, $C(O)OH$, OH, CN, $NO_2$, F, Cl, Br and I; wherein each $R^7$ aryl, cycloalkyl, cycloalkenyl, heteroaryl, heterocycloalkyl, and heterocycloalkenyl is optionally substituted with one or more substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $SO_2NHC(O)OH$, $SO_2NR^9C(O)OH$, $SO_2NHC(O)OR^9$, $SO_2NR^9C(O)OR^9$, $C(O)H$, $C(O)OH$, (O), OH, CN, $NO_2$, F, Cl, Br and I. In another embodiment of Formula (IIa), $R^7$, at each occurrence, is independently selected from the group consisting of $C_1$-$C_6$ alkyl, $C_2$-$C_6$ alkenyl, aryl, heteroaryl, heterocycloalkyl, heterocycloalkenyl, and cycloalkyl; wherein each $R^7$ $C_1$-$C_6$ alkyl and $C_2$-$C_6$ alkenyl is optionally substituted with one or more substituents independently selected from the group consisting of $R^8$, $SO_2R^8$, $NH_2$, $NHR^8$, $N(R^8)_2$, $NHS(O)_2R^8$, $NHSO_2N(R^8)_2$, $C(O)NHC(O)NH_2$, $SO_2NH_2$, and OH; wherein each $R^7$ aryl, cycloalkyl, heteroaryl, heterocycloalkenyl, and heterocycloalkyl is optionally substituted with one or more substituents independently selected from the group consisting of $R^9$, $SO_2R^9$, $C(O)R^9$, $CO(O)R^9$, $NH_2$, $NHR^9$, $NHS(O)_2R^9$, $NHC(O)NHR^9$, $C(O)NH_2$, $C(O)NHR^9$, $C(O)N(R^9)_2$, $SO_2NH_2$, $SO_2NHC(O)OR^9$, $C(O)OH$, (O), and OH.

In one embodiment of Formula (IIa), $R^8$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^8$ $C_1$-$C_6$ alkyl, $C_2$-$C_6$ alkenyl, and $C_2$-$C_6$ alkynyl is optionally substituted with one or more substituents independently selected from the group consisting of $NHR^{10}$, and aryl; wherein each $R^8$ aryl, heteroaryl, heterocycloalkyl, heterocycloalkenyl, cycloalkyl, and cycloalkenyl is optionally substituted with one or more substituents independently selected from the group consisting of $R^{11}$, $OR^{11}$, halo, $NH_2$, OH, and (O). In another embodiment of Formula (IIa), $R^8$, at each occurrence, is independently selected from the group consisting of $C_1$-$C_6$ alkyl, aryl, heteroaryl, heterocycloalkyl, heterocycloalkenyl, and cycloalkyl; wherein each $R^8$ $C_1$-$C_6$ alkyl is optionally substituted with one or more aryl; wherein each $R^8$ aryl, heteroaryl, heterocycloalkyl, and cycloalkyl is optionally substituted with one or more substituents independently selected from the group consisting of $R^{11}$, halo, $NH_2$, and OH.

In one embodiment of Formula (IIa), $R^9$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{13}$, $OR^{13}$, $SR^{13}$, $S(O)R^{13}$, $SO_2R^{13}$, $C(O)R^{13}$, $CO(O)R^{13}$, $OC(O)R^{13}$, $OC(O)OR^{13}$, $NH_2$, $NHR^{13}$, $N(R^{13})_2$, $NHC(O)R^{13}$, $NR^{13}C(O)R^{13}$, $NHS(O)_2R^{13}$, $NR^{13}S(O)_2R^{13}$, $NHC(O)OR^{13}$, $NR^{13}C(O)OR^{13}$, $NHC(O)NH_2$, $NHC(O)NHR^{13}$, $NHC(O)N(R^{13})_2$, $NR^{13}C(O)NHR^{13}$, $NR^{13}C(O)N(R^{13})_2$, $C(O)NH_2$, $C(O)NHR^{13}$, $C(O)N(R^{13})_2$, $C(O)NHOH$, $C(O)NHOR^{13}$, $C(O)NHSO_2R^{13}$, $C(O)NR^{13}SO_2R^{13}$, $SO_2NH_2$, $SO_2NHR^{13}$, $SO_2N(R^{13})_2$, $C(O)H$, $C(O)OH$, OH, CN, $NO_2$, F, Cl, Br and I; wherein each $R^9$ aryl, cycloalkyl, cycloalkenyl, heteroaryl, heterocycloalkyl, and heterocycloalkenyl is optionally substituted with one or more substituents independently selected from the group consisting of $R^{14}$, $OR^{14}$, $SR^{14}$, $S(O)R^{14}$, $SO_2R^{14}$, $C(O)R^{14}$, $CO(O)R^{14}$, $OC(O)R^{14}$, $OC(O)OR^{14}$, $NH_2$, $NHR^{14}$, $N(R^{14})_2$, $NHC(O)R^{14}$, $NR^{14}C(O)R^{14}$, $NHS(O)_2R^{14}$, $NR^{14}S(O)_2R^{14}$, $NHC(O)OR^{14}$, $NR^{14}C(O)OR^{14}$, $NHC(O)NH_2$, $NHC(O)NHR^{14}$, $NHC(O)N(R^{14})_2$, $NR^{14}C(O)NHR^{14}$, $NR^{14}C(O)N(R^{14})_2$, $C(O)NH_2$, $C(O)NHR^{14}$, $C(O)N(R^{14})_2$, $C(O)NHOH$, $C(O)NHOR^{14}$, $C(O)NHSO_2R^{14}$, $C(O)NR^{14}SO_2R^{14}$, $SO_2NH_2$, $SO_2NHR^{14}$, $SO_2N(R^{14})_2$, $C(O)H$, $C(O)OH$, (O), OH, CN, $NO_2$, F, Cl, Br and I. In another embodiment of Formula (IIa), $R^9$, at each occurrence, is independently selected from the group consisting of $C_1$-$C_6$ alkyl, aryl, heteroaryl, heterocycloalkyl, and cycloalkyl; wherein each $R^9$ $C_1$-$C_6$ alkyl is optionally substituted with one or more substituents independently selected from the group consisting of $R^{13}$, $OR^{13}$, $S(O)R^{13}$, $SO_2R^{13}$, OH, and F; wherein each $R^9$ aryl, heteroaryl, heterocycloalkyl, and cycloalkyl is optionally substituted with one or more substituents independently selected from the group consisting of $R^{14}$, OH, and F.

In one embodiment of Formula (IIa), $R^{11}$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^{11}$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, CN, $NO_2$, F, Cl, Br and I; wherein each $R^{11}$ aryl, cycloalkyl, cycloalkenyl, heteroaryl, heterocycloalkyl, and heterocycloalkenyl is optionally substituted with one or more substituents independently selected from the group consisting of $C_1$-$C_6$ alkyl, O—$C_1$-$C_6$ alkyl, $NH_2$, $C(O)NH_2$, $C(O)H$, $C(O)$ OH, OH, CN, $NO_2$, F, Cl, Br and I. In another embodiment of Formula (IIa), $R^{11}$, at each occurrence, is independently selected from the group consisting of $C_1$-$C_6$ alkyl and aryl; wherein each $R^{11}$ $C_1$-$C_6$ alkyl is optionally substituted with one or more $NH_2$; wherein each $R^{11}$ aryl is optionally substituted with one or more substituents independently selected from the group consisting of $C_1$-$C_6$ alkyl, and O—$C_1$-$C_6$ alkyl.

In one embodiment of Formula (IIa), $R^{13}$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^{13}$ $C_1$-$C_6$ alkyl, $C_2$-$C_6$ alkenyl, and $C_2$-$C_6$ alkynyl is optionally substituted with one or more substituents independently selected from the group consisting of aryl, $NH_2$, $C(O)NH_2$, $SO_2NH_2$, $C(O)H$, $C(O)OH$, OH, CN, $NO_2$, F, Cl, Br and I; wherein each $R^{13}$ aryl, cycloalkyl, cycloalkenyl, heteroaryl, heterocycloalkyl, and heterocycloalkenyl is optionally substituted with one or more substituents independently selected from the group consisting of $C_1$-$C_6$ alkyl, O—$C_1$-$C_6$ alkyl, $C_1$-$C_6$ alkyl-O—$C_1$-$C_6$ alkyl, $NH_2$, $C(O)NH_2$, $C(O)H$, $C(O)OH$, OH, CN, $NO_2$, F, Cl, Br and I. In another embodiment of Formula (IIa), $R^{13}$, at each occurrence, is independently selected from the group consisting of $C_1$-$C_6$ alkyl, aryl, heteroaryl, heterocycloalkyl, and cycloalkyl; wherein each $R^{13}$ $C_1$-$C_6$ alkyl is optionally substituted with one or more substituents independently aryl; wherein each $R^{13}$ aryl, cycloalkyl, heteroaryl, and heterocycloalkyl is optionally substituted with one or more substituents independently selected from the group consisting of $C_1$-$C_6$ alkyl and O—$C_1$-$C_6$ alkyl, and $C_1$-$C_6$ alkyl-O—$C_1$-$C_6$ alkyl.

In one embodiment of Formula (IIa), $R^{14}$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^{14}$ $C_1$-$C_6$ alkyl, $C_2$-$C_6$ alkenyl, and $C_2$-$C_6$ alkynyl is optionally substituted with one or more substituents independently selected from the group consisting of aryl, $NH_2$, $C(O)NH_2$, $SO_2NH_2$, $C(O)H$, $C(O)OH$, OH, CN, $NO_2$, F, Cl, Br and I; wherein each $R^{14}$ aryl, cycloalkyl, cycloalkenyl, heteroaryl, heterocycloalkyl, and heterocycloalkenyl is optionally substituted with one or more substituents independently selected from the group consisting of $C_1$-$C_6$ alkyl, O—$C_1$-$C_6$ alkyl, $C_1$-$C_6$ alkyl-O—$C_1$-$C_6$ alkyl, $NH_2$, $C(O)NH_2$, $C(O)H$, $C(O)OH$, OH, $NO_2$, F, Cl, Br and I. In another embodiment of Formula (IIa), $R^{14}$, at each occurrence, is $C_1$-$C_6$ alkyl; wherein each $R^{14}$ $C_1$-$C_6$ alkyl is optionally substituted with one or more OH.

In another embodiment of Formula (IIa), $R^2$ is selected from the group consisting of H and $C_1$-$C_6$ alkyl; wherein the $R^2$ $C_1$-$C_6$ alkyl is optionally substituted with one or more substituents independently selected from the group consisting of $R^4$, $SO_2R^4$, $C(O)R^4$, $N(R^4)_2$, $C(O)N(R^4)_2$, $SO_2NH_2$, and OH;

$R^4$, at each occurrence, is independently selected from the group consisting of $C_1$-$C_6$ alkyl, aryl, heteroaryl, heterocycloalkyl, and cycloalkyl; wherein each $R^4$ $C_1$-$C_6$ alkyl is optionally substituted with one or more OH; wherein each $R^4$ aryl, cycloalkyl, heteroaryl, and heterocycloalkyl is optionally substituted with one or more substituents independently selected from the group consisting of $R^6$, $SO_2R^6$, $CO(O)R^6$, $NHS(O)_2R^6$, $SO_2NH_2$, $C(O)OH$, OH, CN, and F;

$R^6$, at each occurrence, is independently selected from the group consisting of $C_1$-$C_6$ alkyl, heteroaryl, and heterocycloalkyl; wherein each $R^6$ $C_1$-$C_6$ alkyl is optionally substituted with one or more substituents independently selected from the group consisting of halo and $R^{6A}$;

$R^{6A}$, at each occurrence, is independently heterocycloalkyl; wherein each $R^{6A}$ heterocycloalkyl is optionally substituted with $C_1$-$C_6$ alkyl;

$R^{16}$ is selected from the group consisting of $NH_2$, $NHR^7$, $NHC(O)R^7$, and $NHC(O)OR^7$;

$R^7$, at each occurrence, is independently selected from the group consisting of $C_1$-$C_6$ alkyl, $C_2$-$C_6$ alkenyl, aryl, heteroaryl, heterocycloalkyl, heterocycloalkenyl, and cycloalkyl; wherein each $R^7 C_1$-$C_6$ alkyl, and $C_2$-$C_6$ alkenyl is optionally substituted with one or more substituents independently selected from the group consisting of $R^8$, $SO_2R^8$, $NH_2$, $NHR^8$, $N(R^8)_2$, $NHS(O)_2R^8$, $NHSO_2N(R^8)_2$, $C(O)NHC(O)NH_2$, $SO_2NH_2$, and OH; wherein each $R^7$ aryl, cycloalkyl, heteroaryl, and heterocycloalkyl is optionally substituted with one or more substituents independently selected from the group consisting of $R^9$, $SO_2R^9$, $C(O)R^9$, $CO(O)R^9$, $NH_2$, $NHR^9$, $NHS(O)_2R^9$, $NHC(O)NHR^9$, $C(O)NH_2$, $C(O)NHR^9$, $C(O)N(R^9)_2$, $SO_2NH_2$, $SO_2NHC(O)OR^9$, $C(O)OH$, (O), and OH;

$R^8$, at each occurrence, is independently selected from the group consisting of $C_1$-$C_6$ alkyl, aryl, heteroaryl, heterocycloalkyl, heterocycloalkenyl, and cycloalkyl; wherein each $R^8$ $C_1$-$C_6$ alkyl is optionally substituted with one or more aryl; wherein each $R^8$ aryl, heteroaryl, heterocycloalkyl, heterocycloalkenyl, and cycloalkyl is optionally substituted with one or more substituents independently selected from the group consisting of $R^{11}$, halo, $NH_2$, and OH;

$R^9$, at each occurrence, is independently selected from the group consisting of $C_1$-$C_6$ alkyl, aryl, heteroaryl, heterocycloalkyl, and cycloalkyl; wherein each $R^9$ $C_1$-$C_6$ alkyl is optionally substituted with one or more substituents independently selected from the group consisting of $R^{13}$, $OR^{13}$, $S(O)R^{13}$, $SO_2R^{13}$, OH, and F; wherein each $R^9$ aryl, heteroaryl, heterocycloalkyl, and cycloalkyl is optionally substituted with one or more substituents independently selected from the group consisting of $R^{14}$, OH, and F;

$R^{11}$, at each occurrence, is independently selected from the group consisting of $C_1$-$C_6$ alkyl and aryl; wherein each $R^{11}$ $C_1$-$C_6$ alkyl is optionally substituted with one or more $NH_2$; wherein each $R^{11}$ aryl is optionally substituted with one or more substituents independently selected from the group consisting of $C_1$-$C_6$ alkyl, and O—$C_1$-$C_6$ alkyl;

$R^{13}$, at each occurrence, is independently selected from the group consisting of $C_1$-$C_6$ alkyl, aryl, heteroaryl, heterocycloalkyl, and cycloalkyl; wherein each $R^{13}$ $C_1$-$C_6$ alkyl is optionally substituted with one or more aryl; wherein each $R^{13}$ aryl, heteroaryl, heterocycloalkyl, and cycloalkyl is optionally substituted with one or more substituents independently selected from the group consisting of $C_1$-$C_6$ alkyl, O—$C_1$-$C_6$ alkyl, and $C_1$-$C_6$ alkyl-O—$C_1$-$C_6$ alkyl; and $R^{14}$, at each occurrence, is independently $C_1$-$C_6$ alkyl; wherein each $R^{14}$ $C_1$-$C_6$ alkyl is optionally substituted with one or more OH.

Still another embodiment pertains to compounds of Formula (IIa), selected from the group consisting of (3R)—N-{5-chloro-4-[1-(3-fluorobenzyl)-2,3-dihydro-1H-indol-6-yl]pyridin-2-yl}piperidine-3-carboxamide;

(3R)—N-[5-chloro-4-(2,3-dihydro-1H-indol-6-yl)pyridin-2-yl]piperidine-3-carboxamide;

(3R)—N-{5-chloro-4-[1-(tetrahydro-2H-pyran-4-ylmethyl)-2,3-dihydro-1H-indol-6-yl]pyridin-2-yl}piperidine-3-carboxamide;

trans-N-{5-chloro-4-[1-(3-fluorobenzyl)-2,3-dihydro-1H-indol-6-yl]pyridin-2-yl}cyclohexane-1,4-diamine;

trans-4-({5-chloro-4-[1-(3-fluorobenzyl)-2,3-dihydro-1H-indol-6-yl]pyridin-2-yl}amino)cyclohexanol;

N-(5-chloro-4-{1-[(5-methylpyrazin-2-yl)methyl]-2,3-dihydro-1H-indol-6-yl}pyridin-2-yl)piperidine-3-carboxamide;

N-[5-chloro-4-(1-{4-[(methylsulfonyl)amino]benzyl}-2,3-dihydro-1H-indol-6-yl)pyridin-2-yl]piperidine-3-carboxamide;

N-(5-chloro-4-{1-[4-fluoro-3-(methylsulfonyl)benzyl]-2,3-dihydro-1H-indol-6-yl}pyridin-2-yl)piperidine-3-carboxamide;

N-(5-chloro-4-{1-[(2-methylpyrimidin-5-yl)methyl]-2,3-dihydro-1H-indol-6-yl}pyridin-2-yl)piperidine-3-carboxamide;

N-(5-chloro-4-{1-[3-(methylsulfonyl)benzyl]-2,3-dihydro-1H-indol-6-yl}pyridin-2-yl)piperidine-3-carboxamide;

N-(5-chloro-4-{1-[(6-methylpyridin-3-yl)methyl]-2,3-dihydro-1H-indol-6-yl}pyridin-2-yl)piperidine-3-carboxamide;

N-{5-chloro-4-[1-(pyrrolidin-3-ylmethyl)-2,3-dihydro-1H-indol-6-yl]pyridin-2-yl}piperidine-3-carboxamide;

4-[(6-{5-chloro-2-[(piperidin-3-ylcarbonyl)amino]pyridin-4-yl}-2,3-dihydro-1H-indol-1-yl)methyl]benzoic acid;

N-(5-chloro-4-{1-[4-(methylsulfonyl)benzyl]-2,3-dihydro-1H-indol-6-yl}pyridin-2-yl)piperidine-3-carboxamide;

methyl 4-[(6-{5-chloro-2-[(piperidin-3-ylcarbonyl)amino]pyridin-4-yl}-2,3-dihydro-1H-indol-1-yl)methyl]benzoate;

N-{5-chloro-4-[1-(pyrimidin-5-ylmethyl)-2,3-dihydro-1H-indol-6-yl]pyridin-2-yl}piperidine-3-carboxamide;

N-[5-chloro-4-(1-{[6-(trifluoromethyl)pyridin-2-yl]methyl}-2,3-dihydro-1H-indol-6-yl)pyridin-2-yl]piperidine-3-carboxamide;

N-{5-chloro-4-[1-(quinolin-6-ylmethyl)-2,3-dihydro-1H-indol-6-yl]pyridin-2-yl}piperidine-3-carboxamide;

N-{4-[1-(1H-benzimidazol-2-ylmethyl)-2,3-dihydro-1H-indol-6-yl]-5-chloropyridin-2-yl}piperidine-3-carboxamide;

N-{5-chloro-4-[1-(2,3-dihydro-1,4-benzodioxin-5-ylmethyl)-2,3-dihydro-1H-indol-6-yl]pyridin-2-yl}piperidine-3-carboxamide;

N-(5-chloro-4-{1-[(1-methyl-1H-benzimidazol-2-yl)methyl]-2,3-dihydro-1H-indol-6-yl}pyridin-2-yl)piperidine-3-carboxamide;

N-(5-chloro-4-{1-[(1-methyl-1H-benzotriazol-5-yl)methyl]-2,3-dihydro-1H-indol-6-yl}pyridin-2-yl)piperidine-3-carboxamide;

N-{4-[1-(1,3-benzodioxol-4-ylmethyl)-2,3-dihydro-1H-indol-6-yl]-5-chloropyridin-2-yl}piperidine-3-carboxamide;

N-{5-chloro-4-[1-(4-methylbenzyl)-2,3-dihydro-1H-indol-6-yl]pyridin-2-yl}piperidine-3-carboxamide;

N-{5-chloro-4-[1-(quinoxalin-6-ylmethyl)-2,3-dihydro-1H-indol-6-yl]pyridin-2-yl}piperidine-3-carboxamide;

N-{5-chloro-4-[1-(pyrazin-2-ylmethyl)-2,3-dihydro-1H-indol-6-yl]pyridin-2-yl}piperidine-3-carboxamide;

N-{5-chloro-4-[1-(2,3-dihydro[1,4]dioxino[2,3-b]pyridin-7-ylmethyl)-2,3-dihydro-1H-indol-6-yl]pyridin-2-yl}piperidine-3-carboxamide;

N-[5-chloro-4-(1-{[6-(methylsulfonyl)pyridin-3-yl]methyl}-2,3-dihydro-1H-indol-6-yl)pyridin-2-yl]piperidine-3-carboxamide;

N-{5-chloro-4-[1-(4-sulfamoylbenzyl)-2,3-dihydro-1H-indol-6-yl]pyridin-2-yl}piperidine-3-carboxamide;

N-(5-chloro-4-{1-[3-fluoro-4-(methylsulfonyl)benzyl]-2,3-dihydro-1H-indol-6-yl}pyridin-2-yl)piperidine-3-carboxamide;

N-(5-chloro-4-{1-[4-(2H-tetrazol-5-yl)benzyl]-2,3-dihydro-1H-indol-6-yl}pyridin-2-yl)piperidine-3-carboxamide;

N-{5-chloro-4-[1-(pyrrolidin-2-ylmethyl)-2,3-dihydro-1H-indol-6-yl]pyridin-2-yl}piperidine-3-carboxamide;

N-(5-chloro-4-{1-[(1-methylpiperidin-4-yl)methyl]-2,3-dihydro-1H-indol-6-yl}pyridin-2-yl)piperidine-3-carboxamide;

N-(5-chloro-4-{1-[2-(dimethylamino)-2-oxoethyl]-2,3-dihydro-1H-indol-6-yl}pyridin-2-yl)piperidine-3-carboxamide;

N-(5-chloro-4-{1-[2-(morpholin-4-yl)-2-oxoethyl]-2,3-dihydro-1H-indol-6-yl}pyridin-2-yl)piperidine-3-carboxamide;

N-(5-chloro-4-{1-[2-oxo-2-(pyrrolidin-1-yl)ethyl]-2,3-dihydro-1H-indol-6-yl}pyridin-2-yl)piperidine-3-carboxamide; or a pharmaceutically acceptable salt thereof.

Embodiments of Formula (IIIa)

In one aspect, the present invention provides compounds of Formula (IIIa) or a pharmaceutically acceptable salt thereof,

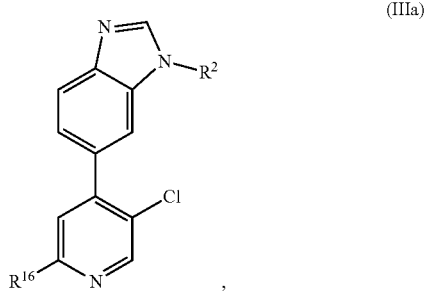

(IIIa)

wherein $R^2$ is selected from the group consisting of H, $C_1$-$C_6$ alkyl, $C_2$-$C_6$ alkenyl, and $C_2$-$C_6$ alkynyl; wherein the $R^2$ $C_1$-$C_6$ alkyl, $C_2$-$C_6$ alkenyl, and $C_2$-$C_6$ alkynyl are optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $SO_2NHC(O)R^4$, $SO_2NR^4C(O)R^4$, $NHS(O)_2R^4$, $NR^4S(O)_2R^4$, $NHC(O)OR^4$, $NR^4C(O)OR^4$, $SO_2NHC(O)OR^4$, $SO_2NR^4C(O)OR^4$, $NHSO_2NHC(O)OR^4$, $NHSO_2NR^4C(O)OR^4$, $NR^4SO_2NR^4C(O)OR^4$, $NR^4SO_2NHC(O)OR^4$, $NHC(O)NH_2$, $NHC(O)NHR^4$, $NHC(O)N(R^4)_2$, $NR^4C(O)NHR^4$, $NR^4C(O)N(R^4)_2$, $OC(O)NH_2$, $OC(O)NHR^4$, $OC(O)N(R^4)_2$, $OC(O)NHSO_2R^4$, $OC(O)NR^4SO_2R^4$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $OSO_2NH_2$, $OSO_2NHR^4$, $OSO_2N(R^4)_2$, $C(O)NHCN$, $C(O)NR^4CN$, $S(O)NR^4$, $S(O)NSO_2R^4$, $C(O)H$, $C(O)OH$, $(O)$, $OH$, $CN$, $NO_2$, $F$, $Cl$, $Br$ and $I$;

$R^4$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^4$ $C_1$-$C_6$ alkyl, $C_2$-$C_6$ alkenyl, and $C_2$-$C_6$ alkynyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $OH$, $CN$, $NO_2$, $F$, $Cl$, $Br$ and $I$; wherein each $R^4$ aryl, cycloalkyl, cycloalkenyl, heteroaryl, heterocycloalkyl, and heterocycloalkenyl is optionally substituted with one or more substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $(O)$, $OH$, $CN$, $NO_2$, $F$, $Br$ and $I$;

$R^5$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl;

$R^6$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^6$ $C_1$-$C_6$ alkyl, $C_2$-$C_6$ alkenyl, and $C_2$-$C_6$ alkynyl is optionally substituted with one or more substituents independently selected from the group consisting of halo and $R^{6A}$;

$R^{6A}$, at each occurrence, is independently selected from the group consisting of aryl, heteroaryl, heterocycloalkyl, heterocycloalkenyl, cycloalkyl, and cycloalkenyl; wherein each $R^{6A}$ aryl, heteroaryl, heterocycloalkyl, heterocycloalkenyl, cycloalkyl, and cycloalkenyl is optionally substituted with $C_1$-$C_6$ alkyl;

$R^{16}$ is selected from the group consisting of $NH_2$, $NHR^7$, $NHC(O)R^7$, $NHS(O)_2R^7$, $NHC(O)OR^7$, $NHC(O)NH_2$, $NHC(O)NHR^7$, and $NHC(O)N(R^7)_2$;

$R^7$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^7$ $C_1$-$C_6$ alkyl, $C_2$-$C_6$ alkenyl, and $C_2$-$C_6$ alkynyl is optionally substituted with one or more substituents independently selected from the group consisting of $R^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHSO_2NH_2$, $NR^8SO_2NH_2$, $NHSO_2NHR^8$, $NR^8SO_2NHR^8$, $NHSO_2N(R^8)_2$, $NR^8SO_2N(R^8)_2$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $C(O)NHC(O)NH_2$, $C(O)NR^8C(O)NH_2$, $C(O)NHC(O)NHR^8$, $C(O)NR^8C(O)NHR^8$, $C(O)NHC(O)N(R^8)_2$, $C(O)NR^8C(O)N(R^8)_2$, $SO_2NH_2$, $SO_2NHR^8$, $SO_2N(R^8)_2$, $C(O)H$, $C(O)OH$, $OH$, $CN$, $NO_2$, $F$, $Cl$, $Br$ and $I$; wherein each $R^7$ aryl, cycloalkyl, cycloalkenyl, heteroaryl, heterocycloalkyl, and heterocycloalkenyl is optionally substituted with one or more substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $SO_2NHC(O)OH$, $SO_2NR^9C(O)OH$, $SO_2NHC(O)OR^9$, $SO_2NR^9C(O)OR^9$, $C(O)H$, $C(O)OH$, $(O)$, $OH$, $CN$, $NO_2$, $F$, $Cl$, $Br$ and $I$;

$R^8$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^8$ $C_1$-$C_6$ alkyl, $C_2$-$C_6$ alkenyl, and $C_2$-$C_6$ alkynyl is optionally substituted with one or more substituents independently selected from the group consisting of $NHR^{10}$, and aryl; wherein each $R^8$ aryl, heteroaryl, heterocycloalkyl, heterocycloalkenyl, cycloalkyl, and cycloalkenyl is optionally substituted with one or more substituents independently selected from the group consisting of $R^{11}$, $OR^{11}$, halo, $NH_2$, $OH$, and $(O)$;

$R^9$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{13}$, $OR^{13}$, $SR^{13}$, $S(O)R^{13}$, $SO_2R^{13}$, $C(O)R^{13}$, $CO(O)R^{13}$, $OC(O)R^{13}$, $OC(O)OR^{13}$, $NH_2$, $NHR^{13}$, $N(R^{13})_2$, $NHC(O)R^{13}$, $NR^{13}C(O)R^{13}$, $NHS(O)_2R^{13}$, $NR^{13}S(O)_2R^{13}$, $NHC(O)OR^{13}$, $NR^{13}C(O)OR^{13}$, $NHC(O)NH_2$, $NHC(O)NHR^{13}$, $NHC(O)N(R^{13})_2$, $NR^{13}C(O)NHR^{13}$, $NR^{13}C(O)N(R^{13})_2$, $C(O)NH_2$, $C(O)NHR^{13}$, $C(O)N(R^{13})_2$, $C(O)NHOH$, $C(O)NHOR^{13}$, $C(O)NHSO_2R^{13}$, $C(O)NR^{13}SO_2R^{13}$, $SO_2NH_2$, $SO_2NHR^{13}$, $SO_2N(R^{13})_2$, $C(O)H$, $C(O)OH$, $OH$, $CN$, $NO_2$, $F$, $Cl$, $Br$ and $I$; wherein each $R^9$ aryl, cycloalkyl, cycloalkenyl, heteroaryl, heterocycloalkyl, and heterocycloalkenyl is optionally substituted with one or more substituents independently selected from the group consisting of $R^{14}$, $OR^{14}$, $SR^{14}$, $S(O)R^{14}$, $SO_2R^{14}$, $C(O)R^{14}$, $CO(O)R^{14}$, $OC(O)R^{14}$, $OC(O)OR^{14}$, $NH_2$, $NHR^{14}$, $N(R^{14})_2$, $NHC(O)R^{14}$, $NR^{14}C(O)R^{14}$, $NHS(O)_2R^{14}$, $NR^{14}S(O)_2R^{14}$, $NHC(O)OR^{14}$, $NR^{14}C(O)OR^{14}$, $NHC(O)NH_2$, $NHC(O)NHR^{14}$, $NHC(O)N(R^{14})_2$, $NR^{14}C(O)NHR^{14}$, $NR^{14}C(O)N(R^{14})_2$, $C(O)NH_2$, $C(O)NHR^{14}$, $C(O)N(R^{14})_2$, $C(O)NHOH$, $C(O)NHOR^{14}$, $C(O)NHSO_2R^{14}$, $C(O)NR^{14}SO_2R^{14}$, $SO_2NH_2$, $SO_2NHR^{14}$, $SO_2N(R^{14})_2$, $C(O)H$, $C(O)OH$, $(O)$, $OH$, $CN$, $NO_2$, $F$, $Cl$, $Br$ and $I$;

$R^{10}$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl;

$R^{11}$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^{11}$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, $OH$, $CN$, $NO_2$, $F$, $Cl$, $Br$ and $I$; wherein each $R^{11}$ aryl, cycloalkyl, cycloalkenyl, heteroaryl, heterocycloalkyl, and heterocycloalkenyl is optionally substituted with one or more substituents independently selected from the group consisting of $C_1$-$C_6$ alkyl, $O$—$C_1$-$C_6$ alkyl, $NH_2$, $C(O)NH_2$, $C(O)H$, $C(O)OH$, $OH$, $CN$, $NO_2$, $F$, $Cl$, $Br$ and $I$;

$R^{13}$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^{13}$ $C_1$-$C_6$ alkyl, $C_2$-$C_6$ alkenyl, and $C_2$-$C_6$ alkynyl is optionally substituted with one or more substituents independently selected from the group consisting of aryl, $NH_2$, $C(O)NH_2$, $SO_2NH_2$, $C(O)H$, $C(O)OH$, $OH$, $CN$, $NO_2$, $F$, $Cl$, $Br$ and $I$; wherein each $R^{13}$ aryl, cycloalkyl, cycloalkenyl, heteroaryl, heterocycloalkyl, and heterocycloalkenyl is optionally substituted with one or more substituents independently selected from the group consisting of $C_1$-$C_6$ alkyl, $O$—$C_1$-$C_6$ alkyl, $C_1$-$C_6$ alkyl-$O$—$C_1$-$C_6$ alkyl, $NH_2$, $C(O)NH_2$, $C(O)H$, $C(O)OH$, $OH$, $CN$, $NO_2$, $F$, $Cl$, $Br$ and $I$; and $R^{14}$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^{14}$ $C_1$-$C_6$ alkyl, $C_2$-$C_6$ alkenyl, and $C_2$-$C_6$ alkynyl is optionally substituted with one or more substituents independently selected from the group consisting of aryl, $NH_2$, $C(O)NH_2$, $SO_2NH_2$, $C(O)H$, $C(O)OH$, $OH$, $CN$, $NO_2$, $F$, $Cl$, $Br$ and $I$; wherein each $R^{14}$ aryl, cycloalkyl, cycloalkenyl, heteroaryl, heterocycloalkyl, and heterocycloalkenyl is optionally substituted with one or more substituents independently selected from the group consisting of $C_1$-$C_6$ alkyl, $O$—$C_1$-$C_6$ alkyl, $C_1$-$C_6$ alkyl-$O$—$C_1$-$C_6$ alkyl, $NH_2$, $C(O)NH_2$, $C(O)H$, $C(O)OH$, $OH$, $NO_2$, $F$, $Cl$, $Br$ and $I$.

In one embodiment of Formula (IIIa), $R^2$ is selected from the group consisting of H, $C_1$-$C_6$ alkyl, $C_2$-$C_6$ alkenyl, and $C_2$-$C_6$ alkynyl; wherein the $R^2$ $C_1$-$C_6$ alkyl, $C_2$-$C_6$ alkenyl, and $C_2$-$C_6$ alkynyl are optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $SO_2NHC(O)R^4$, $SO_2NR^4C(O)R^4$, $NHS(O)_2R^4$, $NR^4S(O)_2R^4$, $NHC(O)OR^4$, $NR^4C(O)OR^4$, $SO_2NHC(O)OR^4$, $SO_2NR^4C(O)OR^4$, $NHSO_2NHC(O)OR^4$, $NHSO_2NR^4C(O)OR^4$, $NR^4SO_2NR^4C(O)OR^4$, $NR^4SO_2NHC(O)OR^4$, $NHC(O)NH_2$, $NHC(O)NHR^4$, $NHC(O)N(R^4)_2$, $NR^4C(O)NHR^4$, $NR^4C(O)N(R^4)_2$, $OC(O)NH_2$, $OC(O)NHR^4$, $OC(O)N(R^4)_2$, $OC(O)NHSO_2R^4$, $OC(O)NR^4SO_2R^4$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $OSO_2NH_2$, $OSO_2NHR^4$, $OSO_2N(R^4)_2$, $C(O)NHCN$, $C(O)NR^4CN$, $S(O)NR^4$, $S(O)NSO_2R^4$, $C(O)H$, $C(O)OH$, $(O)$, $OH$, $CN$, $NO_2$, $F$, $Cl$, $Br$ and $I$. In another embodiment of Formula (IIIa), $R^2$ is selected from the group consisting of H and $C_1$-$C_6$ alkyl; wherein the $R^2$ $C_1$-$C_6$ alkyl is optionally substituted with one or more substituents independently selected from the group consisting of $R^4$, $SO_2R^4$, $C(O)R^4$, $N(R^4)_2$, $C(O)N(R^4)_2$, $SO_2NH_2$, and $OH$. In another embodiment of Formula (IIIa), $R^2$ is H. In another embodiment of Formula (IIIa), $R^2$ is $C_1$-$C_6$ alkyl; wherein the $R^2$ $C_1$-$C_6$ alkyl is optionally substituted with one or more substituents independently selected from the group consisting of $R^4$, $SO_2R^4$, $C(O)R^4$, $N(R^4)_2$, $C(O)N(R^4)_2$, $SO_2NH_2$, and $OH$.

In one embodiment of Formula (IIIa), $R^4$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^4$ $C_1$-$C_6$ alkyl, $C_2$-$C_6$ alkenyl, and $C_2$-$C_6$ alkynyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, $OH$, $CN$, $NO_2$, $F$, $Cl$, $Br$ and $I$; wherein each $R^4$ aryl, cycloalkyl, cycloalkenyl, heteroaryl, heterocycloalkyl, and heterocycloalkenyl is optionally substituted with one or more substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, $(O)$, $OH$, $CN$, $NO_2$, F, Br and I. In another embodiment of Formula (IIIa), $R^4$, at each occurrence, is independently selected from the group consisting of $C_1$-$C_6$ alkyl, aryl, heteroaryl, heterocycloalkyl, and cycloalkyl; wherein each $R^4$ $C_1$-$C_6$ alkyl is optionally substituted with one or more OH; wherein each $R^4$ aryl, cycloalkyl, heteroaryl, and heterocycloalkyl is optionally substituted with one or more substituents independently selected from the group consisting of $R^6$, $SO_2R^6$, $CO(O)R^6$, $NHS(O)_2R^6$, $SO_2NH_2$, $C(O)OH$, $OH$, $CN$, and F. In another embodiment of Formula (IIIa), $R^4$, at each occurrence, is independently $C_1$-$C_6$ alkyl; wherein each $R^4$ $C_1$-$C_6$ alkyl is optionally substituted with one or more OH. In another embodiment of Formula (IIIa), $R^4$, at each occurrence, is independently selected from the group consisting of aryl, heteroaryl, heterocycloalkyl, and cycloalkyl; wherein each $R^4$ aryl, cycloalkyl, heteroaryl, and heterocycloalkyl is optionally substituted with one or more substituents independently selected from the group consisting of $R^6$, $SO_2R^6$, $CO(O)R^6$, $NHS(O)_2R^6$, $SO_2NH_2$, $C(O)OH$, $OH$, CN, and F.

In one embodiment of Formula (IIIa), $R^6$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^6$ $C_1$-$C_6$ alkyl, $C_2$-$C_6$ alkenyl, and $C_2$-$C_6$ alkynyl is optionally substituted with one or more substituents independently selected from the group consisting of halo and $R^{6A}$; and $R^{6A}$, at each occurrence, is independently selected from the group consisting of aryl, heteroaryl, heterocycloalkyl, heterocycloalkenyl, cycloalkyl, and cycloalkenyl; wherein each $R^{6A}$ aryl, heteroaryl, heterocycloalkyl, heterocycloalkenyl, cycloalkyl, and cycloalkenyl is optionally substituted with $C_1$-$C_6$ alkyl. In another embodiment of Formula (Ma), $R^6$, at each occurrence, is independently selected from the group consisting of $C_1$-$C_6$ alkyl, heteroaryl, and heterocycloalkyl; wherein each $R^6$ $C_1$-$C_6$ alkyl is optionally substituted with one or more substituents independently selected from the group consisting of halo and $R^{6A}$; and $R^{6A}$, at each occurrence, is independently heterocycloalkyl; wherein each $R^{6A}$ heterocycloalkyl is optionally substituted with $C_1$-$C_6$ alkyl.

In one embodiment of Formula (Ma), $R^{16}$ is selected from the group consisting of $NH_2$, $NHR^7$, $NHC(O)R^7$, $NHS(O)_2R^7$, $NHC(O)OR^7$, $NHC(O)NH_2$, $NHC(O)NHR^7$, and $NHC(O)N(R^7)_2$. In another embodiment of Formula (Ma), $R^{16}$ is selected from the group consisting of $NH_2$, $NHR^7$, $NHC(O)R^7$, and $NHC(O)OR^7$. In another embodiment of Formula (IIIa), $R^{16}$ is $NH_2$. In another embodiment of Formula (IIIa), $R^{16}$ is $NHR^7$. In another embodiment of Formula (IIIa), $R^{16}$ is $NHC(O)R^7$. In another embodiment of Formula (IIIa), $R^{16}$ is $NHC(O)OR^7$.

In one embodiment of Formula (IIIa), $R^7$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, cycloalkyl, and cycloalkenyl; wherein each $R^7$ $C_1$-$C_6$ alkyl, $C_2$-$C_6$ alkenyl, and $C_2$-$C_6$ alkynyl is optionally substituted with one or more substituents independently selected from the group consisting of $R^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHSO_2NH_2$, $NR^8SO_2NH_2$, $NHSO_2NHR^8$, $NR^8SO_2NHR^8$, $NHSO_2N(R^8)_2$, $NR^8SO_2N(R^8)_2$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $C(O)NHC(O)NH_2$, $C(O)NR^8C(O)NH_2$, $C(O)NHC(O)NHR^8$, $C(O)NR^8C(O)NHR^8$, $C(O)NHC(O)N(R^8)_2$, $C(O)NR^8C(O)N(R^8)_2$, $SO_2NH_2$, $SO_2NHR^8$, $SO_2N(R^8)_2$, $C(O)H$, $C(O)OH$, $OH$, CN, $NO_2$, F, Cl, Br and I; wherein each $R^7$ aryl, cycloalkyl, cycloalkenyl, heteroaryl, heterocycloalkyl, and heterocycloalkenyl is optionally substituted with one or more substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $SO_2NHC(O)OH$, $SO_2NR^9C(O)OH$, $SO_2NHC(O)OR^9$, $SO_2NR^9C(O)OR^9$, $C(O)H$, $C(O)OH$, $(O)$, $OH$, $CN$, $NO_2$, F, Cl, Br and I. In another embodiment of Formula (IIIa), $R^7$, at each occurrence, is independently selected from the group consisting of $C_1$-$C_6$ alkyl, $C_2$-$C_6$ alkenyl, aryl, heteroaryl, heterocycloalkyl, heterocycloalkenyl, and cycloalkyl; wherein each $R^7$ $C_1$-$C_6$ alkyl and $C_2$-$C_6$ alkenyl is optionally substituted with one or more substituents independently selected from the group consisting of $R^8$, $SO_2R^8$, $NH_2$, $NHR^8$, $N(R^8)_2$, $NHS(O)_2R^8$, $NHSO_2N(R^8)_2$, $C(O)NHC(O)NH_2$, $SO_2NH_2$, and OH; wherein each $R^7$ aryl, cycloalkyl, heteroaryl, heterocycloalkenyl, and heterocycloalkyl is optionally substituted with one or more substituents independently selected from the group consisting of $R^9$, $SO_2R^9$, $C(O)R^9$, $CO(O)R^9$, $NH_2$, $NHR^9$, $NHS(O)_2R^9$, $NHC(O)NHR^9$, $C(O)NH_2$, $C(O)NHR^9$, $C(O)N(R^9)_2$, $SO_2NH_2$, $SO_2NHC(O)OR^9$, $C(O)OH$, $(O)$, and OH.

In one embodiment of Formula (IIIa), $R^8$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^8$ $C_1$-$C_6$ alkyl, $C_2$-$C_6$ alkenyl, and $C_2$-$C_6$ alkynyl is optionally substituted with one or more substituents independently selected from the group consisting of $NHR^{10}$, and aryl; wherein each $R^8$ aryl, heteroaryl, heterocycloalkyl, heterocycloalkenyl, cycloalkyl, and cycloalkenyl is optionally substituted with one or more substituents independently selected from the group consisting of $R^{11}$, $OR^{11}$, halo, $NH_2$, OH, and $(O)$. In another embodiment of Formula (IIIa), $R^8$, at each occurrence, is independently selected from the group consisting of $C_1$-$C_6$ alkyl, aryl, heteroaryl, heterocycloalkyl, heterocycloalkenyl, and cycloalkyl; wherein each $R^8$ $C_1$-$C_6$ alkyl is optionally substituted with one or more aryl; wherein each $R^8$ aryl, heteroaryl, heterocycloalkyl, and cycloalkyl is optionally substituted with one or more substituents independently selected from the group consisting of $R^{11}$, halo, $NH_2$, and OH.

In one embodiment of Formula (IIIa), $R^9$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{13}$, $OR^{13}$, $SR^{13}$, $S(O)R^{13}$, $SO_2R^{13}$, $C(O)R^{13}$, $CO(O)R^{13}$, $OC(O)R^{13}$, $OC(O)OR^{13}$, $NH_2$, $NHR^{13}$, $N(R^{13})_2$, $NHC(O)R^{13}$, $NR^{13}C(O)R^{13}$, $NHS(O)_2R^{13}$, $NR^{13}S(O)_2R^{13}$, $NHC(O)OR^{13}$, $NR^{13}C(O)OR^{13}$, $NHC(O)NH_2$, $NHC(O)NHR^{13}$, $NHC(O)N(R^{13})_2$, $NR^{13}C(O)NHR^{13}$, $NR^{13}C(O)N(R^{13})_2$, $C(O)NH_2$, $C(O)NHR^{13}$, $C(O)N(R^{13})_2$, $C(O)NHOH$, $C(O)NHOR^{13}$, $C(O)NHSO_2R^{13}$, $C(O)NR^{13}SO_2R^{13}$, $SO_2NH_2$, $SO_2NHR^{13}$, $SO_2N(R^{13})_2$, $C(O)H$, $C(O)OH$, $OH$, $CN$, $NO_2$, F, Cl, Br and I; wherein each $R^9$ aryl, cycloalkyl, cycloalkenyl, heteroaryl, heterocycloalkyl, and heterocycloalkenyl is optionally substituted with one or more substituents independently selected from the group consisting of $R^{14}$, $OR^{14}$, $SR^{14}$, $S(O)R^{14}$, $SO_2R^{14}$, $C(O)R^{14}$, $CO(O)R^{14}$, $OC(O)R^{14}$, $OC(O)OR^{14}$, $NH_2$, $NHR^{14}$, $N(R^{14})_2$, $NHC(O)R^{14}$, $NR^{14}C(O)R^{14}$, $NHS(O)_2R^{14}$, $NR^{14}S(O)_2R^{14}$, $NHC(O)OR^{14}$, $NR^{14}C(O)OR^{14}$, $NHC(O)NH_2$, $NHC(O)NHR^{14}$, $NHC(O)N(R^{14})_2$, $NR^{14}C(O)NHR^{14}$, $NR^{14}C(O)N(R^{14})_2$, $C(O)NH_2$, $C(O)NHR^{14}$, $C(O)N(R^{14})_2$, $C(O)NHOH$, $C(O)NHOR^{14}$, $C(O)NHSO_2R^{14}$, $C(O)NR^{14}SO_2R^{14}$, $SO_2NH_2$, $SO_2NHR^{14}$, $SO_2N(R^{14})_2$, $C(O)H$, $C(O)OH$, (O), $OH$, $CN$, $NO_2$, F, Cl, Br and I. In another embodiment of Formula (IIIa), $R^9$, at each occurrence, is independently selected from the group consisting of $C_1$-$C_6$ alkyl, aryl, heteroaryl, heterocycloalkyl, and cycloalkyl; wherein each $R^9$ $C_1$-$C_6$ alkyl is optionally substituted with one or more substituents independently selected from the group consisting of $R^{13}$, $OR^{13}$, $S(O)R^{13}$, $SO_2R^{13}$, $OH$, and F; wherein each $R^9$ aryl, heteroaryl, heterocycloalkyl, and cycloalkyl is optionally substituted with one or more substituents independently selected from the group consisting of $R^{14}$, $OH$, and F.

In one embodiment of Formula (IIIa), $R^{11}$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^{11}$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, $OH$, $CN$, $NO_2$, F, Cl, Br and I; wherein each $R^{11}$ aryl, cycloalkyl, cycloalkenyl, heteroaryl, heterocycloalkyl, and heterocycloalkenyl is optionally substituted with one or more substituents independently selected from the group consisting of $C_1$-$C_6$ alkyl, O—$C_1$-$C_6$ alkyl, $NH_2$, $C(O)NH_2$, $C(O)H$, $C(O)OH$, $OH$, $CN$, $NO_2$, F, Cl, Br and I. In another embodiment of Formula (IIIa), $R^{11}$, at each occurrence, is independently selected from the group consisting of $C_1$-$C_6$ alkyl and aryl; wherein each $R^{11}$ $C_1$-$C_6$ alkyl is optionally substituted with one or more $NH_2$; wherein each $R^{11}$ aryl is optionally substituted with one or more substituents independently selected from the group consisting of $C_1$-$C_6$ alkyl, and O—$C_1$-$C_6$ alkyl.

In one embodiment of Formula (IIIa), $R^{13}$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^{13}$ $C_1$-$C_6$ alkyl, $C_2$-$C_6$ alkenyl, and $C_2$-$C_6$ alkynyl is optionally substituted with one or more substituents independently selected from the group consisting of aryl, $NH_2$, $C(O)NH_2$, $SO_2NH_2$, $C(O)H$, $C(O)OH$, $OH$, $CN$, $NO_2$, F, Cl, Br and I; wherein each $R^{13}$ aryl, cycloalkyl, cycloalkenyl, heteroaryl, heterocycloalkyl, and heterocycloalkyl is optionally substituted with one or more substituents independently selected from the group consisting of $C_1$-$C_6$ alkyl, O—$C_1$-$C_6$ alkyl, $C_1$-$C_6$ alkyl-O—$C_1$-$C_6$ alkyl, $NH_2$, $C(O)NH_2$, $C(O)H$, $C(O)OH$, $OH$, $CN$, $NO_2$, F, Cl, Br and I. In another embodiment of Formula (IIIa), $R^{13}$, at each occurrence, is independently selected from the group consisting of $C_1$-$C_6$ alkyl, aryl, heteroaryl, heterocycloalkyl, and cycloalkyl; wherein each $R^{13}$ $C_1$-$C_6$ alkyl is optionally substituted with one or more substituents independently aryl; wherein each $R^{13}$ aryl, cycloalkyl, heteroaryl, and heterocycloalkyl is optionally substituted with one or more substituents independently selected from the group consisting of $C_1$-$C_6$ alkyl and O—$C_1$-$C_6$ alkyl, and $C_1$-$C_6$ alkyl-O—$C_1$-$C_6$ alkyl.

In one embodiment of Formula (IIIa), $R^{14}$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^{14}$ $C_1$-$C_6$ alkyl, $C_2$-$C_6$ alkenyl, and $C_2$-$C_6$ alkynyl is optionally substituted with one or more substituents independently selected from the group consisting of aryl, $NH_2$, $C(O)NH_2$, $SO_2NH_2$, $C(O)H$, $C(O)OH$, $OH$, $CN$, $NO_2$, F, Cl, Br and I; wherein each $R^{14}$ aryl, cycloalkyl, cycloalkenyl, heteroaryl, heterocycloalkyl, and heterocycloalkenyl is optionally substituted with one or more substituents independently selected from the group consisting of $C_1$-$C_6$ alkyl, O—$C_1$-$C_6$ alkyl, $C_1$-$C_6$ alkyl-O—$C_1$-$C_6$ alkyl, $NH_2$, $C(O)NH_2$, $C(O)H$, $C(O)OH$, $OH$, $NO_2$, F, Cl, Br and I. In another embodiment of Formula (IIIa), $R^{14}$, at each occurrence, is $C_1$-$C_6$ alkyl; wherein each $R^{14}$ $C_1$-$C_6$ alkyl is optionally substituted with one or more OH.

In another embodiment of Formula (IIIa), $R^2$ is selected from the group consisting of H and $C_1$-$C_6$ alkyl; wherein the $R^2$ $C_1$-$C_6$ alkyl is optionally substituted with one or more substituents independently selected from the group consisting of $R^4$, $SO_2R^4$, $C(O)R^4$, $N(R^4)_2$, $C(O)N(R^4)_2$, $SO_2NH_2$, and OH;

$R^4$, at each occurrence, is independently selected from the group consisting of $C_1$-$C_6$ alkyl, aryl, heteroaryl, heterocycloalkyl, and cycloalkyl; wherein each $R^4$ $C_1$-$C_6$ alkyl is optionally substituted with one or more OH; wherein each $R^4$ aryl, cycloalkyl, heteroaryl, and heterocycloalkyl is optionally substituted with one or more substituents independently selected from the group consisting of $R^6$, $SO_2R^6$, $CO(O)R^6$, $NHS(O)_2R^6$, $SO_2NH_2$, $C(O)OH$, $OH$, $CN$, and F;

$R^6$, at each occurrence, is independently selected from the group consisting of $C_1$-$C_6$ alkyl, heteroaryl, and heterocycloalkyl; wherein each $R^6$ $C_1$-$C_6$ alkyl is optionally substituted with one or more substituents independently selected from the group consisting of halo and $R^{6A}$;

$R^{6A}$, at each occurrence, is independently heterocycloalkyl; wherein each $R^{6A}$ heterocycloalkyl is optionally substituted with $C_1$-$C_6$ alkyl;

$R^{16}$ is selected from the group consisting of $NH_2$, $NHR^7$, $NHC(O)R^7$, and $NHC(O)OR^7$;

$R^7$, at each occurrence, is independently selected from the group consisting of $C_1$-$C_6$ alkyl, $C_2$-$C_6$ alkenyl, aryl, heteroaryl, heterocycloalkyl, heterocycloalkenyl, and cycloalkyl; wherein each $R^7$$C_1$-$C_6$ alkyl, and $C_2$-$C_6$ alkenyl is optionally substituted with one or more substituents independently selected from the group consisting of $R^8$, $SO_2R^8$, $NH_2$, $NHR^8$, $N(R^8)_2$, $NHS(O)_2R^8$, $NHSO_2N(R^8)_2$, $C(O)NHC(O)NH_2$, $SO_2NH_2$, and OH; wherein each $R^7$ aryl, cycloalkyl, heteroaryl, and heterocycloalkyl is optionally substituted with one or more substituents independently selected from the group consisting of $R^9$, $SO_2R^9$, $C(O)R^9$, $CO(O)R^9$, $NH_2$, $NHR^9$, $NHS(O)_2R^9$, $NHC(O)NHR^9$, $C(O)NH_2$, $C(O)NHR^9$, $C(O)N(R^9)_2$, $SO_2NH_2$, $SO_2NHC(O)OR^9$, $C(O)OH$, (O), and OH;

$R^8$, at each occurrence, is independently selected from the group consisting of $C_1$-$C_6$ alkyl, aryl, heteroaryl, heterocycloalkyl, heterocycloalkenyl, and cycloalkyl; wherein each $R^8$ $C_1$-$C_6$ alkyl is optionally substituted with one or more aryl; wherein each $R^8$ aryl, heteroaryl, heterocycloalkyl, heterocycloalkenyl, and cycloalkyl is optionally substituted with one or more substituents independently selected from the group consisting of $R^{11}$, halo, $NH_2$, and OH;

$R^9$, at each occurrence, is independently selected from the group consisting of $C_1$-$C_6$ alkyl, aryl, heteroaryl, heterocycloalkyl, and cycloalkyl; wherein each $R^9$ $C_1$-$C_6$ alkyl is optionally substituted with one or more substituents independently selected from the group consisting of $R^{13}$, $OR^{13}$, $S(O)R^{13}$, $SO_2R^{13}$, OH, and F; wherein each $R^9$ aryl, heteroaryl, heterocycloalkyl, and cycloalkyl is optionally substituted with one or more substituents independently selected from the group consisting of $R^{14}$, OH, and F;

$R^{11}$, at each occurrence, is independently selected from the group consisting of $C_1$-$C_6$ alkyl and aryl; wherein each $R^{11}$ $C_1$-$C_6$ alkyl is optionally substituted with one or more $NH_2$; wherein each $R^{11}$ aryl is optionally substituted with one or more substituents independently selected from the group consisting of $C_1$-$C_6$ alkyl, and O—$C_1$-$C_6$ alkyl;

$R^{13}$, at each occurrence, is independently selected from the group consisting of $C_1$-$C_6$ alkyl, aryl, heteroaryl, heterocycloalkyl, and cycloalkyl; wherein each $R^{13}$ $C_1$-$C_6$ alkyl is optionally substituted with one or more aryl; wherein each $R^{13}$ aryl, heteroaryl, heterocycloalkyl, and cycloalkyl is optionally substituted with one or more substituents independently selected from the group consisting of $C_1$-$C_6$ alkyl, O—$C_1$-$C_6$ alkyl, and $C_1$-$C_6$ alkyl-O—$C_1$-$C_6$ alkyl; and $R^{14}$, at each occurrence, is independently $C_1$-$C_6$ alkyl; wherein each $R^{14}$ $C_1$-$C_6$ alkyl is optionally substituted with one or more OH.

Still another embodiment pertains to compounds of Formula (Ma), selected from the group consisting of (3R)—N-[5-chloro-4-(1-methyl-1H-benzimidazol-6-yl)pyridin-2-yl]piperidine-3-carboxamide;

(3R)—N-{5-chloro-4-[1-(3-fluorobenzyl)-1H-benzimidazol-5-yl]pyridin-2-yl}piperidine-3-carboxamide;

(3R)—N-{5-chloro-4-[1-(3-fluorobenzyl)-1H-benzimidazol-6-yl]pyridin-2-yl}piperidine-3-carboxamide;

trans-N-{5-chloro-4-[1-(3-fluorobenzyl)-1H-benzimidazol-6-yl]pyridin-2-yl}cyclohexane-1,4-diamine;

trans-4-({5-chloro-4-[1-(3-fluorobenzyl)-1H-benzimidazol-6-yl]pyridin-2-yl}amino)cyclohexanol;

trans-N-[5-chloro-4-(1-methyl-1H-benzimidazol-6-yl)pyridin-2-yl]cyclohexane-1,4-diamine;

(3R)—N-{5-chloro-4-[1-(tetrahydro-2H-pyran-4-ylmethyl)-1H-benzimidazol-6-yl]pyridin-2-yl}piperidine-3-carboxamide;

(3R)—N-(5-chloro-4-{1-[2-(morpholin-4-yl)ethyl]-1H-benzimidazol-6-yl}pyridin-2-yl)piperidine-3-carboxamide;

(3R)—N-{5-chloro-4-[1-(3-hydroxy-3-methylbutyl)-1H-benzimidazol-6-yl]pyridin-2-yl}piperidine-3-carboxamide;

(3R)—N-{5-chloro-4-[1-(4-fluorobenzyl)-1H-benzimidazol-6-yl]pyridin-2-yl}piperidine-3-carboxamide;

(3R)—N-{5-chloro-4-[1-(3,4-difluorobenzyl)-1H-benzimidazol-6-yl]pyridin-2-yl}piperidine-3-carboxamide;

(3R)—N-(5-chloro-4-{1-[2-(3-fluorophenyl)ethyl]-1H-benzimidazol-6-yl}pyridin-2-yl)piperidine-3-carboxamide;

(3R)—N-{5-chloro-4-[1-(2-sulfamoylethyl)-1H-benzimidazol-6-yl]pyridin-2-yl}piperidine-3-carboxamide;

(3R)—N-(5-chloro-4-{1-[(1,1-dioxidotetrahydrothiophen-3-yl)methyl]-1H-benzimidazol-6-yl}pyridin-2-yl)piperidine-3-carboxamide;

(3R)—N-{5-chloro-4-[1-(2-fluorobenzyl)-1H-benzimidazol-6-yl]pyridin-2-yl}piperidine-3-carboxamide;

(3R)—N-{5-chloro-4-[1-(pyridin-3-ylmethyl)-1H-benzimidazol-6-yl]pyridin-2-yl}piperidine-3-carboxamide;

(3R)—N-(5-chloro-4-{1-[(1,1-dioxidotetrahydro-2H-thiopyran-4-yl)methyl]-1H-benzimidazol-6-yl}pyridin-2-yl)piperidine-3-carboxamide;

(3R)—N-(5-chloro-4-{1-[(5-methyl-4H-1,2,4-triazol-3-yl)methyl]-1H-benzimidazol-6-yl}pyridin-2-yl)piperidine-3-carboxamide;

(3R)—N-{5-chloro-4-[1-(1,3-thiazol-4-ylmethyl)-1H-benzimidazol-5-yl]pyridin-2-yl}piperidine-3-carboxamide-(3R)—N-{5-chloro-4-[1-(1,3-thiazol-4-ylmethyl)-1H-benzimidazol-6-yl]pyridin-2-yl}piperidine-3-carboxamide (1:1);

5-chloro-N-cyclopentyl-4-[1-(3-fluorobenzyl)-1H-benzimidazol-6-yl]pyridin-2-amine;

1-[trans-4-({5-chloro-4-[1-(3-fluorobenzyl)-1H-benzimidazol-6-yl]pyridin-2-yl}amino)cyclohexyl]-3-methylurea;

N-[trans-4-({5-chloro-4-[1-(3-fluorobenzyl)-1H-benzimidazol-6-yl]pyridin-2-yl}amino)cyclohexyl]methanesulfonamide;

N'-{5-chloro-4-[1-(3-fluorobenzyl)-1H-benzimidazol-6-yl]pyridin-2-yl}-N-methyl-N-(pyridin-2-yl)propane-1,3-diamine;

1-({5-chloro-4-[1-(3-fluorobenzyl)-1H-benzimidazol-6-yl]pyridin-2-yl}amino)-3-(dimethylamino)propan-2-ol;

5-chloro-4-[1-(3-fluorobenzyl)-1H-benzimidazol-6-yl]-N-[(5-methyl-4H-1,2,4-triazol-3-yl)methyl]pyridin-2-amine;

N-{5-chloro-4-[1-(3-fluorobenzyl)-1H-benzimidazol-6-yl]pyridin-2-yl}-N'-(pyridin-3-yl)ethane-1,2-diamine;

N-[(5-amino-4H-1,2,4-triazol-3-yl)methyl]-5-chloro-4-[1-(3-fluorobenzyl)-1H-benzimidazol-6-yl]pyridin-2-amine;

N-benzyl-N'-{5-chloro-4-[1-(3-fluorobenzyl)-1H-benzimidazol-6-yl]pyridin-2-yl}-N-methylpropane-1,3-diamine;

5-chloro-4-[1-(3-fluorobenzyl)-1H-benzimidazol-6-yl]-N-(pyrimidin-2-ylmethyl)pyridin-2-amine;

5-chloro-4-[1-(3-fluorobenzyl)-1H-benzimidazol-6-yl]-N-[1-(pyridin-4-yl)propan-2-yl]pyridin-2-amine;

5-chloro-4-[1-(3-fluorobenzyl)-1H-benzimidazol-6-yl]-N-[1-(1-methyl-1H-pyrazol-4-yl)piperidin-3-yl]pyridin-2-amine;

5-[({5-chloro-4-[1-(3-fluorobenzyl)-1H-benzimidazol-6-yl]pyridin-2-yl}amino)methyl]pyrimidin-2-amine;

5-chloro-N-[2-(1-ethylpiperidin-4-yl)ethyl]-4-[1-(3-fluorobenzyl)-1H-benzimidazol-6-yl]pyridin-2-amine;

5-chloro-4-[1-(3-fluorobenzyl)-1H-benzimidazol-6-yl]-N-[2-(5-methyl-4H-1,2,4-triazol-3-yl)ethyl]pyridin-2-amine;

N-{5-chloro-4-[1-(3-fluorobenzyl)-1H-benzimidazol-6-yl]pyridin-2-yl}-N'-(pyridin-4-yl)ethane-1,2-diamine;

5-chloro-4-[1-(3-fluorobenzyl)-1H-benzimidazol-6-yl]-N-[2-(1-methylpiperidin-4-yl)ethyl]pyridin-2-amine;

5-chloro-4-[1-(3-fluorobenzyl)-1H-benzimidazol-6-yl]-N-[2-(pyridin-4-yl)propyl]pyridin-2-amine;

$N^1$-{5-chloro-4-[1-(3-fluorobenzyl)-1H-benzimidazol-6-yl]pyridin-2-yl}-$N^2$,$N^2$,2-trimethylpropane-1,2-diamine;

N-{5-chloro-4-[1-(3-fluorobenzyl)-1H-benzimidazol-6-yl]pyridin-2-yl}-N'-phenylpropane-1,3-diamine;

$N^3$-{5-chloro-4-[1-(3-fluorobenzyl)-1H-benzimidazol-6-yl]pyridin-2-yl}butane-1,3-diamine;

5-chloro-4-[1-(3-fluorobenzyl)-1H-benzimidazol-6-yl]pyridin-2-amine;

5-chloro-4-[1-(3-fluorobenzyl)-1H-benzimidazol-6-yl]-N-(1H-imidazol-4-ylmethyl)pyridin-2-amine;

5-chloro-4-[1-(3-fluorobenzyl)-1H-benzimidazol-6-yl]-N-(pyrazin-2-ylmethyl)pyridin-2-amine;

5-chloro-4-[1-(3-fluorobenzyl)-1H-benzimidazol-6-yl]-N-[1-(pyrazin-2-yl)propan-2-yl]pyridin-2-amine;

5-chloro-4-[1-(3-fluorobenzyl)-1H-benzimidazol-6-yl]-N-(1-methylpyrrolidin-3-yl)pyridin-2-amine;

5-chloro-4-[1-(3-fluorobenzyl)-1H-benzimidazol-6-yl]-N-[2-(pyridin-3-yl)ethyl]pyridin-2-amine;

N'-{5-chloro-4-[1-(3-fluorobenzyl)-1H-benzimidazol-6-yl]pyridin-2-yl}-N,N-dimethylbutane-1,4-diamine;

5-chloro-4-[1-(3-fluorobenzyl)-1H-benzimidazol-6-yl]-N-[(1-methylpiperidin-4-yl)methyl]pyridin-2-amine;

N-benzyl-N'-{5-chloro-4-[1-(3-fluorobenzyl)-1H-benzimidazol-6-yl]pyridin-2-yl}-N-methylethane-1,2-diamine;

5-chloro-4-[1-(3-fluorobenzyl)-1H-benzimidazol-6-yl]-N-[2-(pyridin-2-yl)ethyl]pyridin-2-amine;

4-({5-chloro-4-[1-(3-fluorobenzyl)-1H-benzimidazol-6-yl]pyridin-2-yl}amino)-2-methylbutan-2-ol;

N'-{5-chloro-4-[1-(3-fluorobenzyl)-1H-benzimidazol-6-yl]pyridin-2-yl}-N-methyl-N-phenylpropane-1,3-diamine;

5-chloro-4-[1-(3-fluorobenzyl)-1H-benzimidazol-6-yl]-N-(1-methylpiperidin-4-yl)pyridin-2-amine;

5-chloro-4-[1-(3-fluorobenzyl)-1H-benzimidazol-6-yl]-N-[2-(pyridin-4-yl)ethyl]pyridin-2-amine;

5-chloro-4-[1-(3-fluorobenzyl)-1H-benzimidazol-6-yl]-N-(pyrimidin-5-ylmethyl)pyridin-2-amine;

$N^2$-{5-chloro-4-[1-(3-fluorobenzyl)-1H-benzimidazol-6-yl]pyridin-2-yl}-2-methylpropane-1,2-diamine;

5-chloro-N-(2-cyclohexylethyl)-4-[1-(3-fluorobenzyl)-1H-benzimidazol-6-yl]pyridin-2-amine;

N-{5-chloro-4-[1-(3-fluorobenzyl)-1H-benzimidazol-6-yl]pyridin-2-yl}-N'-phenylethane-1,2-diamine;

N'-{5-chloro-4-[1-(3-fluorobenzyl)-1H-benzimidazol-6-yl]pyridin-2-yl}-N,N,2,2-tetramethylpropane-1,3-diamine;

2-({5-chloro-4-[1-(3-fluorobenzyl)-1H-benzimidazol-6-yl]pyridin-2-yl}amino)ethanol;

N-benzyl-5-chloro-4-[1-(3-fluorobenzyl)-1H-benzimidazol-6-yl]pyridin-2-amine;

N'-{5-chloro-4-[1-(3-fluorobenzyl)-1H-benzimidazol-6-yl]pyridin-2-yl}-N,N-dimethylpropane-1,3-diamine;

3-({5-chloro-4-[1-(3-fluorobenzyl)-1H-benzimidazol-6-yl]pyridin-2-yl}amino)propan-1-ol;

N-{5-chloro-4-[1-(3-fluorobenzyl)-1H-benzimidazol-6-yl]pyridin-2-yl}propane-1,3-diamine;

4-[({5-chloro-4-[1-(3-fluorobenzyl)-1H-benzimidazol-6-yl]pyridin-2-yl}amino)methyl]phenol;

N-{5-chloro-4-[1-(3-fluorobenzyl)-1H-benzimidazol-6-yl]pyridin-2-yl}butane-1,4-diamine;

N-[2-(4-aminophenyl)ethyl]-5-chloro-4-[1-(3-fluorobenzyl)-1H-benzimidazol-6-yl]pyridin-2-amine;

N-{5-chloro-4-[1-(3-fluorobenzyl)-1H-benzimidazol-6-yl]pyridin-2-yl}-2,2-dimethylpropane-1,3-diamine;

N-{5-chloro-4-[1-(3-fluorobenzyl)-1H-benzimidazol-6-yl]pyridin-2-yl}ethane-1,2-diamine;

N-[4-(aminomethyl)benzyl]-5-chloro-4-[1-(3-fluorobenzyl)-1H-benzimidazol-6-yl]pyridin-2-amine;

1-({5-chloro-4-[1-(3-fluorobenzyl)-1H-benzimidazol-6-yl]pyridin-2-yl}amino)-2-methylpropan-2-ol;

1-amino-3-{5-chloro-4-[1-(3-fluorobenzyl)-1H-benzimidazol-6-yl]pyridin-2-yl}amino)propan-2-ol;

N-{5-chloro-4-[1-(3-fluorobenzyl)-1H-benzimidazol-6-yl]pyridin-2-yl}-N'-(pyridin-2-yl)ethane-1,2-diamine;

(3R)—N-{5-chloro-4-[1-(3-fluorobenzyl)-1H-benzimidazol-6-yl]pyridin-2-yl}-1-azabicyclo[2.2.2]octan-3-amine;

(3S)—N-{5-chloro-4-[1-(3-fluorobenzyl)-1H-benzimidazol-6-yl]pyridin-2-yl}-1-azabicyclo[2.2.2]octan-3-amine;

2-benzyl-N-{5-chloro-4-[1-(3-fluorobenzyl)-1H-benzimidazol-6-yl]pyridin-2-yl}octahydro-1H-isoindol-4-amine;

2-benzyl-N-{5-chloro-4-[1-(3-fluorobenzyl)-1H-benzimidazol-6-yl]pyridin-2-yl}octahydrocyclopenta[c]pyrrol-4-amine;

N-{5-chloro-4-[1-(3-fluorobenzyl)-1H-benzimidazol-6-yl]pyridin-2-yl}-9-(cyclopropylmethyl)-9-azabicyclo[3.3.1]nonan-3-amine;

benzyl 4-({5-chloro-4-[1-(3-fluorobenzyl)-1H-benzimidazol-6-yl]pyridin-2-yl}amino)-4-(4-fluorophenyl)piperidine-1-carboxylate;

tert-butyl {5-chloro-4-[1-(3-fluorobenzyl)-1H-benzimidazol-6-yl]pyridin-2-yl}carbamate;

(3R)—N-(5-chloro-4-{1-[(5-methyl-1,3,4-thiadiazol-2-yl)methyl]-1H-benzimidazol-6-yl}pyridin-2-yl)piperidine-3-carboxamide;

(3R)—N-(5-chloro-4-{1-[2-(pyridin-3-yl)ethyl]-1H-benzimidazol-6-yl}pyridin-2-yl)piperidine-3-carboxamide;

N-{5-chloro-4-[1-(3-fluorobenzyl)-1H-benzimidazol-6-yl]pyridin-2-yl}-N'-methylpropane-1,3-diamine;

N-[(trans-4-aminocyclohexyl)methyl]-5-chloro-4-[1-(3-fluorobenzyl)-1H-benzimidazol-6-yl]pyridin-2-amine;

N-{5-chloro-4-[1-(3-fluorobenzyl)-1H-benzimidazol-6-yl]pyridin-2-yl}-N'-methylbutane-1,4-diamine;

N-benzyl-N'-{5-chloro-4-[1-(3-fluorobenzyl)-1H-benzimidazol-6-yl]pyridin-2-yl}ethane-1,2-diamine;

5-chloro-4-[1-(3-fluorobenzyl)-1H-benzimidazol-6-yl]-N-[2-(piperidin-4-yl)ethyl]pyridin-2-amine;

5-chloro-4-[1-(3-fluorobenzyl)-1H-benzimidazol-6-yl]-N-[2-(piperidin-3-yl)ethyl]pyridin-2-amine;

$N^2$-{5-chloro-4-[1-(3-fluorobenzyl)-1H-benzimidazol-6-yl]pyridin-2-yl}-1-phenylethane-1,2-diamine;

5-chloro-4-[1-(3-fluorobenzyl)-1H-benzimidazol-6-yl]-N-(piperidin-3-yl)pyridin-2-amine;

N-[(2R)-azetidin-2-ylmethyl]-5-chloro-4-[1-(3-fluorobenzyl)-1H-benzimidazol-6-yl]pyridin-2-amine;

N-[2-(azetidin-2-yl)ethyl]-5-chloro-4-[1-(3-fluorobenzyl)-1H-benzimidazol-6-yl]pyridin-2-amine;

(4aS,8R,8aS)—N-{5-chloro-4-[1-(3-fluorobenzyl)-1H-benzimidazol-6-yl]pyridin-2-yl}decahydroisoquinolin-8-amine;

5-chloro-4-[1-(3-fluorobenzyl)-1H-benzimidazol-6-yl]-N-[2-(pyrrolidin-2-yl)ethyl]pyridin-2-amine;

N-{5-chloro-4-[1-(3-fluorobenzyl)-1H-benzimidazol-6-yl]pyridin-2-yl}-6-azaspiro[3.5]nonan-2-amine;

N-{5-chloro-4-[1-(3-fluorobenzyl)-1H-benzimidazol-6-yl]pyridin-2-yl}-7-azaspiro[3.5]nonan-2-amine;

N-{5-chloro-4-[1-(3-fluorobenzyl)-1H-benzimidazol-6-yl]pyridin-2-yl}-7-azaspiro[3.5]nonan-1-amine;

5-chloro-4-[1-(3-fluorobenzyl)-1H-benzimidazol-6-yl]-N-{[(2R,4S)-4-fluoropyrrolidin-2-yl]methyl}pyridin-2-amine;

5-chloro-4-[1-(3-fluorobenzyl)-1H-benzimidazol-6-yl]-N-[(4-fluoropyrrolidin-3-yl)methyl]pyridin-2-amine;

N-{5-chloro-4-[1-(3-fluorobenzyl)-1H-benzimidazol-6-yl]pyridin-2-yl}-6-azaspiro[3.4]octan-2-amine;

(3R)—N-(5-chloro-4-{1-[2-(methylsulfonyl)ethyl]-1H-benzimidazol-6-yl}pyridin-2-yl)piperidine-3-carboxamide;

5-chloro-4-[1-(3-fluorobenzyl)-1H-benzimidazol-6-yl]-N-{2-[4-(4-methylphenyl)piperidin-4-yl]ethyl}pyridin-2-amine;

5-chloro-4-[1-(3-fluorobenzyl)-1H-benzimidazol-6-yl]-N-{2-[4-(4-methoxyphenyl)piperidin-4-yl]ethyl}pyridin-2-amine;

5-chloro-4-[1-(3-fluorobenzyl)-1H-benzimidazol-6-yl]-N-[(4-fluoropiperidin-4-yl)methyl]pyridin-2-amine;

5-chloro-4-[1-(3-fluorobenzyl)-1H-benzimidazol-6-yl]-N-{2-[3-(4-methoxyphenyl)pyrrolidin-3-yl]ethyl}pyridin-2-amine;

N-{5-chloro-4-[1-(3-fluorobenzyl)-1H-benzimidazol-6-yl]
pyridin-2-yl}-6-azaspiro[3.4]octan-1-amine;
(1S,4R)—N-{5-chloro-4-[1-(3-fluorobenzyl)-1H-benzimi-
dazol-6-yl]pyridin-2-yl}-6-azaspiro[3.5]nonan-1-amine;
N-{5-chloro-4-[1-(3-fluorobenzyl)-1H-benzimidazol-6-yl]
pyridin-2-yl}-5-thia-2-azaspiro[3.4]octan-8-amine 5,5-
dioxide;
N-{5-chloro-4-[1-(3-fluorobenzyl)-1H-benzimidazol-6-yl]
pyridin-2-yl}-9-azabicyclo[3.3.1]nonan-3-amine;
(3S)—N-{5-chloro-4-[1-(3-fluorobenzyl)-1H-benzimida-
zol-6-yl]pyridin-2-yl}azepan-3-amine;
(3R)—N-{5-chloro-4-[1-(3-fluorobenzyl)-1H-benzimida-
zol-6-yl]pyridin-2-yl}azepan-3-amine;
(1R,4R)—N-{5-chloro-4-[1-(3-fluorobenzyl)-1H-benzimi-
dazol-6-yl]pyridin-2-yl}-6-azaspiro[3.5]nonan-1-amine;
N-{[3-(aminomethyl)cyclohexyl]methyl}-5-chloro-4-[1-(3-
fluorobenzyl)-1H-benzimidazol-6-yl]pyridin-2-amine;
N-{5-chloro-4-[1-(3-fluorobenzyl)-1H-benzimidazol-6-yl]
pyridin-2-yl}-2-(piperidin-4-yl)acetamide;
4-({5-chloro-4-[1-(3-fluorobenzyl)-1H-benzimidazol-6-yl]
pyridin-2-yl}amino)benzenesulfonamide;
(3R)—N-(5-chloro-4-{1-[(5-fluoropyridin-3-yl)methyl]-
1H-benzimidazol-6-yl}pyridin-2-yl)piperidine-3-carbox-
amide;
(3R)—N-(5-chloro-4-{1-[(4-cyanotetrahydro-2H-pyran-4-
yl)methyl]-1H-benzimidazol-6-yl}pyridin-2-yl)piperi-
dine-3-carboxamide;
(3R)—N-(5-chloro-4-{1-[3-(dimethylamino)propyl]-1H-
benzimidazol-6-yl}pyridin-2-yl)piperidine-3-carboxam-
ide;
(3R)—N-(5-chloro-4-{1-[(1R)-1-(3-fluorophenyl)ethyl]-
1H-benzimidazol-6-yl}pyridin-2-yl)piperidine-3-carbox-
amide;
(3R)—N-[5-chloro-4-(1-{[3-(morpholin-4-yl)oxetan-3-yl]
methyl}-1H-benzimidazol-6-yl)pyridin-2-yl]piperidine-
3-carboxamide;
(3R)—N-[5-chloro-4-(1-{[3-(pyrrolidin-1-yl)oxetan-3-yl]
methyl}-1H-benzimidazol-6-yl)pyridin-2-yl]piperidine-
3-carboxamide;
N-{5-chloro-4-[1-(tetrahydro-2H-pyran-4-ylmethyl)-1H-
benzimidazol-6-yl]pyridin-2-yl}-7-azaspiro[3.5]nonan-2-
amine;
N-{5-chloro-4-[1-(tetrahydro-2H-pyran-4-ylmethyl)-1H-
benzimidazol-6-yl]pyridin-2-yl}-7-(methylsulfonyl)-7-
azaspiro[3.5]nonan-2-amine;
(2E)-N-{5-chloro-4-[1-(3-fluorobenzyl)-1H-benzimidazol-
6-yl]pyridin-2-yl}-3-(pyridin-4-yl)prop-2-enamide;
(1R,2S)—N-{5-chloro-4-[1-(3-fluorobenzyl)-1H-benzimi-
dazol-6-yl]pyridin-2-yl}-N'-cyclopentylcyclobutane-1,2-
dicarboxamide;
N-{5-chloro-4-[1-(3-fluorobenzyl)-1H-benzimidazol-6-yl]
pyridin-2-yl}-2-(2-oxopyridin-1(2H)-yl)propanamide;
N-{5-chloro-4-[1-(3-fluorobenzyl)-1H-benzimidazol-6-yl]
pyridin-2-yl}-2-(methylsulfonyl)acetamide;
N-{5-chloro-4-[1-(3-fluorobenzyl)-1H-benzimidazol-6-yl]
pyridin-2-yl}-1-(3-chlorophenyl)-5-oxopyrrolidine-3-
carboxamide;
1-benzyl-N-{5-chloro-4-[1-(3-fluorobenzyl)-1H-benzimi-
dazol-6-yl]pyridin-2-yl}-5-oxopyrrolidine-3-carboxam-
ide;
N-{5-chloro-4-[1-(3-fluorobenzyl)-1H-benzimidazol-6-yl]
pyridin-2-yl}-2,3-dihydro[1,4]dioxino[2,3-b]pyridine-7-
carboxamide;
(3R)—N-{5-chloro-4-[1-(3-fluorobenzyl)-1H-benzimida-
zol-6-yl]pyridin-2-yl}-3-(pyridin-3-yl)-1H-pyrrolo[1,2-c]
[1,3]thiazole-7-carboxamide;
N-{5-chloro-4-[1-(3-fluorobenzyl)-1H-benzimidazol-6-yl]
pyridin-2-yl}-3-oxocyclobutanecarboxamide;
N-{5-chloro-4-[1-(3-fluorobenzyl)-1H-benzimidazol-6-yl]
pyridin-2-yl}-6-oxospiro[3.3]heptane-2-carboxamide;
benzyl (1R,5S,6r)-6-({5-chloro-4-[1-(3-fluorobenzyl)-1H-
benzimidazol-6-yl]pyridin-2-yl}carbamoyl)-3-azabicyclo
[3.1.0]hexane-3-carboxylate;
N-{5-chloro-4-[1-(3-fluorobenzyl)-1H-benzimidazol-6-yl]
pyridin-2-yl}-1-methylazetidine-3-carboxamide;
N-{5-chloro-4-[1-(3-fluorobenzyl)-1H-benzimidazol-6-yl]
pyridin-2-yl}-3-methyloxetane-3-carboxamide;
N-{5-chloro-4-[1-(3-fluorobenzyl)-1H-benzimidazol-6-yl]
pyridin-2-yl}-4-hydroxy-4-(trifluoromethyl)cyclohexan-
ecarboxamide;
N-{5-chloro-4-[1-(3-fluorobenzyl)-1H-benzimidazol-6-yl]
pyridin-2-yl}-1-(2,2-dimethylpropanoyl)-2,3-dihydro-
1H-pyrido[2,3-b][1,4]oxazine-6-carboxamide;
N-{5-chloro-4-[1-(3-fluorobenzyl)-1H-benzimidazol-6-yl]
pyridin-2-yl}-2-(methylsulfonyl)-5-thia-2-azaspiro[3.4]
octane-8-carboxamide 5,5-dioxide;
$N^8$-{5-chloro-4-[1-(3-fluorobenzyl)-1H-benzimidazol-6-yl]
pyridin-2-yl}-$N^2$-ethyl-5-thia-2-azaspiro[3.4]octane-2,8-
dicarboxamide 5,5-dioxide;
$N^8$-{5-chloro-4-[1-(3-fluorobenzyl)-1H-benzimidazol-6-yl]
pyridin-2-yl}-$N^2$-phenyl-5-thia-2-azaspiro[3.4]octane-2,
8-dicarboxamide 5,5-dioxide;
N-{5-chloro-4-[1-(3-fluorobenzyl)-1H-benzimidazol-6-yl]
pyridin-2-yl}-7-(cyclohexylcarbonyl)-1-thia-7-azaspiro
[4.4]nonane-4-carboxamide 1,1-dioxide;
N-{5-chloro-4-[1-(3-fluorobenzyl)-1H-benzimidazol-6-yl]
pyridin-2-yl}-7-(2-methylpropanoyl)-1-thia-7-azaspiro
[4.4]nonane-4-carboxamide 1,1-dioxide;
N-{5-chloro-4-[1-(3-fluorobenzyl)-1H-benzimidazol-6-yl]
pyridin-2-yl}-7-(phenylsulfonyl)-1-thia-7-azaspiro[4.4]
nonane-4-carboxamide 1,1-dioxide;
7-benzoyl-N-{5-chloro-4-[1-(3-fluorobenzyl)-1H-benzimi-
dazol-6-yl]pyridin-2-yl}-1-thia-7-azaspiro[4.4]nonane-4-
carboxamide 1,1-dioxide;
N-{5-chloro-4-[1-(3-fluorobenzyl)-1H-benzimidazol-6-yl]
pyridin-2-yl}-7-ethyl-1-thia-7-azaspiro[4.4]nonane-4-
carboxamide 1,1-dioxide;
N-{5-chloro-4-[1-(3-fluorobenzyl)-1H-benzimidazol-6-yl]
pyridin-2-yl}-2-oxohexahydro-2H-cyclopenta[d][1,3]ox-
azole-5-carboxamide;
N-{5-chloro-4-[1-(3-fluorobenzyl)-1H-benzimidazol-6-yl]
pyridin-2-yl}-7-(methylsulfonyl)-1-thia-7-azaspiro[4.4]
nonane-4-carboxamide 1,1-dioxide;
(2E)-N-carbamoyl-N'-{5-chloro-4-[1-(3-fluorobenzyl)-1H-
benzimidazol-6-yl]pyridin-2-yl}but-2-enediamide;
N-{5-chloro-4-[1-(3-fluorobenzyl)-1H-benzimidazol-6-yl]
pyridin-2-yl}cyclopropane-1,1-dicarboxamide;
N-{5-chloro-4-[1-(3-fluorobenzyl)-1H-benzimidazol-6-yl]
pyridin-2-yl}-1H-pyrazole-4-carboxamide;
trans-N-{5-chloro-4-[1-(tetrahydro-2H-pyran-4-ylmethyl)-
1H-benzimidazol-6-yl]pyridin-2-yl}cyclohexane-1,4-di-
amine;
N-{5-chloro-4-[1-(tetrahydro-2H-pyran-4-ylmethyl)-1H-
benzimidazol-6-yl]pyridin-2-yl}piperidine-4-carboxam-
ide;
N-{5-chloro-4-[1-(tetrahydro-2H-pyran-4-ylmethyl)-1H-
benzimidazol-6-yl]pyridin-2-yl}-2-oxohexahydro-2H-
cyclopenta[d][1,3]oxazole-5-carboxamide;
(2s,4r)-N-{5-chloro-4-[1-(3-fluorobenzyl)-1H-benzimida-
zol-6-yl]pyridin-2-yl}-6-azaspiro[3.4]octan-2-amine;
(2r,4s)-N-{5-chloro-4-[1-(3-fluorobenzyl)-1H-benzimida-
zol-6-yl]pyridin-2-yl}-6-azaspiro[3.4]octan-2-amine;

(2s,4r)-N-{5-chloro-4-[1-(3-fluorobenzyl)-1H-benzimidazol-6-yl]pyridin-2-yl}-6-azaspiro[3.5]nonan-2-amine;
(2r,4s)-N-{5-chloro-4-[1-(3-fluorobenzyl)-1H-benzimidazol-6-yl]pyridin-2-yl}-6-azaspiro[3.5]nonan-2-amine;
(3S)—N-{5-chloro-4-[1-(tetrahydro-2H-pyran-4-ylmethyl)-1H-benzimidazol-6-yl]pyridin-2-yl}piperidine-3-carboxamide;
4-[(6-{5-chloro-2-[(2-hydroxyethyl)amino]pyridin-4-yl}-1H-benzimidazol-1-yl)methyl]tetrahydro-2H-pyran-4-carbonitrile;
2-[(5-chloro-4-{1-[(5-fluoropyridin-3-yl)methyl]-1H-benzimidazol-6-yl}pyridin-2-yl)amino]ethanol;
trans-N-{5-chloro-4-[1-(3-fluorobenzyl)-1H-benzimidazol-6-yl]pyridin-2-yl}-N'-(pyridin-2-ylmethyl)cyclohexane-1,4-diamine;
trans-N-{5-chloro-4-[1-(3-fluorobenzyl)-1H-benzimidazol-6-yl]pyridin-2-yl}-N'-(pyridin-3-ylmethyl)cyclohexane-1,4-diamine;
trans-N-{5-chloro-4-[1-(3-fluorobenzyl)-1H-benzimidazol-6-yl]pyridin-2-yl}-N'-(pyridin-4-ylmethyl)cyclohexane-1,4-diamine;
trans-N-(1,3-benzodioxol-5-ylmethyl)-N'-{5-chloro-4-[1-(3-fluorobenzyl)-1H-benzimidazol-6-yl]pyridin-2-yl}cyclohexane-1,4-diamine;
trans-N-{5-chloro-4-[1-(3-fluorobenzyl)-1H-benzimidazol-6-yl]pyridin-2-yl}-N'-(1,3-thiazol-2-ylmethyl)cyclohexane-1,4-diamine;
trans-N-{5-chloro-4-[1-(3-fluorobenzyl)-1H-benzimidazol-6-yl]pyridin-2-yl}-N'-{[1-(methoxymethyl)-2,3-dihydro-1H-1,2,3-triazol-4-yl]methyl}cyclohexane-1,4-diamine;
trans-N-{5-chloro-4-[1-(3-fluorobenzyl)-1H-benzimidazol-6-yl]pyridin-2-yl}-N'-[2-(morpholin-4-yl)ethyl]cyclohexane-1,4-diamine;
trans-N-{5-chloro-4-[1-(3-fluorobenzyl)-1H-benzimidazol-6-yl]pyridin-2-yl}-N'-[2-methyl-2-(morpholin-4-yl)propyl]cyclohexane-1,4-diamine;
trans-N-{5-chloro-4-[1-(3-fluorobenzyl)-1H-benzimidazol-6-yl]pyridin-2-yl}-N'-(tetrahydrofuran-2-ylmethyl)cyclohexane-1,4-diamine;
trans-N-{5-chloro-4-[1-(3-fluorobenzyl)-1H-benzimidazol-6-yl]pyridin-2-yl}-N'-[(2,5-dimethoxytetrahydrofuran-3-yl)methyl]cyclohexane-1,4-diamine;
trans-N-{5-chloro-4-[1-(3-fluorobenzyl)-1H-benzimidazol-6-yl]pyridin-2-yl}-N'-(cyclopropylmethyl)cyclohexane-1,4-diamine;
3-{[trans-4-({5-chloro-4-[1-(3-fluorobenzyl)-1H-benzimidazol-6-yl]pyridin-2-yl}amino)cyclohexyl]amino}propane-1,2-diol;
trans-N-{5-chloro-4-[1-(3-fluorobenzyl)-1H-benzimidazol-6-yl]pyridin-2-yl}-N'-(1-methoxypropan-2-yl)cyclohexane-1,4-diamine;
trans-N-{5-chloro-4-[1-(3-fluorobenzyl)-1H-benzimidazol-6-yl]pyridin-2-yl}-N'-(1,3-dimethoxypropan-2-yl)cyclohexane-1,4-diamine;
trans-N-{5-chloro-4-[1-(3-fluorobenzyl)-1H-benzimidazol-6-yl]pyridin-2-yl}-N'-(2-phenoxyethyl)cyclohexane-1,4-diamine;
trans-N-[3-(benzyloxy)propyl]-N'-{5-chloro-4-[1-(3-fluorobenzyl)-1H-benzimidazol-6-yl]pyridin-2-yl}cyclohexane-1,4-diamine;
trans-N-{5-chloro-4-[1-(3-fluorobenzyl)-1H-benzimidazol-6-yl]pyridin-2-yl}-N'-[2,2-dimethyl-3-(phenylsulfinyl)propyl]cyclohexane-1,4-diamine;
trans-N-{5-chloro-4-[1-(3-fluorobenzyl)-1H-benzimidazol-6-yl]pyridin-2-yl}-N'-(2-methoxypropyl)cyclohexane-1,4-diamine;
trans-N-{5-chloro-4-[1-(3-fluorobenzyl)-1H-benzimidazol-6-yl]pyridin-2-yl}-N'-[2-(cyclohexyloxy)propyl]cyclohexane-1,4-diamine;
trans-N-{5-chloro-4-[1-(3-fluorobenzyl)-1H-benzimidazol-6-yl]pyridin-2-yl}-N'-[(5,5-dimethyltetrahydrofuran-2-yl)methyl]cyclohexane-1,4-diamine;
trans-N-{5-chloro-4-[1-(3-fluorobenzyl)-1H-benzimidazol-6-yl]pyridin-2-yl}-N'-(3-methoxypropyl)cyclohexane-1,4-diamine;
2-{[trans-4-({5-chloro-4-[1-(3-fluorobenzyl)-1H-benzimidazol-6-yl]pyridin-2-yl}amino)cyclohexyl]amino}propan-1-ol;
N-{5-chloro-4-[1-(3-fluorobenzyl)-1H-benzimidazol-6-yl]pyridin-2-yl}cyclohexane-1,3-diamine;
N-{5-chloro-4-[1-(tetrahydro-2H-pyran-4-ylmethyl)-1H-benzimidazol-6-yl]pyridin-2-yl}pyridine-4-carboxamide;
N-{5-chloro-4-[1-(tetrahydro-2H-pyran-4-ylmethyl)-1H-benzimidazol-6-yl]pyridin-2-yl}pyridine-3-carboxamide;
N-{5-chloro-4-[1-(tetrahydro-2H-pyran-4-ylmethyl)-1H-benzimidazol-6-yl]pyridin-2-yl}-1-methyl-1H-imidazole-4-carboxamide;
N-{5-chloro-4-[1-(tetrahydro-2H-pyran-4-ylmethyl)-1H-benzimidazol-6-yl]pyridin-2-yl}-1H-imidazole-4-carboxamide;
N-{5-chloro-4-[1-(tetrahydro-2H-pyran-4-ylmethyl)-1H-benzimidazol-6-yl]pyridin-2-yl}-1,3-thiazole-4-carboxamide;
N-{5-chloro-4-[1-(tetrahydro-2H-pyran-4-ylmethyl)-1H-benzimidazol-6-yl]pyridin-2-yl}-1H-1,2,4-triazole-3-carboxamide;
N-{5-chloro-4-[1-(tetrahydro-2H-pyran-4-ylmethyl)-1H-benzimidazol-6-yl]pyridin-2-yl}pyrimidine-5-carboxamide;
N-{5-chloro-4-[1-(tetrahydro-2H-pyran-4-ylmethyl)-1H-benzimidazol-6-yl]pyridin-2-yl}pyrazine-2-carboxamide;
N-{5-chloro-4-[1-(tetrahydro-2H-pyran-4-ylmethyl)-1H-benzimidazol-6-yl]pyridin-2-yl}-1H-pyrazole-3-carboxamide;
N-{5-chloro-4-[1-(tetrahydro-2H-pyran-4-ylmethyl)-1H-benzimidazol-6-yl]pyridin-2-yl}-1H-1,2,3-triazole-4-carboxamide;
N-{5-chloro-4-[1-(tetrahydro-2H-pyran-4-ylmethyl)-1H-benzimidazol-6-yl]pyridin-2-yl}azetidine-3-carboxamide;
N-{5-chloro-4-[1-(tetrahydro-2H-pyran-4-ylmethyl)-1H-benzimidazol-6-yl]pyridin-2-yl}-1H-pyrazole-4-carboxamide;
(3aR,6aS)—N-{5-chloro-4-[1-(tetrahydro-2H-pyran-4-ylmethyl)-1H-benzimidazol-6-yl]pyridin-2-yl}octahydrocyclopenta[c]pyrrole-5-carboxamide;
N-{5-chloro-4-[1-(tetrahydro-2H-pyran-4-ylmethyl)-1H-benzimidazol-6-yl]pyridin-2-yl}-2-azaspiro[3.3]heptane-6-carboxamide;
N-{5-chloro-4-[1-(tetrahydro-2H-pyran-4-ylmethyl)-1H-benzimidazol-6-yl]pyridin-2-yl}-3-azabicyclo[3.1.0]hexane-6-carboxamide;
N-{5-chloro-4-[1-(tetrahydro-2H-pyran-4-ylmethyl)-1H-benzimidazol-6-yl]pyridin-2-yl}-3-oxocyclobutanecarboxamide;
N-{5-chloro-4-[1-(tetrahydro-2H-pyran-4-ylmethyl)-1H-benzimidazol-6-yl]pyridin-2-yl}-1,2,5,6-tetrahydropyridine-3-carboxamide;
N-{5-chloro-4-[1-(3-fluorobenzyl)-1H-benzimidazol-6-yl]pyridin-2-yl}-2-(tetrahydro-2H-pyran-4-ylsulfonyl)propanamide;

N-{5-chloro-4-[1-(3-fluorobenzyl)-1H-benzimidazol-6-yl]
pyridin-2-yl}-5,6,7,8-tetrahydro[1,2,4]triazolo[4,3-a]
pyridine-6-carboxamide;

N-{5-chloro-4-[1-(3-fluorobenzyl)-1H-benzimidazol-6-yl]
pyridin-2-yl}-5,6,7,8-tetrahydroimidazo[1,2-a]pyridine-
6-carboxamide;

N-{5-chloro-4-[1-(3-fluorobenzyl)-1H-benzimidazol-6-yl]
pyridin-2-yl}-3,4-dihydro-2H-pyrano[2,3-b]pyridine-6-
carboxamide;

N-{5-chloro-4-[1-(3-fluorobenzyl)-1H-benzimidazol-6-yl]
pyridin-2-yl}-2-sulfamoylacetamide;

N-{5-chloro-4-[1-(3-fluorobenzyl)-1H-benzimidazol-6-yl]
pyridin-2-yl}-2-[(4-methylpiperazin-1-yl)sulfonyl]acet-
amide;

N-{5-chloro-4-[1-(3-fluorobenzyl)-1H-benzimidazol-6-yl]
pyridin-2-yl}-5-oxo-D-prolinamide;

N-{5-chloro-4-[1-(3-fluorobenzyl)-1H-benzimidazol-6-yl]
pyridin-2-yl}-$N^2$-(dimethylsulfamoyl)glycinamide;

N-{5-chloro-4-[1-(tetrahydro-2H-pyran-4-ylmethyl)-1H-
benzimidazol-6-yl]pyridin-2-yl}-2-(tetrahydro-2H-
pyran-4-ylsulfonyl)propanamide;

N-{5-chloro-4-[1-(tetrahydro-2H-pyran-4-ylmethyl)-1H-
benzimidazol-6-yl]pyridin-2-yl}-5,6,7,8-tetrahydro[1,2,
4]triazolo[4,3-a]pyridine-6-carboxamide;

N-{5-chloro-4-[1-(tetrahydro-2H-pyran-4-ylmethyl)-1H-
benzimidazol-6-yl]pyridin-2-yl}-5,6,7,8-tetrahydroimi-
dazo[1,2-a]pyridine-6-carboxamide;

N-{5-chloro-4-[1-(tetrahydro-2H-pyran-4-ylmethyl)-1H-
benzimidazol-6-yl]pyridin-2-yl}-3,4-dihydro-2H-pyrano
[2,3-b]pyridine-6-carboxamide;

N-{5-chloro-4-[1-(tetrahydro-2H-pyran-4-ylmethyl)-1H-
benzimidazol-6-yl]pyridin-2-yl}-2-sulfamoylacetamide;

N-{5-chloro-4-[1-(tetrahydro-2H-pyran-4-ylmethyl)-1H-
benzimidazol-6-yl]pyridin-2-yl}-$N^2$-(ethylsulfonyl)
glycinamide;

N-{5-chloro-4-[1-(tetrahydro-2H-pyran-4-ylmethyl)-1H-
benzimidazol-6-yl]pyridin-2-yl}-5-oxo-D-prolinamide;

N-{5-chloro-4-[1-(tetrahydro-2H-pyran-4-ylmethyl)-1H-
benzimidazol-6-yl]pyridin-2-yl}-$N^2$-(dimethylsulfamoyl)
glycinamide;

N-{5-chloro-4-[1-(tetrahydro-2H-pyran-4-ylmethyl)-1H-
benzimidazol-6-yl]pyridin-2-yl}-2-[(4-methylpiperazin-
1-yl)sulfonyl]acetamide;

cis-3-amino-N-{5-chloro-4-[1-(tetrahydro-2H-pyran-4-yl-
methyl)-1H-benzimidazol-6-yl]pyridin-2-
yl}cyclobutanecarboxamide;

trans-3-amino-N-{5-chloro-4-[1-(tetrahydro-2H-pyran-4-
ylmethyl)-1H-benzimidazol-6-yl]pyridin-2-
yl}cyclobutanecarboxamide;

(1R,5S,6r)-N-{5-chloro-4-[1-(tetrahydro-2H-pyran-4-ylm-
ethyl)-1H-benzimidazol-6-yl]pyridin-2-yl}-3-azabicyclo
[3.1.0]hexane-6-carboxamide;

(2R)—N-{5-chloro-4-[1-(tetrahydro-2H-pyran-4-ylm-
ethyl)-1H-benzimidazol-6-yl]pyridin-2-yl}azetidine-2-
carboxamide;

6-amino-N-{5-chloro-4-[1-(tetrahydro-2H-pyran-4-ylm-
ethyl)-1H-benzimidazol-6-yl]pyridin-2-yl}spiro[3.3]hep-
tane-2-carboxamide;

N-{5-chloro-4-[1-(tetrahydro-2H-pyran-4-ylmethyl)-1H-
benzimidazol-6-yl]pyridin-2-yl}-2-(furan-2-yl)-2-(piper-
azin-1-yl)acetamide;

1-amino-N-{5-chloro-4-[1-(tetrahydro-2H-pyran-4-ylm-
ethyl)-1H-benzimidazol-6-yl]pyridin-2-
yl}cyclopentanecarboxamide;

N-{5-chloro-4-[1-(tetrahydro-2H-pyran-4-ylmethyl)-1H-
benzimidazol-6-yl]pyridin-2-yl}-5-thia-2-azaspiro[3.4]
octane-8-carboxamide 5,5-dioxide;

(2S,3R)—N-{5-chloro-4-[1-(tetrahydro-2H-pyran-4-ylm-
ethyl)-1H-benzimidazol-6-yl]pyridin-2-yl}-3-ethylazeti-
dine-2-carboxamide;

N-{5-chloro-4-[1-(tetrahydro-2H-pyran-4-ylmethyl)-1H-
benzimidazol-6-yl]pyridin-2-yl}-4-(4-fluorophenyl)pip-
eridine-4-carboxamide;

N-{5-chloro-4-[1-(tetrahydro-2H-pyran-4-ylmethyl)-1H-
benzimidazol-6-yl]pyridin-2-yl}-1-thia-7-azaspiro[4.4]
nonane-4-carboxamide 1,1-dioxide;

methyl 4-{[6-(5-chloro-2-{[(3R)-piperidin-3-ylcarbonyl]
amino}pyridin-4-yl)-1H-benzimidazol-1-yl]
methyl}benzoate;

(3R)—N-(5-chloro-4-{1-[3-(3-fluorophenyl)propyl]-1H-
benzimidazol-6-yl}pyridin-2-yl)piperidine-3-carboxam-
ide;

4-{[6-(5-chloro-2-{[(3R)-piperidin-3-ylcarbonyl]
amino}pyridin-4-yl)-1H-benzimidazol-1-yl]
methyl}benzoic acid;

(1R,4R,6R)—N-{5-chloro-4-[1-(tetrahydro-2H-pyran-4-yl-
methyl)-1H-benzimidazol-6-yl]pyridin-2-yl}-2-azabicy-
clo[2.2.1]heptane-6-carboxamide;

(1R,4R,6S)—N-{5-chloro-4-[1-(tetrahydro-2H-pyran-4-yl-
methyl)-1H-benzimidazol-6-yl]pyridin-2-yl}-2-azabicy-
clo[2.2.1]heptane-6-carboxamide;

(3R)—N-{5-chloro-4-[1-(thiophen-2-ylmethyl)-1H-benz-
imidazol-6-yl]pyridin-2-yl}piperidine-3-carboxamide;

5-chloro-4-[1-(3-fluorobenzyl)-1H-benzimidazol-6-yl]-N-
{3-[(methylsulfonyl)methyl]phenyl}pyridin-2-amine;

ethyl {[(3R)-3-({5-chloro-4-[1-(tetrahydro-2H-pyran-4-yl-
methyl)-1H-benzimidazol-6-yl]pyridin-2-yl}carbamoyl)
piperidin-1-yl]sulfonyl}carbamate;

methyl (cis)-3-({5-chloro-4-[1-(tetrahydro-2H-pyran-4-yl-
methyl)-1H-benzimidazol-6-yl]pyridin-2-yl}carbamoyl)
cyclohexanecarboxylate;

(cis)-3-({5-chloro-4-[1-(tetrahydro-2H-pyran-4-ylmethyl)-
1H-benzimidazol-6-yl]pyridin-2-yl}carbamoyl)cyclo-
hexanecarboxylic acid;

(cis)-N-{5-chloro-4-[1-(tetrahydro-2H-pyran-4-ylmethyl)-
1H-benzimidazol-6-yl]pyridin-2-yl}-3-[(3-hydroxyazeti-
din-1-yl)carbonyl]cyclohexanecarboxamide;

(cis)-N'-{5-chloro-4-[1-(tetrahydro-2H-pyran-4-ylmethyl)-
1H-benzimidazol-6-yl]pyridin-2-yl}-N-(2-hydroxy-
ethyl)-N-methylcyclohexane-1,3-dicarboxamide;

(cis)-N-{5-chloro-4-[1-(tetrahydro-2H-pyran-4-ylmethyl)-
1H-benzimidazol-6-yl]pyridin-2-yl}-3-{[(2S)-2-(hy-
droxymethyl)pyrrolidin-1-yl]
carbonyl}cyclohexanecarboxamide;

(3R)—N-[4-(1-methyl-1H-benzimidazol-6-yl)pyridin-2-yl]
piperidine-3-carboxamide;

tert-butyl (3aR,6aS)-5-({5-chloro-4-[1-(tetrahydro-2H-
pyran-4-ylmethyl)-1H-benzimidazol-6-yl]pyridin-2-
yl}carbamoyl)hexahydrocyclopenta[c]pyrrole-2(1H)-car-
boxylate;

cis-4-({5-chloro-4-[1-(3-fluorobenzyl)-1H-benzimidazol-6-
yl]pyridin-2-yl}amino)cyclohexanecarboxylic acid; or a
pharmaceutically acceptable salt thereof.

Schemes

Compounds of the present invention (e.g., compounds of
Formula I) can be prepared by applying synthetic method-
ology known in the art and synthetic methodology outlined
in the schemes set forth below.

Scheme 1

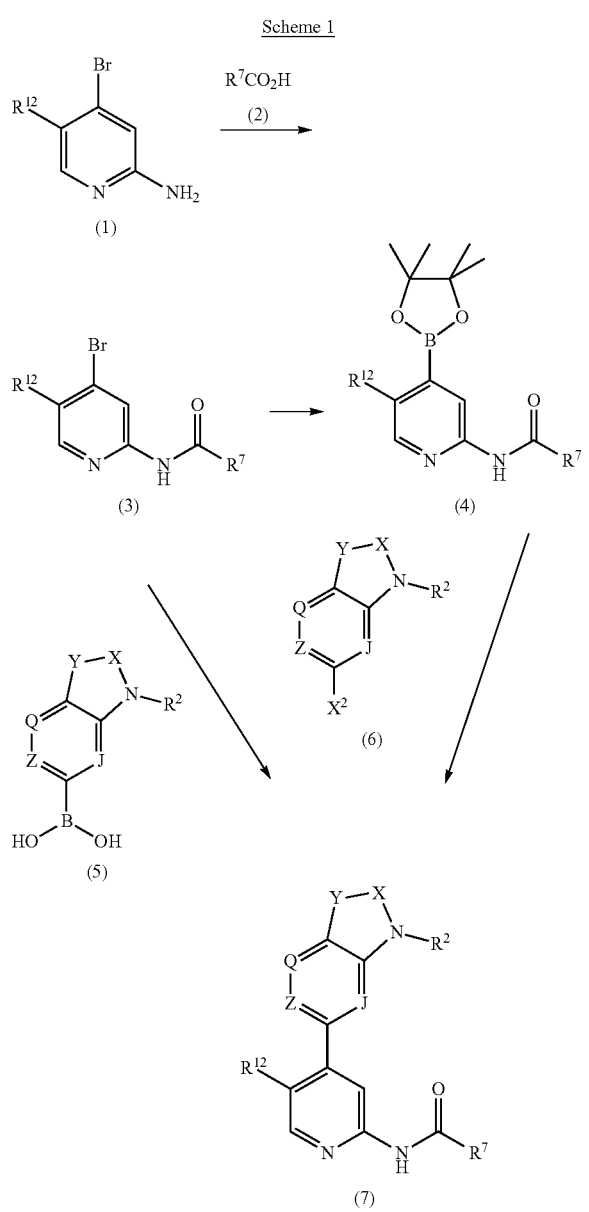

Examples of the palladium catalyst include, but are not limited to, 1,1'-bis(diphenylphosphino)ferrocene-palladium (II)dichloride dichloromethane complex, tetrakis(triphenylphosphine)palladium(0), tris(dibenzylideneacetone)dipalladium(0), bis(triphenylphosphine)palladium(II) dichloride, and palladium(II)acetate. Examples of suitable bases that may be employed include, but are not limited to, carbonates or phosphates of sodium, potassium, and cesium, acetates of sodium or potassium, and cesium fluoride. Examples of suitable ligands include, but are not limited to, 2-(dicyclohexylphosphino)biphenyl, 1,3,5,7-tetramethyl-6-phenyl-2,4,8-trioxa-6-phosphaadamante, 2-dicyclohexylphosphino-2',4',6'-triisopropylbiphenyl (X-phos), and 1,1'-bis (diphenylphosphanyl) ferrocene. Non-limiting examples of suitable solvent include methanol, ethanol, dimethoxyethane, N,N-dimethylformamide, dimethylsulfoxide, dioxane, tetrahydrofuran, and water, or mixtures thereof. Compounds of formula (4) can be reacted with compounds of formula (6), wherein X, Y, Z, J, and $R^2$ are as described herein and $X^2$ is a suitable halide or triflate, under Suzuki Coupling reaction conditions as described above to provide compounds of formula (7), which are representative of compounds of Formula (Ia).

Alternatively, compounds of formula (3) can be reacted with compounds of formula (5) (or an equivalent boronic ester), wherein $R^2$ is as described herein, under Suzuki Coupling reaction conditions as described above to provide compounds of formula (7), which are representative of compounds of Formula (Ia).

Scheme 2

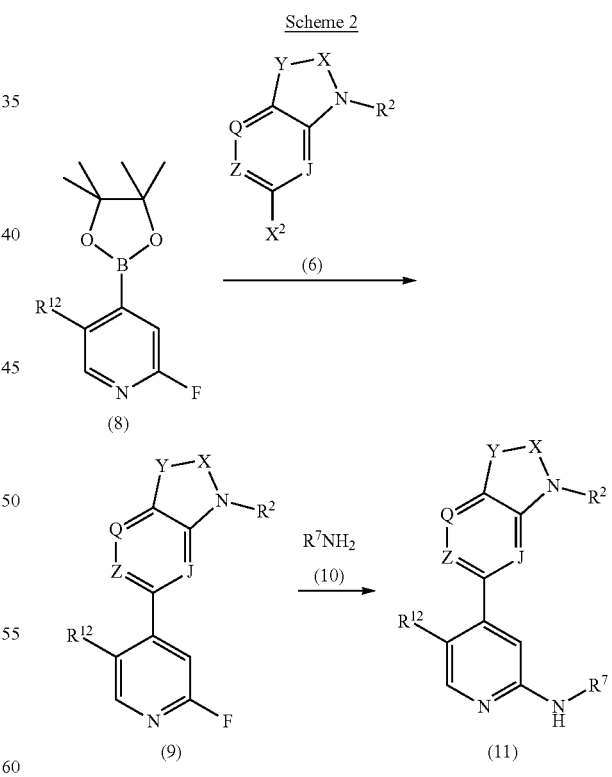

As shown in Scheme 1, compounds of formula (2), wherein $R^7$ is as described herein, can be treated with 1-chloro-N,N,2-trimethylprop-1-en-1-amine at low temperature (e.g., 0° C.), followed by the addition of compounds of formula (1), wherein $R^{12}$ is as described herein, in the presence of a base such as but limited to pyridine, to provide compounds of formula (3). The reaction is typically performed in a solvent such as, but not limited to dichloromethane, tetrahydrofuran, or mixtures thereof. Compounds of formula (4), can be prepared from compounds of formula (3), by reacting the latter with 4,4,4',4',5,5,5',5'-octamethyl-2,2'-bi(1,3,2-dioxaborolane) under Suzuki coupling reaction conditions (N. Miyama and A. Suzuki, Chem. Rev. 1995, 95:2457-2483, J. Organomet. Chem. 1999, 576:147-148). For example, the coupling reaction may be conducted in the presence of a palladium catalyst and a base, and optionally in the presence of a ligand, and in a suitable solvent at elevated temperature (about 80° C. to about 150° C.). The reaction may be facilitated by microwave irradiation.

As shown in Scheme 2, compounds of formula (8), wherein $R^{12}$ is as described herein, can be reacted with compounds of formula (6) under Suzuki Coupling reaction conditions as described in Scheme 1 to provide compounds of formula (9). Compounds of formula (10) wherein $R^7$ is as described herein for Formula (Ia) can be reacted with compounds of formula (9), to provide compounds of formula (11) which are representative of compounds of Formula (Ia). The reaction is typically performed at an elevated temperature (e.g., 105° C.), in a solvent such as but not limited to dimethyl sulfoxide.

Alternatively, compounds of formula (13) may be reacted with compounds of formula (2), wherein $R^7$ is as described herein, under acylation conditions which typically include one or more coupling agents and a suitable base in a suitable solvent to provide compounds of formula (17) which are Scheme 3

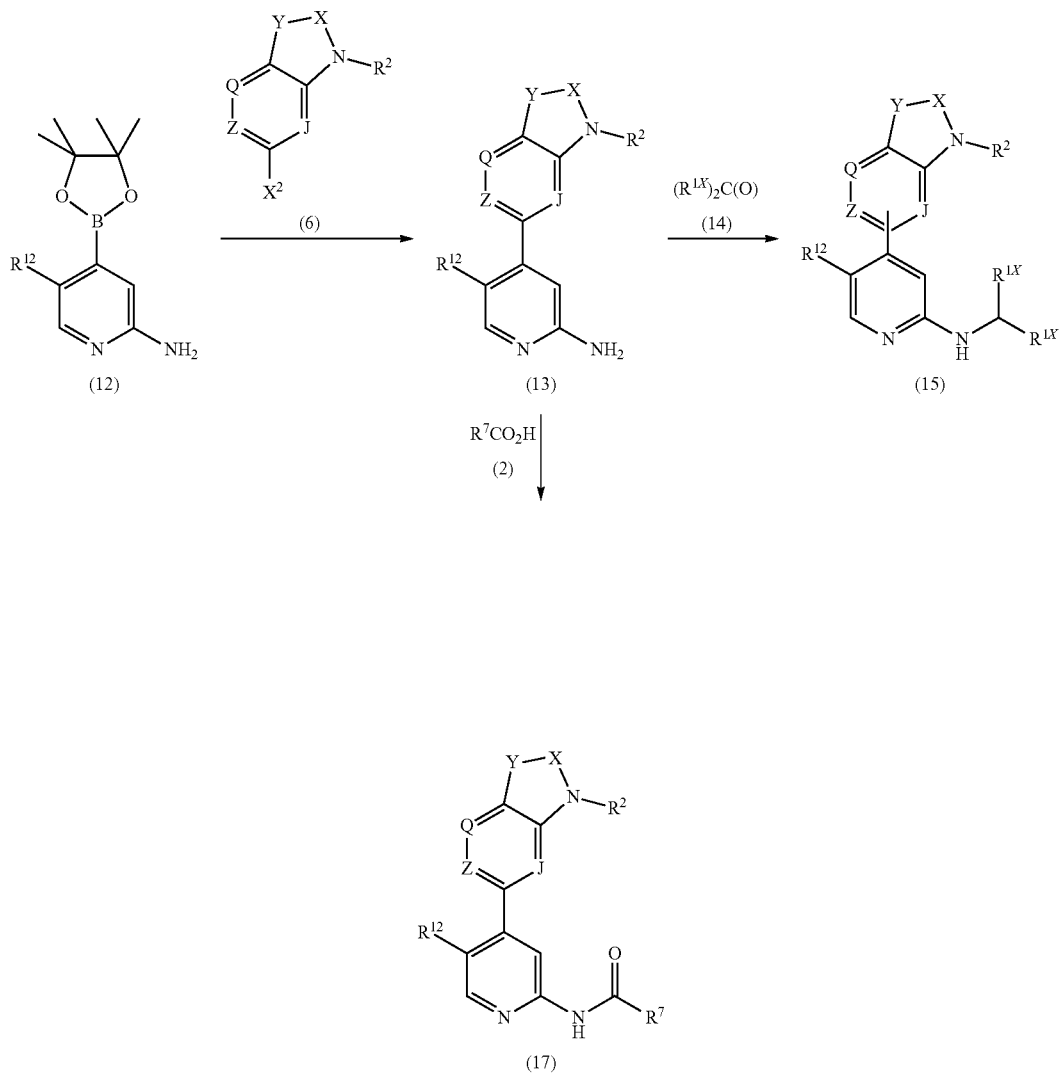

As shown in Scheme 3, compounds of formula (12), wherein $R^{12}$ is as described herein, can be reacted with compounds of formula (6) under Suzuki Coupling reaction conditions as described in Scheme 1 to provide compounds of formula (13). Compounds of formula (14) wherein each $R^{LX}$ is alkyl or as described in Formula (Ia) for substituents on alkyl, can be reacted with compounds of formula (13) under reductive amination conditions to provide compounds of formula (15). For example, a reducing agent and acetic acid are typically employed. Examples of reducing agents used include but are not limited to sodium borohydride, sodium cyanohydride, sodium triacetoxyborohydride, and polymer supported cyanoborohydride. The reaction is typically performed in a solvent such as but not limited to methanol, tetrahydrofuran, and dichloromethane or mixtures thereof.

representative of compounds of Formula (Ia). Examples of coupling agents include, but are not limited to 1-hydroxy-7-aza-benzotriazole, hydroxybenzotriazole, 1-ethyl-3-[3-(dimethylamino)propyl]-carbodiimide hydrochloride, 1,1'-carbonyldiimidazole, benzotriazol-1-yl-oxytripyrrolidinophosphonium hexafluorophosphate, ethyl 2-cyano-2-(hydroxyimino)acetate, (O-(7-azabenzotriazol-1-yl)-N,N,N',N'-tetramethyluronium hexafluorophosphate), and (benzotriazol-1-yloxy)tris(dimethylamino)phosphonium hexafluorophosphate. Examples of suitable bases include, but are not limited to triethylamine, N,N-diisopropylethylamine, 4-(dimethylamino)pyridine, and mixtures thereof. Examples of solvents include, but are not limited to dichloromethane, N,N-dimethylformamide, and mixtures thereof.

Scheme 4

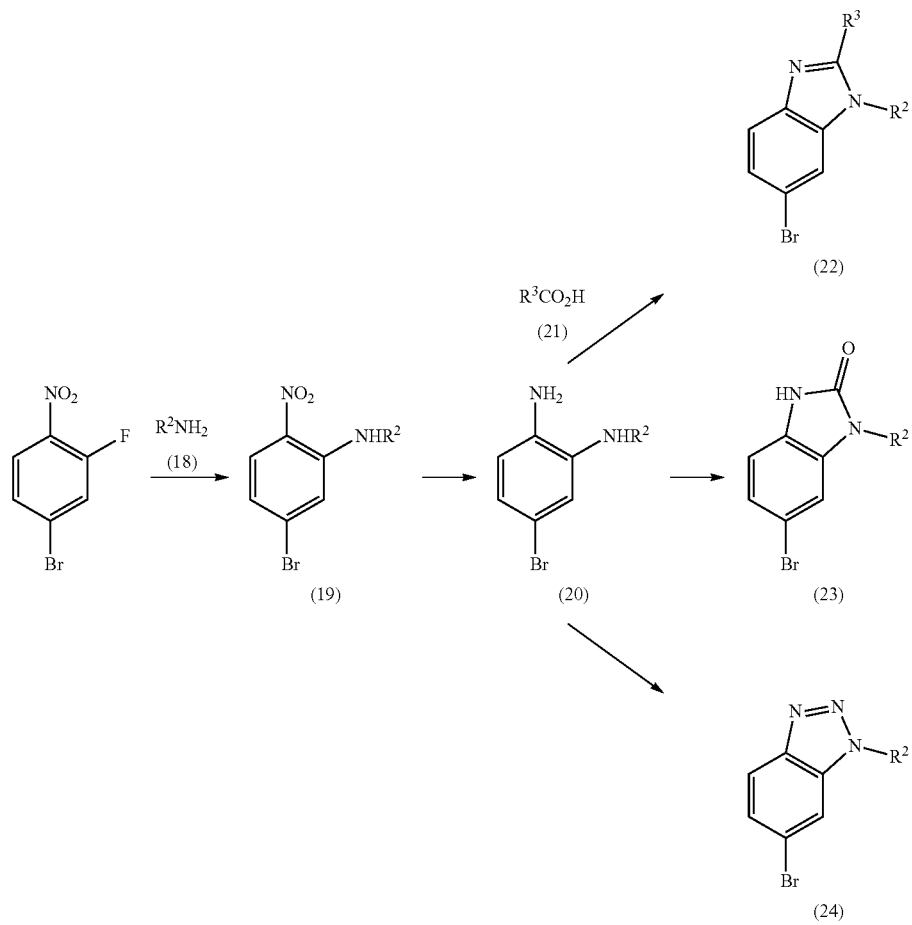

4-Bromo-2-fluoro-1-nitrobenzene can be reacted with compounds of formula (18) wherein $R^2$ is as described for Formula (I), in the presence of a base such as but not limited to potassium carbonate, to provide compounds of formula (19). The reaction is typically performed at an elevated temperature (e.g., 80° C.), in a solvent such as but not limited to N,N-dimethylformamide. Compounds of formula (20) can be prepared under reducing conditions such as hydrazine monohydrate in the presence of Raney® nickel in water. The reaction is typically performed at an elevated temperature (e.g., 50° C.), in a solvent such as but not limited to methanol.

Compounds of formula (20) can be reacted with compounds of formula (21) wherein $R^3$ is as described herein for Formula (Ia), at an elevated temperature (e.g., 90° C.) to provide compounds of formula (22).

Compounds of formula (20) can be reacted with carbonyl diimidazole to provide compounds of formula (23). The reaction is typically performed at ambient temperature in a solvent such as but not limited to tetrahydrofuran.

Compounds of formula (20) can be reacted with sodium nitrite in glacial acetic acid to provide compounds of formula (24). The reaction is typically performed at ambient temperature.

Scheme 5

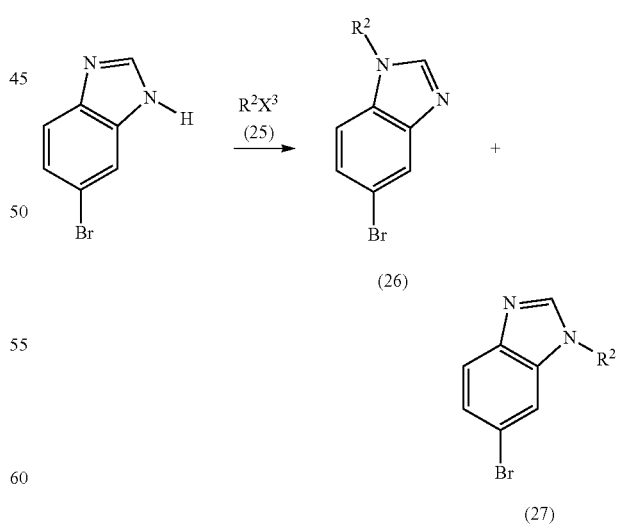

As shown in Scheme (5), 6-bromo-1H-benzo[d]imidazole can be reacted with compounds of formula (25), wherein $R^2$ is as described herein and $X^3$ is an appropriate halide, in the presence of a base such as but not limited to cesium carbonate to provide compounds of formula (26) and (27). The reaction is typically performed at an elevated temperature (e.g., 110° C.) in a solvent such as but not limited to N,N-dimethylformamide.

Scheme 6

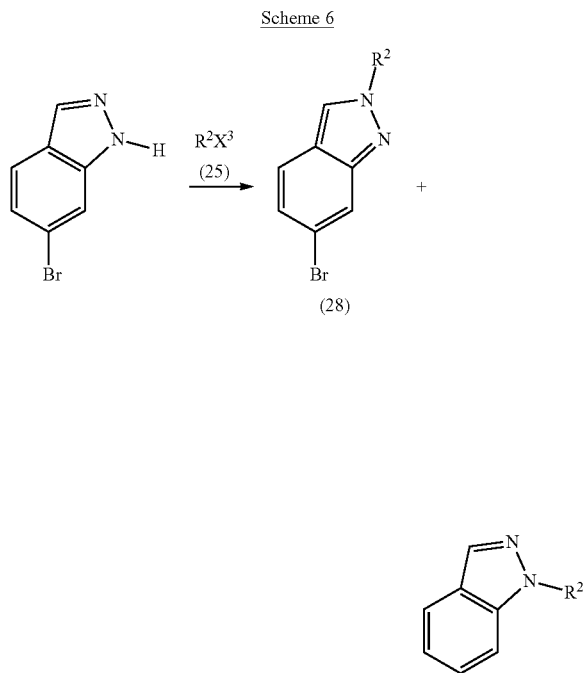

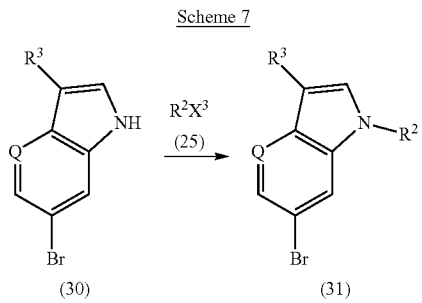

As shown in Scheme (6), 6-bromo-1H-indazole can be reacted with compounds of formula (25), wherein $R^2$ is as described herein and $X^3$ is an appropriate halide, in the presence of a base such as but not limited to potassium tert-butoxide to provide compounds of formula (28) and (29). The reaction is typically performed at an ambient temperature in a solvent such as but not limited to dimethylsulfoxide.

Scheme 7

As shown in Scheme (7), compounds of formula (30), wherein Q and $R^3$ are as described herein, can be reacted with compounds of formula (25), wherein $R^2$ is as described herein and $X^3$ is an appropriate halide, in the presence of a base such as but not limited to sodium hydride to provide compounds of formula (31). The reaction is typically performed at an elevated temperature (e.g., 100° C.) in a solvent such as but not limited to N,N-dimethylformamide.

Scheme 8

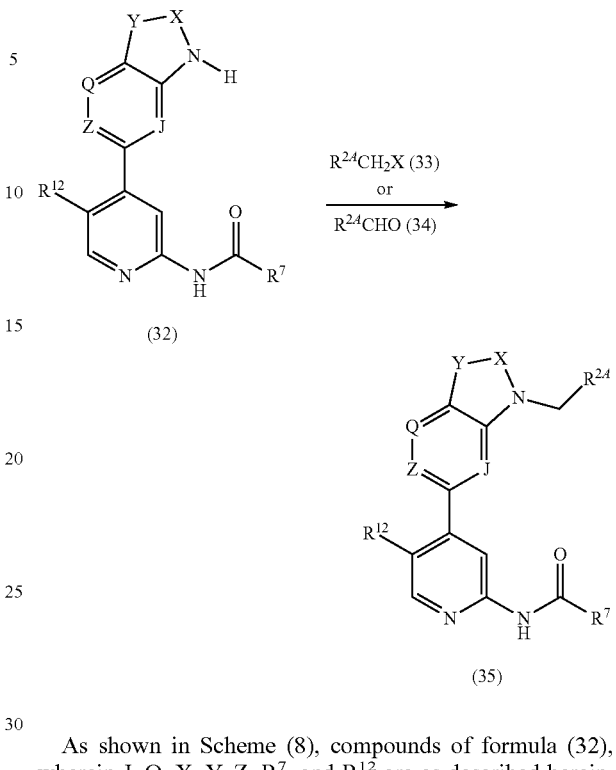

As shown in Scheme (8), compounds of formula (32), wherein J, Q, X, Y, Z, $R^7$, and $R^{12}$ are as described herein, can be reacted with compounds of formula (33), wherein $R^{24}$ is as described herein for substituents on $R^2$ when $R^2$ is alkyl, under appropriate alkylation conditions to provide compounds of formula (35), which are representative of compounds of Formula (Ia). Alternatively, compounds of formula (34), wherein $R^{24}$ is as described herein for substituents on $R^2$ when $R^2$ is alkyl, can be reacted with compounds of Formula (32) under appropriate reductive amination conditions to provide compounds of formula (35), which are representative of compounds of Formula (Ia).

Pharmaceutically acceptable salts have been described in S. M. Berge et al. J. Pharmaceutical Sciences, 1977, 66: 1-19.

Compounds of formula (I) may contain either a basic or an acidic functionality, or both, and can be converted to a pharmaceutically acceptable salt, when desired, by using a suitable acid or base. The salts may be prepared in situ during the final isolation and purification of the compounds of the invention.

Examples of acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts may be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other examples of organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use.

The present invention contemplates compounds of formula (I) formed by synthetic means or formed by in vivo biotransformation of a prodrug.

Compounds described herein can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

Pharmaceutical Compositions

This invention also provides for pharmaceutical compositions comprising a therapeutically effective amount of a compound of Formula I, or a pharmaceutically acceptable salt thereof together with a pharmaceutically acceptable carrier, diluent, or excipient therefor. The phrase "pharmaceutical composition" refers to a composition suitable for administration in medical or veterinary use.

The pharmaceutical compositions that comprise a compound of formula (I), alone or in combination with a second active pharmaceutical agent, may be administered to the subjects orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents, which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally-administered drug form may be accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In certain embodiments, solid dosage forms may contain from 1% to 95% (w/w) of a compound of Formula (Ia). In certain embodiments, the compound of Formula (Ia) may be present in the solid dosage form in a range of from 5% to 70% (w/w). In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

The pharmaceutical composition may be a unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form can be a capsule, tablet, cachet, or lozenge itself, or it can be the appropriate number of any of these in packaged form. The quantity of active component in a unit dose preparation may be varied or adjusted from 0.1 mg to 1000 mg, from 1 mg to 100 mg, or from 1% to 95% (w/w) of a unit dose, according to the particular application and the potency of the active component. The composition can, if desired, also contain other compatible therapeutic agents.

The dose to be administered to a subject may be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician can evaluate factors such as the circulating plasma levels of the compound, compound toxicities, and/or the progression of the disease, etc. In general, the dose equivalent of a compound is from about 1 μg/kg to 100 mg/kg for a typical subject.

For administration, compounds of the Formula (Ia) can be administered at a rate determined by factors that can include, but are not limited to, the $LD_{50}$ of the compound, the pharmacokinetic profile of the compound, contraindicated drugs, and the side-effects of the compound at various concentrations, as applied to the mass and overall health of the subject. Administration can be accomplished via single or divided doses.

The compounds utilized in the pharmaceutical method of the invention can be administered at the initial dosage of about 0.001 mg/kg to about 100 mg/kg daily. In certain embodiments, the daily dose range is from about 0.1 mg/kg to about 10 mg/kg. The dosages, however, may be varied depending upon the requirements of the subject, the severity of the condition being treated, and the compound being employed. Determination of the proper dosage for a particular situation is within the skill of the practitioner. Treatment may be initiated with smaller dosages, which are less than the optimum dose of the compound. Thereafter, the dosage is increased by small increments until the optimum effect under circumstances is reached. For convenience, the total daily dosage may be divided and administered in portions during the day, if desired.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of Formula (Ia) may also be administered in the form of liposomes. Liposomes generally may be derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form may contain, in addition to a compound of formula (I), stabilizers, preservatives, excipients and the like. Examples of lipids include, but are not limited to, natural and synthetic phospholipids and phosphatidyl cholines (lecithins), used separately or together.

Methods to form liposomes have been described, see example, Prescott, Ed., Methods in Cell Biology, Volume XIV, Academic Press, New York, N.Y. (1976), p. 33 et seq.

Dosage forms for topical administration of a compound described herein include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

Methods of Use

The compounds of Formula (Ia), or pharmaceutically acceptable salts thereof, and pharmaceutical compositions comprising a compound of formula I, or a pharmaceutically acceptable salt thereof, can be administered to a subject suffering from a CDK9-mediated disorder or condition. A "CDK9-mediated disorder or condition" is characterized by the participation of one or more CDK9 kinases in the inception, manifestation of one or more symptoms or disease markers, severity, or progression of a disorder or condition. An example of a CDK9-mediated disorder or condition is cancer, including cancers such as, not limited to, acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophoblastic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcoma, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synovioma, sweat gland carcinoma, testicular cancer (including germ cell testicular cancer), thyroid cancer, Waldenström's macroglobulinemia, testicular tumors, uterine cancer, Wilms' tumor and the like.

The term "administering" or "administered" refers to the method of contacting a compound with a subject. Thus, the compounds of Formula (Ia) can be administered by injection, that is, intravenously, intramuscularly, intracutaneously, subcutaneously, intraduodenally, parentally, or intraperitoneally. In certain embodiments, a compound of Formula (Ia) may be administered orally. Also, the compounds described herein can be administered by inhalation, for example, intranasally. Additionally, the compounds of Formula (Ia) can be administered transdermally, topically, via implantation, transdermally, topically, and via implantation. In certain embodiments, the compounds of the Formula (Ia) may be delivered orally. The compounds can also be delivered rectally, bucally, intravaginally, ocularly, andially, or by insufflation. CDK9-mediated disorders and conditions can be treated prophylactically, acutely, and chronically using compounds of Formula (Ia), depending on the nature of the disorder or condition. Typically, the host or subject in each of these methods is human, although other mammals can also benefit from the administration of a compound of Formula (Ia).

The compounds of Formula (Ia) can be co-administered to a subject. The term "co-administered" means the administration of two or more different pharmaceutical agents or treatments (e.g., radiation treatment) that are administered to a subject by combination in the same pharmaceutical composition or separate pharmaceutical compositions. Thus co-administration involves administration at the same time of a single pharmaceutical composition comprising two or more pharmaceutical agents or administration of two or more different compositions to the same subject at the same or different times.

The compounds of the invention can be co-administered with a therapeutically effective amount of one or more agents to treat a cancer, where examples of the agents include, such as radiation, alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs (dual variable domain antibodies), leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (bromodomain) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, *J. of Immunology* 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, singledouble strands, bulges, nicksgaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include EGFR antibodies, ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, pertuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecific antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FCl, PU-3, radicicol, SNX-2112, STA-9090 VER49009 and the like.

Inhibitors of inhibitors of apoptosis proteins include HGS1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirubicin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzumab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofuran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radio-sensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EPO906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces* staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

The following Examples may be used for illustrative purposes and should not be deemed to narrow the scope of the invention.

EXAMPLES

The following examples are presented to provide what is believed to be the most useful and readily understood description of procedures and conceptual aspects of this invention. The exemplified compounds were named using ACD/ChemSketch Version 5.06 (5 Jun. 2001, Advanced Chemistry Development Inc., Toronto, Ontario), ACD/ChemSketch Version 12.01 (13 May 2009), Advanced Chemistry Development Inc., Toronto, Ontario), or ChemDraw® Ver. 9.0.5 (CambridgeSoft, Cambridge, Mass.). Intermediates were named using ChemDraw® Ver. 9.0.5 (CambridgeSoft, Cambridge, Mass.).

Example 1

(3R)—N-{5-chloro-4-[1-(3-fluorobenzyl)-2,3-dihydro-1H-indol-6-yl]pyridin-2-yl}piperidine-3-carboxamide Example 1A 4-bromo-5-chloropyridin-2-amine To a solution of 4-bromopyridin-2-amine (12.0 g, 69.4 mmol) in N,N-dimethylformamide (200 mL) at −20° C. was slowly added a solution of 1-chloropyrrolidine-2,5-dione (10.24 g, 77.0 mmol) in N,N-dimethylformamide (200 mL). The mixture was stirred at room temperature for 16 hours and the mixture was poured into cold 1M aqueous sodium hydroxide (1000 mL) and extracted with ethyl acetate. The organic layer was washed with water and brine, dried over sodium sulfate, filtered and concentrated. Purification by column chromatography on silica (Analogix 280), eluting with a gradient of 5-65% ethyl acetate/hexanes gave the title compound. MS (ESI) m/e 208 (M+H)⁺.

Example 1B (R)-tert-butyl 3-((4-bromo-5-chloropyridin-2-yl)carbamoyl)piperidine-1-carboxylate To a solution of (R)-1-(tert-butoxycarbonyl)piperidine-3-carboxylic acid (6.61 g, 28.8 mmol) in 70 mL of dichloromethane at 0° C. was added 1-chloro-N,N,2-trimethyl-prop-1-en-1-amine (3.70 g, 27.7 mmol). The mixture was stirred at room temperature for 30 minutes and a solution of Example 1A (4.6 g, 22.17 mmol) and pyridine (2.24 mL, 27.7 mmol) in tetrahydrofuran (70 mL) was added. The mixture was stirred at room temperature overnight, diluted with ethyl acetate, washed with saturated aqueous sodium bicarbonate and brine, dried over sodium sulfate, filtered and concentrated. Purification by column chromatography on silica (Analogix 280), eluting with a gradient of 10-90% ethyl acetate/hexane afforded the title compound. MS (ESI) m/e 420 (M+H)⁺.

Example 1C (R)-tert-butyl 3-((5-chloro-4-(4,4,5,5-tetramethyl-1,3,2-dioxaborolan-2-yl)pyridin-2-yl)carbamoyl)piperidine-1-carboxylate A mixture of Example 1B (1.20 g, 2.87 mmol), 4,4,4',4',5,5,5',5'-octamethyl-2,2'-bi(1,3,2-dioxaborolane) (0.73 g, 2.87 mmol), 1,1'-bis(diphenylphosphino)ferrocene-palladium(II)dichloride dichloromethane complex (0.14 g, 0.17 mmol) and potassium acetate (0.844 g, 8.60 mmol) in 1,4-dioxane (12 mL) was flushed with nitrogen and stirred at 95° C. overnight. After cooling, the solution was used directly without further purification.

Example 1D 6-bromo-1-(3-fluorobenzyl)indoline

A mixture of 6-bromoindoline (750 mg, 3.79 mmol), 1-(bromomethyl)-3-fluorobenzene (697 μL, 5.68 mmol), and cesium carbonate (1.851 g, 5.68 mmol) in N,N-dimethylformamide (7.573 mL) was stirred at 110° C. for 2 hours. The mixture was cooled, diluted with ethyl acetate, washed with water and brine, dried over magnesium sulfate, filtered and concentrated. Purification by silica gel flash chromatography (Isco®, Redi-Sep® column) eluting with a gradient of 2-50% ethyl acetate/hexane afforded the title compound.

Example 1E (3R)—N-{5-chloro-4-[1-(3-fluorobenzyl)-2,3-dihydro-1H-indol-6-yl]pyridin-2-yl}piperidine-3-carboxamide A mixture of Example 1C (0.107 mmol), Example 1D (32.9 mg, 0.107 mmol), 1,1'-bis(diphenylphosphino)ferrocene-palladium(II)dichloride dichloromethane complex (5.3 mg, 6.5 μmol) and 2M aqueous sodium carbonate (0.295 mL, 0.590 mmol) in 1,4-dioxane (1 mL) was flushed with nitrogen and stirred at 95° C. for 1 hour. The mixture was cooled, concentrated and purified by reverse-phase HPLC (Phenomenex Luna C8(2) 5 μm 100 Å AXIA column) using a gradient of 10-95% acetonitrile/0.1% trifluoroacetic acid in water with 10 mM ammonium acetate to afford 6.5 mg of the protected intermediate. To this intermediate was added 2M hydrogen chloride in diethyl ether (0.5 mL) and the mixture was stirred at room temperature for 1 hour. Concentration gave the title compound as the hydrochloride salt. ¹H NMR (400 MHz, methanol-d₄) δ 1.85-2.28 (m, 4H) 3.08-3.18 (m, 2H) 3.22 (t, J=7.78 Hz, 2H) 3.27-3.39 (m, 3H) 3.47 (dd, J=12.66, 3.20 Hz, 1H) 3.84 (t, J=7.63 Hz, 2H) 4.66 (s, 2H) 7.08-7.18 (m, 1H) 7.19-7.55 (m, 7H) 8.00 (s, 1H) 8.46 (s, 1H). MS (ESI) m/e 465 (M+H)⁺.

Example 2

(3R)—N-[5-chloro-4-(2,3-dihydro-1H-indol-6-yl)pyridin-2-yl]piperidine-3-carboxamide To a mixture of Example 1B (72 mg, 0.172 mmol), 4,4,4',4',5,5,5',5'-octamethyl-2,2'-bi(1,3,2-dioxaborolane) (44 mg, 0.172 mmol), 1,1'-bis(diphenylphosphino)ferrocene-palladium(II)dichloride dichloromethane complex (8.4 mg, 0.010 mmol) and potassium acetate (51 mg, 0.516 mmol) was added dioxane (855 μL). The mixture was flushed with nitrogen and stirred at 100° C. for 3 hours under nitrogen. A solution of 6-bromoindoline (30.6 mg, 0.155 mmol) in dioxane (0.5 mL) was added, followed by 1,1'-bis(diphenylphosphino)ferrocene-palladium(II)dichloride dichloromethane complex (8.4 mg, 0.010 mmol) and 2M aqueous sodium carbonate solution (473 μL, 0.946 mmol). The mixture was stirred at 100° C. for 3 hours. After cooling, the mixture was filtered through diatomaceous earth with ethyl acetate and concentrated. Purification of the residue by silica gel flash chromatography (Isco®, Redi-Sep® column) eluting with a gradient of 10-100% ethyl acetate/hexane, afforded the BOC-protected intermediate which was dissolved in 1 mL of dichloromethane and treated with 1 mL of trifluoroacetic acid. The mixture was stirred at ambient temperature for 15 minutes, concentrated and purified by reverse-phase preparative HPLC (Phenomenex Luna C8(2) 5 μm 100 Å AXIA column) using a gradient of 10-95% acetonitrile/0.1% trifluoroacetic acid in water to afford the title compound as the bis-trifluoroacetate salt. ¹H NMR (300 MHz, methanol-d₄) δ 8.42 (s, 1H), 8.21 (s, 1H), 7.61 (d, J=8.1, 1H), 7.55-7.47 (m, 2H), 3.89 (t, J=7.9, 2H), 3.45-3.34 (m, 2H), 3.28-3.21 (m, 1H), 3.16-2.98 (m, 3H), 2.22-2.10 (m, 1H), 2.02-1.79 (m, 4H).). MS (ESI) m/z 357 (M+H)⁺.

Example 3

(3R)—N-[5-chloro-4-(1-methyl-1H-benzimidazol-6-yl)pyridin-2-yl]piperidine-3-carboxamide The title compound was prepared as described in Example 2, using 6-bromo-1-methyl-1H-benzo[d]imidazole in place of 6-bromoindoline. The BOC-protected intermediate was purified by reverse-phase preparative HPLC (Phenomenex Luna C8(2) 5 μm 100 Å AXIA column) using a gradient of 10-95% acetonitrile/0.1% trifluoroacetic acid in water and the intermediate obtained was dissolved in 1 mL dichloromethane and treated with 1 mL trifluoroacetic acid. The mixture was stirred at ambient temperature for 15 minutes, concentrated and purified by reverse-phase preparative HPLC (Phenomenex Luna C8(2) 5 μm 100 Å AXIA column) using a gradient of 10-95% acetonitrile/0.1% trifluoroacetic acid in water to afford the title compound as the trifluoroacetate salt. ¹H NMR (400 MHz, methanol-d₄) δ 9.46 (s, 1H), 8.47 (s, 1H), 8.30 (s, 1H), 8.10 (s, 1H), 7.99 (d, J=8.6, 1H), 7.79 (dd, J=8.6, 1.4, 1H), 4.19 (s, 3H), 3.42-3.34 (m, 2H), 3.27-3.22 (m, 1H), 3.16-2.99 (m, 2H), 2.21-2.12 (m, 1H), 2.03-1.79 (m, 3H). MS (ESI) m/z 370 (M+H)⁺.

Example 4

(3R)—N-{5-chloro-4-[1-(tetrahydro-2H-pyran-4-ylmethyl)-2,3-dihydro-1H-indol-6-yl]pyridin-2-yl}piperidine-3-carboxamide Example 4A 6-bromo-1-((tetrahydro-2H-pyran-4-yl)methyl)indoline A mixture of 6-bromoindoline (500 mg, 2.52 mmol), 4-(bromomethyl)tetrahydro-2H-pyran (678 mg, 3.79 mmol) and cesium carbonate (1.234 g, 3.79 mmol) in N,N-dimethylformamide (5.049 mL) was stirred at 110° C. for 2 hours. The mixture was cooled and diluted with 200 mL ethyl acetate. The mixture was washed with water and brine, dried over magnesium sulfate, filtered and concentrated. Purification by silica gel flash chromatography (Isco®, Redi-Sep® column) eluting with a gradient of 2-60% ethyl acetate/hexane yielded the title compound. MS (ESI) m/z 297 (M+H)⁺.

Example 4B (3R)—N-{5-chloro-4-[1-(tetrahydro-2H-pyran-4-ylmethyl)-2,3-dihydro-1H-indol-6-yl]pyridin-2-yl}piperidine-3-carboxamide The title compound was prepared as described in Example 2, using Example 4A in place of 6-bromoindoline. Purification by silica gel flash chromatography (Isco®, Redi-Sep® column) eluting with a gradient of 2-60% ethyl acetate/hexane afforded the BOC-protected intermediate which was dissolved in 1 mL dichloromethane and treated with 1 mL trifluoroacetic acid. The mixture was stirred at ambient for 15 minutes, concentrated and purified by reverse-phase preparative HPLC (Phenomenex Luna C8(2) 5 µm 100 Å AXIA column) using a gradient of 10-95% acetonitrile/0.1% trifluoroacetic acid in water to afford the title compound as the trifluoroacetate salt. ¹H NMR (400 MHz, methanol-d₄) δ 8.34 (s, 1H), 8.15 (s, 1H), 7.13 (d, J=7.4, 1H), 6.70 (dd, J=7.4, 1.3, 1H), 6.54 (s, 1H), 3.96 (dd, J=11.3, 3.5, 2H), 3.52-3.40 (m, 4H), 3.39-3.33 (m, 2H), 3.27-3.19 (m, 1H), 3.18-3.09 (m, 1H), 3.06-2.97 (m, 5H), 2.18-2.09 (m, 1H), 2.03-1.79 (m, 4H), 1.77-1.70 (m, 2H), 1.42-1.29 (m, 2H). MS (ESI) m/z 455 (M+H)⁺.

Example 5

(3R)—N-{5-chloro-4-[1-(3-fluorobenzyl)-1H-benzimidazol-5-yl]pyridin-2-yl}piperidine-3-carboxamide Example 5A 5-bromo-1-(3-fluorobenzyl)-1H-benzo[d]imidazole A mixture of 6-bromo-1H-benzo[d]imidazole (500 mg, 2.54 mmol), 1-(bromomethyl)-3-fluorobenzene (720 mg, 3.81 mmol) and cesium carbonate (1.24 g, 3.81 mmol) in N,N-dimethylformamide (5.075 mL) was stirred at 110° C. for 2 hours. The mixture was cooled and diluted with 50 mL ethyl acetate. The mixture was washed with water and brine, dried over magnesium sulfate, filtered and concentrated. Purification by silica gel flash chromatography (Isco®, Redi-Sep® column) eluting with a gradient of 10-100% ethyl acetate/hexane afforded the two regioisomers. The faster eluting regioisomer was isolated and determined to be the title compound by NOE experiments. MS (ESI) m/z 306 (M+H)⁺.

Example 5B (3R)—N-{5-chloro-4-[1-(3-fluorobenzyl)-1H-benzimidazol-5-yl]pyridin-2-yl}piperidine-3-carboxamide The title compound was prepared as described in Example 2, using Example 5A in place of 6-bromoindoline. Purification of the residue by silica gel flash chromatography (Isco®, Redi-Sep® column) eluting with a gradient of 20-100% ethyl acetate/hexane afforded the BOC-protected intermediate which was dissolved in 1 mL dichloromethane and treated with 1 mL trifluoroacetic acid. The mixture was stirred at ambient temperature for 15 minutes, concentrated and purified by reverse-phase preparative HPLC on a (Phenomenex Luna C8(2) 5 µm 100 Å AXIA column) using a gradient of 10-95% acetonitrile/0.1% trifluoroacetic acid in water to afford the title compound as the trifluoroacetate salt. ¹H NMR (400 MHz, methanol-d₄) δ 9.48 (s, 1H), 8.44 (s, 1H), 8.26 (s, 1H), 7.99 (s, 1H), 7.89 (d, J=8.7, 1H), 7.69 (dd, J=8.7, 1.4, 1H), 7.51-7.42 (m, 1H), 7.31-7.22 (m, 2H), 7.15 (td, J=8.6, 2.4, 1H), 5.80 (s, 2H), 3.40-3.33 (m, 2H), 3.28-3.20 (m, 1H), 3.15-2.98 (m, 2H), 2.20-2.11 (m, 1H), 2.01-1.79 (m, 3H). MS (ESI) m/z 464 (M+H)⁺.

Example 6

(3R)—N-{5-chloro-4-[1-(3-fluorobenzyl)-1H-benzimidazol-6-yl]pyridin-2-yl}piperidine-3-carboxamide Example 6A 6-bromo-1-(3-fluorobenzyl)-1H-benzo[d]imidazole The slower eluting regioisomer from Example 5A was isolated and determined to be the title compound by NOE experiments. MS (ESI) m/z 306 (M+H)⁺.

Example 6B (3R)—N-{5-chloro-4-[1-(3-fluorobenzyl)-1H-benzimidazol-6-yl]pyridin-2-yl}piperidine-3-carboxamide The title compound was prepared as described in Example 2, using Example 6A in place of 6-bromoindoline. Purification by silica gel flash chromatography (Isco®, Redi-Sep® column) eluting with a gradient of 20-100% ethyl acetate/hexane afforded the BOC-protected intermediate which was dissolved in 1 mL dichloromethane and treated with 1 mL trifluoroacetic acid. The mixture was stirred at ambient temperature for 15 minutes, concentrated and purified by reverse-phase preparative HPLC (Phenomenex Luna C8(2) 5 µm 100 Å AXIA column) using a gradient of 10-95% acetonitrile/0.1% trifluoroacetic acid in water to afford the title compound as the trifluoroacetate salt. ¹H NMR (400 MHz, methanol-d₄) δ 9.56 (s, 1H), 8.43 (s, 1H), 8.24 (s, 1H), 8.02-7.95 (m, 2H), 7.74 (dd, J=8.6, 1.3, 1H), 7.49-7.41 (m, 1H), 7.30-7.22 (m, 2H), 7.14 (td, J=8.6, 2.5, 1H), 5.80 (s, 2H), 3.43-3.33 (m, 2H), 3.27-3.21 (m, 1H), 3.16-2.97 (m, 2H), 2.21-2.12 (m, 1H), 2.01-1.79 (m, 3H). MS (ESI) m/z 464 (M+H)$^+$.

Example 7

(3R)—N-{5-chloro-4-[1-(3-fluorobenzyl)-1H-indol-6-yl]pyridin-2-yl}piperidine-3-carboxamide Example 7A 6-bromo-1-(3-fluorobenzyl)-1H-indole A mixture of 6-bromo-1H-indole (400 mg, 2.04 mmol) and sodium hydride (53.9 mg, 2.244 mmol) in N,N-dimethylformamide (4.081 mL) was stirred at ambient temperature for 10 minutes and 1-(bromomethyl)-3-fluorobenzene (250 μL, 2.04 mmol) was added. After stirring at 100° C. overnight, the mixture was cooled and diluted with 50 mL ethyl acetate. The mixture was washed with water and brine, dried over magnesium sulfate, filtered and concentrated. Purification by silica gel flash chromatography (Isco®, Redi-Sep® column) eluting with a gradient of 2-30% ethyl acetate/hexane afforded the title compound. MS (ESI) m/z 306 (M+H)$^+$.

Example 7B (3R)—N-{5-chloro-4-[1-(3-fluorobenzyl)-1H-indol-6-yl]pyridin-2-yl}piperidine-3-carboxamide The title compound was prepared as described in Example 2, using Example 7A in place of 6-bromoindoline. Purification by silica gel flash chromatography (Isco®, Redi-Sep® column) eluting with a gradient of 10-60% ethyl acetate/hexane afforded the BOC-protected intermediate which was dissolved in 1 mL dichloromethane and treated with 1 mL trifluoroacetic acid. The mixture was stirred at ambient temperature for 15 minutes, concentrated and purified by reverse-phase preparative HPLC (Phenomenex Luna C8(2) 5 μm 100 Å AXIA column) using a gradient of 10-95% acetonitrile/0.1% trifluoroacetic acid in water to afford the title compound as the trifluoroacetate salt. $^1$H NMR (300 MHz, methanol-d$_4$) δ 8.33 (s, 1H), 8.19 (s, 1H), 7.69 (d, J=8.1, 1H), 7.49 (s, 1H), 7.43 (d, J=3.1, 1H), 7.34-7.25 (m, 1H), 7.17 (dd, J=8.2, 1.6, 1H), 7.01-6.94 (m, 2H), 6.89-6.82 (m, 1H), 6.60 (dd, J=3.2, 0.7, 1H), 5.45 (s, 2H), 3.38-3.32 (m, 2H), 3.25-2.96 (m, 3H), 2.20-2.08 (m, 1H), 2.03-1.78 (m, 3H). MS (ESI) m/z 463 (M+H)$^+$.

Example 8 trans-N-{5-chloro-4-[1-(3-fluorobenzyl)-1H-benzimidazol-6-yl]pyridin-2-yl}cyclohexane-1,4-diamine Example 8A 5-bromo-N-(3-fluorobenzyl)-2-nitroaniline A mixture of 4-bromo-2-fluoro-1-nitrobenzene (500 mg, 2.273 mmol) and 3-fluorobenzylamine (370 mg, 2.95 mmol) in 7 mL N,N-dimethylformamide was treated with potassium carbonate (1.00 g, 7.24 mmol) and the mixture was heated at 80° C. for 1 hour. The mixture was diluted with ethyl acetate and the mixture was washed with brine, dried over magnesium sulfate, filtered and concentrated to give the crude title compound which was used without further purification.

Example 8B 5-bromo-N$^1$-(3-fluorobenzyl)benzene-1,2-diamine

To suspension of Example 8A (700 mg, 2.153 mmol) in 10 mL methanol was added hydrazine monohydrate (0.2 mL, 4.08 mmol) followed by 50% Raney® nickel in water (100 mg). The mixture was stirred at 50° C. for 2 hours, filtered through diatomaceous earth with dichloromethane, concentrated and purified by flash chromatography eluting with 100% dichloromethane to give the title compound.

Example 8C 6-bromo-1-(3-fluorobenzyl)-1H-benzo[d]imidazole

A mixture of Example 8B (299 mg, 1.013 mmol) in formic acid (500 μL, 13.25 mmol) was stirred at 90° C. for 1 hour. The cooled mixture was diluted with ethyl acetate, washed with water and brine, dried over magnesium sulfate, filtered, concentrated and purified by silica gel flash chromatography eluting with 80% ethyl acetate/hexane to afford the title compound.

Example 8D 6-(5-chloro-2-fluoropyridin-4-yl)-1-(3-fluorobenzyl)-1H-benzo[d]imidazole A mixture of Example 8C (91 mg, 0.298 mmol), 5-chloro-2-fluoro-4-(4,4,5,5-tetramethyl-1,3,2-dioxaborolan-2-yl)pyridine (100 mg, 0.388 mmol), bis(diphenylphosphino)ferrocene-palladium(II)dichloride dichloromethane complex (24.4 mg, 0.030 mmol), sodium carbonate (0.373 mL, 0.746 mmol) and dimethoxyethane (1.5 mL) was heated in a Biotage Initiator® microwave reactor at 110° C. for 30 minutes. The mixture was filtered through diatomaceous earth with ethyl acetate, concentrated and purified by silica gel flash chromatography (Isco®, Redi-Sep® column) eluting with a gradient of 2-75% ethyl acetate/hexane to give the title compound. MS (ESI) m/e 356 (M+H)$^+$.

Example 8E trans-N-{5-chloro-4-[1-(3-fluorobenzyl)-1H-benzimidazol-6-yl]pyridin-2-yl}cyclohexane-1,4-diamine A mixture of Example 8D (42 mg, 0.118 mmol) and trans-cyclohexane-1,4-diamine (135 mg, 1.181 mmol) in dimethyl sulfoxide (0.5 mL) was heated at 105° C. overnight. After cooling, the mixture was treated with trifluoroacetic acid (239 μL, 3.11 mmol) and diluted with methanol (1.5 mL). Purification by reverse-phase HPLC (Phenomenex Luna C8(2) 100 Å AXIA column) using a gradient of 10-95% acetonitrile/0.1% trifluoroacetic acid in water afforded the title compound as the trifluoroacetate salt. $^1$H NMR (400 MHz, dimethylsulfoxide-d$_6$) δ 1.23-1.38 (m, 2H) 1.39-1.55 (m, 2H) 1.95-2.11 (m, 4H) 2.97-3.11 (m, 1H) 3.62-3.73 (m, 1H) 5.62 (s, 1H) 6.55 (s, 1H) 7.07-7.14 (m, 1H) 7.16-7.23 (m, 2H) 7.34-7.43 (m, 2H) 7.72 (s, 1H) 7.74-7.80 (m, 2H) 7.81 (s, 1H) 7.83 (s, 1H) 8.05 (s, 1H) 8.86 (s, 1H). MS (ESI) m/e 450 (M+H)$^+$.

Example 9 trans-N-{5-chloro-4-[1-(3-fluorobenzyl)-2,3-dihydro-1H-indol-6-yl]pyridin-2-yl}cyclohexane-1,4-diamine

Example 9A 6-(5-chloro-2-fluoropyridin-4-yl)-1-(3-fluorobenzyl) indoline

The title compound was prepared as described in Example 8D using Example 1D in place of Example 8C. MS (ESI) m/e 357 (M+H)$^+$.

Example 9B trans-N-{5-chloro-4-[1-(3-fluorobenzyl)-2,3-dihydro-1H-indol-6-yl]pyridin-2-yl}cyclohexane-1,4-diamine A mixture of Example 9A (40 mg, 0.112 mmol) and trans-cyclohexane-1,4-diamine (128 mg, 1.1821 mmol) in dimethylsulfoxide (0.5 mL) was stirred at 105° C. overnight. After cooling, the mixture was treated with trifluoroacetic acid (239 µL, 3.11 mmol) and was diluted with methanol (1.5 mL). Purification by reverse-phase HPLC (Phenomenex Luna C8(2) 100 Å AXIA column) using a gradient of 10-95% acetonitrile/0.1% trifluoroacetic acid in water afforded the title compound as the trifluoroacetate salt. $^1$H NMR (400 MHz, dimethylsulfoxide-d$_6$) δ 1.21-1.36 (m, 2H) 1.38-1.53 (m, 2H) 1.90-2.10 (m, 4H) 2.98 (t, J=8.39 Hz, 2H) 3.01-3.07 (m, 1H) 3.41 (t, J=8.39 Hz, 2H) 3.56-3.69 (m, 1H) 4.32 (s, 2H) 6.48 (s, 1H) 6.50 (s, 1H) 6.60 (d, J=7.32 Hz, 1H) 6.98-7.21 (m, 4H) 7.31-7.40 (m, 1H) 7.67-7.81 (m, 3H) 7.98 (s, 1H). MS (ESI) m/e 451 (M+H)$^+$.

Example 10 trans-4-({5-chloro-4-[1-(3-fluorobenzyl)-2,3-dihydro-1H-indol-6-yl]pyridin-2-yl}amino)cyclohexanol The title compound was prepared as described in Example 9B using trans-4-aminocyclohexanol in place of trans-cyclohexane-1,4-diamine. $^1$H NMR (400 MHz, dimethylsulfoxide-d$_6$) δ 1.14-1.35 (m, 4H) 1.79-1.99 (m, 4H) 2.98 (t, J=8.39 Hz, 2H) 3.41 (t, J=8.39 Hz, 2H) 3.44-3.48 (m, 1H) 3.52-3.68 (m, 1H) 4.15 (s, 1H) 4.32 (s, 2H) 6.13 (d, J=7.63 Hz, 1H) 6.41 (s, 1H) 6.50 (d, J=1.22 Hz, 1H) 6.60 (dd, J=7.48, 1.37 Hz, 1H) 6.99-7.21 (m, 4H) 7.32-7.42 (m, 1H) 7.95 (s, 1H). MS (ESI) m/e 452 (M+H)$^+$.

Example 11 trans-4-({5-chloro-4-[1-(3-fluorobenzyl)-1H-benzimidazol-6-yl]pyridin-2-yl}amino)cyclohexanol The title compound was prepared as described in Example 8E using trans-4-aminocyclohexanol in place of trans-cyclohexane-1,4-diamine. $^1$H NMR (400 MHz, dimethylsulfoxide-d$_6$) δ 1.16-1.35 (m, 4H) 1.80-1.99 (m, 4H) 3.38-3.50 (m, 1H) 3.57-3.68 (m, 1H) 4.13 (d, J=4.27 Hz, 1H) 5.52 (s, 2H) 6.20 (d, J=7.32 Hz, 1H) 6.46 (s, 1H) 7.03-7.16 (m, 2H) 7.23 (dd, J=8.39, 1.68 Hz, 1H) 7.23 (dd, J=8.39, 1.68 Hz, 1H) 7.33-7.41 (m, 1H) 7.57 (s, 1H) 7.71 (d, J=8.24 Hz, 1H) 8.00 (s, 1H) 8.37 (s, 1H). MS (ESI) m/e 451 (M+H)$^+$.

Example 12 trans-N-[5-chloro-4-(1-methyl-1H-benzimidazol-6-yl)pyridin-2-yl]cyclohexane-1,4-diamine

Example 12A 6-(5-chloro-2-fluoropyridin-4-yl)-1-methyl-1H-benzo[d]imidazole

The title compound was prepared as described in Example 8D using 6-bromo-1-methyl-1H-benzo[d]imidazole in place of Example 8C. MS (ESI) m/e 262 (M+H)$^+$.

Example 12B trans-N-[5-chloro-4-(1-methyl-1H-benzimidazol-6-yl)pyridin-2-yl]cyclohexane-1,4-diamine The title compound was prepared as the bis-trifluoroacetate salt as described in Example 8E using Example 12A in place of Example 8D. $^1$H NMR (400 MHz, dimethylsulfoxide-d$_6$) δ 1.19-1.33 (m, 2H) 1.35-1.51 (m, 2H) 1.90-2.05 (m, 4H) 2.86-3.00 (m, 1H) 3.80-3.90 (m, 1H) 3.97 (s, 3H) 7.37-7.45 (m, 2H) 7.72 (s, 2H) 7.79 (s, 1H) 7.83 (d, J=8.54 Hz, 1H) 8.06 (d, J=2.44 Hz, 1H) 8.83 (s, 1H). MS (ESI) m/e 356 (M+H)$^+$.

Example 13

(3R)—N-{5-chloro-4-[1-(tetrahydro-2H-pyran-4-ylmethyl)-1H-benzimidazol-6-yl]pyridin-2-yl}piperidine-3-carboxamide

Example 13A 5-bromo-2-nitro-N-((tetrahydro-2H-pyran-4-yl)methyl)aniline

A mixture of 4-bromo-2-fluoro-1-nitrobenzene (6.5 g, 29.5 mmol), (tetrahydro-2H-pyran-4-yl)methanamine (4.25 g, 36.9 mmol) and potassium carbonate (16.33 g, 118 mmol) in N,N-dimethylformamide (130 mL) was heated at 80° C. for 1 hour. After cooling, the mixture was diluted with ethyl acetate. The mixture was washed with water and brine, dried over magnesium sulfate, filtered and concentrated to give the crude title compound which was used without further purification.

Example 13B 5-bromo-N$^1$-((tetrahydro-2H-pyran-4-yl)methyl)benzene-1,2-diamine To a suspension of Example 13A (9.30 g, 29.5 mmol) in methanol (150 mL) was added hydrazine hydrate (5 g, 100 mmol) followed by Raney nickel (1000 mg, 5.84 mmol) and the mixture was heated at 50° C. for 60 minutes. After cooling, diatomaceous earth was added and the slurry was filtered through with added dichloromethane. After concentration, the crude title compound was used without further purification.

Example 13C 6-bromo-1-((tetrahydro-2H-pyran-4-yl)methyl)-1H-benzo[d]imidazole A solution of Example 13B (8.41 g, 29.5 mmol) in formic acid (10 mL, 261 mmol) was heated at 95° C. for 1 hour. After cooling, the mixture was concentrated and dissolved in 200 mL ethyl acetate. The mixture was washed with dilute aqueous potassium carbonate and brine, dried over magnesium sulfate, filtered and concentrated. Purification by silica gel flash chromatography (Isco®, Redi-Sep® column) eluting with 50-100% ethyl acetate/hexane followed by 10% 2:1 methanol/water in ethyl acetate provided a solid that was precipitated from ethyl acetate/hexane to afford the title compound. MS (ESI) m/z 297 (M+H)$^+$.

Example 13D (R)-tert-butyl 3-(5-chloro-4-(1-((tetrahydro-2H-pyran-4-yl)methyl)-1H-benzo[d]imidazol-6-yl)pyridin-2-ylcarbamoyl)piperidine-1-carboxylate To a mixture of Example 1B (1.0 g, 2.388 mmol), 4,4,4',4',5,5,5',5'-octamethyl-2,2'-bi(1,3,2-dioxaborolane) (606 mg, 2.388 mmol), 1,1'-bis(diphenylphosphino)ferrocene-palladium(II)dichloride dichloromethane complex (117 mg, 0.143 mmol) and potassium acetate (7.16 mmol) was added dioxane (11.9 mL). The mixture was flushed with nitrogen and stirred at 100° for 3 hours. A solution of Example 13C (705 mg, 2.388 mmol) in dioxane (5 mL) was added, followed by 1,1'-bis(diphenylphosphino)ferrocene-palladium(II)dichloride dichloromethane complex (117 mg, 0.143 mmol) and 2M aqueous sodium carbonate (6.57 mL, 13.14 mmol) and the mixture was stirred at 100° C. for 3 hours. After cooling, the mixture was filtered through diatomaceous earth with ethyl acetate. Purification by silica gel flash chromatography (Isco®, Redi-Sep® column) eluting with 50-100% ethyl acetate/hexane followed by 10% 2:1 methanol/water in ethyl acetate) afforded the title compound which was purified further by reverse-phase preparative HPLC (Phenomenex Luna C8(2) 5 μm 100 Å AXIA column) using a gradient of 10-95% acetonitrile/0.1% trifluoroacetic acid in water to afford the title compound as the trifluoroacetate salt. The salt was dissolved in ethyl acetate and washed with saturated aqueous bicarbonate and brine, dried over magnesium sulfate, filtered and concentrated to give the title compound as the free base. MS (ESI) m/z 554 (M+H)$^+$.

Example 13E (3R)—N-{5-chloro-4-[1-(tetrahydro-2H-pyran-4-ylmethyl)-1H-benzimidazol-6-yl]pyridin-2-yl}piperidine-3-carboxamide A solution of Example 13D (609.5 mg, 1.1 mmol) in 1:1 dichloromethane/methanol (4 mL) was cooled to 0° C. 2M Hydrogen chloride in diethyl ether (8 mL) was added slowly and the mixture was stirred at ambient temperature for 2 hours (3 mL methanol was added to dissolved the precipitate). The mixture was concentrated to afford the title compound as the bis-hydrochloride salt. $^1$H NMR (400 MHz, methanol-d$_4$) δ 9.67 (s, 1H), 8.53 (s, 1H), 8.29 (s, 1H), 8.20 (s, 1H), 8.04 (d, J=8.6, 1H), 7.84 (dd, J=8.6, 1.3, 1H), 4.54 (d, J=7.3, 2H), 3.98-3.90 (m, 2H), 3.48-3.35 (m, 3H), 3.35-3.27 (m, 2H), 3.18-3.03 (m, 2H), 2.39-2.29 (m, 1H), 2.26-2.17 (m, 1H), 2.04-1.96 (m, 1H), 1.93-1.84 (m, 2H), 1.63-1.41 (m, 4H). MS (ESI) m/z 454 (M+H)$^+$.

Example 14

(3R)—N-(5-chloro-4-{1-[2-(morpholin-4-yl)ethyl]-1H-benzimidazol-6-yl}pyridin-2-yl)piperidine-3-carboxamide

Example 14A (R)-tert-butyl 3-((5-chloro-4-(4,4,5,5-tetramethyl-1,3,2-dioxaborolan-2-yl)pyridin-2-yl)carbamoyl)piperidine-1-carboxylate A solution of Example 1B (1.53 g, 3.65 mmol), bis(pinacolatato)diboron (0.928 g, 3.65 mmol), [1,1'-bis(diphenylphosphino)ferrocene]dichloropalladium(II)-dichloromethane complex (0.179 g, 0.219 mmol) and potassium acetate (1.19 g, 12.13 mmol) in 10 mL dioxane was flushed with nitrogen and heated at 95° C. for 20 hours. After cooling and concentration, the residue was suspended in 36.5 mL dioxane to give a 0.10 M solution which was used without further purification.

Example 14B 5-bromo-N-(2-morpholinoethyl)-2-nitroaniline

The title compound was prepared as described in Example 8A using 2-morpholinoethanamine in place of 3-fluorobenzylamine. The crude product was used without further purification.

Example 14C 5-bromo-N$^1$-(2-morpholinoethyl)benzene-1,2-diamine

The title compound was prepared as described in Example 8B using Example 14B in place of Example 8A.

Example 14D 4-(2-(6-bromo-1H-benzo[d]imidazol-1-yl)ethyl)morpholine

The title compound was prepared as described in Example 8C using Example 14C in place of Example 8B.

Example 14E (3R)—N-(5-chloro-4-{1-[2-(morpholin-4-yl)ethyl]-1H-benzimidazol-6-yl}pyridin-2-yl)piperidine-3-carboxamide A solution of Example 14A (0.10 M in dioxane, 4.6 mL, 0.46 mmol), Example 14D (146 mg, 0.47 mmol), [1,1'-bis(diphenylphosphino)ferrocene]dichloropalladium(II)-dichloromethane complex (23 mg, 0.028 mmol) and 2M aqueous sodium carbonate (1.1 mL, 2.2 mmol) in 2 mL dioxane was flushed with nitrogen. The mixture was heated at 95° C. for 24 hours, cooled and concentrated. The residue was filtered through silica gel/diatomaceous earth, eluting with 10/90 methanol/dichloromethane and stirred in 2 mL 1:1 trifluoroacetic acid/dichloromethane for 24 hours. Concentration and purification by reverse phase HPLC on a Water LC with a C18 column eluting with a gradient of 10:90 to 40:60 acetonitrile/0.1% trifluoroacetic acid in water, provided the trifluoroacetate salt, which was dissolved in methanol and eluted from an SCX column (5 g) with 2M ammonia in methanol to provide the title compound. $^1$H NMR (400 MHz, DMSO-d$_6$) δ 1.46 (m, 1H), 1.65 (m, 2H), 1.92 (m, 1H), 2.49 (m, 4H), 2.76 (m, 5H), 2.86 (m, 1H), 3.04 (m, 1H), 3.58 (t, 4H), 4.47 (t, 2H), 7.36 (d, 1H), 7.83 (m, 2H), 8.31 (s, 1H), 8.40 (s, 1H), 8.52 (s, 1H), 10.99 (br s, 1H). MS (ESI) m/e 469.2 (M+H)$^+$.

Example 15

(3R)—N-{5-chloro-4-[1-(3-hydroxy-3-methylbutyl)-1H-benzimidazol-6-yl]pyridin-2-yl}piperidine-3-carboxamide The title compound was prepared as described in Examples 14B-E using 4-amino-2-methylbutan-2-ol in place of 2-morpholinoethanamine. $^1$H NMR (400 MHz, DMSO-d$_6$) δ 1.15 (m, 6H), 1.38 (m, 1H), 1.58 (m, 2H), 1.88 (m, 3H), 2.57 (m, 2H), 2.67 (t, 1H), 2.78 (m, 1H), 2.97 (m, 1H), 4.35 (m, 2H), 7.28 (d, 1H), 7.71 (s, 1H), 7.75 (d, 1H), 8.23 (s, 1H), 8.34 (s, 1H), 8.45 (s, 1H), 10.92 (br s, 1H). MS (ESI) m/e 442.3 (M+H)$^+$.

Example 16

(3R)—N-{5-chloro-4-[1-(4-fluorobenzyl)-1H-benzimidazol-6-yl]pyridin-2-yl}piperidine-3-carboxamide The title compound was prepared as described in Examples 14B-E using (4-fluorophenyl)methanamine in place of 2-morpholinoethanamine. $^1$H NMR (400 MHz, DMSO-d$_6$) δ 1.38 (m, 1H), 1.57 (m, 2H), 1.84 (m, 1H), 2.56 (m, 2H), 2.67 (m, 1H), 2.78 (m, 1H), 2.96 (m, 1H), 5.53 (s, 2H), 7.16 (t, 2H), 7.29 (d, 1H), 7.42 (m, 2H), 7.72 (s, 1H), 7.76 (d, 1H), 8.18 (s, 1H), 8.42 (s, 1H), 8.51 (s, 1H), 10.90 (br s, 1H). MS (ESI) m/e 464.1 (M+H)$^+$.

Example 17

(3R)—N-{5-chloro-4-[1-(3,4-difluorobenzyl)-1H-benzimidazol-6-yl]pyridin-2-yl}piperidine-3-carboxamide The title compound was prepared as described in Examples 14B-E using (3,4-difluorophenyl)methanamine in place of 2-morpholinoethanamine. $^1$H NMR (400 MHz, DMSO-d$_6$) δ 1.40 (m, 1H), 1.60 (m, 2H), 1.85 (m, 1H), 2.60 (m, 2H), 2.70 (m, 1H), 2.82 (m, 1H), 2.99 (m, 1H), 5.55 (s, 2H), 7.23 (m, 1H), 7.31 (d, 1H), 7.40 (m, 1H), 7.55 (m, 1H), 7.77 (m, 2H), 8.20 (s, 1H), 8.44 (s, 1H), 8.54 (s, 1H), 10.93 (br s, 1H). MS (ESI) m/e 482.1 (M+H)$^+$.

Example 18

(3R)—N-(5-chloro-4-{1-[2-(3-fluorophenyl)ethyl]-1H-benzimidazol-6-yl}pyridin-2-yl)piperidine-3-carboxamide The title compound was prepared as described in Examples 14B-E using 2-(3-fluorophenyl)ethanamine in place of 2-morpholinoethanamine. $^1$H NMR (400 MHz, DMSO-d$_6$) δ 1.40 (m, 1H), 1.60 (m, 2H), 1.86 (m, 1H), 2.62 (m, 2H), 2.71 (m, 1H), 2.81 (m, 1H), 2.98 (m, 1H), 3.16 (t, 2H), 4.57 (t, 2H), 7.00 (m, 3H), 7.28 (m, 2H), 7.74 (d, 1H), 7.78 (s, 1H), 8.22 (d, 2H), 8.45 (s, 1H), 10.94 (br s, 1H). MS (ESI) m/e 478.2 (M+H)$^+$.

Example 19

(3R)—N-{5-chloro-4-[1-(2-sulfamoylethyl)-1H-benzimidazol-6-yl]pyridin-2-yl}piperidine-3-carboxamide The title compound was prepared as described in Examples 14B-E using 2-aminoethanesulfonamide in place of 2-morpholinoethanamine. $^1$H NMR (400 MHz, DMSO-d$_6$) δ 1.39 (m, 1H), 1.61 (m, 2H), 1.86 (m, 1H), 2.60 (m, 2H), 2.70 (t, 1H), 2.82 (m, 1H), 3.00 (m, 1H), 3.56 (t, 2H), 4.71 (t, 2H), 7.32 (d, 1H), 7.77 (s, 1H), 7.79 (s, 1H), 8.25 (s, 1H), 8.36 (s, 1H), 8.47 (s, 1H), 10.95 (br s, 1H). MS (ESI) m/e 463.2 (M+H)$^+$.

Example 20

(3R)—N-(5-chloro-4-{1-[(1,1-dioxidotetrahydrothiophen-3-yl)methyl]-1H-benzimidazol-6-yl}pyridin-2-yl)piperidine-3-carboxamide The title compound was prepared as described in Examples 14B-E using 3-(aminoethyl)tetrahydrothiophene 1,1-dioxide in place of 2-morpholinoethanamine. $^1$H NMR (400 MHz, DMSO-d$_6$) δ 1.40 (m, 1H), 1.61 (m, 2H), 1.89 (m, 2H), 2.10 (m, 1H), 2.57 (m, 1H), 2.70 (t, 1H), 2.81 (m, 1H), 2.97 (m, 4H), 3.23 (m, 3H), 4.46 (m, 2H), 7.30 (d, 1H), 7.79 (d, 1H), 7.90 (s, 1H), 8.25 (s, 1H), 8.39 (s, 1H), 8.47 (s, 1H), 10.95 (br s, 1H). MS (ESI) m/e 488.2 (M+H)$^+$.

Example 21

(3R)—N-{5-chloro-4-[1-(2-fluorobenzyl)-1H-benzimidazol-6-yl]pyridin-2-yl}piperidine-3-carboxamide The title compound was prepared as described in Examples 14B-E using (2-fluorophenyl)methanamine in place of 2-morpholinoethanamine. $^1$H NMR (400 MHz, DMSO-d$_6$) δ 1.40 (m, 1H), 1.58 (m, 2H), 1.85 (m, 1H), 2.58 (m, 2H), 2.70 (t, 1H), 2.80 (m, 1H), 2.98 (m, 1H), 5.63 (s, 2H), 7.25 (m, 5H), 7.73 (s, 1H), 7.79 (d, 1H), 8.21 (s, 1H), 8.45 (d, 2H), 10.93 (br s, 1H). MS (ESI) m/e 464.2 (M+H)$^+$.

Example 22

(3R)—N-{5-chloro-4-[1-(pyridin-3-ylmethyl)-1H-benzimidazol-6-yl]pyridin-2-yl}piperidine-3-carboxamide Example 22A 6-bromo-1-(pyridin-3-ylmethyl)-1H-benzo[d]imidazole The title compound was prepared as described in Examples 8A-C using pyridin-3-ylmethanamine in place of 3-fluorobenzylamine MS (ESI) m/e 289 (M+H)$^+$.

Example 22B ((3R)—N-{5-chloro-4-[1-(pyridin-3-ylmethyl)-1H-benzimidazol-6-yl]pyridin-2-yl}piperidine-3-carboxamide The title compound was prepared as the trifluoroacetate salt as described in Example 1E using Example 22A in place of Example 1D. $^1$H NMR (400 MHz, dimethylsulfoxide-d$_6$) δ 1.60-2.13 (m, 4H) 2.80-3.21 (m, 4H) 3.27-3.35 (m, 1H) 5.78 (s, 2H) 7.46 (d, J=8.54 Hz, 1H) 7.57 (dd, J=7.48, 5.34 Hz, 1H) 7.84-7.92 (m, 2H) 8.03 (d, J=7.94 Hz, 1H) 8.10 (s, 1H) 8.44 (s, 1H) 8.62 (d, J=4.88 Hz, 1H) 8.80 (s, 1H) 9.02-9.24 (m, 2H) 10.71 (s, 1H). MS (ESI) m/e 447 (M+H)$^+$.

Example 23

(3R)—N-(5-chloro-4-{1-[(1,1-dioxidotetrahydro-2H-thiopyran-4-yl)methyl]-1H-benzimidazol-6-yl}pyridin-2-yl)piperidine-3-carboxamide

Example 23A 4-((6-bromo-1H-benzo[d]imidazol-1-yl)methyl)tetrahydro-2H-thiopyran 1,1-dioxide The title compound was prepared as described in Examples 8A-C using 4-(aminomethyl)tetrahydro-2H-thiopyran 1,1-dioxide in place of 3-fluorobenzylamine. MS (ESI) m/e 344 (M+H)$^+$.

Example 23B (3R)—N-(5-chloro-4-{1-[(1,1-dioxidotetrahydro-2H-thiopyran-4-yl)methyl]-1H-benzimidazol-6-yl}pyridin-2-yl)piperidine-3-carboxamide The title compound was prepared as the bis-hydrochloride salt as described in Example 1E using Example 23A in place of Example 1D. $^1$H NMR (400 MHz, dimethylsulfoxide-d$_6$) δ 1.59-2.39 (m, 9H) 2.78-3.35 (m, 9H) 4.41 (d, J=7.32 Hz, 2H) 7.48 (d, J=8.54 Hz, 1H) 7.89 (d, J=8.54 Hz, 1H) 8.00 (s, 1H) 8.16 (s, 1H) 8.47 (s, 1H) 8.99 (s, 1H) 9.02-9.29 (m, 2H) 10.73 (s, 1H). MS (ESI) m/e 502 (M+H)$^+$.

Example 24

(3R)—N-(5-chloro-4-{1-[(5-methyl-4H-1,2,4-triazol-3-yl)methyl]-1H-benzimidazol-6-yl}pyridin-2-yl)piperidine-3-carboxamide

Example 24A 6-bromo-1-((5-methyl-4H-1,2,4-triazol-3-yl)methyl)-1H-benzo[d]imidazole The title compound was prepared as described in Examples 8A-C using (5-methyl-4H-1,2,4-triazol-3-yl)methanamine in place of 3-fluorobenzylamine. MS (ESI) m/e 292 (M+H)$^+$.

Example 24B (3R)—N-(5-chloro-4-{1-[(5-methyl-4H-1,2,4-triazol-3-yl)methyl]-1H-benzimidazol-6-yl}pyridin-2-yl)piperidine-3-carboxamide The title compound was prepared as the a hydrochloride salt as described in Example 1E using Example 24A in place of Example 1D. $^1$H NMR (400 MHz, dimethylsulfoxide-d$_6$) δ 1.61-2.15 (m, 4H) 2.31 (s, 3H) 2.74-3.35 (m, 5H) 5.68 (s, 2H) 7.50 (d, J=8.54 Hz, 1H) 7.83-7.97 (m, 2H) 8.13 (s, 1H) 8.47 (s, 1H) 9.06-9.34 (m, 3H) 10.72 (s, 1H). MS (ESI) m/e 451 (M+H)$^+$.

Example 25

(3R)—N-{5-chloro-4-[1-(1,3-thiazol-4-ylmethyl)-1H-benzimidazol-5-yl]pyridin-2-yl}piperidine-3-carboxamide-(3R)—N-{5-chloro-4-[1-(1,3-thiazol-4-ylmethyl)-1H-benzimidazol-6-yl]pyridin-2-yl}piperidine-3-carboxamide (1:1)

Example 25A 4-((6-bromo-1H-benzo[d]imidazol-1-yl)methyl)thiazole and 4-((5-bromo-1H-benzo[d]imidazol-1-yl)methyl)thiazole A solution of 6-bromo-1H-benzo[d]imidazole (500 mg, 2.54 mmol) in 5 mL N,N-dimethylformamide was treated with 4-(chloromethyl)thiazole hydrochloride (518 mg, 3.05 mmol) and cesium carbonate (1.819 g, 5.58 mmol) and the mixture was heated overnight at 110° C. The mixture was diluted with ethyl acetate, washed with water and brine, dried over magnesium sulfate, filtered, and concentrated. Flash chromatography on silica eluting with 3.5% methanol/dichloromethane provided the title compound as a mixture of regioisomers.

Example 25B (R)-tert-butyl 3-((5-chloro-4-(1-(thiazol-4-ylmethyl)-1H-benzo[d]imidazol-5-yl)pyridin-2-yl)carbamoyl)piperidine-1-carboxylate and (R)-tert-butyl 3-((5-chloro-4-(1-(thiazol-4-ylmethyl)-1H-benzo[d]imidazol-6-yl)pyridin-2-yl)carbamoyl)piperidine-1-carboxylate A solution of Example 1B (100 mg, 0.239 mmol), bis(pinacolato)diboron (60.6 mg, 0.239 mmol), 1,1'-bis(diphenylphosphino)ferrocene-palladium(II)dichloride-dichloromethane complex (11.70 mg, 0.014 mmol) and potassium acetate (70.3 mg, 0.716 mmol) in 1.5 mL dioxane was flushed with nitrogen for 5 minutes and heated at 110° C. for 1 hour. The mixture was cooled and Example 25A mixture (38.6 mg, 0.131 mmol), 1,1'-bis(diphenylphosphino)ferrocene-palladium(II)dichloride-dichloromethane complex (11.70 mg, 0.014 mmol) and 2M aqueous sodium carbonate (700 μL, 1.400 mmol) were added. The mixture was flushed with nitrogen and heated at 100° C. for 2 hours. The mixture was cooled, filtered through diatomaceous earth, concentrated and purified by flash chromatography on silica, eluting with 4% methanol/dichloromethane to obtain the title compound as a mixture of regioisomers.

Example 25C (3R)—N-{5-chloro-4-[1-(1,3-thiazol-4-ylmethyl)-1H-benzimidazol-5-yl]pyridine-2-yl}piperidine-3-carboxamide and (3R)—N-{5-chloro-4-[1-(1,3-thiazol-4-ylmethyl)-1H-benzimidazol-6-yl]pyridin-2-yl}piperidine-3-carboxamide (1:1)

A solution of Example 25B (32 mg, 0.058 mmol) in 2 mL dichloromethane was treated with 0.25 mL trifluoroacetic acid and the mixture was stirred at room temperature for 2 hours. The mixture was concentrated and dried under vacuum to obtain the title compound as a 1:1 mixture of regioisomers. $^1$H NMR (300 MHz, DMSO-d$_6$) δ 1.61-2.06 (m, 4H) 2.80-3.34 (m, 5H) 5.71 (s, 2H) 7.31-7.40 (m, 1H) 7.79-7.81 (m, 3H) 8.18 (s, 1H) 8.42-8.63 (m, 3H) 11.00 (s, 1H). MS (DCI) m/e 453 (M+H)$^+$.

Example 26

5-chloro-N-cyclopentyl-4-[1-(3-fluorobenzyl)-1H-benzimidazol-6-yl]pyridin-2-amine A solution of Example 8D (10.0 mg, 0.0281 mmol) in dimethyl sulfoxide (0.1 mL), a solution of cyclopentanamine (11.48 mg, 0.0843 mmol) in dimethyl sulfoxide (0.1 mL) and N,N-diisopropylethylamine (14.69 μL, 0.0843 mmol) was heated in an Anton Paar Synthos 3000 microwave optimizer at 150° C. for 30 minutes. Dimethyl sulfoxide (800 μL) was added and the mixture was purified by reverse-phase preparative HPLC (Phenomenex Luna C8(2) 5 μm 100 Å AXIA column) using a gradient of 10-95% acetonitrile/0.1% trifluoroacetic acid in water to yield the title compound as the bis-trifluoroacetate salt. $^1$H NMR (400 MHz, dimethylsulfoxide-d$_6$) δ 1.39-1.51 (m, 2H), 1.53-1.60 (m, 2H), 1.62-1.74 (m, 2H), 1.88-1.98 (m, 2H), 4.07-4.11 (m, 1H), 5.68 (s, 2H), 6.55 (s, 1H), 7.12-7.20 (m, 1H), 7.26 (d, J=7.7 Hz, 1H), 7.33 (d, J=9.9 Hz, 1H), 7.39-7.49 (m, 2H), 7.83-7.93 (m, 2H), 8.10 (s, 1H), 9.17 (s, 1H). MS (ESI$^+$) m/z 421.1 (M−H)$^+$.

Example 27

1-[trans-4-({5-chloro-4-[1-(3-fluorobenzyl)-1H-benzimidazol-6-yl]pyridin-2-yl}amino)cyclohexyl]-3-methylurea To Example 8E (100 mg, 0.22 mmol) in N,N-dimethylformamide (1.5 mL) was added isocyanatomethane (12.7 mg, 0.22 mmol) and triethylamine (0.5 mL) and the mixture was stirred at 0° C. for 10 minutes, concentrated and purified by reverse-phase HPLC (Phenomenex Luna C8(2) 100 Å AXIA column) using a gradient of 10-95% acetonitrile/0.1% trifluoroacetic acid in water to afford the title compound as the trifluoroacetate salt. $^1$H NMR (400 MHz, dimethylsulfoxide-d$_6$) δ 1.11-1.43 (m, 4H) 1.77-2.07 (m, 4H) 2.55 (s, 3H) 3.27-3.44 (m, 1H) 3.56-3.70 (m, 1H) 5.63 (s, 2H) 6.55 (s, 1H) 7.06-7.14 (m, 1H) 7.17-7.25 (m, 2H) 7.33-7.44 (m, 2H) 7.75 (s, 1H) 7.82 (d, J=8.24 Hz, 1H) 8.04 (s, 1H) 8.90 (s, 1H). MS (ESI) m/e 507 (M+H)$^+$.

Example 28

N-[trans-4-({5-chloro-4-[1-(3-fluorobenzyl)-1H-benzimidazol-6-yl]pyridin-2-yl}amino)cyclohexyl]methanesulfonamide To Example 8E (120 mg, 0.27 mmol) in N,N-dimethylformamide (2 mL) was added methanesulfonyl chloride (0.04 mL, 0.48 mmol) and triethylamine (0.22 mL, 1.60 mmol). After stirring at room temperature for 30 minutes, the mixture was treated with 25 mL brine and extracted with ethyl acetate. The organic layer was dried over sodium sulfate, filtered, concentrated and purified by flash chromatography (Analogix 280) on silica gel, eluting with a gradient of 0-6% methanol/ethyl acetate to afford of the title compound. $^1$H NMR (400 MHz, dimethylsulfoxide-d$_6$) δ 1.24-1.44 (m, 4H) 1.89-2.03 (m, 4H) 2.89 (s, 3H) 3.09-3.20 (m, 1H) 3.48-3.71 (m, 1H) 5.53 (s, 2H) 6.26 (d, J=7.32 Hz, 1H) 6.47 (s, 1H) 6.68 (s, 1H) 7.04-7.16 (m, 3H) 7.23 (dd, J=8.24, 1.53 Hz, 1H) 7.32-7.41 (m, 1H) 7.57 (s, 1H) 7.71 (d, J=8.24 Hz, 1H) 8.00 (s, 1H) 8.37 (s, 1H). MS (ESI) m/e 528 (M+H)$^+$.

Example 29

(3R)—N-[4-(1-benzyl-3-benzyl-3-cyano-1H-indol-6-yl)-5-chloropyridin-2-yl]piperidine-3-carboxamide Example 29A benzyl-6-bromo-1H-indole-3-carbonitrile A solution of 6-bromo-1H-indole-3-carbonitrile (400 mg, 1.81 mmol), 2-(tributylphosphoranylidene)acetonitrile (655 mg, 2.71 mmol) and benzyl alcohol (282 μL, 2.71 mmol) in toluene (5 mL) was heated at 75° C. overnight, concentrated and purified by flash chromatography on silica (IntelliFlash Varian 971-FP) eluting with 30% heptanes in ethyl acetate to provide the title compound. LCMS: 312.4 (M+H)$^+$.

Example 29B (R)-tert-butyl 3-((4-(1-benzyl-3-cyano-1H-indol-6-yl)-5-chloropyridin-2-yl)carbamoyl)piperidine-1-carboxylate A mixture of Example 29A (140 mg, 0.45 mmol), 4,4,4',4',5,5,5',5'-octamethyl-2,2'-bi(1,3,2-dioxaborolane) (126 mg, 0.49 mmol), and potassium acetate (132 mg, 1.35 mmol) in dioxane (2.5 mL) was flushed with nitrogen and [1,1'-bis(diphenylphosphino)ferrocene]dichloropalladium(II)-dichloromethane adduct (22 mg, 0.027 mmol) was added. The mixture was stirred at 100° C. overnight and cooled. To this was added Example 1B (148 mg, 0.35 mmol), [1,1'-bis(diphenylphosphino)ferrocene]dichloropalladium(II)-dichloromethane adduct (22 mg, 0.027 mmol), dioxane (3 mL) and 1M aqueous sodium carbonate (1.4 mL). The mixture was heated at 100° C. overnight, cooled, filtered, concentrated and purified by flash chromatography on silica (IntelliFlash Varian 971-FP), eluting with 45% heptanes in ethyl acetate to provide the title compound. LCMS: 571.0 (M+H)$^+$.

Example 29C (3R)—N-[4-(1-benzyl-3-cyano-1H-indol-6-yl)-5-chloropyridin-2-yl]piperidine-3-carboxamide A solution of Example 29B (140 mg, 0.24 mmol) in dichloromethane (5 mL) was treated with trifluoroacetic acid (1.5 mL) for 30 minutes, concentrated and purified by reverse phase chromatography (IntelliFlash Varian 971-FP, C18 column), eluting with a gradient of 10-70% acetonitrile/0.1% trifluoroacetic acid water to provide the title compound. $^1$H NMR (400 MHz, DMSO-d$_6$) δ 1.57-1.70 (m, 2H) 1.76-1.88 (m, 1H) 1.96-2.11 (m, 1H) 2.52-2.54 (m, 1H) 2.85-3.10 (m, 3H) 3.11-3.21 (m, 1H) 5.56 (s, 2H) 7.21-7.40 (m, 6H) 7.79 (d, 1H) 7.85 (s, 1H) 8.15 (s, 1H) 8.38-8.55 (m, 3H) 8.59 (s, 1H) 10.99 (s, 1H). LCMS: 469.8 (M+H)$^+$.

Example 30

N'-{5-chloro-4-[1-(3-fluorobenzyl)-1H-benzimidazol-6-yl]pyridin-2-yl}-N-methyl-N-(pyridin-2-yl)propane-1,3-diamine To a solution of Example 8D (25 mg, 0.07 mmol) in dimethyl sulfoxide (1 mL), was added a solution of $N^1$-methyl-$N^1$-(pyridin-2-yl)propane-1,3-diamine (34 mg, 0.21 mmol) in dimethylsulfoxide (500 μL) and N,N-diisopropylethylamine (37 μL, 0.21 mmol). The mixture was stirred at 120° C. for 16 hours. The mixture was filtered, concentrated and dissolved in 1 mL 1:1 dimethylsulfoxide/methanol. Purification by reverse phase preparative HPLC (Phenomenex Luna C8(2) 100 Å AXIA column) eluting with a gradient of 5-100% acetonitrile/0.1% trifluoroacetic acid in water gave the title compound as the bis-trifluoroacetate salt. $^1$H NMR (400 MHz, dimethylsulfoxide-$d_6$/$D_2O$) δ 1.79-2.00 (m, 2H), 3.19 (d, J=5.7 Hz, 3H), 3.27-3.43 (m, 2H), 3.60-3.70 (m, 2H), 5.74 (d, J=7.6 Hz, 2H), 6.61 (s, 1H), 6.92 (dd, J=9.8, 3.5 Hz, 1H), 7.15-7.24 (m, 1H), 7.29 (dd, J=16.6, 7.4 Hz, 2H), 7.34 (dt, J=9.9, 4.9 Hz, 1H), 7.41-7.48 (m, 1H), 7.53-7.58 (m, 1H), 7.88 (t, J=2.8 Hz, 1H), 7.90-8.00 (m, 3H), 8.08 (s, 1H), 9.41 (s, 1H). MS (ESI$^+$) m/z 501 (M+H)$^+$.

Example 31

1-({5-chloro-4-[1-(3-fluorobenzyl)-1H-benzimidazol-6-yl]pyridin-2-yl}amino)-3-(dimethylamino)propan-2-ol The title compound was prepared as the bis-trifluoroacetate salt as described in Example 30 using 1-amino-3-(dimethylamino)propan-2-ol in place of $N^1$-methyl-$N^1$-(pyridin-2-yl)propane-1,3-diamine. $^1$H NMR (400 MHz, dimethylsulfoxide-$d_6$/$D_2O$) δ 2.73-2.88 (m, 6H), 3.06 (dd, J=12.9, 10.3 Hz, 1H), 3.13-3.21 (m, 1H), 3.31-3.44 (m, 2H), 3.94-4.11 (m, 2H), 5.73 (bs, 2H), 6.65 (s, 1H), 7.15-7.23 (m, 1H), 7.25-7.37 (m, 2H), 7.45 (td, J=7.9, 6.0 Hz, 1H), 7.54 (dd, J=8.4, 1.5 Hz, 1H), 7.85 (d, J=1.5 Hz, 1H), 7.95 (d, J=8.4 Hz, 1H), 8.12 (s, 1H), 9.40 (s, 1H). MS (ESI$^+$) m/z 454 (M+H)$^+$.

Example 32

5-chloro-4-[1-(3-fluorobenzyl)-1H-benzimidazol-6-yl]-N-[(5-methyl-4H-1,2,4-triazol-3-yl)methyl]pyridin-2-amine The title compound was prepared as the bis-trifluoroacetate salt as described in Example 30 using (5-methyl-4H-1,2,4-triazol-3-yl)methanamine in place of $N^1$-methyl-$N^1$-(pyridin-2-yl)propane-1,3-diamine $^1$H NMR (400 MHz, dimethylsulfoxide-$d_6$/$D_2O$) δ 2.41 (s, 3H), 4.60 (s, 2H), 5.72 (bs, 2H), 6.71 (s, 1H), 7.14-7.23 (m, 1H), 7.25-7.36 (m, 2H), 7.40-7.49 (m, 1H), 7.53 (dd, J=8.4, 1.6 Hz, 1H), 7.86 (d, J=1.5 Hz, 1H), 7.91-7.97 (m, 1H), 8.11 (d, J=0.5 Hz, 1H), 9.36 (s, 1H). MS (ESI$^+$) m/z 448 (M+H)$^+$.

Example 33

(3R)—N-{5-chloro-4-[1-(3-fluorobenzyl)-1H-pyrrolo[3,2-b]pyridin-6-yl]pyridin-2-yl}piperidine-3-carboxamide

Example 33A 6-bromo-1-(3-fluorobenzyl)-1H-pyrrolo[3,2-b]pyridine

A mixture of 6-bromo-1H-pyrrolo[3,2-b]pyridine (400 mg, 2.03 mmol) and sodium hydride (89 mg, 2.23 mmol) in N,N-dimethylformamide (4 mL) was stirred at ambient temperature for 10 minutes and 1-(bromomethyl)-3-fluorobenzene (384 mg, 2.03 mmol) was added. After stirring at 100° C. for 3 hours, the mixture was cooled and diluted with ethyl acetate. The mixture was washed with water and brine, dried over magnesium sulfate, filtered, concentrated and purified by flash chromatography (Analogix 280) on silica gel, eluting with a gradient of 10-70% ethyl acetate/hexane to afford the title compound. MS (ESI) m/e 306 (M+H)$^+$.

Example 33B (3R)—N-{5-chloro-4-[1-(3-fluorobenzyl)-1H-pyrrolo[3,2-b]pyridin-6-yl]pyridin-2-yl}piperidine-3-carboxamide The title compound was prepared as described in Example 1E using Example 33A in place of Example 1D. Purification by reverse-phase HPLC (Phenomenex Luna C8(2) 100 Å AXIA column) using a gradient of 10-95% acetonitrile/0.1% trifluoroacetic acid in water afforded the title compound as the trifluoroacetate salt. $^1$H NMR (400 MHz, dimethylsulfoxide-$d_6$) δ 1.61-2.18 (m, 4H) 2.86-3.39 (m, 5H) 5.55 (s, 2H) 6.75 (d, J=3.36 Hz, 1H) 6.98-7.13 (m, 3H) 7.28-7.43 (m, 1H) 7.97 (d, J=3.05 Hz, 1H) 8.16 (s, 1H) 8.20 (s, 1H) 8.40-8.57 (m, 3H) 10.70 (s, 1H). MS (ESI) m/e 454 (M+H)$^+$.

Example 34

N-{5-chloro-4-[1-(3-fluorobenzyl)-1H-benzimidazol-6-yl]pyridin-2-yl}-N'-(pyridin-3-yl)ethane-1,2-diamine The title compound was prepared as the bis-trifluoroacetate salt as described in Example 30 using $N^1$-(pyridin-3-yl)ethane-1,2-diamine in place of $N^1$-methyl-$N^1$-(pyridin-2-yl)propane-1,3-diamine. $^1$H NMR (400 MHz, dimethylsulfoxide-$d_6$/$D_2O$) δ 3.36 (t, J=6.5 Hz, 2H), 3.50 (t, J=6.4 Hz, 2H), 5.74 (bs, 2H), 6.59 (s, 1H), 7.19 (td, J=8.6, 2.7 Hz, 1H), 7.27-7.33 (m, 1H), 7.35 (dd, J=9.8, 2.3 Hz, 1H), 7.45 (td, J=7.9, 6.0 Hz, 1H), 7.55 (dd, J=8.4, 1.5 Hz, 1H), 7.72-7.77 (m, 2H), 7.87 (d, J=1.5 Hz, 1H), 7.92-8.04 (m, 2H), 8.16-8.21 (m, 2H), 9.46 (s, 1H). MS (ESI$^+$) m/z 473 (M+H)$^+$.

Example 35

N-[(5-amino-4H-1,2,4-triazol-3-yl)methyl]-5-chloro-4-[1-(3-fluorobenzyl)-1H-benzimidazol-6-yl]pyridin-2-amine The title compound was prepared as the bis-trifluoroacetate salt as described in Example 30 using 5-(aminomethyl)-4H-1,2,4-triazol-3-amine in place of $N^1$-methyl-$N^1$-

(pyridin-2-yl)propane-1,3-diamine. $^1$H NMR (400 MHz, dimethylsulfoxide-d$_6$/D$_2$O) δ 4.50 (s, 2H), 5.69 (bs, 2H), 6.67 (s, 1H), 7.17 (td, J=8.6, 2.5 Hz, 1H), 7.22-7.34 (m, 2H), 7.39-7.50 (m, 2H), 7.80 (d, J=1.5 Hz, 1H), 7.90 (d, J=8.4 Hz, 2H), 8.12 (d, J=0.5 Hz, 1H), 9.18 (s, 1H). MS (ESI$^+$) m/z 449 (M+H)$^+$

Example 36

N-benzyl-N'-{5-chloro-4-[1-(3-fluorobenzyl)-1H-benzimidazol-6-yl]pyridin-2-yl}-N-methylpropane-1,3-diamine The title compound was prepared as the bis-trifluoroacetate salt as described in Example 30 using N$^1$-benzyl-N$^1$-methylpropane-1,3-diamine in place of N$^1$-methyl-N$^1$-(pyridin-2-yl)propane-1,3-diamine. $^1$H NMR (400 MHz, dimethylsulfoxide-d$_6$/D$_2$O) δ 1.98 (s, 2H), 2.71 (s, 3H), 3.15 (d, J=22.8 Hz, 2H), 3.34 (t, J=6.5 Hz, 2H), 4.31 (s, 2H), 5.75 (s, 2H), 6.57 (s, 1H), 7.19 (td, J=8.4, 2.1 Hz, 1H), 7.32 (dd, J=20.0, 8.7 Hz, 2H), 7.40-7.53 (m, 6H), 7.56 (dd, J=8.5, 1.4 Hz, 1H), 7.83 (d, J=29.6 Hz, 1H), 7.96 (d, J=8.5 Hz, 1H), 8.11 (s, 1H), 9.47 (s, 1H). MS (ESI$^+$) m/z 514 (M+H)$^+$.

Example 37

5-chloro-4-[1-(3-fluorobenzyl)-1H-benzimidazol-6-yl]-N-(pyrimidin-2-ylmethyl)pyridin-2-amine The title compound was prepared as the bis-trifluoroacetate salt as described in Example 30 using pyrimidin-2-ylmethanamine in place of N$^1$-methyl-N$^1$-(pyridin-2-yl)propane-1,3-diamine $^1$H NMR (400 MHz, dimethylsulfoxide-d$_6$/D$_2$O) δ 4.72 (s, 2H), 5.73 (bs, 2H), 6.76 (s, 1H), 7.19 (td, J=8.6, 2.8 Hz, 1H), 7.23-7.38 (m, 2H), 7.37-7.50 (m, 2H), 7.56 (dd, J=8.4, 1.5 Hz, 1H), 7.90 (d, J=1.5 Hz, 1H), 7.94 (d, J=8.4 Hz, 1H), 8.06 (s, 1H), 8.73-8.79 (m, 2H), 9.39 (s, 1H). MS (ESI$^+$) m/z 445 (M+H)$^+$.

Example 38

5-chloro-4-[1-(3-fluorobenzyl)-1H-benzimidazol-6-yl]-N-[1-(pyridin-4-yl)propan-2-yl]pyridin-2-amine The title compound was prepared as the bis-trifluoroacetate salt as described in Example 30 using 1-(1-methyl-1H-pyrazol-4-yl)piperidin-3-amine in place of N$^1$-methyl-N$^1$-(pyridin-2-yl)propane-1,3-diamine. $^1$H NMR (400 MHz, dimethylsulfoxide-d$_6$/D$_2$O) δ 1.21 (d, J=6.5 Hz, 3H), 3.16 (d, J=15.2 Hz, 2H), 4.36 (q, J=6.5 Hz, 1H), 5.75 (bs, 2H), 6.55 (s, 1H), 7.20 (td, J=8.6, 2.6 Hz, 1H), 7.27-7.33 (m, 1H), 7.35 (dd, J=9.8, 2.3 Hz, 1H), 7.45 (td, J=7.9, 6.0 Hz, 1H), 7.56 (dd, J=8.4, 1.6 Hz, 1H), 7.89 (d, J=1.5 Hz, 1H), 7.92-7.99 (m, 3H), 8.09 (s, 1H), 8.74-8.79 (m, 2H), 9.51 (s, 1H). MS (ESI$^+$) m/z 445 (M+H)$^+$.

Example 39

5-chloro-4-[1-(3-fluorobenzyl)-1H-benzimidazol-6-yl]-N-[1-(1-methyl-1H-pyrazol-4-yl)piperidin-3-yl]pyridin-2-amine The title compound was prepared as the bis-trifluoroacetate salt as described in Example 30 using 1-(1-methyl-1H-pyrazol-4-yl)piperidin-3-amine in place of N$^1$-methyl-N$^1$-(pyridin-2-yl)propane-1,3-diamine. $^1$H NMR (400 MHz, dimethylsulfoxide-d$_6$/D$_2$O) δ 1.57 (dd, J=19.9, 10.3 Hz, 1H), 1.83 (d, J=10.9 Hz, 1H), 1.95 (t, J=25.5 Hz, 2H), 2.91-3.03 (m, 1H), 3.11 (d, J=9.7 Hz, 1H), 3.46 (d, J=11.7 Hz, 1H), 3.57-3.72 (m, 1H), 3.82 (s, 3H), 4.17 (t, J=9.7 Hz, 1H), 5.76 (s, 2H), 6.66 (s, 1H), 7.20 (td, J=8.5, 2.1 Hz, 1H), 7.31 (d, J=7.8 Hz, 1H), 7.35 (dd, J=9.7, 1.9 Hz, 1H), 7.45 (td, J=8.0, 6.1 Hz, 1H), 7.55-7.62 (m, 2H), 7.85 (s, 1H), 7.90 (s, 1H), 7.97 (d, J=8.6 Hz, 1H), 8.15 (s, 1H), 9.54 (s, 1H). MS (ESI$^+$) m/z 516 (M+H)$^+$.

Example 40

5-[({5-chloro-4-[1-(3-fluorobenzyl)-1H-benzimidazol-6-yl]pyridin-2-yl}amino)methyl]pyrimidin-2-amine The title compound was prepared as the bis-trifluoroacetate salt as described in Example 30 using 5-(aminomethyl)pyrimidin-2-amine in place of N$^1$-methyl-N-1-(pyridin-2-yl)propane-1,3-diamine. $^1$H NMR (400 MHz, dimethylsulfoxide-d$_6$/D$_2$O) δ 4.38 (bs, 2H), 5.76 (bs, 2H), 6.64 (s, 1H), 7.20 (td, J=8.6, 2.7 Hz, 1H), 7.28-7.34 (m, 1H), 7.36 (dd, J=10.1, 2.1 Hz, 1H), 7.45 (td, J=7.9, 6.0 Hz, 1H), 7.59 (dd, J=8.5, 1.5 Hz, 1H), 7.91 (d, J=1.5 Hz, 1H), 7.94-8.00 (m, 1H), 8.14 (d, J=0.6 Hz, 1H), 8.52 (s, 2H), 9.56 (s, 1H). MS (ESI$^+$) m/z 460 (M+H)$^+$.

Example 41

5-chloro-N-[2-(1-ethylpiperidin-4-yl)ethyl]-4-[1-(3-fluorobenzyl)-1H-benzimidazol-6-yl]pyridin-2-amine The title compound was prepared as the bis-trifluoroacetate salt as described in Example 30 using 2-(1-ethylpiperidin-4-yl)ethanamine in place of N$^1$-methyl-N$^1$-(pyridin-2-yl)propane-1,3-diamine. $^1$H NMR (400 MHz, dimethylsulfoxide-d$_6$/D$_2$O) δ 1.09-1.28 (m, 3H), 1.28-1.44 (m, 2H), 1.44-1.57 (m, 2H), 1.57-1.72 (m, 1H), 1.85-2.01 (m, 2H), 2.74-2.95 (m, 2H), 3.07 (q, J=7.3 Hz, 2H), 3.23-3.37 (m, 2H), 3.37-3.54 (m, 2H), 5.74 (s, 2H), 6.66 (d, J=5.4 Hz, 1H), 7.07-7.25 (m, 1H), 7.24-7.38 (m, 2H), 7.37-7.51 (m, 1H), 7.49-7.64 (m, 1H), 7.90 (d, J=0.9 Hz, 1H), 7.96 (d, J=8.6 Hz, 1H), 8.12 (s, 1H), 9.45 (s, 1H). MS (ESI$^+$) m/z 492 (M+H)$^+$.

Example 42

5-chloro-4-[1-(3-fluorobenzyl)-1H-benzimidazol-6-yl]-N-[2-(5-methyl-4H-1,2,4-triazol-3-yl)ethyl]pyridin-2-amine The title compound was prepared as the bis-trifluoroacetate salt as described in Example 30 using 2-(5-methyl-4H-1,2,4-triazol-3-yl)ethanamine in place of N$^1$-methyl-N$^1$-(pyridin-2-yl)propane-1,3-diamine $^1$H NMR (400 MHz, dimethylsulfoxide-d$_6$/D$_2$O) δ 2.46 (s, 3H), 3.05 (t, J=6.7 Hz, 2H), 3.67 (t, J=6.8 Hz, 2H), 5.72 (s, 2H), 6.57 (s, 1H), 7.18 (td, J=8.4, 2.0 Hz, 1H), 7.31 (dd, J=18.1, 8.6 Hz, 2H), 7.44 (td, J=8.0, 6.1 Hz, 1H), 7.54 (dd, J=8.5, 1.5 Hz, 1H), 7.86 (s, 1H), 7.93 (d, J=8.6 Hz, 1H), 8.11 (s, 1H), 9.38 (s, 1H). MS (ESI$^+$) m/z 462 (M+H)$^+$.

Example 43

N-{5-chloro-4-[1-(3-fluorobenzyl)-1H-benzimidazol-6-yl]pyridin-2-yl}-N'-(pyridin-4-yl)ethane-1,2-diamine The title compound was prepared as the bis-trifluoroacetate salt as described in Example 30 using N$^1$-(pyridin-4- yl)ethane-1,2-diamine in place of $N^1$-methyl-$N^1$-(pyridin-2-yl)propane-1,3-diamine. $^1$H NMR (400 MHz, dimethylsulfoxide-$d_6$/$D_2O$) δ 3.43-3.57 (m, 4H), 5.74 (bs, 2H), 6.58 (s, 1H), 6.85 (dd, J=7.1, 2.6 Hz, 1H), 7.02 (dd, J=7.2, 2.8 Hz, 1H), 7.15-7.24 (m, 1H), 7.26-7.38 (m, 2H), 7.45 (td, J=7.9, 6.0 Hz, 1H), 7.54 (dd, J=8.5, 1.5 Hz, 1H), 7.87 (d, J=1.5 Hz, 1H), 7.95 (d, J=8.5 Hz, 1H), 8.04 (dd, J=7.0, 1.3 Hz, 1H), 8.17 (d, J=0.5 Hz, 1H), 8.21 (d, J=7.2 Hz, 1H), 9.45 (s, 1H). MS (ESI$^+$) m/z 473 (M+H)$^+$.

Example 44

5-chloro-4-[1-(3-fluorobenzyl)-1H-benzimidazol-6-yl]-N-[2-(1-methylpiperidin-4-yl)ethyl]pyridin-2-amine The title compound was prepared as the bis-trifluoroacetate salt as described in Example 30 using 2-(1-methylpiperidin-4-yl)ethanamine in place of $N^1$-methyl-$N^1$-(pyridin-2-yl)propane-1,3-diamine. $^1$H NMR (400 MHz, dimethylsulfoxide-$d_6$/$D_2O$) δ 1.22-1.43 (m, 2H), 1.45-1.72 (m, 3H), 1.87-1.96 (m, 2H), 2.75 (s, 3H), 2.81-3.15 (m, 2H), 3.31 (t, J=7.0 Hz, 2H), 3.37-3.45 (m, 2H), 5.74 (bs, 2H), 6.66 (s, 1H), 7.19 (td, J=8.6, 2.7 Hz, 1H), 7.27-7.33 (m, 1H), 7.35 (dd, J=9.8, 2.3 Hz, 1H), 7.45 (td, J=7.9, 6.0 Hz, 1H), 7.57 (dd, J=8.4, 1.5 Hz, 1H), 7.90 (d, J=1.5 Hz, 1H), 7.96 (d, J=8.5 Hz, 1H), 8.12 (s, 1H), 9.45 (s, 1H). MS (ESI$^+$) m/z 478 (M+H)$^+$.

Example 45

5-chloro-4-[1-(3-fluorobenzyl)-1H-benzimidazol-6-yl]-N-[2-(pyridin-4-yl)propyl]pyridin-2-amine The title compound was prepared as the bis-trifluoroacetate salt as described in Example 30 using $N^2$-(pyridin-4-yl)propane-1,2-diamine in place of $N^1$-methyl-$N^1$-(pyridin-2-yl)propane-1,3-diamine. $^1$H NMR (400 MHz, dimethylsulfoxide-$d_6$/$D_2O$) δ 1.35 (d, J=6.8 Hz, 3H), 3.35-3.48 (m, 1H), 3.60 (d, J=2.2 Hz, 2H), 3.61 (d, J=3.6 Hz, 2H), 5.75 (bs, 2H), 6.57 (s, 1H), 7.19 (td, J=8.6, 2.7 Hz, 1H), 7.30 (d, J=7.8 Hz, 1H), 7.35 (dd, J=9.8, 2.3 Hz, 1H), 7.45 (td, J=7.9, 6.0 Hz, 1H), 7.57 (dd, J=8.4, 1.5 Hz, 1H), 7.90 (d, J=1.5 Hz, 1H), 7.96 (d, J=8.5 Hz, 1H), 7.98-8.04 (m, 2H), 8.10 (s, 1H), 8.77-8.83 (m, 2H), 9.52 (s, 1H). MS (ESI$^+$) m/z 478 (M+H)$^+$.

Example 46

$N^1$-{5-chloro-4-[1-(3-fluorobenzyl)-1H-benzimidazol-6-yl]pyridin-2-yl}-$N^2$,$N^2$,2-trimethylpropane-1,2-diamine The title compound was prepared as the bis-trifluoroacetate salt as described in Example 30 using $N^2$,$N^2$,2-trimethylpropane-1,2-diamine in place of $N^1$-methyl-$N^1$-(pyridin-2-yl)propane-1,3-diamine. $^1$H NMR (400 MHz, dimethylsulfoxide-$d_6$/$D_2O$) δ 1.32 (s, 6H), 2.78 (s, 6H), 3.67 (bs, 2H), 5.74 (bs, 2H), 6.69 (s, 1H), 7.19 (td, J=8.6, 2.6 Hz, 1H), 7.25-7.39 (m, 2H), 7.45 (td, J=7.9, 6.0 Hz, 1H), 7.54 (dd, J=8.4, 1.5 Hz, 1H), 7.86 (d, J=1.5 Hz, 1H), 7.96 (d, J=8.5 Hz, 1H), 8.15 (d, J=0.5 Hz, 1H), 9.43 (s, 1H). MS (ESI$^+$) m/z 472 (M+H)$^+$.

Example 47

N-{5-chloro-4-[1-(3-fluorobenzyl)-1H-benzimidazol-6-yl]pyridin-2-yl}-N'-phenylpropane-1,3-diamine The title compound was prepared as the bis-trifluoroacetate salt as described in Example 30 using $N^1$-phenylpropane-1,3-diamine in place of $N^1$-methyl-$N^1$-(pyridin-2-yl)propane-1,3-diamine. $^1$H NMR (400 MHz, dimethylsulfoxide-$d_6$/$D_2O$) δ 1.84-1.95 (m, 2H), 3.29 (t, J=7.3 Hz, 2H), 3.39 (t, J=6.8 Hz, 2H), 5.74 (bs, 2H), 6.64 (s, 1H), 7.11-7.23 (m, 4H), 7.27-7.33 (m, 1H), 7.31-7.50 (m, 4H), 7.57 (dd, J=8.4, 1.6 Hz, 1H), 7.90 (d, J=1.5 Hz, 1H), 7.96 (d, J=8.4 Hz, 1H), 8.12 (d, J=0.5 Hz, 1H), 9.48 (s, 1H). MS (ESI$^+$) m/z 486 (M+H)$^+$.

Example 48

$N^3$-{5-chloro-4-[1-(3-fluorobenzyl)-1H-benzimidazol-6-yl]pyridin-2-yl}butane-1,3-diamine The title compound was prepared as the bis-trifluoroacetate salt as described in Example 30 using butane-1,3-diamine in place of $N^1$-methyl-$N^1$-(pyridin-2-yl)propane-1,3-diamine. $^1$H NMR (400 MHz, dimethylsulfoxide-$d_6$/$D_2O$) δ 1.24 (d, J=6.5 Hz, 3H), 1.64-1.83 (m, 1H), 1.82-1.95 (m, 1H), 3.16-3.44 (m, 3H), 5.73 (bs, 2H), 6.59 (s, 1H), 7.19 (td, J=8.6, 2.7 Hz, 1H), 7.25-7.37 (m, 2H), 7.45 (td, J=7.9, 6.0 Hz, 1H), 7.55 (dd, J=8.4, 1.6 Hz, 1H), 7.87 (d, J=1.5 Hz, 1H), 7.94 (d, J=8.4 Hz, 1H), 8.12 (d, J=0.5 Hz, 1H), 9.41 (s, 1H). MS (ESI$^+$) m/z 424 (M+H)$^+$.

Example 49

5-chloro-4-[1-(3-fluorobenzyl)-1H-benzimidazol-6-yl]pyridin-2-amine

A mixture of Example 6A (305 mg, 1 mmol), (2-((tert-butoxycarbonyl)amino)-5-chloropyridin-4-yl)boronic acid (354 mg, 1.30 mmol), 1,1'-bis(diphenylphosphino)ferrocene-palladium(II)dichloride dichloromethane complex (82 mg, 0.10 mmol), dimethoxyethane (3.623 mL) and 2M aqueous sodium carbonate (1.26 mL, 2.52 mmol) was heated in a Biotage Initiator® microwave reactor at 110° for 45 minutes. The mixture was filtered through diatomaceous earth with ethyl acetate, concentrated and purified by silica gel flash chromatography (Isco®, Redi-Sep® column) eluting with a gradient of 30-100% ethyl acetate/hexane to afford the BOC-protected intermediate. The mixture was stirred with 3 mL dichloromethane and 3 mL trifluoroacetic acid at ambient temperature for 30 minutes. The mixture was poured into 10% aqueous potassium carbonate and ethyl acetate and the mixture was stirred vigorously for 15 minutes. The solid was filtered and washed with water and hexane to give the title compound. $^1$H NMR (300 MHz, dimethylsulfoxide-$d_6$) δ 8.51 (s, 1H), 7.98 (s, 1H), 7.74 (d, J=8.6, 1H), 7.69-7.65 (m, 1H), 7.43-7.33 (m, 1H), 7.26-7.07 (m, 4H), 6.47 (s, 1H), 6.16 (s, 2H), 5.56 (s, 2H). MS (ESI) m/z 353 (M+H)$^+$.

Example 50

5-chloro-4-[1-(3-fluorobenzyl)-1H-benzimidazol-6-yl]-N-(1H-imidazol-4-ylmethyl)pyridin-2-amine The title compound was prepared as the bis-trifluoroacetate salt as described in Example 30 using 2-(1H-imidazol- 4-yl)ethanamine in place of N$^1$-methyl-N$^1$-(pyridin-2-yl)propane-1,3-diamine. $^1$H NMR (400 MHz, dimethylsulfoxide-d$_6$) δ 4.55 (s, 2H), 5.56 (s, 2H), 6.61 (s, 1H), 7.01-7.20 (m, 3H), 7.27 (dd, J=8.3, 1.6 Hz, 1H), 7.33-7.47 (m, 2H), 7.61 (d, J=1.6 Hz, 1H), 7.76 (d, J=8.3 Hz, 1H), 8.54 (s, 1H), 8.85 (d, J=1.4 Hz, 1H). MS (ESI$^+$) m/z 433 (M+H)$^+$.

Example 51

5-chloro-4-[1-(3-fluorobenzyl)-1H-benzimidazol-6-yl]-N-(pyrazin-2-ylmethyl)pyridin-2-amine The title compound was prepared as the bis-trifluoroacetate salt as described in Example 30 using pyrazin-2-ylmethanamine in place of N$^1$-methyl-N$^1$-(pyridin-2-yl)propane-1,3-diamine. $^1$H NMR (400 MHz, dimethylsulfoxide-d$_6$) δ 5.61 (s, 2H), 6.66 (s, 1H), 7.04-7.14 (m, 1H), 7.19 (d, J=8.8 Hz, 2H), 7.33-7.48 (m, 2H), 7.72 (d, J=0.8 Hz, 1H), 7.80 (d, J=8.4 Hz, 1H), 8.05 (s, 1H), 8.48 (d, J=2.5 Hz, 1H), 8.51-8.57 (m, 1H), 8.62 (s, 1H), 8.80 (s, 1H). MS (ESI$^+$) m/z 445 (M+H)$^+$.

Example 52

5-chloro-4-[1-(3-fluorobenzyl)-1H-benzimidazol-6-yl]-N-[1-(pyrazin-2-yl)propan-2-yl]pyridin-2-amine The title compound was prepared as the bis-trifluoroacetate salt as described in Example 30 using 1-(pyrazin-2-yl)propan-2-amine in place of N$^1$-methyl-N$^1$-(pyridin-2-yl)propane-1,3-diamine. $^1$H NMR (400 MHz, dimethylsulfoxide-d$_6$) δ 1.19 (d, J=6.5 Hz, 3H), 2.95 (dd, J=13.7, 6.5 Hz, 1H), 3.08 (dd, J=13.7, 6.8 Hz, 1H), 4.39 (h, J=6.6 Hz, 1H), 5.62 (s, 2H), 6.49 (s, 1H), 7.06-7.15 (m, 1H), 7.21 (d, J=4.3 Hz, 1H), 7.33-7.43 (m, 2H), 7.71 (d, J=1.5 Hz, 1H), 7.81 (d, J=8.4 Hz, 1H), 8.02 (s, 1H), 8.41 (d, J=2.5 Hz, 1H), 8.47-8.54 (m, 2H), 8.85 (s, 1H). MS (ESI$^+$) m/z 473 (M+H)$^+$.

Example 53

5-chloro-4-[1-(3-fluorobenzyl)-1H-benzimidazol-6-yl]-N-(1-methylpyrrolidin-3-yl)pyridin-2-amine The title compound was prepared as the bis-trifluoroacetate salt as described in Example 30 using 1-methylpyrrolidin-3-amine in place of N$^1$-methyl-N$^1$-(pyridin-2-yl)propane-1,3-diamine. $^1$H NMR (400 MHz, dimethylsulfoxide-d$_6$) δ 1.60-2.18 (m, 2H), 2.76-3.40 (m, 4H), 5.56 (s, 2H), 6.56 (s, 1H), 7.05-7.17 (m, 3H), 7.26 (dd, J=8.3, 1.6 Hz, 1H), 7.33-7.42 (m, 1H), 7.61 (d, J=1.6 Hz, 1H), 7.76 (d, J=8.3 Hz, 1H), 8.52 (s, 1H). MS (ESI$^+$) m/z 436 (M+H)$^+$.

Example 54

5-chloro-4-[1-(3-fluorobenzyl)-1H-benzimidazol-6-yl]-N-[2-(pyridin-3-yl)ethyl]pyridin-2-amine The title compound was prepared as the bis-trifluoroacetate salt as described in Example 30 using 2-(pyridin-3-yl)ethanamine in place of N$^1$-methyl-N$^1$-(pyridin-2-yl)propane-1,3-diamine. $^1$H NMR (400 MHz, dimethylsulfoxide-d$_6$) δ 2.96 (t, J=6.9 Hz, 2H), 3.58 (t, J=7.0 Hz, 2H), 5.58 (s, 2H), 6.50 (s, 1H), 7.08 (d, J=9.8 Hz, 1H), 7.17 (d, J=7.5 Hz, 2H), 7.30 (dd, J=8.4, 1.5 Hz, 1H), 7.38 (dd, J=14.1, 7.8 Hz, 1H), 7.54 (dd, J=7.7, 5.2 Hz, 1H), 7.65 (s, 1H), 7.77 (d, J=8.4 Hz, 1H), 7.96 (d, J=8.1 Hz, 1H), 8.04 (s, 1H), 8.52 (d, J=3.9 Hz, 1H), 8.58 (s, 1H), 8.64 (s, 1H). MS (ESI$^+$) m/z 458 (M+H)$^+$.

Example 55

N'-{5-chloro-4-[1-(3-fluorobenzyl)-1H-benzimidazol-6-yl]pyridin-2-yl}-N,N-dimethylbutane-1,4-diamine The title compound was prepared as the bis-trifluoroacetate salt as described in Example 30 using N$^1$,N$^1$-dimethylbutane-1,4-diamine in place of N$^1$-methyl-N$^1$-(pyridin-2-yl)propane-1,3-diamine. $^1$H NMR (400 MHz, dimethylsulfoxide-d$_6$) δ 1.53-1.65 (m, 2H), 1.64-1.76 (m, 2H), 2.77 (s, 6H), 3.05-3.12 (m, 2H), 3.30 (t, J=6.8 Hz, 2H), 5.58 (s, 2H), 6.50 (s, 1H), 7.05-7.20 (m, 2H), 7.30 (dd, J=8.3, 1.6 Hz, 1H), 7.33-7.43 (m, 1H), 7.64 (d, J=1.6 Hz, 1H), 7.77 (d, J=8.3 Hz, 1H), 8.61 (s, 1H). MS (ESI$^+$) m/z 452 (M+H)$^+$.

Example 56

5-chloro-4-[1-(3-fluorobenzyl)-1H-benzimidazol-6-yl]-N-[(1-methylpiperidin-4-yl)methyl]pyridin-2-amine The title compound was prepared as the bis-trifluoroacetate salt as described in Example 30 using (1-methylpiperidin-4-yl)methanamine in place of N$^1$-methyl-N$^1$-(pyridin-2-yl)propane-1,3-diamine. $^1$H NMR (400 MHz, dimethylsulfoxide-d$_6$) δ 1.26-1.50 (m, 2H), 1.52-2.03 (m, 4H), 2.73-2.78 (m, 3H), 2.82-3.02 (m, 2H), 3.00-3.49 (m, 4H), 5.58 (s, 2H), 6.53 (s, 1H), 7.05-7.14 (m, 1H), 7.13-7.20 (m, 2H), 7.31 (dd, J=8.3, 1.6 Hz, 1H), 7.33-7.43 (m, 1H), 7.65 (d, J=1.6 Hz, 1H), 7.78 (d, J=8.3 Hz, 1H), 8.65 (s, 1H). MS (ESI$^+$) m/z 464 (M+H)$^+$.

Example 57

N-benzyl-N'-{5-chloro-4-[1-(3-fluorobenzyl)-1H-benzimidazol-6-yl]pyridin-2-yl}-N-methylethane-1,2-diamine The title compound was prepared as the bis-trifluoroacetate salt as described in Example 30 using N$^1$-benzyl-N$^1$-methylethane-1,2-diamine in place of N$^1$-methyl-N$^1$-(pyridin-2-yl)propane-1,3-diamine. $^1$H NMR (400 MHz, dimethylsulfoxide-d$_6$) δ 2.80 (s, 3H), 3.66 (t, J=6.1 Hz, 2H), 4.36 (bs, 2H), 5.55 (bs, 2H), 6.55 (s, 1H), 7.05-7.16 (m, 2H), 7.25 (dd, J=8.3, 1.7 Hz, 1H), 7.32-7.40 (m, 1H), 7.38-7.47 (m, 3H), 7.46-7.53 (m, 2H), 7.58 (d, J=1.6 Hz, 1H), 7.76 (d, J=8.3 Hz, 1H), 8.47 (s, 1H). MS (ESI$^+$) m/z 500 (M+H)$^+$.

Example 58

5-chloro-4-[1-(3-fluorobenzyl)-1H-benzimidazol-6-yl]-N-[2-(pyridin-2-yl)ethyl]pyridin-2-amine The title compound was prepared as the bis-trifluoroacetate salt as described in Example 30 using 2-(pyridin-2-yl)ethanamine in place of N$^1$-methyl-N$^1$-(pyridin-2-yl)propane-1,3-diamine. $^1$H NMR (400 MHz, dimethylsulfoxide-d$_6$) δ 3.16 (dd, J=13.8, 6.9 Hz, 2H), 3.70 (t, J=6.9 Hz, 2H), 5.61 (s, 2H), 6.52 (s, 1H), 7.05-7.13 (m, 1H), 7.13-7.25 (m, 2H), 7.32-7.44 (m, 2H), 7.46-7.54 (m, 1H), 7.59 (d, J=7.9

Hz, 1H), 7.69 (d, J=1.1 Hz, 1H), 7.80 (d, J=8.4 Hz, 1H), 7.98-8.11 (m, 1H), 8.61 (d, J=5.1 Hz, 1H), 8.79 (s, 1H). MS (ESI⁺) m/z 458 (M+H)⁺.

Example 59

4-({5-chloro-4-[1-(3-fluorobenzyl)-1H-benzimidazol-6-yl]pyridin-2-yl}amino)-2-methylbutan-2-ol The title compound was prepared as the bis-trifluoroacetate salt as described in Example 30 using 4-amino-2-methylbutan-2-ol in place of $N^1$-methyl-$N^1$-(pyridin-2-yl)propane-1,3-diamine. $^1$H NMR (400 MHz, dimethylsulfoxide-$d_6$) δ 1.15 (s, 6H), 1.64-1.71 (m, 2H), 3.30-3.37 (m, 2H), 3.97 (s, 2H), 5.60 (s, 2H), 6.51 (s, 1H), 7.00-7.14 (m, 1H), 7.15-7.22 (m, 2H), 7.31-7.42 (m, 2H), 7.69 (d, J=1.6 Hz, 1H), 7.79 (d, J=8.3 Hz, 1H), 8.73 (s, 1H). MS (ESI⁺) m/z 439 (M+H)⁺.

Example 60

N'-{5-chloro-4-[1-(3-fluorobenzyl)-1H-benzimidazol-6-yl]pyridin-2-yl}-N-methyl-N-phenylpropane-1,3-diamine The title compound was prepared as the bis-trifluoroacetate salt as described in Example 30 using $N^1$-methyl-$N^1$-phenylpropane-1,3-diamine in place of $N^1$-methyl-$N^1$-(pyridin-2-yl)propane-1,3-diamine. $^1$H NMR (400 MHz, dimethylsulfoxide-$d_6$) δ 1.70-1.88 (m, 2H), 2.90 (s, 3H), 3.31 (t, J=6.9 Hz, 2H), 3.36-3.42 (m, 2H), 5.63 (s, 2H), 6.55 (d, J=5.3 Hz, 1H), 6.59-6.69 (m, 1H), 6.77 (d, J=8.1 Hz, 2H), 7.07-7.24 (m, 4H), 7.32-7.47 (m, 2H), 7.74 (d, J=0.9 Hz, 1H), 7.83 (d, J=8.4 Hz, 1H), 8.05 (s, 1H), 8.91 (s, 1H). MS (ESI⁺) m/z 500 (M+H)⁺.

Example 61

5-chloro-4-[1-(3-fluorobenzyl)-1H-benzimidazol-6-yl]-N-(1-methylpiperidin-4-yl)pyridin-2-amine The title compound was prepared as the bis-trifluoroacetate salt as described in Example using 30 1-methylpiperidin-4-amine in place of $N^1$-methyl-$N^1$-(pyridin-2-yl)propane-1,3-diamine. $^1$H NMR (400 MHz, dimethylsulfoxide-$d_6$) δ 1.91 (d, J=181.3 Hz, 4H), 2.81 (d, J=15.5 Hz, 3H), 3.01-3.56 (m, 4H), 5.60 (s, 2H), 6.53 (d, J=17.5 Hz, 1H), 7.10 (dd, J=10.4, 7.9 Hz, 1H), 7.17 (d, J=8.5 Hz, 2H), 7.29-7.42 (m, 2H), 7.69 (t, J=5.5 Hz, 1H), 7.80 (d, J=8.4 Hz, 1H), 8.06 (s, 1H), 8.76 (d, J=23.2 Hz, 1H). MS (ESI⁺) m/z 450 (M+H)⁺.

Example 62

5-chloro-4-[1-(3-fluorobenzyl)-1H-benzimidazol-6-yl]-N-[2-(pyridin-4-yl)ethyl]pyridin-2-amine The title compound was prepared as the bis-trifluoroacetate salt as described in Example 30 using 2-(pyridin-4-yl)ethanamine in place of $N^1$-methyl-$N^1$-(pyridin-2-yl)propane-1,3-diamine. $^1$H NMR (400 MHz, dimethylsulfoxide-$d_6$) δ 3.10 (t, J=6.8 Hz, 2H), 3.65 (t, J=6.9 Hz, 2H), 5.61 (s, 2H), 6.53 (s, 1H), 7.10 (dd, J=9.0, 6.6 Hz, 1H), 7.16-7.22 (m, 2H), 7.33-7.42 (m, 4H), 7.70 (d, J=0.9 Hz, 1H), 7.73 (d, J=6.3 Hz, 2H), 7.80 (d, J=8.4 Hz, 1H), 8.06 (s, 1H), 8.67 (d, J=6.4 Hz, 2H), 8.80 (s, 1H). MS (ESI⁺) m/z 458 (M+H)⁺.

Example 63

5-chloro-4-[1-(3-fluorobenzyl)-1H-benzimidazol-6-yl]-N-(pyrimidin-5-ylmethyl)pyridin-2-amine The title compound was prepared as the bis-trifluoroacetate salt as described in Example 30 using pyrimidin-5-ylmethanamine in place of $N^1$-methyl-$N^1$-(pyridin-2-yl)propane-1,3-diamine $^1$H NMR (400 MHz, dimethylsulfoxide-$d_6$) δ 4.54 (s, 2H), 5.60 (s, 2H), 6.60 (s, 1H), 7.00-7.13 (m, 1H), 7.19 (d, J=9.1 Hz, 2H), 7.29-7.48 (m, 2H), 7.71 (d, J=1.0 Hz, 1H), 7.79 (d, J=8.4 Hz, 1H), 8.07 (s, 1H), 8.76 (d, J=9.1 Hz, 2H). MS (ESI) m/z 445 (M+H)⁺.

Example 64

$N^2$-{5-chloro-4-[1-(3-fluorobenzyl)-1H-benzimidazol-6-yl]pyridin-2-yl}-2-methylpropane-1,2-diamine The title compound was prepared as the bis-trifluoroacetate salt as described in Example 30 using 2-methylpropane-1,2-diamine in place of $N^1$-methyl-$N^1$-(pyridin-2-yl)propane-1,3-diamine. $^1$H NMR (400 MHz, dimethylsulfoxide-$d_6$) δ 1.28 (s, 6H), 3.49 (s, 2H), 5.59 (s, 2H), 6.64 (s, 1H), 6.81 (s, 1H), 7.08 (dd, J=7.8, 2.0 Hz, 1H), 7.12-7.26 (m, 2H), 7.30 (dd, J=8.4, 1.5 Hz, 1H), 7.38 (dd, J=14.1, 7.7 Hz, 1H), 7.64 (d, J=0.9 Hz, 1H), 7.78 (t, J=11.1 Hz, 2H), 8.07 (s, 1H), 8.65 (s, 1H). MS (ESI⁺) m/z 424 (M+H)⁺.

Example 65

5-chloro-N-(2-cyclohexylethyl)-4-[1-(3-fluorobenzyl)-1H-benzimidazol-6-yl]pyridin-2-amine The title compound was prepared as the bis-trifluoroacetate salt as described in Example 30 using 2-cyclohexylethanamine in place of $N^1$-methyl-$N^1$-(pyridin-2-yl)propane-1,3-diamine. $^1$H NMR (400 MHz, dimethylsulfoxide-$d_6$) δ 0.85-1.03 (m, 2H), 1.09-1.30 (m, 4H), 1.30-1.51 (m, 4H), 1.53-1.75 (m, 4H), 3.20-3.34 (m, 2H), 5.63 (s, 2H), 6.52 (s, 1H), 7.00-7.10 (m, 1H), 7.13-7.24 (m, 2H), 7.31-7.47 (m, 2H), 7.70 (d, J=1.1 Hz, 1H), 7.79 (d, J=8.4 Hz, 1H), 8.04 (s, 1H), 8.77 (s, 1H). MS (ESI⁺) m/z 463 (M+H)⁺.

Example 66

N-{5-chloro-4-[1-(3-fluorobenzyl)-1H-benzimidazol-6-yl]pyridin-2-yl}-N'-phenylethane-1,2-diamine The title compound (34.6 mg) was prepared as the bis-trifluoroacetate salt as described in Example 30 using $N^1$-phenylethane-1,2-diamine in place of $N^1$-methyl-$N^1$-(pyridin-2-yl)propane-1,3-diamine. $^1$H NMR (400 MHz, dimethylsulfoxide-$d_6$) δ 3.26 (t, J=6.4 Hz, 2H), 3.49 (t, J=6.4 Hz, 2H), 5.63 (s, 2H), 6.51-6.60 (m, 2H), 6.65 (d, J=7.8 Hz, 2H), 7.10 (ddd, J=15.8, 8.5, 4.8 Hz, 3H), 7.21 (dd, J=7.7, 4.5 Hz, 2H), 7.33-7.49 (m, 2H), 7.74 (d, J=1.0 Hz, 1H), 7.82 (d, J=8.4 Hz, 1H), 8.08 (s, 1H), 8.90 (s, 1H). MS (ESI⁺) m/z 472 (M+H)⁺.

Example 67

N'-{5-chloro-4-[1-(3-fluorobenzyl)-1H-benzimidazol-6-yl]pyridin-2-yl}-N,N,2,2-tetramethylpropane-1,3-diamine The title compound was prepared as the bis-trifluoroacetate salt as described in Example 30 using $N^1,N^1,2,2$- tetramethylpropane-1,3-diamine in place of N¹-methyl-N¹-(pyridin-2-yl)propane-1,3-diamine. ¹H NMR (400 MHz, dimethylsulfoxide-$d_6$) δ 1.09 (s, 6H), 2.88 (s, 6H), 3.08 (s, 2H), 3.32 (s, 2H), 5.63 (s, 2H) 7.05-7.14 (m, 1H), 7.16 (d, J=1.6 Hz, 1H), 7.26-7.44 (m, 2H), 7.68 (d, J=1.5 Hz, 1H), 7.80 (d, J=8.3 Hz, 1H), 8.09 (s, 1H), 8.70 (s, 1H). MS (ESI⁺) m/z 466 (M+H)⁺.

Example 68

2-({5-chloro-4-[1-(3-fluorobenzyl)-1H-benzimidazol-6-yl]pyridin-2-yl}amino)ethanol The title compound was prepared as the bis-trifluoroacetate salt as described in Example 30 using 2-aminoethanol in place of N¹-methyl-N¹-(pyridin-2-yl)propane-1,3-diamine ¹H NMR (400 MHz, dimethylsulfoxide-$d_6$) δ 3.36 (t, J=5.9 Hz, 2H), 3.57 (t, J=5.9 Hz, 2H), 5.61 (s, 2H), 6.59 (s, 1H), 7.11 (dt, J=9.7, 6.0 Hz, 1H), 7.21 (t, J=8.7 Hz, 2H), 7.30-7.45 (m, 2H), 7.66-7.76 (m, 1H), 7.77-7.85 (m, 1H), 8.04 (s, 1H), 8.80 (s, 1H). MS (ESI⁺) m/z 397 (M+H)⁺.

Example 69

N-benzyl-5-chloro-4-[1-(3-fluorobenzyl)-1H-benzimidazol-6-yl]pyridin-2-amine

The title compound was prepared as the bis-trifluoroacetate salt as described in Example 30 using benzyl amine in place of N¹-methyl-N¹-(pyridin-2-yl)propane-1,3-diamine ¹H NMR (400 MHz, DMSO-$d_6$) δ 4.50 (s, 2H), 5.58 (s, 2H), 6.56 (s, 1H), 6.97-7.16 (m, 1H), 7.13-7.42 (m, 6H), 7.67 (d, J=1.5 Hz, 1H), 7.77 (d, J=8.3 Hz, 1H), 8.70 (s, 1H) MS (ESI⁺) m/z 443 (M+H)⁺.

Example 70

N'-{5-chloro-4-[1-(3-fluorobenzyl)-1H-benzimidazol-6-yl]pyridin-2-yl}-N,N-dimethylpropane-1,3-diamine The title compound was prepared as the bis-trifluoroacetate salt as described in Example 30 using N¹,N¹-dimethylpropane-1,3-diamine in place of N¹-methyl-N¹-(pyridin-2-yl)propane-1,3-diamine. ¹H NMR (400 MHz, dimethylsulfoxide-$d_6$) δ 1.85-1.98 (m, 2H), 2.80 (s, 6H), 3.13 (d, J=2.3 Hz, 2H), 3.17 (d, J=14.3 Hz, 1H), 3.35 (t, J=6.7 Hz, 2H), 5.63 (s, 2H), 6.53 (s, 1H), 7.05-7.14 (m, 1H), 7.14-7.20 (m, 2H), 7.32 (dd, J=8.3, 1.6 Hz, 1H), 7.34-7.43 (m, 1H), 7.66 (d, J=1.5 Hz, 1H), 7.79 (d, J=8.3 Hz, 1H), 8.70 (s, 1H). MS (ESI⁺) m/z 438 (M+H)⁺.

Example 71

3-({5-chloro-4-[1-(3-fluorobenzyl)-1H-benzimidazol-6-yl]pyridin-2-yl}amino)propan-1-ol The title compound was prepared as the bis-trifluoroacetate salt as described in Example 30 using 3-aminopropan-1-ol in place of N¹-methyl-N¹-(pyridin-2-yl)propane-1,3-diamine ¹H NMR (400 MHz, dimethylsulfoxide-$d_6$) δ 1.78-1.91 (m, 2H), 2.89 (s, 2H), 3.35 (t, J=6.7 Hz, 2H), 5.59 (s, 2H), 6.53 (s, 1H), 6.98-7.13 (m, 1H), 7.17 (d, J=8.7 Hz, 2H), 7.35 (ddd, J=11.2, 9.9, 4.7 Hz, 2H), 7.79 (d, J=8.4 Hz, 1H), 8.06 (s, 1H), 8.69 (s, 1H). MS (ESI⁺) m/z 410 (M+H)⁺.

Example 72

N-{5-chloro-4-[1-(3-fluorobenzyl)-1H-benzimidazol-6-yl]pyridin-2-yl}propane-1,3-diamine The title compound was prepared as the bis-trifluoroacetate salt as described in Example 30 using propane-1,3-diamine in place of N¹-methyl-N¹-(pyridin-2-yl)propane-1,3-diamine. ¹H NMR (400 MHz, dimethylsulfoxide-$d_6$) δ 1.84 (p, J=7.1 Hz, 2H), 2.86-2.91 (m, 2H), 3.35 (t, J=6.7 Hz, 2H), 5.57 (s, 2H), 6.52 (s, 1H), 7.05-7.20 (m, 3H), 7.30 (dd, J=8.3, 1.6 Hz, 1H), 7.33-7.54 (m, 1H), 7.61-7.66 (m, 2H), 7.77 (d, J=8.3 Hz, 1H), 8.61 (s, 1H). MS (ESI⁺) m/z 410 (M+H)⁺.

Example 73

4-[({5-chloro-4-[1-(3-fluorobenzyl)-1H-benzimidazol-6-yl]pyridin-2-yl}amino)methyl]phenol The title compound was prepared as the bis-trifluoroacetate salt as described in Example 30 using 4-(aminomethyl)phenol in place of N¹-methyl-N¹-(pyridin-2-yl)propane-1,3-diamine. ¹H NMR (400 MHz, dimethylsulfoxide-$d_6$) δ 4.37 (s, 2H), 5.60 (s, 2H), 6.55 (s, 1H), 6.70 (dd, J=6.5, 4.7 Hz, 2H), 7.02-7.24 (m, 5H), 7.28-7.47 (m, 2H), 7.68 (d, J=1.0 Hz, 1H), 7.77 (t, J=10.4 Hz, 1H), 8.05 (s, 1H), 8.76 (s, 1H). MS (ESI⁺) m/z 459 (M+H)⁺.

Example 74

N-{5-chloro-4-[1-(3-fluorobenzyl)-1H-benzimidazol-6-yl]pyridin-2-yl}butane-1,4-diamine The title compound was prepared as the bis-trifluoroacetate salt as described in Example 30 using butane-1,4-diamine in place of N¹-methyl-N¹-(pyridin-2-yl)propane-1,3-diamine. ¹H NMR (400 MHz, dimethylsulfoxide-$d_6$) δ 1.54-1.69 (m, 4H), 2.79-2.88 (m, 2H), 3.29 (t, J=6.2 Hz, 2H), 5.58 (s, 2H), 6.51 (s, 1H), 7.05-7.20 (m, 3H), 7.30 (dd, J=8.3, 1.6 Hz, 1H), 7.33-7.70 (m, 3H), 7.78 (d, J=8.3 Hz, 1H), 8.64 (s, 1H). MS (ESI⁺) m/z 424 (M+H)⁺.

Example 75

N-[2-(4-aminophenyl)ethyl]-5-chloro-4-[1-(3-fluorobenzyl)-1H-benzimidazol-6-yl]pyridin-2-amine The title compound was prepared as the bis-trifluoroacetate salt as described in Example 30 using 4-(2-aminoethyl)aniline in place of N¹-methyl-N¹-(pyridin-2-yl)propane-1,3-diamine. ¹H NMR (400 MHz, dimethylsulfoxide-$d_6$) δ 2.83 (t, J=7.3 Hz, 2H), 3.49 (t, J=7.3 Hz, 2H), 5.60 (s, 2H), 6.52 (s, 1H), 7.01 (d, J=8.3 Hz, 2H), 7.08 (dd, J=7.8, 2.0 Hz, 1H), 7.19 (dd, J=9.0, 6.1 Hz, 4H), 7.30-7.45 (m, 2H), 7.69 (d, J=0.9 Hz, 1H), 7.79 (d, J=8.4 Hz, 1H), 8.06 (s, 1H), 8.76 (s, 1H). MS (ESI⁺) m/z 472 (M+H)⁺.

Example 76

N-{5-chloro-4-[1-(3-fluorobenzyl)-1H-benzimidazol-6-yl]pyridin-2-yl}-2,2-dimethylpropane-1,3-diamine The title compound was prepared as the bis-trifluoroacetate salt as described in Example 30 using 2,2-dimethylpropane-1,3-diamine in place of N¹-methyl-N¹-(pyridin-2- yl)propane-1,3-diamine ¹H NMR (400 MHz, dimethylsulfoxide-d₆) δ 0.99 (s, 6H), 2.63-2.71 (m, 2H), 3.23 (bs, 2H), 5.56 (s, 2H), 6.63 (s, 1H), 7.04-7.17 (m, 3H), 7.26 (dd, J=8.3, 1.6 Hz, 1H), 7.33-7.42 (m, 1H), 7.53-7.73 (m, 3H), 7.76 (d, J=8.3 Hz, 1H), 8.04 (s, 1H), 8.51 (s, 1H). MS (ESI⁺) m/z 438 (M+H)⁺.

Example 77

N-{5-chloro-4-[1-(3-fluorobenzyl)-1H-benzimidazol-6-yl]pyridin-2-yl}ethane-1,2-diamine The title compound was prepared as the bis-trifluoroacetate salt as described in Example 30 using ethane-1,2-diamine in place of N¹-methyl-N¹-(pyridin-2-yl)propane-1,3-diamine ¹H NMR (400 MHz, dimethylsulfoxide-d₆) δ 2.99-3.06 (m, 2H), 3.53 (t, J=6.2 Hz, 2H), 5.59 (s, 2H); 6.56 (s, 1H), 7.05-7.21 (m, 2H), 7.30 (dd, J=8.3, 1.6 Hz, 1H), 7.33-7.43 (m, 2H), 7.55-7.91 (m, 4H), 8.66 (s, 1H). MS (ESI⁺) m/z 396 (M+H)⁺.

Example 78

N-[4-(aminomethyl)benzyl]-5-chloro-4-[1-(3-fluorobenzyl)-1H-benzimidazol-6-yl]pyridin-2-amine The title compound was prepared as the bis-trifluoroacetate salt as described in Example 30 using 1,4-phenylenedimethanamine in place of N¹-methyl-N¹-(pyridin-2-yl)propane-1,3-diamine ¹H NMR (400 MHz, dimethylsulfoxide-d₆) δ 3.95-4.02 (m, 2H), 4.52 (s, 2H), 5.57 (s, 2H), 6.56 (s, 1H), 7.05-7.23 (m, 2H), 7.24-7.32 (m, 1H), 7.32-7.51 (m, 4H), 7.64 (d, J=1.6 Hz, 1H), 7.76 (d, J=8.4 Hz, 1H), 7.85-8.42 (m, 3H), 8.58 (s, 1H). MS (ESI⁺) m/z 472 (M+H)⁺.

Example 79

1-({5-chloro-4-[1-(3-fluorobenzyl)-1H-benzimidazol-6-yl]pyridin-2-yl}amino)-2-methylpropan-2-ol The title compound was prepared as the bis-trifluoroacetate salt as described in Example 30 using 1-amino-2-methylpropan-2-ol in place of N¹-methyl-N¹-(pyridin-2-yl)propane-1,3-diamine. ¹H NMR (400 MHz, dimethylsulfoxide-d₆) δ 1.15 (s, 6H), 3.27 (s, 2H), 5.62 (s, 2H), 6.71 (s, 1H), 7.06-7.15 (m, 1H), 7.15-7.24 (m, 2H), 7.34-7.43 (m, 2H), 7.73 (d, J=1.6 Hz, 1H), 7.81 (d, J=8.3 Hz, 1H), 8.04 (s, 1H), 8.83 (s, 1H). MS (ESI⁺) m/z 425 (M+H)⁺.

Example 80

1-amino-3-({5-chloro-4-[1-(3-fluorobenzyl)-1H-benzimidazol-6-yl]pyridin-2-yl}amino)propan-2-ol The title compound was prepared as the bis-trifluoroacetate salt as described in Example 30 using 1,3-diaminopropan-2-ol in place of N¹-methyl-N¹-(pyridin-2-yl)propane-1,3-diamine. ¹H NMR (400 MHz, dimethylsulfoxide-d₆) δ 2.73 (dd, J=32.0, 19.3 Hz, 1H), 2.97 (d, J=10.2 Hz, 1H), 3.29-3.45 (m, 2H), 3.90 (ddd, J=9.4, 5.9, 3.6 Hz, 1H), 5.59 (s, 2H), 6.60 (s, 1H), 7.02-7.12 (m, 1H), 7.15 (t, J=12.0 Hz, 2H), 7.32 (dd, J=8.4, 1.5 Hz, 1H), 7.33-7.43 (m, 1H), 7.66 (d, J=1.0 Hz, 2H), 7.79 (d, J=8.4 Hz, 1H), 8.06 (s, 1H), 8.70 (s, 1H). MS (ESI⁺) m/z 426 (M+H)⁺.

Example 81

N-{5-chloro-4-[1-(3-fluorobenzyl)-1H-benzimidazol-6-yl]pyridin-2-yl}-N'-(pyridin-2-yl)ethane-1,2-diamine The title compound was prepared as the bis-trifluoroacetate salt as described in Example 30 using N¹-(pyridin-2-yl)ethane-1,2-diamine in place of N¹-methyl-N¹-(pyridin-2-yl)propane-1,3-diamine. ¹H NMR (400 MHz, dimethylsulfoxide-d₆) δ 3.51 (s, 4H), 5.59 (s, 2H), 6.56 (s, 2H), 6.82 (t, J=6.6 Hz, 2H), 7.08 (ddd, J=19.0, 12.8, 5.3 Hz, 2H), 7.17 (d, J=7.6 Hz, 2H), 7.31 (dd, J=8.4, 1.5 Hz, 1H), 7.33-7.42 (m, 1H), 7.65 (d, J=0.9 Hz, 1H), 7.79 (d, J=8.4 Hz, 1H), 7.84 (ddd, J=14.9, 8.3, 4.8 Hz, 1H), 7.88-7.97 (m, 1H), 8.10 (s, 1H), 8.69 (s, 1H). MS (ESI⁺) m/z 473 (M+H)⁺.

Example 82

(3R)—N-{5-chloro-4-[1-(3-fluorobenzyl)-1H-benzimidazol-6-yl]pyridin-2-yl}-1-azabicyclo[2.2.2]octan-3-amine The title compound was prepared as the bis-trifluoroacetate salt as described in Example 30 using (5S,9R)-1-azabicyclo[3.2.2]nonan-9-amine in place of N¹-methyl-N¹-(pyridin-2-yl)propane-1,3-diamine. ¹H NMR (400 MHz, dimethylsulfoxide-d₆) δ 1.52-1.64 (m, 1H), 1.73-2.25 (m, 4H), 3.14-3.34 (m, 4H), 3.69-3.81 (m, 2H), 3.95-4.08 (m, 1H), 5.56 (s, 2H), 6.76 (s, 1H), 7.04-7.13 (m, 1H), 7.14 (d, J=1.7 Hz, 1H), 7.27-7.41 (m, 2H), 7.61 (d, J=1.6 Hz, 1H), 7.73-7.80 (m, 1H), 8.19 (s, 1H), 8.49 (s, 1H). MS (ESI⁺) m/z 462 (M+H)⁺.

Example 83

(3S)—N-{5-chloro-4-[1-(3-fluorobenzyl)-1H-benzimidazol-6-yl]pyridin-2-yl}-1-azabicyclo[2.2.2]octan-3-amine The title compound was prepared as the bis-trifluoroacetate salt as described in Example 30 using (S)-quinuclidin-3-amine in place of N¹-methyl-N¹-(pyridin-2-yl)propane-1,3-diamine. ¹H NMR (400 MHz, dimethylsulfoxide-d₆) δ 1.51-1.64 (m, 2H), 1.77-2.09 (m, 4H), 2.07-2.33 (m, 2H), 3.69-3.81 (m, 2H), 5.56 (bs, 2H), 6.75 (s, 1H), 7.04-7.13 (m, 1H), 7.11-7.17 (m, 2H), 7.31 (dd, J=8.3, 1.6 Hz, 1H), 7.32-7.42 (m, 1H), 7.60 (d, J=1.6 Hz, 1H), 7.76 (d, J=8.3 Hz, 1H), 8.19 (s, 1H), 8.47 (s, 1H). MS (ESI⁺) m/z 462 (M+H)⁺.

Example 84

2-benzyl-N-{5-chloro-4-[1-(3-fluorobenzyl)-1H-benzimidazol-6-yl]pyridin-2-yl}octahydro-1H-isoindol-4-amine The title compound was prepared as bis-trifluoroacetate salt as described in Example 30 using 2-benzyloctahydro-1H-isoindol-5-amine in place of N¹-methyl-N¹-(pyridin-2-yl)propane-1,3-diamine. ¹H NMR (400 MHz, dimethylsulfoxide-d₆) δ 1.20-2.08 (m, 6H), 2.78-3.42 (m, 4H), 3.46-3.72 (m, 4H), 4.10-4.19 (m, 1H), 4.32-4.48 (m, 2H), 5.58 (bs, 2H), 6.53 (m, 1H), 7.05-7.22 (m, 2H), 7.24-7.48 (m, 5H), 7.50 (bs, 2H), 7.65 (bs, 1H), 7.75-7.81 (m, 1H), 8.65 (s, 1H), 9.74-10.08 (m, 1H). MS (ESI⁺) m/z 566 (M+H)⁺.

Example 85

2-benzyl-N-{5-chloro-4-[1-(3-fluorobenzyl)-1H-benzimidazol-6-yl]pyridin-2-yl}octahydrocyclopenta[c]pyrrol-4-amine The title compound was prepared as the bis-trifluoroacetate salt as described in Example 30 using 2-benzyloctahydrocyclopenta[c]pyrrol-4-amine in place of $N^1$-methyl-$N^1$-(pyridin-2-yl)propane-1,3-diamine $^1$H NMR (400 MHz, dimethylsulfoxide-$d_6$) δ 1.64-2.16 (m, 4H), 2.60-3.37 (m, 65H), 3.59 (bs, 1H), 4.25-4.39 (m, 2H), 5.57 (bs, 2H), 6.58 (bs, 1H), 7.03-7.24 (m, 3H), 7.23-7.35 (m, 1H), 7.33-7.53 (m, 6H), 7.64 (s, 1H), 7.78 (d, J=8.3 Hz, 1H), 8.59 (s, 1H). MS (ESI$^+$) m/z 552 (M+H)$^+$.

Example 86

N-{5-chloro-4-[1-(3-fluorobenzyl)-1H-benzimidazol-6-yl]pyridin-2-yl}-9-(cyclopropylmethyl)-9-azabicyclo[3.3.1]nonan-3-amine The title compound was prepared as the bis-trifluoroacetate salt as described in Example 30 using 9-(cyclopropylmethyl)-9-azabicyclo[3.3.1]nonan-3-amine in place of $N^1$-methyl-$N^1$-(pyridin-2-yl)propane-1,3-diamine. $^1$H NMR (400 MHz, dimethylsulfoxide-$d_6$) δ 0.36-0.49 (m, 2H), 0.60-0.73 (m, 2H), 1.02-1.34 (m, 1H), 1.38-2.43 (m, 10H), 3.11-3.29 (m, 2H), 3.73-3.82 (m, 2H), 5.57 (bs, 2H), 6.46-6.62 (m, 1H), 7.04-7.13 (m, 1H), 7.12-7.18 (m, 2H), 7.29 (dd, J=8.3, 1.6 Hz, 1H), 7.33-7.42 (m, 1H), 7.65 (d, J=1.6 Hz, 1H), 7.77 (d, J=8.3 Hz, 1H), 8.58 (s, 1H). MS (ESI$^+$) m/z 530 (M+H)$^+$.

Example 87 benzyl 4-({5-chloro-4-[1-(3-fluorobenzyl)-1H-benzimidazol-6-yl]pyridin-2-yl}amino)-4-(4-fluorophenyl)piperidine-1-carboxylate The title compound was prepared as the bis-trifluoroacetate salt as described in Example 30 using benzyl 4-amino-4-(4-fluorophenyl)piperidine-1-carboxylate in place of $N^1$-methyl-$N^1$-(pyridin-2-yl)propane-1,3-diamine. $^1$H NMR (400 MHz, dimethylsulfoxide-$d_6$) δ 1.88-1.98 (m, 2H), 2.34-2.43 (m, 2H), 4.02-4.11 (m, 2H), 4.95 (s, 2H), 5.56 (bs, 2H), 6.77 (s, 1H), 7.03-7.14 (m, 3H), 7.13-7.20 (m, 2H), 7.22-7.49 (m, 10H), 7.66 (d, J=1.5 Hz, 1H), 7.75 (d, J=8.3 Hz, 1H), 8.16 (s, 1H), 8.52 (s, 1H). MS (ESI$^+$) m/z 664 (M+H)$^+$.

Example 88 tert-butyl {5-chloro-4-[1-(3-fluorobenzyl)-1H-benzimidazol-6-yl]pyridin-2-yl}carbamate A mixture of Example 6A (305 mg, 1 mmol), (2-((tert-butoxycarbonyl)amino)-5-chloropyridin-4-yl)boronic acid (354 mg, 1.30 mmol), 1,1'-bis(diphenylphosphino)ferrocene-palladium(II)dichloride-dichloromethane complex (82 mg, 0.10 mmol), dimethoxyethane (3.623 mL) and 2M aqueous sodium carbonate (1.26 mL, 2.52 mmol) was heated in a Biotage Initiator® microwave reactor at 110° C. for 45 minutes. The mixture was filtered through diatomaceous earth with ethyl acetate, concentrated and purified by silica gel flash chromatography (Isco®, Redi-Sep® column), eluting with a gradient of 30-100% ethyl acetate/hexane, followed by purification by reverse-phase preparative HPLC (Phenomenex Luna C8(2) 100 Å AXIA column) using a gradient of 10-95% acetonitrile/0.1% trifluoroacetic acid in water to afford the title compound as the trifluoroacetate salt. $^1$H NMR (400 MHz, dimethylsulfoxide-$d_6$) δ 10.12 (s, 1H), 9.30 (s, 1H), 8.41 (s, 1H), 7.98 (s, 1H), 7.93 (d, J=8.5, 1H), 7.89 (s, 1H), 7.53 (dd, J=8.5, 1.1, 1H), 7.46-7.33 (m, 2H), 7.30 (d, J=7.7, 1H), 7.17 (td, J=8.7, 2.5, 1H), 5.71 (s, 2H), 1.46 (s, 9H). MS (ESI) m/z 453 (M+H)$^+$.

Example 89

(3R)—N-(5-chloro-4-{1-[(5-methyl-1,3,4-thiadiazol-2-yl)methyl]-1H-benzimidazol-6-yl}pyridin-2-yl)piperidine-3-carboxamide

Example 89A 2-((6-bromo-1H-benzo[d]imidazol-1-yl)methyl)-5-methyl-1,3,4-thiadiazole The title compound was prepared as described in Examples 8A-C using (5-methyl-1,3,4-thiadiazol-2-yl)methanamine in place of (3-fluorophenyl)methanamine. MS (ESI) m/e 309 (M+H)$^+$.

Example 89B (3R)—N-(5-chloro-4-{1-[(5-methyl-1,3,4-thiadiazol-2-yl)methyl]-1H-benzimidazol-6-yl}pyridin-2-yl)piperidine-3-carboxamide The title compound was prepared as the bis-hydrochloride salt as described in Example 1E using Example 89A in place of Example 1D. $^1$H NMR (400 MHz, dimethylsulfoxide-$d_6$) δ 1.63-2.15 (m, 4H) 2.67 (s, 3H) 2.79-3.36 (m, 5H) 6.08 (s, 2H) 7.40 (d, J=8.54 Hz, 1H) 7.76-7.90 (m, 2H) 8.13 (s, 1H) 8.44 (s, 1H) 8.77 (s, 1H) 8.90-9.24 (m, 2H) 10.70 (s, 1H). MS (ESI) m/e 468 (M+H)$^+$.

Example 90

(3R)—N-(5-chloro-4-{1-[2-(pyridin-3-yl)ethyl]-1H-benzimidazol-6-yl}pyridin-2-yl)piperidine-3-carboxamide

Example 90A 6-bromo-1-(2-(pyridin-3-yl)ethyl)-1H-benzo[d]imidazole

The title compound was prepared as described in Examples 8A-C using 3-(2-bromoethyl)pyridine in place of (3-fluorophenyl)methanamine. MS (ESI) m/e 303 (M+H)$^+$.

Example 90B (3R)—N-(5-chloro-4-{1-[2-(pyridin-3-yl)ethyl]-1H-benzimidazol-6-yl}pyridin-2-yl)piperidine-3-carboxamide The title compound was prepared as the bis-hydrochloride salt as described in Example 1E using Example 90A in place of Example 1D. $^1$H NMR (400 MHz, dimethylsulfoxide-$d_6$) δ 1.63-2.15 (m, 4H) 2.80-3.44 (m, 7H) 4.75 (t, J=7.17 Hz, 2H) 7.44 (d, J=8.54 Hz, 1H) 7.55-7.64 (m, 1H) 7.82-7.93 (m, 2H) 8.03 (d, J=7.63 Hz, 1H) 8.12 (s, 1H) 8.47 (s, 1H) 8.57 (d, J=4.88 Hz, 1H) 8.61 (s, 1H) 8.92 (s, 1H) 9.13 (s, 2H). MS (ESI) m/e 461 (M+H)$^+$.

Example 91

N-{5-chloro-4-[1-(3-fluorobenzyl)-1H-benzimidazol-6-yl]pyridin-2-yl}-N'-methylpropane-1,3-diamine To a solution of Example 8D (25 mg, 0.07 mmol) in dimethyl sulfoxide (1 mL), was added a solution of tert-butyl 3-aminopropyl(methyl)carbamate (40 mg, 0.21 mmol) in dimethylsulfoxide (500 µL) and N,N-diisopropylethylamine (37 µL, 0.21 mmol) and the mixture was stirred at 120° C. for 16 hours. The mixture was filtered, concentrated and dissolved in 200 µL trifluoroacetic acid. After stirring at room temperature for 4 hours the mixture was concentrated and dissolved in 1 mL 1:1 dimethylsulfoxide/methanol. Purification by reverse phase preparative HPLC (Phenomenex Luna C8(2) 100 Å AXIA column) eluting with a gradient of 5-100% acetonitrile/0.1% trifluoroacetic acid in water provided the title compound as the bis-trifluoroacetate salt. $^1$H NMR (400 MHz, dimethylsulfoxide-d$_6$) δ 1.80-1.89 (m, 2H), 2.90-2.98 (m, 2H), 3.34 (t, J=6.7 Hz, 2H), 3.97 (s, 1H), 5.67 (bs, 2H), 6.53 (s, 1H), 7.16 (td, J=8.6, 2.6 Hz, 1H), 7.25 (d, J=7.8 Hz, 1H), 7.32 (d, J=8.9 Hz, 1H), 7.38-7.47 (m, 2H), 7.83 (d, J=1.5 Hz, 1H), 7.88 (d, J=8.4 Hz, 1H), 8.11 (s, 1H), 8.39-8.46 (m, 2H), 9.13 (s, 1H). MS (ESI$^+$) m/z 424 (M+H)$^+$.

Example 92

N-[(trans-4-aminocyclohexyl)methyl]-5-chloro-4-[1-(3-fluorobenzyl)-1H-benzimidazol-6-yl]pyridin-2-amine The title compound was prepared as the bis-trifluoroacetate salt as described in Example 91 using tert-butyl (1r,4r)-4-(aminomethyl)cyclohexylcarbamate in place of tert-butyl 3-aminopropyl(methyl)carbamate. $^1$H NMR (400 MHz, dimethylsulfoxide-d$_6$) δ 0.93-1.10 (m, 2H), 1.18-1.34 (m, 2H), 1.45-1.58 (m, 1H), 1.79-1.87 (m, 2H), 1.89-1.98 (m, 2H), 2.90-2.99 (m, 1H), 3.10-3.19 (m, 2H), 3.97 (s, 1H), 5.69 (bs, 2H), 6.56 (s, 1H), 7.17 (td, J=8.7, 2.6 Hz, 1H), 7.27 (d, J=7.7 Hz, 1H), 7.29-7.37 (m, 1H), 7.38-7.50 (m, 2H), 7.64-7.95 (m, 5H), 8.09 (s, 1H), 9.20 (s, 1H). MS (ESI$^+$) m/z 464 (M+H)$^+$.

Example 93

N-{5-chloro-4-[1-(3-fluorobenzyl)-1H-benzimidazol-6-yl]pyridin-2-yl}-N'-methylbutane-1,4-diamine The title compound was prepared as the bis-trifluoroacetate salt as described in Example 91 using tert-butyl 4-aminobutyl(methyl)carbamate in place of tert-butyl 3-aminopropyl(methyl)carbamate. $^1$H NMR (400 MHz, dimethylsulfoxide-d$_6$) δ 1.48-1.92 (m, 4H), 2.84-2.99 (m, 2H), 3.28 (d, J=12.8 Hz, 2H), 5.67 (bs, 2H), 6.52 (s, 1H), 7.16 (td, J=8.6, 2.5 Hz, 1H), 7.25 (d, J=7.7 Hz, 1H), 7.28-7.35 (m, 1H), 7.37-7.47 (m, 2H), 7.83 (s, 1H), 7.87 (d, J=8.4 Hz, 1H), 8.09 (s, 1H), 8.23-8.50 (m, 2H), 9.12 (s, 1H). MS (ESI$^+$) m/z 438 (M+H)$^+$.

Example 94

N-benzyl-N'-{5-chloro-4-[1-(3-fluorobenzyl)-1H-benzimidazol-6-yl]pyridin-2-yl}ethane-1,2-diamine The title compound was prepared as the bis-trifluoroacetate salt as described in Example 91 using tert-butyl 2-aminoethyl(benzyl)carbamate in place of tert-butyl 3-aminopropyl(methyl)carbamate. $^1$H NMR (400 MHz, dimethylsulfoxide-d$_6$) δ 3.06-3.23 (m, 2H), 3.56-3.64 (m, 2H), 3.97 (s, 1H), 5.67 (bs, 2H), 6.55 (s, 1H), 7.00-7.35 (m, 4H), 7.33-7.56 (m, 5H), 7.80 (s, 1H), 7.88 (d, J=8.4 Hz, 1H), 8.11 (s, 1H), 8.96 (bs, 2H), 9.11 (s, 1H). MS (ESI$^+$) m/z 486 (M+H)$^+$.

Example 95

5-chloro-4-[1-(3-fluorobenzyl)-1H-benzimidazol-6-yl]-N-[2-(piperidin-4-yl)ethyl]pyridin-2-amine The title compound was prepared as the bis-trifluoroacetate salt as described in Example 91 using tert-butyl 4-(2-aminoethyl)piperidine-1-carboxylate in place of tert-butyl 3-aminopropyl(methyl)carbamate. $^1$H NMR (400 MHz, dimethylsulfoxide-d$_6$) δ 1.17-1.36 (m, 2H), 1.50 (q, J=6.9 Hz, 2H), 1.55-1.71 (m, 1H), 1.76-1.96 (m, 2H), 2.68-2.92 (m, 2H), 3.17-3.41 (m, 4H), 5.69 (s, 2H), 6.53 (s, 1H), 7.17 (td, J=8.7, 2.5 Hz, 1H), 7.26 (d, J=7.7 Hz, 1H), 7.33 (d, J=9.8 Hz, 1H), 7.38-7.48 (m, 2H), 7.81-7.90 (m, 2H), 8.10 (s, 1H), 8.25 (d, J=8.6 Hz, 1H), 8.54 (s, 1H), 9.20 (s, 1H). MS (ESI$^+$) m/z 464 (M+H)$^+$.

Example 96

5-chloro-4-[1-(3-fluorobenzyl)-1H-benzimidazol-6-yl]-N-[2-(piperidin-3-yl)ethyl]pyridin-2-amine The title compound was prepared as the bis-trifluoroacetate salt as described in Example 91 using tert-butyl 3-(2-aminoethyl)piperidine-1-carboxylate in place of tert-butyl 3-aminopropyl(methyl)carbamate. $^1$H NMR (400 MHz, dimethylsulfoxide-d$_6$) δ 1.18 (dq, J=11.8, 8.8 Hz, 1H), 1.35-1.63 (m, 4H), 1.81 (dd, J=24.0, 13.8 Hz, 2H), 2.59 (t, J=11.2 Hz, 1H), 2.68-2.81 (m, 1H), 3.09-3.40 (m, 4H), 5.68 (s, 2H), 6.53 (s, 1H), 7.17 (td, J=8.6, 2.4 Hz, 1H), 7.29 (dd, J=26.4, 8.8 Hz, 2H), 7.36-7.49 (m, 2H), 7.75-7.94 (m, 2H), 8.10 (s, 1H), 8.33 (d, J=10.4 Hz, 1H), 8.63 (d, J=10.6 Hz, 1H), 9.19 (s, 1H). MS (ESI$^+$) m/z 464 (M+H)$^+$.

Example 97

N$^2$-{5-chloro-4-[1-(3-fluorobenzyl)-1H-benzimidazol-6-yl]pyridin-2-yl}-1-phenylethane-1,2-diamine The title compound was prepared as the bis-trifluoroacetate salt as described in Example 91 using tert-butyl 2-amino-1-phenylethylcarbamate in place of tert-butyl 3-aminopropyl(methyl)carbamate. $^1$H NMR (400 MHz, dimethylsulfoxide-d$_6$) δ 3.96 (s, 2H), 4.52 (d, J=5.9 Hz, 1H), 5.64 (s, 2H), 6.54 (s, 1H), 7.08 (d, J=41.1 Hz, 1H), 7.11-7.37 (m, 4H), 7.38-7.49 (m, 4H), 7.74 (s, 1H), 7.84 (d, J=8.4 Hz, 1H), 8.15 (s, 1H), 8.38 (s, 3H), 8.95 (s, 1H). MS (ESI$^+$) m/z 472 (M+H)$^+$.

Example 98

5-chloro-4-[1-(3-fluorobenzyl)-1H-benzimidazol-6-yl]-N-(piperidin-3-yl)pyridin-2-amine The title compound was prepared as the bis-trifluoroacetate salt as described in Example 91 using tert-butyl 3-aminopiperidine-1-carboxylate in place of tert-butyl 3-aminopropyl(methyl)carbamate. $^1$H NMR (400 MHz, dimethylsulfoxide-$d_6$) δ 1.51 (dd, J=20.6, 10.2 Hz, 1H), 1.70 (d, J=11.5 Hz, 1H), 1.85-2.03 (m, 2H), 2.64-2.79 (m, 1H), 2.88 (d, J=8.8 Hz, 1H), 3.15-3.25 (m, 1H), 3.41 (d, J=10.7 Hz, 2H), 4.07 (s, 2H), 5.64 (s, 2H), 6.55 (s, 1H), 6.96 (d, J=6.9 Hz, 1H), 7.08-7.19 (m, 1H), 7.22 (d, J=7.7 Hz, 1H), 7.28 (d, J=10.0 Hz, 1H), 7.32-7.47 (m, 2H), 7.78 (s, 1H), 7.84 (d, J=8.4 Hz, 1H), 8.11 (s, 1H), 8.60 (s, 2H), 8.97 (s, 1H).). MS (ESI$^+$) m/z 436 (M+H)$^+$.

Example 99

N-[(2R)-azetidin-2-ylmethyl]-5-chloro-4-[1-(3-fluorobenzyl)-1H-benzimidazol-6-yl]pyridin-2-amine The title compound was prepared as the bis-trifluoroacetate salt as described in Example 91 using tert-butyl 2-(aminomethyl)azetidine-1-carboxylate in place of tert-butyl 3-aminopropyl(methyl)carbamate. $^1$H NMR (400 MHz, dimethylsulfoxide-$d_6$) δ 2.20-2.41 (m, 2H), 3.07-3.25 (m, 2H), 3.88-3.94 (m, 2H), 4.47 (dt, J=13.1, 6.7 Hz, 1H), 5.64 (s, 2H), 6.48 (s, 1H), 7.07-7.20 (m, 1H), 7.23 (d, J=7.7 Hz, 1H), 7.29 (d, J=9.8 Hz, 1H), 7.34-7.51 (m, 2H), 7.77 (s, 1H), 7.84 (d, J=8.4 Hz, 1H), 8.02 (s, 2H), 8.22 (s, 1H), 8.93 (d, J=13.1 Hz, 1H). MS (ESI$^+$) m/z 422 (M+H)$^+$.

Example 100

N-[2-(azetidin-2-yl)ethyl]-5-chloro-4-[1-(3-fluorobenzyl)-1H-benzimidazol-6-yl]pyridin-2-amine The title compound was prepared as the bis-trifluoroacetate salt as described in Example 91 using tert-butyl 2-(2-aminoethyl)azetidine-1-carboxylate in place of tert-butyl 3-aminopropyl(methyl)carbamate. $^1$H NMR (400 MHz, dimethylsulfoxide-$d_6$) δ 1.94-2.07 (m, 1H), 2.07-2.17 (m, 1H), 2.17-2.30 (m, 1H), 2.40-2.49 (m, 1H), 3.20-3.39 (m, 2H), 3.78 (m, J=9.4, 7.1 Hz, 1H), 3.88-3.95 (m, 1H), 4.41 (dt, J=14.3, 7.3 Hz, 2H), 5.69 (s, 2H), 6.53 (s, 1H), 7.17 (td, J=8.6, 2.5 Hz, 1H), 7.26 (d, J=7.7 Hz, 1H), 7.33 (d, J=9.9 Hz, 1H), 7.38-7.51 (m, 2H), 7.84 (s, 1H), 7.89 (d, J=8.5 Hz, 1H), 8.12 (s, 1H), 8.64 (d, J=69.6 Hz, 2H), 9.19 (s, 1H). MS (ESI$^+$) m/z 436 (M+H)$^+$.

Example 101

(4aS,8R,8aS)—N-{5-chloro-4-[1-(3-fluorobenzyl)-1H-benzimidazol-6-yl]pyridin-2-yl}decahydroisoquinolin-8-amine The title compound was prepared as the bis-trifluoroacetate salt as described in Example 91 using (4aS,8R,8aS)-tert-butyl 8-aminooctahydroisoquinoline-2(1H)-carboxylate in place of tert-butyl 3-aminopropyl(methyl)carbamate. $^1$H NMR (400 MHz, dimethylsulfoxide-$d_6$) δ 1.20-1.47 (m, 2H), 1.46-1.74 (m, 4H), 1.73-1.85 (m, 1H), 1.90-1.99 (m, 1H), 2.22-2.35 (m, 2H), 2.69-2.84 (m, 1H), 2.96-3.07 (m, 1H), 3.09-3.19 (m, 1H), 3.23-3.32 (m, 1H), 3.97 (s, 2H), 5.67 (bs, 2H), 6.57 (s, 1H), 6.83-6.98 (m, 1H), 7.16 (td, J=8.7, 2.7 Hz, 1H), 7.21-7.27 (m, 1H), 7.27-7.35 (m, 1H), 7.38-7.47 (m, 2H), 7.81-7.90 (m, 2H), 7.88-8.01 (m, 1H), 8.08 (s, 1H), 8.63-8.75 (m, 1H), 9.12 (s, 1H). MS (ESI$^+$) m/z 490 (M+H)$^+$.

Example 102

5-chloro-4-[1-(3-fluorobenzyl)-1H-benzimidazol-6-yl]-N-[2-(pyrrolidin-2-yl)ethyl]pyridin-2-amine The title compound was prepared as the bis-trifluoroacetate salt as described in Example 91 using tert-butyl 2-(2-aminoethyl)pyrrolidine-1-carboxylate in place of tert-butyl 3-aminopropyl(methyl)carbamate. $^1$H NMR (400 MHz, dimethylsulfoxide-$d_6$) δ 1.56 (dt, J=17.7, 8.6 Hz, 1H), 1.84 (dt, J=14.0, 7.0 Hz, 2H), 1.88-2.02 (m, 2H), 2.06-2.22 (m, 1H), 3.09-3.23 (m, 4H), 3.29-3.37 (m, 2H), 5.63 (s, 2H), 6.51 (s, 1H), 7.15 (dd, J=14.0, 5.6 Hz, 1H), 7.21 (d, J=7.7 Hz, 1H), 7.27 (d, J=9.7 Hz, 1H), 7.35 (d, J=8.5 Hz, 1H), 7.41 (dd, J=14.0, 7.9 Hz, 1H), 7.76 (s, 1H), 7.83 (d, J=8.4 Hz, 1H), 8.10 (s, 1H), 8.38 (s, 1H), 8.76 (d, J=24.0 Hz, 1H), 8.89 (s, 1H). MS (ESI$^+$) m/z 450 (M+H)$^+$.

Example 103

11-{5-chloro-4-[1-(3-fluorobenzyl)-1H-benzimidazol-6-yl]pyridin-2-yl}-1,8-dioxa-4,11-diazaspiro[5.6]dodecane The title compound was prepared as the bis-trifluoroacetate salt as described in Example 91 using tert-butyl 1,8-dioxa-4,11-diazaspiro[5.6]dodecane-4-carboxylate in place of tert-butyl 3-aminopropyl(methyl)carbamate. $^1$H NMR (400 MHz, dimethylsulfoxide-$d_6$) δ 3.01-3.18 (m, 4H), 3.69-3.95 (m, 8H), 4.16-4.24 (m, 1H), 5.63 (bs, 2H), 6.80 (s, 1H), 7.11-7.34 (m, 3H), 7.36-7.46 (m, 2H), 7.80 (s, 1H), 7.84 (d, J=8.3 Hz, 1H), 8.19 (s, 1H), 8.74-8.87 (m, 1H), 8.91 (bs, 1H), 8.93-9.07 (m, 1H). MS (ESI$^+$) m/z 508 (M+H)$^+$.

Example 104

N-{5-chloro-4-[1-(3-fluorobenzyl)-1H-benzimidazol-6-yl]pyridin-2-yl}-6-azaspiro[3.5]nonan-2-amine The title compound was prepared as the bis-trifluoroacetate salt as described in Example 91 using tert-butyl 2-amino-6-azaspiro[3.5]nonane-6-carboxylate in place of tert-butyl 3-aminopropyl(methyl)carbamate. $^1$H NMR (400 MHz, dimethylsulfoxide-$d_6$) δ 1.68 (s, 4H), 1.73-1.86 (m, 2H), 2.17-2.28 (m, 2H), 2.96 (s, 4H), 4.24 (s, 1H), 5.63 (s, 2H), 6.44 (s, 1H), 7.15 (t, J=8.5 Hz, 1H), 7.22 (d, J=7.9 Hz, 1H), 7.28 (d, J=9.9 Hz, 1H), 7.35 (d, J=8.4 Hz, 1H), 7.41 (dd, J=14.1, 8.0 Hz, 1H), 7.76 (s, 1H), 7.82 (d, J=8.4 Hz, 1H), 8.07 (d, J=6.6 Hz, 1H), 8.35 (s, 2H), 8.91 (s, 1H). MS (ESI$^+$) m/z 476 (M+H)$^+$.

Example 105

N-{5-chloro-4-[1-(3-fluorobenzyl)-1H-benzimidazol-6-yl]pyridin-2-yl}-7-azaspiro[3.5]nonan-2-amine The title compound was prepared as the bis-trifluoroacetate salt as described in Example 91 using tert-butyl 2-amino-7-azaspiro[3.5]nonane-7-carboxylate in place of tert-butyl 3-aminopropyl(methyl)carbamate. $^1$H NMR (400 MHz, dimethylsulfoxide-$d_6$) δ 1.58-1.81 (m, 6H), 2.20-2.38 (m, 2H), 2.99 (d, J=31.9 Hz, 4H), 4.20-4.27 (m, 2H), 5.66 (s, 2H), 6.45 (s, 1H), 7.16 (td, J=8.7, 2.5 Hz, 1H), 7.25 (d, J=7.7 Hz, 1H), 7.31 (d, J=9.8 Hz, 1H), 7.36-7.46 (m, 2H), 7.82 (s, 1H), 7.86 (d, J=8.4 Hz, 1H), 8.08 (s, 1H), 8.33 (s, 2H), 9.08 (s, 1H). MS (ESI$^+$) m/z 476 (M+H)$^+$.

Example 106

N-{5-chloro-4-[1-(3-fluorobenzyl)-1H-benzimidazol-6-yl]pyridin-2-yl}-7-azaspiro[3.5]nonan-1-amine The title compound was prepared as the bis-trifluoroacetate salt as described in Example 91 using tert-butyl 1-amino-7-azaspiro[3.5]nonane-7-carboxylate in place of tert-butyl 3-aminopropyl(methyl)carbamate. $^1$H NMR (400 MHz, dimethylsulfoxide-d$_6$) δ 1.45-1.80 (m, 5H), 1.85-2.05 (m, 2H), 2.16-2.29 (m, 1H), 2.74-2.90 (m, 1H), 2.87-3.09 (m, 2H), 3.09-3.20 (m, 1H), 4.16-4.26 (m, 1H), 5.69 (bs, 2H), 6.56 (s, 1H), 7.09-7.30 (m, 3H), 7.32 (d, J=9.0 Hz, 1H), 7.37-7.47 (m, 2H), 7.84 (d, J=1.5 Hz, 1H), 7.89 (d, J=8.4 Hz, 1H), 8.09 (s, 1H), 8.39-8.49 (m, 1H), 9.21 (s, 1H). MS (ESI$^+$) m/z 476 (M+H)$^+$.

Example 107

5-chloro-4-[1-(3-fluorobenzyl)-1H-benzimidazol-6-yl]-N-{[(2R,4S)-4-fluoropyrrolidin-2-yl]methyl}pyridin-2-amine The title compound was prepared as the bis-trifluoroacetate salt as described in Example 91 using (2R,4S)-tert-butyl 2-(aminomethyl)-4-fluoropyrrolidine-1-carboxylate in place of tert-butyl 3-aminopropyl(methyl)carbamate. $^1$H NMR (400 MHz, dimethylsulfoxide-d$_6$) δ 1.87-2.08 (m, 1H), 2.26-2.45 (m, 1H), 3.48 (d, J=22.8 Hz, 2H), 3.63 (dd, J=15.4, 10.6 Hz, 4H), 5.45 (d, J=52.7 Hz, 1H), 5.66 (s, 2H), 6.63 (s, 1H), 7.16 (td, J=8.7, 2.5 Hz, 1H), 7.23 (d, J=7.7 Hz, 2H), 7.29 (d, J=9.9 Hz, 1H), 7.36-7.45 (m, 2H), 7.78 (s, 1H), 7.86 (d, J=8.4 Hz, 1H), 8.16 (s, 1H), 9.03 (s, 1H), 9.11 (s, 1H), 9.55 (s, 1H). MS (ESI$^+$) m/z 454 (M+H)$^+$.

Example 108

5-chloro-4-[1-(3-fluorobenzyl)-1H-benzimidazol-6-yl]-N-[(4-fluoropyrrolidin-3-yl)methyl]pyridin-2-amine The title compound was prepared as the bis-trifluoroacetate salt as described in Example 91 using tert-butyl 3-(aminomethyl)-4-fluoropyrrolidine-1-carboxylate in place of tert-butyl 3-aminopropyl(methyl)carbamate. $^1$H NMR (400 MHz, dimethylsulfoxide-d$_6$) δ 2.54 (s, 1H), 2.83 (d, J=24.8 Hz, 2H), 3.09 (dd, J=11.9, 5.7 Hz, 2H), 3.96 (s, 1H), 5.27 (d, J=53.1 Hz, 1H), 5.63 (s, 2H), 6.59 (d, J=31.1 Hz, 1H), 7.14 (dd, J=19.1, 8.1 Hz, 2H), 7.21 (d, J=7.7 Hz, 1H), 7.27 (d, J=9.8 Hz, 1H), 7.31-7.46 (m, 2H), 7.78 (s, 1H), 7.83 (d, J=8.4 Hz, 1H), 8.10 (d, J=6.3 Hz, 1H), 8.89 (s, 1H), 9.17 (d, J=59.4 Hz, 2H). MS (ESI$^+$) m/z 454 (M+H)$^+$.

Example 109

N-{5-chloro-4-[1-(3-fluorobenzyl)-1H-benzimidazol-6-yl]pyridin-2-yl}-6-azaspiro[3.4]octan-2-amine The title compound was prepared as the bis-trifluoroacetate salt as described in Example 91 using tert-butyl 2-amino-6-azaspiro[3.4]octane-6-carboxylate in place of tert-butyl 3-aminopropyl(methyl)carbamate. $^1$H NMR (400 MHz, dimethylsulfoxide-d$_6$) δ 1.88-2.05 (m, 4H), 2.32-2.45 (m, 2H), 3.05-3.26 (m, 4H), 5.67 (bs, 2H), 6.47 (s, 1H), 7.16 (td, J=8.7, 2.6 Hz, 1H), 7.26 (d, J=7.7 Hz, 1H), 7.28-7.36 (m, 1H), 7.38-7.49 (m, 2H), 7.87 (d, J=8.4 Hz, 1H), 8.09 (d, J=2.4 Hz, 1H), 8.64-8.90 (m, 2H), 9.13 (s, 1H). MS (ESI$^+$) m/z 462 (M+H)$^+$.

Example 110

(3R)—N-{5-chloro-4-[1-(3-fluorobenzyl)-1H-benzotriazol-6-yl]pyridin-2-yl}piperidine-3-carboxamide Example 110A 6-bromo-1-(3-fluorobenzyl)-1H-benzo[d][1,2,3]triazole To Example 8B (245 mg, 0.830 mmol) in glacial acetic acid (5 mL) was added a solution of sodium nitrite (200 mg, 2.90 mmol) in water (0.5 mL) and the mixture was stirred at room temperature for 1 hour. The mixture was diluted with water and extracted with ethyl acetate. The organic extracts were rinsed with brine, dried over magnesium sulfate, filtered, and concentrated to provide the title compound which was used without further purification.

Example 110B (3R)—N-{5-chloro-4-[1-(3-fluorobenzyl)-1H-benzotriazol-6-yl]pyridin-2-yl}piperidine-3-carboxamide A solution of Example 14A (0.10M in dioxane, 2.6 mL, 0.26 mmol), Example 110A (80.9 mg, 0.26 mmol), [1,1'-bis(diphenylphosphino)ferrocene]dichloropalladium(II)-dichloromethane complex (14.7 mg, 0.018 mmol) and 2M aqueous sodium carbonate (0.7 mL, 1.4 mmol) in dioxane (2 mL) was flushed with nitrogen and heated at 95° C. for 24 hours. The mixture was cooled, concentrated, filtered through silica gel/diatomaceous earth with 10/90 methanol/dichloromethane and concentrated. The residue was stirred in 1:1 trifluoroacetic acid:dichloromethane (2 mL) for 24 hours, concentrated and purified by reverse phase HPLC on a Waters LC system (C18 column) using a gradient of 10:90 to 40:60 acetonitrile/0.1% trifluoroacetic acid in water. The trifluoroacetate salt obtained was dissolved in methanol and eluted from an SCX column (5 g) with 2M ammonia in methanol to provide the title compound. $^1$H NMR (400 MHz, DMSO-d$_6$) δ 1.59 (m, 3H), 1.90 (m, 1H), 2.74 (m, 3H), 2.93 (m, 1H), 3.10 (m, 1H), 6.06 (s, 2H), 7.17 (m, 2H), 7.26 (d, 1H), 7.41 (m, 1H), 7.49 (d, 1H), 8.10 (s, 1H), 8.23 (m, 2H), 8.52 (s, 1H), 11.03 (br s, 1H). MS (ESI) m/e 465.2 (M+H)$^+$.

Example 111

(3R)—N-(5-chloro-4-{1-[2-(methylsulfonyl)ethyl]-1H-benzimidazol-6-yl}pyridin-2-yl)piperidine-3-carboxamide The title compound was prepared as described in Examples 14B-E using 2-(methylsulfonyl)ethanamine in place of 2-morpholinoethanamine. $^1$H NMR (400 MHz, DMSO-d$_6$) δ 1.38 (m, 1H), 1.58 (m, 2H), 1.83 (m, 1H), 2.57 (m, 2H), 2.68 (t, 1H), 2.79 (m, 1H), 2.97 (m, 1H), 3.00 (s, 3H), 3.75 (t, 2H), 4.74 (t, 2H), 7.30 (d, 1H), 7.77 (d, 1H), 7.82 (s, 1H), 8.24 (s, 1H), 8.36 (s, 1H), 8.45 (s, 1H), 10.93 (br s, 1H). MS (ESI) m/e 462.1 (M+H)+.

Example 112

(3R)—N-(5-chloro-4-{1-[2-(methylsulfonyl)ethyl]-1H-benzotriazol-6-yl}pyridin-2-yl)piperidine-3-carboxamide The title compound was prepared as described in Examples 8A-B followed by Examples 110A-B using 2-(methylsulfonyl)ethanamine in place of (3-fluorophenyl)methanamine. $^1$H NMR (400 MHz, DMSO-$d_6$) δ 1.39 (m, 1H), 1.57 (m, 2H), 1.83 (m, 1H), 2.57 (m, 2H), 2.69 (t, 1H), 2.81 (m, 1H), 2.98 (m, 1H), 3.03 (s, 3H), 3.92 (t, 2H), 5.19 (t, 2H), 7.50 (d, 1H), 8.12 (s, 1H), 8.17 (d, 1H), 8.26 (s, 1H), 8.50 (s, 1H), 11.00 (br s, 1H). MS (ESI) m/e 463.1 (M+H)+.

Example 113

(3R)—N-{5-chloro-4-[1-(4-fluorobenzyl)-1H-benzotriazol-6-yl]pyridin-2-yl}piperidine-3-carboxamide The title compound was prepared as described in Examples 8A-B followed by Examples 110A-B using (4-fluorophenyl)methanamine in place of (3-fluorophenyl)methanamine. $^1$H NMR (400 MHz, DMSO-$d_6$) δ 1.40 (m, 1H), 1.60 (m, 2H), 1.85 (m, 1H), 2.57 (m, 1H), 2.69 (m, 1H), 2.81 (m, 1H), 2.99 (m, 2H), 6.03 (s, 2H), 7.19 (t, 2H), 7.48 (m, 3H), 8.08 (s, 1H), 8.19 (d, 1H), 8.24 (s, 1H), 8.50 (s, 1H), 11.00 (br s, 1H). MS (ESI) m/e 465.1 (M+H)+.

Example 114

(3R)—N-{5-chloro-4-[1-(3,4-difluorobenzyl)-1H-benzotriazol-6-yl]pyridin-2-yl}piperidine-3-carboxamide The title compound was prepared as described in Examples 8A-B followed by Examples 110A-B using (3,4-difluorophenyl)methanamine in place of (3-fluorophenyl)methanamine. $^1$H NMR (400 MHz, DMSO-$d_6$) δ 1.40 (m, 1H), 1.60 (m, 2H), 1.85 (m, 1H), 2.58 (m, 2H), 2.70 (m, 1H), 2.82 (m, 1H), 2.99 (m, 1H), 6.04 (s, 2H), 7.23 (m, 1H), 7.50 (m, 3H), 8.12 (s, 1H), 8.20 (d, 1H), 8.26 (s, 1H), 8.51 (s, 1H), 11.01 (br s, 1H). MS (ESI) m/e 483.1 (M+H)+.

Example 115

(3R)—N-(5-chloro-4-{1-[2-(3-fluorophenyl)ethyl]-1H-benzotriazol-6-yl}pyridin-2-yl)piperidine-3-carboxamide The title compound was prepared as described in Examples 8A-B followed by Examples 110A-B using 2-(3,4-difluorophenyl)ethanamine in place of (3-fluorophenyl)methanamine. $^1$H NMR (400 MHz, DMSO-$d_6$) δ 1.40 (m, 1H), 1.59 (m, 2H), 1.86 (m, 1H), 2.59 (m, 2H), 2.71 (t, 1H), 2.82 (m, 1H), 3.00 (m, 1H), 3.28 (t, 2H), 5.04 (t, 2H), 6.97 (m, 2H), 7.06 (m, 1H), 7.24 (q, 1H), 7.42 (d, 1H), 7.93 (s, 1H), 8.12 (d, 1H), 8.21 (s, 1H), 8.50 (s, 1H), 11.00 (br s, 1H). MS (ESI) m/e 479.1 (M+H)+.

Example 116

(3R)—N-{5-chloro-4-[1-(2-sulfamoylethyl)-1H-benzotriazol-6-yl]pyridin-2-yl}piperidine-3-carboxamide The title compound was prepared as described in Examples 8A-B followed by Examples 110A-B using 2-aminoethanesulfonamide in place of (3-fluorophenyl)methanamine. $^1$H NMR (400 MHz, DMSO-$d_6$) δ 1.62 (m, 1H), 1.77 (m, 2H), 2.02 (m, 1H), 2.73 (m, 2H), 2.94 (m, 1H), 3.08 (m, 1H), 3.74 (t, 2H), 5.12 (t, 2H), 7.46 (m, 1H), 8.08 (s, 1H), 8.19 (m, 2H), 8.54 (s, 1H), 11.05 (br s, 1H). MS (ESI) m/e 464.1 (M+H)+.

Example 117

5-chloro-4-[1-(3-fluorobenzyl)-1H-benzimidazol-6-yl]-N-{2-[4-(4-methylphenyl)piperidin-4-yl]ethyl}pyridin-2-amine The title compound was prepared as the bis-trifluoroacetate salt as described in Example 91 using tert-butyl 4-(2-aminoethyl)-4-p-tolylpiperidine-1-carboxylate in place of tert-butyl 3-aminopropyl(methyl)carbamate. $^1$H NMR (400 MHz, dimethylsulfoxide-$d_6$) δ 1.74-1.88 (m, 2H), 1.93 (t, J=10.8 Hz, 2H), 2.25 (s, 3H), 2.32 (d, J=14.3 Hz, 2H), 2.79 (d, J=8.9 Hz, 2H), 2.87 (dd, J=17.5, 9.4 Hz, 2H), 3.17 (s, 2H), 5.67 (s, 2H), 6.33 (s, 1H), 7.11-7.22 (m, 3H), 7.29 (dt, J=18.5, 10.1 Hz, 4H), 7.40 (ddd, J=11.2, 9.8, 4.7 Hz, 2H), 7.81 (s, 1H), 7.87 (d, J=8.5 Hz, 1H), 8.04 (s, 1H), 8.43 (d, J=23.8 Hz, 2H), 9.18 (s, 1H). MS (ESI+) m/z 554 (M+H)+.

Example 118

5-chloro-4-[1-(3-fluorobenzyl)-1H-benzimidazol-6-yl]-N-{2-[4-(4-methoxyphenyl)piperidin-4-yl]ethyl}pyridin-2-amine The title compound was prepared as the bis-trifluoroacetate salt as described in Example 91 using tert-butyl 4-(2-aminoethyl)-4-(4-methoxyphenyl)piperidine-1-carboxylate in place of tert-butyl 3-aminopropyl(methyl)carbamate. $^1$H NMR (400 MHz, dimethylsulfoxide-$d_6$) δ 1.76-2.10 (m, 4H), 2.24-2.37 (m, 2H), 2.66-3.06 (m, 4H), 3.15-3.23 (m, 2H), 3.72 (s, 3H), 3.97 (s, 1H), 5.67 (bs, 2H), 6.33 (s, 1H), 6.88-6.95 (m, 2H), 7.16 (td, J=8.6, 2.6 Hz, 1H), 7.23-7.36 (m, 4H), 7.35-7.48 (m, 2H), 7.81 (s, 1H), 7.87 (d, J=8.4 Hz, 1H), 8.04 (s, 1H), 8.22-8.84 (m, 2H), 9.18 (s, 1H). MS (ESI+) m/z 570 (M+H)+.

Example 119

5-chloro-4-[1-(3-fluorobenzyl)-1H-benzimidazol-6-yl]-N-[(4-fluoropiperidin-4-yl)methyl]pyridin-2-amine The title compound was prepared as the bis-trifluoroacetate salt as described in Example 91 using tert-butyl 4-(aminomethyl)-4-fluoropiperidine-1-carboxylate in place of tert-butyl 3-aminopropyl(methyl)carbamate. $^1$H NMR (400 MHz, dimethylsulfoxide-$d_6$) δ 1.71-2.06 (m, 4H), 2.91-3.09 (m, 2H), 3.23-3.33 (m, 2H), 3.60-3.71 (m, 2H), 5.68 (bs, 2H), 6.65 (s, 1H), 7.13-7.30 (m, 3H), 7.29-7.36 (m, 1H), 7.38-7.48 (m, 2H), 7.88 (d, J=8.4 Hz, 1H), 8.08 (s, 1H), 8.35-8.43 (m, 1H), 8.69-8.76 (m, 1H), 9.18 (s, 1H). MS (ESI+) m/z 468 (M+H)+.

Example 120

5-chloro-4-[1-(3-fluorobenzyl)-1H-benzimidazol-6-yl]-N-{2-[3-(4-methoxyphenyl)pyrrolidin-3-yl]ethyl}pyridin-2-amine The title compound was prepared as the bis-trifluoroacetate salt as described in Example 91 using tert-butyl 3(2-aminoethyl)-3-(4-methoxyphenyl)pyrrolidine-1-carboxylate in place of tert-butyl 3-aminopropyl(methyl)carbamate. $^1$H NMR (400 MHz, dimethylsulfoxide-$d_6$) δ 1.71-2.20 (m, 2H), 2.18-2.38 (m, 2H), 2.80-2.94 (m, 1H), 2.97-3.08 (m, 1H), 3.12-3.24 (m, 1H), 3.25-3.50 (m, 2H), 3.72 (s, 2H), 3.97 (s, 1H), 5.68 (bs, 2H), 6.38 (s, 1H), 6.88-6.94 (m, 2H), 7.16 (td, J=8.6, 2.5 Hz, 1H), 7.20-7.37 (m, 3H), 7.36-7.46 (m, 2H), 7.82 (s, 1H), 7.88 (d, J=8.4 Hz, 1H), 8.05 (s, 1H), 8.91 (dd, J=6.4, 3.2 Hz, 1H), 9.02-9.08 (m, 1H), 9.20 (s, 1H). MS (ESI$^+$) m/z 556 (M+H)$^+$.

Example 121

N-{5-chloro-4-[1-(3-fluorobenzyl)-1H-benzimidazol-6-yl]pyridin-2-yl}-6-azaspiro[3.4]octan-1-amine The title compound was prepared as the bis-trifluoroacetate salt as described in Example 91 using tert-butyl 1-amino-6-azaspiro[3.4]octane-6-carboxylate in place of tert-butyl 3-aminopropyl(methyl)carbamate. $^1$H NMR (400 MHz, dimethylsulfoxide-$d_6$) δ 1.71-2.06 (m, 4H), 2.11-2.36 (m, 2H), 3.01-3.21 (m, 4H), 3.97 (s, 12H), 4.36 (d, J=6.4 Hz, 2H), 5.66 (s, 2H), 6.57 (s, 1H), 7.09-7.33 (m, 4H), 7.41 (dt, J=12.7, 7.4 Hz, 2H), 7.79 (d, J=8.9 Hz, 1H), 7.86 (d, J=8.4 Hz, 1H), 8.08 (d, J=4.0 Hz, 1H), 8.43 (s, 1H), 8.71 (s, 1H), 9.03 (s, 1H). MS (ESI$^+$) m/z 462 (M+H)$^+$.

Example 122

(1S,4R)—N-{5-chloro-4-[1-(3-fluorobenzyl)-1H-benzimidazol-6-yl]pyridin-2-yl}-6-azaspiro[3.5]nonan-1-amine The title compound was prepared as the bis-trifluoroacetate salt as described in Example 91 using (1S,4R)-tert-butyl 1-amino-6-azaspiro[3.5]nonane-6-carboxylate in place of tert-butyl 3-aminopropyl(methyl)carbamate. $^1$H NMR (400 MHz, dimethylsulfoxide-$d_6$) δ 1.47-1.83 (m, 6H), 1.94-2.08 (m, 1H), 2.79-2.93 (m, 1H), 2.94-3.01 (m, 1H), 3.03-3.23 (m, 2H), 5.66 (bs, 2H), 6.60 (s, 1H), 7.12-7.20 (m, 1H), 7.20-7.26 (m, 1H), 7.26-7.33 (m, 2H), 7.37-7.47 (m, 2H), 7.86 (d, J=8.4 Hz, 1H), 8.11 (s, 1H), 8.15-8.34 (m, 1H), 8.59-8.75 (m, 1H), 9.05 (s, 1H). MS (ESI$^+$) m/z 476 (M+H)$^+$.

Example 123

N-{5-chloro-4-[1-(3-fluorobenzyl)-1H-benzimidazol-6-yl]pyridin-2-yl}-5-thia-2-azaspiro[3.4]octan-8-amine 5,5-dioxide The title compound was prepared as the bis-trifluoroacetate salt as described in Example 91 using tert-butyl 8-amino-5-thia-2-azaspiro[3.4]octane-2-carboxylate 5,5-dioxide in place of tert-butyl 3-aminopropyl(methyl)carbamate. $^1$H NMR (400 MHz, dimethylsulfoxide-$d_6$) δ 1.82-2.04 (m, 1H), 3.32 (ddd, J=13.4, 10.6, 7.4 Hz, 1H), 3.54 (ddd, J=13.4, 7.6, 3.8 Hz, 1H), 3.96 (s, 2H), 4.03-4.17 (m, 2H), 4.25 (d, J=3.0 Hz, 2H), 4.30 (d, J=9.4 Hz, 1H), 5.64 (bs, 2H), 6.63 (s, 1H), 7.15 (td, J=8.6, 2.7 Hz, 1H), 7.24 (d, J=7.8 Hz, 1H), 7.26-7.33 (m, 1H), 7.35-7.52 (m, 2H), 7.82 (s, 1H), 7.85 (d, J=8.4 Hz, 1H), 8.41-8.77 (m, 2H), 8.94 (s, 1H). MS (ESI$^+$) m/z 512 (M+H)$^+$.

Example 124

N-{5-chloro-4-[1-(3-fluorobenzyl)-1H-benzimidazol-6-yl]pyridin-2-yl}-9-azabicyclo[3.3.1]nonan-3-amine The title compound was prepared as the bis-trifluoroacetate salt as described in Example 91 using tert-butyl 3-amino-9-azabicyclo[3.3.1]nonane-9-carboxylate in place of tert-butyl 3-aminopropyl(methyl)carbamate. $^1$H NMR (400 MHz, dimethylsulfoxide-$d_6$) δ 1.70 (d, J=7.0 Hz, 1H), 1.74-2.06 (m, 5H), 2.17-2.35 (m, 2H), 3.70 (s, 2H), 4.67 (d, J=5.4 Hz, 2H), 5.68 (s, 2H), 6.57 (s, 1H), 6.91 (s, 1H), 7.17 (td, J=8.6, 2.3 Hz, 1H), 7.26 (d, J=7.8 Hz, 1H), 7.32 (d, J=9.8 Hz, 1H), 7.37-7.48 (m, 2H), 7.88 (d, J=8.8 Hz, 2H), 8.13 (s, 1H), 8.60 (s, 2H), 9.18 (s, 1H). MS (ESI$^+$) m/z 476 (M+H)$^+$.

Example 125

(3S)—N-{5-chloro-4-[1-(3-fluorobenzyl)-1H-benzimidazol-6-yl]pyridin-2-yl}azepan-3-amine The title compound was prepared as the bis-trifluoroacetate salt as described in Example 91 using (S)-tert-butyl 3-aminoazepane-1-carboxylate in place of tert-butyl 3-aminopropyl(methyl)carbamate. $^1$H NMR (400 MHz, dimethylsulfoxide-$d_6$) δ 1.65 (dt, J=24.5, 11.4 Hz, 2H), 1.82 (dd, J=16.6, 6.2 Hz, 3H), 1.96 (t, J=17.1 Hz, 1H), 3.11 (dt, J=14.2, 8.2 Hz, 4H), 3.33 (d, J=10.1 Hz, 1H), 4.10-4.19 (m, 1H), 5.64 (s, 2H), 6.58 (s, 1H), 6.94 (d, J=6.2 Hz, 1H), 7.15 (td, J=8.7, 2.6 Hz, 1H), 7.22 (d, J=7.7 Hz, 1H), 7.28 (d, J=9.9 Hz, 1H), 7.31-7.47 (m, 2H), 7.78 (s, 1H), 7.84 (d, J=8.4 Hz, 1H), 8.13 (s, 1H), 8.72 (s, 2H), 8.97 (s, 1H). MS (ESI$^+$) m/z 450 (M+H)$^+$.

Example 126

(3R)—N-{5-chloro-4-[1-(3-fluorobenzyl)-1H-benzimidazol-6-yl]pyridin-2-yl}azepan-3-amine The title compound was prepared as the bis-trifluoroacetate salt as described in Example 91 using (R)-tert-butyl 3-aminoazepane-1-carboxylate in place of tert-butyl 3-aminopropyl(methyl)carbamate. $^1$H NMR (400 MHz, dimethylsulfoxide-$d_6$) δ 1.46-1.70 (m, 2H), 1.70-1.91 (m, 3H), 1.92-2.05 (m, 1H), 2.95-3.21 (m, 3H), 3.33 (dd, J=13.2, 3.5 Hz, 1H), 4.19 (s, 2H), 5.66 (s, 2H), 6.58 (s, 1H), 6.96 (s, 1H), 7.16 (td, J=8.6, 2.5 Hz, 1H), 7.23 (d, J=7.7 Hz, 1H), 7.30 (d, J=9.7 Hz, 1H), 7.37-7.52 (m, 2H), 7.74-7.92 (m, 2H), 8.13 (s, 1H), 8.75 (s, 2H), 9.06 (s, 1H). MS (ESI$^+$) m/z 450 (M+H)$^+$.

Example 127

(1R,4R)—N-{5-chloro-4-[1-(3-fluorobenzyl)-1H-benzimidazol-6-yl]pyridin-2-yl}-6-azaspiro[3.5]nonan-1-amine The title compound was prepared as the bis-trifluoroacetate salt as described in Example 91 using (1R,4R)-tert-butyl 1-amino-6-azaspiro[3.5]nonane-6-carboxylate in place of tert-butyl 3-aminopropyl(methyl)carbamate. $^1$H NMR (400 MHz, dimethylsulfoxide-d$_6$) δ 1.43-1.88 (m, 4H), 1.90-2.05 (m, 2H), 2.16-2.35 (m, 1H), 2.63-2.90 (m, 2H), 3.03-3.19 (m, 1H), 3.27-3.35 (m, 1H), 3.96 (s, 1H), 4.13-4.26 (m, 1H), 5.65 (bs, 2H), 6.53 (s, 1H), 7.04-7.26 (m, 3H), 7.25-7.32 (m, 1H), 7.32-7.48 (m, 1H), 7.78 (s, 1H), 7.85 (d, J=8.4 Hz, 1H), 8.09 (s, 2H), 8.53-8.75 (m, 1H), 8.99 (bs, 1H). MS (ESI$^+$) m/z 476 (M+H)$^+$.

Example 128

N-{[3-(aminomethyl)cyclohexyl]methyl}-5-chloro-4-[1-(3-fluorobenzyl)-1H-benzimidazol-6-yl]pyridin-2-amine The title compound was prepared as the bis-trifluoroacetate salt as described in Example 91 using tert-butyl (3-(aminomethyl)cyclohexyl)methylcarbamate in place of tert-butyl 3-aminopropyl(methyl)carbamate. $^1$H NMR (400 MHz, dimethylsulfoxide-d$_6$) δ 0.65 (q, J=12.1 Hz, 1H), 0.76-0.94 (m, 2H), 1.12-1.33 (m, 1H), 1.33-1.70 (m, 2H), 1.72-1.93 (m, 4H), 2.59-2.93 (m, 2H), 3.08 (dd, J=13.2, 7.1 Hz, 1H), 3.14-3.23 (m, 1H), 3.97 (s, 1H), 5.68 (bs, 2H), 6.55 (s, 1H), 7.04-7.21 (m, 1H), 7.25 (d, J=7.7 Hz, 1H), 7.28-7.35 (m, 2H), 7.38-7.47 (m, 2H), 7.62-7.94 (m, 5H), 8.08 (s, 1H), 9.15 (s, 1H). MS (ESI$^+$) m/z 478 (M+H)$^+$.

Example 129

N-{5-chloro-4-[1-(3-fluorobenzyl)-1H-benzimidazol-6-yl]pyridin-2-yl}-2-(piperidin-4-yl)acetamide To a solution of 2-(1-(tert-butoxycarbonyl)piperidin-4-yl)acetic acid (41.4 mg, 0.170 mmol) in dichloromethane (472 μL) at 0° C., was added 1-chloro-N,N,2-trimethylpropenylamine (20.62 μL, 0.156 mmol). The mixture was stirred at ambient temperature for 30 minutes and a solution of Example 49 (50 mg, 0.142 mmol) and pyridine (12.61 μL, 0.156 mmol) in tetrahydrofuran (472 μL) and N,N-dimethylformamide (472 μL) was added and the mixture was stirred at ambient temperature overnight. The mixture was diluted with 1.5 mL methanol and purified by reverse-phase preparative HPLC (Phenomenex Luna C8(2) 100 Å AXIA column) using a gradient of 10-95% acetonitrile/0.1% trifluoroacetic acid in water to afford the BOC-protected intermediate. The crude material was dissolved in methanol, loaded on a Bond Elut® MEGA BE-SCX (5 GM) cartridge, washed with 2M ammonia solution in methanol and concentrated to give the free-base of the BOC-protected intermediate. The material was dissolved in 1:1 methanol/dichloromethane (1 mL) and 2M hydrogen chloride in diethyl ether (4 mL, 8 mmol) was added. After stirring at 50° C. for 2 hours, the mixture was cooled and concentrated to give the title compound as the tris-hydrochloride salt. $^1$H NMR (300 MHz, methanol-d$_4$) δ 9.69 (s, 1H), 8.43 (s, 1H), 8.20 (s, 1H), 8.05-7.97 (m, 2H), 7.83-7.72 (m, 1H), 7.51-7.39 (m, 1H), 7.35-7.25 (m, 2H), 7.22-7.08 (m, 1H), 5.83 (s, 2H), 3.47-3.35 (m, 2H), 3.11-2.96 (m, 2H), 2.49 (d, J=7.0, 2H), 2.29-2.12 (m, 1H), 2.10-1.96 (m, 2H), 1.64-1.44 (m, 2H). MS (ESI) m/z 478 (M+H)$^+$.

Example 130

4-({5-chloro-4-[1-(3-fluorobenzyl)-1H-benzimidazol-6-yl]pyridin-2-yl}amino)benzenesulfonamide A mixture of Example 8D (50 mg, 0.141 mmol), 4-aminobenzenesulfonamide (72.6 mg, 0.422 mmol) and cesium carbonate (68.7 mg, 0.211 mmol) in dimethylsulfoxide (281 μL) was stirred at 120° C. for 24 hours. After cooling, trifluoroacetic acid was added (100 μL). The mixture was diluted with methanol (1 mL) and purified by reverse-phase preparative HPLC (Phenomenex Luna C8(2) 100 Å AXIA column) using a gradient of 10-95% acetonitrile/0.1% trifluoroacetic acid in water to afford the title compound as the bis-trifluoroacetate salt. $^1$H NMR (400 MHz, methanol-d$_4$) δ 9.52 (s, 1H), 8.22 (d, J=2.5, 1H), 8.00-7.91 (m, 2H), 7.77 (d, J=2.5, 1H), 7.71 (dd, J=8.6, 1.4, 1H), 7.54 (t, J=1.9, 1H), 7.48-7.41 (m, 2H), 7.40-7.30 (m, 2H), 7.28-7.23 (m, 1H), 7.17-7.09 (m, 2H), 5.77 (s, 2H). MS (ESI) m/z 508 (M+H)$^+$.

Example 131

(3R)—N-(5-chloro-4-{1-[(5-fluoropyridin-3-yl)methyl]-1H-yl}pyridin-2-yl)piperidine-3-carboxamide Example 131A 6-bromo-((5-fluoropyridin-3-yl)methyl)-1H-benzo[d]imidazole The title compound was prepared as described in Examples 8A-C using 3-(2-bromoethyl)pyridine with (5-fluoropyridin-3-yl)methanamine in place of (3-fluorophenyl)methanamine. MS (ESI) m/e 307 (M+H)$^+$.

Example 131B (3R)—N-(5-chloro-4-{1-[(5-fluoropyridin-3-yl)methyl]-1H-yl}pyridin-2-yl)piperidine-3-carboxamide The title compound was prepared as the bis-hydrochloride salt as described in Example 1E using Example 131A in place of Example 1D. $^1$H NMR (400 MHz, dimethylsulfoxide-d$_6$) δ 1.62-2.13 (m, 4H) 2.79-3.36 (m, 5H) 5.76 (s, 2H) 7.46 (d, J=8.24 Hz, 1H) 7.78 (d, J=9.46 Hz, 1H) 7.87-7.93 (m, 2H) 8.11 (s, 1H) 8.45 (s, 1H) 8.51 (d, J=2.75 Hz, 1H) 8.56 (s, 1H) 8.98 (s, 1H) 9.09 (s, 1H) 10.71 (s, 1H). MS (ESI) m/e 465 (M+H)$^+$.

Example 132

(3R)—N-(5-chloro-4-{1-[(4-cyanotetrahydro-2H-pyran-4-yl)methyl]-1H-yl}pyridin-2-yl)piperidine-3-carboxamide Example 132A 4-((6-bromo-1H-benzo[d]imidazol-1-yl)methyl)tetrahydro-2H-pyran-4-carbonitrile The title compound was prepared as described in Examples 8A-C using 4-(aminomethyl)tetrahydro-2H-pyran-4-carbonitrile in place of (3-fluorophenyl)methanamine. MS (ESI) m/e 307 (M+H)$^+$.

Example 132B

The title compound was prepared as the bis-hydrochloride salt as described in Example 1E using Example 132A in place of Example 1D. $^1$H NMR (400 MHz, dimethylsulfoxide-d$_6$) δ 1.61-2.14 (m, 8H) 2.76-3.52 (m, 7H) 3.92 (dd, J=12.21, 2.44 Hz, 2H) 4.76 (s, 2H) 7.43 (d, J=8.24 Hz, 1H)

7.87 (d, J=8.24 Hz, 1H) 8.07 (s, 1H) 8.15 (s, 1H) 8.46 (s, 1H) 8.78 (s, 1H) 9.06 (s, 1H) 9.16 (s, 1H) 10.71 (s, 1H). MS (ESI) m/e 479 (M+H)$^+$.

Example 133

(3R)—N-{5-chloro-4-[1-(3-fluorobenzyl)-1H-pyrrolo[3,2-c]pyridin-6-yl]pyridin-2-yl}piperidine-3-carboxamide Example 133A 6-bromo-1-(3-fluorobenzyl)-1H-pyrrolo[3,2-c]pyridine The title compound was prepared as described in Example 33A using 6-bromo-1H-pyrrolo[3,2-c]pyridine in place of 6-bromo-1H-pyrrolo[3,2-b]pyridine. MS (ESI) m/e 306 (M+H)$^+$.

Example 133B (3R)—N-{5-chloro-4-[1-(3-fluorobenzyl)-1H-pyrrolo[3,2-c]pyridin-6-yl]pyridin-2-yl}piperidine-3-carboxamide The title compound was prepared as the bis-hydrochloride salt as described in Example 1E using Example 133A in place of Example 1D. $^1$H NMR (400 MHz, dimethylsulfoxide-d$_6$) δ 1.62-2.16 (m, 4H) 2.77-3.47 (m, 5H) 5.61 (s, 2H) 6.97 (d, J=2.75 Hz, 1H) 7.05-7.16 (m, 3H) 7.32-7.42 (m, 1H) 7.89 (d, J=3.05 Hz, 1H) 8.14 (s, 1H) 8.34 (s, 1H) 8.51 (s, 1H) 9.00 (s, 2H) 9.16 (s, 1H) 10.78 (s, 1H). MS (ESI) m/e 464 (M+H)$^+$.

Example 134

(3R)—N-{5-chloro-4-[1-(3-fluorobenzyl)-1H-pyrrolo[2,3-b]pyridin-6-yl]pyridin-2-yl}piperidine-3-carboxamide Example 134A 6-bromo-1-(3-fluorobenzyl)-1H-pyrrolo[2,3-b]pyridine The title compound was prepared as described in Example 33A using 6-bromo-1H-pyrrolo[2,3-b]pyridine in place of 6-bromo-1H-pyrrolo[3,2-b]pyridine. MS (ESI) m/e 306 (M+H)$^+$.

Example 134B (3R)—N-{5-chloro-4-[1-(3-fluorobenzyl)-1H-pyrrolo[2,3-b]pyridin-6-yl]pyridin-2-yl}piperidine-3-carboxamide The title compound was prepared as the bis-hydrochloride salt as described in Example 1E using Example 134A in place of Example 1D. $^1$H NMR (400 MHz, dimethylsulfoxide-d$_6$) δ 1.63-2.14 (m, 4H) 2.81-3.39 (m, 5H) 5.51 (s, 2H) 6.60 (d, J=3.66 Hz, 1H) 6.99-7.07 (m, 1H) 7.11 (d, J=10.07 Hz, 1H) 7.18 (d, J=7.93 Hz, 1H) 7.31-7.38 (m, 1H) 7.45 (d, J=7.93 Hz, 1H) 7.71 (d, J=3.36 Hz, 1H) 8.12 (d, J=7.93 Hz, 1H) 8.35 (s, 1H) 8.44 (s, 1H) 8.90 (s, 2H) 10.66 (s, 1H). MS (ESI) m/e 464 (M+H)$^+$.

Example 135

(3R)—N-{5-chloro-4-[5-fluoro-1-(3-fluorobenzyl)-1H-benzimidazol-6-yl]pyridin-2-yl}piperidine-3-carboxamide Example 135A 5-bromo-4-fluoro-N-(3-fluorobenzyl)-2-nitroaniline A mixture of 1-bromo-2,5-difluoro-4-nitrobenzene (950 mg, 3.99 mmol), (3-fluorophenyl)methanamine (0.797 mL, 6.99 mmol) and potassium carbonate (2.207 g, 15.97 mmol) in N,N-dimethylformamide (20 mL) was heated at 80° for 1 hour. After cooling, the mixture was diluted with diethyl ether. The mixture was washed with water and brine, dried over magnesium sulfate, filtered and concentrated to give the crude title compound which was used without further purification. MS (ESI) m/e 343 (M+H)$^+$.

Example 135B 5-bromo-4-fluoro-N$^1$-(3-fluorobenzyl)benzene-1,2-diamine

To a suspension of Example 135A (1.369 g, 3.99 mmol) in methanol (20 mL) was added hydrazine hydrate (923 mg, 18.43 mmol) followed by 50% Raney® nickel in water (400 mg, 2.334 mmol) and the mixture was heated at 50° C. for 30 minutes. After cooling, diatomaceous earth was added and the slurry was filtered through diatomaceous earth with dichloromethane and concentrated to provide the crude title compound which was used without further purification. MS (ESI) m/e 313 (M+H)$^+$.

Example 135C 6-bromo-5-fluoro-1-(3-fluorobenzyl)-1H-benzo[d]imidazole

A solution of Example 135B (1.249 g, 3.99 mmol) in formic acid (3 mL, 78 mmol) was stirred at 95° C. for 1 hour. After cooling, the mixture was concentrated and dissolved in 80 mL ethyl acetate. The mixture was washed with 10% aqueous potassium carbonate and brine, dried over magnesium sulfate, filtered and concentrated. Purification by silica gel flash chromatography (Isco®, Redi-Sep® column) eluting with a gradient of 30-100% ethyl acetate/hexane, followed by recrystallization from ethyl acetate/hexane afforded the title compound. MS (ESI) m/e 324 (M+H)$^+$.

Example 135D (3R)—N-{5-chloro-4-[5-fluoro-1-(3-fluorobenzyl)-1H-benzimidazol-6-yl]pyridin-2-yl}piperidine-3-carboxamide The title compound was prepared as the bis-hydrochloride salt as described in Example 1E using Example 135C in place of Example 1D. $^1$H NMR (400 MHz, dimethylsulfoxide-d$_6$) δ 1.60-2.12 (m, 4H) 2.80-3.35 (m, 5H) 5.58 (s, 2H) 7.04-7.14 (m, 1H) 7.17 (t, J=7.17 Hz, 2H) 7.30-7.43 (m, 1H) 7.59-7.69 (m, 2H) 8.08 (s, 1H) 8.46 (s, 1H) 8.67 (s, 1H) 8.91 (s, 1H) 8.95-9.07 (m, 1H) 10.73 (s, 1H). MS (ESI) m/e 482 (M+H)$^+$.

Example 136

(3R)—N-{5-chloro-4-[1-(3-fluorobenzyl)-1H-indazol-6-yl]pyridin-2-yl}piperidine-3-carboxamide

Example 136A 6-bromo-1-(3-fluorobenzyl)-1H-indazole

A solution of 6-bromo-1H-indazole (500 mg, 2.54 mmol) in dimethylsulfoxide (5 mL) was treated with potassium tert-butoxide (327 mg, 2.92 mmol) and stirred at room temperature for 10 minutes. 1-(Bromomethyl)-3-fluorobenzene (528 mg, 2.79 mmol) was added and the mixture was stirred overnight. The mixture was quenched with 10% hydrochloric acid and extracted with ethyl acetate. The organic extracts were rinsed with brine, dried over magnesium sulfate, filtered and concentrated. The two regioisomeric products were separated by flash chromatography on silica eluting with 15% ethyl acetate/hexane to provide the title compound as the faster eluting isomer.

Example 136B (3R)—N-{5-chloro-4-[1-(3-fluorobenzyl)-1H-indazol-6-yl]pyridin-2-yl}piperidine-3-carboxamide The title compound was prepared as described in Example 14E using Example 136A in place of Example 14D. $^1$H NMR (400 MHz, DMSO-$d_6$) δ 1.40 (m, 1H), 1.59 (m, 2H), 1.86 (m, 1H), 2.59 (m, 2H), 2.72 (m, 1H), 2.83 (m, 1H), 2.98 (m, 1H), 5.75 (s, 2H), 7.09 (t, 3H), 7.22 (d, 1H), 7.34 (q, 1H), 7.92 (m, 2H), 8.24 (m, 2H), 8.48 (s, 1H), 10.98 (br s, 1H). MS (ESI) m/e 464.1 (M+H)$^+$.

Example 137

(3R)—N-[4-(1-{2-[bis(2-hydroxyethyl)amino]ethyl}-1H-benzotriazol-6-yl)-5-chloropyridin-2-yl]piperidine-3-carboxamide The title compound was prepared as described Examples 8A-B followed by Examples 110A-B using 2,2'-((2-aminoethyl)azanediyl)diethanol in place of (3-fluorophenyl)methanamine. $^1$H NMR (400 MHz, DMSO-$d_6$) δ 1.43 (m, 1H), 1.61 (m, 2H), 1.86 (m, 1H), 2.58 (m, 5H), 2.65 (m, 1H), 2.73 (t, 1H), 2.84 (m, 1H), 3.00 (m, 1H), 3.09 (t, 2H), 3.26 (t, 4H), 4.81 (t, 2H), 7.46 (d, 1H), 8.10 (s, 1H), 8.15 (d, 1H), 8.26 (s, 1H), 8.51 (s, 1H), 11.01 (br s, 1H). MS (ESI) m/e 488.2 (M+H)$^+$.

Example 138

(3R)—N-[5-chloro-4-(2-oxo-2,3-dihydro-1H-indol-6-yl)pyridin-2-yl]piperidine-3-carboxamide The title compound was prepared as the bis-hydrochloride salt as described in Example 1E using 6-bromoindolin-2-one in place of Example 1D. $^1$H NMR (400 MHz, dimethylsulfoxide-$d_6$) δ 1.63-2.13 (m, 4H) 2.77-3.45 (m, 5H) 3.52 (s, 2H) 6.91 (s, 1H) 7.01 (dd, J=7.63, 1.53 Hz, 1H) 7.32 (d, J=7.63 Hz, 1H) 8.08 (s, 1H) 8.42 (s, 1H) 8.84 (s, 1H) 8.94 (s, 1H) 10.24 (s, 1H) 10.70 (s, 1H). MS (ESI) m/e 371 (M+H)$^+$.

Example 139

(3R)—N-(5-chloro-4-{1-[3-(dimethylamino)propyl]-1H-benzimidazol-6-yl}pyridin-2-yl)piperidine-3-carboxamide The title compound was prepared as described in Examples 14B-E using N',N'-dimethylpropane-1,3-diamine in place of 2-morpholinoethanamine. $^1$H NMR (400 MHz, DMSO-$d_6$) δ 1.41 (m, 1H), 1.59 (m, 2H), 1.85 (m, 1H), 1.93 (t, 2H), 2.10 (m, 6H), 2.16 (t, 2H), 2.55 (m, 1H), 2.61 (m, 1H), 2.71 (t, 1H), 2.82 (m, 1H), 2.98 (m, 1H), 4.32 (t, 2H), 7.30 (d, 1H), 7.76 (s, 1H), 7.78 (s, 1H), 8.25 (s, 1H), 8.32 (s, 1H), 8.46 (s, 1H), 10.94 (br s, 1H). MS (ESI) m/e 441.2 (M+H)$^+$.

Example 140

(3R)—N-(5-chloro-4-{1-[3-(dimethylamino)propyl]-1H-benzotriazol-6-yl}pyridin-2-yl)piperidine-3-carboxamide The title compound was prepared as described in Examples 8A-B followed by Examples 110A-B using N',N'-dimethylpropane-1,3-diamine in place of (3-fluorophenyl)methanamine. $^1$H NMR (400 MHz, DMSO-$d_6$) δ 1.38 (m, 1H), 1.59 (m, 2H), 1.85 (m, 1H), 2.09 (m, 8H), 2.19 (t, 2H), 2.53 (m, 1H), 2.60 (m, 1H), 2.66 (m, 1H), 2.81 (m, 1H), 2.98 (m, 1H), 4.78 (t, 2H), 7.49 (d, 1H), 8.04 (s, 1H), 8.16 (d, 1H), 8.28 (s, 1H), 8.51 (s, 1H), 11.01 (br s, 1H). MS (ESI) m/e 442.1 (M+H)$^+$.

Example 141

(3R)—N-(5-chloro-4-{1-[2-(morpholin-4-yl)ethyl]-1H-benzotriazol-6-yl}pyridin-2-yl)piperidine-3-carboxamide The title compound was prepared as described in Examples 8A-B followed by Examples 110A-B using 2-morpholinoethanamine in place of (3-fluorophenyl)methanamine. $^1$H NMR (400 MHz, DMSO-$d_6$) δ 1.39 (m, 1H), 1.60 (m 2H), 1.85 (m, 1H), 2.44 (m, 3H), 2.53 (m, 1H), 2.59 (m, 1H), 2.70 (t, 1H), 2.81 (m, 1H), 2.87 (t, 2H), 2.99 (m, 2H), 3.46 (t, 4H), 4.89 (t, 2H), 7.48 (d, 1H), 8.09 (s, 1H), 8.15 (d, 1H), 8.27 (s, 1H), 8.51 (s, 1H), 11.01 (br s, 1H). MS (ESI) m/e 470.2 (M+H)$^+$.

Example 142

(3R)—N-{5-chloro-4-[1-(3-fluorobenzyl)-2-methyl-1H-benzimidazol-6-yl]pyridin-2-yl}piperidine-3-carboxamide

Example 142A 6-bromo-1-(3-fluorobenzyl)-2-methyl-1H-benzo[d]imidazole

A solution of Example 8B (250 mg, 0.847 mmol) in glacial acetic acid (0.5 mL) was heated at 100° C. for 4 hours. The mixture was cooled, diluted with water and extracted with ethyl acetate. The organic extracts were washed with brine, dried over magnesium sulfate, filtered, concentrated and purified by flash chromatography on silica, eluting with 30% ethyl acetate/dichloromethane to provide the title compound.

Example 142B (3R)—N-{5-chloro-4-[1-(3-fluorobenzyl)-2-methyl-1H-benzimidazol-6-yl]pyridin-2-yl}piperidine-3-carboxamide The title compound was prepared as described in Example 14E using Example 142A in place of Example 14D. $^1$H NMR (400 MHz, DMSO-d$_6$) δ 1.38 (m, 1H), 1.57 (m, 2H), 1.84 (m, 1H), 3.57 (s, 3H), 2.60 (m, 1H), 2.69 (t, 1H), 2.80 (m, 1H), 2.98 (m 2H), 5.56 (s, 2H), 6.95 (d, 1H), 7.04 (d, 1H), 7.21 (t, 2H), 7.26 (d, 1H), 7.38 (q, 1H), 7.67 (s, 1H), 8.20 (s, 1H), 8.42 (s, 1H), 10.91 (br s, 1H). MS (ESI) m/e 478.1 (M+H)$^+$.

Example 143

(3R)—N-{5-chloro-4-[3-(tetrahydro-2H-pyran-4-ylmethyl)-3H-imidazo[4,5-b]pyridin-5-yl]pyridin-2-yl}piperidine-3-carboxamide

Example 143A 6-chloro-3-nitro-N-((tetrahydro-2H-pyran-4-yl)methyl)pyridin-2-amine A mixture of 2,6-dichloro-3-nitropyridine (1 g, 5.18 mmol)), (tetrahydro-2H-pyran-4-yl)methanamine (1.044 g, 9.07 mmol) and triethylamine (2.167 mL, 15.55 mmol) in tetrahydrofuran (22.83 mL) was stirred at 0° C. for 30 minutes and at ambient temperature for 2 hours. Methanol (10 mL) was added, followed by silica gel and the mixture was concentrated and purified by silica gel flash chromatography (Isco®, Redi-Sep® column) eluting with a gradient of 30% ethyl acetate/hexane to afford the title compound. MS (ESI) m/z 272 (M+H)$^+$.

Example 143B 6-chloro-N$^2$-((tetrahydro-2H-pyran-4-yl)methyl)pyridine-2,3-diamine A solution of Example 143A (1.057 g, 3.89 mmol) in tetrahydrofuran (1 mL) was added to 50% Raney nickel in water (335.5 mg, 5.72 mmol) in a 20 mL pressure bottle and the mixture was stirred under 60 psi of hydrogen at room temperature for 13 hours. The mixture was filtered and concentrated to provide the crude title compound which was used without further purification.

Example 143C 5-chloro-3-((tetrahydro-2H-pyran-4-yl)methyl)-3H-imidazo[4,5-b]pyridine A solution of the crude product of Example 143B (0.979 g, 4.05 mmol) in formic acid (2 mL, 52.1 mmol) was heated at 95° C. for 1 hour. The mixture was cooled, concentrated and dissolved in 50 mL ethyl acetate. The mixture was washed with dilute potassium carbonate and brine, dried over magnesium sulfate, filtered and concentrated. Recrystallization from ethyl acetate/hexane afforded the title compound. MS (ESI) m/z 252 (M+H)$^+$.

Example 143D (3R)—N-{5-chloro-4-[3-(tetrahydro-2H-pyran-4-ylmethyl)-3H-imidazo[4,5-b]pyridin-5-yl]pyridin-2-yl}piperidine-3-carboxamide A mixture of Example 1B (150 mg, 0.358 mmol), 4,4,4',4',5,5,5',5'-octamethyl-2,2'-bi(1,3,2-dioxaborolane) (91 mg, 0.358 mmol), 1,1'-bis(diphenylphosphino)ferrocene-palladium(II)dichloride-dichloromethane complex (17.55 mg, 0.021 mmol) and potassium acetate (105 mg, 1.075 mmol) in dioxane (1.791 mL) was flushed with nitrogen and stirred at 100° C. for 3 hours. A solution of Example 143C (90 mg, 0.358 mmol) in dioxane (0.5 mL) was added, followed by 1,1'-bis(diphenylphosphino)ferrocene-palladium(II)dichloride-dichloromethane complex (17.55 mg, 0.021 mmol) and 2M aqueous sodium carbonate (985 μL, 1.970 mmol). The mixture was stirred at 100° C. for 3 hours, cooled and filtered through diatomaceous earth with ethyl acetate. Purification by silica gel flash chromatography (Isco®, Redi-Sep® column) eluting with a gradient of 50-100% ethyl acetate/hexane followed by 10% 2:1 methanol/water in ethyl acetate, afforded the BOC-protected intermediate. The material was further purified by reverse-phase preparative HPLC (Phenomenex Luna C8(2) 100 Å AXIA column) using a gradient of 10-95% acetonitrile/0.1% trifluoroacetic acid in water. A solution of this intermediate in dichloromethane (2 mL) and trifluoroacetic acid (2 mL) was stirred at ambient temperature for 15 minutes, concentrated, dissolved in methanol (2 mL) and loaded on a Bond Elut® MEGA BE-SCX (5 GM, prewashed with 50% methanol/dichloromethane) cartridge. The cartridge was washed with 2M ammonia in methanol and concentrated to give the title compound as the free base. $^1$H NMR (300 MHz, dimethylsulfoxide-d$_6$) δ 11.04 (s, 1H), 8.80 (s, 3H), 8.55 (s, 1H), 8.41 (s, 1H), 8.30 (d, J=8.3, 1H), 7.68 (d, J=8.3, 1H), 4.25 (d, J=7.2, 2H), 3.89-3.79 (m, 2H), 3.36-3.13 (m, 4H), 3.12-2.83 (m, 3H), 2.39-2.18 (m, 1H), 2.12-2.00 (m, 1H), 1.87-1.56 (m, 3H), 1.50-1.19 (m, 4H). MS (ESI) m/z 455 (M+H)$^+$.

Example 144

(3R)—N-(5-chloro-4-{1-[(1R)-1-(3-fluorophenyl)ethyl]-1H-benzimidazol-6-yl}pyridin-2-yl)piperidine-3-carboxamide The title compound was prepared as described in Examples 14B-E using (R)-1-(3-fluorophenyl)ethanamine in place of 2-morpholinoethanamine. $^1$H NMR (400 MHz, DMSO-d$_6$) δ 1.39 (m, 1H), 1.59 (m, 2H), 1.84 (m, 1H), 1.98 (d, 3H), 2.56 (m, 2H), 2.69 (t, 1H), 2.80 (m, 1H), 2.96 (m, 1H), 5.95 (q, 1H), 7.10 (m, 1H), 7.18 (d, 1H), 7.27 (m, 2H), 7.38 (m, 1H), 7.65 (s, 1H), 7.78 (d, 1H), 8.18 (s, 1H), 8.42 (s, 1H), 8.71 (s, 1H), 10.91 (br s, 1H). MS (ESI) m/e 478.1 (M+H)$^+$.

Example 145

(3R)—N-(5-chloro-4-{1-[(1R)-1-(3-fluorophenyl)ethyl]-1H-benzotriazol-6-yl}pyridin-2-yl)piperidine-3-carboxamide The title compound was prepared as described in Examples 8A-B followed by Examples 110A-B using (R)-

1-(3-fluorophenyl)ethanamine in place of (3-fluorophenyl) methanamine. $^1$H NMR (400 MHz, DMSO-$d_6$) δ 1.39 (m, 1H), 1.59 (m, 2H), 1.84 (m, 1H), 2.10 (d, 3H), 2.53 (m, 1H), 2.59 (m, 1H), 2.69 (t, 1H), 2.80 (m, 1H), 2.97 (m, 1H), 6.45 (q, 1H), 7.13 (m, 1H), 7.21 (d, 1H), 7.40 (m, 3H), 7.99 (s, 1H), 8.20 (m, 2H), 8.48 (s, 1H), 11.00 (br s, 1H). MS (ESI) m/e 479.1 (M+H)$^+$.

Example 146

(3R)—N-{5-chloro-4-[3-(3-fluorobenzyl)-2-oxo-2,3-dihydro-1H-benzimidazol-5-yl]pyridin-2-yl}piperidine-3-carboxamide Example 146A 6-bromo-1-(3-fluorobenzyl)-1H-benzo[d]imidazol-2 (3H)-one A solution of Example 8B (375 mg, 1.271 mmol) in tetrahydrofuran (6 mL) was treated with carbonyl diimidazole (206 mg, 1.271 mmol) and stirred at room temperature overnight. The mixture was concentrated and purified by flash chromatography on silica, eluting with 40% ethyl acetate/hexane to provide the title compound.

Example 146B (3R)—N-{5-chloro-4-[3-(3-fluorobenzyl)-2-oxo-2,3-dihydro-1H-benzimidazol-5-yl]pyridin-2-yl}piperidine-3-carboxamide The title compound was prepared as described in Example 14E using Example 146A in place of Example 14D. $^1$H NMR (400 MHz, DMSO-$d_6$) δ 1.39 (m, 1H), 1.58 (m, 2H), 1.83 (m, 1H), 2.56 (m, 2H), 2.69 (t, 1H), 2.81 (m, 1H), 2.98 (m, 1H), 5.07 (s, 2H), 7.15 (m, 5H), 7.26 (s, 1H), 7.38 (q, 1H), 8.16 (s, 1H), 8.40 (s, 1H), 10.89 (br s, 1H). MS (ESI) m/e 480.1 (M+H)$^+$.

Example 147

(3R)—N-{5-chloro-4-[5-chloro-1-(tetrahydro-2H-pyran-4-ylmethyl)-1H-benzimidazol-6-yl]pyridin-2-yl}piperidine-3-carboxamide Example 147A 5 5-bromo-4-chloro-2-nitro-N-((tetrahydro-2H-pyran-4-yl)methyl)aniline A solution of 1-bromo-2-chloro-5-fluoro-4-nitrobenzene (800 mg, 3.14 mmol) and (tetrahydro-2H-pyran-4-yl)methanamine (362 mg, 3.14 mmol) in N,N-dimethylformamide (7 mL) was treated with potassium carbonate (1.738 g, 12.58 mmol) and stirred at room temperature for 30 minutes and at 55° C. for 2 hours. The mixture was partitioned between ethyl acetate and brine and the aqueous layer was extracted with ethyl acetate. The combined extracts were washed with brine, dried over magnesium sulfate and concentrated to provide the title compound which was used without further purification.

Example 147B 5-bromo-4-chloro-N$^1$-((tetrahydro-2H-pyran-4-yl)methyl)benzene-1,2-diamine To a suspension of Example 147A in methanol (25 mL) and hydrazine monohydrate (0.412 mL, 8.49 mmol)) was added 50% Raney® nickel in water (104 mg, 0.364 mmol). After stirring at room temperature for 1 hour, the mixture was filtered and concentrated to give the crude title compound which was used without further purification.

Example 147C 6-bromo-5-chloro-1-((tetrahydro-2H-pyran-4-yl) methyl)-1H-benzo[d]imidazole To the crude product of Example 147B was added formic acid (3.66 mL, 97 mmol) and the mixture was heated at 95° C. for 16 hours. The mixture was partitioned between ethyl acetate and saturated aqueous sodium bicarbonate and the aqueous layer was extracted with ethyl acetate. The combined extracts were washed with brine, dried over magnesium sulfate, filtered and concentrated to give the crude title compound which was used without further purification. MS (ESI) m/e 330 (M+H)$^+$.

Example 147D (3R)—N-{5-chloro-4-[5-chloro-1-(tetrahydro-2H-pyran-4-ylmethyl)-1H-benzimidazol-6-yl]pyridin-2-yl}piperidine-3-carboxamide The title compound was prepared as the bis-hydrochloride salt as described in Example 1E using Example 147C in place of Example 1D. $^1$H NMR (400 MHz, dimethylsulfoxide-$d_6$) δ 1.20-2.20 (m, 9H) 2.73-3.89 (m, 9H) 4.21 (d, J=7.02 Hz, 2H) 7.79 (s, 1H) 7.90 (s, 1H) 8.08 (s, 1H) 8.49 (s, 1H) 8.55 (s, 1H) 9.01 (s, 1H) 9.14 (s, 1H) 10.77 (s, 1H). MS (ESI) m/e 488 (M+H)$^+$.

Example 148

N-(5-chloro-4-{1-[(5-methylpyrazin-2-yl)methyl]-2,3-dihydro-1H-indol-6-yl}pyridin-2-yl)piperidine-3-carboxamide To a solution of the BOC-protected intermediate from Example 2 (32 mg, 0.07 mmol) in 1/1 dichloromethane/methanol (1 mL) was added a solution of 5-methylpyrazine-2-carbaldehyde (11 mg, 0.09 mmol) in 1/1 dichloromethane/methanol (0.3 mL), followed by acetic acid (20 µL, 0.35 mmol) and the mixture was stirred at 50° C. for 15 minutes. MP-cyanoborohydride resin (327 mg, 0.07 mmol) was added and the mixture was shaken at 50° C. overnight, filtered and concentrated. To the residue was added 4M hydrogen chloride in dioxane (2 mL) and the mixture was shaken at 50° C. for 2 hours. The mixture was concentrated, dissolved in 1:1 dimethylsulfoxide/methanol and purified by preparative HPLC (Phenomenex Luna C8(2) 5 µm 100 Å AXIA column) eluting with a gradient of 5-100% acetonitrile/0.1% trifluoroacetic acid in water to afford the title compound as the trifluoroacetate salt. $^1$H NMR (400 MHz, pyridine-d5) δ 12.04 (s, 1H) 8.74 (s, 1H) 8.69 (s, 1H) 8.49-8.51 (m, 1H) 8.46 (s, 1H) 7.18 (d, J=7.32 Hz, 1H) 6.91-6.96 (m, 2H) 4.53 (s, 2H) 3.91-4.03 (m, J=8.55 Hz, 1H) 3.63-3.71 (m, J=8.70, 8.70 Hz, 2H) 3.61 (s, 1H) 3.53-3.60 (m, 1H) 3.47 (t, J=8.39 Hz, 2H) 3.07-3.16 (m, 1H) 2.92 (t, J=8.54 Hz, 2H) 2.44 (s, 3H) 2.19-2.27 (m, J=2.44 Hz, 1H) 1.87-2.11 (m, J=28.08 Hz, 2H) 1.76-1.86 (m, J=14.34 Hz, 1H). MS (ESI) m/z 463 (M+H)$^+$.

Example 149

N-[5-chloro-4-(1-{4-[(methylsulfonyl)amino]benzyl}-2,3-dihydro-1H-indol-6-yl)pyridin-2-yl]piperidine-3-carboxamide The title compound was prepared as the trifluoroacetate salt as described in Example 148, using N-(4-formylphenyl)methanesulfonamide in place of 5-methylpyrazine-2-carbaldehyde. $^1$H NMR (400 MHz, pyridine-$d_5$) δ 12.06 (s, 1H) 8.49-8.54 (m, 1H) 7.64-7.70 (m, 2H) 7.48 (d, J=8.54 Hz, 2H) 6.96 (d, J=8.85 Hz, 1H) 6.90 (s, 1H) 4.31 (s, 2H) 3.88-4.02 (m, 1H) 3.64-3.74 (m, J=9.46 Hz, 2H) 3.53-3.63 (m, 2H) 3.27-3.34 (m, 2H) 3.19 (s, 3H) 3.05-3.17 (m, 1H) 2.90 (t, J=8.39 Hz, 2H) 2.22 (s, 1H) 1.90-2.12 (m, J=14.95 Hz, 2H) 1.75-1.85 (m, 1H). MS (ESI) m/z 540 (M+H)$^+$.

Example 150

N-(5-chloro-4-{1-[4-fluoro-3-(methylsulfonyl)benzyl]-2,3-dihydro-1H-indol-6-yl}pyridin-2-yl)piperidine-3-carboxamide The title compound was prepared as the trifluoroacetate salt as described in Example 148, using 4-fluoro-3-(methylsulfonyl)benzaldehyde in place of 5-methylpyrazine-2-carbaldehyde. $^1$H NMR (400 MHz, pyridine-$d_5$) δ 12.06 (s, 1H) 8.68 (s, 1H) 8.52 (s, 1H) 8.22 (dd, J=6.71, 2.14 Hz, 1H) 7.63-7.70 (m, 1H) 7.28-7.35 (m, 1H) 7.19 (d, J=7.63 Hz, 1H) 6.98 (d, J=7.32 Hz, 1H) 6.82 (s, 1H) 4.28 (s, 2H) 3.92-4.02 (m, J=8.85 Hz, 1H) 3.63-3.72 (m, J=8.85 Hz, 2H) 3.56-3.63 (m, 2H) 3.43-3.47 (m, 3H) 3.22 (t, J=8.24 Hz, 2H) 3.05-3.17 (m, 1H) 2.87 (t, J=8.24 Hz, 2H) 2.19-2.27 (m, J=13.12 Hz, 1H) 1.89-2.11 (m, 2H) 1.75-1.85 (m, J=10.38, 3.36 Hz, 1H). MS (ESI) m/z 543 (M+H)$^+$.

Example 151

N-(5-chloro-4-{1-[(2-methylpyrimidin-5-yl)methyl]-2,3-dihydro-1H-indol-6-yl}pyridin-2-yl)piperidine-3-carboxamide The title compound was prepared as the trifluoroacetate salt as described in Example 148, using 2-methylpyrimidine-5-carbaldehyde in place of 5-methylpyrazine-2-carbaldehyde. $^1$H NMR (400 MHz, pyridine-$d_5$) δ 12.07 (s, 1H) 8.82 (s, 1H) 8.71 (s, 1H) 8.52 (s, 1H) 7.18 (s, 1H) 6.94-7.04 (m, 2H) 6.93 (s, 1H) 4.27 (s, 2H) 3.94-4.01 (m, 1H) 3.63-3.69 (m, 2H) 3.56-3.63 (m, 2H) 3.23 (t, J=8.24 Hz, 2H) 3.05-3.15 (m, 1H) 2.87 (t, J=8.24 Hz, 2H) 2.79 (s, 3H) 2.22 (s, 1H) 1.89-2.07 (m, 2H) 1.76-1.85 (m, 1H). MS (ESI) m/z 463 (M+H)$^+$.

Example 152

N-(5-chloro-4-{1-[3-(methylsulfonyl)benzyl]-2,3-dihydro-1H-indol-6-yl}pyridin-2-yl)piperidine-3-carboxamide The title compound was prepared as the trifluoroacetate salt as described in Example 148, using 3-(methylsulfonyl)benzaldehyde in place of 5-methylpyrazine-2-carbaldehyde. $^1$H NMR (400 MHz, pyridine-$d_5$) δ 12.06 (s, 1H) 8.68 (s, 1H) 8.52 (s, 1H) 8.29 (s, 1H) 8.08 (d, J=7.93 Hz, 1H) 7.64-7.70 (m, 1H) 7.50-7.56 (m, 1H) 7.19 (d, J=7.63 Hz, 1H) 6.94-6.99 (m, J=7.32, 1.22 Hz, 1H) 6.82 (s, 1H) 4.33 (s, 2H) 3.91-4.02 (m, J=8.54 Hz, 1H) 3.64-3.74 (m, 2H) 3.54-3.63 (m, 2H) 3.28-3.31 (m, 3H) 3.18-3.27 (m, 2H) 3.06-3.16 (m, 1H) 2.86 (t, J=8.24 Hz, 2H) 2.19-2.28 (m, 1H) 1.87-2.13 (m, 2H) 1.75-1.85 (m, 1H). MS (ESI) m/z 525 (M+H)$^+$.

Example 153

N-(5-chloro-4-{1-[(6-methylpyridin-3-yl)methyl]-2,3-dihydro-1H-indol-6-yl}pyridin-2-yl)piperidine-3-carboxamide The title compound was prepared as the trifluoroacetate salt as described in Example 148, using 6-methylnicotinaldehyde in place of 5-methylpyrazine-2-carbaldehyde. $^1$H NMR (400 MHz, pyridine-$d_5$) δ 12.06 (s, 1H) 8.69-8.70 (m, 1H) 8.53 (s, 1H) 7.41 (s, 1H) 7.18 (s, 1H) 7.11-7.15 (m, J=7.63 Hz, 1H) 7.01 (s, 1H) 6.93-6.98 (m, J=7.63 Hz, 1H) 6.91 (s, 1H) 4.26 (s, 2H) 3.92-4.00 (m, 1H) 3.62-3.71 (m, 2H) 3.57-3.62 (m, 2H) 3.23 (t, J=8.24 Hz, 2H) 3.05-3.16 (m, 1H) 2.82-2.91 (m, 2H) 2.50-2.56 (m, 3H) 2.17-2.27 (m, 1H) 1.90-2.09 (m, 2H) 1.77-1.87 (m, 1H). MS (ESI) m/z 462 (M+H)$^+$.

Example 154

N-{5-chloro-4-[1-(pyrrolidin-3-ylmethyl)-2,3-dihydro-1H-indol-6-yl]pyridin-2-yl}piperidine-3-carboxamide The title compound was prepared as the trifluoroacetate salt as described in Example 148, using tert-butyl 3-formylpyrrolidine-1-carboxylate in place of 5-methylpyrazine-2-carbaldehyde. $^1$H NMR (400 MHz, pyridine-$d_5$) δ 12.07 (s, 1H) 8.67 (s, 1H) 8.54 (s, 1H) 7.17 (d, J=7.63 Hz, 1H) 6.94 (d, J=7.32 Hz, 1H) 6.77 (s, 1H) 3.89-4.01 (m, J=7.93 Hz, 1H) 3.71-3.81 (m, J=11.29, 7.63 Hz, 1H) 3.64-3.70 (m, 2H) 3.57-3.63 (m, 2H) 3.43-3.55 (m, 2H) 3.09-3.37 (m, 5H) 2.86 (t, J=8.54 Hz, 2H) 2.75-2.83 (m, 1H) 2.20-2.28 (m, 1H) 2.10-2.19 (m, 1H) 1.90-2.08 (m, 2H) 1.77-1.89 (m, 2H). MS (ESI) m/z 440 (M+H)$^+$.

Example 155

4-[(6-{5-chloro-2-[(piperidin-3-ylcarbonyl)amino]pyridin-4-yl}-2,3-dihydro-1H-indol-1-yl)methyl]benzoic acid The title compound was prepared as the trifluoroacetate salt as described in Example 148, using 4-formylbenzoic acid in place of 5-methylpyrazine-2-carbaldehyde. $^1$H NMR (400 MHz, pyridine-$d_5$) δ 12.05 (s, 1H) 8.71 (s, 1H) 8.51 (s, 1H) 8.45 (d, J=8.24 Hz, 2H) 7.53-7.56 (m, 2H) 7.20 (s, 1H) 6.95-6.99 (m, 1H) 6.86 (s, 1H) 4.35 (s, 2H) 3.92-4.02 (m, J=8.24 Hz, 1H) 3.63-3.73 (m, 2H) 3.57-3.64 (m, 2H) 3.23-3.35 (m, 2H) 3.04-3.17 (m, 1H) 2.92 (t, J=8.39 Hz, 2H) 2.20-2.26 (m, 1H) 1.88-2.11 (m, 2H) 1.73-1.84 (m, 1H). MS (ESI) m/z 491 (M+H)$^+$.

Example 156

N-(5-chloro-4-{1-[4-(methylsulfonyl)benzyl]-2,3-dihydro-1H-indol-6-yl}pyridin-2-yl)piperidine-3-carboxamide The title compound was prepared as the trifluoroacetate salt as described in Example 148, using 4-(methylsulfonyl)benzaldehyde in place of 5-methylpyrazine-2-carbaldehyde. $^1$H NMR (400 MHz, pyridine-$d_5$) δ 12.06 (s, 1H) 8.68 (s, 1H) 8.47-8.56 (m, 1H) 8.15 (d, J=8.24 Hz, 2H) 7.60 (s, 1H) 6.99 (d, J=7.63 Hz, 1H) 6.80 (s, 1H) 4.35 (s, 2H) 3.92-4.03 (m, J=8.24 Hz, 1H) 3.64-3.74 (m, 3H) 3.55-3.64 (m, 3H) 3.28 (s, 3H) 3.05-3.17 (m, 1H) 2.93 (t, J=8.24 Hz, 2H) 2.17-2.27 (m, 1H) 1.90-2.12 (m, 2H) 1.75-1.85 (m, 1H). MS (ESI) m/z 525 (M+H)$^+$.

Example 157 methyl 4-[(6-{5-chloro-2-[(piperidin-3-ylcarbonyl) amino]pyridin-4-yl}-2,3-dihydro-1H-indol-1-yl) methyl]benzoate The title compound was prepared as the trifluoroacetate salt as described in Example 148, using methyl 4-formylbenzoate in place of 5-methylpyrazine-2-carbaldehyde. $^1$H NMR (400 MHz, pyridine-d$_5$) δ 12.05 (s, 1H) 8.70 (s, 1H) 8.50-8.52 (m, 1H) 8.14-8.19 (m, 2H) 7.51 (d, J=8.24 Hz, 2H) 6.97 (d, J=7.02 Hz, 1H) 6.83 (s, 1H) 4.33 (s, 2H) 3.91-4.03 (m, 1H) 3.79-3.86 (m, 3H) 3.63-3.71 (m, J=8.39, 8.39 Hz, 2H) 3.55-3.63 (m, 2H) 3.29 (t, J=8.24 Hz, 2H) 3.04-3.17 (m, 1H) 2.92 (t, J=8.39 Hz, 2H) 2.23 (d, J=11.60 Hz, 1H) 1.87-2.11 (m, J=27.47 Hz, 2H) 1.73-1.85 (m, J=14.34 Hz, 1H). MS (ESI) m/z 505 (M+H)$^+$.

Example 158

N-{5-chloro-4-[1-(pyrimidin-5-ylmethyl)-2,3-dihydro-1H-indol-6-yl]pyridin-2-yl}piperidine-3-carboxamide The title compound was prepared as the trifluoroacetate salt as described in Example 148, using pyrimidine-5-carbaldehyde in place of 5-methylpyrazine-2-carbaldehyde. $^1$H NMR (400 MHz, pyridine-d$_5$) δ 12.07 (s, 1H) 9.42 (s, 1H) 8.93 (s, 2H) 8.70 (s, 1H) 8.48-8.54 (m, 1H) 7.19 (s, 1H) 6.93-6.99 (m, J=7.32, 1.22 Hz, 1H) 6.91 (s, 1H) 4.30 (s, 2H) 3.88-4.03 (m, 1H) 3.62-3.73 (m, J=8.54 Hz, 2H) 3.53-3.63 (m, 2H) 3.23 (t, J=8.39 Hz, 2H) 3.05-3.17 (m, 1H) 2.88 (t, J=8.39 Hz, 2H) 2.17-2.31 (m, 1H) 1.98 (s, 2H) 1.71-1.85 (m, J=13.73 Hz, 1H). MS (ESI) m/z 449 (M+H)$^+$.

Example 159

N-[5-chloro-4-(1-{[6-(trifluoromethyl)pyridin-2-yl] methyl}-2,3-dihydro-1H-indol-6-yl)pyridin-2-yl] piperidine-3-carboxamide The title compound was prepared as the trifluoroacetate salt as described in Example 148, using 6-(trifluoromethyl) picolinaldehyde in place of 5-methylpyrazine-2-carbaldehyde. $^1$H NMR (400 MHz, pyridine-d$_5$) δ 12.04 (s, 1H) 8.67 (s, 1H) 8.50 (s, 1H) 7.84 (t, J=7.78 Hz, 1H) 7.61-7.65 (m, 2H) 7.19 (s, 1H) 6.94-6.99 (m, 1H) 6.81 (s, 1H) 4.56 (s, 2H) 3.91-4.02 (m, J=7.93 Hz, 1H) 3.63-3.70 (m, J=7.93 Hz, 2H) 3.53-3.62 (m, 2H) 3.44 (t, J=8.39 Hz, 2H) 3.05-3.18 (m, 1H) 2.95 (t, J=8.54 Hz, 2H) 2.17-2.28 (m, 1H) 1.88-2.10 (m, J=42.11 Hz, 2H) 1.75-1.87 (m, 1H). MS (ESI) m/z 516 (M+H)$^+$.

Example 160

N-{5-chloro-4-[1-(quinolin-6-ylmethyl)-2,3-dihydro-1H-indol-6-yl]pyridin-2-yl}piperidine-3-carboxamide The title compound was prepared as the trifluoroacetate salt as described in Example 148, using quinoline-6-carbaldehyde in place of 5-methylpyrazine-2-carbaldehyde. $^1$H NMR (400 MHz, pyridine-d$_5$) δ 12.04 (s, 1H) 9.02 (dd, J=4.12, 1.68 Hz, 1H) 8.71 (s, 1H) 8.50 (s, 1H) 8.33 (d, J=8.55 Hz, 1H) 8.20 (d, J=8.24 Hz, 1H) 7.92 (s, 1H) 7.80 (dd, J=8.70, 1.68 Hz, 1H) 7.37 (dd, J=8.24, 3.97 Hz, 1H) 6.98 (d, J=7.32 Hz, 1H) 6.93 (s, 1H) 4.47 (s, 2H) 3.93-4.00 (m, J=7.93 Hz, 1H) 3.64-3.72 (m, J=8.70, 8.70 Hz, 2H) 3.57-3.62 (m, 3H) 3.33 (t, J=8.39 Hz, 2H) 3.04-3.18 (m, 1H) 2.93 (t, J=8.24 Hz, 2H) 2.19-2.28 (m, 1H) 1.87-2.10 (m, 2H) 1.75-1.85 (m, J=10.22, 3.81 Hz, 1H). MS (ESI) m/z 498 (M+H)$^+$.

Example 161

N-{4-[1-(1H-benzimidazol-2-ylmethyl)-2,3-dihydro-1H-indol-6-yl]-5-chloropyridin-2-yl}piperidine-3-carboxamide The title compound was prepared as the trifluoroacetate salt as described in Example 148, using 1H-benzo[d]imidazole-2-carbaldehyde in place of 5-methylpyrazine-2-carbaldehyde. $^1$H NMR (400 MHz, pyridine-d$_5$) δ 12.02 (s, 1H) 8.61 (s, 1H) 8.46 (s, 1H) 7.79-7.87 (m, 2H) 7.28-7.34 (m, 2H) 7.10 (d, J=7.63 Hz, 1H) 6.87-6.95 (m, 2H) 4.79 (s, 2H) 3.93-4.04 (m, J=7.93, 7.93 Hz, 1H) 3.64-3.74 (m, 2H) 3.58-3.64 (m, 2H) 3.47 (t, J=8.39 Hz, 2H) 3.05-3.20 (m, 1H) 2.77 (t, J=8.24 Hz, 2H) 2.18-2.31 (m, J=14.95 Hz, 1H) 1.89-2.10 (m, 2H) 1.77-1.85 (m, 1H). MS (ESI) m/z 487 (M+H)$^+$.

Example 162

N-{5-chloro-4-[1-(2,3-dihydro-1,4-benzodioxin-5-ylmethyl)-2,3-dihydro-1H-indol-6-yl]pyridin-2-yl}piperidine-3-carboxamide The title compound was prepared as the trifluoroacetate salt as described in Example 148, using 2,3-dihydrobenzo[b][1,4]dioxine-5-carbaldehyde in place of 5-methylpyrazine-2-carbaldehyde. $^1$H NMR (400 MHz, pyridine-d$_5$) δ 12.04 (s, 1H) 8.52 (s, 1H) 7.18 (d, J=7.63 Hz, 1H) 7.06 (d, J=7.32 Hz, 1H) 6.99-7.02 (m, 1H) 6.96-6.98 (m, J=1.53 Hz, 1H) 6.91-6.95 (m, 2H) 6.87-6.90 (m, 1H) 4.39 (s, 2H) 4.09-4.25 (m, 4H) 3.90-4.00 (m, J=8.85 Hz, 1H) 3.52-3.71 (m, 4H) 3.40 (t, J=8.39 Hz, 2H) 3.04-3.17 (m, 1H) 2.90 (t, J=8.24 Hz, 2H) 2.21 (s, 1H) 1.89-2.11 (m, 2H) 1.75-1.85 (m, 1H). MS (ESI) m/z 505 (M+H)$^+$.

Example 163

N-(5-chloro-4-{1-[(1-methyl-1H-benzimidazol-2-yl) methyl]-2,3-dihydro-1H-indol-6-yl}pyridin-2-yl) piperidine-3-carboxamide The title compound was prepared as the trifluoroacetate salt as described in Example 148, using 1-methyl-1H-benzo[d]imidazole-2-carbaldehyde in place of 5-methylpyrazine-2-carbaldehyde. $^1$H NMR (400 MHz, pyridine-d$_5$) δ 12.05 (s, 1H) 8.71 (s, 1H) 8.52 (s, 1H) 7.95-8.01 (m, 1H) 7.41-7.48 (m, 1H) 7.31-7.38 (m, 2H) 7.18-7.20 (m, 2H) 6.97-7.03 (m, 1H) 4.68 (s, 2H) 3.91-4.12 (m, 1H) 3.72 (s, 3H) 3.64-3.70 (m, 2H) 3.54-3.64 (m, 2H) 3.36 (t, J=8.39 Hz, 2H) 3.05-3.20 (m, 1H) 2.87 (t, J=8.24 Hz, 2H) 2.20-2.31 (m, 1H) 1.88-2.11 (m, 2H) 1.76-1.83 (m, 1H). MS (ESI) m/z 501 (M+H)$^+$.

Example 164

N-(5-chloro-4-{1-[(1-methyl-1H-benzotriazol-5-yl)methyl]-2,3-dihydro-1H-indol-6-yl}pyridin-2-yl)piperidine-3-carboxamide The title compound was prepared as the trifluoroacetate salt as described in Example 148, using 1-methyl-1H-benzo[d][1,2,3]triazole-5-carbaldehyde in place of 5-methylpyrazine-2-carbaldehyde. $^1$H NMR (400 MHz, pyridine-$d_5$) δ 12.04 (s, 1H) 8.71 (s, 1H) 8.51 (s, 1H) 8.24 (s, 1H) 6.98 (d, J=8.24 Hz, 1H) 6.94 (s, 1H) 4.46 (s, 2H) 4.16 (s, 3H) 3.91-4.02 (m, 1H) 3.63-3.74 (m, 2H) 3.56-3.63 (m, 2H) 3.32 (t, J=8.39 Hz, 2H) 3.05-3.20 (m, J=10.22, 10.22 Hz, 1H) 2.92 (t, J=8.24 Hz, 2H) 2.15-2.29 (m, 1H) 1.90-2.09 (m, 2H) 1.77-1.86 (m, 1H). MS (ESI) m/z 502 (M+H)$^+$.

Example 165

N-{4-[1-(1,3-benzodioxol-4-ylmethyl)-2,3-dihydro-1H-indol-6-yl]-5-chloropyridin-2-yl}piperidine-3-carboxamide The title compound was prepared as the trifluoroacetate salt as described in Example 148, using benzo[d][1,3]dioxole-4-carbaldehyde in place of 5-methylpyrazine-2-carbaldehyde. $^1$H NMR (400 MHz, pyridine-$d_5$) δ 12.05 (s, 1H) 8.69-8.71 (m, 1H) 8.53 (s, 1H) 7.17 (d, J=7.32 Hz, 1H) 6.91-7.04 (m, 3H) 6.85-6.90 (m, 2H) 6.00 (s, 2H) 4.34 (s, 2H) 3.90-4.02 (m, J=9.16 Hz, 1H) 3.49-3.76 (m, 4H) 3.36 (t, J=8.39 Hz, 2H) 3.05-3.19 (m, 1H) 2.88 (t, J=8.39 Hz, 2H) 2.18-2.29 (m, 1H) 1.90-2.09 (m, 2H) 1.74-1.85 (m, 1H). MS (ESI) m/z 491 (M+H)$^+$.

Example 166

N-{5-chloro-4-[1-(4-methylbenzyl)-2,3-dihydro-1H-indol-6-yl]pyridin-2-yl}piperidine-3-carboxamide The title compound was prepared as the trifluoroacetate salt as described in Example 148, using 4-methylbenzaldehyde in place of 5-methylpyrazine-2-carbaldehyde. $^1$H NMR (400 MHz, pyridine-$d_5$) δ 11.97-12.09 (m, 1H) 8.71 (s, 1H) 8.52 (s, 1H) 7.34 (d, J=7.93 Hz, 2H) 7.15-7.20 (m, J=7.02, 7.02 Hz, 3H) 6.91-6.95 (m, 1H) 6.89 (s, 1H) 4.27 (s, 2H) 3.91-4.01 (m, J=7.93 Hz, 1H) 3.53-3.71 (m, 4H) 3.27 (t, J=8.39 Hz, 2H) 3.07-3.16 (m, 1H) 2.88 (t, J=8.39 Hz, 2H) 2.18-2.29 (m, 4H) 1.93-2.08 (m, 2H) 1.76-1.84 (m, 1H). MS (ESI) m/z 461 (M+H)$^+$.

Example 167

N-{5-chloro-4-[1-(quinoxalin-6-ylmethyl)-2,3-dihydro-1H-indol-6-yl]pyridin-2-yl}piperidine-3-carboxamide The title compound was prepared as the trifluoroacetate salt as described in Example 148, using quinoxaline-6-carbaldehyde in place of 5-methylpyrazine-2-carbaldehyde. $^1$H NMR (400 MHz, pyridine-$d_5$) δ 12.03 (s, 1H) 8.90 (d, J=3.36 Hz, 2H) 8.70 (s, 1H) 8.49 (s, 1H) 8.32 (s, 1H) 8.25 (d, J=8.54 Hz, 1H) 7.85 (dd, J=8.70, 1.68 Hz, 1H) 7.23 (s, 1H) 6.97 (d, J=7.32 Hz, 1H) 6.92 (s, 1H) 4.52 (s, 2H) 3.89-3.99 (m, J=8.54, 8.54 Hz, 1H) 3.57-3.70 (m, 4H) 3.34 (t, J=8.39 Hz, 2H) 3.03-3.16 (m, 1H) 2.93 (t, J=8.24 Hz, 2H) 2.17-2.30 (m, 1H) 1.86-2.12 (m, 2H) 1.74-1.83 (m, J=13.89, 3.51 Hz, 1H). MS (ESI) m/z 499 (M+H)$^+$.

Example 168

N-{5-chloro-4-[1-(pyrazin-2-ylmethyl)-2,3-dihydro-1H-indol-6-yl]pyridin-2-yl}piperidine-3-carboxamide The title compound was prepared as the trifluoroacetate salt as described in Example 148, using pyrazine-2-carbaldehyde in place of 5-methylpyrazine-2-carbaldehyde. $^1$H NMR (400 MHz, pyridine-$d_5$) δ 12.04 (s, 1H) 8.88 (s, 1H) 8.68 (s, 1H) 8.53-8.59 (m, 2H) 8.50 (s, 1H) 7.18 (d, J=7.32 Hz, 1H) 6.89-6.97 (m, 2H) 4.55 (s, 2H) 3.90-4.03 (m, J=9.16, 9.16 Hz, 1H) 3.52-3.72 (m, 4H) 3.46 (t, J=8.54 Hz, 2H) 3.06-3.18 (m, 1H) 2.93 (t, J=8.39 Hz, 2H) 2.18-2.28 (m, 1H) 1.88-2.06 (m, 2H) 1.74-1.84 (m, 1H). MS (ESI) m/z 449 (M+H)$^+$.

Example 169

N-{5-chloro-4-[1-(2,3-dihydro[1,4]dioxino[2,3-b]pyridin-7-ylmethyl)-2,3-dihydro-1H-indol-6-yl]pyridin-2-yl}piperidine-3-carboxamide The title compound was prepared as the trifluoroacetate salt as described in Example 148, using 2,3-dihydro-[1,4]dioxino[2,3-b]pyridine-7-carbaldehyde in place of 5-methylpyrazine-2-carbaldehyde. $^1$H NMR (400 MHz, pyridine-$d_5$) δ 12.05 (s, 1H) 8.68-8.71 (m, 1H) 8.51-8.53 (m, 1H) 8.08 (d, J=1.83 Hz, 1H) 7.41 (d, J=1.83 Hz, 1H) 7.18 (d, J=7.32 Hz, 1H) 6.90-6.99 (m, 2H) 4.32-4.37 (m, 2H) 4.24 (s, 2H) 4.12-4.18 (m, J=5.04, 3.20 Hz, 2H) 3.64-3.72 (m, 2H) 3.56-3.63 (m, 2H) 3.26 (t, J=8.24 Hz, 2H) 3.08-3.18 (m, 1H) 2.87 (t, J=8.24 Hz, 2H) 2.18-2.28 (m, 1H) 1.90-2.08 (m, 2H) 1.74-1.85 (m, 1H). MS (ESI) m/z 506 (M+H)$^+$.

Example 170

N-[5-chloro-4-(1-{[6-(methylsulfonyl)pyridin-3-yl]methyl}-2,3-dihydro-1H-indol-6-yl)pyridin-2-yl]piperidine-3-carboxamide The title compound was prepared as the trifluoroacetate salt as described in Example 148, using 6-(methylsulfonyl)nicotinaldehyde in place of 5-methylpyrazine-2-carbaldehyde. $^1$H NMR (400 MHz, pyridine-$d_5$) δ 12.06 (s, 1H) 8.82-8.86 (m, 1H) 8.66 (s, 1H) 8.52 (s, 1H) 8.25 (d, J=7.93 Hz, 1H) 7.97 (dd, J=8.09, 1.98 Hz, 1H) 7.22-7.24 (m, 1H) 7.00 (d, J=7.63 Hz, 1H) 6.82 (s, 1H) 4.38 (s, 2H) 3.92-4.01 (m, 1H) 3.64-3.74 (m, 2H) 3.60-3.63 (m, 2H) 3.47 (s, 3H) 3.26 (t, J=8.39 Hz, 2H) 3.05-3.17 (m, 1H) 2.92 (t, J=8.24 Hz, 2H) 2.18-2.27 (m, J=14.65 Hz, 1H) 1.90-2.11 (m, 2H) 1.76-1.86 (m, J=13.73, 3.36 Hz, 1H). MS (ESI) m/z 526 (M+H)$^+$.

Example 171

N-{5-chloro-4-[1-(4-sulfamoylbenzyl)-2,3-dihydro-1H-indol-6-yl]pyridin-2-yl}piperidine-3-carboxamide The title compound was prepared as the trifluoroacetate salt as described in Example 148, using 4-formylbenzenesulfonamide in place of 5-methylpyrazine-2-carbaldehyde.

¹H NMR (400 MHz, pyridine-d₅) δ 12.07 (s, 1H) 8.97-9.00 (m, 1H) 8.67 (s, 1H) 8.51 (s, 1H) 8.28 (d, J=8.24 Hz, 2H) 7.51 (d, J=8.24 Hz, 2H) 6.94-7.00 (m, 1H) 6.80 (s, 1H) 4.29 (s, 2H) 3.91-4.02 (m, 1H) 3.65-3.74 (m, J=9.16 Hz, 2H) 3.56-3.63 (m, 2H) 3.24 (t, J=8.39 Hz, 2H) 3.06-3.17 (m, 1H) 2.90 (t, J=8.39 Hz, 2H) 2.15-2.28 (m, 1H) 1.87-2.11 (m, J=1.22 Hz, 2H) 1.76-1.84 (m, 1H). MS (ESI) m/z 526 (M+H)⁺.

Example 172

N-(5-chloro-4-{1-[3-fluoro-4-(methylsulfonyl)benzyl]-2,3-dihydro-1H-indol-6-yl}pyridin-2-yl)piperidine-3-carboxamide The title compound was prepared as the trifluoroacetate salt as described in Example 148, using 3-fluoro-4-(methylsulfonyl)benzaldehyde in place of 5-methylpyrazine-2-carbaldehyde. ¹H NMR (400 MHz, pyridine-d₅) δ 12.05 (s, 1H) 8.67 (s, 1H) 8.49-8.51 (m, 1H) 8.10 (t, J=7.63 Hz, 1H) 7.32-7.44 (m, 2H) 7.24 (s, 1H) 7.00 (d, J=7.63 Hz, 1H) 6.76-6.80 (m, 1H) 4.34 (s, 2H) 3.89-4.03 (m, J=8.70, 8.70 Hz, 1H) 3.63-3.74 (m, 2H) 3.57-3.63 (m, 2H) 3.42 (s, 3H) 3.31 (t, J=8.39 Hz, 2H) 3.06-3.18 (m, 1H) 2.95 (t, J=8.24 Hz, 2H) 2.18-2.30 (m, J=13.12 Hz, 1H) 1.88-2.13 (m, 2H) 1.73-1.86 (m, 1H). MS (ESI) m/z 543 (M+H)⁺.

Example 173

N-(5-chloro-4-{1-[4-(2H-tetrazol-5-yl)benzyl]-2,3-dihydro-1H-indol-6-yl}pyridin-2-yl)piperidine-3-carboxamide The title compound was prepared as the trifluoroacetate salt as described in Example 148, using 4-(2H-tetrazol-5-yl)benzaldehyde in place of 5-methylpyrazine-2-carbaldehyde. ¹H NMR (400 MHz, pyridine-d₅) δ 12.03 (s, 1H) 8.67 (s, 1H) 8.50-8.51 (m, 1H) 8.37 (d, J=7.93 Hz, 2H) 7.59-7.61 (m, 2H) 7.20 (s, 1H) 6.95-7.01 (m, 1H) 6.83 (s, 1H) 4.34 (s, 2H) 3.89-3.98 (m, J=8.24 Hz, 1H) 3.52-3.69 (m, 5H) 3.33 (t, J=9.00 Hz, 2H) 3.08-3.22 (m, 1H) 2.93 (t, J=8.54 Hz, 2H) 2.15-2.25 (m, J=3.36 Hz, 1H) 1.86-2.07 (m, 2H) 1.73-1.84 (m, J=9.46 Hz, 1H). MS (ESI) m/z 515 (M+H)⁺.

Example 174

N-{5-chloro-4-[1-(pyrrolidin-2-ylmethyl)-2,3-dihydro-1H-indol-6-yl]pyridin-2-yl}piperidine-3-carboxamide The title compound was prepared as the trifluoroacetate salt as described in Example 148, using tert-butyl 2-formylpyrrolidine-1-carboxylate in place of 5-methylpyrazine-2-carbaldehyde. ¹H NMR (400 MHz, pyridine-d₅) δ 12.05 (s, 1H) 8.60 (s, 1H) 8.53 (s, 1H) 7.08 (d, J=7.32 Hz, 1H) 6.89 (d, J=7.63 Hz, 1H) 6.80 (s, 1H) 4.11-4.24 (m, 1H) 3.94-4.03 (m, 1H) 3.51-3.87 (m, 8H) 3.41-3.51 (m, 1H) 3.22-3.38 (m, 2H) 3.05-3.18 (m, 1H) 2.78 (t, J=8.24 Hz, 2H) 2.16-2.33 (m, J=13.12 Hz, 1H) 1.89-2.19 (m, 5H) 1.73-1.87 (m, 2H). MS (ESI) m/z 440 (M+H)⁺.

Example 175

N-(5-chloro-4-{1-[(1-methylpiperidin-4-yl)methyl]-2,3-dihydro-1H-indol-6-yl}pyridin-2-yl)piperidine-3-carboxamide The title compound was prepared as the trifluoroacetate salt as described in Example 148, using 1-methylpiperidine-4-carbaldehyde in place of 5-methylpyrazine-2-carbaldehyde. ¹H NMR (400 MHz, pyridine-d₅) δ 12.07 (s, 1H) 8.68 (s, 1H) 8.55 (s, 1H) 7.17 (d, J=7.63 Hz, 1H) 6.92 (d, J=7.32 Hz, 1H) 6.68 (s, 1H) 3.91-4.03 (m, J=8.54 Hz, 1H) 3.46-3.74 (m, 6H) 3.25 (t, J=8.39 Hz, 2H) 3.04-3.19 (m, 1H) 2.73-2.98 (m, 8H) 2.17-2.33 (m, 1H) 1.69-2.14 (m, 8H). MS (ESI) m/z 440 (M+H)⁺.

Example 176

N-{5-chloro-4-[1-(3-fluorobenzyl)-1H-imidazo[4,5-b]pyridin-6-yl]pyridin-2-yl}piperidine-3-carboxamide Example 176A 6-bromo-1-(3-fluorobenzyl)-1H-imidazo[4,5-b]pyridine A suspension of 6-bromo-3H-imidazo[4,5-b]pyridine (1 g, 5.05 mmol), 1-(bromomethyl)-3-fluorobenzene (1.050 g, 5.55 mmol) and cesium carbonate (3.29 g, 10.10 mmol) in N,N-dimethylformamide (5 mL) was stirred at 60° C. for 14 hours. The mixture was concentrated and purified by flash chromatography on silica (Analogix, Intelliflash 310), eluting with a gradient of 30-100% ethyl acetate/heptanes to provide the title compound. MS (ESI⁺) m/z 306.0 (M+H)⁺.

Example 176B tert-butyl 3-((5-chloro-4-(1-(3-fluorobenzyl)-1H-imidazo[4,5-b]pyridin-6-yl)pyridin-2-yl)carbamoyl)piperidine-1-carboxylate A suspension of Example 176A (100 mg, 0.327 mmol), Example 1C (3.27 mL, 0.327 mmol), 1,1'-bis(diphenylphosphino)ferrocene-palladium(II)dichloride-dichloromethane complex (16.01 mg, 0.020 mmol) and sodium carbonate (1.574 mL, 1.633 mmol) in 1,4-dioxane (3 mL) was heated at 90° C. for 90 minutes. The mixture was diluted with ethyl acetate and the organic layer was dried over magnesium sulfate, filtered and concentrated. Purification by reverse phase flash chromatography (Analogix, Intelliflash 310, C18 column), eluting with a gradient of 20-100% acetonitrile/0.1% trifluoroacetic acid in water provided the title compound. MS (ESI⁺) m/z 565.0 (M+H)⁺.

Example 176C

N-{5-chloro-4-[1-(3-fluorobenzyl)-1H-imidazo[4,5-b]pyridin-6-yl]pyridin-2-yl}piperidine-3-carboxamide A suspension of Example 176B (130 mg, 0.230 mmol) and trifluoroacetic acid (0.5 mL, 6.49 mmol) in dichloromethane (1.5 mL) was stirred at room temperature for 150 minutes. The mixture was concentrated and purified by reverse phase flash chromatography (Analogix, Intelliflash 310, C18 column), eluting with a gradient of 20-100% acetonitrile/0.1% trifluoroacetic acid in water to provide the title compound. ¹H NMR (300 MHz, DMSO-d₆) δ 11.05 (s, 1H), 8.83 (s, 1H), 8.54 (s, 1H), 8.49 (s, 1H), 8.48 (d, J=2.08 Hz, 1H), 8.27 (d, J=2.06 Hz, 1H), 8.20 (s, 1H), 7.44-7.35 (m, 1H), 7.30 (dd, J=2.05, 9.68 Hz, 1H), 7.21 (d, J=7.81 Hz, 1H), 7.18-7.10 (m, 1H), 5.61 (s, 2H), 3.33 (d, J=9.22 Hz, 1H), 3.16 (s, 1H), 3.13-2.82 (m, 4H), 2.05 (s, 1H), 1.82 (s, 1H), 1.71-1.53 (m, 2H). MS (ESI⁺) m/z 465.1 (M+H)⁺.

Example 177

(3R)—N-[5-chloro-4-(1-{[3-(morpholin-4-yl)oxetan-3-yl]methyl}-1H-benzimidazol-6-yl)pyridin-2-yl]piperidine-3-carboxamide Example 177A 4-(3-((6-bromo-1H-benzo[d]imidazol-1-yl)methyl)oxetan-3-yl)morpholine The title compound was prepared as described in Examples 8A-C using (3-morpholinooxetan-3-yl)methanamine in place of (3-fluorophenyl)methanamine. MS (ESI) m/e 353 (M+H)⁺.

Example 177B (3R)—N-[5-chloro-4-(1-{[3-(morpholin-4-yl)oxetan-3-yl]methyl}-1H-benzimidazol-6-yl)pyridin-2-yl]piperidine-3-carboxamide A mixture of Example 1C (0.215 mmol), Example 177A (76 mg, 0.215 mmol) 1,1'-bis(diphenylphosphino)ferrocene-palladium(II)dichloride-dichloromethane complex (10.5 mg, 0.013 mmol) and sodium carbonate (0.59 mL, 1.18 mmol) in 1,4-dioxane (2 mL) was flushed with nitrogen and stirred at 95° C. for 2 hours. The mixture was cooled, concentrated, and purified by reverse-phase HPLC (Phenomenex Luna C8(2) 100 Å AXIA column) using a gradient of 10-95% acetonitrile/0.1% trifluoroacetic acid in water to afford the BOC-protected intermediate as the trifluoroacetate salt. To the intermediate was added 1:1 trifluoroacetic acid/dichloromethane (0.3 mL) and the mixture was stirred at ambient temperature for 20 minutes and concentrated to give the title compound as the trifluoroacetate salt. ¹H NMR (400 MHz, dimethylsulfoxide-d₆) δ 1.62-2.11 (m, 4H) 2.59-2.68 (m, 4H) 2.85-3.38 (m, 5H) 3.55-3.60 (m, 4H) 4.34 (d, J=7.02 Hz, 2H) 4.64 (d, J=7.02 Hz, 2H) 4.73 (s, 2H) 7.37 (dd, J=8.54, 1.53 Hz, 1H) 7.83 (d, J=8.24 Hz, 1H) 7.88 (s, 1H) 8.17 (s, 1H) 8.46 (s, 1H) 8.52 (s, 1H) 8.64 (s, 1H) 10.69 (s, 1H). MS (ESI) m/e 511 (M+H)⁺.

Example 178

(3R)—N-[5-chloro-4-(1-{[3-(pyrrolidin-1-yl)oxetan-3-yl]methyl}-1H-benzimidazol-6-yl)pyridin-2-yl]piperidine-3-carboxamide Example 178A 6-bromo-1-((3-(pyrrolidin-1-yl)oxetan-3-yl)methyl)-1H-benzo[d]imidazole The title compound was prepared as described in Examples 8A-C using (3-(pyrrolidin-1-yl)oxetan-3-yl)methanamine in place of (3-fluorophenyl)methanamine. MS (ESI) m/e 337 (M+H)⁺.

Example 178B (3R)—N-[5-chloro-4-(1-{[3-(pyrrolidin-1-yl)oxetan-3-yl]methyl}-1H-benzimidazol-6-yl)pyridin-2-yl]piperidine-3-carboxamide The title compound was prepared as the trifluoroacetate salt as described in Example 177B using Example 178A in place of Example 177A. ¹H NMR (400 MHz, dimethylsulfoxide-d₆) δ 1.63-2.12 (m, 8H) 2.86-3.38 (m, 9H) 4.51 (d, J=7.93 Hz, 2H) 4.75 (d, J=7.93 Hz, 2H) 4.80 (s, 2H) 7.35 (dd, J=8.24, 1.53 Hz, 1H) 7.83 (d, J=8.54 Hz, 1H) 7.87 (s, 1H) 8.16 (s, 1H) 8.46 (s, 1H) 8.53 (s, 1H) 8.55 (s, 1H) 10.69 (s, 1H). MS (ESI) m/e 495 (M+H)⁺.

Example 179

N-{5-chloro-4-[1-(tetrahydro-2H-pyran-4-ylmethyl)-1H-benzimidazol-6-yl]pyridin-2-yl}-7-azaspiro[3.5]nonan-2-amine Example 179A 6-(5-chloro-2-fluoropyridin-4-yl)-1-((tetrahydro-2H-pyran-4-yl)methyl)-1H-benzo[d]imidazole The title compound was prepared as described in Example 88, using Example 13C in place of Example 6A and (5-chloro-2-fluoropyridin-4-yl)boronic acid in place of (2-((tert-butoxycarbonyl)amino)-5-chloropyridine. Purification by silica gel flash chromatography (Isco®, Redi-Sep® column) eluting with a gradient of 50-100% ethyl acetate/hexane followed by 10% 2:1 methanol/water in ethyl acetate, followed by recrystallization from ethyl acetate/hexane afforded the title compound. MS (ESI) m/z 346 (M+H)⁺.

Example 179B

N-{5-chloro-4-[1-(tetrahydro-2H-pyran-4-ylmethyl)-1H-benzimidazol-6-yl]pyridin-2-yl}-7-azaspiro[3.5]nonan-2-amine A mixture of Example 179A (300 mg, 0.868 mmol), tert-butyl 2-amino-7-azaspiro[3.5]nonane-7-carboxylate (626 mg, 2.60 mmol) and N,N-diisopropylethylamine (227 μL, 1.301 mmol) in dimethylsulfoxide (1.735 mL) was stirred at 120° C. for 24 hours. After cooling, water and ethyl acetate were added and the organic layer was washed with brine, dried over magnesium sulfate, filtered and concentrated. Purification by silica gel flash chromatography (Isco®, Redi-Sep® column) eluting with a gradient of 50-100% ethyl acetate/hexane afforded the BOC-protected intermediate (418 mg) which was dissolved in 1.5 mL ethyl acetate. 2M Hydrogen chloride in diethyl ether (5 mL, 10.0 mmol) was added and the mixture was stirred at 45° C. for 2 hours. After cooling, the solid was filtered and washed with diethyl ether to obtain the title compound as the tris-hydrochloride salt. ¹H NMR (400 MHz, methanol-d₄) δ 9.49 (s, 1H), 8.20 (s, 1H), 8.12 (s, 1H), 7.98 (d, J=8.6, 1H), 7.76 (dd, J=8.6, 1.4, 1H), 7.00 (s, 1H), 4.50 (d, J=7.3, 2H), 4.38 (p, J=7.8, 1H), 3.99-3.90 (m, 2H), 3.43-3.34 (m, 2H), 3.23-3.09 (m, 4H), 2.61-2.50 (m, 2H), 2.40-2.23 (m, 1H), 2.01-1.83 (m, 6H), 1.61-1.41 (m, 4H). MS (ESI) m/z 467 (M+H)⁺.

Example 180

N-{5-chloro-4-[1-(tetrahydro-2H-pyran-4-ylmethyl)-1H-benzimidazol-6-yl]pyridin-2-yl}-7-(methylsulfonyl)-7-azaspiro[3.5]nonan-2-amine To a solution of Example 179 (150 mg, 0.261 mmol) in N,N-dimethylformamide (1.043 mL) and N,N-diisopropylethylamine (228 μL, 1.303 mmol) at −30° C. was added methanesulfonyl chloride (22.35 μL, 0.287 mmol). After stirring for 10 minutes, water and ethyl acetate were added followed by 10% aqueous potassium carbonate. The organic layer was washed with 10% aqueous potassium carbonate, saturated aqueous sodium bicarbonate and brine, dried over magnesium sulfate, filtered and concentrated. Purification by silica gel flash chromatography (Isco®, Redi-Sep® column) eluting with a gradient of 50-100% ethyl acetate/hexane followed by 10% 2:1 methanol/water in ethyl acetate afforded the title compound. $^1$H NMR (500 MHz, dimethylsulfoxide-$d_6$) δ 8.30 (s, 1H), 8.07 (s, 1H), 7.77-7.68 (m, 2H), 7.25 (d, J=8.3, 1H), 7.06 (d, J=6.8, 1H), 6.49 (s, 1H), 4.33-4.23 (m, 1H), 4.19 (d, J=7.1, 2H), 3.86-3.77 (m, 2H), 3.26-3.16 (m, 2H), 3.11-2.96 (m, 4H), 2.83 (s, 3H), 2.33-2.24 (m, 2H), 2.14-2.02 (m, 1H), 1.74-1.55 (m, 6H), 1.44-1.21 (m, 4H). MS (ESI) m/z 544 (M+H)$^+$.

Example 181

(2E)-N-{5-chloro-4-[1-(3-fluorobenzyl)-1H-benzimidazol-6-yl]pyridin-2-yl}-3-(pyridin-4-yl)prop-2-enamide The title compound was prepared as the bis-trifluoroacetate salt as described in Example 189 using (E)-3-(pyridin-4-yl)acrylic acid in place of 3-oxocyclobutanecarboxylic acid. $^1$H NMR (400 MHz, dimethylsulfoxide-$d_6$/D$_2$O) δ 8.67 (s, 1H), 8.62-8.52 (m, 4H), 8.39 (s, 1H), 8.14 (s, 1H), 7.83 (d, J=8.3 Hz, 1H), 7.78-7.73 (m, 1H), 7.47-7.42 (m, 1H), 7.42-7.36 (m, 3H), 7.24-7.15 (m, 2H), 7.15-7.07 (m, 1H), 5.63 (s, 2H). (ESI) m/z 484 (M+H)$^+$.

Example 182

(1R,2S)—N-{5-chloro-4-[1-(3-fluorobenzyl)-1H-benzimidazol-6-yl]pyridin-2-yl}-N'-cyclopentylcyclobutane-1,2-dicarboxamide The title compound was prepared as the bis-trifluoroacetate salt as described in Example 189 using (1S,2R)-2-(cyclopentylcarbamoyl)cyclobutanecarboxylic acid in place of 3-oxocyclobutanecarboxylic acid. $^1$H NMR (400 MHz, dimethylsulfoxide-$d_6$/D$_2$O) δ 8.79 (s, 1H), 8.40-8.35 (m, 1H), 8.12 (d, J=0.6 Hz, 1H), 7.87 (dd, J=8.4, 0.7 Hz, 1H), 7.73-7.69 (m, 1H), 7.45-7.36 (m, 2H), 7.23-7.15 (m, 2H), 7.15-7.06 (m, 1H), 5.63 (s, 2H), 3.91-3.81 (m, 1H), 3.60-3.50 (m, 1H), 3.46-3.32 (m, 1H), 2.43-2.14 (m, 2H), 2.07-1.91 (m, 2H), 1.85-1.64 (m, 1H), 1.65-1.46 (m, 2H), 1.46-1.24 (m, 4H), 1.22-1.04 (m, 1H). MS (ESI) m/z 546 (M+H)$^+$.

Example 183

N-{5-chloro-4-[1-(3-fluorobenzyl)-1H-benzimidazol-6-yl]pyridin-2-yl}-2-(2-oxopyridin-1(2H)-yl)propanamide The title compound was prepared as the bis-trifluoroacetate salt as described in Example 189 using 2-(2-oxopyridin-1(2H)-yl)propanoic acid in place of 3-oxocyclobutanecarboxylic acid. $^1$H NMR (400 MHz, dimethylsulfoxide-$d_6$/D$_2$O) δ 8.84 (s, 1H), 8.44 (s, 1H), 8.05 (s, 1H), 7.86 (dd, J=8.4, 0.7 Hz, 1H), 7.77-7.73 (m, 1H), 7.66 (dd, J=7.0, 2.0 Hz, 1H), 7.49-7.34 (m, 3H), 7.23-7.15 (m, 2H), 7.13-7.05 (m, 1H), 6.46-6.39 (m, 1H), 6.32 (td, J=6.8, 1.4 Hz, 1H), 5.67-5.58 (m, 3H), 1.64 (d, J=7.3 Hz, 3H). MS (ESI$^+$) m/z 502 (M+H)$^+$.

Example 184

N-{5-chloro-4-[1-(3-fluorobenzyl)-1H-benzimidazol-6-yl]pyridin-2-yl}-2-(methylsulfonyl)acetamide The title compound was prepared as the bis-trifluoroacetate salt as described in Example 189 using 2-(methylsulfonyl)acetic acid in place of 3-oxocyclobutanecarboxylic acid. $^1$H NMR (400 MHz, dimethylsulfoxide-$d_6$/D$_2$O) δ 8.73 (s, 1H), 8.46 (s, 1H), 8.09 (s, 1H), 7.86 (dd, J=8.3, 0.7 Hz, 1H), 7.76-7.71 (m, 1H), 7.45-7.36 (m, 2H), 7.24-7.14 (m, 2H), 7.15-7.06 (m, 1H), 5.62 (s, 2H), 4.40 (d, J=0.6 Hz, 2H), 3.14 (s, 3H). MS (ESI) m/z 473 (M+H)$^+$.

Example 185

N-{5-chloro-4-[1-(3-fluorobenzyl)-1H-benzimidazol-6-yl]pyridin-2-yl}-1-(3-chlorophenyl)-5-oxopyrrolidine-3-carboxamide The title compound was prepared as the bis-trifluoroacetate salt as described in Example 189 using 1-(3-chlorophenyl)-5-oxopyrrolidine-3-carboxylic acid in place of 3-oxocyclobutanecarboxylic acid. $^1$H NMR (400 MHz, dimethylsulfoxide-$d_6$/D$_2$O) δ 8.77 (s, 1H), 8.43 (s, 1H), 8.13 (s, 1H), 7.86 (dd, J=8.3, 0.7 Hz, 1H), 7.80 (t, J=2.1 Hz, 1H), 7.75-7.71 (m, 1H), 7.50 (ddd, J=8.3, 2.1, 1.0 Hz, 1H), 7.46-7.34 (m, 3H), 7.22-7.14 (m, 3H), 7.08 (td, J=8.7, 2.6 Hz, 1H), 5.62 (s, 2H), 4.14 (dd, J=9.9, 8.4 Hz, 1H), 4.00 (dd, J=9.9, 5.3 Hz, 1H), 3.69-3.58 (m, 1H), 2.89 (dd, J=17.1, 9.3 Hz, 1H), 2.77 (dd, J=17.1, 6.3 Hz, 1H). MS (ESI$^+$) m/z 574 (M+H)$^+$.

Example 186

1-benzyl-N-{5-chloro-4-[1-(3-fluorobenzyl)-1H-benzimidazol-6-yl]pyridin-2-yl}-5-oxopyrrolidine-3-carboxamide The title compound was prepared as the bis-trifluoroacetate salt as described in Example 189 using 1-benzyl-5-oxopyrrolidine-3-carboxylic acid in place of 3-oxocyclobutanecarboxylic acid. $^1$H NMR (400 MHz, dimethylsulfoxide-$d_6$/D$_2$O) δ 8.76 (s, 1H), 8.09 (d, J=0.6 Hz, 1H), 7.86 (dd, J=8.4, 0.7 Hz, 1H), 7.72 (dd, J=1.6, 0.8 Hz, 1H), 7.44-7.34 (m, 2H), 7.35-7.27 (m, 2H), 7.29-7.20 (m, 3H), 7.21-7.14 (m, 2H), 7.14-7.05 (m, 1H), 5.62 (s, 2H), 4.39 (q, J=15.0 Hz, 2H), 3.60-3.43 (m, 2H), 3.40 (dd, J=9.0, 5.1 Hz, 1H), 2.64 (d, J=8.9 Hz, 2H). MS (ESI) m/z 554 (M+H)$^+$.

Example 187

N-{5-chloro-4-[1-(3-fluorobenzyl)-1H-benzimidazol-6-yl]pyridin-2-yl}-2,3-dihydro[1,4]dioxino[2,3-b]pyridine-7-carboxamide The title compound was prepared as the bis-trifluoroacetate salt as described in Example 189 using 2,3-dihydro-[1,4]dioxino[2,3-b]pyridine-7-carboxylic acid in place of 3-oxocyclobutanecarboxylic acid. $^1$H NMR (400 MHz, dimethylsulfoxide-$d_6$/D$_2$O) δ 8.46 (s, 1H), 8.41 (d, J=8.0 Hz, 1H), 8.20 (s, 1H), 7.84 (d, J=2.2, 1.7 Hz, 1H), 7.80 (d, J=8.5 Hz, 1H), 7.69-7.66 (m, 1H), 7.48 (dt, J=9.6, 3.1 Hz, 1H), 7.46-7.36 (m, 1H), 7.25-7.17 (m, 2H), 7.16-7.07 (m, 1H), 5.64 (s, 1H), 4.49 (dd, J=5.0, 3.2 Hz, 2H), 4.31 (dd, J=5.0, 3.2 Hz, 2H). MS (ESI) m/z 516 (M+H)⁺.

Example 188

(3R)—N-{5-chloro-4-[1-(3-fluorobenzyl)-1H-benzimidazol-6-yl]pyridin-2-yl}-3-(pyridin-3-yl)-1H-pyrrolo[1,2-c][1,3]thiazole-7-carboxamide The title compound was prepared as the bis-trifluoroacetate salt as described in Example 189 using 3-(pyridin-3-yl)-1,3-dihydropyrrolo[1,2-c]thiazole-7-carboxylic acid in place of 3-oxocyclobutanecarboxylic acid. $^1$H NMR (400 MHz, dimethylsulfoxide-d₆/D₂O) δ 8.54 (dd, J=4.7, 1.5 Hz, 1H), 8.43 (d, J=8.6 Hz, 1H), 8.25 (d, J=0.6 Hz, 1H), 7.82 (dd, J=8.2, 0.7 Hz, 1H), 7.68 (d, J=1.4 Hz, 1H), 7.66-7.60 (m, 1H), 7.44-7.32 (m, 3H), 7.16 (m, 2H), 7.12-7.04 (m, 1H), 7.03 (d, J=3.1 Hz, 1H), 6.70-6.65 (m, 1H), 6.58 (d, J=3.1 Hz, 1H), 5.57 (s, 2H), 4.55 (dd, J=14.9, 1.9 Hz, 1H), 4.41 (d, J=14.8 Hz, 1H), 1.35-1.18 (m, 1H). MS (ESI) m/z 581 (M+H)⁺.

Example 189

N-{5-chloro-4-[1-(3-fluorobenzyl)-1H-benzimidazol-6-yl]pyridin-2-yl}-3-oxocyclobutanecarboxamide To a solution of 3-oxocyclobutanecarboxylic acid (68.4 mg, 0.6 mmol) in dichloromethane (2 mL) at 0° C. was added 1-chloro-N,N,2-trimethylpropenylamine (88 μL, 0.66 mmol) and the mixture was stirred for 1 hour. A 750 μL (0.225 mmol) portion of this solution was added to a solution of Example 49 (30 mg, 0.085 mmol) in 1:1 tetrahydrofuran/pyridine (1 mL) and the mixture was stirred at 40° C. for 16 hours. The mixture was concentrated and dissolved in 1:1 dimethylsulfoxide/methanol (1.5 mL). Purification by preparative HPLC (Phenomenex Luna C8(2) 100 Å AXIA column) eluting with a gradient of 5-100% acetonitrile/0.1% trifluoroacetic acid in water afforded the title compound as the bis-trifluoroacetate salt. $^1$H NMR (400 MHz, dimethylsulfoxide-d₆/D₂O) δ 8.62 (s, 1H), 8.16 (s, 1H), 7.84 (dd, J=8.3, 0.7 Hz, 1H), 7.72-7.68 (m, 1H), 7.43-7.32 (m, 2H), 7.23-7.12 (m, 2H), 7.14-7.05 (m, 1H), 5.60 (s, 2H), 3.57-3.46 (m, 1H), 3.30-3.26 (m, 4H). MS (ESI) m/z 449 (M+H)⁺.

Example 190

N-{5-chloro-4-[1-(3-fluorobenzyl)-1H-benzimidazol-6-yl]pyridin-2-yl}-6-oxo spiro[3.3]heptane-2-carboxamide The title compound was prepared as the bis-trifluoroacetate salt as described in Example 189 using 6-oxospiro[3.3]heptane-2-carboxylic acid in place of 3-oxocyclobutanecarboxylic acid. $^1$H NMR (400 MHz, dimethylsulfoxide-d₆/D₂O) δ 8.70 (s, 1H), 8.39 (s, 1H), 8.15 (s, 1H), 8.03 (s, 1H), 7.85 (d, J=8.4 Hz, 1H), 7.72 (s, 1H), 7.45-7.37 (m, 2H), 7.21-7.16 (m, 2H), 7.14-7.07 (m, 1H), 5.61 (s, 2H), 3.42-3.31 (m, 1H), 3.16-3.13 (m, 2H), 3.05-3.00 (m, 3H), 2.50-2.44 (m, 3H), 2.41 (d, J=8.4 Hz, 3H). MS (ESI) m/z 489 (M+H)⁺.

Example 191 benzyl (1R,5S,6r)-6-({5-chloro-4-[1-(3-fluorobenzyl)-1H-benzimidazol-6-yl]pyridin-2-yl}carbamoyl)-3-azabicyclo[3.1.0]hexane-3-carboxylate The title compound was prepared as the bis-trifluoroacetate salt as described in Example 189 using 2-((1R,5S,6s)-3-(benzyloxycarbonyl)-3-azabicyclo[3.1.0]hexan-6-yl)acetic acid in place of 3-oxocyclobutanecarboxylic acid. $^1$H NMR (400 MHz, dimethylsulfoxide-d₆/D₂O) δ 8.56 (s, 1H), 8.08 (d, J=0.6 Hz, 1H), 7.81 (dd, J=8.3, 0.7 Hz, 1H), 7.69-7.65 (m, 1H), 7.44-7.28 (m, 7H), 7.19-7.05 (m, 3H), 5.57 (s, 2H), 5.08 (s, 2H), 3.64 (d, J=11.0 Hz, 2H), 3.49 (d, J=11.4 Hz, 2H), 2.11-2.02 (m, 2H), 1.89 (t, J=3.1 Hz, 1H). MS (ESI) m/z 596 (M+H)⁺.

Example 192

N-{5-chloro-4-[1-(3-fluorobenzyl)-1H-benzimidazol-6-yl]pyridin-2-yl}-1-methylazetidine-3-carboxamide The title compound was prepared as the bis-trifluoroacetate salt as described in Example 189 using 1-methylazetidine-3-carboxylic acid in place of 3-oxocyclobutanecarboxylic acid. $^1$H NMR (400 MHz, dimethylsulfoxide-d₆/D₂O) δ 8.62 (s, 1H), 8.16 (s, 1H), 7.84 (dd, J=8.3, 0.7 Hz, 1H), 7.72-7.68 (m, 1H), 7.43-7.32 (m, 2H), 7.23-7.12 (m, 2H), 7.14-7.05 (m, 1H), 5.65 (s, 2H), 3.65-3.46 (m, 2H), 3.45-3.26 (m, 2H), 2.78 (m, 1H), 2.55 (s, 3H). MS (ESI) m/z 450 (M+H)⁺.

Example 193

N-{5-chloro-4-[1-(3-fluorobenzyl)-1H-benzimidazol-6-yl]pyridin-2-yl}-3-methyloxetane-3-carboxamide The title compound was prepared as the bis-trifluoroacetate salt as described in Example 189 using 3-methyloxetane-3-carboxylic acid in place of 3-oxocyclobutanecarboxylic acid. $^1$H NMR (400 MHz, dimethylsulfoxide-d₆/D₂O) δ 8.89 (s, 1H), 8.54 (s, 1H), 7.89 (d, J=8.4 Hz, 1H), 7.78 (d, J=1.2 Hz, 1H), 7.44 (dd, J=8.5, 1.7 Hz, 1H), 7.41-7.34 (m, 1H), 7.22-6.97 (m, 1H), 5.59 (s, 1H), 4.76 (dd, J=62.2, 14.4 Hz, 1H), 3.65 (dd, J=73.0, 11.0 Hz, 1H), 1.21 (s, 1H). MS (ESI) m/z 451 (M+H)⁺.

Example 194

N-{5-chloro-4-[1-(3-fluorobenzyl)-1H-benzimidazol-6-yl]pyridin-2-yl}-4-hydroxy-4-(trifluoromethyl)cyclohexanecarboxamide The title compound was prepared as the bis-trifluoroacetate salt as described in Example 189 using 4-hydroxy-4-(trifluoromethyl)cyclohexanecarboxylic acid in place of 3-oxocyclobutanecarboxylic acid. $^1$H NMR (400 MHz, dimethylsulfoxide-d₆/D₂O) δ 8.81 (s, 1H), 8.40 (s, 1H), 8.13 (s, 1H), 7.87 (d, J=8.3 Hz, 1H), 7.78-7.73 (m, 1H), 7.47-7.42 (m, 1H), 7.42-7.36 (m, 1H), 7.24-7.15 (m, 2H), 7.15-7.07 (m, 1H), 5.63 (s, 2H), 1.89-1.69 (m, 7H), 1.65-1.44 (m, 2H). MS (ESI) m/z 547 (M+H)⁺.

Example 195

N-{5-chloro-4-[1-(3-fluorobenzyl)-1H-benzimidazol-6-yl]pyridin-2-yl}-1-(2,2-dimethylpropanoyl)-2,3-dihydro-1H-pyrido[2,3-b][1,4]oxazine-6-carboxamide The title compound was prepared as the bis-trifluoroacetate salt as described in Example 189 using 4-pivaloyl-3,4-dihydro-2H-benzo[b][1,4]oxazine-7-carboxylic acid in place of 3-oxocyclobutanecarboxylic acid. $^1$H NMR (400 MHz, dimethylsulfoxide-$d_6$/$D_2O$) δ 8.81 (s, 1H), 8.48 (s, 1H), 8.31 (d, J=8.0 Hz, 1H), 8.296 (s, 1H), 7.89 (dt, J=4.2, 1.7 Hz, 1H), 7.80 (d, J=1.1 Hz, 1H), 7.79-7.73 (m, 1H), 7.48 (dt, J=9.6, 3.1 Hz, 1H), 7.46-7.36 (m, 1H), 7.25-7.17 (m, 2H), 7.16-7.07 (m, 1H), 5.64 (s, 1H), 4.51 (dd, J=9.8, 5.0 Hz, 2H), 4.09 (dd, J=10.1, 5.6 Hz, 2H), 1.35 (s, 9H). MS (ESI) m/z 599 (M+H)$^+$.

Example 196

N-{5-chloro-4-[1-(3-fluorobenzyl)-1H-benzimidazol-6-yl]pyridin-2-yl}-2-(methylsulfonyl)-5-thia-2-azaspiro[3.4]octane-8-carboxamide 5,5-dioxide The title compound was prepared as the bis-trifluoroacetate salt as described in Example 189 using 2-(methylsulfonyl)-5-thia-2-azaspiro[3.4]octane-8-carboxylic acid 5,5-dioxide in place of 3-oxocyclobutanecarboxylic acid. $^1$H NMR (400 MHz, dimethylsulfoxide-$d_6$/$D_2O$) δ 8.75 (s, 1H), 8.11 (d, J=0.6 Hz, 1H), 7.86 (dd, J=8.3, 0.7 Hz, 1H), 7.75-7.70 (m, 1H), 7.46-7.36 (m, 2H), 7.24-7.14 (m, 2H), 7.15-7.06 (m, 1H), 5.62 (s, 2H), 4.25-4.17 (m, 2H), 4.12 (q, J=9.6 Hz, 2H), 3.67 (dd, J=8.7, 6.2 Hz, 1H), 2.90 (s, 3H), 2.40-2.25 (m, 1H), 2.27-2.15 (m, 1H). MS (ESI) m/z 618 (M+H)$^+$.

Example 197

N$^8$-(5-chloro-4-(1-(3-fluorobenzyl)-1H-benzo[d]imidazol-6-yl)pyridin-2-yl)-N$^2$-ethyl-5-thia-2-azaspiro[3.4]octane-2,8-dicarboxamide 5,5-dioxide The title compound was prepared as the bis-trifluoroacetate salt as described in Example 189 using 2-(ethylcarbamoyl)-5-thia-2-azaspiro[3.4]octane-8-carboxylic acid 5,5-dioxide in place of 3-oxocyclobutanecarboxylic acid. $^1$H NMR (400 MHz, dimethylsulfoxide-$d_6$/$D_2O$) δ 8.59 (s, 1H), 8.48-8.41 (m, 1H), 8.10 (d, J=0.6 Hz, 1H), 7.83 (dd, J=8.3, 0.7 Hz, 1H), 7.71-7.67 (m, 1H), 7.43-7.33 (m, 2H), 7.23-7.13 (m, 2H), 7.13-7.04 (m, 1H), 5.59 (s, 2H), 4.18 (d, J=9.7 Hz, 1H), 4.11-4.02 (m, 2H), 3.99 (d, J=9.6 Hz, 1H), 3.63 (dd, J=8.7, 6.3 Hz, 1H), 3.38-3.28 (m, 1H), 3.23-3.12 (m, 1H), 2.94 (q, J=7.1 Hz, 2H), 2.35-2.11 (m, 2H), 0.91 (t, J=7.1 Hz, 3H). MS (ESI) m/z 611 (M+H)$^+$.

Example 198

N$^8$-(5-chloro-4-(1-(3-fluorobenzyl)-1H-benzo[d]imidazol-6-yl)pyridin-2-yl)-N$^2$-phenyl-5-thia-2-azaspiro[3.4]octane-2,8-dicarboxamide 5,5-dioxide The title compound was prepared as the bis-trifluoroacetate salt as described in Example 189 using 2-(phenylcarbamoyl)-5-thia-2-azaspiro[3.4]octane-8-carboxylic acid 5,5-dioxide in place of 3-oxocyclobutanecarboxylic acid. $^1$H NMR (400 MHz, dimethylsulfoxide-$d_6$/$D_2O$) δ 8.73 (s, 1H), 8.42 (s, 1H), 8.11 (s, 1H), 7.83 (dd, J=8.3, 0.7 Hz, 1H), 7.72-7.68 (m, 1H), 7.47-7.30 (m, 4H), 7.26-7.06 (m, 4H), 7.14-7.05 (m, 1H), 6.96-6.88 (m, 1H), 5.60 (s, 2H), 4.36 (d, J=10.1 Hz, 1H), 4.29-4.21 (m, 2H), 4.18 (d, J=9.9 Hz, 1H), 3.68 (dd, J=8.8, 6.3 Hz, 1H), 3.41-3.32 (m, 1H), 3.26-3.14 (m, 1H), 2.45-2.10 (m, 2H). MS (ESI) m/z 659 (M+H)$^+$.

Example 199

N-{5-chloro-4-[1-(3-fluorobenzyl)-1H-benzimidazol-6-yl]pyridin-2-yl}-7-(cyclohexylcarbonyl)-1-thia-7-azaspiro[4.4]nonane-4-carboxamide 1,1-dioxide The title compound was prepared as the bis-trifluoroacetate salt as described in Example 189 using 7-(cyclohexylcarbonyl)-1-thia-7-azaspiro[4.4]nonane-4-carboxylic acid 1,1-dioxide in place of 3-oxocyclobutanecarboxylic acid. $^1$H NMR (400 MHz, dimethylsulfoxide-$d_6$/$D_2O$) δ 8.80 (s, 0.5H), 8.79 (s, 0.5H), 8.44 (s, 0.5H), 8.43 (s, 0.5H), 8.09 (s, 0.5H), 8.06 (s, 0.5H), 7.87 (d, J=8.6 Hz, 0.5H), 7.86 (d, J=8.6 Hz, 0.5H), 7.72 (bs, 1H), 7.48-7.36 (m, 2H), 7.25-7.16 (m, 2H), 7.11 (td, J=8.7, 2.4 Hz, 1H), 5.63 (bs, 2H), 4.11-3.65 (m, 2H), 3.75-3.58 (m, 4H), 3.26-3.12 (m, 1H), 2.46-2.04 (m, 4H), 1.87-1.40 (m, 5H), 1.39-0.99 (m, 6H). MS (ESI) m/z 664 (M+H)$^+$.

Example 200

N-{5-chloro-4-[1-(3-fluorobenzyl)-1H-benzimidazol-6-yl]pyridin-2-yl}-7-(2-methylpropanoyl)-1-thia-7-azaspiro[4.4]nonane-4-carboxamide 1,1-dioxide The title compound was prepared as the bis-trifluoroacetate salt as described in Example 189 using 7-(2-methylpropan-1-one)-1-thia-7-azaspiro[4.4]nonane-4-carboxylic acid 1,1-dioxide in place of 3-oxocyclobutanecarboxylic acid. $^1$H NMR (400 MHz, dimethylsulfoxide-$d_6$/$D_2O$) δ 8.83 (s, 0.5H), 8.81 (s, 0.5H), 8.47 (s, 0.5H), 8.44 (s, 0.5H), 8.011 (s, 0.5H), 8.04 (s, 0.5H), 7.87 (d, J=8.6 Hz, 0.5H), 7.86 (d, J=8.6 Hz, 0.5H), 7.75 (bs, 1H), 7.49-7.36 (m, 2H), 7.23-7.16 (m, 2H), 7.11 (td, J=8.7, 2.4 Hz, 1H), 5.64 (bs, 2H), 4.11-3.65 (m, 2H), 3.58-3.75 (m, 4H), 3.26-3.12 (m, 1H), 2.59-2.70 (m, 1H), 2.51-2.17 (m, 4H), (d, J=6.7 Hz, 6H). MS (ESI) m/z 624 (M+H)$^+$.

Example 201

N-{5-chloro-4-[1-(3-fluorobenzyl)-1H-benzimidazol-6-yl]pyridin-2-yl}-7-(phenylsulfonyl)-1-thia-7-azaspiro[4.4]nonane-4-carboxamide 1,1-dioxide The title compound was prepared as the bis-trifluoroacetate salt as described in Example 189 using 7-(phenylsulfonyl)-1-thia-7-azaspiro[4.4]nonane-4-carboxylic acid 1,1-dioxide in place of 3-oxocyclobutanecarboxylic acid. $^1$H NMR (400 MHz, dimethylsulfoxide-$d_6$/$D_2O$) δ 8.82 (s, 1H), 8.79 (s, 0.5H), 8.47 (s, 0.5H), 8.47 (s, 0.5H), 8.44 (s, 0.5H), 7.99 (s, 0.5H), 7.91 (s, 0.5), 7.91 (dd, J=5.1, 4.7 Hz, 0.5H), 7.88 (dd, J=5.1, 4.7 Hz, 0.5H), 7.80-7.64 (m, 3H), 7.23-7.14 (m, 2H), 7.10 (td, J=8.3, 2.3 Hz, 1H), 5.61 (s, 2H), 3.82 (d, J=11.9 Hz, 1H), 3.63 (d, J=11.2 Hz, 1H), 3.58-3.30 (m, 4H), 3.26-3.08 (m, 2H), 2.48-2.11 (m, 4H); (ESI) m/z 694 (M+H)$^+$.

Example 202

7-benzoyl-N-{5-chloro-4-[1-(3-fluorobenzyl)-1H-benzimidazol-6-yl]pyridin-2-yl}-1-thia-7-azaspiro[4.4]nonane-4-carboxamide 1,1-dioxide The title compound was prepared as the bis-trifluoroacetate salt as described in Example 189 using 7-benzoyl-1-thia-7-azaspiro[4.4]nonane-4-carboxylic acid 1,1-dioxide in place of 3-oxocyclobutanecarboxylic acid. $^1$H NMR (400 MHz, dimethylsulfoxide-$d_6$/$D_2O$) δ 8.73 (s, 1H), 8.46 (d, J=1.7 Hz, 1H), 8.09 (s, 1H), 7.86 (d, J=8.6 Hz, 1H), 7.70 (d, J=1.6 Hz, 1H), 7.70 (s, 1H), 7.50-7.24 (m, 7H), 7.23-7.14 (m, 2H), 7.10 (td, J=8.3, 2.3 Hz, 1H), 5.61 (s, 2H), 4.09 (d, J=13.0 Hz, 1H), 3.85 (d, J=13.0 Hz, 1H), 3.73-3.33 (m, 4H), 3.25-3.06 (m, 1H), 2.48-2.10 (m, 4H). MS (ESI) m/z 658 (M+H)$^+$.

Example 203

N-{5-chloro-4-[1-(3-fluorobenzyl)-1H-benzimidazol-6-yl]pyridin-2-yl}-7-ethyl-1-thia-7-azaspiro[4.4]nonane-4-carboxamide 1,1-dioxide The title compound was prepared as the bis-trifluoroacetate salt as described in Example 189 using 7-ethyl-1-thia-7-azaspiro[4.4]nonane-4-carboxylic acid 1,1-dioxide in place of 3-oxocyclobutanecarboxylic acid. $^1$H NMR (400 MHz, dimethylsulfoxide-$d_6$/$D_2O$) δ 8.55 (d, J=1.7 Hz, 1H), 8.46 (s, 1H), 8.11 (s, 1H), 7.84 (d, J=8.3 Hz, 1H), 7.68-7.63 (m, 1H), 7.43-7.31 (m, 2H), 7.19-7.05 (m, 3H), 5.58 (bs, 2H), 4.14-3.70 (m, 2H), 3.69-3.29 (m, 5H), 3.24-3.14 (m, 2H), 2.84-2.64 (m, 1H), 2.49-2.13 (m, 3H), 1.27-1.11 (m, 3H). MS (ESI) m/z 582 (M+H)$^+$.

Example 204

N-{5-chloro-4-[1-(3-fluorobenzyl)-1H-benzimidazol-6-yl]pyridin-2-yl}-2-oxohexahydro-2H-cyclopenta[d][1,3]oxazole-5-carboxamide The title compound was prepared as the bis-trifluoroacetate salt as described in Example 189 using 2-oxohexahydro-2H-cyclopenta[d]oxazole-5-carboxylic acid in place of 3-oxocyclobutanecarboxylic acid. $^1$H NMR (400 MHz, dimethylsulfoxide-$d_6$/$D_2O$) δ 8.68 (s, 1H), 8.40 (s, 1H), 8.11 (d, J=0.6 Hz, 1H), 7.84 (dd, J=8.3, 0.7 Hz, 1H), 7.71 (dd, J=1.6, 0.8 Hz, 1H), 7.44-7.35 (m, 2H), 7.24-7.14 (m, 2H), 7.15-7.03 (m, 1H), 5.60 (s, 2H), 4.98-4.89 (m, 1H), 4.16-4.07 (m, 1H), 3.16-2.97 (m, 1H), 2.35 (dt, J=14.1, 7.0 Hz, 1H), 2.29-2.19 (m, 1H), 2.15-2.04 (m, 1H), 1.98-1.86 (m, 1H). MS (ESI) m/z 506 (M+H)$^+$.

Example 205

N-{5-chloro-4-[1-(3-fluorobenzyl)-1H-benzimidazol-6-yl]pyridin-2-yl}-7-(methylsulfonyl)-1-thia-7-azaspiro[4.4]nonane-4-carboxamide 1,1-dioxide The title compound was prepared as a 1:1 mixture of stereoisomeric bis-trifluoroacetate salts as described in Example 189 using 7-(methylsulfonyl)-1-thia-7-azaspiro[4.4]nonane-4-carboxylic acid 1,1-dioxide in place of 3-oxocyclobutanecarboxylic acid. $^1$H NMR (400 MHz, dimethylsulfoxide-$d_6$/$D_2O$) δ 8.57 (s, 0.5H), 8.56 (s, 0.5H), 8.44 (s, 0.5H), 8.44 (s, 0.5H), 8.011 (m, 1H), 7.86-7.80 (m, 1H, overlapping doublets), 7.70-7.66 (m, 1H), 7.45-7.33 (m, 2H), 7.21-7.03 (m, 3H), 5.58 (bs, 2H), 3.89 (d, J=11.9 Hz, 0.5H), 3.77 (d, J=11.5 Hz, 0.5H), 3.66 (d, J=6.2 Hz, 0.5H), 3.64 (d, J=6.7 Hz, 0.5H), 3.59-3.47 (m, 1H), 3.46-3.31 (m, 3H) 2.85 (s, 1.5H), 2.83 (s, 1.5H), 2.70-2.57 (m, 1H), 2.48-2.14 (m, 4H). MS (ESI) m/z 632 (M+H)$^+$.

Example 206

(2E)-N-carbamoyl-N'-{5-chloro-4-[1-(3-fluorobenzyl)-1H-benzimidazol-6-yl]pyridin-2-yl}but-2-enediamide The title compound was prepared as the bis-trifluoroacetate salt as described in Example 189 using (E)-4-oxo-4-ureidobut-2-enoic acid in place of 3-oxocyclobutanecarboxylic acid. $^1$H NMR (400 MHz, dimethylsulfoxide-$d_6$/$D_2O$) δ 8.49 (s, 1H), 8.45 (s, 1H), 8.05 (s, 1H), 7.87 (d, J=8.3 Hz, 1H), 7.82-7.73 (m, 2H), 7.68-7.60 (m, 1H), 7.47-7.42 (m, 1H), 7.42-7.36 (m, 3H), 7.24-7.15 (m, 2H), 7.19-7.07 (m, 1H), 5.64 (s, 2H). MS (ESI) m/z 493 (M+H)$^+$.

Example 207

N-{5-chloro-4-[1-(3-fluorobenzyl)-1H-benzimidazol-6-yl]pyridin-2-yl}cyclopropane-1,1-dicarboxamide The title compound was prepared as the bis-trifluoroacetate salt as described in Example 189 using 1-carbamoylcyclopropanecarboxylic acid in place of 3-oxocyclobutanecarboxylic acid. $^1$H NMR (400 MHz, dimethylsulfoxide-$d_6$/$D_2O$) δ 8.61 (s, 1H), 8.42 (s, 1H), 8.11 (s, 1H), 7.82 (dd, J=7.5, 5.1 Hz, 1H), 7.69 (s, 1H), 7.44-7.32 (m, 2H), 7.23-7.13 (m, 2H), 7.13-7.04 (m, 1H), 5.59 (s, 2H), 1.65-1.55 (m, 2H), 1.54-1.36 (m, 2H). MS (ESI) m/z 464 (M+H)$^+$.

Example 208

N-{5-chloro-4-[1-(3-fluorobenzyl)-1H-benzimidazol-6-yl]pyridin-2-yl}-1H-pyrazole-4-carboxamide The title compound was prepared as the bis-trifluoroacetate salt as described in Example 189 using 1H-pyrazole-4-carboxylic acid in place of 3-oxocyclobutanecarboxylic acid. $^1$H NMR (400 MHz, dimethylsulfoxide-$d_6$/$D_2O$) δ 8.62 (s, 1H), 8.16 (s, 1H), 7.84 (dd, J=8.3, 0.7 Hz, 1H), 7.72-7.68 (m, 1H), 7.43-7.32 (m, 2H), 7.23-7.12 (m, 2H), 7.14-7.05 (m, 1H), 5.60 (s, 2H), 3.57-3.46 (m, 1H). MS (ESI) m/z 447 (M+H)$^+$.

Example 209 trans-N-{5-chloro-4-[1-(tetrahydro-2H-pyran-4-ylmethyl)-1H-benzimidazol-6-yl]pyridin-2-yl}cyclohexane-1,4-diamine The title compound was prepared as described in Example 179B, using (1r,4r)-cyclohexane-1,4-diamine in place of tert-butyl 2-amino-7-azaspiro[3.5]nonane-7-carboxylate. Purification by reverse-phase preparative HPLC (Phenomenex Luna C8(2) 100 Å AXIA column) using a gradient of 10-95% acetonitrile/0.1% trifluoroacetic acid in water afforded the title compound as the trifluoroacetate salt. This was dissolved in methanol and loaded on a Bond Elut® MEGA BE-SCX (5 GM, prewashed with 50% methanol/dichloromethane) cartridge with methanol and washed with 2M ammonia in methanol and concentrated to give the title compound (100 mg). ¹H NMR (400 MHz, dimethylsulfoxide-$d_6$) δ 8.30 (s, 1H), 8.06 (s, 1H), 7.76-7.67 (m, 2H), 7.24 (dd, J=8.3, 1.6, 1H), 6.69 (d, J=7.6, 1H), 6.53 (s, 1H), 4.19 (d, J=7.2, 2H), 3.86-3.78 (m, 2H), 3.70-3.57 (m, 2H), 3.25-3.18 (m, 2H), 2.87-2.78 (m, 1H), 2.15-2.04 (m, 1H), 2.04-1.83 (m, 4H), 1.43-1.16 (m, 7H). MS (ESI) m/z 440 (M+H)⁺.

Example 210

N-{5-chloro-4-[1-(tetrahydro-2H-pyran-4-ylmethyl)-1H-benzimidazol-6-yl]pyridin-2-yl}piperidine-4-carboxamide Example 210A 5-chloro-4-(4,4,5,5-tetramethyl-1,3,2-dioxaborolan-2-yl)pyridin-2-amine A mixture of 4-bromo-5-chloropyridin-2-amine (7 g, 33.7 mmol), 4,4,4',4',5,5,5',5'-octamethyl-2,2'-bi(1,3,2-dioxaborolane) (25.7 g, 101 mmol) and potassium acetate (4.97 g, 50.6 mmol) in N,N-dimethylformamide (200 mL) was stirred under nitrogen atmosphere. Pd(dppf)Cl$_2$·dichloromethane adduct (0.741 g, 1.012 mmol) was added rapidly to the suspension. The resulting suspension was stirred at about 80° C. for 16 hours. After cooling to room temperature, the suspension was filtered and the filtrate was diluted with water. The aqueous layer was back extracted with methylene chloride (3×50 mL). The combined aqueous layers were concentrated. The crude product was washed with ethanol and filtered. The filtrate was combined with the organic layer from the previous extraction and concentrated in vacuo to afford the title compound (~60% purity by ¹HNMR analysis). MS (ESI⁺) m/z 255.1 (M+H)⁺.

Example 210B 5-chloro-4-(1-((tetrahydro-2H-pyran-4-yl)methyl)-1H-benzo[d]imidazol-6-yl)pyridin-2-amine A mixture of Example 13C (12 g, 40.7 mmol), Example 210A (12.42 g, 48.8 mmol) and saturated aqueous sodium carbonate (40 mL, 122 mmol) in dimethoxyethane (150 mL) was stirred under nitrogen atmosphere. Pd(dppf)Cl$_2$·dichloromethane adduct (0.892 g, 1.220 mmol) was added rapidly to the suspension. The resulting suspension was stirred at about 110° C. for 3 hours. After cooling to room temperature, the suspension was filtered and the filtrate was concentrated onto silica gel. Silica gel flash chromatography (eluting with 100% ethyl acetate) afforded the title compound. MS (ESI⁺) m/z 343.0 (M+H)⁺.

Example 210C

N-{5-chloro-4-[1-(tetrahydro-2H-pyran-4-ylmethyl)-1H-benzimidazol-6-yl]pyridin-2-yl}piperidine-4-carboxamide To a solution of 1-(tert-butoxycarbonyl)piperidine-4-carboxylic acid (201 mg, 0.875 mmol) in N,N-dimethylformamide (875 µl) at 0° C. was added 1-chloro-N,N,2-trimethylpropenylamine (116 µl, 0.875 mmol). The mixture was stirred at ambient for 30 minutes then a solution of Example 210B (120 mg, 0.350 mmol) and pyridine (70.8 µl, 0.875 mmol) in N,N-dimethylformamide (875 µl) was added. The reaction mixture was then stirred at ambient temperature overnight. The reaction mixture was then poured into a 60 mL separatory funnel, and 25 mL of ethyl acetate was added. The organic mixture was washed with two portions of 10% aqueous potassium carbonate (20 mL each), saturated aqueous sodium bicarbonate (25 mL), and saturated aqueous brine (20 mL), dried over anhydrous magnesium sulfate, filtered and concentrated. Purification was by silica gel flash chromatography (Isco®, Redi-Sep® column) eluting with a gradient of 50-100% ethyl acetate/hexane followed by 10% of a 2:1 methanol:water mixture in ethyl acetate. The product obtained was purified further by recrystallization in ethyl acetate/hexane to afford the pure tert-butyloxycarbonyl protected intermediate. The intermediate was dissolved in 1:1 dichloromethane/methanol mixture (2 mL) and cooled to 0° C. A 2 molar solution of hydrochloric acid in diethyl ether (4 mL) was slowly added and the mixture was then stirred at ambient temperature for 2 hours. Methanol was added (2 mL) to dissolve the solids that precipitated and then the mixture was concentrated to afford the title compound as a bis hydrochloric acid salt. ¹H NMR (500 MHz, methanol-$d_4$) δ ppm 1.40-1.53 (m, 2H), 1.53-1.65 (m, 2H), 1.93-2.05 (m, 2H), 2.08-2.20 (m, 2H), 2.24-2.40 (m, 1H), 2.81-2.92 (m, 1H), 3.05-3.16 (m, 2H), 3.33-3.44 (m, 2H), 3.49 (dt, J=13.0, 3.8 Hz, 2H), 3.91-4.02 (m, 2H), 4.49 (d, J=7.3 Hz, 2H), 7.76 (dd, J=8.5, 1.4 Hz, 1H), 7.98 (d, J=8.6 Hz, 1H), 8.17 (s, 1H), 8.30 (s, 1H), 8.46 (s, 1H), 9.47 (s, 1H). MS (ESI⁺) m/z 454.1 (M+H)⁺.

Example 211

N-{5-chloro-4-[1-(tetrahydro-2H-pyran-4-ylmethyl)-1H-benzimidazol-6-yl]pyridin-2-yl}-2-oxohexahydro-2H-cyclopenta[d][1,3]oxazole-5-carboxamide To a solution of 2-oxohexahydro-2H-cyclopenta[d]oxazole-5-carboxylic acid (374 mg, 2.188 mmol) in N,N-dimethylformamide (2188 µl) at 0° C. was added 1-chloro-N,N,2-trimethylpropenylamine (289 µl, 2.188 mmol). The mixture was stirred at ambient temperature for 30 minutes then a solution of Example 210B (300 mg, 0.875 mmol) and pyridine (177 µl, 2.188 mmol) in N,N-dimethylformamide (2188 µl) was added. The reaction mixture was then stirred at ambient temperature. After stirring at ambient temperature for 16 hours the reaction mixture was poured into a 60 mL separatory funnel, 25 mL of ethyl acetate was added and the organic mixture was washed with two portions of 10% aqueous potassium carbonate solution (20 mL each), saturated aqueous sodium bicarbonate (25 mL), and saturated aqueous brine (20 mL), dried over anhydrous magnesium sulfate, filtered, and concentrated. Purification by silica gel flash chromatography (Isco®, Redi-Sep® column, eluted with a gradient of 50-100% ethyl acetate/hexane then switched to 10% of a 2:1 methanol:water mixture in ethyl acetate) provided the crude title compound. The crude material was purified further by reverse-phase HPLC (Phenomenex Luna C8(2) 100 Å AXIA column) using a gradient of 10-95% acetonitrile/0.1% trifluoroacetic acid in water to afford the title compound as a trifluoroacetic acid salt. The product was dissolved in 25 mL of ethyl acetate, poured into a 60 mL separatory funnel and washed with an aqueous solution of 10% potassium carbonate (25 mL), and saturated aqueous brine (20 mL), dried over anhydrous magnesium sulfate, filtered and concentrated to afford the title compound. ¹H NMR (400 MHz, DMSO-$d_6$) δ ppm 1.22-1.36 (m, 2H), 1.35-1.46 (m, 2H), 1.79-1.91 (m, 1H), 1.99-2.15 (m, 2H), 2.14-2.27 (m, 1H), 2.31 (dt, J=14.0, 7.1 Hz, 1H), 2.94-3.08 (m, 1H), 3.22 (td, J=11.6, 2.2 Hz, 2H), 3.75-3.89 (m, 2H), 4.05-4.14 (m, 1H), 4.21 (d, J=7.2 Hz, 2H), 4.86-4.99 (m, 1H), 7.29 (dd, J=8.3, 1.6 Hz, 1H), 7.70 (s, 1H), 7.77 (d, J=8.4 Hz, 1H), 7.81 (d, J=1.4 Hz, 1H), 8.22 (s, 1H), 8.33 (s, 1H), 8.48 (s, 1H), 10.77 (s, 1H). MS (ESI$^+$) m/z 496.4 (M+H)$^+$.

Example 212

(2s,4r)-N-{5-chloro-4-[1-(3-fluorobenzyl)-1H-benzimidazol-6-yl]pyridin-2-yl}-6-azaspiro[3.4]octan-2-amine Example 212A tert-butyl 2-(5-chloro-4-(1-(3-fluorobenzyl)-1H-benzo[d]imidazol-6-yl)pyridin-2-ylamino)-6-azaspiro[3.4]octane-6-carboxylate A mixture of Example 8D (300 mg, 0.843 mmol), tert-butyl 2-amino-6-azaspiro[3.4]octane-6-carboxylate (573 mg, 2.53 mmol) and diisopropylethyl amine (221 µl, 1.265 mmol) in dimethylsulfoxide (1686 µl) was stirred at 120° C. for 24 hours. After cooling to ambient temperature, water (25 mL) and ethyl acetate (25 mL) were added and the mixture was poured into a 60 mL separatory funnel. The aqueous layer was removed and the organic layer was washed with 20 mL of saturated aqueous brine, dried over anhydrous magnesium sulfate, filtered and concentrated. The crude material obtained was purified by silica gel flash chromatography (Isco®, Redi-Sep® column) eluting with a gradient of 50-100% ethyl acetate/hexane to afford the title compound. MS (ESI$^+$) m/z 562.5 (M+H)$^+$.

Example 212B (2s,4r)-tert-butyl 2-(5-chloro-4-(1-(3-fluorobenzyl)-1H-benzo[d]imidazol-6-yl)pyridin-2-ylamino)-6-azaspiro[3.4]octane-6-carboxylate Preparative SFC chiral separation of Example 212A (393 mg) was performed on a THAR/Waters SFC 80 system running under SuperChrom software control and equipped with an 8-way preparative column switcher, carbon dioxide pump, modifier pump, automated back pressure regulator, UV detector, and 6-position fraction collector. The mobile phase comprised of supercritical carbon dioxide supplied by a Dewar of bone-dry non-certified carbon dioxide pressurized to 350 psi with a modifier of methanol with 0.5% of diethyl amine at a flow rate of 70 g/min. UV detection was set to collect at a wavelength of 220 nm, the column was at ambient temperature, and the backpressure regulator was set to maintain 100 bar. The sample was dissolved in methanol at a concentration of 50 mg/mL. The sample was loaded into the modifier stream in 0.5 mL (50 mg) injections. The mobile phase was held isocraticly at 30% methanol:carbon dioxide. Fraction collection was time triggered. The instrument was fitted with a CHIRALPAK IA column (21 mm i.d.×250 mm length with 5 µm particles). The chiral separation afforded the title compound as the faster eluting enantiomer and Example 213A (slower eluting enantiomer). MS (ESI$^+$) m/z 562.5 (M+H)$^+$.

Example 212C (2s,4r)-N-{5-chloro-4-[1-(3-fluorobenzyl)-1H-benzimidazol-6-yl]pyridin-2-yl}-6-azaspiro[3.4]octan-2-amine Example 212B (140 mg, 0.249 mmol) was dissolved in 1:1 dichloromethane/methanol mixture (2 mL) and the mixture was cooled to 0° C. A 2 molar solution of hydrochloric acid in diethyl ether (6 mL, 10.00 mmol) was slowly added and the mixture was stirred at ambient temperature for 2 hours. Methanol was added (3 mL) to dissolve the precipitate and the mixture was concentrated to give to title compound as a bis hydrochloric acid salt. $^1$H NMR (400 MHz, Methanol-d$_4$) δ ppm 2.14 (t, J=7.4 Hz, 2H), 2.24-2.34 (m, 2H), 2.70-2.83 (m, 2H), 3.28-3.34 (m, 2H), 3.41 (s, 2H), 4.38 (p, J=7.7 Hz, 1H), 5.86 (s, 2H), 7.10 (s, 1H), 7.11-7.19 (m, 1H), 7.25-7.34 (m, 2H), 7.41-7.50 (m, 1H), 7.79 (dd, J=8.7, 1.5 Hz, 1H), 8.00-8.08 (m, 2H), 8.11 (s, 1H), 9.67 (s, 1H). MS (ESI$^+$) m/z 462.4 (M+H)$^+$.

Example 213

(2r,4s)-N-{5-chloro-4-[1-(3-fluorobenzyl)-1H-benzimidazol-6-yl]pyridin-2-yl}-6-azaspiro[3.4]octan-2-amine Example 213A (2r,4s)-tert-butyl 2-(5-chloro-4-(1-(3-fluorobenzyl)-1H-benzo[d]imidazol-6-yl)pyridin-2-ylamino)-6-azaspiro[3.4]octane-6-carboxylate The title compound was prepared as described in Example 212B, and corresponds to the slower eluting enantiomer under the SFC conditions described in Example 212B. MS (ESI$^+$) m/z 562.5 (M+H)$^+$.

Example 213B (2r,4s)-N-{5-chloro-4-[1-(3-fluorobenzyl)-1H-benzimidazol-6-yl]pyridin-2-yl}-6-azaspiro[3.4]octan-2-amine The title compound was prepared using the conditions described in Example 212C using Example 213A in place of Example 212B to afford the bis hydrochloric acid salt. $^1$H NMR (400 MHz, Methanol-d$_4$) δ ppm 2.14 (t, J=7.4 Hz, 2H), 2.24-2.34 (m, 2H), 2.70-2.83 (m, 2H), 3.28-3.34 (m, 2H), 3.41 (s, 2H), 4.38 (p, J=7.7 Hz, 1H), 5.86 (s, 2H), 7.10 (s, 1H), 7.11-7.19 (m, 1H), 7.25-7.34 (m, 2H), 7.41-7.50 (m, 1H), 7.79 (dd, J=8.7, 1.5 Hz, 1H), 8.00-8.08 (m, 2H), 8.11 (s, 1H), 9.67 (s, 1H). MS (ESI$^+$) m/z 462.4 (M+H)$^+$.

Example 214

(2s,4r)-N-{5-chloro-4-[1-(3-fluorobenzyl)-1H-benzimidazol-6-yl]pyridin-2-yl}-6-azaspiro[3.5]nonan-2-amine Example 214A tert-butyl 2-(5-chloro-4-(1-(3-fluorobenzyl)-1H-benzo[d]imidazol-6-yl)pyridin-2-ylamino)-6-azaspiro[3.5]nonane-6-carboxylate The title compound was prepared using the conditions described in Example 212A using tert-butyl 2-amino-6-azaspiro[3.5]nonane-6-carboxylate in place of tert-butyl 2-amino-6-azaspiro[3.4]octane-6-carboxylate. MS (ESI$^+$) m/z 576.4 (M+H)$^+$.

Example 214B (2s,4r)-tert-butyl 2-(5-chloro-4-(1-(3-fluorobenzyl)-1H-benzo[d]imidazol-6-yl)pyridin-2-ylamino)-6-azaspiro[3.5]nonane-6-carboxylate Preparative SFC chiral separation of Example 214A (485 mg) was performed on a THAR/Waters SFC 80 system running under SuperChrom software control and equipped with an 8-way preparative column switcher, carbon dioxide pump, modifier pump, automated back pressure regulator, UV detector, and 6-position fraction collector. The mobile phase comprised of supercritical carbon dioxide supplied by a Dewar of bone-dry non-certified carbon dioxide pressurized to 350 psi with a modifier of methanol with 0.5% of diethyl amine at a flow rate of 70 g/min. UV detection was set to collect at a wavelength of 220 nm, the column was at ambient temperature, and the backpressure regulator was set to maintain 100 bar. The sample was dissolved in methanol at a concentration of 50 mg/mL. The sample was loaded into the modifier stream in 0.5 mL (50 mg) injections. The mobile phase was held isocraticly at 30% methanol:carbon dioxide. Fraction collection was time triggered. The instrument was fitted with a CHIRALPAK IA column (21 mm i.d.×250 mm length with 5 μm particles). The chiral separation afforded the title compound as the faster eluting enantiomer and Example 215A (slower eluting enantiomer). MS (ESI$^+$) m/z 576.4 (M+H)$^+$.

Example 214C (2s,4r)-N-{5-chloro-4-[1-(3-fluorobenzyl)-1H-benzimidazol-6-yl]pyridin-2-yl}-6-azaspiro[3.5]nonan-2-amine The title compound was prepared using the conditions described in Example 212C using Example 214B in place of Example 212B to afford the bis hydrochloric acid salt. $^1$H NMR (400 MHz, Methanol-$d_4$) δ ppm 1.70-1.86 (m, 4H), 1.96-2.10 (m, 2H), 2.64-2.77 (m, 2H), 3.07-3.17 (m, 2H), 3.28 (s, 2H), 4.43 (p, J=7.9 Hz, 1H), 5.87 (s, 2H), 7.08-7.19 (m, 2H), 7.26-7.35 (m, 2H), 7.41-7.51 (m, 1H), 7.79 (dd, J=8.7, 1.5 Hz, 1H), 8.01-8.09 (m, 2H), 8.11 (s, 1H), 9.68 (s, 1H). MS (ESI$^+$) m/z 475.8 (M+H)$^+$.

Example 215

(2r,4s)-N-{5-chloro-4-[1-(3-fluorobenzyl)-1H-benzimidazol-6-yl]pyridin-2-yl}-6-azaspiro[3.5]nonan-2-amine

Example 215A ((2r,4s)-tert-butyl 2-(5-chloro-4-(1-(3-fluorobenzyl)-1H-benzo[d]imidazol-6-yl)pyridin-2-ylamino)-6-azaspiro[3.5]nonane-6-carboxylate The title compound was prepared as described in Example 214B, and corresponds to the slower eluting enantiomer under the SFC conditions described in Example 214B. MS (ESI$^+$) m/z 576.4 (M+H)$^+$.

Example 215B (2r,4s)-N-{5-chloro-4-[1-(3-fluorobenzyl)-1H-benzimidazol-6-yl]pyridin-2-yl}-6-azaspiro[3.5]nonan-2-amine The title compound was prepared as described in Example 212C, using Example 215A in place of Example 212B to afford the bis hydrochloric acid salt. $^1$H NMR (400 MHz, Methanol-$d_4$) δ ppm 1.77-1.95 (m, 4H), 2.06-2.19 (m, 2H), 2.46-2.60 (m, 2H), 3.06-3.14 (m, 2H), 3.14-3.22 (m, 2H), 4.39 (p, J=7.8 Hz, 1H), 5.86 (s, 2H), 7.08-7.19 (m, 2H), 7.26-7.35 (m, 2H), 7.41-7.51 (m, 1H), 7.79 (dd, J=8.7, 1.5 Hz, 1H), 8.01-8.09 (m, 2H), 8.11 (s, 1H), 9.68 (s, 1H). MS (ESI$^+$) m/z 475.7 (M+H)$^+$.

Example 216

(3S)—N-{5-chloro-4-[1-(tetrahydro-2H-pyran-4-ylmethyl)-1H-benzimidazol-6-yl]pyridin-2-yl}piperidine-3-carboxamide The title compound was prepared using the conditions described in Example 210C using (S)-1-(tert-butoxycarbonyl)piperidine-3-carboxylic acid in place of 1-(tert-butoxycarbonyl)piperidine-4-carboxylic acid to afford the bis hydrochloric acid salt. $^1$H NMR (500 MHz, Methanol-$d_4$) δ ppm 1.42-1.55 (m, 2H), 1.55-1.65 (m, 2H), 1.83-1.95 (m, 2H), 1.95-2.05 (m, 1H), 2.16-2.26 (m, 1H), 2.28-2.42 (m, 1H), 3.04-3.16 (m, 2H), 3.28-3.49 (m, 4H), 3.90-4.02 (m, 2H), 4.53 (d, J=7.3 Hz, 2H), 7.83 (dd, J=8.7, 1.4 Hz, 1H), 8.03 (d, J=8.5 Hz, 1H), 8.22 (s, 1H), 8.28 (d, J=1.4 Hz, 1H), 8.52 (s, 1H), 9.66 (s, 1H). MS (ESI$^+$) m/z 454.4 (M+H)$^+$.

Example 217

(3R)—N-{5-chloro-4-[3-(3-fluorobenzoyl)-1H-indol-5-yl]pyridin-2-yl}piperidine-3-carboxamide

Example 217A (5-bromo-1H-indol-3-yl)(3-fluorophenyl)methanone

5-Bromo-1H-indole (482 mg, 2.5 mmol), 3-fluorobenzoyl chloride (390 mg, 2.5 mmol) and aluminum trichloride (328 mg, 2.5 mmol) were dissolved in 5 mL of 1,2-dichloroethane. The reaction mixture was heated at 110° C. for 2 minutes in a Biotage® Initiator® microwave reactor then quenched with 50 mL of water. The aqueous phase was extracted with three 20 mL portions of ethyl acetate. The organic extracts were then combined, dried over sodium sulfate, filtered, and concentrated to give the title compound.

Example 217B (3R)—N-{5-chloro-4-[3-(3-fluorobenzoyl)-1H-indol-5-yl]pyridin-2-yl}piperidine-3-carboxamide The title compound was prepared as described in Example 14E using Example 217A in place of Example 14D. $^1$H NMR (400 MHz, DMSO-$d_6$) δ 1.78 (m, 3H), 2.08 (m, 1H), 3.10 (m, 4H), 3.32 (m, 1H), 7.39 (m, 2H), 7.58 (m, 4H), 8.00 (s, 1H), 8.17 (s, 1H), 8.35 (s, 1H), 8.44 (s, 1H), 10.67 (br s, 1H), 12.18 (br s, 1H). MS (ESI) m/e 477.1 (M+H)$^+$.

Example 218

(3R)—N-{5-chloro-4-[1-(3-fluorobenzyl)-1H-imidazo[4,5-b]pyrazin-6-yl]pyridin-2-yl}piperidine-3-carboxamide

Example 218A 6-bromo-N2-(3-fluorobenzyl)pyrazine-2,3-diamine 3,5-Dibromopyrazin-2-amine (2 g, 7.9 mmol), 3-fluorobenzylamine (0.99 g, 7.9 mmol) and N,N-diisopropylethylamine (1.5 mL, 8.6 mmol) were dissolved in 50 mL of n-butanol and refluxed for 48 hours. After cooling to room temperature, the reaction was partitioned between ethyl acetate and water (100 mL each). The aqueous layer was removed and the organic phase was washed with 50 mL of aqueous saturated aqueous brine followed by 50 mL of aqueous saturated ammonium chloride, and was dried over magnesium sulfate, filtered and concentrated. Purification by silica gel flash chromatography eluting with 20% ethyl acetate in dichloromethane provided the title compound.

Example 218B 6-bromo-1-(3-fluorobenzyl)-1H-imidazo[4,5-b]pyrazine

The title compound was prepared as described in Example 8C, using Example 218A in place of Example 8B.

Example 218C (3R)—N-{5-chloro-4-[1-(3-fluorobenzyl)-1H-imidazo[4,5-b]pyrazin-6-yl]pyridin-2-yl}piperidine-3-carboxamide The title compound was prepared as described in Example 14E, using Example 218B in place of Example 14D. The hydrochloride salt was prepared by dissolving the resultant solid in methanol and adding 2 molar hydrogen chloride in diethyl ether. After concentrating under reduced pressure, the title compound was obtained. $^1$H NMR (400 MHz, DMSO-$d_6$) δ 1.77 (m, 3H), 2.10 (m, 1H), 2.89 (m, 1H), 3.11 (m, 3H), 3.34 (br d, 1H), 5.57 (s, 2H), 7.10 (br t, 1H), 7.28 (m, 2H), 7.40 (m, 1H), 8.36 (s, 1H), 8.52 (s, 1H), 8.83 (s, 1H), 8.99 (s, 1H), 10.77 (br s, 1H). MS (ESI) m/e 466.1 (M+H)$^+$.

Example 219

N-(5-chloro-4-{1-[2-(dimethylamino)-2-oxoethyl]-2,3-dihydro-1H-indol-6-yl}pyridin-2-yl)piperidine-3-carboxamide The title compound was prepared as described in Example 1D using N,N-dimethyl-2-chloroacetamide in place of 1-(bromomethyl)-3-fluorobenzene and also using the BOC-protected intermediate from Example 2 in place of 6-bromoindoline. $^1$H NMR (400 MHz, DMSO-$d_6$) δ 10.94 (s, 1H), 8.46 (dd, J=6.4, 4.2 Hz, 1H), 8.43 (s, 1H), 8.08 (s, 1H), 7.12 (d, J=7.4 Hz, 1H), 6.56 (dd, J=7.4, 1.5 Hz, 1H), 6.46 (d, J=1.5 Hz, 1H), 4.04 (s, 2H), 3.51 (t, J=8.5 Hz, 2H), 3.15 (dd, J=10.0, 6.2 Hz, 2H), 3.12-3.01 (m, 2H), 2.99 (s, 3H), 2.97-2.85 (m, 3H), 2.81 (s, 3H), 2.03 (d, J=8.4 Hz, 1H), 1.81 (s, 1H), 1.62 (d, J=10.6 Hz, 2H). MS (ESI) m/z 442 (M+H)$^+$.

Example 220

N-(5-chloro-4-{1-[2-(morpholin-4-yl)-2-oxoethyl]-2,3-dihydro-1H-indol-6-yl}pyridin-2-yl)piperidine-3-carboxamide The title compound was prepared as described in Example 1D using 4-(chloroacetyl)morpholine in place of 1-(bromomethyl)-3-fluorobenzene and also using the BOC-protected intermediate from Example 2 in place of 6-bromoindoline. $^1$H NMR (400 MHz, DMSO-$d_6$) δ 10.94 (s, 1H), 8.46 (s, 1H), 8.44 (s, 1H), 8.09 (s, 1H), 7.13 (d, J=7.5 Hz, 1H), 6.59 (dd, J=7.4, 1.5 Hz, 1H), 6.49 (d, J=1.5 Hz, 1H), 4.07 (s, 2H), 3.64-3.37 (m, 6H), 3.17 (d, J=12.6 Hz, 4H), 3.12-2.82 (m, 7H), 2.03 (s, 1H), 1.81 (s, 1H), 1.64 (s, 2H). MS (ESI) m/z 484 (M+H)$^+$.

Example 221

N-(5-chloro-4-{1-[2-oxo-2-(pyrrolidin-1-yl)ethyl]-2,3-dihydro-1H-indol-6-yl}pyridin-2-yl)piperidine-3-carboxamide The title compound was prepared as described in Example 1D using 1-(chloroacetyl)pyrrolidine in place of 1-(bromomethyl)-3-fluorobenzene and also using the BOC-protected intermediate from Example 2 in place of 6-bromoindoline. $^1$H NMR (400 MHz, DMSO-$d_6$) δ 10.94 (s, 1H), 8.43 (s, 1H), 8.08 (s, 1H), 7.12 (d, J=7.4 Hz, 1H), 6.57 (dd, J=7.4, 1.5 Hz, 1H), 6.47 (d, J=1.6 Hz, 1H), 3.96 (s, 2H), 3.54 (t, J=8.5 Hz, 2H), 3.45 (q, J=6.5 Hz, 2H), 3.16 (d, J=12.3 Hz, 2H), 3.11-2.83 (m, 7H), 2.03 (s, 1H), 1.97-1.70 (m, 5H), 1.63 (s, 2H). MS (ESI) m/z 468 (M+H)$^+$.

Example 222

(3R)—N-{5-chloro-4-[3-cyano-1-(tetrahydro-2H-pyran-4-ylmethyl)-1H-pyrrolo[3,2-b]pyridin-6-yl]pyridin-2-yl}piperidine-3-carboxamide Example 222A 6-bromo-1-((tetrahydro-2H-pyran-4-yl)methyl)-1H-pyrrolo[3,2-b]pyridine-3-carbonitrile To a solution mixture of 6-bromo-1H-pyrrolo[3,2-b]pyridine-3-carbonitrile (500 mg, 2.252 mmol) in N,N-dimethylformamide (4504 μl) was added sodium hydride (59.4 mg, 2.477 mmol) followed by 4-(bromomethyl)tetrahydro-2H-pyran (444 mg, 2.477 mmol). The mixture was then stirred at 100° C. After 2 hours, the mixture was cooled to ambient temperature and poured into a 120 mL separatory funnel. The mixture was diluted with 50 mL of ethyl acetate and the organic mixture was washed with a 0.5 molar solution of aqueous sodium bicarbonate (1×50 mL), water (1×50 mL), and saturated aqueous brine (1×30 mL), dried over anhydrous magnesium sulfate, filtered and concentrated. Purification by silica gel flash chromatography (Isco®, Redi-Sep® column) eluting with a gradient of 30-100% ethyl acetate/hexane afforded the title compound. MS (ESI$^+$) m/z 320.1 (M+H)$^+$.

Example 222B (R)-tert-butyl 3-(5-chloro-4-(3-cyano-1-((tetrahydro-2H-pyran-4-yl)methyl)-1H-pyrrolo[3,2-b]pyridin-6-yl)pyridin-2-ylcarbamoyl)piperidine-1-carboxylate To a mixture of Example 1B (250 mg, 0.597 mmol), 4,4,4',4',5,5,5',5'-octamethyl-2,2'-bi(1,3,2-dioxaborolane) (152 mg, 0.597 mmol), 1,1'-bis(diphenylphosphino)ferrocene-palladium(II)dichloride dichloromethane complex (29.3 mg, 0.036 mmol) and potassium acetate (1.791 mmol) was added dioxane (2970 μl). The mixture was evacuated and backfilled with nitrogen twice, then stirred at 100° C. for 3 hours. Example 222A (172 mg, 0.537 mmol) was added as a dioxane (5 mL) solution followed by another portion of 1,1'-bis(diphenylphosphino)ferrocene-palladium(II)dichloride dichloromethane complex (15 mg, 0.018 mmol) and 2 molar aqueous sodium carbonate (1642 µl, 3.28 mmol). The mixture was stirred at 100° C. for an additional 3 hours. After cooling to ambient temperature, the mixture was filtered through diatomaceous earth and the filter cake was washed with 20 mL of ethyl acetate. Purification by silica gel flash chromatography (Isco®, Redi-Sep® column) eluting with a gradient of 50-100% ethyl acetate/hexane afforded the title compound. MS (ESI$^+$) m/z 579.4 (M+H)$^+$.

Example 222C (3R)—N-{5-chloro-4-[3-cyano-1-(tetrahydro-2H-pyran-4-ylmethyl)-1H-pyrrolo[3,2-b]pyridin-6-yl]pyridin-2-yl}piperidine-3-carboxamide Example 222B (245 mg, 0.423 mmol) was dissolved in 1:1 dichloromethane/methanol (4 mL) and the mixture was cooled to 0° C. A 2 molar solution of hydrochloric acid (solution in diethyl ether, 5 mL, 10.00 mmol) was slowly added and the mixture was then stirred at ambient temperature for 2 hours. Methanol was added (3 mL) to dissolve the precipitate and the mixture was concentrated. The residue was treated with 25 mL of ethyl acetate and poured into a 60 mL separatory funnel. The organic layer was washed with diluted aqueous potassium carbonate (10% weight in water, 1×20 mL), saturated aqueous sodium carbonate (1×20 mL), and saturated aqueous brine (1×20 mL), dried over anhydrous magnesium sulfate, filtered and concentrated. Purification by silica gel flash chromatography (Isco®, Redi-Sep® column) eluting with a gradient of 50-100% ethyl acetate/hexane followed by 10% of a 2:1 methanol:water mixture in ethyl acetate and finally a 30% solution of a 2:1 mixture of methanol/water in ethyl acetate containing 5% of triethylamine provided the title compound. $^1$H NMR (400 MHz, DMSO-d$_6$) δ ppm 1.23-1.41 (m, 4H), 1.41-1.54 (m, 1H), 1.55-1.72 (m, 2H), 1.86-1.95 (m, 1H), 2.04-2.17 (m, 1H), 2.58-2.82 (m, 3H), 2.85-2.94 (m, 1H), 3.03-3.11 (m, 1H), 3.16-3.27 (m, 2H), 3.78-3.87 (m, 2H), 4.26 (d, J=7.3 Hz, 2H), 8.27 (s, 1H), 8.47 (d, J=1.9 Hz, 1H), 8.54 (s, 1H), 8.59 (d, J=1.8 Hz, 1H), 8.68 (s, 1H), 11.04 (s, 1H). MS (ESI$^+$) m/z 479.4 (M+H)$^+$.

Example 223

4-[(6-{5-chloro-2-[(2-hydroxyethyl)amino]pyridin-4-yl}-1H-benzimidazol-1-yl)methyl]tetrahydro-2H-pyran-4-carbonitrile Example 223A 4-((6-(5-chloro-2-fluoropyridin-4-yl)-1H-benzo[d]imidazol-1-yl)methyl)tetrahydro-2H-pyran-4-carbonitrile A microwave reaction vial, equipped with stir bar, was charged with Example 132A (160 mg, 0.500 mmol), (5-chloro-2-fluoropyridin-4-yl)boronic acid (114 mg, 0.650 mmol), 1,1'-bis(diphenylphosphino)ferrocene-palladium(II) dichloride dichloromethane complex (61.2 mg, 0.075 mmol), dimethoxyethane (1.8 mL) and 2 molar aqueous sodium carbonate (630 µl, 1.259 mmol). The reaction vial was heated with stirring at 110° C. for 45 minutes in a Biotage Initiator® microwave reactor. The mixture was filtered through diatomaceous earth and the filter cake was washed with ethyl acetate and the filtrate was concentrated onto silica gel. Purification by silica gel flash chromatography (Isco®, Redi-Sep® column) eluting with a gradient of 50-100% ethyl acetate/hexane and then a 10% solution of a 2:1 methanol:water mixture in ethyl acetate followed by recrystallization from an ethyl acetate/hexane mixture afforded the title compound. MS (ESI$^+$) m/z 371.2 (M+H)$^+$.

Example 223B

4-[(6-{5-chloro-2-[(2-hydroxyethyl)amino]pyridin-4-yl}-1H-benzimidazol-1-yl)methyl]tetrahydro-2H-pyran-4-carbonitrile To a mixture of Example 223A (100 mg, 0.270 mmol) and 2-aminoethanol (81 µl, 1.348 mmol) in dimethylsulfoxide (539 µl) was added diisopropylethyl amine (70.7 µl, 0.405 mmol). The mixture was heated at 120° C. for 24 hours. After cooling to ambient temperature, the mixture was poured into a 60 mL separatory funnel and diluted with 25 mL of ethyl acetate. The organic layer was washed with saturated aqueous sodium bicarbonate (1×20 mL), water (1×20 mL), and saturated aqueous brine (1×20 mL), dried over anhydrous magnesium sulfate, filtered and concentrated. Purification by silica gel flash chromatography (Isco®, Redi-Sep® column) eluting with a gradient of 50-100% ethyl acetate/hexane followed by a 10% solution of a 2:1 methanol:water mixture in ethyl acetate afforded the title compound. $^1$H NMR (400 MHz, DMSO-d$_6$) δ ppm 1.75 (dd, J=13.3, 2.0 Hz, 2H), 1.83-1.96 (m, 2H), 3.33-3.38 (m, 2H), 3.42 (td, J=12.1, 2.0 Hz, 2H), 3.53 (q, J=5.8 Hz, 2H), 3.86-3.99 (m, 2H), 4.64-4.73 (m, 3H), 6.56 (s, 1H), 6.78 (t, J=5.7 Hz, 1H), 7.27 (dd, J=8.3, 1.6 Hz, 1H), 7.75 (d, J=8.4 Hz, 1H), 7.92 (d, J=1.5 Hz, 1H), 8.07 (s, 1H), 8.34 (s, 1H). MS (ESI$^+$) m/z 411.9 (M+H)$^+$.

Example 224

2-[(5-chloro-4-{1-[(5-fluoropyridin-3-yl)methyl]-1H-benzimidazol-6-yl}pyridin-2-yl)amino]ethanol Example 224A 6-(5-chloro-2-fluoropyridin-4-yl)-1-((5-fluoropyridin-3-yl)methyl)-1H-benzo[d]imidazole The title compound was prepared as described in Example 223A using Example 131A in place of Example 132A. MS (ESI$^+$) m/z 357.3 (M+H)$^+$.

Example 224B

2-[(5-chloro-4-{1-[(5-fluoropyridin-3-yl)methyl]-1H-benzimidazol-6-yl}pyridin-2-yl)amino]ethanol The title compound was prepared as described in Example 223B using Example 224A in place of Example 223A. $^1$H NMR (500 MHz, DMSO-d$_6$) δ ppm 3.29-3.39 (m, 2H), 3.53 (q, J=5.9 Hz, 2H), 4.71 (t, J=5.4 Hz, 1H), 5.64 (s, 2H), 6.54 (s, 1H), 6.80 (t, J=5.7 Hz, 1H), 7.24 (dd, J=8.3, 1.7 Hz, 1H), 7.72-7.82 (m, 3H), 8.05 (s, 1H), 8.48-8.60 (m, 3H). MS (ESI$^+$) m/z 398.3 (M+H)$^+$.

Example 225 trans-N-{5-chloro-4-[1-(3-fluorobenzyl)-1H-benzimidazol-6-yl]pyridin-2-yl}-N'-(pyridin-2-ylmethyl)cyclohexane-1,4-diamine In a 4 mL vial was added Example 8E (27 mg, 0.06 mmol) followed by 1 mL of a 1 molar solution in methanol of ammonium acetate/acetic acid buffer (pH=4). To this solution was added picolinaldehyde, (7 mg, 0.07 mmol) dissolved in 1 mL of a 1 molar solution in methanol of ammonium acetate/acetic acid buffer (pH=4). MP-Cyanoborohydride resin (Biotage®, 200 mg, 0.88 mmol/g) was added and the resulting mixture was shaken at room temperature for 5 hours. The reaction mixture was filtered and concentrated then purified by reverse-phase HPLC (Phenomenex Luna C8(2) 100 Å AXIA column) using a gradient of 10-95% acetonitrile/0.1% trifluoroacetic acid in water to afford the title compound as a trifluoroacetic acid salt. $^1$H NMR (400 MHz, DMSO-d$_6$/D$_2$O) δ ppm 1.21-1.34 (m, 2H), 1.49-1.63 (m, 2H), 2.04-2.22 (m, 4H), 3.10-3.20 (m, 1H), 3.59-3.70 (m, 1H), 4.36 (s, 2H), 5.72 (s, 2H), 6.59 (s, 1H), 7.19 (td, J=8.7, 2.6 Hz, 1H), 7.27-7.36 (m, 2H), 7.41-7.56 (m, 4H), 7.87 (s, 1H), 7.88-7.98 (m, 2H), 8.10 (s, 1H), 8.67 (d, J=4.8, 1.3 Hz, 1H), 9.38 (d, J=3.3 Hz, 1H). MS (ESI) m/e 541 (M+H)$^+$.

The following Examples (Example 226 to Example 246) were prepared essentially as described in Example 225, substituting the appropriate aldehyde. All products were purified by reverse-phase HPLC and were isolated as trifluoroacetic acid salts.

Example 226 trans-N-{5-chloro-4-[1-(3-fluorobenzyl)-1H-benzimidazol-6-yl]pyridin-2-yl}-N'-(pyridin-3-ylmethyl)cyclohexane-1,4-diamine $^1$H NMR (400 MHz, DMSO-d$_6$/D$_2$O) δ ppm 1.29 (q, J=13.1, 12.6 Hz, 2H), 1.52 (q, J=12.2 Hz, 2H), 2.14 (dd, J=39.6, 12.1 Hz, 4H), 3.09-3.23 (m, 1H), 3.59-3.71 (m, 1H), 4.29 (s, 2H), 5.71 (s, 2H), 6.58 (s, 1H), 7.19 (td, J=8.7, 2.6 Hz, 1H), 7.26-7.35 (m, 2H), 7.41-7.48 (m, 1H), 7.52 (dd, J=8.4, 1.5 Hz, 1H), 7.65 (dd, J=7.9, 5.0 Hz, 1H), 7.85 (s, 1H), 7.92 (d, J=8.4 Hz, 1H), 8.05-8.12 (m, 2H), 8.70 (dd, J=5.0, 1.5 Hz, 1H), 8.75 (d, J=2.1 Hz, 1H), 9.33 (s, 1H). MS (ESI) m/e 541 (M+H)$^+$.

Example 227 trans-N-{5-chloro-4-[1-(3-fluorobenzyl)-1H-benzimidazol-6-yl]pyridin-2-yl}-N'-(pyridin-4-ylmethyl)cyclohexane-1,4-diamine $^1$H NMR (400 MHz, DMSO-d$_6$/D$_2$O) δ ppm 1.29 (q, J=12.3 Hz, 2H), 1.38-1.59 (m, 2H), 1.98-2.23 (m, 4H), 3.10-3.25 (m, 1H), 3.59-3.70 (m, 1H), 4.36 (s, 2H), 5.72 (s, 2H), 6.55-6.60 (m, 1H), 7.19 (td, J=8.7, 2.6 Hz, 1H), 7.26-7.35 (m, 2H), 7.40-7.48 (m, 1H), 7.51-7.55 (m, 1H), 7.72-7.77 (m, 2H), 7.85-7.88 (m, 1H), 7.93 (d, J=8.5 Hz, 1H), 8.09-8.11 (m, 1H), 8.75-8.81 (m, 2H), 9.34-9.40 (m, 1H); MS (ESI) m/e 541 (M+H)$^+$.

Example 228 trans-N-(1,3-benzodioxol-5-ylmethyl)-N'-{5-chloro-4-[1-(3-fluorobenzyl)-1H-benzimidazol-6-yl]pyridin-2-yl}cyclohexane-1,4-diamine $^1$H NMR (400 MHz, DMSO-d$_6$/D$_2$O) δ ppm 1.19-1.32 (m, 2H), 1.43-1.55 (m, 2H), 2.01-2.22 (m, 4H), 2.94-3.12 (m, 1H), 4.08 (s, 2H), 5.64 (s, 2H), 6.05 (s, 2H), 6.52 (s, 1H), 6.95-7.04 (m, 2H), 7.07 (s, 1H), 7.11-7.32 (m, 3H), 7.34-7.47 (m, 2H), 7.74 (s, 1H), 7.85 (d, J=8.5 Hz, 1H), 8.07 (s, 1H), 8.95 (s, 1H). MS (ESI) m/e 584 (M+H)$^+$.

Example 229 trans-N-{5-chloro-4-[1-(3-fluorobenzyl)-1H-benzimidazol-6-yl]pyridin-2-yl}-N'-(1,3-thiazol-2-ylmethyl)cyclohexane-1,4-diamine $^1$H NMR (400 MHz, DMSO-d$_6$/D$_2$O) δ ppm 1.19-1.36 (m, 2H), 1.47-1.59 (m, 1H), 1.64-1.74 (m, 1H), 2.02-2.23 (m, 4H), 3.27-3.39 (m, 1H), 3.62-3.70 (m, 1H), 4.60-4.88 (m, 2H), 5.69 (s, 2H), 6.54 (d, J=6.1 Hz, 1H), 7.11-7.36 (m, 3H), 7.37-7.53 (m, 2H), 7.77-7.98 (m, 3H), 8.02 (d, J=3.3 Hz, 1H), 8.04-8.10 (m, 1H), 9.20 (s, 1H); MS (ESI) m/e 547 (M+H)$^+$.

Example 230 trans-N-{5-chloro-4-[1-(3-fluorobenzyl)-1H-benzimidazol-6-yl]pyridin-2-yl}-N'-{[1-(methoxymethyl)-2,3-dihydro-1H-1,2,3-triazol-4-yl]methyl}cyclohexane-1,4-diamine $^1$H NMR (400 MHz, DMSO-d$_6$/D$_2$O) δ ppm 1.18-1.36 (m, 2H), 1.41-1.58 (m, 2H), 2.00-2.29 (m, 4H), 3.05-3.17 (m, 1H), 3.29-3.36 (m, 3H), 3.61-3.71 (m, 1H), 4.35 (d, J=6.3 Hz, 2H), 5.63-5.76 (m, 4H), 6.49-6.65 (m, 1H), 7.18 (td, J=8.7, 2.6 Hz, 1H), 7.26 (d, J=7.7 Hz, 1H), 7.28-7.34 (m, 1H), 7.44 (td, J=8.0, 6.2 Hz, 1H), 7.48 (dd, J=8.7, 1.5 Hz, 1H), 7.82 (d, J=1.5 Hz, 1H), 7.90 (d, J=8.5 Hz, 1H), 8.09 (s, 1H), 8.35 (s, 1H), 9.21 (s, 1H); MS (ESI) m/e 575 (M+H)+.

Example 231 trans-N-{5-chloro-4-[1-(3-fluorobenzyl)-1H-benzimidazol-6-yl]pyridin-2-yl}-N'-[2-(morpholin-4-yl)ethyl]cyclohexane-1,4-diamine $^1$H NMR (400 MHz, DMSO-d$_6$/D$_2$O) δ ppm 1.19-1.37 (m, 2H), 1.37-1.56 (m, 2H), 1.93-2.14 (m, 4H), 2.96-3.50 (m, 9H), 3.76-3.90 (m, 5H), 5.70 (s, 2H), 6.52-6.58 (m, 1H), 7.18 (td, J=8.7, 2.5 Hz, 1H), 7.23-7.33 (m, 2H), 7.39-7.53 (m, 2H), 7.78-7.86 (m, 1H), 7.86-7.97 (m, 1H), 8.09 (s, 1H), 9.25 (s, 1H). MS (ESI) m/e 563 (M+H)+.

Example 232 trans-N-{5-chloro-4-[1-(3-fluorobenzyl)-1H-benzimidazol-6-yl]pyridin-2-yl}-N'-[2-methyl-2-(morpholin-4-yl)propyl]cyclohexane-1,4-diamine $^1$H NMR (400 MHz, DMSO-d$_6$/D$_2$O) δ ppm 1.18-1.46 (m, 8H), 1.47-1.65 (m, 2H), 1.94-2.05 (m, 1H), 2.06-2.20 (m, 3H), 2.94-3.30 (m, 6H), 3.51-3.70 (m, 2H), 3.75-3.89 (m, 4H), 5.70 (s, 2H), 6.51-6.62 (m, 1H), 7.18 (td, J=8.8, 2.6 Hz, 1H), 7.24-7.34 (m, 2H), 7.40-7.53 (m, 2H), 7.81-7.86 (m, 1H), 7.91 (d, J=8.4 Hz, 1H), 8.09 (s, 1H), 9.25-9.35 (m, 1H). MS (ESI) m/e 591 (M+H)+.

Example 233 trans-N-{5-chloro-4-[1-(3-fluorobenzyl)-1H-benzimidazol-6-yl]pyridin-2-yl}-N'-(tetrahydrofuran-2-ylmethyl)cyclohexane-1,4-diamine $^1$H NMR (400 MHz, DMSO-d$_6$/D$_2$O) δ ppm 1.16-1.32 (m, 2H), 1.39-1.62 (m, 3H), 1.81-1.97 (m, 2H), 1.99-2.18

(m, 5H), 2.88-2.97 (m, 1H), 3.00-3.16 (m, 2H), 3.57-3.66 (m, 1H), 3.75-3.78 (m, 1H), 3.81-3.87 (m, 1H), 4.04-4.13 (m, 1H), 5.70 (s, 2H), 6.56 (s, 1H), 7.18 (td, J=8.7, 2.6 Hz, 1H), 7.27 (d, J=7.8 Hz, 1H), 7.29-7.34 (m, 1H), 7.40-7.47 (m, 1H), 7.50 (dd, J=8.5, 1.5 Hz, 1H), 7.84 (s, 1H), 7.91 (d, J=8.5 Hz, 1H), 8.09 (s, 1H), 9.28 (s, 1H). MS (ESI) m/e 534 (M+H)+.

Example 234 trans-N-{5-chloro-4-[1-(3-fluorobenzyl)-1H-benzimidazol-6-yl]pyridin-2-yl}-N'-[(2,5-dimethoxytetrahydrofuran-3-yl)methyl]cyclohexane-1,4-diamine $^1$H NMR (400 MHz, DMSO-d$_6$/D$_2$O) δ ppm 1.17-1.56 (m, 4H), 1.65-1.91 (m, 2H), 1.94-2.20 (m, 6H), 2.91-3.13 (m, 2H), 3.20-3.44 (m, 5H), 3.59-3.70 (m, 1H), 3.98-4.26 (m, 1H), 4.80-5.16 (m, 2H), 5.70 (s, 2H), 6.56 (s, 1H), 7.18 (td, J=8.6, 2.6 Hz, 1H), 7.23-7.33 (m, 2H), 7.40-7.54 (m, 2H), 7.83-7.85 (m, 1H), 7.91 (d, J=8.5 Hz, 1H), 8.06-8.13 (m, 1H), 9.26-9.32 (m, 1H). MS (ESI) m/e 594 (M+H)+.

Example 235 trans-N-{5-chloro-4-[1-(3-fluorobenzyl)-1H-benzimidazol-6-yl]pyridin-2-yl}-N'-(cyclopropylmethyl)cyclohexane-1,4-diamine $^1$H NMR (400 MHz, DMSO-d$_6$/D$_2$O) δ ppm 0.29-0.42 (m, 2H), 0.55-0.68 (m, 2H), 0.95-1.08 (m, 1H), 1.19-1.35 (m, 2H), 1.35-1.53 (m, 2H), 2.00-2.14 (m, 4H), 2.84 (d, J=7.4 Hz, 2H), 2.98-3.12 (m, 1H), 3.58-3.72 (m, 1H), 5.71 (s, 2H), 6.57 (s, 1H), 7.18 (td, J=8.7, 2.6 Hz, 1H), 7.24-7.34 (m, 2H), 7.40-7.48 (m, 1H), 7.51 (dd, J=8.4, 1.5 Hz, 1H), 7.81-7.88 (m, 1H), 7.92 (d, J=8.4 Hz, 1H), 8.09 (s, 1H), 9.31 (s, 1H). MS (ESI) m/e 504 (M+H)+.

Example 236

3-{[trans-4-({5-chloro-4-[1-(3-fluorobenzyl)-1H-benzimidazol-6-yl]pyridin-2-yl}amino)cyclohexyl]amino}propane-1,2-diol $^1$H NMR (400 MHz, DMSO-d$_6$/D$_2$O) δ ppm 1.20-1.36 (m, 2H), 1.39-1.56 (m, 2H), 1.98-2.18 (m, 4H), 2.74-2.94 (m, 1H), 3.00-3.14 (m, 2H), 3.32-3.52 (m, 2H), 3.59-3.71 (m, 1H), 3.76-3.89 (m, 1H), 5.71 (s, 2H), 6.57-6.58 (m, 1H), 7.19 (td, J=8.7, 2.6 Hz, 1H), 7.28 (d, J=7.7 Hz, 1H), 7.30-7.35 (m, 1H), 7.40-7.48 (m, 1H), 7.52 (dd, J=8.4, 1.5 Hz, 1H), 7.82-7.87 (m, 1H), 7.92 (d, J=8.5 Hz, 1H), 8.09 (s, 1H), 9.34 (s, 1H). MS (ESI) m/e 524 (M+H)+.

Example 237 trans-N-{5-chloro-4-[1-(3-fluorobenzyl)-1H-benzimidazol-6-yl]pyridin-2-yl}-N-(1-methoxypropan-2-yl)cyclohexane-1,4-diamine $^1$H NMR (400 MHz, DMSO-d$_6$/D$_2$O) δ ppm 1.23 (d, J=6.4 Hz, 3H), 1.25-1.37 (m, 2H), 1.39-1.60 (m, 2H), 1.97-2.14 (m, 4H), 3.06-3.22 (m, 1H), 3.35 (s, 3H), 3.41-3.47 (m, 1H), 3.49-3.59 (m, 2H), 3.60-3.72 (m, 1H), 5.71 (s, 2H), 6.57 (s, 1H), 7.18 (td, J=8.7, 2.6 Hz, 1H), 7.27 (d, J=7.8 Hz, 1H), 7.29-7.33 (m, 1H), 7.41-7.47 (m, 1H), 7.51 (dd, J=8.4, 1.5 Hz, 1H), 7.83-7.86 (m, 1H), 7.92 (d, J=8.4 Hz, 1H), 8.09 (s, 1H), 9.31 (s, 1H). MS (ESI) m/e 522 (M+H)+.

Example 238 trans-N-{5-chloro-4-[1-(3-fluorobenzyl)-1H-benzimidazol-6-yl]pyridin-2-yl}-N-(1,3-dimethoxypropan-2-yl)cyclohexane-1,4-diamine $^1$H NMR (400 MHz, DMSO-d$_6$/D$_2$O) δ ppm 1.20-1.33 (m, 2H), 1.43-1.56 (m, 2H), 2.00-2.15 (m, 4H), 3.07-3.22 (m, 1H), 3.33 (s, 6H), 3.46-3.68 (m, 6H), 5.69 (s, 2H), 6.56 (s, 1H), 7.18 (td, J=8.6, 2.6 Hz, 1H), 7.27 (d, J=7.8 Hz, 1H), 7.29-7.34 (m, 1H), 7.40-7.47 (m, 1H), 7.49 (dd, J=8.5, 1.6 Hz, 1H), 7.79-7.84 (m, 1H), 7.91 (d, J=8.5 Hz, 1H), 8.08 (s, 1H), 9.24 (s, 1H). MS (ESI) m/e 552 (M+H)+.

Example 239 trans-N-{5-chloro-4-[1-(3-fluorobenzyl)-1H-benzimidazol-6-yl]pyridin-2-yl}-N'-(2-phenoxyethyl)cyclohexane-1,4-diamine $^1$H NMR (400 MHz, DMSO-d$_6$/D$_2$O) δ ppm 1.20-1.37 (m, 2H), 1.43-1.60 (m, 2H), 2.03-2.20 (m, 4H), 3.08-3.22 (m, 1H), 3.40 (t, J=5.0 Hz, 2H), 3.59-3.70 (m, 1H), 4.24 (t, J=4.9 Hz, 2H), 5.70 (s, 2H), 6.56 (s, 1H), 6.99-7.04 (m, 3H), 7.18 (td, J=8.8, 2.6 Hz, 1H), 7.25-7.39 (m, 4H), 7.40-7.47 (m, 1H), 7.49 (dd, J=8.5, 1.5 Hz, 1H), 7.79-7.87 (m, 1H), 7.91 (d, J=8.5 Hz, 1H), 8.09 (s, 1H), 9.24 (s, 1H). MS (ESI) m/e 570 (M+H)+.

Example 240 trans-N-[3-(benzyloxy)propyl]-N'-{5-chloro-4-[1-(3-fluorobenzyl)-1H-benzimidazol-6-yl]pyridin-2-yl}cyclohexane-1,4-diamine $^1$H NMR (400 MHz, DMSO-d$_6$/D$_2$O) δ ppm 1.19-1.34 (m, 2H), 1.34-1.51 (m, 2H), 1.81-1.93 (m, 2H), 2.00-2.10 (m, 4H), 2.96-3.09 (m, 3H), 3.54 (t, J=6.0 Hz, 2H), 3.60-3.69 (m, 1H), 4.44-4.54 (m, 2H), 5.67 (s, 2H), 6.53 (s, 1H), 7.17 (td, J=8.6, 2.6 Hz, 1H), 7.23-7.46 (m, 9H), 7.74-7.83 (m, 1H), 7.87 (d, J=8.5 Hz, 1H), 8.07 (s, 1H), 9.09 (s, 1H). MS (ESI) m/e 598 (M+H)+.

Example 241 trans-N-{5-chloro-4-[1-(3-fluorobenzyl)-1H-benzimidazol-6-yl]pyridin-2-yl}-N'-[2,2-dimethyl-3-(phenylsulfinyl)propyl]cyclohexane-1,4-diamine $^1$H NMR (400 MHz, DMSO-d$_6$/D$_2$O) δ ppm 1.18 (s, 3H), 1.22-1.30 (m, 2H), 1.34 (s, 3H), 1.51 (s, 2H), 2.02-2.23 (m, 4H), 2.86-3.22 (m, 4H), 3.78-4.02 (m, 2H), 5.62 (s, 2H), 6.51 (s, 1H), 7.11-7.28 (m, 4H), 7.33-7.44 (m, 2H), 7.59-7.66 (m, 2H), 7.68-7.75 (m, 3H), 7.83 (d, J=8.5 Hz, 1H), 8.06 (s, 1H), 8.84 (s, 1H). MS (ESI) m/e 644 (M+H)+.

Example 242 trans-N-{5-chloro-4-[1-(3-fluorobenzyl)-1H-benzimidazol-6-yl]pyridin-2-yl}-N'-(2-methoxypropyl)cyclohexane-1,4-diamine $^1$H NMR (400 MHz, DMSO-d$_6$/D$_2$O) δ ppm 1.15 (d, J=6.2 Hz, 3H), 1.21-1.34 (m, 2H), 1.37-1.59 (m, 2H), 2.01-2.17 (m, 4H), 2.83-2.98 (m, 1H), 2.98-3.10 (m, 2H), 3.31 (s, 3H), 3.55-3.67 (m, 2H), 5.69 (s, 2H), 6.55 (s, 1H), 7.18 (td, J=8.8, 2.7 Hz, 1H), 7.23-7.36 (m, 2H), 7.40-7.51

(m, 2H), 7.78-7.86 (m, 1H), 7.90 (d, J=8.4 Hz, 1H), 8.08 (s, 1H), 9.23 (s, 1H). MS (ESI) m/e 522 (M+H)+.

Example 243 trans-N-{5-chloro-4-[1-(3-fluorobenzyl)-1H-benzimidazol-6-yl]pyridin-2-yl}-N'-[2-(cyclohexyloxy)propyl]cyclohexane-1,4-diamine $^1$H NMR (400 MHz, DMSO-d$_6$/D$_2$O) δ ppm 1.14 (d, J=6.1 Hz, 3H), 1.15-1.34 (m, 7H), 1.44-1.56 (m, 3H), 1.63-1.94 (m, 4H), 2.01-2.15 (m, 4H), 2.81-2.95 (m, 1H), 2.95-3.14 (m, 2H), 3.33-3.43 (m, 1H), 3.59-3.67 (m, 1H), 3.79-3.91 (m, 1H), 5.69 (s, 2H), 6.55 (s, 1H), 7.18 (td, J=8.6, 2.4 Hz, 1H), 7.24-7.33 (m, 2H), 7.40-7.50 (m, 2H), 7.78-7.86 (m, 1H), 7.90 (d, J=8.5 Hz, 1H), 8.08 (s, 1H), 9.23 (s, 1H). MS (ESI) m/e 590 (M+H)+.

Example 244 trans-N-{5-chloro-4-[1-(3-fluorobenzyl)-1H-benzimidazol-6-yl]pyridin-2-yl}-N'-[(5,5-dimethyltetrahydrofuran-2-yl)methyl]cyclohexane-1,4-diamine $^1$H NMR (400 MHz, DMSO-d$_6$/D$_2$O) δ ppm 1.17-1.34 (m, 8H), 1.37-1.55 (m, 2H), 1.65-1.84 (m, 3H), 1.96-2.20 (m, 5H), 2.85-3.00 (m, 1H), 3.00-3.16 (m, 2H), 3.57-3.66 (m, 1H), 4.08-4.22 (m, 1H), 5.69 (s, 2H), 6.55 (s, 1H), 7.18 (td, J=8.7, 2.6 Hz, 1H), 7.23-7.33 (m, 2H), 7.36-7.50 (m, 2H), 7.76-7.85 (m, 1H), 7.90 (d, J=8.4 Hz, 1H), 8.08 (s, 1H), 9.21 (s, 1H)). MS (ESI) m/e 562 (M+H)+.

Example 245 trans-N-{5-chloro-4-[1-(3-fluorobenzyl)-1H-benzimidazol-6-yl]pyridin-2-yl}-N'-(3-methoxypropyl)cyclohexane-1,4-diamine $^1$H NMR (400 MHz, DMSO-d$_6$/D$_2$O) δ ppm 1.29 (dd, J=13.5, 10.4 Hz, 2H), 1.36-1.52 (m, 2H), 1.76-1.91 (m, 2H), 2.01-2.12 (m, 4H), 2.93-3.10 (m, 3H), 3.26 (s, 3H), 3.42 (t, J=6.0 Hz, 2H), 3.59-3.71 (m, 1H), 5.70 (s, 2H), 6.56 (s, 1H), 7.18 (td, J=8.7, 2.6 Hz, 1H), 7.27 (d, J=7.7 Hz, 1H), 7.29-7.34 (m, 1H), 7.40-7.47 (m, 1H), 7.50 (dd, J=8.4, 1.5 Hz, 1H), 7.80-7.87 (m, 1H), 7.91 (d, J=8.5 Hz, 1H), 8.09 (s, 1H), 9.27 (s, 1H). MS (ESI) m/e 522 (M+H)+.

Example 246

2-{[trans-4-({5-chloro-4-[1-(3-fluorobenzyl)-1H-benzimidazol-6-yl]pyridin-2-yl}amino)cyclohexyl]amino}propan-1-ol $^1$H NMR (400 MHz, DMSO-d$_6$/D$_2$O) δ ppm 1.13-1.60 (m, 6H), 1.93-2.15 (m, 4H), 2.95-3.23 (m, 1H), 3.29-3.41 (m, 1H), 3.43-3.55 (m, 1H), 3.59-3.68 (m, 2H), 5.71 (s, 2H), 6.58 (s, 1H), 7.18 (td, J=8.8, 2.6 Hz, 1H), 7.28 (d, J=7.7 Hz, 1H), 7.30-7.35 (m, 1H), 7.40-7.48 (m, 1H), 7.52 (dd, J=8.5, 1.5 Hz, 1H), 7.81-7.88 (m, 1H), 7.92 (d, J=8.5 Hz, 1H), 8.09 (s, 1H), 9.33 (s, 1H). MS (ESI) m/e 508 (M+H)+.

Example 247

(3R)—N-{5-chloro-4-[1-(3-fluorobenzyl)-1H-[1,2,3]triazolo[4,5-b]pyrazin-6-yl]pyridin-2-yl}piperidine-3-carboxamide Example 247A 6-bromo-(3-fluorobenzyl)-1H-[1,2,3]triazolo[4,5-b]pyrazine The title compound was prepared as described in Example 110A using Example 218A in place of Example 8B.

Example 247B (3R)—N-{5-chloro-4-[1-(3-fluorobenzyl)-1H-[1,2,3]triazolo[4,5-b]pyrazin-6-yl]pyridin-2-yl}piperidine-3-carboxamide The title compound was prepared as described in Example 14E using Example 247A in place of Example 14D. $^1$H NMR (400 MHz, DMSO-d$_6$) δ 1.42 (m, 1H), 1.62 (m, 2H), 1.88 (m, 1H), 2.65 (m, 3H), 2.83 (m, 1H), 3.02 (m, 1H), 6.07 (s, 2H), 7.18 (t, 1H), 7.29 (t, 2H), 7.44 (m, 1H), 8.48 (s, 1H), 8.61 (s, 1H), 9.18 (s, 1H), 11.12 (br s, 1H). MS (ESI) m/e 467.0 (M+H)$^+$.

Example 248

(3R)—N-{5-chloro-4-[1-(tetrahydro-2H-pyran-4-ylmethyl)-1H-benzotriazol-6-yl]pyridin-2-yl}piperidine-3-carboxamide Example 248A 6-bromo-1-((tetrahydro-2H-pyran-4-yl)methyl)-1H-benzo[d][1,2,3]triazole The title compound was prepared as described in Example 110A using Example 13B in place of Example 8B.

Example 248B (3R)—N-{5-chloro-4-[1-(tetrahydro-2H-pyran-4-ylmethyl)-1H-benzotriazol-6-yl]pyridin-2-yl}piperidine-3-carboxamide The title compound was prepared as described in Example 14E using Example 248A in place of Example 14D. $^1$H NMR (400 MHz, DMSO-d$_6$) δ 1.40 (m, 5H), 1.59 (m, 2H), 1.86 (m, 1H), 2.24 (m, 1H), 2.63 (m, 2H), 2.83 (m, 1H), 2.99 (m, 1H), 3.24 (m, 3H), 3.83 (m, 2H), 4.69 (d, 2H), 7.49 (d, 1H), 8.16 (m, 2H), 8.28 (s, 1H), 8.52 (s, 1H), 11.02 (br s, 1H). MS (ESI) m/e 455.2 (M+H)$^+$.

Example 249

N-{5-chloro-4-[1-(3-fluorobenzyl)-1H-pyrrolo[3,2-b]pyridin-6-yl]pyridin-2-yl}-6-azaspiro[3.4]octan-2-amine

Example 249A 6-(5-chloro-2-fluoropyridin-4-yl)-1-(3-fluorobenzyl)-1H-pyrrolo[3,2-b]pyridine The title compound was prepared as described in Example 223A, using Example 33A in place of Example 132A. MS (ESI$^+$) m/z 356.3 (M+H)$^+$.

Example 249B

N-{5-chloro-4-[1-(3-fluorobenzyl)-1H-pyrrolo[3,2-b]pyridin-6-yl]pyridin-2-yl}-6-azaspiro[3.4]octan-2-amine A mixture of Example 249A (86 mg, 0.242 mmol), tert-butyl 2-amino-6-azaspiro[3.4]octane-6-carboxylate (164 mg, 0.725 mmol) and diisopropylethyl amine (63.3 µl, 0.363 mmol) in dimethylsulfoxide (483 µl) was stirred at 120° C. for 24 hours. After cooling to ambient temperature, water (25 mL) and ethyl acetate (25 mL) were added and the mixture was poured into a 60 mL separatory funnel. The aqueous layer was removed and the organic layer was washed with saturated aqueous brine (20 mL), dried over anhydrous magnesium sulfate, filtered and concentrated. The crude material obtained was purified by silica gel flash chromatography (Isco®, Redi-Sep® column) eluting with a gradient of 50-100% ethyl acetate/hexane to afford the tert-butyloxycarbonyl protected intermediate. The intermediate was dissolved in 1 mL of dichloromethane and 1 mL of methanol was added. After cooling the mixture to 0° C., 5 mL of a 2 molar solution of hydrochloric acid (solution in diethyl ether) was added and the cooling bath was removed to allow the mixture to stir at ambient temperature. After stirring for 2 hours, the reaction mixture was concentrated to give the title compound as a bis hydrochloric acid salt. $^1$H NMR (400 MHz, Methanol-d$_4$) δ ppm 2.15 (t, J=7.5 Hz, 1H), 2.22 (t, J=7.2 Hz, 1H), 2.27-2.41 (m, 2H), 2.62-2.84 (m, 2H), 3.29-3.46 (m, 4H), 4.35-4.51 (m, 1H), 5.77 (s, 2H), 7.02-7.20 (m, 4H), 7.28-7.35 (m, 1H), 7.35-7.44 (m, 1H), 8.19 (s, 1H), 8.43 (d, J=3.2 Hz, 1H), 8.87-8.98 (m, 2H). MS (ESI$^+$) m/z 462.4 (M+H)$^+$.

Example 250

N-{5-chloro-4-[1-(3-fluorobenzyl)-1H-benzimidazol-6-yl]pyridin-2-yl}cyclohexane-1,3-diamine The title compound was prepared using the conditions described in Example 223B using Example 8D in place of Example 223A and using cyclohexane-1,3-diamine in place of 2-aminoethanol. $^1$H NMR (400 MHz, DMSO-d$_6$) δ ppm 0.85-1.05 (m, 2H), 1.13-1.78 (m, 5H), 1.85-1.94 (m, 1H), 2.00-2.10 (m, 1H), 2.53-2.68 (m, 1H), 2.96-3.08 (m, 1H), 3.56-3.77 (m, 1H), 5.56 (s, 2H), 6.42-6.56 (m, 1H), 6.57-6.69 (m, 1H), 7.06-7.28 (m, 4H), 7.36-7.44 (m, 1H), 7.67 (s, 1H), 7.72-7.77 (m, 1H), 8.03 (s, 1H), 8.52 (s, 1H). MS (ESI$^+$) m/z 450.4 (M+H)$^+$.

Example 251

(3R)—N-{5-chloro-4-[1-(3-fluorobenzyl)-2-(trifluoromethyl)-1H-benzimidazol-6-yl]pyridin-2-yl}piperidine-3-carboxamide

Example 251A 6-bromo-1-(3-fluorobenzyl)-2-(trifluoromethyl)-1H-benzo[d]imidazole To a mixture of 6-bromo-2-(trifluoromethyl)-1H-benzo[d]imidazole (500 mg, 1.887 mmol) in N,N-dimethylformamide (3773 µl) was added sodium hydride (49.8 mg, 2.075 mmol) followed by 1-(bromomethyl)-3-fluorobenzene (255 µl, 2.075 mmol). The mixture was stirred at 100° C. for two hours and cooled to ambient temperature. The mixture was diluted with 25 mL of ethyl acetate and was poured into a 60 mL separatory funnel. The organics were washed with saturated aqueous sodium bicarbonate (1×20 mL), and saturated aqueous brine (1×20 mL), dried over anhydrous magnesium sulfate, filtered and concentrated. Purification by silica gel flash chromatography (Isco®, Redi-Sep® column) eluting with a gradient of 2-30% ethyl acetate/hexane afforded the title compound as the faster eluting isomer. $^1$H NMR (400 MHz, DMSO-d$_6$) δ ppm 5.75 (s, 2H), 6.84 (dt, J=7.6, 1.2 Hz, 1H), 7.01 (dt, J=10.0, 2.2 Hz, 1H), 7.11-7.19 (m, 1H), 7.33-7.42 (m, 1H), 7.63 (dd, J=8.8, 1.8 Hz, 1H), 7.71 (d, J=8.8 Hz, 1H), 8.15 (d, J=1.7 Hz, 1H).

Example 251B (3R)—N-{5-chloro-4-[1-(3-fluorobenzyl)-2-(trifluoromethyl)-1H-benzimidazol-6-yl]pyridin-2-yl}piperidine-3-carboxamide The tert-butyloxocarbony protected title compound was prepared as described in Example 2 using Example 251A in place of 6-bromoindoline. The intermediate was dissolved in 1 mL of dichloromethane and 1 mL of methanol was added. After cooling the mixture to 0° C., 5 mL of a 2 molar solution of hydrochloric acid (solution in diethyl ether) was added and the cooling bath was removed to allow the mixture to stir at ambient temperature. After stirring for 2 hours, the reaction mixture was concentrated to afford the title compound as a bis hydrochloric acid salt. $^1$H NMR (400 MHz, Methanol-d$_4$) δ ppm 1.81-2.07 (m, 3H), 2.18-2.32 (m, 1H), 3.05-3.23 (m, 2H), 3.33-3.37 (m, 2H), 3.46-3.55 (m, 1H), 5.80 (s, 2H), 6.89-6.97 (m, 2H), 7.01-7.09 (m, 1H), 7.31-7.41 (m, 1H), 7.63 (dd, J=8.6, 1.5 Hz, 1H), 7.84-7.91 (m, 2H), 8.03 (d, J=8.5 Hz, 1H), 8.52 (s, 1H). MS (ESI$^+$) m/z 532.3 (M+H)$^+$.

Example 252

(3R)—N-{5-chloro-4-[2-(trifluoromethyl)-1H-benzimidazol-6-yl]pyridin-2-yl}piperidine-3-carboxamide The tert-butyloxocarbony protected title compound was prepared using the conditions described in Example 2 using 6-bromo-2-(trifluoromethyl)-1H-benzo[d]imidazole in place of 6-bromoindoline. The tert-butyloxocarbony protected intermediate was dissolved in 1 mL of dichloromethane and 1 mL of methanol was added. After cooling the mixture to 0° C., 5 mL of a 2 molar solution of hydrochloric acid (solution in diethyl ether) was added and the cooling bath was removed to allow the mixture to stir at ambient temperature. After stirring for 2 hours, the reaction mixture was concentrated to afford the title compound as a bis hydrochloric acid salt. $^1$H NMR (500 MHz, Methanol-d$_4$) δ ppm 1.78-2.05 (m, 3H), 2.12-2.28 (m, 1H), 3.06-3.19 (m, 2H), 3.22-3.40 (m, 2H), 3.43 (dd, J=12.8, 3.9 Hz, 1H), 7.59 (dd, J=8.5, 1.6 Hz, 1H), 7.86 (d, J=8.4 Hz, 1H), 7.91 (d, J=1.6 Hz, 1H), 8.13 (s, 1H), 8.48 (s, 1H). MS (ESI$^+$) m/z 424.0 (M+H)$^+$.

Example 253

(3R)—N-{5-chloro-4-[1-(3-fluorobenzyl)-3-(methoxymethyl)-1H-pyrrolo[3,2-b]pyridin-6-yl]pyridin-2-yl}piperidine-3-carboxamide Example 253A 6-bromo-1-(3-fluorobenzyl)-1H-pyrrolo[3,2-b]pyridine-3-carbaldehyde The title compound was prepared using the conditions described in Example 251A using 6-bromo-1H-pyrrolo[3,2-b]pyridine-3-carbaldehyde in place of 6-bromo-2-(trifluoromethyl)-1H-benzo[d]imidazole. MS (ESI$^+$) m/z 335.0 (M+H)$^+$.

Example 253B (R)-tert-butyl 3-(5-chloro-4-(1-(3-fluorobenzyl)-3-formyl-1H-pyrrolo[3,2-b]pyridin-6-yl)pyridin-2-ylcarbamoyl)piperidine-1-carboxylate A 20 mL microwave reaction vial was charged with Example 253A (213 mg, 0.640 mmol), 4,4,4',4',5,5,5',5'-octamethyl-2,2'-bi(1,3,2-dioxaborolane) (163 mg, 0.640 mmol), potassium acetate (188 mg, 1.92 mmol) and 1,1'-bis(diphenylphosphino)ferrocene-palladium(II)dichloride dichloromethane complex (31.4 mg, 0.038 mmol). The vial was capped with a septa and evacuated and backfilled with nitrogen twice. Dioxane (4 mL) was added and the mixture was and backfilled with nitrogen twice and stirred under nitrogen at 100° C. for 3 hours. Example 1B (268 mg, 0.640 mmol), followed by another portion of 1,1'-bis(diphenylphosphino)ferrocene-palladium(II)dichloride dichloromethane complex (15.7 mg, 0.019 mmol) and by a 2 molar aqueous sodium carbonate solution (1.76 mL, 3.52 mmol) was added. The reaction mixture was stirred at 100° C. for 3 hours. After cooling to ambient temperature, the mixture was filtered through a ¼ inch diatomaceous earth pad and the filter cake was washed with 30 mL of ethyl acetate. The filtrate was concentrated and purification by silica gel flash chromatography (Isco®, Redi-Sep® column) eluting with a gradient of 30-100% ethyl acetate/hexane afforded the title compound. MS (ESI$^+$) m/z 592.4 (M+H)$^+$.

Example 253C (3R)—N-{5-chloro-4-[1-(3-fluorobenzyl)-3-(methoxymethyl)-1H-pyrrolo[3,2-b]pyridin-6-yl]pyridin-2-yl}piperidine-3-carboxamide Example 253B (120 mg, 0.203 mmol) was dissolved in methanol (1.5 mL) and dichloromethane (0.25 mL). The mixture was stirred at ambient temperature and sodium borohydride (15.34 mg, 0.405 mmol) was added in one portion. The mixture was stirred for 30 minutes and diluted with 15 mL of ethyl acetate and poured into a separatory funnel. The organic layer was washed with water (2×10 mL), and saturated aqueous brine (1×10 mL), dried over anhydrous magnesium sulfate, filtered and concentrated. Purification by silica gel flash chromatography (Isco®, Redi-Sep® column) eluting with a gradient of 50-100% ethyl acetate/hexane then switched to 10% of a 2:1 methanol:water mixture in ethyl acetate afforded the tert-butyloxocarbonyl protected intermediate. The intermediate was dissolved in 1 mL of dichloromethane and 1 mL of methanol was added. After cooling the mixture to 0° C., 5 mL of a 2 molar solution of hydrochloric acid (solution in ether) was added and the cooling was removed to allow the mixture to stir at ambient temperature. After stirring for 2 hours, the reaction mixture was concentrated. The product was purified by reverse-phase HPLC (Phenomenex Luna C8(2) 100 Å AXIA column) using a gradient of 10-95% acetonitrile/0.1% trifluoroacetic acid in water to afford the title compound as a bis trifluoroacetic acid salt. $^1$H NMR (400 MHz, DMSO-d$_6$) δ ppm 1.53-1.73 (m, 2H), 1.78-1.92 (m, 1H), 1.99-2.15 (m, 1H), 2.84-3.13 (m, 3H), 3.16-3.27 (m, 1H), 3.33-3.41 (m, 1H), 4.66 (s, 2H), 5.57 (s, 2H), 7.08-7.16 (m, 2H), 7.16-7.23 (m, 1H), 7.34-7.42 (m, 1H), 8.15 (s, 1H), 8.23 (s, 1H), 8.40 (d, J=1.8 Hz, 1H), 8.53-8.57 (m, 2H), 8.59-8.76 (m, 2H), 11.06 (s, 1H). MS (ESI$^+$) m/z 508.4 (M+H)$^+$.

Example 254

(3R)—N-{5-chloro-4-[3-(methoxymethyl)-1-(tetrahydro-2H-pyran-4-ylmethyl)-1H-pyrrolo[3,2-b]pyridin-6-yl]pyridin-2-yl}piperidine-3-carboxamide Example 254A 6-bromo-1-((tetrahydro-2H-pyran-4-yl)methyl)-1H-pyrrolo[3,2-b]pyridine-3-carbaldehyde The title compound was prepared using the conditions described in Example 251A using 6-bromo-1H-pyrrolo[3,2-b]pyridine-3-carbaldehyde in place of 6-bromo-2-(trifluoromethyl)-1H-benzo[d]imidazole and using 4-(bromomethyl)tetrahydro-2H-pyran in place of 1-(bromomethyl)-3-fluorobenzene. $^1$H NMR (400 MHz, DMSO-d$_6$) δ ppm 1.23-1.40 (m, 4H), 2.02-2.19 (m, 1H), 3.15-3.28 (m, 2H), 3.74-3.87 (m, 2H), 4.22 (d, J=7.4 Hz, 2H), 8.51 (s, 1H), 8.57-8.62 (m, 2H), 10.14 (s, 1H).

Example 254B (R)-tert-butyl 3-(5-chloro-4-(3-formyl-1-((tetrahydro-2H-pyran-4-yl)methyl)-1H-pyrrolo[3,2-b]pyridin-6-yl)pyridin-2-ylcarbamoyl)piperidine-1-carboxylate The title compound was prepared as described in Example 253B using Example 254A in place of Example 253A. MS (ESI) m/z 582.4 (M+H)$^+$.

Example 254C (3R)—N-{5-chloro-4-[3-(methoxymethyl)-1-(tetrahydro-2H-pyran-4-ylmethyl)-1H-pyrrolo[3,2-b]pyridin-6-yl]pyridin-2-yl}piperidine-3-carboxamide The title compound was prepared as described in Example 253C using Example 254B in place of Example 253B. $^1$H NMR (400 MHz, DMSO-d$_6$) δ ppm 1.22-1.43 (m, 4H), 1.55-1.75 (m, 2H), 1.79-1.91 (m, 1H), 2.00-2.15 (m, 2H), 2.84-3.10 (m, 3H), 3.15-3.27 (m, 3H), 3.33-3.40 (m, 1H), 3.74-3.87 (m, 2H), 4.24 (d, J=7.2 Hz, 2H), 4.66 (s, 2H), 8.06 (s, 1H), 8.27 (s, 1H), 8.52-8.56 (m, 1H), 8.57-8.62 (m, 2H), 8.62-8.79 (m, 2H), 11.09 (s, 1H). MS (ESI+) m/z 498.3 (M+H)+.

The following Examples (Example 255 to Example 270) were prepared essentially as described in Example 189 using Example 210B in place of Example 49 and substituting the appropriate carboxylic acid. All products were purified by reverse-phase HPLC and were isolated as trifluoroacetic acid salts.

Example 255

N-{5-chloro-4-[1-(tetrahydro-2H-pyran-4-ylmethyl)-1H-benzimidazol-6-yl]pyridin-2-yl}pyridine-4-carboxamide $^1$H NMR (400 MHz, DMSO-$d_6$) δ 9.58 (s, 1H), 8.95-8.83 (m, 2H), 8.66 (s, 1H), 8.36 (s, 1H), 8.31 (d, J=1.5 Hz, 1H), 8.10-8.06 (m, 2H), 8.05 (d, J=8.5 Hz, 1H), 7.76 (dd, J=8.5, 1.5 Hz, 1H), 4.47 (d, J=7.3 Hz, 2H), 3.88-3.81 (m, 2H), 3.26 (td, J=11.6, 2.1 Hz, 2H), 2.22 (ddp, J=11.4, 7.5, 3.8 Hz, 1H), 1.57-1.46 (m, 2H), 1.38 (qd, J=11.9, 4.4 Hz, 2H). MS (ESI) m/z 448 (M+H)+.

Example 256

N-{5-chloro-4-[1-(tetrahydro-2H-pyran-4-ylmethyl)-1H-benzimidazol-6-yl]pyridin-2-yl}pyridine-3-carboxamide $^1$H NMR (400 MHz, DMSO-$d_6$) δ 9.59 (s, 1H), 9.20 (d, J=2.2 Hz, 1H), 8.85 (dd, J=5.1, 1.7 Hz, 1H), 8.65 (s, 1H), 8.52 (dt, J=8.2, 1.9 Hz, 1H), 8.37 (s, 1H), 8.32 (d, J=1.5 Hz, 1H), 8.05 (d, J=8.6 Hz, 1H), 7.77 (dd, J=8.4, 1.6 Hz, 1H), 7.75-7.72 (m, 1H), 4.47 (d, J=7.2 Hz, 2H), 3.85 (dd, J=4.3, 1.9 Hz, 2H), 3.26 (td, J=11.6, 2.2 Hz, 2H), 2.23 (ddd, J=11.5, 7.6, 3.9 Hz, 1H), 1.51 (dd, J=13.2, 3.4 Hz, 2H), 1.46-1.29 (m, 2H). MS (ESI) m/z 448 (M+H)+.

Example 257

N-{5-chloro-4-[1-(tetrahydro-2H-pyran-4-ylmethyl)-1H-benzimidazol-6-yl]pyridin-2-yl}-1-methyl-1H-imidazole-4-carboxamide $^1$H NMR (400 MHz, DMSO-$d_6$) δ 9.56 (s, 1H), 8.60 (s, 1H), 8.34 (d, J=1.2 Hz, 1H), 8.33 (s, 1H), 8.30 (d, J=1.5 Hz, 1H), 8.16 (d, J=1.3 Hz, 1H), 8.04 (d, J=8.6 Hz, 1H), 7.74 (dd, J=8.6, 1.5 Hz, 1H), 4.46 (d, J=7.3 Hz, 2H), 3.86-3.84 (m, 2H), 3.83 (s, 3H), 3.25 (td, J=11.6, 2.2 Hz, 2H), 2.22 (ddq, J=11.3, 7.7, 3.8 Hz, 1H), 1.50 (ddd, J=11.7, 4.3, 2.5 Hz, 2H), 1.46-1.25 (m, 2H). MS (ESI) m/z 451 (M+H)+.

Example 258

N-{5-chloro-4-[1-(tetrahydro-2H-pyran-4-ylmethyl)-1H-benzimidazol-6-yl]pyridin-2-yl}-1H-imidazole-4-carboxamide $^1$H NMR (400 MHz, DMSO-$d_6$) δ 9.47 (s, 1H), 8.66 (d, J=1.8 Hz, 1H), 8.63 (s, 1H), 8.33 (s, 1H), 8.31 (s, 1H), 8.27 (d, J=1.5 Hz, 1H), 8.02 (d, J=8.6 Hz, 1H), 7.72 (dd, J=8.6, 1.5 Hz, 1H), 4.44 (d, J=7.2 Hz, 2H), 3.92-3.82 (m, 2H), 3.25 (td, J=11.7, 2.2 Hz, 2H), 2.21 (tt, J=8.9, 4.8 Hz, 1H), 1.49 (d, J=12.4 Hz, 2H), 1.44-1.29 (m, 2H). MS (ESI) m/z 437 (M+H)+.

Example 259

N-{5-chloro-4-[1-(tetrahydro-2H-pyran-4-ylmethyl)-1H-benzimidazol-6-yl]pyridin-2-yl}-1,3-thiazole-4-carboxamide $^1$H NMR (400 MHz, DMSO-$d_6$) δ 9.41 (s, 1H), 9.27 (d, J=2.0 Hz, 1H), 8.61 (d, J=2.0 Hz, 1H), 8.60 (s, 1H), 8.36 (s, 1H), 8.26 (d, J=1.5 Hz, 1H), 8.01 (d, J=8.5 Hz, 1H), 7.71 (dd, J=8.5, 1.5 Hz, 1H), 4.44 (d, J=7.2 Hz, 2H), 3.86 (ddd, J=11.4, 4.5, 1.8 Hz, 2H), 3.25 (td, J=11.7, 2.2 Hz, 2H), 2.21 (ddp, J=11.2, 7.4, 3.7 Hz, 1H), 1.58-1.45 (m, 2H), 1.45-1.27 (m, 2H). MS (ESI) m/z 454 (M+H)+.

Example 260

N-{5-chloro-4-[1-(tetrahydro-2H-pyran-4-ylmethyl)-1H-benzimidazol-6-yl]pyridin-2-yl}-1H-1,2,4-triazole-3-carboxamide $^1$H NMR (400 MHz, DMSO-$d_6$) δ 9.31 (s, 1H), 8.72 (s, 1H), 8.61 (s, 1H), 8.31 (s, 1H), 8.22 (d, J=1.5 Hz, 1H), 8.00 (d, J=8.5 Hz, 1H), 7.69 (dd, J=8.5, 1.5 Hz, 1H), 4.41 (d, J=7.2 Hz, 2H), 3.92-3.81 (m, 2H), 3.25 (td, J=11.6, 2.2 Hz, 2H), 2.19 (ddp, J=11.6, 7.7, 3.8 Hz, 1H), 1.49 (dd, J=13.0, 3.5 Hz, 2H), 1.36 (qd, J=12.2, 4.6 Hz, 2H). MS (ESI) m/z 438 (M+H)+.

Example 261

N-{5-chloro-4-[1-(tetrahydro-2H-pyran-4-ylmethyl)-1H-benzimidazol-6-yl]pyridin-2-yl}pyrimidine-5-carboxamide $^1$H NMR (400 MHz, DMSO-$d_6$) δ 9.53 (s, 1H), 9.37 (s, 1H), 9.29 (s, 2H), 8.65 (s, 1H), 8.36 (s, 1H), 8.32-8.26 (m, 1H), 8.04 (d, J=8.6 Hz, 1H), 7.74 (dd, J=8.6, 1.5 Hz, 1H), 4.46 (d, J=7.2 Hz, 2H), 3.91-3.83 (m, 2H), 3.26 (td, J=11.7, 2.3 Hz, 2H), 2.22 (ddd, J=11.5, 7.6, 4.1 Hz, 1H), 1.58-1.45 (m, 2H), 1.45-1.34 (m, 2H). MS (ESI) m/z 449 (M+H)+.

Example 262

N-{5-chloro-4-[1-(tetrahydro-2H-pyran-4-ylmethyl)-1H-benzimidazol-6-yl]pyridin-2-yl}pyrazine-2-carboxamide $^1$H NMR (400 MHz, DMSO-$d_6$) δ 9.42 (s, 1H), 9.31 (d, J=1.5 Hz, 1H), 8.97 (d, J=2.4 Hz, 1H), 8.85 (dd, J=2.5, 1.5 Hz, 1H), 8.63 (s, 1H), 8.39 (s, 1H), 8.27 (d, J=1.6 Hz, 1H), 8.02 (d, J=8.5 Hz, 1H), 7.72 (dd, J=8.5, 1.5 Hz, 1H), 4.44 (d, J=7.2 Hz, 2H), 3.86 (ddd, J=11.5, 4.4, 1.9 Hz, 2H), 3.26 (td, J=11.7, 2.2 Hz, 2H), 2.21 (ddt, J=11.4, 7.7, 3.8 Hz, 1H), 1.60-1.45 (m, 2H), 1.45-1.30 (m, 2H). MS (ESI) m/z 449 (M+H)+.

Example 263

N-{5-chloro-4-[1-(tetrahydro-2H-pyran-4-ylmethyl)-1H-benzimidazol-6-yl]pyridin-2-yl}-1H-pyrazole-3-carboxamide $^1$H NMR (400 MHz, DMSO-$d_6$) δ 9.43 (s, 1H), 8.59 (s, 1H), 8.34 (s, 1H), 8.26 (d, J=1.6 Hz, 1H), 8.01 (d, J=8.5 Hz, 1H), 7.90 (d, J=2.4 Hz, 1H), 7.72 (dd, J=8.5, 1.5 Hz, 1H), 6.93 (d, J=2.4 Hz, 1H), 4.43 (d, J=7.2 Hz, 2H), 3.92-3.80 (m, 3H), 3.25 (td, J=11.6, 2.2 Hz, 2H), 2.21 (ddq, J=11.5, 7.8, 4.1 Hz, 1H), 1.49 (dd, J=13.2, 3.6 Hz, 2H), 1.44-1.29 (m, 2H). MS (ESI) m/z 437 (M+H)$^+$.

Example 264

N-{5-chloro-4-[1-(tetrahydro-2H-pyran-4-ylmethyl)-1H-benzimidazol-6-yl]pyridin-2-yl}-1H-1,2,3-triazole-4-carboxamide $^1$H NMR (400 MHz, DMSO-d$_6$) δ 9.39 (s, 1H), 8.66 (s, 1H), 8.61 (s, 1H), 8.33 (s, 1H), 8.25 (d, J=1.6 Hz, 1H), 8.01 (d, J=8.5 Hz, 1H), 7.71 (dd, J=8.5, 1.5 Hz, 1H), 4.43 (d, J=7.2 Hz, 2H), 3.85 (ddd, J=11.2, 4.4, 1.8 Hz, 2H), 3.25 (td, J=11.7, 2.2 Hz, 2H), 2.21 (ddq, J=11.3, 7.7, 3.9 Hz, 1H), 1.59-1.44 (m, 2H), 1.36 (qd, J=12.0, 4.5 Hz, 2H). MS (ESI) m/z 438 (M+H)$^+$.

Example 265

N-{5-chloro-4-[1-(tetrahydro-2H-pyran-4-ylmethyl)-1H-benzimidazol-6-yl]pyridin-2-yl}azetidine-3-carboxamide $^1$H NMR (400 MHz, DMSO-d$_6$) δ 9.12 (s, 1H), 8.77 (s, 1H), 8.08 (d, J=1.6 Hz, 1H), 7.95 (d, J=8.5 Hz, 1H), 7.57 (s, 1H), 7.53 (dd, J=8.4, 1.6 Hz, 1H), 4.31 (d, J=7.2 Hz, 2H), 3.90-3.78 (m, 2H), 3.39 (dt, J=12.4, 5.9 Hz, 1H), 3.32-3.11 (m, 4H), 2.12 (ddp, J=11.6, 7.6, 3.7 Hz, 1H), 1.51-1.21 (m, 4H). MS (ESI) m/z 426 (M+H)$^+$.

Example 266

N-{5-chloro-4-[1-(tetrahydro-2H-pyran-4-ylmethyl)-1H-benzimidazol-6-yl]pyridin-2-yl}-1H-pyrazole-4-carboxamide $^1$H NMR (400 MHz, DMSO-d$_6$) δ 9.35 (s, 1H), 8.58 (s, 1H), 8.35 (s, 1H), 8.34 (s, 2H), 8.22 (d, J=1.7 Hz, 1H), 7.99 (d, J=8.6 Hz, 1H), 7.68 (dd, J=8.5, 1.5 Hz, 1H), 4.41 (d, J=7.2 Hz, 2H), 3.93-3.81 (m, 2H), 3.25 (td, J=11.7, 2.3 Hz, 2H), 2.20 (ddd, J=11.5, 7.5, 3.9 Hz, 1H), 1.57-1.43 (m, 2H), 1.35 (qd, J=11.9, 4.5 Hz, 2H). MS (ESI) m/z 437 (M+H)$^+$.

Example 267

(3aR,6aS)—N-{5-chloro-4-[1-(tetrahydro-2H-pyran-4-ylmethyl)-1H-benzimidazol-6-yl]pyridin-2-yl}octahydrocyclopenta[c]pyrrole-5-carboxamide $^1$H NMR (400 MHz, DMSO-d$_6$) δ 9.46 (d, J=2.2 Hz, 1H), 8.52 (d, J=1.1 Hz, 1H), 8.26 (d, J=5.4 Hz, 1H), 8.23 (d, J=1.7 Hz, 1H), 7.99 (d, J=8.5 Hz, 1H), 7.67 (dd, J=8.5, 1.5 Hz, 1H), 4.43 (d, J=7.3 Hz, 2H), 3.92-3.82 (m, 2H), 3.55-3.30 (m, 2H), 3.31-2.96 (m, 5H), 2.70 (d, J=52.3 Hz, 2H), 2.28-1.85 (m, 3H), 1.84-1.52 (m, 2H), 1.54-1.30 (m, 4H). MS (ESI) m/z 480 (M+H)$^+$.

Example 268

N-{5-chloro-4-[1-(tetrahydro-2H-pyran-4-ylmethyl)-1H-benzimidazol-6-yl]pyridin-2-yl}-2-azaspiro[3.3]heptane-6-carboxamide $^1$H NMR (400 MHz, DMSO-d$_6$) δ 9.47 (d, J=1.5 Hz, 1H), 8.51 (s, 1H), 8.27 (s, 1H), 8.25-8.19 (m, 1H), 8.00 (d, J=8.6 Hz, 1H), 7.68 (dd, J=8.5, 1.5 Hz, 1H), 4.44 (d, J=7.2 Hz, 2H), 3.85 (ddd, J=11.6, 4.3, 2.0 Hz, 4H), 3.77 (s, 2H), 3.34-3.20 (m, 3H), 2.47-2.27 (m, 4H), 2.20 (ddq, J=11.8, 8.1, 3.9 Hz, 1H), 1.57-1.37 (m, 4H). MS (ESI) m/z 466 (M+H)$^+$.

Example 269

N-{5-chloro-4-[1-(tetrahydro-2H-pyran-4-ylmethyl)-1H-benzimidazol-6-yl]pyridin-2-yl}-3-azabicyclo[3.1.0]hexane-6-carboxamide $^1$H NMR (400 MHz, DMSO-d$_6$) δ 9.39 (s, 1H), 8.52 (s, 1H), 8.20 (s, 1H), 8.19 (d, J=1.5 Hz, 1H), 7.97 (d, J=8.5 Hz, 1H), 7.64 (dd, J=8.5, 1.5 Hz, 1H), 4.41 (d, J=7.3 Hz, 2H), 3.90-3.81 (m, 2H), 3.52 (dd, J=18.3, 11.2 Hz, 3H), 3.38 (t, J=12.9 Hz, 3H), 3.30-3.14 (m, 2H), 2.18 (ddd, J=11.5, 7.6, 4.0 Hz, 1H), 2.02 (t, J=3.1 Hz, 2H), 1.88 (t, J=3.1 Hz, 1H), 1.53-1.43 (m, 2H), 1.37-1.31 (m, 2H). MS (ESI) m/z 452 (M+H)$^+$.

Example 270

N-{5-chloro-4-[1-(tetrahydro-2H-pyran-4-ylmethyl)-1H-benzimidazol-6-yl]pyridin-2-yl}-3-oxocyclobutanecarboxamide $^1$H NMR (400 MHz, DMSO-d$_6$) δ 9.54 (s, 1H), 8.56 (s, 1H), 8.29 (s, 1H), 8.26 (dd, J=2.6, 1.8 Hz, 1H), 8.02 (d, J=8.6 Hz, 1H), 7.71 (dd, J=8.5, 1.5 Hz, 1H), 4.45 (d, J=7.3 Hz, 2H), 3.85 (ddd, J=12.1, 4.6, 2.0 Hz, 3H), 3.62-3.46 (m, 1H), 3.43-3.19 (m, 4H), 2.21 (ddd, J=11.3, 7.4, 3.7 Hz, 1H), 1.49 (dd, J=13.1, 3.4 Hz, 2H), 1.44-1.34 (m, 2H). MS (ESI) m/z 439 (M+H)$^+$.

Example 271

(3R)—N-{5-chloro-4-[2-(3-fluorophenyl)-1-methyl-1H-benzimidazol-6-yl]pyridin-2-yl}piperidine-3-carboxamide Example 271A 5-bromo-N-methyl-2-nitroaniline The title compound was prepared as described in Example 8A using methanamine in place of 3-fluorobenzylamine.

Example 271B 5-bromo-N$^1$-methylbenzene-1,2-diamine

The title compound was prepared as described in Example 8B using Example 271A in place of Example 8A. MS (DCI) m/e 200.9 (M+H)$^+$.

Example 271C 6-bromo-2-(3-fluorophenyl)-1-methyl-1H-benzo[d]imidazole

2-Fluorobenzoic acid (128 mg, 0.91 mmol) and carbonyl diimidazole (170 mg, 1.05 mmol) were dissolved in butyronitrile (3 mL). After stirring at room temperature for 15 minutes, Example 271B (183 mg, 0.91 mmol) was added. The reaction mixture was heated at 180° C. for 30 minutes in a Biotage® Initiator® microwave reactor. The reaction mixture was concentrated and acetic acid (2 mL) was added. After heating at 150° C. for 20 minutes, the residue was partitioned between 50 mL of ethyl acetate and 50 mL of water. The aqueous layer was removed and the organic layer was washed with aqueous saturated sodium bicarbonate (30 mL), dried over sodium sulfate, filtered and concentrated. Purification by silica gel flash chromatography eluting with 20% ethyl acetate in hexanes gave the title compound. MS (DCI) m/e 305.0 (M+H)$^+$.

Example 271D (3R)—N-{5-chloro-4-[2-(3-fluorophenyl)-1-methyl-1H-benzimidazol-6-yl]pyridin-2-yl}piperidine-3-carboxamide The title compound was prepared as described in Example 14E using Example 271C in place of Example 14D. $^1$H NMR (400 MHz, DMSO-d$_6$) δ 1.40 (m, 1H), 1.58 (m, 2H), 1.84 (m, 1H), 2.69 (m, 4H), 2.99 (m, 1H), 3.95 (s, 3H), 7.37 (d, 1H), 7.44 m, 1H), 7.65 (m, 1H), 7.75 (m, 2H), 7.81 (m, 2H), 8.28 (s, 1H), 8.48 (s, 1H), 10.96 (br s, 1H). MS (ESI) m/e 464.2 (M+H)$^+$.

Example 272

(3R)—N-{5-chloro-4-[2-(3-fluorobenzyl)-1-methyl-1H-benzimidazol-6-yl]pyridin-2-yl}piperidine-3-carboxamide Example 272A 6-bromo-2-(3-fluorobenzyl)-1-methyl-1H-benzo[d]imidazole The title compound was prepared as described in Example 271C using 2-(3-fluorophenyl)acetic acid in place of 2-fluorobenzoic acid. MS (DCI) m/e 318.9 (M+H)$^+$.

Example 272B (3R)—N-{5-chloro-4-[2-(3-fluorobenzyl)-1-methyl-1H-benzimidazol-6-yl]pyridin-2-yl}piperidine-3-carboxamide The title compound was prepared as described in Example 14E using Example 272A in place of Example 14D. $^1$H NMR (400 MHz, DMSO-d$_6$) δ 1.39 (m, 1H), 1.60 (m, 2H), 1.85 (m, 1H), 2.2.61 (m, 3H), 2.81 (m, 1H), 2.99 (m, 1H), 3.77 (s, 3H), 4.38 (s, 2H), 7.16 (m, 3H), 7.28 (m, 1H), 7.39 (m, 1H), 7.64 (br s, 1H), 7.70 (d, 1H), 8.24 (s, 1H), 8.45 9s, 1H), 10.93 (br s, 1H). MS (ESI) m/e 478.2 (M+H)$^+$.

Example 273

N-{5-chloro-4-[1-(tetrahydro-2H-pyran-4-ylmethyl)-1H-benzimidazol-6-yl]pyridin-2-yl}-1,2,5,6-tetrahydropyridine-3-carboxamide The title compound was prepared as described in Example 210C using 1-(tert-butoxycarbonyl)-1,2,5,6-tetrahydropyridine-3-carboxylic acid in place of 1-(tert-butoxycarbonyl)piperidine-4-carboxylic acid to afford the bis hydrochloric acid salt. $^1$H NMR (400 MHz, DMSO-d$_6$) δ ppm 1.26-1.57 (m, 4H), 2.08-2.25 (m, 1H), 2.48-2.56 (m, 2H), 3.15-3.30 (m, 4H), 3.78-3.90 (m, 4H), 4.37 (d, J=7.2 Hz, 2H), 7.12-7.23 (m, 1H), 7.57 (dd, J=8.4, 1.5 Hz, 1H), 7.95 (d, J=8.5 Hz, 1H), 8.15 (d, J=1.6 Hz, 1H), 8.21 (s, 1H), 8.60 (s, 1H), 9.03 (s, 2H), 9.22 (s, 1H), 10.88 (s, 1H). MS (ESI$^+$) m/z 452.2 (M+H)$^+$.

The following Examples (Example 274 to Example 290) were prepared essentially as described in Example 189 using the appropriate aminopyridine (Example 49 or Example 210B) and substituting the appropriate carboxylic acid. All Examples were purified by reverse-phase HPLC and were isolated as trifluoroacetic acid salts.

Example 274

N-{5-chloro-4-[1-(3-fluorobenzyl)-1H-benzimidazol-6-yl]pyridin-2-yl}-2-(tetrahydro-2H-pyran-4-ylsulfonyl)propanamide $^1$H NMR (400 MHz, DMSO-d$_6$/D$_2$O) δ ppm 1.53 (s, 3H), 1.58-1.80 (m, 2H), 1.87-2.01 (m, 2H), 3.30-3.46 (m, 2H), 3.59-3.71 (m, 2H), 3.91-4.03 (m, 2H), 5.59 (s, 2H), 7.13 (td, J=8.9, 2.8 Hz, 1H), 7.17-7.27 (m, 2H), 7.34 (dd, J=8.4, 1.7 Hz, 1H), 7.36-7.47 (m, 1H), 7.70-7.78 (m, 1H), 7.83 (d, J=8.4 Hz, 1H), 8.16 (s, 1H), 8.51 (s, 1H), 8.57 (s, 1H). MS (ESI) m/e 557 (M+H)+.

Example 275

N-{5-chloro-4-[1-(3-fluorobenzyl)-1H-benzimidazol-6-yl]pyridin-2-yl}-5,6,7,8-tetrahydro[1,2,4]triazolo[4,3-a]pyridine-6-carboxamide $^1$H NMR (400 MHz, DMSO-d$_6$/D$_2$O) δ ppm 1.96-2.13 (m, 1H), 2.17-2.31 (m, 1H), 2.71-2.99 (m, 2H), 3.11-3.30 (m, 1H), 4.06-4.19 (m, 1H), 4.22-4.35 (m, 1H), 5.58 (s, 2H), 7.11 (td, J=8.4, 2.5 Hz, 1H), 7.15-7.24 (m, 2H), 7.33 (dd, J=8.4, 1.7 Hz, 1H), 7.34-7.41 (m, 1H), 7.67-7.76 (m, 1H), 7.81 (d, J=8.4 Hz, 1H), 8.15 (s, 1H), 8.42 (s, 1H), 8.48 (s, 1H), 8.56 (s, 1H). MS (ESI) m/e 502 (M+H)+.

Example 276

N-{5-chloro-4-[1-(3-fluorobenzyl)-1H-benzimidazol-6-yl]pyridin-2-yl}-5,6,7,8-tetrahydroimidazo[1,2-a]pyridine-6-carboxamide $^1$H NMR (400 MHz, DMSO-d$_6$) δ ppm 1.94-2.07 (m, 1H), 2.17-2.29 (m, 1H), 2.66-2.92 (m, 2H), 3.14-3.29 (m, 1H), 3.97-4.11 (m, 1H), 4.15-4.28 (m, 1H), 5.58 (s, 2H), 6.82-6.84 (m, 1H), 7.04-7.07 (m, 1H), 7.08-7.15 (m, 1H), 7.16-7.25 (m, 2H), 7.33 (dd, J=8.4, 1.7 Hz, 1H), 7.35-7.42 (m, 1H), 7.71-7.74 (m, 1H), 7.81 (d, J=8.3 Hz, 1H), 8.18 (s, 1H), 8.48 (s, 1H), 8.56 (s, 1H). MS (ESI) m/e 501 (M+H)+.

Example 277

N-{5-chloro-4-[1-(3-fluorobenzyl)-1H-benzimidazol-6-yl]pyridin-2-yl}-3,4-dihydro-2H-pyrano[2,3-b]pyridine-6-carboxamide $^1$H NMR (400 MHz, DMSO-d$_6$/D$_2$O) δ ppm 1.88-1.94 (m, 2H), 2.72-2.81 (m, 2H), 4.32-4.36 (m, 2H), 5.59 (s, 2H), 7.06-7.16 (m, 1H), 7.17-7.26 (m, 2H), 7.33-7.43 (m, 2H), 7.76-7.86 (m, 3H), 7.90-7.93 (m, 1H), 8.40-8.42 (m, 1H), 8.47-8.53 (m, 1H), 8.56-8.58 (m, 1H). MS (ESI) m/e 514 (M+H)+.

Example 278

N-{5-chloro-4-[1-(3-fluorobenzyl)-1H-benzimidazol-6-yl]pyridin-2-yl}-2-sulfamoylacetamide $^1$H NMR (400 MHz, DMSO-d$_6$/D$_2$O) δ ppm 3.76-3.79 (m, 1H), 4.18-4.29 (m, 1H), 5.58 (s, 2H), 7.06-7.24 (m, 3H), 7.32 (dd, J=8.4, 1.7 Hz, 1H), 7.36-7.43 (m, 1H), 7.70-7.78 (m, 1H), 7.83 (d, J=8.3 Hz, 1H), 8.19 (s, 1H), 8.50 (s, 1H), 8.56 (s, 1H). MS (ESI) m/e 474 (M+H)+.

Example 279

N-{5-chloro-4-[1-(3-fluorobenzyl)-1H-benzimidazol-6-yl]pyridin-2-yl}-2-[(4-methylpiperazin-1-yl)sulfonyl]acetamide $^1$H NMR (400 MHz, DMSO-d$_6$/D$_2$O) δ ppm 2.18 (s, 3H), 2.33-2.43 (m, 4H), 3.18-3.29 (m, 4H), 3.74-3.79 (m, 2H), 5.58 (s, 2H), 7.13 (td, J=8.6, 2.5 Hz, 1H), 7.16-7.25 (m, 2H), 7.31-7.36 (m, 1H), 7.37-7.44 (m, 1H), 7.71-7.77 (m, 1H), 7.83 (d, J=8.4 Hz, 1H), 8.14 (s, 1H), 8.51 (s, 1H), 8.57 (s, 1H). MS (ESI) m/e 557 (M+H)+.

Example 280

N-{5-chloro-4-[1-(3-fluorobenzyl)-1H-benzimidazol-6-yl]pyridin-2-yl}-5-oxo-D-prolinamide $^1$H NMR (400 MHz, DMSO-d$_6$/D$_2$O) δ ppm 1.95-2.06 (m, 1H), 2.11-2.28 (m, 2H), 2.32-2.45 (m, 1H), 4.30-4.42 (m, 1H), 5.58 (s, 2H), 7.09-7.16 (m, 1H), 7.16-7.20 (m, 1H), 7.20-7.24 (m, 1H), 7.33 (dd, J=8.3, 1.7 Hz, 1H), 7.36-7.44 (m, 1H), 7.70-7.74 (m, 1H), 7.82 (d, J=8.5 Hz, 1H), 8.18 (s, 1H), 8.48 (s, 1H), 8.56 (s, 1H). MS (ESI) m/e 464 (M+H)+.

Example 281

N-{5-chloro-4-[1-(3-fluorobenzyl)-1H-benzimidazol-6-yl]pyridin-2-yl}-N$^2$-(dimethylsulfamoyl)glycinamide $^1$H NMR (400 MHz, DMSO-d$_6$/D$_2$O) δ ppm 2.68 (s, 6H), 3.88 (s, 2H), 5.58 (s, 2H), 7.13 (td, J=9.1, 2.8 Hz, 1H), 7.17-7.26 (m, 2H), 7.33 (dd, J=8.4, 1.7 Hz, 1H), 7.36-7.45 (m, 1H), 7.69-7.77 (m, 1H), 7.82 (d, J=8.6 Hz, 1H), 8.15 (s, 1H), 8.47 (s, 1H), 8.57 (s, 1H). MS (ESI) m/e 517 (M+H)+.

Example 282

N-{5-chloro-4-[1-(tetrahydro-2H-pyran-4-ylmethyl)-1H-benzimidazol-6-yl]pyridin-2-yl}-2-(tetrahydro-2H-pyran-4-ylsulfonyl)propanamide $^1$H NMR (400 MHz, DMSO-d$_6$/D$_2$O) δ ppm 1.21-1.47 (m, 4H), 1.53 (s, 3H), 1.59-1.81 (m, 2H), 1.87-2.02 (m, 2H), 3.13-3.29 (m, 2H), 3.31-3.46 (m, 2H), 3.58-3.73 (m, 2H), 3.76-3.88 (m, 3H), 3.91-4.03 (m, 2H), 4.23 (d, J=7.2 Hz, 2H), 7.34 (dd, J=8.4, 1.7 Hz, 1H), 7.81 (d, J=8.4 Hz, 1H), 7.83-7.89 (m, 1H), 8.21 (s, 1H), 8.35 (s, 1H), 8.54 (s, 1H). MS (ESI) m/e 547 (M+H)+.

Example 283

N-{5-chloro-4-[1-(tetrahydro-2H-pyran-4-ylmethyl)-1H-benzimidazol-6-yl]pyridin-2-yl}-5,6,7,8-tetrahydro[1,2,4]triazolo[4,3-a]pyridine-6-carboxamide $^1$H NMR (400 MHz, DMSO-d$_6$/D$_2$O) δ ppm 1.20-1.46 (m, 4H), 1.97-2.15 (m, 2H), 2.18-2.32 (m, 1H), 2.76-3.05 (m, 2H), 3.14-3.29 (m, 3H), 3.75-3.87 (m, 2H), 4.07-4.15 (m, 1H), 4.22 (d, J=7.1 Hz, 2H), 4.26-4.36 (m, 1H), 7.32 (dd, J=8.4, 1.7 Hz, 1H), 7.79 (d, J=8.5 Hz, 1H), 7.82-7.85 (m, 1H), 8.21 (s, 1H), 8.35 (s, 1H), 8.42 (s, 1H), 8.51 (s, 1H). MS (ESI) m/e 492 (M+H)+.

Example 284

N-{5-chloro-4-[1-(tetrahydro-2H-pyran-4-ylmethyl)-1H-benzimidazol-6-yl]pyridin-2-yl}-5,6,7,8-tetrahydroimidazo[1,2-a]pyridine-6-carboxamide $^1$H NMR (400 MHz, DMSO-d$_6$/D$_2$O) δ ppm 1.20-1.46 (m, 4H), 1.94-2.17 (m, 2H), 2.19-2.27 (m, 1H), 2.69-2.89 (m, 2H), 3.16-3.26 (m, 3H), 3.79-3.86 (m, 2H), 3.97-4.11 (m, 1H), 4.17-4.26 (m, 3H), 6.83 (d, J=1.4 Hz, 1H), 7.05 (d, J=1.4 Hz, 1H), 7.33 (dd, J=8.4, 1.7 Hz, 1H), 7.80 (d, J=8.3 Hz, 1H), 7.82-7.86 (m, 1H), 8.23 (s, 1H), 8.35 (s, 1H), 8.51 (s, 1H). MS (ESI) m/e 491 (M+H)+.

Example 285

N-{5-chloro-4-[1-(tetrahydro-2H-pyran-4-ylmethyl)-1H-benzimidazol-6-yl]pyridin-2-yl}-3,4-dihydro-2H-pyrano[2,3-b]pyridine-6-carboxamide $^1$H NMR (400 MHz, DMSO-d$_6$/D$_2$O) δ ppm 1.23-1.47 (m, 4H), 1.87-1.99 (m, 2H), 2.03-2.17 (m, 1H), 2.76-2.87 (m, 2H), 3.18-3.27 (m, 2H), 3.79-3.85 (m, 2H), 4.20-4.26 (m, 2H), 4.33-4.40 (m, 2H), 7.32-7.41 (m, 1H), 7.79-7.85 (m, 1H), 7.85-7.94 (m, 2H), 8.12-8.63 (m, 4H). MS (ESI) m/e 504 (M+H)+.

Example 286

N-{5-chloro-4-[1-(tetrahydro-2H-pyran-4-ylmethyl)-1H-benzimidazol-6-yl]pyridin-2-yl}-2-sulfamoylacetamide $^1$H NMR (400 MHz, DMSO-d$_6$/D$_2$O) δ ppm 1.20-1.46 (m, 4H), 2.02-2.17 (m, 1H), 3.13-3.29 (m, 2H), 3.76-3.88 (m, 4H), 4.17-4.28 (m, 2H), 7.33 (dd, J=8.4, 1.6 Hz, 1H), 7.81 (d, J=8.5 Hz, 1H), 7.83-7.85 (m, 1H), 8.24 (s, 1H), 8.35 (s, 1H), 8.53 (s, 1H). MS (ESI) m/e 464 (M+H)+.

Example 287

N-{5-chloro-4-[1-(tetrahydro-2H-pyran-4-ylmethyl)-1H-benzimidazol-6-yl]pyridin-2-yl}-N$^2$-(ethylsulfonyl)glycinamide $^1$H NMR (400 MHz, DMSO-d$_6$/D$_2$O) δ ppm 1.24 (t, J=7.3 Hz, 3H), 1.27-1.37 (m, 2H), 1.36-1.46 (m, 2H), 2.03-2.16 (m, 1H), 3.07 (q, J=7.4 Hz, 2H), 3.18-3.27 (m, 2H), 3.80-3.85 (m, 2H), 3.93 (s, 2H), 4.16-4.28 (m, 2H), 7.34 (dd, J=8.4, 1.7 Hz, 1H), 7.80 (d, J=8.4 Hz, 1H), 7.82-7.84 (m, 1H), 8.20 (s, 1H), 8.35 (s, 1H), 8.50 (s, 1H). MS (ESI) m/e 492 (M+H)+.

Example 288

N-{5-chloro-4-[1-(tetrahydro-2H-pyran-4-ylmethyl)-1H-benzimidazol-6-yl]pyridin-2-yl}-5-oxo-D-prolinamide $^1$H NMR (400 MHz, DMSO-d$_6$/D$_2$O) δ ppm 1.21-1.46 (m, 4H), 1.93-2.31 (m, 4H), 2.31-2.47 (m, 1H), 3.18-3.29

(m, 2H), 3.80-3.88 (m, 2H), 4.18-4.28 (m, 2H), 4.32-4.43 (m, 1H), 7.33 (dd, J=8.3, 1.7 Hz, 1H), 7.80 (d, J=8.5 Hz, 1H), 7.82-7.86 (m, 1H), 8.23 (s, 1H), 8.35 (s, 1H), 8.51 (s, 1H). MS (ESI) m/e 454 (M+H)+.

Example 289

N-{5-chloro-4-[1-(tetrahydro-2H-pyran-4-ylmethyl)-1H-benzimidazol-6-yl]pyridin-2-yl}-N²-(dimethylsulfamoyl)glycinamide ¹H NMR (400 MHz, DMSO-d₆/D₂O) δ ppm 1.19-1.46 (m, 4H), 2.03-2.14 (m, 1H), 2.68 (s, 6H), 3.15-3.29 (m, 2H), 3.79-3.87 (m, 2H), 3.89 (s, 2H), 4.18-4.28 (m, 2H), 7.34 (dd, J=8.4, 1.6 Hz, 1H), 7.81 (d, J=8.4 Hz, 1H), 7.82-7.86 (m, 1H), 8.21 (s, 1H), 8.35 (s, 1H), 8.50 (s, 1H). MS (ESI) m/e 507 (M+H)+.

Example 290

N-{5-chloro-4-[1-(tetrahydro-2H-pyran-4-ylmethyl)-1H-benzimidazol-6-yl]pyridin-2-yl}-2-[(4-methylpiperazin-1-yl)sulfonyl]acetamide ¹H NMR (400 MHz, DMSO-d₆/D₂O) δ ppm 1.26-1.49 (m, 6H), 2.15 (s, 1H), 2.83 (s, 3H), 2.96-3.34 (m, 7H), 3.81-3.86 (m, 3H), 4.31-4.38 (m, 2H), 4.49 (s, 2H), 7.54 (dd, J=8.4, 1.6 Hz, 1H), 7.93 (d, J=8.5 Hz, 1H), 8.03-8.15 (m, 1H), 8.20 (s, 1H), 8.59 (s, 1H), 9.07 (s, 1H). MS (ESI) m/e 547 (M+H)+.

Example 291

(3R)—N-(5-chloro-4-{1-[4-(methylsulfonyl)benzyl]-1H-benzotriazol-6-yl}pyridin-2-yl)piperidine-3-carboxamide Example 291A 5-bromo-N-(4-(methylsulfonyl)benzyl)-2-nitroaniline The title compound was prepared as described in Example 8A using 4-methylsulfonylbenzylamine hydrochloride in place of 3-fluorobenzylamine.

Example 291B 5-bromo-N-1-(4-(methylsulfonyl)benzyl)benzene-1,2-diamine

The title compound was prepared as described in Example 8B using Example 291A in place of Example 8A.

Example 291C 6-bromo-1-(4-(methylsulfonyl)benzyl)-1H-benzo[d][1,2,3]triazole

The title compound was prepared as described in Example 110A using Example 291B in place of Example 8B.

Example 291D (3R)—N-(5-chloro-4-{1-[4-(methylsulfonyl)benzyl]-1H-benzotriazol-6-yl}pyridin-2-yl)piperidine-3-carboxamide The title compound was prepared as described in Example 14E using Example 291C in place of Example 14D. ¹H NMR (400 MHz, DMSO-d₆) δ 1.61 (m, 3H), 1.93 (m, 1H), 2.71 (m, 3H), 2.92 (m, 2H), 3.09 (m, 1H), 2.18 (s, 3H), 6.18 (m, 2H), 7.49 (d, 1H), 7.61 (d, 2H), 7.91 (d, 2H), 8.10 (br s, 1H), 8.22 (br s, 2H), 8.52 (s, 1H), 11.03 (br s, 1H). MS (ESI) m/e 525.1 (M+H)⁺.

The following Examples (Example 292 to Example 302) were prepared essentially as described in Example 189 using Example 210B in place of Example 49 and substituting the appropriate carboxylic acid. All products were purified by reverse-phase HPLC and were isolated as trifluoroacetic acid salts.

Example 292 cis-3-amino-N-{5-chloro-4-[1-(tetrahydro-2H-pyran-4-ylmethyl)-1H-benzimidazol-6-yl]pyridin-2-yl}cyclobutanecarboxamide ¹H NMR (500 MHz, DMSO-d₆/D₂O) δ ppm 1.24-1.35 (m, 2H), 1.38-1.45 (m, 2H), 1.98-2.18 (m, 3H), 2.35-2.45 (m, 2H), 2.81-2.92 (m, 1H), 3.14-3.28 (m, 2H), 3.31-3.45 (m, 1H), 3.80-3.88 (m, 2H), 4.19-4.27 (m, 2H), 7.33 (dd, J=8.5, 1.7 Hz, 1H), 7.80 (d, J=8.4 Hz, 1H), 7.82-7.87 (m, 1H), 8.25 (s, 1H), 8.35 (s, 1H), 8.47 (s, 1H). MS (ESI) m/e 440 (M+H)+.

Example 293 trans-3-amino-N-{5-chloro-4-[1-(tetrahydro-2H-pyran-4-ylmethyl)-1H-benzimidazol-6-yl]pyridin-2-yl}cyclobutanecarboxamide ¹H NMR (500 MHz, DMSO-d₆/D₂O) δ ppm 1.24-1.36 (m, 2H), 1.36-1.46 (m, 2H), 2.06-2.21 (m, 3H), 2.36-2.47 (m, 2H), 3.17-3.34 (m, 3H), 3.55-3.68 (m, 1H), 3.79-3.88 (m, 2H), 4.19-4.27 (m, 2H), 7.34 (dd, J=8.3, 1.7 Hz, 1H), 7.80 (d, J=8.4 Hz, 1H), 7.83-7.87 (m, 1H), 8.26 (s, 1H), 8.35 (s, 1H), 8.47 (s, 1H). MS (ESI) m/e 440 (M+H)+.

Example 294

(1R,5S,6r)-N-{5-chloro-4-[1-(tetrahydro-2H-pyran-4-ylmethyl)-1H-benzimidazol-6-yl]pyridin-2-yl}-3-azabicyclo[3.1.0]hexane-6-carboxamide ¹H NMR (500 MHz, DMSO-d₆/D₂O) δ ppm 1.20-1.35 (m, 2H), 1.35-1.45 (m, 2H), 1.80-1.83 (m, 1H), 2.05-2.13 (m, 1H), 2.76-2.85 (m, 3H), 2.93-3.04 (m, 3H), 3.14-3.28 (m, 2H), 3.80-3.85 (m, 2H), 4.18-4.26 (m, 2H), 7.32 (dd, J=8.4, 1.6 Hz, 1H), 7.79 (d, J=8.3 Hz, 1H), 7.81-7.86 (m, 1H), 8.18 (s, 1H), 8.34 (s, 1H), 8.46 (s, 1H). MS (ESI) m/e 452 (M+H)+.

Example 295

(2R)—N-{5-chloro-4-[1-(tetrahydro-2H-pyran-4-ylmethyl)-1H-benzimidazol-6-yl]pyridin-2-yl}azetidine-2-carboxamide ¹H NMR (500 MHz, DMSO-d₆) δ ppm 1.19-1.46 (m, 6H), 2.05-2.16 (m, 1H), 3.17-3.29 (m, 4H), 3.79-3.87 (m, 3H), 4.23 (d, J=7.3 Hz, 2H), 7.35 (dd, J=8.4, 1.7 Hz, 1H), 7.81 (d, J=8.4 Hz, 1H), 7.85 (d, J=1.8 Hz, 1H), 8.25 (s, 1H), 8.35 (s, 1H), 8.51 (s, 1H). MS (ESI) m/e 426 (M+H)+.

Example 296

6-amino-N-{5-chloro-4-[1-(tetrahydro-2H-pyran-4-ylmethyl)-1H-benzimidazol-6-yl]pyridin-2-yl}spiro[3.3]heptane-2-carboxamide $^1$H NMR (500 MHz, DMSO-d$_6$/D$_2$O) δ ppm 1.20-1.36 (m, 2H), 1.36-1.45 (m, 2H), 1.85-1.93 (m, 1H), 1.94-2.03 (m, 1H), 2.05-2.16 (m, 2H), 2.15-2.27 (m, 4H), 2.34-2.42 (m, 1H), 3.14-3.32 (m, 3H), 3.32-3.46 (m, 1H), 3.80-3.86 (m, 2H), 4.19-4.27 (m, 2H), 7.33 (dd, J=8.3, 1.6 Hz, 1H), 7.76-7.86 (m, 2H), 8.24 (s, 1H), 8.35 (s, 1H), 8.46 (s, 1H). MS (ESI) m/e 480 (M+H)+.

Example 297

N-{5-chloro-4-[1-(tetrahydro-2H-pyran-4-ylmethyl)-1H-benzimidazol-6-yl]pyridin-2-yl}-2-(furan-2-yl)-2-(piperazin-1-yl)acetamide $^1$H NMR (500 MHz, DMSO-d$_6$/D$_2$O) δ ppm 1.23-1.43 (m, 6H), 2.06-2.13 (m, 1H), 2.42-2.46 (m, 1H), 2.79-2.84 (m, 4H), 3.22 (t, J=11.4 Hz, 3H), 3.80-3.84 (m, 2H), 4.21-4.26 (m, 2H), 4.57 (s, 1H), 6.46-6.50 (m, 2H), 7.34 (dd, J=8.3, 1.6 Hz, 1H), 7.63-7.68 (m, 1H), 7.76-7.88 (m, 2H), 8.22 (s, 1H), 8.35 (s, 1H), 8.53 (s, 1H). MS (ESI) m/e 535 (M+H)+.

Example 298

1-amino-N-{5-chloro-4-[1-(tetrahydro-2H-pyran-4-ylmethyl)-1H-benzimidazol-6-yl]pyridin-2-yl}cyclopentanecarboxamide $^1$H NMR (500 MHz, DMSO-d$_6$/D$_2$O) δ ppm 1.25-1.45 (m, 5H), 1.56-1.62 (m, 2H), 1.66-1.74 (m, 2H), 1.78-1.83 (m, 2H), 1.99-2.13 (m, 2H), 3.17-3.28 (m, 2H), 3.80-3.84 (m, 2H), 4.21-4.24 (m, 2H), 7.31-7.36 (m, 1H), 7.78-7.82 (m, 1H), 7.82-7.88 (m, 1H), 8.28 (s, 1H), 8.35 (s, 1H), 8.49 (s, 1H). MS (ESI) m/e 454 (M+H)+.

Example 299

N-{5-chloro-4-[1-(tetrahydro-2H-pyran-4-ylmethyl)-1H-benzimidazol-6-yl]pyridin-2-yl}-5-thia-2-azaspiro[3.4]octane-8-carboxamide 5,5-dioxide $^1$H NMR (500 MHz, DMSO-d$_6$/D$_2$O) δ ppm 1.22-1.36 (m, 2H), 1.36-1.46 (m, 2H), 2.04-2.27 (m, 2H), 3.08-3.16 (m, 1H), 3.18 (s, 1H), 3.19-3.28 (m, 2H), 3.49-3.58 (m, 2H), 3.62-3.73 (m, 4H), 3.81-3.86 (m, 2H), 4.20-4.26 (m, 2H), 7.31-7.38 (m, 1H), 7.78-7.83 (m, 1H), 7.83-7.89 (m, 1H), 8.27 (s, 1H), 8.35 (s, 1H), 8.54 (s, 1H). MS (ESI) m/e 530 (M+H)+.

Example 300

(2S,3R)—N-{5-chloro-4-[1-(tetrahydro-2H-pyran-4-ylmethyl)-1H-benzimidazol-6-yl]pyridin-2-yl}-3-ethylazetidine-2-carboxamide $^1$H NMR (500 MHz, DMSO-d$_6$/D$_2$O) δ ppm 0.72-0.81 (m, 2H), 1.23-1.36 (m, 2H), 1.36-1.47 (m, 2H), 1.45-1.60 (m, 1H), 2.04-2.17 (m, 1H), 2.73-2.83 (m, 2H), 2.96-3.04 (m, 2H), 3.18-3.27 (m, 2H), 3.64-3.72 (m, 2H), 3.80-3.95 (m, 2H), 4.20-4.42 (m, 2H), 7.30-7.39 (m, 1H), 7.78-7.83 (m, 1H), 7.83-7.87 (m, 1H), 8.20-8.31 (m, 1H), 8.35 (s, 1H), 8.51 (s, 1H). MS (ESI) m/e 454 (M+H)+.

Example 301

N-{5-chloro-4-[1-(tetrahydro-2H-pyran-4-ylmethyl)-1H-benzimidazol-6-yl]pyridin-2-yl}-4-(4-fluorophenyl)piperidine-4-carboxamide $^1$H NMR (500 MHz, DMSO-d$_6$/D$_2$O) δ ppm 1.23-1.36 (m, 2H), 1.36-1.45 (m, 2H), 1.94-2.07 (m, 2H), 2.06-2.16 (m, 1H), 2.64-2.73 (m, 2H), 2.78-2.90 (m, 2H), 2.97-3.07 (m, 2H), 3.20-3.28 (m, 2H), 3.80-3.88 (m, 2H), 4.19-4.27 (m, 2H), 7.18-7.26 (m, 2H), 7.32 (dd, J=8.3, 1.6 Hz, 1H), 7.46-7.51 (m, 2H), 7.80 (d, J=8.4 Hz, 1H), 7.82-7.84 (m, 1H), 8.15 (s, 1H), 8.35 (s, 1H), 8.46 (s, 1H). MS (ESI) m/e 548 (M+H)+.

Example 302

N-{5-chloro-4-[1-(tetrahydro-2H-pyran-4-ylmethyl)-1H-benzimidazol-6-yl]pyridin-2-yl}-1-thia-7-azaspiro[4.4]nonane-4-carboxamide 1,1-dioxide $^1$H NMR (500 MHz, DMSO-d$_6$/D$_2$O) δ ppm 1.24-1.36 (m, 2H), 1.36-1.46 (m, 2H), 2.04-2.15 (m, 2H), 2.21-2.36 (m, 3H), 2.62-2.75 (m, 1H), 2.80-2.91 (m, 1H), 3.00-3.11 (m, 1H), 3.18-3.27 (m, 4H), 3.32-3.40 (m, 1H), 3.43-3.55 (m, 1H), 3.80-3.87 (m, 2H), 4.19-4.25 (m, 2H), 7.34 (dd, J=8.3, 1.6 Hz, 1H), 7.81 (d, J=8.3 Hz, 1H), 7.83-7.86 (m, 1H), 8.17-8.24 (m, 1H), 8.35 (s, 1H), 8.52 (s, 1H). MS (ESI) m/e 544 (M+H)+.

Example 303

(3R)—N-(5-chloro-4-{1-[2-(3-fluorophenyl)-2-oxoethyl]-1H-pyrrolo[3,2-b]pyridin-6-yl}pyridin-2-yl)piperidine-3-carboxamide Example 303A 2-(6-bromo-1H-pyrrolo[3,2-b]pyridin-1-yl)-1-(3-fluorophenyl)ethanone A two dram vial equipped with septa was charged with 6-bromo-1H-pyrrolo[3,2-b]pyridine (1.04 g, 5.28 mmol), 2-bromo-1-(3-fluorophenyl)ethanone (1.489 g, 6.86 mmol) and N,N-dimethylformamide (12.48 mL). N-ethyl-N-isopropylpropan-2-amine (1.844 mL, 10.56 mmol) was then added and the mixture was stirred at 80° C. for 2 hours. After cooling to ambient temperature, the mixture was diluted with 50 mL of ethyl acetate and poured into a 125 mL separatory funnel. The organic layer was washed with water (50 mL) and saturated aqueous brine (40 mL), dried over anhydrous magnesium sulfate, filtered and concentrated. Purification by silica gel flash chromatography (Isco®, Redi-Sep® column) eluting with a gradient of 10-80% ethyl acetate/hexane afforded the title compound. MS (ESI$^+$) m/z 335.0 (M+H)$^+$.

Example 303B (3R)—N-(5-chloro-4-{1-[2-(3-fluorophenyl)-2-oxoethyl]-1H-pyrrolo[3,2-b]pyridin-6-yl}pyridin-2-yl)piperidine-3-carboxamide The tert-butyloxocarbonyl protected title compound was prepared as described in Example 253B using Example 303A in place of Example 253A. The tert-butyloxocarbonyl intermediate was dissolved into 3 mL of dichloromethane and treated with 3 mL of trifluoroacetic acid. The mixture was stirred at ambient for 10 minutes then concentrated. The residue was treated with 25 mL of ethyl acetate and poured into a 60 mL separatory funnel. The organic mixture was washed with diluted aqueous potassium carbonate (10% weight in water, 1×20 mL), saturated aqueous sodium carbonate (1×20 mL), and saturated aqueous brine (1×20 mL), dried over anhydrous magnesium sulfate, filtered and concentrated. Purification by silica gel flash chromatography (Isco®, Redi-Sep® column) eluting with a gradient of 50-100% ethyl acetate/hexane, followed by 10% of a 2:1 methanol:water mixture in ethyl acetate and finally a 30% solution of a 2:1 mixture of methanol/water in ethyl acetate containing 5% of triethylamine afforded the title compound. $^1$H NMR (400 MHz, DMSO-d$_6$) δ ppm 1.43-1.74 (m, 3H), 1.87-1.99 (m, 1H), 2.57-2.89 (m, 3H), 2.92-3.01 (m, 1H), 3.09-3.16 (m, 1H), 6.05 (s, 2H), 6.73 (d, J=3.2 Hz, 1H), 7.59 (td, J=8.5, 2.6 Hz, 1H), 7.63-7.72 (m, 1H), 7.76 (d, J=3.3 Hz, 1H), 7.84-7.91 (m, 1H), 7.93 (d, J=7.6 Hz, 1H), 8.13 (d, J=1.9 Hz, 1H), 8.21 (s, 1H), 8.44 (d, J=1.8 Hz, 1H), 8.49 (s, 1H), 10.98 (s, 1H). MS (ESI$^+$) m/z 492.4 (M+H)$^+$.

Example 304

N-(5-chloro-4-{1-[(5-fluoropyridin-3-yl)methyl]-1H-pyrrolo[3,2-b]pyridin-6-yl}pyridin-2-yl)-3-oxo-cyclobutanecarboxamide Example 304A 6-bromo-((5-fluoropyridin-3-yl)methyl)-1H-pyrrolo[3,2-b]pyridine The title compound was prepared using the conditions described in Example 251A using 6-bromo-1H-pyrrolo[3,2-b]pyridine in place of 6-bromo-2-(trifluoromethyl)-1H-benzo[d]imidazole and also using 3-(chloromethyl)-5-fluoropyridine in place of 1-(bromomethyl)-3-fluorobenzene. MS (ESI$^+$) m/z 306.0 (M+H)$^+$.

Example 304B 5-chloro-4-(1-((5-fluoropyridin-3-yl)methyl)-1H-pyrrolo[3,2-b]pyridin-6-yl)pyridin-2-amine The title compound was prepared as described in Example 210B using Example 304A in place of Example 13C. MS (ESI$^+$) m/z 354.0 (M+H)$^+$.

Example 304C

N-(5-chloro-4-{1-[(5-fluoropyridin-3-yl)methyl]-1H-pyrrolo[3,2-b]pyridin-6-yl}pyridin-2-yl)-3-oxo-cyclobutanecarboxamide The title compound was prepared as described in Example 211 using 3-oxocyclobutanecarboxylic acid in place of 2-oxohexahydro-2H-cyclopenta[d]oxazole-5-carboxylic acid and Example 304B in place of Example 210B. $^1$H NMR (500 MHz, DMSO-d$_6$) δ ppm 3.22-3.32 (m, 4H), 3.46-3.57 (m, 1H), 5.62 (s, 2H), 6.74 (d, J=3.3 Hz, 1H), 7.71 (dt, J=9.7, 2.3 Hz, 1H), 8.04 (d, J=3.3 Hz, 1H), 8.25-8.28 (m, 1H), 8.30 (s, 1H), 8.44 (d, J=1.8 Hz, 1H), 8.45-8.48 (m, 1H), 8.50 (d, J=2.8 Hz, 1H), 8.53 (s, 1H), 11.08 (s, 1H). MS (ESI$^+$) m/z 450.3 (M+H)$^+$.

Example 305

(3R)—N-(5-chloro-4-{1-[(1-methyl-1H-benzotriazol-6-yl)methyl]-1H-pyrrolo[3,2-b]pyridin-6-yl}pyridin-2-yl)piperidine-3-carboxamide Example 305A (R)-tert-butyl 3-(5-chloro-4-(1H-pyrrolo[3,2-b]pyridin-6-yl)pyridin-2-ylcarbamoyl)piperidine-1-carboxylate The title compound was prepared as described in Example 253B using 6-bromo-1H-pyrrolo[3,2-b]pyridine in place of Example 253A. MS (ESI$^+$) m/z 456.0 (M+H)$^+$.

Example 305B (R)-tert-butyl 3-(5-chloro-4-(1-((1-methyl-1H-benzo[d][1,2,3]triazol-6-yl)methyl)-1H-pyrrolo[3,2-b]pyridin-6-yl)pyridin-2-ylcarbamoyl)piperidine-1-carboxylate To a two dram vial was added Example 305A (52 mg, 0.114 mmol), 5-(bromomethyl)-1-methyl-1H-benzo[d][1,2,3]triazole (51.6 mg, 0.228 mmol), cesium carbonate (111 mg, 0.342 mmol) and tetrabutylammonium iodide (42.1 mg, 0.114 mmol) in N,N-dimethylformamide (570 μl). The vial was capped with a septa and the mixture was stirred at 75° C. for 16 hours. After cooling to ambient temperature, the mixture was partitioned between water and ethyl acetate (10 mL each). The organic layer was removed and dried over anhydrous magnesium sulfate, filtered and concentrated, and purified by silica gel flash chromatography (Isco®, Redi-Sep® column) eluting with a gradient of 40-100% ethyl acetate/hexane to give the title compound. MS (ESI$^+$) m/z 599.3 (M+H)$^+$.

Example 305C (3R)—N-(5-chloro-4-{1-[(1-methyl-1H-benzotriazol-6-yl)methyl]-1H-pyrrolo[3,2-b]pyridin-6-yl}pyridin-2-yl)piperidine-3-carboxamide Example 305B (63 mg, 0.105 mmol) was dissolved in 1.5 mL of dichloromethane and trifluoroacetic acid (1.5 mL) was added and the mixture stirred at ambient for 10 minutes and concentrated. Purification by reverse-phase HPLC (Phenomenex Luna C8(2) 100 Å AXIA column) using a gradient of 10-95% acetonitrile/0.1% trifluoroacetic acid in water afforded the title compound as a bis trifluoroacetate salt. $^1$H NMR (500 MHz, Methanol-d$_4$) δ ppm 1.79-2.07 (m, 3H), 2.09-2.22 (m, 1H), 3.00-3.12 (m, 1H), 3.21-3.30 (m, 2H), 3.33-3.46 (m, 2H), 4.32 (s, 3H), 5.86 (s, 2H), 6.99 (d, J=3.1 Hz, 1H), 7.56 (dd, J=8.7, 1.5 Hz, 1H), 7.77 (d, J=8.6 Hz, 1H), 8.10 (s, 1H), 8.32 (s, 1H), 8.39 (d, J=3.3 Hz, 1H), 8.47 (s, 1H), 8.76-8.87 (m, 2H). MS (ESI$^+$) m/z 501.4 (M+H)$^+$.

Example 306

(3R)—N-(5-chloro-4-{1-[2-oxo-2-(tetrahydro-2H-pyran-4-yl)ethyl]-1H-pyrrolo[3,2-b]pyridin-6-yl}pyridin-2-yl)piperidine-3-carboxamide Example 306A 2-(6-bromo-1H-pyrrolo[3,2-b]pyridin-1-yl)-1-(tetrahydro-2H-pyran-4-yl)ethanone The title compound was prepared using the conditions described in Example 303A using 2-bromo-1-(tetrahydro- 2H-pyran-4-yl)ethanone in place of 2-bromo-1-(3-fluorophenyl)ethanone. MS (ESI+) m/z 325.0 (M+H)+.

Example 306B (R)-tert-butyl 3-(5-chloro-4-(1-(2-oxo-2-(tetrahydro-2H-pyran-4-yl)ethyl)-1H-pyrrolo[3,2-b]pyridin-6-yl)pyridin-2-ylcarbamoyl)piperidine-1-carboxylate The title compound was prepared using the conditions described in Example 253B using Example 306A in place of Example 253A. MS (ESI+) m/z 582.3 (M+H)+.

Example 306C (3R)—N-(5-chloro-4-{1-[2-oxo-2-(tetrahydro-2H-pyran-4-yl)ethyl]-1H-pyrrolo[3,2-b]pyridin-6-yl}pyridin-2-yl)piperidine-3-carboxamide Example 306B was dissolved into 3 mL of dichloromethane and the mixture was treated with 3 mL of trifluoroacetic acid. The mixture was stirred at ambient temperature for 10 minutes and concentrated. The residue was added to 25 mL of ethyl acetate and poured into a 60 mL separatory funnel. The organic mixture was washed with diluted aqueous potassium carbonate (10% weight in water, 1×20 mL), saturated aqueous sodium carbonate (1×20 mL), and saturated aqueous brine (1×20 mL), dried over anhydrous magnesium sulfate, filtered and concentrated. Purification by silica gel flash chromatography (Isco®, Redi-Sep® column) eluting with a gradient of 50-100% ethyl acetate/hexane followed by 10% of a 2:1 methanol:water mixture in ethyl acetate and finally a 30% solution of a 2:1 mixture of methanol/water in ethyl acetate containing 5% of triethylamine afforded the title compound. $^1$H NMR (500 MHz, DMSO-$d_6$) δ ppm 1.32-1.44 (m, 1H), 1.51-1.66 (m, 4H), 1.79-1.90 (m, 3H), 2.54-2.64 (m, 1H), 2.64-2.72 (m, 1H), 2.74-2.82 (m, 1H), 2.82-2.92 (m, 1H), 2.96 (dd, J=12.0, 3.4 Hz, 1H), 3.33-3.43 (m, 3H), 3.85-3.96 (m, 2H), 5.44 (s, 2H), 6.68 (d, J=3.1 Hz, 1H), 7.67 (d, J=3.3 Hz, 1H), 7.95-8.01 (m, 1H), 8.24 (s, 1H), 8.43 (d, J=1.9 Hz, 1H), 8.48 (s, 1H), 10.96 (s, 1H). MS (ESI+) m/z 482.3 (M+H)+.

Example 307

(3R)—N-(5-chloro-4-{1-[2-hydroxy-2-(tetrahydro-2H-pyran-4-yl)ethyl]-1H-pyrrolo[3,2-b]pyridin-6-yl}pyridin-2-yl)piperidine-3-carboxamide Example 306B (140 mg, 0.241 mmol) was dissolved in methanol (1203 μl) and sodium borohydride (27.3 mg, 0.722 mmol) was added. The reaction mixture was stirred at ambient temperature for 20 minutes then diluted with 20 mL of ethyl acetate and poured into a separatory funnel. The organic layer was washed with water (1×25 mL) and saturated aqueous brine (1×25 mL), dried over anhydrous magnesium sulfate, filtered and concentrated. Purification by silica gel flash chromatography (Isco®, Redi-Sep® column) eluting with a gradient of 50-100% ethyl acetate/hexane followed by 10% of a 2:1 methanol:water mixture in ethyl acetate afforded the tert-butyloxocarbonyl protected intermediate. The intermediate was then treated with 2 mL of dichloromethane and 2 mL of trifluoroacetic acid. The mixture was stirred at ambient temperature for 10 minutes and concentrated. The residue obtained was purified by reverse phase HPLC (Phenomenex Luna C8(2) 100 Å AXIA column) using a gradient of 10-95% acetonitrile/0.1% trifluoroacetic acid in water to afford the title compound as a bis trifluoroacetate salt. $^1$H NMR (400 MHz, Methanol-$d_4$) δ ppm 1.44-2.06 (m, 8H), 2.10-2.23 (m, 1H), 2.98-3.17 (m, 2H), 3.24-3.34 (m, 2H), 3.36-3.51 (m, 3H), 3.63-3.75 (m, 1H), 3.95-4.05 (m, 2H), 4.37 (dd, J=14.5, 9.2 Hz, 1H), 4.59 (dd, J=14.7, 2.7 Hz, 1H), 6.93 (d, J=3.2 Hz, 1H), 8.20 (d, J=3.3 Hz, 1H), 8.38 (s, 1H), 8.52 (s, 1H), 8.75 (s, 1H), 8.80 (s, 1H). MS (ESI+) m/z 484.4 (M+H)+.

Example 308

(3R)—N-(5-chloro-4-{1-[(trans-4-hydroxy-4-methylcyclohexyl)methyl]-1H-benzotriazol-6-yl}pyridin-2-yl)piperidine-3-carboxamide Example 308A (1R,4R)-4-(((5-bromo-2-nitrophenyl)amino)methyl)-1-methylcyclohexanol The title compound was prepared as described in Example 8A using (1r,4r)-4-(aminomethyl)-1-methylcyclohexanol, hydrochloride in place of 3-fluorobenzylamine.

Example 308B (1R,4R)-4-(((2-amino-5-bromophenyl)amino)methyl)-1-methylcyclohexanol The title compound was prepared as described in Example 8B using Example 308A in place of Example 8A.

Example 308C (1R,4R)-4-((6-bromo-1H-benzo[d][1,2,3]triazol-1-yl)methyl)-1-methylcyclohexanol The title compound was prepared as described in Example 110A using Example 308B in place of Example 8B.

Example 308D (3R)—N-(5-chloro-4-{1-[(trans-4-hydroxy-4-methylcyclohexyl)methyl]-1H-benzotriazol-6-yl}pyridin-2-yl)piperidine-3-carboxamid The title compound was prepared as described in Example 14E using Example 308C in place of Example 14D. $^1$H NMR (400 MHz, DMSO-$d_6$) δ 1.18 (m, 5H), 1.33 (m, 2H), 1.44 (m, 1H), 1.61 (m, 6H), 1.88 (m, 1H), 2.05 (m, 1H), 2.63 (m, 2H), 2.81 (m, 2H), 4.64 (d, 2H), 7.44 (d, 1H), 7.99 (s, 1H), 8.12 (d, 1H), 8.22 (s, 1H), 8.45 (s, 1H), 10.66 (br s, 1H).). MS (ESI) m/e 483.1 (M+H)+.

Example 309

(3R)—N-(5-chloro-4-{5-fluoro-1-[(1R)-1-(3-fluorophenyl)ethyl]-1H-benzotriazol-6-yl}pyridin-2-yl)piperidine-3-carboxamide Example 309A (R)-5-bromo-4-fluoro-N-(1-(3-fluorophenyl)ethyl)-2-nitroaniline The title compound was prepared as described in Example 8A using 4-bromo-2,5-difluoronitrobenzene in place of 4-bromo-2-fluoro-1-nitrobenzene and also using (R)-1-(3-fluorophenyl)ethanamine in place of 3-fluorobenzylamine.

Example 309B (R)-5-bromo-4-fluoro-N-1-(1-(3-fluorophenyl)ethyl)benzene-1,2-diamine The title compound was prepared as described in Example 8B using Example 309A in place of Example 8A.

Example 309C (R)-6-bromo-5-fluoro-1-(1-(3-fluorophenyl)ethyl)-1H-benzo[d][1,2,3]triazole The title compound was prepared as described in Example 110A using Example 309B in place of Example 8B.

Example 309D (3R)—N-(5-chloro-4-{5-fluoro-1-[(1R)-1-(3-fluorophenyl)ethyl]-1H-benzotriazol-6-yl}pyridin-2-yl)piperidine-3-carboxamide The title compound was prepared as described in Example 14E using Example 309C in place of Example 14D. $^1$H NMR (400 MHz, DMSO-d$_6$) δ 1.40 (m, 1H), 1.58 (m, 2H), 1.84 (m, 1H), 2.08 (d, 3H), 2.63 (m, 3H), 2.80 (m, 1H), 2.98 (m, 1H), 8.42 (q, 1H), 7.14 (m, 1H), 7.21 (m, 1H), 7.32 (m, 1H), 7.39 (m, 1H), 8.11 (m, 2H), 8.23 (s, 1H), 8.52 (s, 1H), 11.08 (br s, 1H). MS (ESI) m/e 497.1 (M+H)$^+$.

Example 310 methyl 4-{[6-(5-chloro-2-{[(3R)-piperidin-3-ylcarbonyl]amino}pyridin-4-yl)-1H-benzimidazol-1-yl]methyl}benzoate Example 310A methyl 4-(((5-bromo-2-nitrophenyl)amino)methyl)benzoate The title compound was prepared as described in Example 8A using methyl 4-(aminomethyl)benzoate hydrochloride in place of 3-fluorobenzylamine.

Example 310B methyl 4-(((2-amino-5-bromophenyl)amino)methyl)benzoate

The title compound was prepared as described in Example 8B using Example 310A in place of Example 8A.

Example 310C methyl 4-((6-bromo-1H-benzo[d]imidazol-1-yl)methyl)benzoate

The title compound was prepared as described in Example 8C using Example 310B in place of Example 8B.

Example 310D methyl 4-{[6-(5-chloro-2-{[(3R)-piperidin-3-ylcarbonyl]amino}pyridin-4-yl)-1H-benzimidazol-1-yl]methyl}benzoate The title compound was prepared as described in Example 14E using Example 310C in place of Example 14D. $^1$H NMR (400 MHz, DMSO-d$_6$) δ 1.42 (m, 1H), 1.59 (m, 2H), 1.85 (m, 1H), 2.63 (m, 3H), 2.82 (m, 1H), 2.99 (m, 1H), 3.82 (s, 3H), 5.68 (br s, 2H), 7.29 (d, 1H), 7.46 (d, 2H), 7.68 (s, 1H), 7.79 (d, 1H), 7.93 (d, 2H), 8.18 (s, 1H), 8.42 (s, 1H), 8.55 (s, 1H), 10.91 (br s, 1H). MS (ESI) m/e 504.1 (M+H)$^+$.

Example 311 methyl 4-{[6-(5-chloro-2-{[(3R)-piperidin-3-ylcarbonyl]amino}pyridin-4-yl)-1H-benzotriazol-1-yl]methyl}benzoate Example 311A methyl 4-((6-bromo-1H-benzo[d][1,2,3]triazol-1-yl)methyl)benzoate The title compound was prepared as described in Example 110A using Example 310B in place of Example 8B.

Example 311B methyl 4-{[6-(5-chloro-2-{[(3R)-piperidin-3-ylcarbonyl]amino}pyridin-4-yl)-1H-benzotriazol-1-yl]methyl}benzoate The title compound was prepared as described in Example 14E using Example 311A in place of Example 14D. $^1$H NMR (400 MHz, DMSO-d$_6$) δ 1.40 (m, 1H), 1.59 (m, 2H), 1.85 (m, 1H), 2.63 (m, 3H), 2.83 (m, 1H), 2.99 (m, 1H), 3.83 (s, 3H), 6.15 (s, 2H), 7.49 (m, 3H), 7.95 (d, 2H), 8.07 (s, 1H), 8.21 (d, 1H), 8.24 (s, 1H), 8.49 (s, 1H), 11.00 (br s, 1H). MS (ESI) m/e 505.1 (M+H)$^+$.

Example 312

(3R)—N-(5-chloro-4-{1-[3-(3-fluorophenyl)propyl]-1H-benzimidazol-6-yl}pyridin-2-yl)piperidine-3-carboxamide Example 312A 5-bromo-N-(3-(3-fluorophenyl)propyl)-2-nitroaniline The title compound was prepared as described in Example 8A using 3-(3-fluorophenyl)propan-1-amine hydrochloride in place of 3-fluorobenzylamine.

Example 312B 5-bromo-N$^1$-(3-(3-fluorophenyl)propyl)benzene-1,2-diamine

The title compound was prepared as described in Example 8B using Example 312A in place of Example 8A.

Example 312C 6-bromo-1-(3-(3-fluorophenyl)propyl)-1H-benzo[d]
imidazole

The title compound was prepared as described in Example 8C using Example 312B in place of Example 8B.

Example 312D (3R)—N-(5-chloro-4-{1-[3-(3-fluorophenyl)propyl]-1H-benzimidazol-6-yl}pyridin-2-yl)piperidine-3-carboxamide The title compound was prepared as described in Example 14E using Example 312C in place of Example 14D. $^1$H NMR (400 MHz, DMSO-d$_6$) δ 1.42 (m, 1H), 1.60 (m, 2H), 1.87 (m, 1H), 2.15 (m, 2H), 2.56 (m, 1H), 2.64 (m, 3H), 2.73 (t, 1H), 2.84 (m, 1H), 3.01 (m, 1H), 4.33 (t, 2H), 7.03 (m, 3H), 7.30 (m, 2H), 7.76 (m, 2H), 8.25 (s, 1H), 8.36 (s, 1H), 8.47 (s, 1H), 10.95 (br s, 1H). MS (ESI) m/e 492.2 (M+H)$^+$.

Example 313

(3R)—N-(5-chloro-4-{1-[3-(3-fluorophenyl)propyl]-1H-benzotriazol-6-yl}pyridin-2-yl)piperidine-3-carboxamide

Example 313A 6-bromo-1-(3-(3-fluorophenyl)propyl)-1H-benzo[d][1,2,3]triazole The title compound was prepared as described in Example 110A using Example 312B in place of Example 8B.

Example 313B (3R)—N-(5-chloro-4-{1-[3-(3-fluorophenyl)propyl]-1H-benzotriazol-6-yl}pyridin-2-yl)piperidine-3-carboxamide The title compound was prepared as described in Example 14E using Example 313A in place of Example 14D. $^1$H NMR (400 MHz, DMSO-d$_6$) δ 1.40 (m, 1H), 1.60 (m, 2H), 1.86 (m, 1H), 2.27 (m, 2H), 2.59 (m, 1H), 2.67 (m, 4H), 2.82 (m, 1H), 3.00 (m, 1H), 4.79 (t, 2H), 7.00 (m, 3H), 7.29 (q, 1H), 7.48 (d, 1H), 8.05 (s, 1H), 8.17 (d, 1H), 8.29 (s, 1H), 8.51 (s, 1H), 11.01 (br s, 1H). MS (ESI) m/e 493.1 (M+H)$^+$.

Example 314

4-{[6-(5-chloro-2-{[(3R)-piperidin-3-ylcarbonyl]amino}pyridin-4-yl)-1H-benzotriazol-1-yl]methyl}benzoic acid Example 311B (52 mg, 0.10 mmol) was dissolved in tetrahydrofuran and an aqueous lithium hydroxide solution (1 mL, 1M) was added. After stirring at room temperature for 24 hours, the reaction was acidified with a 2 molar aqueous hydrochloric acid solution and concentrated. Purification by reverse phase-HPLC (Sunfire 5 μM, 50×250 mm) eluting with 5-50% acetonitrile in water (containing 0.1% trifluoroacetic acid) provided the title compound as a trifluoroacetate salt. $^1$H NMR (400 MHz, DMSO-d$_6$) δ 1.65 (m, 2H), 1.84 (m, 1H), 2.05 (m, 1H), 2.91 (m, 1H), 3.04 (m, 2H), 3.18 (m, 1H), 3.33 (m, 1H), 6.14 (s, 2H), 7.44 (d, 2H), 7.49 (d, 1H), 7.92 (d, 2H), 8.06 (s, 1H), 8.21 (m, 2H), 8.54 (s, 1H), 11.07 (s, 1H). MS (ESI) m/e 491.1 (M+H)$^+$.

Example 315

4-{[6-(2-amino-5-chloropyridin-4-yl)-1H-benzotriazol-1-yl]methyl}benzoic acid

The title compound was isolated as a side-product in Example 314. $^1$H NMR (400 MHz, DMSO-d$_6$) δ 6.12 (s, 2H), 6.63 (s, 1H), 7.45 (m, 3H), 7.91 (d, 2H), 8.02 (s, 1H), 8.12 (s, 1H), 8.18 (d, 1H). MS (ESI) m/e 380.1 (M+H)$^+$.

Example 316

(3R)—N-{4-[1-(tetrahydro-2H-pyran-4-ylmethyl)-1H-benzimidazol-6-yl]pyridin-2-yl}piperidine-3-carboxamide

Example 316A (R)-tert-butyl 3-(4-bromopyridin-2-ylcarbamoyl)piperidine-1-carboxylate The title compound was prepared using the conditions described in Example 211 using (R)-1-(tert-butoxycarbonyl)piperidine-3-carboxylic acid in place of 2-oxohexahydro-2H-cyclopenta[d]oxazole-5-carboxylic acid and also using 4-bromopyridin-2-amine in place of Example 210B. MS (ESI$^+$) m/z 384.2 (M+H)$^+$.

Example 316B (3R)—N-{4-[1-(tetrahydro-2H-pyran-4-ylmethyl)-1H-benzimidazol-6-yl]pyridin-2-yl}piperidine-3-carboxamide The tert-butyloxocarbonyl protected title compound was prepared using the conditions described in Example 253B using Example 13C in place of Example 253A and also using Example 316A in place of Example 1B. The intermediate was dissolved into 3 mL of dichloromethane and treated with 3 mL of trifluoroacetic acid. The mixture was stirred at ambient temperature for 10 minutes and concentrated. The residue was treated with 25 mL of ethyl acetate and poured into a 60 mL separatory funnel. The organic mixture was washed with diluted aqueous potassium carbonate (10% weight in water, 1×20 mL), saturated aqueous sodium carbonate (1×20 mL), and saturated aqueous brine (1×20 mL), dried over anhydrous magnesium sulfate, filtered and concentrated. Purification by silica gel flash chromatography (Isco®, Redi-Sep® column) eluting with a gradient of 50-100% ethyl acetate/hexane followed by 10% of a 2:1 methanol:water mixture in ethyl acetate and finally a 30% solution of a 2:1 mixture of methanol/water in ethyl acetate containing 5% of triethylamine afforded the title compound. $^1$H NMR (400 MHz, DMSO-d$_6$) δ ppm 1.29-1.49 (m, 5H), 1.56-1.71 (m, 2H), 1.80-1.94 (m, 1H), 2.06-2.21 (m, 1H), 2.53-2.67 (m, 2H), 2.67-2.87 (m, 2H), 2.95-3.05 (m, 1H), 3.18-3.28 (m, 2H), 3.76-3.89 (m, 2H), 4.25 (d, J=7.2 Hz, 2H), 7.49 (dd, J=5.3, 1.6 Hz, 1H), 7.53 (dd, J=8.4, 1.6 Hz, 1H), 7.77 (d, J=8.4 Hz, 1H), 8.04 (d, J=1.6 Hz, 1H), 8.31 (s, 1H), 8.36 (d, J=5.2 Hz, 1H), 8.46 (d, J=1.5 Hz, 1H), 10.74 (s, 1H). MS (ESI+) m/z 420.3 (M+H)+.

Example 317

(3R)—N-(5-chloro-4-{1-[(5-fluoropyridin-3-yl)methyl]-1H-pyrrolo[3,2-b]pyridin-6-yl}pyridin-2-yl)piperidine-3-carboxamide Example 317A 6-bromo-((5-fluoropyridin-3-yl)methyl)-1H-pyrrolo[3,2-b]pyridine A mixture of 6-bromo-1H-pyrrolo[3,2-b]pyridine (4.00 g, 20.30 mmol), sodium hydride (0.89 g, 22.33 mmol) in N,N-dimethylformamide (20 mL) was stirred at ambient for 30 minutes. 3-(Chloromethyl)-5-fluoropyridine (3.25 g, 22.33) was added. The mixture was stirred at 80° C. for 16 hours. The reaction mixture was cooled to ambient temperature and diluted with 100 mL of ethyl acetate. The mixture was washed with water and brine, dried over anhydrous sodium sulfate, filtered and concentrated to obtain the crude title compound which was used directly in next step.

Example 317B (3R)—N-(5-chloro-4-{1-[(5-fluoropyridin-3-yl)methyl]-1H-pyrrolo[3,2-b]pyridin-6-yl}pyridin-2-yl)piperidine-3-carboxamide The title compound was prepared as described in Example 1E using Example 317A in place of Example 1D. Purification by reverse-phase HPLC (Phenomenex Luna C8(2) 100 Å AXIA column) using a gradient of 10-95% acetonitrile/0.1% trifluoroacetic acid in water afforded the title compound as the bis-trifluoroacetate salt. $^1$H NMR (400 MHz, DMSO-$d_6$) δ ppm 1.63-2.15 (m, 4H) 2.86-3.43 (m, 5H) 5.64 (s, 2H) 6.79 (d, J=3.05 Hz, 1H) 7.60 (d, J=9.46 Hz, 1H) 8.06 (d, J=3.36 Hz, 1H) 8.18 (s, 1H) 8.34 (s, 1H) 8.41-8.49 (m, 2H) 8.52 (d, J=1.83 Hz, 1H) 8.63 (s, br, 2H) 10.75 (s, 1H). MS (ESI) m/e 465 (M+H)+.

Example 318

(3R)—N-(5-chloro-4-{1-[1-(pyridin-3-yl)ethyl]-1H-benzotriazol-6-yl}pyridin-2-yl)piperidine-3-carboxamide Example 318A 5-bromo-2-nitro-N-(1-(pyridin-3-yl)ethyl)aniline The title compound was prepared as described in Example 8A using 1-(pyridin-3-yl)ethanamine dihydrochloride in place of 3-fluorobenzylamine.

Example 318B 5-bromo-N$^1$-(1-(pyridin-3-yl)ethyl)benzene-1,2-diamine

The title compound was prepared as described in Example 8B using Example 318A in place of Example 8A.

Example 318C 6-bromo-1-(1-(pyridin-3-yl)ethyl)-1H-benzo[d][1,2,3]triazole

The title compound was prepared as described in Example 110A using Example 318B in place of Example 8B.

Example 318D (3R)—N-(5-chloro-4-{1-[1-(pyridin-3-yl)ethyl]-1H-benzotriazol-6-yl}pyridin-2-yl)piperidine-3-carboxamide The title compound was prepared as described in Example 14E using Example 318C in place of Example 14D. $^1$H NMR (400 MHz, DMSO-$d_6$) δ 1.61 (m, 3H), 1.87 (m, 1H), 2.13 (m, 3H), 2.67 (m, 3H), 2.86 (m, 1H), 3.02 (m, 1H), 6.51 (q, 1H), 7.39 (m, 1H), 7.47 (d, 1H), 7.81 (d, 1H), 8.04 (s, 1H), 8.21 (m, 2H), 8.51 (m, 2H), 8.71 (s, 1H), 11.01 (br s, 1H). MS (ESI) m/e 462.1 (M+H)+.

Example 319

(3R)—N-{5-chloro-4-[1-(3-fluorobenzyl)-5-methoxy-1H-benzimidazol-6-yl]pyridin-2-yl}piperidine-3-carboxamide Example 319A 5-bromo-N-(3-fluorobenzyl)-4-methoxy-2-nitroaniline The title compound was prepared as described in Example 8A using 1-bromo-5-fluoro-2-methoxy-4-nitrobenzene in place of 4-bromo-2-fluoro-1-nitrobenzene.

Example 319B 5-bromo-N$^1$-(3-fluorobenzyl)-4-methoxybenzene-1,2-diamine

The title compound was prepared as described in Example 8B using Example 319A in place of Example 8A.

Example 319C 6-bromo-1-(3-fluorobenzyl)-5-methoxy-1H-benzo[d]imidazole

The title compound was prepared as described in Example 8C using Example 319B in place of Example 8B.

Example 319D (3R)—N-{5-chloro-4-[1-(3-fluorobenzyl)-5-methoxy-1H-benzimidazol-6-yl]pyridin-2-yl}piperidine-3-carboxamide The title compound was prepared as described in Example 14E using Example 319C in place of Example 14D. $^1$H NMR (400 MHz, DMSO-$d_6$) δ 1.43 (m, 1H), 1.65 (m, 2H), 1.86 (m, 1H), 2.62 (m, 2H), 2.83 (m, 2H), 3.02 (m, 1H), 3.76 (s, 3H), 5.48 (s, 2H), 7.08 (m, 3H), 7.36 (m, 3H), 8.04 (s, 1H), 8.30 (d, 2H), 10.62 (br s, 1H). MS (ESI) m/e 494.1 (M+H)+.

Example 320

4-{[6-(5-chloro-2-{[(3R)-piperidin-3-ylcarbonyl]amino}pyridin-4-yl)-1H-benzimidazol-1-yl]methyl}benzoic acid The title compound was prepared as described in Example 314 using Example 310D in place of Example 311B. $^1$H NMR (400 MHz, DMSO-$d_6$) δ 1.65 (m, 2H), 1.82 (m, 1H), 2.04 (m, 1H), 2.98 (m, 3H), 3.18 (m, 1H), 3.33 (m, 1H), 5.70 (s, 2H), 7.36 (d, 1H), 7.45 (d, 2H), 7.74 (s, 1H), 7.85 (d, 1H), 7.92 (d, 2H), 8.15 (s, 1H), 8.49 (s, 1H), 8.78 (s, 1H), 11.01 (s, 1H). MS (ESI) m/e 490.1 (M+H)$^+$.

Example 321

(3R)—N-{5-chloro-4-[1-(3-fluorobenzyl)-5-methoxy-1H-benzotriazol-6-yl]pyridin-2-yl}piperidine-3-carboxamide

Example 321A 6-bromo-1-(3-fluorobenzyl)-5-methoxy-1H-benzo[d][1,2,3]triazole The title compound was prepared as described in Example 110A using Example 319B in place of Example 8B.

Example 321B (3R)—N-{5-chloro-4-[1-(3-fluorobenzyl)-5-methoxy-1H-benzotriazol-6-yl]pyridin-2-yl}piperidine-3-carboxamide The title compound was prepared as described in Example 14E using Example 321A in place of Example 14D. $^1$H NMR (400 MHz, DMSO-$d_6$) δ 1.68 (m, 2H), 1.81 (m, 2H), 2.04 (m, 1H), 2.84 (m, 1H), 3.09 (m, 2H), 3.24 (m, 1H), 3.87 (s, 3H), 5.98 (s, 2H), 7.18 (m, 3H), 7.41 (m, 1H), 7.68 (m, 1H), 7.79 (m, 1H), 8.09 (s, 1H), 8.46 (s, 1H), 10.78 (br s, 1H). MS (ESI) m/e 495.1 (M+H)$^+$.

Example 322

(1R,4R,6R)—N-{5-chloro-4-[1-(tetrahydro-2H-pyran-4-ylmethyl)-1H-benzimidazol-6-yl]pyridin-2-yl}-2-azabicyclo[2.2.1]heptane-6-carboxamide The tert-butyloxocarbonyl protected title compound was prepared as described in Example 210C using (1R,4R,6R)-2-(tert-butoxycarbonyl)-2-azabicyclo[2.2.1]heptane-6-carboxylic acid in place of 1-(tert-butoxycarbonyl)piperidine-4-carboxylic acid. The intermediate was dissolved in 3 mL of dichloromethane and 3 mL of trifluoroacetic acid was added. The mixture was stirred for 15 minutes and concentrated. The residue obtained was purified by reverse phase HPLC (Phenomenex Luna C8(2) 100 Å AXIA column) using a gradient of 10-95% acetonitrile/0.1% trifluoroacetic acid in water to afford the title compound as a bis trifluoroacetate salt. $^1$H NMR (400 MHz, Methanol-$d_4$) δ ppm 1.40-1.64 (m, 4H), 1.74-1.83 (m, 1H), 1.96-2.15 (m, 3H), 2.26-2.40 (m, 1H), 2.75-2.83 (m, 1H), 3.03-3.16 (m, 2H), 3.19 (dt, J=11.1, 3.2 Hz, 1H), 3.38 (td, J=11.7, 2.3 Hz, 2H), 3.91-4.00 (m, 2H), 4.26 (s, 1H), 4.50 (d, J=7.3 Hz, 2H), 7.78 (dd, J=8.7, 1.4 Hz, 1H), 8.00 (d, J=8.6 Hz, 1H), 8.18 (d, J=1.5 Hz, 1H), 8.26 (s, 1H), 8.46 (s, 1H), 9.54 (s, 1H). MS (ESI$^+$) m/z 466.3 (M+H)$^+$.

Example 323

(1R,4R,6S)—N-{5-chloro-4-[1-(tetrahydro-2H-pyran-4-ylmethyl)-1H-benzimidazol-6-yl]pyridin-2-yl}-2-azabicyclo[2.2.1]heptane-6-carboxamide The tert-butyloxocarbonyl protected title compound was prepared using the conditions described in Example 210C using (1R,4R,6S)-2-(tert-butoxycarbonyl)-2-azabicyclo[2.2.1]heptane-6-carboxylic acid in place of 1-(tert-butoxycarbonyl)piperidine-4-carboxylic acid. The intermediate was dissolved in 3 mL of dichloromethane and 3 mL of trifluoroacetic acid was added. The mixture was stirred for 15 minutes and concentrated. The residue obtained was purified by reverse phase HPLC (Phenomenex Luna C8(2) 100 Å AXIA column) using a gradient of 10-95% acetonitrile/0.1% trifluoroacetic acid in water to afford the title compound as a bis trifluoroacetate salt. $^1$H NMR (400 MHz, Methanol-$d_4$) δ ppm 1.39-1.63 (m, 4H), 1.66-1.77 (m, 1H), 1.84-1.99 (m, 2H), 2.20-2.40 (m, 2H), 2.78-2.87 (m, 1H), 3.15-3.27 (m, 3H), 3.38 (td, J=11.7, 2.3 Hz, 2H), 3.89-4.01 (m, 2H), 4.27-4.35 (m, 1H), 4.49 (d, J=7.3 Hz, 2H), 7.76 (d, J=8.6 Hz, 1H), 8.00 (d, J=8.6 Hz, 1H), 8.18 (s, 1H), 8.34 (s, 1H), 8.48 (s, 1H), 9.51 (s, 1H). MS (ESI$^+$) m/z 466.3 (M+H)$^+$.

Example 324

(3R)—N-{5-chloro-4-[1-(thiophen-2-ylmethyl)-1H-benzimidazol-6-yl]pyridin-2-yl}piperidine-3-carboxamide

Example 324A 5-bromo-2-nitro-N-(thiophen-2-ylmethyl)aniline

The title compound was prepared as described in Example 8A using 2-thiophenemethylamine in place of 3-fluorobenzylamine.

Example 324B 5-bromo-N-1-(thiophen-2-ylmethyl)benzene-1,2-diamine

The title compound was prepared as described in Example 8B using Example 324A in place of Example 8A.

Example 324C 6-bromo-1-(thiophen-2-ylmethyl)-1H-benzo[d]imidazole

The title compound was prepared as described in Example 8C using Example 324B in place of Example 8B.

Example 324D (3R)—N-{5-chloro-4-[1-(thiophen-2-ylmethyl)-1H-benzimidazol-6-yl]pyridin-2-yl}piperidine-3-carboxamide The title compound was prepared as described in Example 14E using Example 324C in place of Example 14D. $^1$H NMR (400 MHz, DMSO-$d_6$) δ 1.48 (m, 1H), 1.65 (m, 2H), 1.93 (m, 1H), 2.71 (m, 3H), 2.89 (m, 1H), 3.07 (m, 1H), 5.84 (s, 2H), 7.04 (m, 1H), 7.30 (m, 1H), 7.38 (m, 1H), 7.50 (d, 1H), 7.82 (d, 1H), 7.89 (s, 1H), 8.28 (s, 1H), 8.51 (s, 1H), 8.55 (s, 1H), 11.00 (br s, 1H). MS (ESI) m/e 452.1 (M+H)+.

Example 325

(3R)—N-{5-chloro-4-[1-(thiophen-2-ylmethyl)-1H-benzotriazol-6-yl]pyridin-2-yl}piperidine-3-carboxamide Example 325A 6-bromo-1-(thiophen-2-ylmethyl)-1H-benzo[d][1,2,3]triazole The title compound was prepared as described in Example 110A using Example 324B in place of Example 8B.

Example 325B (3R)—N-{5-chloro-4-[1-(thiophen-2-ylmethyl)-1H-benzotriazol-6-yl]pyridin-2-yl}piperidine-3-carboxamide The title compound was prepared as described in Example 14E using Example 325A in place of Example 14D. $^1$H NMR (400 MHz, DMSO-$d_6$) δ 1.40 (m, 1H), 1.59 (m, 2H), 1.85 (m, 1H), 2.61 (m, 3H), 2.81 (m, 1H), 2.97 (m, 1H), 6.26 (s, 2H), 7.00 (m, 1H), 7.31 (m, 1H), 7.48 (m, 2H), 8.14 (s, 1H), 8.19 (d, 1H), 8.28 (s, 1H), 8.51 (s, 1H), 11.02 (br s, 1H). MS (ESI) m/e 453.1 (M+H)+.

Example 326

(3R)—N-(5-chloro-4-{1-[2-(dimethylamino)-2-(3-fluorophenyl)ethyl]-1H-benzotriazol-6-yl}pyridin-2-yl)piperidine-3-carboxamide Example 326A $N^2$-(5-bromo-2-nitrophenyl)-1-(3-fluorophenyl)-$N^1$,$N^1$-dimethylethane-1,2-diamine The title compound was prepared as described in Example 8A using 1-(3-fluorophenyl)-N1,N1-dimethylethane-1,2-diamine in place of 3-fluorobenzylamine.

Example 326B 5-bromo-$N^1$-(2-(dimethylamino)-2-(3-fluorophenyl)ethyl)benzene-1,2-diamine The title compound was prepared as described in Example 8B using Example 326A in place of Example 8A.

Example 326C 2-(6-bromo-1H-benzo[d][1,2,3]triazol-1-yl)-1-(3-fluorophenyl)-N,N-dimethylethanamine The title compound was prepared as described in Example 110A using Example 326B in place of Example 8B.

Example 326D (3R)—N-(5-chloro-4-{1-[2-(dimethylamino)-2-(3-fluorophenyl)ethyl]-1H-benzotriazol-6-yl}pyridin-2-yl)piperidine-3-carboxamide The title compound was prepared as described in Example 14E using Example 326C in place of Example 14D. $^1$H NMR (400 MHz, DMSO-$d_6$) δ 1.42 (m, 1H), 1.59 (m, 2H), 1.85 (m, 1H), 2.12 (br s, 6H), 2.57 (m, 1H), 2.62 (m, 1H), 2.71 (m, 1H), 2.82 (m, 1H), 2.98 (m, 1H), 4.26 (t, 1H), 5.02 (m, 1H), 5.38 (m, 1H), 7.05 (t, 1H), 7.13 (d, 1H), 7.18 (d, 1H), 7.33 (q, 1H), 7.41 (d, 1H), 8.01 (s, 1H), 8.08 (d, 1H), 8.23 (s, 1H), 8.51 (s, 1H), 11.02 (br s, 1H). MS (ESI) m/e 522.2 (M+H)+.

Example 327

(3R)—N-[5-chloro-4-(1-{3-[(4-methylpiperazin-1-yl)methyl]benzyl}-1H-benzotriazol-6-yl)pyridin-2-yl]piperidine-3-carboxamide Example 327A 5-bromo-N-(3-((4-methylpiperazin-1-yl)methyl)benzyl)-2-nitroaniline The title compound was prepared as described in Example 8A using (3-((4-methylpiperazin-1-yl)methyl)phenyl)methanamine in place of 3-fluorobenzylamine.

Example 327B 5-bromo-N-1-(3-((4-methylpiperazin-1-yl)methyl)benzyl)benzene-1,2-diamine The title compound was prepared as described in Example 8B using Example 327A in place of Example 8A.

Example 327C 6-bromo-1-(3-((4-methylpiperazin-1-yl)methyl)benzyl)-1H-benzo[d][1,2,3]triazole The title compound was prepared as described in Example 110A using Example 327B in place of Example 8B.

Example 327D (3R)—N-[5-chloro-4-(1-{3-[(4-methylpiperazin-1-yl)methyl]benzyl}-1H-benzotriazol-6-yl)pyridin-2-yl]piperidine-3-carboxamide The title compound was prepared as described in Example 14E using Example 327C in place of Example 14D. $^1$H NMR (400 MHz, DMSO-$d_6$) δ 1.59 (m, 2H), 1.80 (m, 1H), 2.03 (m, 1H), 2.16 (m, 2H), 2.28 (m, 7H), 2.68 (m, 1H), 2.85 (m, 1H), 2.97 (m, 2H), 3.14 (m, 2H), 3.42 (m, 1H), 3.41 (s, 2H), 6.04 (s, 2H), 7.30 (m, 4H), 7.47 (m, 1H), 7.98 (d, 1H), 8.19 (m, 2H), 8.54 (m, 1H), 11.07 (br s, 1H). MS (ESI) m/e 559.3 (M+H)+.

Example 328

5-chloro-4-[1-(3-fluorobenzyl)-1H-benzimidazol-6-yl]-N-{3-[(methylsulfonyl)methyl]phenyl}pyridin-2-amine Example 328A methyl(3-nitrobenzyl)sulfane To a stirred solution of 1-(chloromethyl)-3-nitrobenzene (4.00 g, 23.31 mmol) in ethanol (48 mL) at −15° C. was added sodium methanethiolate (1.80 g, 25.60 mmol) in two portions. The cold bath was removed and the mixture was stirred at room temperature for 16 hours. The mixture was diluted with saturated aqueous brine (150 mL) and extracted with ethyl acetate (2×100 mL). The organic extracts were combined then washed with water (100 mL), dried over anhydrous sodium sulfate, filtered and concentrated to give the crude title product which was used without further purification.

Example 328B 1-((methylsulfonyl)methyl)-3-nitrobenzene

To a stirred solution of Example 328A (1.50 g, 8.19 mmol) in dichloromethane (180 mL) at 0° C. was added 3-chlorobenzoperoxoic acid (4.04 g, 18.01 mmol). The mixture was stirred at 0° C. for 30 minutes and at room temperature for 2.5 hours. The mixture was diluted with water (60 mL) before sodium bicarbonate (1.65 g) was added. The mixture was extracted with dichloromethane (2×50 mL). The organic extracts were combined and dried over anhydrous sodium sulfate, filtered and concentrated. The residue was purified by reverse-phase HPLC performed on Waters PrepLC 4000 System with a Phenomenex Luna C8 AXIA column (30×75 mm, 100 Å) using a gradient of 10% to 95% acetonitrile:0.1% trifluoroacetic acid in water to afford the title compound. $^1$H NMR (400 MHz, DMSO-$d_6$) δ ppm 2.94-3.00 (m, 3H) 4.73 (s, 2H) 7.73 (t, J=7.93 Hz, 1H) 7.88 (d, J=7.93 Hz, 1H) 8.26 (dd, J=8.24, 2.14 Hz, 1H) 8.33 (s, 1H).

Example 328C 3-((methylsulfonyl)methyl)aniline

Example 328B (150 mg, 0.697 mmol) was suspended in 3 mL of methanol, and hydrazine monohydrate (0.169 mL, 3.48 mmol) was added. A Raney Nickel slurry (23.9 mg, 0.139 mmol) (approximate amount) was added and the mixture was stirred at room temperature for 1.5 hours and at 40° C. for 1 hour. The cold mixture was filtered through a diatomaceous earth pad and the filtrate was concentrated to afford the title compound. $^1$H NMR (500 MHz, DMSO-$d_6$) δ ppm 2.86 (s, 3H) 4.26 (s, 2H) 5.15 (s, 2H) 6.51-6.56 (m, J=12.66, 7.78 Hz, 2H) 6.58 (s, 1H) 7.01 (t, J=7.78 Hz, 1H).

Example 328D 5-chloro-4-[1-(3-fluorobenzyl)-1H-benzimidazol-6-yl]-N-{3-[(methylsulfonyl)methyl]phenyl}pyridin-2-amine A mixture of Example 8D (65.3 mg, 0.184 mmol), Example 328C (51 mg, 0.275 mmol) and cesium carbonate (90 mg, 0.275 mmol) in dimethyl sulfoxide (1 mL) was stirred in a Biotage Initiator® microwave reactor at 200° C. for 75 minutes. The reaction mixture was purified by reverse-phase HPLC performed on Waters PrepLC 4000 System with a Phenomenex Luna C8 AXIA column (30×75 mm, 100 Å) using a gradient of 10% to 95% acetonitrile:10 mM ammonium acetate in water to afford the crude product. The crude product was purified by thin layer chromatography on Silica Gel 60 $F_{254}$ EMD (elute: $CH_2Cl_2$/$CH_3OH$=20/1) to afford the title compound. $^1$H NMR (400 MHz, Methanol-$d_4$) δ ppm 2.88 (s, 3H) 4.38 (s, 2H) 4.56 (s, 1H) 5.58 (s, 2H) 6.86 (s, 1H) 6.99-7.07 (m, 3H) 7.10 (d, J=7.93 Hz, 1H) 7.26-7.42 (m, 3H) 7.52-7.58 (m, 1H) 7.59 (s, 1H) 7.70 (s, 1H) 7.78 (d, J=8.54 Hz, 1H) 8.17 (s, 1H) 8.39 (s, 1H). MS (ESI$^+$) m/z 521 (M+H)$^+$.

Example 329

(3R)—N-{5-chloro-4-[4-fluoro-1-(tetrahydro-2H-pyran-4-ylmethyl)-1H-benzimidazol-6-yl]pyridin-2-yl}piperidine-3-carboxamide The title compound was prepared as described in Example 13A to Example 13E using 5-bromo-1,3-difluoro-2-nitrobenzene in place of 4-bromo-2-fluoro-1-nitrobenzene. $^1$H NMR (501 MHz, DMSO-$d_6$) δ ppm 1.23-1.87 (m, 8H) 2.06-2.18 (m, 1H) 2.54-2.84 (m, 5H) 2.92-3.02 (m, 1H) 3.19-3.28 (m, 2H) 3.79-3.86 (m, 2H) 4.22 (d, J=7.34 Hz, 2H) 7.10 (dd, J=11.37, 1.28 Hz, 1H) 7.62 (d, J=1.28 Hz, 1H) 8.21 (s, 1H) 8.30 (s, 1H) 8.42 (s, 1H) 10.68 (s, 1H). MS (ESI$^+$) m/z 472 (M+H)$^+$.

Example 330 ethyl {[(3R)-3-({5-chloro-4-[1-(tetrahydro-2H-pyran-4-ylmethyl)-1H-benzimidazol-6-yl]pyridin-2-yl}carbamoyl)piperidin-1-yl]sulfonyl}carbamate Example 330A ((4-(dimethylamino)pyridin-1-ium-1-yl)sulfonyl)(ethoxycarbonyl)amide To a solution of ethanol (1.61 mL, 27.2 mmol) in anhydrous methylene chloride (100 mL) was added dropwise under cooling with ice chlorosulfonyl isocyanate (2.4 mL, 27.6 mmol) over 15 minutes. After stirring for 15 minutes, N,N-dimethylpyridin-4-amine (6.9 g, 56.5 mmol) was added. The cooling bath was removed, and the reaction mixture was stirred for 1 hour at room temperature. The mixture was washed three times with water and finally with a saturated solution of sodium chloride in water. After drying with sodium sulfate and filtration, the organic layer was concentrated under vacuum to provide title compound. $^1$H NMR (500 MHz, DMSO-$d_6$) δ ppm 1.07 (t, J=7.02 Hz, 3H) 3.23 (s, 6H) 3.82 (q, J=7.12 Hz, 2H) 6.97 (d, J=7.93 Hz, 2H) 8.47 (d, J=7.93 Hz, 2H).

Example 330B ethyl {[(3R)-3-({5-chloro-4-[1-(tetrahydro-2H-pyran-4-ylmethyl)-1H-benzimidazol-6-yl]pyridin-2-yl}carbamoyl)piperidin-1-yl]sulfonyl}carbamate To a suspension of Example 13E (58 mg, 0.110 mmol) in $CH_2Cl_2$ (3 mL) was added triethylamine (77 μl, 0.551 mmol) and Example 330A (36.1 mg, 0.132 mmol). The mixture was stirred at room temperature overnight and concentrated in vacuo. The residue was purified by reverse-phase HPLC performed on Waters PrepLC 4000 System with a Phenomenex Luna C8 AXIA column (30×75 mm, 100 Å) using a gradient of 10% to 95% acetonitrile:0.1% trifluoroacetic acid in water to afford the title compound as the bis-trifluoroacetate salt. $^1$H NMR (500 MHz, DMSO-$d_6$) δ ppm 1.19 (t, J=7.02 Hz, 3H) 1.27-1.55 (m, 6H) 1.75-1.85 (m, 1H) 1.90-1.99 (m, J=8.54 Hz, 1H) 2.10-2.21 (m, 1H) 2.73-2.84 (m, 2H) 2.93-3.01 (m, 1H) 3.19-3.27 (m, 2H) 3.57 (d, J=11.90 Hz, 1H) 3.75 (dd, J=11.90, 3.36 Hz, 1H) 3.84 (dd, J=11.29, 3.05 Hz, 2H) 4.10 (q, J=7.02 Hz, 2H) 4.37 (d, J=7.32 Hz, 2H) 7.55-7.57 (m, 1H) 7.93 (d, J=8.54 Hz, 1H)

8.15 (s, 1H) 8.23 (s, 1H) 8.54 (s, 1H) 9.21 (s, 1H) 10.96 (s, 1H) 11.29 (s, 1H). MS (ESI+) m/z 605 (M+H)+.

Example 331 methyl (cis)-3-({5-chloro-4-[1-(tetrahydro-2H-pyran-4-ylmethyl)-1H-benzimidazol-6-yl]pyridin-2-yl}carbamoyl)cyclohexanecarboxylate Cis-3-(methoxycarbonyl)cyclohexanecarboxylic acid (815 mg; 4.4 mmol) in 7 mL dimethylformamide was cooled to 0° C., 1-chloro-N,N,2-trimethylprop-1-en-1-amine (0.6 mL; 4.5 mmol) was added and the mixture was stirred at 0° C. for 30 minutes. A mixture of Example 210B (750 mg; 2.2 mmol) and pyridine (0.4 mL, 5 mmol) in 7 mL dimethylformamide was added and the reaction was stirred for 16 hours at room temperature. The reaction mixture was diluted with water (60 mL) and extracted with three 50 mL portions of ethyl acetate. The combined extracts were rinsed with water (60 mL) and saturated aqueous brine (50 mL), dried over anhydrous magnesium sulfate, filtered and concentrated. The title compound was isolated as after flash chromatography (eluting with 3% methanol/dichloromethane). $^1$H NMR (500 MHz, DMSO-$d_6$) δ 10.69 (s, 1H), 8.47 (s, 1H), 8.33 (s, 1H), 8.25 (s, 1H), 7.83 (d, J=1.6 Hz, 1H), 7.7 (d, J=8.4 Hz, 1H), 7.29 (dd, J=8.4, 1.6 Hz, 1H), 4.21 (d, J=7.2 Hz, 2H), 3.82 (m, 2H), 3.60 (s, 3H), 3.21 (td, J=11.7, 2.2 Hz, 2H), 2.63-2.55 (m, 1H), 2.42-2.31 (m, 2H), 2.29-2.23 (m, 1H), 2.17-1.96 (m, 2H), 1.94-1.72 (m, 3H), 1.53-1.12 (m, 6H). MS (ESI) m/e 511/513 (M+H)+.

Example 332

(cis)-3-({5-chloro-4-[1-(tetrahydro-2H-pyran-4-ylmethyl)-1H-benzimidazol-6-yl]pyridin-2-yl}carbamoyl)cyclohexanecarboxylic acid Example 331 (679 mg; 1.3 mmol) in 10 mL 1:2:2 tetrahydrofuran:methanol:water was treated with lithium hydroxide monohydrate (150 mg; 3.6 mmol) and stirred for 16 hours at room temperature and concentrated. The residue was suspended in 50 mL of water and made slightly acidic with citric acid. The product was extracted with three 50 mL portions of ethyl acetate. The combined extracts were rinsed with water (50 mL) and saturated aqueous brine (40 mL), dried over anhydrous magnesium sulfate, filtered, and concentrated to give the title compound. $^1$H NMR (500 MHz, DMSO-$d_6$) δ 12.10 (s, 1H), 10.67 (s, 1H), 8.47 (s, 1H), 8.33 (s, 1H), 8.29 (d, J=40.0 Hz, 1H), 7.83 (d, J=1.6 Hz, 1H), 7.77 (d, J=8.4 Hz, 1H), 7.29 (dd, J=8.3, 1.6 Hz, 1H), 4.34 (s, 1H), 4.21 (d, J=7.1 Hz, 2H), 3.82 (dd, J=11.6, 4.5 Hz, 2H), 3.50-3.35 (m, 2H), 3.21 (td, J=11.6, 2.2 Hz, 2H), 2.58 (dq, J=11.9, 5.0, 4.1 Hz, 1H), 2.28-2.20 (m, 2H), 2.14-1.98 (m, 2H), 1.94-1.73 (m, 3H), 1.49-1.16 (m, 4H). MS (ESI) m/e 497/499 (M+H)+.

Example 333

(cis)-N-{5-chloro-4-[1-(tetrahydro-2H-pyran-4-ylmethyl)-1H-benzimidazol-6-yl]pyridin-2-yl}-3-[(3-hydroxyazetidin-1-yl)carbonyl]cyclohexanecarboxamide To a mixture of Example 332 (100 mg, 0.2 mmol) and azetidin-3-ol hydrochloride (24 mg; 0.22 mmol) in 3 mL dimethylformamide and diisopropylethylamine (0.1 mL, 0.6 mmol) was added 2-(3H-[1,2,3]triazolo[4,5-b]pyridin-3-yl)-1,1,3,3-tetramethylisouronium hexafluorophosphate (80 mg; 0.21 mmol) and the mixture was stirred for 16 hours at room temperature. The reaction mixture was diluted with water (30 mL) and extracted with three 20 mL portions of ethyl acetate. The combined extracts were rinsed with brine (30 mL), dried over MgSO$_4$, filtered, concentrated, and isolated by silica gel flash chromatography (eluting with 7% methanol/dichloromethane) to yield the title compound. $^1$H NMR (400 MHz, DMSO-$d_6$) δ 10.67 (d, J=5.4 Hz, 1H), 8.47 (s, 1H), 8.33 (s, 1H), 8.24 (s, 1H), 7.83 (s, 1H), 7.77 (d, J=8.4 Hz, 1H), 7.29 (d, J=8.4 Hz, 1H), 5.70 (d, J=6.1 Hz, 1H), 4.47-4.27 (m, 2H), 4.21 (d, J=7.2 Hz, 2H), 4.04-3.78 (m, 4H), 3.57-3.53 (m, 1H), 3.26-3.15 (m, 3H), 2.62-2.52 (m, 1H), 2.28-2.18 (m, 1H), 2.15-203 (m, 1H), 1.85-1.73 (m, 2H), 1.66-1.59 (m, 1H), 1.49-1.20 (m, 8H). MS (ESI) m/e 552/554 (M+H)+.

Example 334

(cis)-N'-{5-chloro-4-[1-(tetrahydro-2H-pyran-4-ylmethyl)-1H-benzimidazol-6-yl]pyridin-2-yl}-N-(2-hydroxyethyl)-N-methylcyclohexane-1,3-dicarboxamide The title compound was prepared using the procedure as described in Example 333 using 2-(methylamino)ethanol in place of azetidin-3-ol hydrochloride. $^1$H NMR (400 MHz, DMSO-$d_6$) δ 10.68 (d, J=2.7 Hz, 1H), 8.47 (s, 1H), 8.33 (s, 1H), 8.25 (s, 1H), 7.83 (s, 1H), 7.77 (d, J=8.4 Hz, 1H), 7.29 (dd, J=8.4, 1.6 Hz, 1H), 4.21 (d, J=7.1 Hz, 2H), 3.85-3.79 (m, 2H), 3.56-3.25 (m, 4H), 3.21 (td, J=11.6, 2.3 Hz, 2H), 2.80 (s, 3H), 2.76-2.56 (m, 2H), 2.14-2.04 (m, 1H), 1.85-1.44 (m, 4H), 1.44-1.22 (m, 8H). MS (ESI) m/e 554/556 (M+H)+.

Example 335

(cis)-N-{5-chloro-4-[1-(tetrahydro-2H-pyran-4-ylmethyl)-1H-benzimidazol-6-yl]pyridin-2-yl}-3-{[(2S)-2-(hydroxymethyl)pyrrolidin-1-yl]carbonyl}cyclohexanecarboxamide The title compound was prepared as described in Example 333 using (S)-pyrrolidin-2-ylmethanol in place of azetidin-3-ol hydrochloride. $^1$H NMR (400 MHz, DMSO-$d_6$) δ 10.68 (s, 1H), 8.47 (s, 1H), 8.33 (s, 1H), 8.25 (s, 1H), 7.83 (s, 1H), 7.76 (d, J=8.1 Hz, 1H), 7.29 (d, J=8.1 Hz, 1H), 4.21 (d, J=7.1 Hz, 2H), 3.96-3.77 (m, 3H), 3.56-3.40 (m, 2H), 3.28-3.17 (m, 4H), 2.64-2.38 (m, 2H), 2.09 (ddd, J=12.1, 7.9, 4.6 Hz, 1H), 2.00-1.57 (m, 7H), 1.56-1.18 (m, 9H). MS (ESI) m/e 580/582 (M+H)+.

Example 336

(3R)—N-[4-(1-methyl-1H-benzimidazol-6-yl)pyridin-2-yl]piperidine-3-carboxamide

The tert-butyloxocarbonyl protected title compound was prepared using the conditions described in Example 253B using 6-bromo-1-methyl-1H-benzo[d]imidazole in place of Example 253A and also using Example 316A in place of Example 1B. The intermediate was dissolved in 3 mL of dichloromethane and treated with 3 mL of trifluoroacetic acid. The mixture was stirred at ambient temperature for 10 minutes and was concentrated. The residue was treated with 25 mL of ethyl acetate and poured into a 60 mL separatory funnel. The organic mixture was washed with diluted aqueous potassium carbonate (10% weight in water, 1×20 mL), saturated aqueous sodium carbonate (1×20 mL), and saturated aqueous brine (1×20 mL), dried over anhydrous magnesium sulfate, filtered and concentrated. Purification by recrystallization from hot ethyl acetate afforded the title compound. $^1$H NMR (400 MHz, DMSO-d$_6$) δ ppm 1.41-1.56 (m, 1H), 1.61-1.75 (m, 2H), 1.87-1.99 (m, 1H), 2.60-2.79 (m, 2H), 2.78-2.89 (m, 1H), 2.89-2.98 (m, 1H), 3.10 (dd, J=12.1, 3.5 Hz, 1H), 3.92 (s, 3H), 7.50 (dd, J=5.2, 1.7 Hz, 1H), 7.57 (dd, J=8.4, 1.7 Hz, 1H), 7.78 (d, J=8.5 Hz, 1H), 7.95 (d, J=1.6 Hz, 1H), 8.28 (s, 1H), 8.37 (d, J=5.2 Hz, 1H), 8.44-8.54 (m, 1H), 10.76 (s, 1H). MS (ESI$^+$) m/z 336.1 (M+H)$^+$.

Example 337 tert-butyl (3aR,6aS)-5-({5-chloro-4-[1-(tetrahydro-2H-pyran-4-ylmethyl)-1H-benzimidazol-6-yl]pyridin-2-yl}carbamoyl)hexahydrocyclopenta[c]pyrrole-2(1H)-carboxylate The title compound was prepared using the procedure described in Example 331 using (3aR,6aS)-2-(tert-butoxycarbonyl)octahydrocyclopenta[c]pyrrole-5-carboxylic acid in place of cis-3-(methoxycarbonyl)cyclohexanecarboxylic acid. $^1$H NMR (DMSO-d$_6$) δ: 1.03-1.65 (m, 8H), 1.37 (s, 9H), 2.05-2.17 (m, 4H), 2.55-2.64 (m, 2H), 3.08-3.26 (m, 4H), 3.77-3.85 (m, 2H), 4.21 (d, J=7.2 Hz, 2H), 7.29 (dd, J=8.3, 1.6 Hz, 1H), 7.71-7.78 (d, J=8.3 Hz, 1H), 7.83 (s, 1H), 8.26 (s, 1H), 8.33 (s, 1H), 8.46 (s, 1H), 10.73 (s, 1H). MS (ESI) m/e 578 (M−H)$^+$.

Example 338

(3aR,6aS)—N$^5$-{5-chloro-4-[1-(tetrahydro-2H-pyran-4-ylmethyl)-1H-benzimidazol-6-yl]pyridin-2-yl}-N$^2$-methylhexahydrocyclopenta[c]pyrrole-2,5 (1H)-dicarboxamide To Example 337 (120 mg; 0.21 mmol) in 4 mL of dichloromethane was added 1 mL trifluoroacetic acid. The mixture was stirred at room temperature for 4 hours and concentrated. The residue was dissolved in 1.5 mL N,N-dimethylformamide. Triethylamine (0.1 mL; 0.72 mmol) and N-succinimidyl-N-methylcarbamate (50 mg, 0.290 mmol) were added and the reaction was stirred for 16 hours at room temperature. The reaction mixture was partitioned between water (10 mL) and ethyl acetate (10 mL). The organic layer was removed and the aqueous phase was extracted with two 10 mL portions of ethyl acetate. The combined extracts were rinsed with brine (20 mL), dried over magnesium sulfate, filtered, and concentrated. The product was isolated by HPLC (Phenomenex Luna C8(2) 5 μm 100 Å AXIA column) using a gradient of 10-95% acetonitrile/0.1% trifluoroacetic acid in water to afford the title compound as the trifluoroacetate salt. $^1$H NMR (DMSO-d$_6$) δ: 1.34 (qd, J=12.0, 4.5 Hz, 2H), 1.42-1.61 (m, 4H), 2.10-2.21 (m, 3H), 2.56-2.66 (m, 2H), 3.03-3.32 (m, 9H), 3.84 (dd, J=11.8, 4.5 Hz, 2H), 4.37 (d, J=8.4 Hz, 3H), 6.02 (bs, 1H), 7.58 (dd, J=8.5, 1.6 Hz, 1H), 7.94 (d, J=8.5 Hz, 1H), 8.17 (d, J=1.6 Hz, 1H), 8.28 (s, 1H), 8.52 (s, 1H), 9.29 (s, 1H), 10.79 (s, 1H). MS (ESI) m/e 537 (M−H)$^1$.

Example 339 cis-4-({5-chloro-4-[1-(3-fluorobenzyl)-1H-benzimidazol-6-yl]pyridin-2-yl}amino)cyclohexanecarboxylic acid Example 339A cis-ethyl 4-((5-chloro-4-(1-(3-fluorobenzyl)-1H-benzo[d]imidazol-6-yl)pyridin-2-yl)amino)cyclohexanecarboxylate To Example 8D (250 mg, 0.70 mmol) in 3 mL dimethylsulfoxide was added cis-ethyl 4-aminocyclohexanecarboxylate hydrochloride (250 mg, 1.204 mmol) and diisopropylethylamine (0.25 mL, 1.431 mmol). The reaction was heated at 120° C. for 48 hours. The cooled mixture was diluted with 20 mL of water and extracted with three 20 mL portions of ethyl acetate. The combined extracts were rinsed successively with water (30 mL) and brine (30 mL), dried over magnesium sulfate, filtered and concentrated. The product was isolated by flash column chromatography (eluting with 1:1 ethyl acetate:dichloromethane) to yield the title compound.

Example 339B cis-4-({5-chloro-4-[1-(3-fluorobenzyl)-1H-benzimidazol-6-yl]pyridin-2-yl}amino)cyclohexanecarboxylic acid To Example 339A (130 mg, 0.26 mmol) in 2.5 mL 1:2:2 tetrahydrofuran:methanol:water was added lithium hydroxide monohydrate (40 mg, 0.95 mmol) and the reaction was stirred at room temperature for 16 hours. The reaction was concentrated and the residue was subjected to reverse phase HPLC on a Waters LC with a C18 column eluting with a gradient of 10:90 to 40:60 acetonitrile/0.1% trifluoroacetic acid in water, to yield the title compound as the trifluoroacetate salt. $^1$H NMR (DMSO-d$_6$) δ: 1.50-1.64 (m, 4H), 1.66-1.77 (m, 2H), 1.82-1.96 (m, 2H), 2.38-2.47 (m, 1H), 3.85 (d, J=7.9 Hz, 1H), 5.20 (bs, 1H), 5.68 (s, 2H), 6.62 (s, 1H), 7.06 (bs, 1H), 7.17 (td, J=8.7, 2.6 Hz, 1H), 7.22-7.38 (m, 2H), 7.38-7.50 (m, 2H), 7.88 (d, J=8.5 Hz, 2H), 8.09 (s, 1H), 9.22 (s, 1H). MS (ESI) m/e 479 (M−H)$^+$.

Biological Examples

CDK9 Enzyme Protocol

CDK9 enzyme activities were measured using LANCE ULight TR-FRET kinase assay reagents (PerkinElmer, Waltham, Mass.). Compounds were directly added in 100% DMSO to white low volume assay plates (Perkin Elmer Proxiplate 6008289) using a Labcyte Echo acoustic dispenser. Assay reagents in serine/threonine kinase assay buffer containing 20 mM HEPES, 10 mM MgCl$_2$, 100 mM Na$_3$VO$_4$, and 0.0075% Triton X-100. were added for final reaction mixture concentrations of 1000 μM ATP, 100 nM U-light MBP peptide (Perkin Elmer TRF0109M) and reaction initiated with 4 nM CDK9/Cyclin T1 (Carna Biosciences 04-110). The kinase reaction was carried out for 30 minutes before addition of stopping buffer to a final of 20 mM EDTA and 0.5 nM of LANCE Ultra Europium anti-phospho-MBP antibody (PerkinElmer TRF0201M) in LANCE detection buffer (PerkinElmer CR97-100). The reaction was equilibrated for 1 hour and the signal read in the Perkin Elmer Envision in TR-FRET mode (excitation at 320 nm and emission at 615665 nm).

Cell Viability Protocol

Cell viability assays were performed using A431 or H929 cells. A431 cells were seeded in 96-well plates at 10,000 cells/well and, after overnight incubation, treated with compounds at 2-times the final concentration to result in a dose response of 3-fold dilutions from 10 μM to 0.0005 μM (50 μL/well, 0.1% final DMSO concentration). H929 cells were seeded in 96-well plates at 10,000 cells/well and treated immediately with compounds as described above. After 24 hours at 37° C., cell viability was measured Cell TiterGlo reagent (Promega) with a luminescence reader. Alternately, cell viability assays were performed in 384-well format. A431 cells were seeded in 384-well plates at 2500 cells/well and, after overnight incubation, treated with compounds in a dose response of 3-fold dilutions from 10 μM to 0.0005 μM (25 nL/well, 0.1% final DMSO concentration). For the H929 viability assay, 25 nL/well of the compounds was dispensed into 384-well plates in a dose response as described above and cells were immediately seeded in 384-well plates at 2500 cells/well. After 24 hours at 37° C., cell viability was measured using Cell TiterGlo reagent (Promega) with a luminescence reader. The results are reported in Table 1.

TABLE 1

| Example | CDK9 IC$_{50}$ (μM) | A431 viability EC$_{50}$ (μM) | H929 viability EC$_{50}$ (μM) |
|---|---|---|---|
| 1 | 0.024 | 1.6 | 0.53 |
| 2 | 0.26 | ND | 6.4 |
| 3 | 0.038 | ND | 3 |
| 4 | 0.065 | ND | 2.7 |
| 5 | 2.2 | ND | ND |
| 6 | 0.027 | 0.034 | 0.11 |
| 7 | 0.051 | ND | 0.68 |
| 8 | 0.22 | 0.017 | 0.12 |
| 9 | 0.24 | ND | 1.4 |
| 10 | 0.41 | ND | 3.6 |
| 11 | 0.035 | 0.029 | 0.032 |
| 12 | 5.2 | ND | ND |
| 13 | 0.15 | 0.069 | 0.27 |
| 14 | 0.1 | ND | 0.75 |
| 15 | 0.068 | ND | 0.73 |
| 16 | 0.019 | 0.025 | 0.084 |
| 17 | 0.015 | 0.009 | 0.073 |
| 18 | 0.013 | 0.019 | 0.11 |
| 19 | 0.039 | ND | 1.45 |
| 20 | 0.066 | ND | 0.68 |
| 21 | 0.017 | 0.02 | 0.17 |
| 22 | 0.05 | ND | 0.39 |
| 23 | 0.087 | ND | 0.69 |
| 24 | 0.2 | ND | >10 |
| 25 | 0.082 | ND | 1.3 |
| 26 | 0.17 | ND | ND |
| 27 | 0.046 | ND | 0.34 |
| 28 | 0.065 | 0.29 | 0.17 |
| 29 | 0.012 | ND | 1 |
| 30 | 0.36 | ND | ND |
| 31 | 1.2 | ND | ND |
| 32 | 1.6 | ND | ND |
| 33 | 0.014 | ND | 0.43 |
| 34 | 0.042 | ND | 1.1 |
| 35 | 1.2 | ND | ND |
| 36 | 0.76 | ND | ND |
| 37 | 1.4 | ND | ND |
| 38 | 0.17 | ND | 3.9 |
| 39 | 0.27 | ND | 0.75 |
| 40 | 0.52 | ND | ND |
| 41 | 0.028 | ND | 0.69 |
| 42 | 0.091 | ND | 3.1 |
| 43 | 0.043 | ND | 1.2 |
| 44 | 0.019 | 0.071 | 0.26 |
| 45 | 0.11 | ND | 2.3 |
| 46 | 1.6 | ND | ND |
| 47 | 0.057 | ND | 0.97 |
| 48 | 0.078 | ND | 1.3 |
| 49 | 0.13 | ND | 3.7 |
| 50 | 0.26 | ND | 1.8 |
| 51 | 0.31 | ND | ND |
| 52 | 0.054 | ND | 1.1 |
| 53 | 1.9 | ND | ND |
| 54 | 0.61 | ND | ND |
| 55 | 0.036 | ND | 0.86 |
| 56 | 0.03 | ND | 0.44 |
| 57 | 1.5 | ND | ND |
| 58 | 0.087 | ND | 3.1 |
| 59 | 0.019 | ND | 0.84 |
| 60 | 0.39 | ND | ND |
| 61 | 0.41 | ND | ND |
| 62 | 0.13 | ND | 3.2 |
| 63 | 0.39 | ND | ND |
| 64 | 0.39 | ND | ND |
| 65 | 1.2 | ND | ND |
| 66 | 0.15 | ND | 2.6 |
| 67 | 0.045 | ND | 3 |
| 68 | 0.023 | ND | 0.62 |
| 69 | 2.5 | ND | ND |
| 70 | 0.31 | ND | ND |
| 71 | 0.045 | ND | 1 |
| 72 | 0.043 | ND | 0.85 |
| 73 | 0.55 | ND | ND |
| 74 | 0.017 | ND | 1.3 |
| 75 | 0.052 | ND | 1.7 |
| 76 | 0.082 | ND | 1.6 |
| 77 | 1 | ND | ND |
| 78 | 0.16 | ND | 9.3 |
| 79 | 0.039 | ND | 0.72 |
| 80 | 0.068 | ND | 3.6 |
| 81 | 0.072 | ND | 1.6 |
| 82 | 2.3 | ND | ND |
| 83 | 2.7 | ND | ND |
| 84 | 2.3 | ND | ND |
| 85 | 1.3 | ND | ND |
| 86 | 1.5 | ND | ND |
| 87 | 14.1 | ND | ND |
| 88 | 0.54 | ND | ND |
| 89 | 0.11 | ND | 2.4 |
| 90 | 0.08 | ND | 1.7 |
| 91 | 0.47 | ND | ND |
| 92 | 0.039 | ND | 0.39 |
| 93 | 0.014 | ND | 0.53 |
| 94 | 0.79 | ND | ND |
| 95 | 0.012 | ND | 0.61 |
| 96 | 0.035 | ND | 0.42 |
| 97 | 0.8 | ND | ND |
| 98 | 0.12 | ND | 2.2 |
| 99 | 1.5 | ND | ND |
| 100 | 0.24 | ND | 5 |
| 101 | 0.13 | ND | 3.3 |
| 102 | 0.033 | ND | 3.1 |
| 103 | 2.6 | ND | ND |
| 104 | 0.033 | 0.029 | 0.082 |
| 105 | 0.037 | 0.015 | 0.095 |
| 106 | 0.13 | ND | 1.7 |
| 107 | 1.3 | ND | ND |
| 108 | 0.049 | ND | 1.7 |
| 109 | 0.019 | 0.026 | 0.095 |
| 110 | 0.056 | ND | 0.46 |
| 111 | 0.069 | ND | 1.1 |
| 112 | 0.2 | ND | 3.5 |
| 113 | 0.022 | ND | 0.44 |
| 114 | 0.019 | ND | 0.31 |
| 115 | 0.043 | 0.17 | 0.25 |
| 116 | 0.34 | ND | ND |
| 117 | 0.13 | ND | 1.5 |
| 118 | 0.083 | ND | 1.7 |
| 119 | 0.12 | ND | 1.5 |

TABLE 1-continued

| Example | CDK9 IC$_{50}$ (μM) | A431 viability EC$_{50}$ (μM) | H929 viability EC$_{50}$ (μM) |
|---|---|---|---|
| 120 | 0.12 | ND | 1.3 |
| 121 | 0.1 | ND | 2.3 |
| 122 | 0.51 | ND | ND |
| 123 | 1.8 | ND | ND |
| 124 | 0.06 | ND | 4.5 |
| 125 | 0.11 | ND | 7.3 |
| 126 | 0.095 | ND | 5 |
| 127 | 0.27 | ND | 2.8 |
| 128 | 0.093 | ND | 1.6 |
| 129 | 0.026 | ND | 0.97 |
| 130 | 15.1 | ND | ND |
| 131 | 0.04 | ND | 0.36 |
| 132 | 0.13 | ND | 0.86 |
| 133 | 0.3 | ND | ND |
| 134 | 0.024 | ND | 0.78 |
| 135 | 0.025 | 0.011 | 0.11 |
| 136 | 0.14 | ND | 3.5 |
| 137 | 0.54 | ND | >10 |
| 138 | 5.4 | ND | ND |
| 139 | 0.44 | ND | ND |
| 140 | 2.5 | ND | ND |
| 141 | 0.26 | ND | 2.1 |
| 142 | 0.03 | ND | 0.44 |
| 143 | 0.29 | ND | 0.56 |
| 144 | 0.019 | 0.006 | 0.048 |
| 145 | 0.056 | ND | 0.37 |
| 146 | 0.96 | ND | ND |
| 147 | 0.25 | ND | 0.85 |
| 148 | 0.85 | ND | ND |
| 149 | 0.2 | ND | 5.7 |
| 150 | 0.11 | ND | 1.4 |
| 151 | 0.68 | ND | ND |
| 152 | 0.3 | ND | 3.2 |
| 153 | 0.73 | ND | ND |
| 154 | 0.61 | ND | ND |
| 155 | 0.72 | ND | ND |
| 156 | 0.38 | ND | ND |
| 157 | 1.2 | ND | ND |
| 158 | 0.21 | ND | 1.8 |
| 159 | 1.3 | ND | ND |
| 160 | 0.5 | ND | ND |
| 161 | 0.2 | ND | 4.8 |
| 162 | 0.47 | ND | ND |
| 163 | 0.95 | ND | ND |
| 164 | 0.17 | ND | 1.5 |
| 165 | 0.59 | ND | ND |
| 166 | 0.55 | ND | ND |
| 167 | 0.11 | ND | 3 |
| 168 | 0.11 | ND | 3.2 |
| 169 | 0.21 | ND | 2.4 |
| 170 | 0.29 | ND | 2 |
| 171 | 0.29 | ND | 3.6 |
| 172 | 0.23 | ND | 1.1 |
| 173 | 1.4 | ND | ND |
| 174 | 0.43 | ND | ND |
| 175 | 0.47 | ND | ND |
| 176 | 0.023 | ND | 0.22 |
| 177 | 0.34 | ND | ND |
| 178 | 0.016 | ND | 0.59 |
| 179 | 0.042 | ND | 1.6 |
| 180 | 0.18 | ND | 1.3 |
| 181 | 0.074 | ND | 0.4 |
| 182 | 0.97 | ND | ND |
| 183 | 0.083 | 0.031 | 0.05 |
| 184 | 0.022 | ND | 0.27 |
| 185 | 0.29 | ND | 0.27 |
| 186 | 0.094 | ND | 0.22 |
| 187 | 0.27 | ND | 0.14 |
| 188 | 1.2 | ND | ND |
| 189 | 0.027 | 0.078 | 0.073 |
| 190 | 0.033 | ND | 0.12 |
| 191 | 1.5 | ND | ND |
| 192 | 0.081 | 0.14 | 0.096 |
| 193 | >12.5 | ND | ND |
| 194 | 0.13 | ND | 0.27 |
| 195 | >12.5 | ND | ND |
| 196 | 0.081 | ND | 0.45 |
| 197 | 0.26 | ND | 4 |
| 198 | 0.75 | ND | ND |
| 199 | 1.9 | ND | ND |
| 200 | 1.3 | ND | ND |
| 201 | 1.6 | ND | ND |
| 202 | 1.8 | ND | ND |
| 203 | 2.8 | ND | ND |
| 204 | 0.016 | 0.27 | 0.056 |
| 205 | 0.13 | ND | 1.7 |
| 206 | 0.13 | ND | 2.5 |
| 207 | 0.23 | ND | 1.1 |
| 208 | 0.074 | 3.5 | 0.038 |
| 209 | 0.066 | ND | 0.81 |
| 210 | 0.25 | ND | 1.3 |
| 211 | 0.05 | ND | 0.8 |
| 212 | 0.014 | ND | 0.17 |
| 213 | 0.054 | 0.086 | 0.092 |
| 214 | 0.022 | ND | 0.2 |
| 215 | 0.039 | 0.047 | 0.082 |
| 216 | 0.28 | ND | ND |
| 217 | 0.95 | ND | ND |
| 218 | 0.042 | ND | 0.19 |
| 219 | 2 | ND | ND |
| 220 | 0.21 | ND | 2.3 |
| 221 | 0.67 | ND | ND |
| 222 | 0.67 | ND | >10 |
| 223 | 0.25 | ND | 6 |
| 224 | 0.27 | ND | 2.7 |
| 225 | 0.049 | 0.027 | 0.076 |
| 226 | 0.037 | ND | 0.18 |
| 227 | 0.04 | 0.024 | 0.096 |
| 228 | 0.086 | ND | 0.38 |
| 229 | 0.11 | ND | 0.16 |
| 230 | 0.045 | ND | 0.16 |
| 231 | 0.036 | ND | 0.14 |
| 232 | 0.082 | ND | 0.19 |
| 233 | 0.042 | 0.008 | 0.044 |
| 234 | 0.086 | ND | 0.32 |
| 235 | 0.044 | ND | 0.15 |
| 236 | 0.043 | ND | 0.32 |
| 237 | 0.053 | 0.015 | 0.075 |
| 238 | 0.049 | ND | 0.11 |
| 239 | 0.097 | ND | 0.23 |
| 240 | 0.11 | ND | 0.48 |
| 241 | 0.11 | ND | 0.19 |
| 242 | 0.05 | ND | 0.21 |
| 243 | 0.19 | ND | 0.47 |
| 244 | 0.055 | ND | 0.29 |
| 245 | 0.049 | 0.031 | 0.079 |
| 246 | 0.061 | ND | 0.14 |
| 247 | 0.14 | ND | 1.5 |
| 248 | 0.33 | ND | 2.1 |
| 249 | 0.025 | ND | 0.95 |
| 250 | 0.068 | ND | 0.72 |
| 251 | 1.4 | ND | ND |
| 252 | 3.2 | ND | ND |
| 253 | 1.8 | ND | ND |
| 254 | 6.8 | ND | ND |
| 255 | 1.9 | ND | ND |
| 256 | 0.69 | ND | ND |
| 257 | 5 | ND | ND |
| 258 | 1.4 | ND | ND |
| 259 | 1.1 | ND | ND |
| 260 | 1.2 | ND | ND |
| 261 | 0.77 | ND | ND |
| 262 | 2.3 | ND | ND |
| 263 | 1.1 | ND | ND |
| 264 | 2.1 | ND | ND |
| 265 | 7.9 | ND | ND |
| 266 | 0.19 | ND | 0.35 |
| 267 | 0.14 | ND | 1.4 |
| 268 | 0.13 | ND | 0.68 |
| 269 | 0.58 | ND | ND |

TABLE 1-continued

| Example | CDK9 IC$_{50}$ (μM) | A431 viability EC$_{50}$ (μM) | H929 viability EC$_{50}$ (μM) |
|---|---|---|---|
| 270 | 0.18 | ND | 0.59 |
| 271 | 2.7 | ND | ND |
| 272 | 0.29 | ND | ND |
| 273 | 1.5 | ND | ND |
| 274 | 0.043 | ND | 0.36 |
| 275 | 0.063 | ND | 1.5 |
| 276 | 0.032 | ND | 0.12 |
| 277 | 2.3 | ND | ND |
| 278 | 0.021 | ND | 0.42 |
| 279 | 0.13 | ND | 1.7 |
| 280 | 0.023 | ND | 0.29 |
| 281 | 0.053 | ND | 0.69 |
| 282 | 0.28 | ND | ND |
| 283 | 0.16 | ND | >10 |
| 284 | 0.22 | ND | 2.8 |
| 285 | 0.51 | ND | ND |
| 286 | 0.088 | ND | 2.4 |
| 287 | 0.12 | ND | 1.1 |
| 288 | 0.15 | ND | 1.4 |
| 289 | 0.23 | ND | 2.4 |
| 290 | 0.29 | ND | ND |
| 291 | 0.64 | ND | ND |
| 292 | 0.097 | ND | 0.59 |
| 293 | 0.11 | ND | 0.28 |
| 294 | 0.29 | ND | ND |
| 295 | 0.43 | ND | ND |
| 296 | 0.16 | ND | 0.89 |
| 297 | 6.7 | ND | ND |
| 298 | 1.7 | ND | ND |
| 299 | 1.3 | ND | ND |
| 300 | 3.1 | ND | ND |
| 301 | 3.5 | ND | ND |
| 302 | 1.5 | ND | ND |
| 303 | 0.2 | ND | 1.8 |
| 304 | 0.1 | ND | 0.69 |
| 305 | 0.041 | ND | 2.3 |
| 306 | 0.04 | ND | 6.9 |
| 307 | 0.26 | ND | >10 |
| 308 | 0.17 | ND | 1.3 |
| 309 | 0.062 | ND | 0.97 |
| 310 | 0.13 | ND | 0.36 |
| 311 | 0.18 | ND | 0.35 |
| 312 | 0.025 | ND | 0.71 |
| 313 | 0.37 | ND | ND |
| 314 | 1.4 | ND | ND |
| 315 | 12.5 | ND | ND |
| 316 | 0.083 | ND | 0.47 |
| 317 | 0.056 | ND | 0.96 |
| 318 | 0.23 | ND | ND |
| 319 | 0.021 | ND | 0.54 |
| 320 | 0.091 | ND | >10 |
| 321 | 0.2 | ND | ND |
| 322 | 0.22 | ND | 2.6 |
| 323 | 0.1 | ND | 0.55 |
| 324 | 0.027 | ND | 0.28 |
| 325 | 0.099 | ND | 1.6 |
| 326 | 0.73 | ND | ND |
| 327 | 0.66 | ND | ND |
| 328 | 0.17 | ND | 1.2 |
| 329 | 0.22 | ND | 0.28 |
| 330 | 1.3 | ND | 6.4 |
| 331 | 0.31 | ND | 0.18 |
| 332 | 0.33 | ND | >10 |
| 333 | 0.58 | ND | 4.8 |
| 334 | 0.53 | ND | 1.8 |
| 335 | 0.4 | ND | 0.64 |
| 336 | 0.2 | ND | 0.48 |
| 337 | 0.21 | ND | 0.17 |
| 338 | 0.29 | ND | 0.2 |
| 339 | 0.59 | ND | 8.9 |

ND = not determined

Xenograft Tumor Growth Inhibition Assay

The effect of Examples 6 and 13 to inhibit the growth of H929 xenograft tumors implanted in mice was evaluated. NCI-H929 cells obtained from culture were suspended in cell culture medium (MEM, no calcium, no glutamine, Life Technologies Corporation) and diluted 1:1 with a solution of Matrigel™ (BD Biosciences, Franklin Lakes, N.J.). Tumor cells 5 million per site were inoculated subcutaneously into the right hind flank of female nude or SCID-beige mice (Charles River Labs). Randomization into treatment and vehicle control groups (9-10/group) occurred when the mean tumor volume reached approximately 200 mm$^3$. Compounds were formulated in 2% DMSO, 5% Tween80, 20% PEG400, 73% HPMC. Administration of compound or vehicle was initiated on the day following randomization and continued for the indicated time. Tumors were measured twice a week throughout the treatment period using a pair of calipers and tumor volumes were calculated according to the formula V=L×W$^2$/2 (V: volume, mm$^3$; L: length, mm. W: width, m) Tumor growth inhibition was calculated based on the mean tumor volume measured at the end of the treatment period according to the formula % TGI=100−mean tumor volume of treatment group/mean tumor volume of control group× 100. Results are given in Table 2.

TABLE 2

H929 human multiple myeloma cancer xenograft model.

| Compound of Example | Dose mg/kg | route, regimen | % TGI$^a$ | % TGD$^b$ |
|---|---|---|---|---|
| 6 | 3.75 | IP, TW$^c$ × 3 | 48** | 36* |
| 6 | 7.50 | IP, TW × 3 | 51** | 53 |
| 13 | 7.5 | IP, TW × 3 | 40 | 29** |
| 13 | 15 | IP, TW × 3 | 70*** | 95*** |

$^a$The p values (as indicated by asterisks) are derived from Student's T test comparison of treatment group vs. control group: *p < 0.05, p < 0.01, *p < 0.001.
$^b$Tumor growth delay, % TGD = (T − C)/C × 100, where T = median time to reach 500 mm$^3$ of treatment group and C = median time to endpoint of control group. The p values (as indicated by asterisks) derived from Kaplan Meier log-rank comparison of treatment group vs. treatment control group based on an endpoint of 1000 mm$^3$. *p < 0.05, p < 0.01, *p < 0.001.
$^c$Twice a week, 3 and 4 days apart.

It is meant to be understood that the examples and embodiments described herein are for illustrative purposes only and that various modifications or changes in light thereof will be suggested to persons skilled in the art and are to be included within the spirit and purview of the appended claims. All publications, patents, and patent applications cited herein are hereby incorporated by reference in their entirety for all purposes.

What is claimed is:
1. A compound having Formula (Ia), or a pharmaceutically acceptable salt thereof,

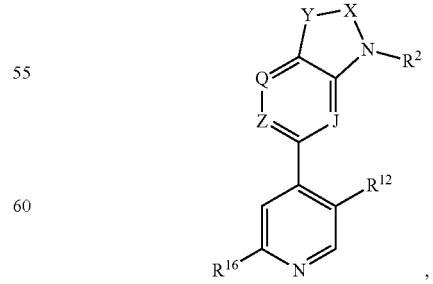

(Ia)

wherein
R$^{12}$ is halo;
J is N or CH;

Q is N or $CR^1$;
Z is N or $CR^1$;
wherein the bond between X and Y may be a single or a double bond; and
if a double bond is present, then Y is $CR^3$ and X is CH, Y is CH and X is CH, Y is N and X is CH, Y is N and X is $CR^3$, Y is $CR^3$ and X is N, Y is N and X is N, or Y is CH and X is N; and
if a single bond is present, then Y is $CH_2$ and X is $CH_2$ or C(O), or Y is NH or $N(C_1\text{-}C_3$ alkyl) and X is C(O);
$R^3$ is selected from the group consisting of $R^{3A}$, $C(O)R^{3A}$, and CN;
$R^{3A}$ is selected from the group consisting of $C_1$-$C_6$ alkyl, $C_2$-$C_6$ alkenyl, $C_2$-$C_6$ alkynyl, aryl, cycloalkyl, cycloalkenyl, heteroaryl, heterocycloalkyl, and heterocycloalkenyl; wherein the $R^{3A}$ $C_1$-$C_6$ alkyl, $C_2$-$C_6$ alkenyl, and $C_2$-$C_6$ alkynyl are optionally substituted with one or more substituents independently selected from the group consisting of $R^{3B}$, $OR^{3B}$, and halo; wherein the $R^{3A}$ aryl, cycloalkyl, cycloalkenyl, heteroaryl, heterocycloalkyl, and heterocycloalkenyl are optionally substituted with one or more halo;
$R^{3B}$ is selected from the group consisting of $C_1$-$C_6$ alkyl, $C_2$-$C_6$ alkenyl, $C_2$-$C_6$ alkynyl, and aryl, wherein the $R^{3B}$ aryl is optionally substituted with one or more substituents independently selected from the group consisting of F, Cl, Br, and I;
$R^1$ is selected from the group consisting of H, CN, Cl, Br, I, F, $R^{1A}$; and $OR^{1A}$;
$R^{1A}$ is selected from the group consisting of $C_1$-$C_6$ alkyl, $C_2$-$C_6$ alkenyl, and $C_2$-$C_6$ alkynyl;
$R^2$ is selected from the group consisting of H, $C_1$-$C_6$ alkyl, $C_2$-$C_6$ alkenyl, and $C_2$-$C_6$ alkynyl; wherein the $R^2$ $C_1$-$C_6$ alkyl, $C_2$-$C_6$ alkenyl, and $C_2$-$C_6$ alkynyl are optionally substituted with one or more substituents independently selected from the group consisting of $R^4$, $OR^4$, $SR^4$, $S(O)R^4$, $SO_2R^4$, $C(O)R^4$, $CO(O)R^4$, $OC(O)R^4$, $OC(O)OR^4$, $NH_2$, $NHR^4$, $N(R^4)_2$, $NHC(O)R^4$, $NR^4C(O)R^4$, $SO_2NHC(O)R^4$, $SO_2NR^4C(O)R^4$, $NHS(O)_2R^4$, $NR^4S(O)_2R^4$, $NHC(O)OR^4$, $NR^4C(O)OR^4$, $SO_2NHC(O)OR^4$, $SO_2NR^4C(O)OR^4$, $NHSO_2NHC(O)OR^4$, $NHSO_2NR^4C(O)OR^4$, $NR^4SO_2NR^4C(O)OR^4$, $NR^4SO_2NHC(O)OR^4$, $NHC(O)NH_2$, $NHC(O)NHR^4$, $NHC(O)N(R^4)_2$, $NR^4C(O)NHR^4$, $NR^4C(O)N(R^4)_2$, $OC(O)NH_2$, $OC(O)NHR^4$, $OC(O)N(R^4)_2$, $OC(O)NHSO_2R^4$, $OC(O)NR^4SO_2R^4$, $C(O)NH_2$, $C(O)NHR^4$, $C(O)N(R^4)_2$, $C(O)NHOH$, $C(O)NHOR^4$, $C(O)NHSO_2R^4$, $C(O)NR^4SO_2R^4$, $SO_2NH_2$, $SO_2NHR^4$, $SO_2N(R^4)_2$, $OSO_2NH_2$, $OSO_2NHR^4$, $OSO_2N(R^4)_2$, $C(O)NHCN$, $C(O)NR^4CN$, $S(O)NR^4$, $S(O)NSO_2R^4$, $C(O)H$, $C(O)OH$, (O), OH, CN, $NO_2$, F, Cl, Br and I;
$R^4$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^4$ $C_1$-$C_6$ alkyl, $C_2$-$C_6$ alkenyl, and $C_2$-$C_6$ alkynyl is optionally substituted with one or more substituents independently selected from the group consisting of $R^5$, $OR^5$, $SR^5$, $S(O)R^5$, $SO_2R^5$, $C(O)R^5$, $CO(O)R^5$, $OC(O)R^5$, $OC(O)OR^5$, $NH_2$, $NHR^5$, $N(R^5)_2$, $NHC(O)R^5$, $NR^5C(O)R^5$, $NHS(O)_2R^5$, $NR^5S(O)_2R^5$, $NHC(O)OR^5$, $NR^5C(O)OR^5$, $NHC(O)NH_2$, $NHC(O)NHR^5$, $NHC(O)N(R^5)_2$, $NR^5C(O)NHR^5$, $NR^5C(O)N(R^5)_2$, $C(O)NH_2$, $C(O)NHR^5$, $C(O)N(R^5)_2$, $C(O)NHOH$, $C(O)NHOR^5$, $C(O)NHSO_2R^5$, $C(O)NR^5SO_2R^5$, $SO_2NH_2$, $SO_2NHR^5$, $SO_2N(R^5)_2$, $C(O)H$, $C(O)OH$, OH, CN, $NO_2$, F, Cl, Br and I; wherein each $R^4$ aryl, cycloalkyl, cycloalkenyl, heteroaryl, heterocycloalkyl, and heterocycloalkenyl is optionally substituted with one or more substituents independently selected from the group consisting of $R^6$, $OR^6$, $SR^6$, $S(O)R^6$, $SO_2R^6$, $C(O)R^6$, $CO(O)R^6$, $OC(O)R^6$, $OC(O)OR^6$, $NH_2$, $NHR^6$, $N(R^6)_2$, $NHC(O)R^6$, $NR^6C(O)R^6$, $NHS(O)_2R^6$, $NR^6S(O)_2R^6$, $NHC(O)OR^6$, $NR^6C(O)OR^6$, $NHC(O)NH_2$, $NHC(O)NHR^6$, $NHC(O)N(R^6)_2$, $NR^6C(O)NHR^6$, $NR^6C(O)N(R^6)_2$, $C(O)NH_2$, $C(O)NHR^6$, $C(O)N(R^6)_2$, $C(O)NHOH$, $C(O)NHOR^6$, $C(O)NHSO_2R^6$, $C(O)NR^6SO_2R^6$, $SO_2NH_2$, $SO_2NHR^6$, $SO_2N(R^6)_2$, $C(O)H$, $C(O)OH$, (O), OH, CN, $NO_2$, F, Br and I;
$R^5$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl;
$R^6$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^6$ $C_1$-$C_6$ alkyl, $C_2$-$C_6$ alkenyl, and $C_2$-$C_6$ alkynyl is optionally substituted with one or more substituents independently selected from the group consisting of halo and $R^{6A}$;
$R^{6A}$, at each occurrence, is independently selected from the group consisting of aryl, heteroaryl, heterocycloalkyl, heterocycloalkenyl, cycloalkyl, and cycloalkenyl; wherein each $R^{6A}$ aryl, heteroaryl, heterocycloalkyl, heterocycloalkenyl, cycloalkyl, and cycloalkenyl is optionally substituted with $C_1$-$C_6$ alkyl;
$R^{16}$ is selected from the group consisting of $NH_2$, $NHR^7$, $NHC(O)R^7$, $NHS(O)_2R^7$, $NHC(O)OR^7$, $NHC(O)NH_2$, $NHC(O)NHR^7$, and $NHC(O)N(R^7)_2$;
$R^7$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^7$ $C_1$-$C_6$ alkyl, $C_2$-$C_6$ alkenyl, and $C_2$-$C_6$ alkynyl is optionally substituted with one or more substituents independently selected from the group consisting of $R^8$, $SR^8$, $S(O)R^8$, $SO_2R^8$, $C(O)R^8$, $CO(O)R^8$, $OC(O)R^8$, $OC(O)OR^8$, $NH_2$, $NHR^8$, $N(R^8)_2$, $NHC(O)R^8$, $NR^8C(O)R^8$, $NHS(O)_2R^8$, $NR^8S(O)_2R^8$, $NHSO_2NH_2$, $NR^8SO_2NH_2$, $NHSO_2NHR^8$, $NR^8SO_2NHR^8$, $NHSO_2N(R^8)_2$, $NR^8SO_2N(R^8)_2$, $NHC(O)OR^8$, $NR^8C(O)OR^8$, $NHC(O)NH_2$, $NHC(O)NHR^8$, $NHC(O)N(R^8)_2$, $NR^8C(O)NHR^8$, $NR^8C(O)N(R^8)_2$, $C(O)NH_2$, $C(O)NHR^8$, $C(O)N(R^8)_2$, $C(O)NHOH$, $C(O)NHOR^8$, $C(O)NHSO_2R^8$, $C(O)NR^8SO_2R^8$, $C(O)NHC(O)NH_2$, $C(O)NR^8C(O)NH_2$, $C(O)NHC(O)NHR^8$, $C(O)NR^8C(O)NHR^8$, $C(O)NHC(O)N(R^8)_2$, $C(O)NR^8C(O)N(R^8)_2$, $SO_2NH_2$, $SO_2NHR^8$, $SO_2N(R^8)_2$, $C(O)H$, $C(O)OH$, OH, CN, $NO_2$, F, Cl, Br and I; wherein each $R^7$ aryl, cycloalkyl, cycloalkenyl, heteroaryl, heterocycloalkyl, and heterocycloalkenyl is optionally substituted with one or more substituents independently selected from the group consisting of $R^9$, $OR^9$, $SR^9$, $S(O)R^9$, $SO_2R^9$, $C(O)R^9$, $CO(O)R^9$, $OC(O)R^9$, $OC(O)OR^9$, $NH_2$, $NHR^9$, $N(R^9)_2$, $NHC(O)R^9$, $NR^9C(O)R^9$, $NHS(O)_2R^9$, $NR^9S(O)_2R^9$, $NHC(O)OR^9$, $NR^9C(O)OR^9$, $NHC(O)NH_2$, $NHC(O)NHR^9$, $NHC(O)N(R^9)_2$, $NR^9C(O)NHR^9$, $NR^9C(O)N(R^9)_2$, $C(O)NH_2$, $C(O)NHR^9$, $C(O)N(R^9)_2$, $C(O)NHOH$, $C(O)NHOR^9$, $C(O)NHSO_2R^9$, $C(O)NR^9SO_2R^9$, $SO_2NH_2$, $SO_2NHR^9$, $SO_2N(R^9)_2$, $SO_2NHC(O)OH$, $SO_2NR^9C(O)OH$, $SO_2NHC(O)OR^9$, $SO_2NR^9C(O)OR^9$, $C(O)H$, $C(O)OH$, (O), OH, CN, $NO_2$, F, Cl, Br and I;

$R^8$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^8$ $C_1$-$C_6$ alkyl, $C_2$-$C_6$ alkenyl, and $C_2$-$C_6$ alkynyl is optionally substituted with one or more substituents independently selected from the group consisting of $NHR^{10}$, and aryl; wherein each $R^8$ aryl, heteroaryl, heterocycloalkyl, heterocycloalkenyl, cycloalkyl, and cycloalkenyl is optionally substituted with one or more substituents independently selected from the group consisting of $R^{11}$, $OR^{11}$, halo, $NH_2$, OH, and (O);

$R^9$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^9$ $C_1$-$C_6$ alkyl, $C_2$-$C_6$ alkenyl, and $C_2$-$C_6$ alkynyl is optionally substituted with one or more substituents independently selected from the group consisting of $R^{13}$, $OR^{13}$, $SR^{13}$, $S(O)R^{13}$, $SO_2R^{13}$, $C(O)R^{13}$, $CO(O)R^{13}$, $OC(O)R^{13}$, $OC(O)OR^{13}$, $NH_2$, $NHR^{13}$, $N(R^{13})_2$, $NHC(O)R^{13}$, $NR^{13}C(O)R^{13}$, $NHS(O)_2R^{13}$, $NR^{13}S(O)_2R^{13}$, $NHC(O)OR^{13}$, $NR^{13}C(O)OR^{13}$, $NHC(O)NH_2$, $NHC(O)NHR^{13}$, $NHC(O)N(R^{13})_2$, $NR^{13}C(O)NHR^{13}$, $NR^{13}C(O)N(R^{13})_2$, $C(O)NH_2$, $C(O)NHR^{13}$, $C(O)N(R^{13})_2$, $C(O)NHOH$, $C(O)NHOR^{13}$, $C(O)NHSO_2R^{13}$, $C(O)NR^{13}SO_2R^{13}$, $SO_2NH_2$, $SO_2NHR^{13}$, $SO_2N(R^{13})_2$, $C(O)H$, $C(O)OH$, OH, CN, $NO_2$, F, Cl, Br and I; wherein each $R^9$ aryl, cycloalkyl, cycloalkenyl, heteroaryl, heterocycloalkyl, and heterocycloalkenyl is optionally substituted with one or more substituents independently selected from the group consisting of $R^{14}$, $OR^{14}$, $SR^{14}$, $S(O)R^{14}$, $SO_2R^{14}$, $C(O)R^{14}$, $CO(O)R^{14}$, $OC(O)R^{14}$, $OC(O)OR^{14}$, $NH_2$, $NHR^{14}$, $N(R^{14})_2$, $NHC(O)R^{14}$, $NR^{14}C(O)R^{14}$, $NHS(O)_2R^{14}$, $NR^{14}S(O)_2R^{14}$, $NHC(O)OR^{14}$, $NR^{14}C(O)OR^{14}$, $NHC(O)NH_2$, $NHC(O)NHR^{14}$, $NHC(O)N(R^{14})_2$, $NR^{14}C(O)NHR^{14}$, $NR^{14}C(O)N(R^{14})_2$, $C(O)NH_2$, $C(O)NHR^{14}$, $C(O)N(R^{14})_2$, $C(O)NHOH$, $C(O)NHOR^{14}$, $C(O)NHSO_2R^{14}$, $C(O)NR^{14}SO_2R^{14}$, $SO_2NH_2$, $SO_2NHR^{14}$, $SO_2N(R^{14})_2$, $C(O)H$, $C(O)OH$, (O), OH, CN, $NO_2$, F, Cl, Br and I;

$R^{10}$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl;

$R^{11}$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^{11}$ $C_1$-$C_6$ alkyl, $C_2$-$C_6$ alkenyl, and $C_2$-$C_6$ alkynyl is optionally substituted with one or more substituents independently selected from the group consisting of $NH_2$, $C(O)NH_2$, $SO_2NH_2$, $C(O)H$, $C(O)OH$, OH, CN, $NO_2$, F, Cl, Br and I; wherein each $R^{11}$ aryl, cycloalkyl, cycloalkenyl, heteroaryl, heterocycloalkyl, and heterocycloalkenyl is optionally substituted with one or more substituents independently selected from the group consisting of $C_1$-$C_6$ alkyl, O—$C_1$-$C_6$ alkyl, $NH_2$, $C(O)NH_2$, $C(O)H$, $C(O)OH$, OH, CN, $NO_2$, F, Cl, Br and I;

$R^{13}$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^{13}$ $C_1$-$C_6$ alkyl, $C_2$-$C_6$ alkenyl, and $C_2$-$C_6$ alkynyl is optionally substituted with one or more substituents independently selected from the group consisting of aryl, $NH_2$, $C(O)NH_2$, $SO_2NH_2$, $C(O)H$, $C(O)OH$, OH, CN, $NO_2$, F, Cl, Br and I; wherein each $R^{13}$ aryl, cycloalkyl, cycloalkenyl, heteroaryl, heterocycloalkyl, and heterocycloalkenyl is optionally substituted with one or more substituents independently selected from the group consisting of $C_1$-$C_6$ alkyl, O—$C_1$-$C_6$ alkyl, $C_1$-$C_6$ alkyl-O—$C_1$-$C_6$ alkyl, $NH_2$, $C(O)NH_2$, $C(O)H$, $C(O)OH$, OH, CN, $NO_2$, F, Cl, Br and I; and $R^{14}$, at each occurrence, is independently selected from the group consisting of $C_1$-$C_6$ alkyl, $C_2$-$C_6$ alkenyl, $C_2$-$C_6$ alkynyl, aryl, heteroaryl, heterocycloalkyl, heterocycloalkenyl, cycloalkyl, and cycloalkenyl; wherein each $R^{14}$ $C_1$-$C_6$ alkyl, $C_2$-$C_6$ alkenyl, and $C_2$-$C_6$ alkynyl is optionally substituted with one or more substituents independently selected from the group consisting of aryl, $NH_2$, $C(O)NH_2$, $SO_2NH_2$, $C(O)H$, $C(O)OH$, OH, CN, $NO_2$, F, Cl, Br and I; wherein each $R^{14}$ aryl, cycloalkyl, cycloalkenyl, heteroaryl, heterocycloalkyl, and heterocycloalkenyl is optionally substituted with one or more substituents independently selected from the group consisting of $C_1$-$C_6$ alkyl, O—$C_1$-$C_6$ alkyl, $C_1$-$C_6$ alkyl-O—$C_1$-$C_6$ alkyl, $NH_2$, $C(O)NH_2$, $C(O)H$, $C(O)OH$, OH, $NO_2$, F, Cl, Br and I.

2. The compound of claim 1, or a pharmaceutically acceptable salt thereof, wherein $R^{12}$ is Cl.

3. The compound of claim 2, or a pharmaceutically acceptable salt thereof, wherein $R^{16}$ is selected from the group consisting of $NHR^7$ and $NHC(O)R^7$.

4. The compound of claim 3, or a pharmaceutically acceptable salt thereof, wherein J is CH; Q is $CR^1$; Z is $CR^1$; wherein the bond between X and Y is a single bond; Y is $CH_2$ and X is $CH_2$; and $R^1$ is H.

5. The compound of claim 3, or a pharmaceutically acceptable salt thereof, wherein J is CH; Q is $CR^1$; Z is $CR^1$; wherein the bond between X and Y is a double bond; Y is N and X is CH; and $R^1$ is H.

6. The compound of claim 4, or a pharmaceutically acceptable salt thereof, wherein $R^2$ is $C_1$-$C_6$ alkyl; wherein the $R^2$ $C_1$-$C_6$ alkyl is optionally substituted with one or more substituents independently selected from the group consisting of $R^4$, $SO_2R^4$, $C(O)R^4$, $N(R^4)_2$, $C(O)N(R^4)_2$, $SO_2NH_2$, and OH.

7. The compound of claim 5, or a pharmaceutically acceptable salt thereof, wherein $R^2$ is $C_1$-$C_6$ alkyl; wherein the $R^2$ $C_1$-$C_6$ alkyl is optionally substituted with one or more substituents independently selected from the group consisting of $R^4$, $SO_2R^4$, $C(O)R^4$, $N(R^4)_2$, $C(O)N(R^4)_2$, $SO_2NH_2$, and OH.

8. The compound of claim 6, or a pharmaceutically acceptable salt thereof, wherein $R^4$, at each occurrence, is independently selected from the group consisting of $C_1$-$C_6$ alkyl, aryl, heteroaryl, heterocycloalkyl, and cycloalkyl; wherein each $R^4$ $C_1$-$C_6$ alkyl is optionally substituted with one or more OH; wherein each $R^4$ aryl, cycloalkyl, heteroaryl, and heterocycloalkyl is optionally substituted with one or more substituents independently selected from the group consisting of $R^6$, $SO_2R^6$, $CO(O)R^6$, $NHS(O)_2R^6$, $SO_2NH_2$, $C(O)OH$, OH, CN, and F.

9. The compound of claim 7, or a pharmaceutically acceptable salt thereof, wherein $R^4$, at each occurrence, is independently selected from the group consisting of $C_1$-$C_6$ alkyl, aryl, heteroaryl, heterocycloalkyl, and cycloalkyl; wherein each $R^4$ $C_1$-$C_6$ alkyl is optionally substituted with one or more OH; wherein each $R^4$ aryl, cycloalkyl, heteroaryl, and heterocycloalkyl is optionally substituted with one or more substituents independently selected from the group consisting of $R^6$, $SO_2R^6$, $CO(O)R^6$, $NHS(O)_2R^6$, $SO_2NH_2$, $C(O)OH$, OH, CN, and F.

10. The compound of claim 6, or a pharmaceutically acceptable salt thereof, wherein $R^4$, at each occurrence, is independently $C_1$-$C_6$ alkyl; wherein each $R^4$ $C_1$-$C_6$ alkyl is optionally substituted with one or more OH.

11. The compound of claim 7, or a pharmaceutically acceptable salt thereof, wherein $R^4$, at each occurrence, is independently $C_1$-$C_6$ alkyl; wherein each $R^4$ $C_1$-$C_6$ alkyl is optionally substituted with one or more OH.

12. The compound of claim 6, or a pharmaceutically acceptable salt thereof, wherein $R^4$, at each occurrence, is independently selected from the group consisting of aryl, heteroaryl, heterocycloalkyl, and cycloalkyl; wherein each $R^4$ aryl, cycloalkyl, heteroaryl, and heterocycloalkyl is optionally substituted with one or more substituents independently selected from the group consisting of $R^6$, $SO_2R^6$, $CO(O)R^6$, $NHS(O)_2R^6$, $SO_2NH_2$, $C(O)OH$, OH, CN, and F.

13. The compound of claim 7, or a pharmaceutically acceptable salt thereof, wherein $R^4$, at each occurrence, is independently selected from the group consisting of aryl, heteroaryl, heterocycloalkyl, and cycloalkyl; wherein each $R^4$ aryl, cycloalkyl, heteroaryl, and heterocycloalkyl is optionally substituted with one or more substituents independently selected from the group consisting of $R^6$, $SO_2R^6$, $CO(O)R^6$, $NHS(O)_2R^6$, $SO_2NH_2$, $C(O)OH$, OH, CN, and F.

14. A compound selected from the group consisting of:
(3R)—N-{5-chloro-4-[1-(3-fluorobenzyl)-2,3-dihydro-1H-indol-6-yl]pyridin-2-yl}piperidine-3-carboxamide;
(3R)—N-[5-chloro-4-(2,3-dihydro-1H-indol-6-yl)pyridin-2-yl]piperidine-3-carboxamide;
(3R)—N-[5-chloro-4-(1-methyl-1H-benzimidazol-6-yl)pyridin-2-yl]piperidine-3-carboxamide;
(3R)—N-{5-chloro-4-[1-(tetrahydro-2H-pyran-4-ylmethyl)-2,3-dihydro-1H-indol-6-yl]pyridin-2-yl}piperidine-3-carboxamide;
(3R)—N-{5-chloro-4-[1-(3-fluorobenzyl)-1H-benzimidazol-5-yl]pyridin-2-yl}piperidine-3-carboxamide;
(3R)—N-{5-chloro-4-[1-(3-fluorobenzyl)-1H-benzimidazol-6-yl]pyridin-2-yl}piperidine-3-carboxamide;
(3R)—N-{5-chloro-4-[1-(3-fluorobenzyl)-1H-indol-6-yl]pyridin-2-yl}piperidine-3-carboxamide;
trans-N-{5-chloro-4-[1-(3-fluorobenzyl)-1H-benzimidazol-6-yl]pyridin-2-yl}cyclohexane-1,4-diamine;
trans-N-{5-chloro-4-[1-(3-fluorobenzyl)-2,3-dihydro-1H-indol-6-yl]pyridin-2-yl}cyclohexane-1,4-diamine;
trans-4-({5-chloro-4-[1-(3-fluorobenzyl)-2,3-dihydro-1H-indol-6-yl]pyridin-2-yl}amino)cyclohexanol;
trans-4-({5-chloro-4-[1-(3-fluorobenzyl)-1H-benzimidazol-6-yl]pyridin-2-yl}amino)cyclohexanol;
trans-N-[5-chloro-4-(1-methyl-1H-benzimidazol-6-yl)pyridin-2-yl]cyclohexane-1,4-diamine;
(3R)—N-{5-chloro-4-[1-(tetrahydro-2H-pyran-4-ylmethyl)-1H-benzimidazol-6-yl]pyridin-2-yl}piperidine-3-carboxamide;
(3R)—N-(5-chloro-4-{1-[2-(morpholin-4-yl)ethyl]-1H-benzimidazol-6-yl}pyridin-2-yl)piperidine-3-carboxamide;
(3R)—N-{5-chloro-4-[1-(3-hydroxy-3-methylbutyl)-1H-benzimidazol-6-yl]pyridin-2-yl}piperidine-3-carboxamide;
(3R)—N-{5-chloro-4-[1-(4-fluorobenzyl)-1H-benzimidazol-6-yl]pyridin-2-yl}piperidine-3-carboxamide;
(3R)—N-{5-chloro-4-[1-(3,4-difluorobenzyl)-1H-benzimidazol-6-yl]pyridin-2-yl}piperidine-3-carboxamide;
(3R)—N-(5-chloro-4-{1-[2-(3-fluorophenyl)ethyl]-1H-benzimidazol-6-yl}pyridin-2-yl)piperidine-3-carboxamide;
(3R)—N-{5-chloro-4-[1-(2-sulfamoylethyl)-1H-benzimidazol-6-yl]pyridin-2-yl}piperidine-3-carboxamide;
(3R)—N-(5-chloro-4-{1-[(1,1-dioxidotetrahydrothiophen-3-yl)methyl]-1H-benzimidazol-6-yl}pyridin-2-yl)piperidine-3-carboxamide;
(3R)—N-{5-chloro-4-[1-(2-fluorobenzyl)-1H-benzimidazol-6-yl]pyridin-2-yl}piperidine-3-carboxamide;
(3R)—N-{5-chloro-4-[1-(pyridin-3-ylmethyl)-1H-benzimidazol-6-yl]pyridin-2-yl}piperidine-3-carboxamide;
(3R)—N-(5-chloro-4-{1-[(1,1-dioxidotetrahydro-2H-thiopyran-4-yl)methyl]-1H-benzimidazol-6-yl}pyridin-2-yl)piperidine-3-carboxamide;
(3R)—N-(5-chloro-4-{1-[(5-methyl-4H-1,2,4-triazol-3-yl)methyl]-1H-benzimidazol-6-yl}pyridin-2-yl)piperidine-3-carboxamide;
(3R)—N-{5-chloro-4-[1-(1,3-thiazol-4-ylmethyl)-1H-benzimidazol-5-yl]pyridin-2-yl}piperidine-3-carboxamide-(3R)—N-{5-chloro-4-[1-(1,3-thiazol-4-ylmethyl)-1H-benzimidazol-6-yl]pyridin-2-yl}piperidine-3-carboxamide (1:1);
5-chloro-N-cyclopentyl-4-[1-(3-fluorobenzyl)-1H-benzimidazol-6-yl]pyridin-2-amine;
1-[trans-4-({5-chloro-4-[1-(3-fluorobenzyl)-1H-benzimidazol-6-yl]pyridin-2-yl}amino)cyclohexyl]-3-methylurea;
N-[trans-4-({5-chloro-4-[1-(3-fluorobenzyl)-1H-benzimidazol-6-yl]pyridin-2-yl}amino)cyclohexyl]methanesulfonamide;
(3R)—N-[4-(1-benzyl-3-cyano-1H-indol-6-yl)-5-chloropyridin-2-yl]piperidine-3-carboxamide;
N'-{5-chloro-4-[1-(3-fluorobenzyl)-1H-benzimidazol-6-yl]pyridin-2-yl}-N-methyl-N-(pyridin-2-yl)propane-1,3-diamine;
1-({5-chloro-4-[1-(3-fluorobenzyl)-1H-benzimidazol-6-yl]pyridin-2-yl}amino)-3-(dimethylamino)propan-2-ol;
5-chloro-4-[1-(3-fluorobenzyl)-1H-benzimidazol-6-yl]-N-[(5-methyl-4H-1,2,4-triazol-3-yl)methyl]pyridin-2-amine;
(3R)—N-{5-chloro-4-[1-(3-fluorobenzyl)-1H-pyrrolo[3,2-b]pyridin-6-yl]pyridin-2-yl}piperidine-3-carboxamide;
N-{5-chloro-4-[1-(3-fluorobenzyl)-1H-benzimidazol-6-yl]pyridin-2-yl}-N'-(pyridin-3-yl)ethane-1,2-diamine;
N-[(5-amino-4H-1,2,4-triazol-3-yl)methyl]-5-chloro-4-[1-(3-fluorobenzyl)-1H-benzimidazol-6-yl]pyridin-2-amine;
N-benzyl-N'-{5-chloro-4-[1-(3-fluorobenzyl)-1H-benzimidazol-6-yl]pyridin-2-yl}-N-methylpropane-1,3-diamine;
5-chloro-4-[1-(3-fluorobenzyl)-1H-benzimidazol-6-yl]-N-(pyrimidin-2-ylmethyl)pyridin-2-amine;
5-chloro-4-[1-(3-fluorobenzyl)-1H-benzimidazol-6-yl]-N-[1-(pyridin-4-yl)propan-2-yl]pyridin-2-amine;
5-chloro-4-[1-(3-fluorobenzyl)-1H-benzimidazol-6-yl]-N-[1-(1-methyl-1H-pyrazol-4-yl)piperidin-3-yl]pyridin-2-amine;
5-[({5-chloro-4-[1-(3-fluorobenzyl)-1H-benzimidazol-6-yl]pyridin-2-yl}amino)methyl]pyrimidin-2-amine;
5-chloro-N-[2-(1-ethylpiperidin-4-yl)ethyl]-4-[1-(3-fluorobenzyl)-1H-benzimidazol-6-yl]pyridin-2-amine;
5-chloro-4-[1-(3-fluorobenzyl)-1H-benzimidazol-6-yl]-N-[2-(5-methyl-4H-1,2,4-triazol-3-yl)ethyl]pyridin-2-amine;
N-{5-chloro-4-[1-(3-fluorobenzyl)-1H-benzimidazol-6-yl]pyridin-2-yl}-N'-(pyridin-4-yl)ethane-1,2-diamine;

5-chloro-4-[1-(3-fluorobenzyl)-1H-benzimidazol-6-yl]-N-[2-(1-methylpiperidin-4-yl)ethyl]pyridin-2-amine;

5-chloro-4-[1-(3-fluorobenzyl)-1H-benzimidazol-6-yl]-N-[2-(pyridin-4-yl)propyl]pyridin-2-amine;

$N^1$-{5-chloro-4-[1-(3-fluorobenzyl)-1H-benzimidazol-6-yl]pyridin-2-yl}-$N^2$,$N^2$,2-trimethylpropane-1,2-diamine;

N-{5-chloro-4-[1-(3-fluorobenzyl)-1H-benzimidazol-6-yl]pyridin-2-yl}-N'-phenylpropane-1,3-diamine;

$N^3$-{5-chloro-4-[1-(3-fluorobenzyl)-1H-benzimidazol-6-yl]pyridin-2-yl}butane-1,3-diamine;

5-chloro-4-[1-(3-fluorobenzyl)-1H-benzimidazol-6-yl]pyridin-2-amine;

5-chloro-4-[1-(3-fluorobenzyl)-1H-benzimidazol-6-yl]-N-(1H-imidazol-4-ylmethyl)pyridin-2-amine;

5-chloro-4-[1-(3-fluorobenzyl)-1H-benzimidazol-6-yl]-N-(pyrazin-2-ylmethyl)pyridin-2-amine;

5-chloro-4-[1-(3-fluorobenzyl)-1H-benzimidazol-6-yl]-N-[1-(pyrazin-2-yl)propan-2-yl]pyridin-2-amine;

5-chloro-4-[1-(3-fluorobenzyl)-1H-benzimidazol-6-yl]-N-(1-methylpyrrolidin-3-yl)pyridin-2-amine;

5-chloro-4-[1-(3-fluorobenzyl)-1H-benzimidazol-6-yl]-N-[2-(pyridin-3-yl)ethyl]pyridin-2-amine;

N'-{5-chloro-4-[1-(3-fluorobenzyl)-1H-benzimidazol-6-yl]pyridin-2-yl}-N,N-dimethylbutane-1,4-diamine;

5-chloro-4-[1-(3-fluorobenzyl)-1H-benzimidazol-6-yl]-N-[(1-methylpiperidin-4-yl)methyl]pyridin-2-amine;

N-benzyl-N'-{5-chloro-4-[1-(3-fluorobenzyl)-1H-benzimidazol-6-yl]pyridin-2-yl}-N-methylethane-1,2-diamine;

5-chloro-4-[1-(3-fluorobenzyl)-1H-benzimidazol-6-yl]-N-[2-(pyridin-2-yl)ethyl]pyridin-2-amine;

4-({5-chloro-4-[1-(3-fluorobenzyl)-1H-benzimidazol-6-yl]pyridin-2-yl}amino)-2-methylbutan-2-ol;

N'-{5-chloro-4-[1-(3-fluorobenzyl)-1H-benzimidazol-6-yl]pyridin-2-yl}-N-methyl-N-phenylpropane-1,3-diamine;

5-chloro-4-[1-(3-fluorobenzyl)-1H-benzimidazol-6-yl]-N-(1-methylpiperidin-4-yl)pyridin-2-amine;

5-chloro-4-[1-(3-fluorobenzyl)-1H-benzimidazol-6-yl]-N-[2-(pyridin-4-yl)ethyl]pyridin-2-amine;

5-chloro-4-[1-(3-fluorobenzyl)-1H-benzimidazol-6-yl]-N-(pyrimidin-5-ylmethyl)pyridin-2-amine;

$N^2$-{5-chloro-4-[1-(3-fluorobenzyl)-1H-benzimidazol-6-yl]pyridin-2-yl}-2-methylpropane-1,2-diamine;

5-chloro-N-(2-cyclohexylethyl)-4-[1-(3-fluorobenzyl)-1H-benzimidazol-6-yl]pyridin-2-amine;

N-{5-chloro-4-[1-(3-fluorobenzyl)-1H-benzimidazol-6-yl]pyridin-2-yl}-N-phenylethane-1,2-diamine;

N'-{5-chloro-4-[1-(3-fluorobenzyl)-1H-benzimidazol-6-yl]pyridin-2-yl}-N,N,2,2-tetramethylpropane-1,3-diamine;

2-({5-chloro-4-[1-(3-fluorobenzyl)-1H-benzimidazol-6-yl]pyridin-2-yl}amino)ethanol;

N-benzyl-5-chloro-4-[1-(3-fluorobenzyl)-1H-benzimidazol-6-yl]pyridin-2-amine;

N'-{5-chloro-4-[1-(3-fluorobenzyl)-1H-benzimidazol-6-yl]pyridin-2-yl}-N,N-dimethylpropane-1,3-diamine;

3-({5-chloro-4-[1-(3-fluorobenzyl)-1H-benzimidazol-6-yl]pyridin-2-yl}amino)propan-1-ol;

N-{5-chloro-4-[1-(3-fluorobenzyl)-1H-benzimidazol-6-yl]pyridin-2-yl}propane-1,3-diamine;

4-[({5-chloro-4-[1-(3-fluorobenzyl)-1H-benzimidazol-6-yl]pyridin-2-yl}amino)methyl]phenol;

N-{5-chloro-4-[1-(3-fluorobenzyl)-1H-benzimidazol-6-yl]pyridin-2-yl}butane-1,4-diamine;

N-[2-(4-aminophenyl)ethyl]-5-chloro-4-[1-(3-fluorobenzyl)-1H-benzimidazol-6-yl]pyridin-2-amine;

N-{5-chloro-4-[1-(3-fluorobenzyl)-1H-benzimidazol-6-yl]pyridin-2-yl}-2,2-dimethylpropane-1,3-diamine;

N-{5-chloro-4-[1-(3-fluorobenzyl)-1H-benzimidazol-6-yl]pyridin-2-yl}ethane-1,2-diamine;

N-[4-(aminomethyl)benzyl]-5-chloro-4-[1-(3-fluorobenzyl)-1H-benzimidazol-6-yl]pyridin-2-amine;

1-({5-chloro-4-[1-(3-fluorobenzyl)-1H-benzimidazol-6-yl]pyridin-2-yl}amino)-2-methylpropan-2-ol;

1-amino-3-({5-chloro-4-[1-(3-fluorobenzyl)-1H-benzimidazol-6-yl]pyridin-2-yl}amino)propan-2-ol;

N-{5-chloro-4-[1-(3-fluorobenzyl)-1H-benzimidazol-6-yl]pyridin-2-yl}-N'-(pyridin-2-yl)ethane-1,2-diamine;

(3R)—N-{5-chloro-4-[1-(3-fluorobenzyl)-1H-benzimidazol-6-yl]pyridin-2-yl}-1-azabicyclo[2.2.2]octan-3-amine;

(3S)—N-{5-chloro-4-[1-(3-fluorobenzyl)-1H-benzimidazol-6-yl]pyridin-2-yl}-1-azabicyclo[2.2.2]octan-3-amine;

2-benzyl-N-{5-chloro-4-[1-(3-fluorobenzyl)-1H-benzimidazol-6-yl]pyridin-2-yl}octahydro-1H-isoindol-4-amine;

2-benzyl-N-{5-chloro-4-[1-(3-fluorobenzyl)-1H-benzimidazol-6-yl]pyridin-2-yl}octahydrocyclopenta[c]pyrrol-4-amine;

N-{5-chloro-4-[1-(3-fluorobenzyl)-1H-benzimidazol-6-yl]pyridin-2-yl}-9-(cyclopropylmethyl)-9-azabicyclo[3.3.1]nonan-3-amine;

benzyl 4-({5-chloro-4-[1-(3-fluorobenzyl)-1H-benzimidazol-6-yl]pyridin-2-yl}amino)-4-(4-fluorophenyl)piperidine-1-carboxylate;

tert-butyl {5-chloro-4-[1-(3-fluorobenzyl)-1H-benzimidazol-6-yl]pyridin-2-yl}carbamate;

(3R)—N-(5-chloro-4-{1-[(5-methyl-1,3,4-thiadiazol-2-yl)methyl]-1H-benzimidazol-6-yl}pyridin-2-yl)piperidine-3-carboxamide;

(3R)—N-(5-chloro-4-{1-[2-(pyridin-3-yl)ethyl]-1H-benzimidazol-6-yl}pyridin-2-yl)piperidine-3-carboxamide;

N-{5-chloro-4-[1-(3-fluorobenzyl)-1H-benzimidazol-6-yl]pyridin-2-yl}-N'-methylpropane-1,3-diamine;

N-[(trans-4-aminocyclohexyl)methyl]-5-chloro-4-[1-(3-fluorobenzyl)-1H-benzimidazol-6-yl]pyridin-2-amine;

N-{5-chloro-4-[1-(3-fluorobenzyl)-1H-benzimidazol-6-yl]pyridin-2-yl}-N'-methylbutane-1,4-diamine;

N-benzyl-N'-{5-chloro-4-[1-(3-fluorobenzyl)-1H-benzimidazol-6-yl]pyridin-2-yl}ethane-1,2-diamine;

5-chloro-4-[1-(3-fluorobenzyl)-1H-benzimidazol-6-yl]-N-[2-(piperidin-4-yl)ethyl]pyridin-2-amine;

5-chloro-4-[1-(3-fluorobenzyl)-1H-benzimidazol-6-yl]-N-[2-(piperidin-3-yl)ethyl]pyridin-2-amine;

$N^2$-{5-chloro-4-[1-(3-fluorobenzyl)-1H-benzimidazol-6-yl]pyridin-2-yl}-1-phenylethane-1,2-diamine;

5-chloro-4-[1-(3-fluorobenzyl)-1H-benzimidazol-6-yl]-N-(piperidin-3-yl)pyridin-2-amine;

N-[(2R)-azetidin-2-ylmethyl]-5-chloro-4-[1-(3-fluorobenzyl)-1H-benzimidazol-6-yl]pyridin-2-amine;

N-[2-(azetidin-2-yl)ethyl]-5-chloro-4-[1-(3-fluorobenzyl)-1H-benzimidazol-6-yl]pyridin-2-amine;

(4aS,8R,8aS)—N-{5-chloro-4-[1-(3-fluorobenzyl)-1H-benzimidazol-6-yl]pyridin-2-yl}decahydroisoquinolin-8-amine;

5-chloro-4-[1-(3-fluorobenzyl)-1H-benzimidazol-6-yl]-N-[2-(pyrrolidin-2-yl)ethyl]pyridin-2-amine;

N-{5-chloro-4-[1-(3-fluorobenzyl)-1H-benzimidazol-6-yl]pyridin-2-yl}-6-azaspiro[3.5]nonan-2-amine;

N-{5-chloro-4-[1-(3-fluorobenzyl)-1H-benzimidazol-6-yl]pyridin-2-yl}-7-azaspiro[3.5]nonan-2-amine;
N-{5-chloro-4-[1-(3-fluorobenzyl)-1H-benzimidazol-6-yl]pyridin-2-yl}-7-azaspiro[3.5]nonan-1-amine;
5-chloro-4-[1-(3-fluorobenzyl)-1H-benzimidazol-6-yl]-N-{[(2R,4S)-4-fluoropyrrolidin-2-yl]methyl}pyridin-2-amine;
5-chloro-4-[1-(3-fluorobenzyl)-1H-benzimidazol-6-yl]-N-[(4-fluoropyrrolidin-3-yl)methyl]pyridin-2-amine;
N-{5-chloro-4-[1-(3-fluorobenzyl)-1H-benzimidazol-6-yl]pyridin-2-yl}-6-azaspiro[3.4]octan-2-amine;
(3R)—N-{5-chloro-4-[1-(3-fluorobenzyl)-1H-benzotriazol-6-yl]pyridin-2-yl}piperidine-3-carboxamide;
(3R)—N-(5-chloro-4-{1-[2-(methylsulfonyl)ethyl]-1H-benzimidazol-6-yl}pyridin-2-yl)piperidine-3-carboxamide;
(3R)—N-(5-chloro-4-{1-[2-(methylsulfonyl)ethyl]-1H-benzotriazol-6-yl}pyridin-2-yl)piperidine-3-carboxamide;
(3R)—N-{5-chloro-4-[1-(4-fluorobenzyl)-1H-benzotriazol-6-yl]pyridin-2-yl}piperidine-3-carboxamide;
(3R)—N-{5-chloro-4-[1-(3,4-difluorobenzyl)-1H-benzotriazol-6-yl]pyridin-2-yl}piperidine-3-carboxamide;
(3R)—N-(5-chloro-4-{1-[2-(3-fluorophenyl)ethyl]-1H-benzotriazol-6-yl}pyridin-2-yl)piperidine-3-carboxamide;
(3R)—N-{5-chloro-4-[1-(2-sulfamoylethyl)-1H-benzotriazol-6-yl]pyridin-2-yl}piperidine-3-carboxamide;
5-chloro-4-[1-(3-fluorobenzyl)-1H-benzimidazol-6-yl]-N-{2-[4-(4-methylphenyl)piperidin-4-yl]ethyl}pyridin-2-amine;
5-chloro-4-[1-(3-fluorobenzyl)-1H-benzimidazol-6-yl]-N-{2-[4-(4-methoxyphenyl)piperidin-4-yl]ethyl}pyridin-2-amine;
5-chloro-4-[1-(3-fluorobenzyl)-1H-benzimidazol-6-yl]-N-[(4-fluoropiperidin-4-yl)methyl]pyridin-2-amine;
5-chloro-4-[1-(3-fluorobenzyl)-1H-benzimidazol-6-yl]-N-{2-[3-(4-methoxyphenyl)pyrrolidin-3-yl]ethyl}pyridin-2-amine;
N-{5-chloro-4-[1-(3-fluorobenzyl)-1H-benzimidazol-6-yl]pyridin-2-yl}-6-azaspiro[3.4]octan-1-amine;
(1S,4R)—N-{5-chloro-4-[1-(3-fluorobenzyl)-1H-benzimidazol-6-yl]pyridin-2-yl}-6-azaspiro[3.5]nonan-1-amine;
N-{5-chloro-4-[1-(3-fluorobenzyl)-1H-benzimidazol-6-yl]pyridin-2-yl}-5-thia-2-azaspiro[3.4]octan-8-amine 5,5-dioxide;
N-{5-chloro-4-[1-(3-fluorobenzyl)-1H-benzimidazol-6-yl]pyridin-2-yl}-9-azabicyclo[3.3.1]nonan-3-amine;
(3S)—N-{5-chloro-4-[1-(3-fluorobenzyl)-1H-benzimidazol-6-yl]pyridin-2-yl}azepan-3-amine;
(3R)—N-{5-chloro-4-[1-(3-fluorobenzyl)-1H-benzimidazol-6-yl]pyridin-2-yl}azepan-3-amine;
(1R,4R)—N-{5-chloro-4-[1-(3-fluorobenzyl)-1H-benzimidazol-6-yl]pyridin-2-yl}-6-azaspiro[3.5]nonan-1-amine;
N-{[3-(aminomethyl)cyclohexyl]methyl}-5-chloro-4-[1-(3-fluorobenzyl)-1H-benzimidazol-6-yl]pyridin-2-amine;
N-{5-chloro-4-[1-(3-fluorobenzyl)-1H-benzimidazol-6-yl]pyridin-2-yl}-2-(piperidin-4-yl)acetamide;
4-({5-chloro-4-[1-(3-fluorobenzyl)-1H-benzimidazol-6-yl]pyridin-2-yl}amino)benzenesulfonamide;
(3R)—N-(5-chloro-4-{1-[(5-fluoropyridin-3-yl)methyl]-1H-benzimidazol-6-yl}pyridin-2-yl)piperidine-3-carboxamide;
(3R)—N-(5-chloro-4-{1-[(4-cyanotetrahydro-2H-pyran-4-yl)methyl]-1H-benzimidazol-6-yl}pyridin-2-yl)piperidine-3-carboxamide;
(3R)—N-{5-chloro-4-[1-(3-fluorobenzyl)-1H-pyrrolo[3,2-c]pyridin-6-yl]pyridin-2-yl}piperidine-3-carboxamide;
(3R)—N-{5-chloro-4-[1-(3-fluorobenzyl)-1H-pyrrolo[2,3-b]pyridin-6-yl]pyridin-2-yl}piperidine-3-carboxamide;
(3R)—N-{5-chloro-4-[5-fluoro-1-(3-fluorobenzyl)-1H-benzimidazol-6-yl]pyridin-2-yl}piperidine-3-carboxamide;
(3R)—N-{5-chloro-4-[1-(3-fluorobenzyl)-1H-indazol-6-yl]pyridin-2-yl}piperidine-3-carboxamide;
(3R)—N-[4-(1-{2-[bis(2-hydroxyethyl)amino]ethyl}-1H-benzotriazol-6-yl)-5-chloropyridin-2-yl]piperidine-3-carboxamide;
(3R)—N-[5-chloro-4-(2-oxo-2,3-dihydro-1H-indol-6-yl)pyridin-2-yl]piperidine-3-carboxamide;
(3R)—N-(5-chloro-4-{1-[3-(dimethylamino)propyl]-1H-benzimidazol-6-yl}pyridin-2-yl)piperidine-3-carboxamide;
(3R)—N-(5-chloro-4-{1-[3-(dimethylamino)propyl]-1H-benzotriazol-6-yl}pyridin-2-yl)piperidine-3-carboxamide;
(3R)—N-(5-chloro-4-{1-[2-(morpholin-4-yl)ethyl]-1H-benzotriazol-6-yl}pyridin-2-yl)piperidine-3-carboxamide;
(3R)—N-{5-chloro-4-[1-(3-fluorobenzyl)-2-methyl-1H-benzimidazol-6-yl]pyridin-2-yl}piperidine-3-carboxamide;
(3R)—N-{5-chloro-4-[3-(tetrahydro-2H-pyran-4-ylmethyl)-3H-imidazo[4,5-b]pyridin-5-yl]pyridin-2-yl}piperidine-3-carboxamide;
(3R)—N-(5-chloro-4-{1-[(1R)-1-(3-fluorophenyl)ethyl]-1H-benzimidazol-6-yl}pyridin-2-yl)piperidine-3-carboxamide;
(3R)—N-(5-chloro-4-{1-[(1R)-1-(3-fluorophenyl)ethyl]-1H-benzotriazol-6-yl}pyridin-2-yl)piperidine-3-carboxamide;
(3R)—N-{5-chloro-4-[3-(3-fluorobenzyl)-2-oxo-2,3-dihydro-1H-benzimidazol-5-yl]pyridin-2-yl}piperidine-3-carboxamide;
(3R)—N-{5-chloro-4-[5-chloro-1-(tetrahydro-2H-pyran-4-ylmethyl)-1H-benzimidazol-6-yl]pyridin-2-yl}piperidine-3-carboxamide;
N-(5-chloro-4-{1-[(5-methylpyrazin-2-yl)methyl]-2,3-dihydro-1H-indol-6-yl}pyridin-2-yl)piperidine-3-carboxamide;
N-[5-chloro-4-(1-{4-[(methylsulfonyl)amino]benzyl}-2,3-dihydro-1H-indol-6-yl)pyridin-2-yl]piperidine-3-carboxamide;
N-(5-chloro-4-{1-[4-fluoro-3-(methylsulfonyl)benzyl]-2,3-dihydro-1H-indol-6-yl}pyridin-2-yl)piperidine-3-carboxamide;
N-(5-chloro-4-{1-[(2-methylpyrimidin-5-yl)methyl]-2,3-dihydro-1H-indol-6-yl}pyridin-2-yl)piperidine-3-carboxamide;
N-(5-chloro-4-{1-[3-(methylsulfonyl)benzyl]-2,3-dihydro-1H-indol-6-yl}pyridin-2-yl)piperidine-3-carboxamide;
N-(5-chloro-4-{1-[(6-methylpyridin-3-yl)methyl]-2,3-dihydro-1H-indol-6-yl}pyridin-2-yl)piperidine-3-carboxamide;
N-{5-chloro-4-[1-(pyrrolidin-3-ylmethyl)-2,3-dihydro-1H-indol-6-yl]pyridin-2-yl}piperidine-3-carboxamide;

4-[(6-{5-chloro-2-[(piperidin-3-ylcarbonyl)amino]pyridin-4-yl}-2,3-dihydro-1H-indol-1-yl)methyl]benzoic acid;

N-(5-chloro-4-{1-[4-(methylsulfonyl)benzyl]-2,3-dihydro-1H-indol-6-yl}pyridin-2-yl)piperidine-3-carboxamide;

methyl 4-[(6-{5-chloro-2-[(piperidin-3-ylcarbonyl)amino]pyridin-4-yl}-2,3-dihydro-1H-indol-1-yl)methyl]benzoate;

N-{5-chloro-4-[1-(pyrimidin-5-ylmethyl)-2,3-dihydro-1H-indol-6-yl]pyridin-2-yl}piperidine-3-carboxamide;

N-[5-chloro-4-(1-{[6-(trifluoromethyl)pyridin-2-yl]methyl}-2,3-dihydro-1H-indol-6-yl)pyridin-2-yl]piperidine-3-carboxamide;

N-{5-chloro-4-[1-(quinolin-6-ylmethyl)-2,3-dihydro-1H-indol-6-yl]pyridin-2-yl}piperidine-3-carboxamide;

N-{4-[1-(1H-benzimidazol-2-ylmethyl)-2,3-dihydro-1H-indol-6-yl]-5-chloropyridin-2-yl}piperidine-3-carboxamide;

N-{5-chloro-4-[1-(2,3-dihydro-1,4-benzodioxin-5-ylmethyl)-2,3-dihydro-1H-indol-6-yl]pyridin-2-yl}piperidine-3-carboxamide;

N-(5-chloro-4-{1-[(1-methyl-1H-benzimidazol-2-yl)methyl]-2,3-dihydro-1H-indol-6-yl}pyridin-2-yl)piperidine-3-carboxamide;

N-(5-chloro-4-{1-[(1-methyl-1H-benzotriazol-5-yl)methyl]-2,3-dihydro-1H-indol-6-yl}pyridin-2-yl)piperidine-3-carboxamide;

N-{4-[1-(1,3-benzodioxol-4-ylmethyl)-2,3-dihydro-1H-indol-6-yl]-5-chloropyridin-2-yl}piperidine-3-carboxamide;

N-{5-chloro-4-[1-(4-methylbenzyl)-2,3-dihydro-1H-indol-6-yl]pyridin-2-yl}piperidine-3-carboxamide;

N-{5-chloro-4-[1-(quinoxalin-6-ylmethyl)-2,3-dihydro-1H-indol-6-yl]pyridin-2-yl}piperidine-3-carboxamide;

N-{5-chloro-4-[1-(pyrazin-2-ylmethyl)-2,3-dihydro-1H-indol-6-yl]pyridin-2-yl}piperidine-3-carboxamide;

N-{5-chloro-4-[1-(2,3-dihydro[1,4]dioxino[2,3-b]pyridin-7-ylmethyl)-2,3-dihydro-1H-indol-6-yl]pyridin-2-yl}piperidine-3-carboxamide;

N-[5-chloro-4-(1-{[6-(methylsulfonyl)pyridin-3-yl]methyl}-2,3-dihydro-1H-indol-6-yl)pyridin-2-yl]piperidine-3-carboxamide;

N-{5-chloro-4-[1-(4-sulfamoylbenzyl)-2,3-dihydro-1H-indol-6-yl]pyridin-2-yl}piperidine-3-carboxamide;

N-(5-chloro-4-{1-[3-fluoro-4-(methylsulfonyl)benzyl]-2,3-dihydro-1H-indol-6-yl}pyridin-2-yl)piperidine-3-carboxamide;

N-(5-chloro-4-{1-[4-(2H-tetrazol-5-yl)benzyl]-2,3-dihydro-1H-indol-6-yl}pyridin-2-yl)piperidine-3-carboxamide;

N-{5-chloro-4-[1-(pyrrolidin-2-ylmethyl)-2,3-dihydro-1H-indol-6-yl]pyridin-2-yl}piperidine-3-carboxamide;

N-(5-chloro-4-{1-[(1-methylpiperidin-4-yl)methyl]-2,3-dihydro-1H-indol-6-yl}pyridin-2-yl)piperidine-3-carboxamide;

N-{5-chloro-4-[1-(3-fluorobenzyl)-1H-imidazo[4,5-b]pyridin-6-yl]pyridin-2-yl}piperidine-3-carboxamide;

(3R)—N-[5-chloro-4-(1-{[3-(morpholin-4-yl)oxetan-3-yl]methyl}-1H-benzimidazol-6-yl)pyridin-2-yl]piperidine-3-carboxamide;

(3R)—N-[5-chloro-4-(1-{[3-(pyrrolidin-1-yl)oxetan-3-yl]methyl}-1H-benzimidazol-6-yl)pyridin-2-yl]piperidine-3-carboxamide;

N-{5-chloro-4-[1-(tetrahydro-2H-pyran-4-ylmethyl)-1H-benzimidazol-6-yl]pyridin-2-yl}-7-azaspiro[3.5]nonan-2-amine;

N-{5-chloro-4-[1-(tetrahydro-2H-pyran-4-ylmethyl)-1H-benzimidazol-6-yl]pyridin-2-yl}-7-(methylsulfonyl)-7-azaspiro[3.5]nonan-2-amine;

(2E)-N-{5-chloro-4-[1-(3-fluorobenzyl)-1H-benzimidazol-6-yl]pyridin-2-yl}-3-(pyridin-4-yl)prop-2-enamide;

(1R,2S)—N-{5-chloro-4-[1-(3-fluorobenzyl)-1H-benzimidazol-6-yl]pyridin-2-yl}-N'-cyclopentylcyclobutane-1,2-dicarboxamide;

N-{5-chloro-4-[1-(3-fluorobenzyl)-1H-benzimidazol-6-yl]pyridin-2-yl}-2-(2-oxopyridin-1(2H)-yl)propanamide;

N-{5-chloro-4-[1-(3-fluorobenzyl)-1H-benzimidazol-6-yl]pyridin-2-yl}-2-(methylsulfonyl)acetamide;

N-{5-chloro-4-[1-(3-fluorobenzyl)-1H-benzimidazol-6-yl]pyridin-2-yl}-1-(3-chlorophenyl)-5-oxopyrrolidine-3-carboxamide;

1-benzyl-N-{5-chloro-4-[1-(3-fluorobenzyl)-1H-benzimidazol-6-yl]pyridin-2-yl}-5-oxopyrrolidine-3-carboxamide;

N-{5-chloro-4-[1-(3-fluorobenzyl)-1H-benzimidazol-6-yl]pyridin-2-yl}-2,3-dihydro[1,4]dioxino[2,3-b]pyridine-7-carboxamide;

(3R)—N-{5-chloro-4-[1-(3-fluorobenzyl)-1H-benzimidazol-6-yl]pyridin-2-yl}-3-(pyridin-3-yl)-1H-pyrrolo[1,2-c][1,3]thiazole-7-carboxamide;

N-{5-chloro-4-[1-(3-fluorobenzyl)-1H-benzimidazol-6-yl]pyridin-2-yl}-3-oxocyclobutanecarboxamide;

N-{5-chloro-4-[1-(3-fluorobenzyl)-1H-benzimidazol-6-yl]pyridin-2-yl}-6-oxospiro[3.3]heptane-2-carboxamide;

benzyl (1R,5S,6r)-6-({5-chloro-4-[1-(3-fluorobenzyl)-1H-benzimidazol-6-yl]pyridin-2-yl}carbamoyl)-3-azabicyclo[3.1.0]hexane-3-carboxylate;

N-{5-chloro-4-[1-(3-fluorobenzyl)-1H-benzimidazol-6-yl]pyridin-2-yl}-1-methylazetidine-3-carboxamide;

N-{5-chloro-4-[1-(3-fluorobenzyl)-1H-benzimidazol-6-yl]pyridin-2-yl}-3-methyloxetane-3-carboxamide;

N-{5-chloro-4-[1-(3-fluorobenzyl)-1H-benzimidazol-6-yl]pyridin-2-yl}-4-hydroxy-4-(trifluoromethyl)cyclohexanecarboxamide;

N-{5-chloro-4-[1-(3-fluorobenzyl)-1H-benzimidazol-6-yl]pyridin-2-yl}-1-(2,2-dimethylpropanoyl)-2,3-dihydro-1H-pyrido[2,3-b][1,4]oxazine-6-carboxamide;

N-{5-chloro-4-[1-(3-fluorobenzyl)-1H-benzimidazol-6-yl]pyridin-2-yl}-2-(methylsulfonyl)-5-thia-2-azaspiro[3.4]octane-8-carboxamide 5,5-dioxide;

$N^8$-{5-chloro-4-[1-(3-fluorobenzyl)-1H-benzimidazol-6-yl]pyridin-2-yl}-$N^2$-ethyl-5-thia-2-azaspiro[3.4]octane-2,8-dicarboxamide 5,5-dioxide;

$N^8$-{-chloro-4-[1-(3-fluorobenzyl)-1H-benzimidazol-6-yl]pyridin-2-yl}-$N^2$-phenyl-5-thia-2-azaspiro[3.4]octane-2,8-dicarboxamide 5,5-dioxide;

N-{5-chloro-4-[1-(3-fluorobenzyl)-1H-benzimidazol-6-yl]pyridin-2-yl}-7-(cyclohexylcarbonyl)-1-thia-7-azaspiro[4.4]nonane-4-carboxamide 1,1-dioxide;

N-{5-chloro-4-[1-(3-fluorobenzyl)-1H-benzimidazol-6-yl]pyridin-2-yl}-7-(2-methylpropanoyl)-1-thia-7-azaspiro[4.4]nonane-4-carboxamide 1,1-dioxide;

N-{5-chloro-4-[1-(3-fluorobenzyl)-1H-benzimidazol-6-yl]pyridin-2-yl}-7-(phenylsulfonyl)-1-thia-7-azaspiro[4.4]nonane-4-carboxamide 1,1-dioxide;

7-benzoyl-N-{-chloro-4-[1-(3-fluorobenzyl)-1H-benzimidazol-6-yl]pyridin-2-yl}-1-thia-7-azaspiro[4.4]nonane-4-carboxamide 1,1-dioxide;

N-{5-chloro-4-[1-(3-fluorobenzyl)-1H-benzimidazol-6-yl]pyridin-2-yl}-7-ethyl-1-thia-7-azaspiro[4.4]nonane-4-carboxamide 1,1-dioxide;

N-{5-chloro-4-[1-(3-fluorobenzyl)-1H-benzimidazol-6-yl]pyridin-2-yl}-2-oxohexahydro-2H-cyclopenta[d][1,3]oxazole-5-carboxamide;

N-{5-chloro-4-[1-(3-fluorobenzyl)-1H-benzimidazol-6-yl]pyridin-2-yl}-7-(methylsulfonyl)-1-thia-7-azaspiro[4.4]nonane-4-carboxamide 1,1-dioxide;

(2E)-N-carbamoyl-N'-{5-chloro-4-[1-(3-fluorobenzyl)-1H-benzimidazol-6-yl]pyridin-2-yl}but-2-enediamide;

N-{5-chloro-4-[1-(3-fluorobenzyl)-1H-benzimidazol-6-yl]pyridin-2-yl}cyclopropane-1,1-dicarboxamide;

N-{5-chloro-4-[1-(3-fluorobenzyl)-1H-benzimidazol-6-yl]pyridin-2-yl}-1H-pyrazole-4-carboxamide;

trans-N-{5-chloro-4-[1-(tetrahydro-2H-pyran-4-ylmethyl)-1H-benzimidazol-6-yl]pyridin-2-yl}cyclohexane-1,4-diamine;

N-{5-chloro-4-[1-(tetrahydro-2H-pyran-4-ylmethyl)-1H-benzimidazol-6-yl]pyridin-2-yl}piperidine-4-carboxamide;

N-{5-chloro-4-[1-(tetrahydro-2H-pyran-4-ylmethyl)-1H-benzimidazol-6-yl]pyridin-2-yl}-2-oxohexahydro-2H-cyclopenta[d][1,3]oxazole-5-carboxamide;

(2s,4r)-N-{5-chloro-4-[1-(3-fluorobenzyl)-1H-benzimidazol-6-yl]pyridin-2-yl}-6-azaspiro[3.4]octan-2-amine;

(2r,4s)-N-{5-chloro-4-[1-(3-fluorobenzyl)-1H-benzimidazol-6-yl]pyridin-2-yl}-6-azaspiro[3.4]octan-2-amine;

(2s,4r)-N-{5-chloro-4-[1-(3-fluorobenzyl)-1H-benzimidazol-6-yl]pyridin-2-yl}-6-azaspiro[3.5]nonan-2-amine;

(2r,4s)-N-{5-chloro-4-[1-(3-fluorobenzyl)-1H-benzimidazol-6-yl]pyridin-2-yl}-6-azaspiro[3.5]nonan-2-amine;

(3S)—N-{5-chloro-4-[1-(tetrahydro-2H-pyran-4-ylmethyl)-1H-benzimidazol-6-yl]pyridin-2-yl}piperidine-3-carboxamide;

(3R)—N-{5-chloro-4-[1-(3-fluorobenzyl)-1H-imidazo[4,5-b]pyrazin-6-yl]pyridin-2-yl}piperidine-3-carboxamide;

N-(5-chloro-4-{1-[2-(dimethylamino)-2-oxoethyl]-2,3-dihydro-1H-indol-6-yl}pyridin-2-yl)piperidine-3-carboxamide;

N-(5-chloro-4-{1-[2-(morpholin-4-yl)-2-oxoethyl]-2,3-dihydro-1H-indol-6-yl}pyridin-2-yl)piperidine-3-carboxamide;

N-(5-chloro-4-{1-[2-oxo-2-(pyrrolidin-1-yl)ethyl]-2,3-dihydro-1H-indol-6-yl}pyridin-2-yl)piperidine-3-carboxamide;

(3R)—N-{5-chloro-4-[3-cyano-1-(tetrahydro-2H-pyran-4-ylmethyl)-1H-pyrrolo[3,2-b]pyridin-6-yl]pyridin-2-yl}piperidine-3-carboxamide;

4-[(6-{5-chloro-2-[(2-hydroxyethyl)amino]pyridin-4-yl}-1H-benzimidazol-1-yl)methyl]tetrahydro-2H-pyran-4-carbonitrile;

2-[(5-chloro-4-{1-[(5-fluoropyridin-3-yl)methyl]-1H-benzimidazol-6-yl}pyridin-2-yl)amino]ethanol;

trans-N-{5-chloro-4-[1-(3-fluorobenzyl)-1H-benzimidazol-6-yl]pyridin-2-yl}-N'-(pyridin-2-ylmethyl)cyclohexane-1,4-diamine;

trans-N-{5-chloro-4-[1-(3-fluorobenzyl)-1H-benzimidazol-6-yl]pyridin-2-yl}-N'-(pyridin-3-ylmethyl)cyclohexane-1,4-diamine;

trans-N-{5-chloro-4-[1-(3-fluorobenzyl)-1H-benzimidazol-6-yl]pyridin-2-yl}-N'-(pyridin-4-ylmethyl)cyclohexane-1,4-diamine;

trans-N-(1,3-benzodioxol-5-ylmethyl)-N'-{5-chloro-4-[1-(3-fluorobenzyl)-1H-benzimidazol-6-yl]pyridin-2-yl}cyclohexane-1,4-diamine;

trans-N-{5-chloro-4-[1-(3-fluorobenzyl)-1H-benzimidazol-6-yl]pyridin-2-yl}-N'-(1,3-thiazol-2-ylmethyl)cyclohexane-1,4-diamine;

trans-N-{5-chloro-4-[1-(3-fluorobenzyl)-1H-benzimidazol-6-yl]pyridin-2-yl}-N'-{[1-(methoxymethyl)-2,3-dihydro-1H-1,2,3-triazol-4-yl]methyl}cyclohexane-1,4-diamine;

trans-N-{5-chloro-4-[1-(3-fluorobenzyl)-1H-benzimidazol-6-yl]pyridin-2-yl}-N'-[2-(morpholin-4-yl)ethyl]cyclohexane-1,4-diamine;

trans-N-{5-chloro-4-[1-(3-fluorobenzyl)-1H-benzimidazol-6-yl]pyridin-2-yl}-N'-[2-methyl-2-(morpholin-4-yl)propyl]cyclohexane-1,4-diamine;

trans-N-{5-chloro-4-[1-(3-fluorobenzyl)-1H-benzimidazol-6-yl]pyridin-2-yl}-N'-(tetrahydrofuran-2-ylmethyl)cyclohexane-1,4-diamine;

trans-N-{5-chloro-4-[1-(3-fluorobenzyl)-1H-benzimidazol-6-yl]pyridin-2-yl}-N'-[(2,5-dimethoxytetrahydrofuran-3-yl)methyl]cyclohexane-1,4-diamine;

trans-N-{5-chloro-4-[1-(3-fluorobenzyl)-1H-benzimidazol-6-yl]pyridin-2-yl}-N'-(cyclopropylmethyl)cyclohexane-1,4-diamine;

3-{[trans-4-({5-chloro-4-[1-(3-fluorobenzyl)-1H-benzimidazol-6-yl]pyridin-2-yl}amino)cyclohexyl]amino}propane-1,2-diol;

trans-N-{5-chloro-4-[1-(3-fluorobenzyl)-1H-benzimidazol-6-yl]pyridin-2-yl}-N'-(1-methoxypropan-2-yl)cyclohexane-1,4-diamine;

trans-N-{5-chloro-4-[1-(3-fluorobenzyl)-1H-benzimidazol-6-yl]pyridin-2-yl}-N'-(1,3-dimethoxypropan-2-yl)cyclohexane-1,4-diamine;

trans-N-{5-chloro-4-[1-(3-fluorobenzyl)-1H-benzimidazol-6-yl]pyridin-2-yl}-N'-(2-phenoxyethyl)cyclohexane-1,4-diamine;

trans-N-[3-(benzyloxy)propyl]-N'-{5-chloro-4-[1-(3-fluorobenzyl)-1H-benzimidazol-6-yl]pyridin-2-yl}cyclohexane-1,4-diamine;

trans-N-{5-chloro-4-[1-(3-fluorobenzyl)-1H-benzimidazol-6-yl]pyridin-2-yl}-N'-[2,2-dimethyl-3-(phenylsulfinyl)propyl]cyclohexane-1,4-diamine;

trans-N-{5-chloro-4-[1-(3-fluorobenzyl)-1H-benzimidazol-6-yl]pyridin-2-yl}-N-(2-methoxypropyl)cyclohexane-1,4-diamine;

trans-N-{5-chloro-4-[1-(3-fluorobenzyl)-1H-benzimidazol-6-yl]pyridin-2-yl}-N'-[2-(cyclohexyloxy)propyl]cyclohexane-1,4-diamine;

trans-N-{5-chloro-4-[1-(3-fluorobenzyl)-1H-benzimidazol-6-yl]pyridin-2-yl}-N-[(5,5-dimethyltetrahydrofuran-2-yl)methyl]cyclohexane-1,4-diamine;

trans-N-{5-chloro-4-[1-(3-fluorobenzyl)-1H-benzimidazol-6-yl]pyridin-2-yl}-N-(3-methoxypropyl)cyclohexane-1,4-diamine;

2-{[trans-4-({5-chloro-4-[1-(3-fluorobenzyl)-1H-benzimidazol-6-yl]pyridin-2-yl}amino)cyclohexyl]amino}propan-1-ol;

(3R)—N-{5-chloro-4-[1-(3-fluorobenzyl)-1H-[1,2,3]triazolo[4,5-b]pyrazin-6-yl]pyridin-2-yl}piperidine-3-carboxamide;

(3R)—N-{5-chloro-4-[1-(tetrahydro-2H-pyran-4-ylmethyl)-1H-benzotriazol-6-yl]pyridin-2-yl}piperidine-3-carboxamide;

N-{5-chloro-4-[1-(3-fluorobenzyl)-1H-pyrrolo[3,2-b]pyridin-6-yl]pyridin-2-yl}-6-azaspiro[3.4]octan-2-amine;

N-{5-chloro-4-[1-(3-fluorobenzyl)-1H-benzimidazol-6-yl]pyridin-2-yl}cyclohexane-1,3-diamine;

(3R)—N-{5-chloro-4-[1-(3-fluorobenzyl)-2-(trifluoromethyl)-1H-benzimidazol-6-yl]pyridin-2-yl}piperidine-3-carboxamide;

(3R)—N-{5-chloro-4-[2-(trifluoromethyl)-1H-benzimidazol-6-yl]pyridin-2-yl}piperidine-3-carboxamide;

(3R)—N-{5-chloro-4-[1-(3-fluorobenzyl)-3-(methoxymethyl)-1H-pyrrolo[3,2-b]pyridin-6-yl]pyridin-2-yl}piperidine-3-carboxamide;

(3R)—N-{5-chloro-4-[3-(methoxymethyl)-1-(tetrahydro-2H-pyran-4-ylmethyl)-1H-pyrrolo[3,2-b]pyridin-6-yl]pyridin-2-yl}piperidine-3-carboxamide;

N-{5-chloro-4-[1-(tetrahydro-2H-pyran-4-ylmethyl)-1H-benzimidazol-6-yl]pyridin-2-yl}pyridine-4-carboxamide;

N-{5-chloro-4-[1-(tetrahydro-2H-pyran-4-ylmethyl)-1H-benzimidazol-6-yl]pyridin-2-yl}pyridine-3-carboxamide;

N-{5-chloro-4-[1-(tetrahydro-2H-pyran-4-ylmethyl)-1H-benzimidazol-6-yl]pyridin-2-yl}-1-methyl-1H-imidazole-4-carboxamide;

N-{5-chloro-4-[1-(tetrahydro-2H-pyran-4-ylmethyl)-1H-benzimidazol-6-yl]pyridin-2-yl}-1H-imidazole-4-carboxamide;

N-{5-chloro-4-[1-(tetrahydro-2H-pyran-4-ylmethyl)-1H-benzimidazol-6-yl]pyridin-2-yl}-1,3-thiazole-4-carboxamide;

N-{5-chloro-4-[1-(tetrahydro-2H-pyran-4-ylmethyl)-1H-benzimidazol-6-yl]pyridin-2-yl}-1H-1,2,4-triazole-3-carboxamide;

N-{5-chloro-4-[1-(tetrahydro-2H-pyran-4-ylmethyl)-1H-benzimidazol-6-yl]pyridin-2-yl}pyrimidine-5-carboxamide;

N-{5-chloro-4-[1-(tetrahydro-2H-pyran-4-ylmethyl)-1H-benzimidazol-6-yl]pyridin-2-yl}pyrazine-2-carboxamide;

N-{5-chloro-4-[1-(tetrahydro-2H-pyran-4-ylmethyl)-1H-benzimidazol-6-yl]pyridin-2-yl}-1H-pyrazole-3-carboxamide;

N-{5-chloro-4-[1-(tetrahydro-2H-pyran-4-ylmethyl)-1H-benzimidazol-6-yl]pyridin-2-yl}-1H-1,2,3-triazole-4-carboxamide;

N-{5-chloro-4-[1-(tetrahydro-2H-pyran-4-ylmethyl)-1H-benzimidazol-6-yl]pyridin-2-yl}azetidine-3-carboxamide;

N-{5-chloro-4-[1-(tetrahydro-2H-pyran-4-ylmethyl)-1H-benzimidazol-6-yl]pyridin-2-yl}-1H-pyrazole-4-carboxamide;

(3aR,6aS)—N-{5-chloro-4-[1-(tetrahydro-2H-pyran-4-ylmethyl)-1H-benzimidazol-6-yl]pyridin-2-yl}octahydrocyclopenta[c]pyrrole-5-carboxamide;

N-{5-chloro-4-[1-(tetrahydro-2H-pyran-4-ylmethyl)-1H-benzimidazol-6-yl]pyridin-2-yl}-2-azaspiro[3.3]heptane-6-carboxamide;

N-{5-chloro-4-[1-(tetrahydro-2H-pyran-4-ylmethyl)-1H-benzimidazol-6-yl]pyridin-2-yl}-3-azabicyclo[3.1.0]hexane-6-carboxamide;

N-{5-chloro-4-[1-(tetrahydro-2H-pyran-4-ylmethyl)-1H-benzimidazol-6-yl]pyridin-2-yl}-3-oxocyclobutanecarboxamide;

(3R)—N-{5-chloro-4-[2-(3-fluorophenyl)-1-methyl-1H-benzimidazol-6-yl]pyridin-2-yl}piperidine-3-carboxamide;

(3R)—N-{5-chloro-4-[2-(3-fluorobenzyl)-1-methyl-1H-benzimidazol-6-yl]pyridin-2-yl}piperidine-3-carboxamide;

N-{5-chloro-4-[1-(tetrahydro-2H-pyran-4-ylmethyl)-1H-benzimidazol-6-yl]pyridin-2-yl}-1,2,5,6-tetrahydropyridine-3-carboxamide;

N-{5-chloro-4-[1-(3-fluorobenzyl)-1H-benzimidazol-6-yl]pyridin-2-yl}-2-(tetrahydro-2H-pyran-4-ylsulfonyl)propanamide;

N-{5-chloro-4-[1-(3-fluorobenzyl)-1H-benzimidazol-6-yl]pyridin-2-yl}-5,6,7,8-tetrahydro[1,2,4]triazolo[4,3-a]pyridine-6-carboxamide;

N-{5-chloro-4-[1-(3-fluorobenzyl)-1H-benzimidazol-6-yl]pyridin-2-yl}-5,6,7,8-tetrahydroimidazo[1,2-a]pyridine-6-carboxamide;

N-{5-chloro-4-[1-(3-fluorobenzyl)-1H-benzimidazol-6-yl]pyridin-2-yl}-3,4-dihydro-2H-pyrano[2,3-b]pyridine-6-carboxamide;

N-{5-chloro-4-[1-(3-fluorobenzyl)-1H-benzimidazol-6-yl]pyridin-2-yl}-2-sulfamoylacetamide;

N-{5-chloro-4-[1-(3-fluorobenzyl)-1H-benzimidazol-6-yl]pyridin-2-yl}-2-[(4-methylpiperazin-1-yl)sulfonyl]acetamide;

N-{5-chloro-4-[1-(3-fluorobenzyl)-1H-benzimidazol-6-yl]pyridin-2-yl}-5-oxo-D-prolinamide;

N-{5-chloro-4-[1-(3-fluorobenzyl)-1H-benzimidazol-6-yl]pyridin-2-yl}-$N^2$-(dimethylsulfamoyl)glycinamide;

N-{5-chloro-4-[1-(tetrahydro-2H-pyran-4-ylmethyl)-1H-benzimidazol-6-yl]pyridin-2-yl}-2-(tetrahydro-2H-pyran-4-ylsulfonyl)propanamide;

N-{5-chloro-4-[1-(tetrahydro-2H-pyran-4-ylmethyl)-1H-benzimidazol-6-yl]pyridin-2-yl}-5,6,7,8-tetrahydro[1,2,4]triazolo[4,3-a]pyridine-6-carboxamide;

N-{5-chloro-4-[1-(tetrahydro-2H-pyran-4-ylmethyl)-1H-benzimidazol-6-yl]pyridin-2-yl}-5,6,7,8-tetrahydroimidazo[1,2-a]pyridine-6-carboxamide;

N-{5-chloro-4-[1-(tetrahydro-2H-pyran-4-ylmethyl)-1H-benzimidazol-6-yl]pyridin-2-yl}-3,4-dihydro-2H-pyrano[2,3-b]pyridine-6-carboxamide;

N-{5-chloro-4-[1-(tetrahydro-2H-pyran-4-ylmethyl)-1H-benzimidazol-6-yl]pyridin-2-yl}-2-sulfamoylacetamide;

N-{5-chloro-4-[1-(tetrahydro-2H-pyran-4-ylmethyl)-1H-benzimidazol-6-yl]pyridin-2-yl}-$N^2$-(ethylsulfonyl)glycinamide;

N-{5-chloro-4-[1-(tetrahydro-2H-pyran-4-ylmethyl)-1H-benzimidazol-6-yl]pyridin-2-yl}-5-oxo-D-prolinamide;

N-{5-chloro-4-[1-(tetrahydro-2H-pyran-4-ylmethyl)-1H-benzimidazol-6-yl]pyridin-2-yl}-$N^2$-(dimethylsulfamoyl)glycinamide;

N-{5-chloro-4-[1-(tetrahydro-2H-pyran-4-ylmethyl)-1H-benzimidazol-6-yl]pyridin-2-yl}-2-[(4-methylpiperazin-1-yl)sulfonyl]acetamide;

(3R)—N-(5-chloro-4-{1-[4-(methylsulfonyl)benzyl]-1H-benzotriazol-6-yl}pyridin-2-yl)piperidine-3-carboxamide;

cis-3-amino-N-{5-chloro-4-[1-(tetrahydro-2H-pyran-4-ylmethyl)-1H-benzimidazol-6-yl]pyridin-2-yl}cyclobutanecarboxamide;

trans-3-amino-N-{5-chloro-4-[1-(tetrahydro-2H-pyran-4-ylmethyl)-1H-benzimidazol-6-yl]pyridin-2-yl}cyclobutanecarboxamide;

(1R,5S,6r)-N-{5-chloro-4-[1-(tetrahydro-2H-pyran-4-ylmethyl)-1H-benzimidazol-6-yl]pyridin-2-yl}-3-azabicyclo[3.1.0]hexane-6-carboxamide;

(2R)—N-{5-chloro-4-[1-(tetrahydro-2H-pyran-4-ylm-ethyl)-1H-benzimidazol-6-yl]pyridin-2-yl}azetidine-2-carboxamide;

6-amino-N-{5-chloro-4-[1-(tetrahydro-2H-pyran-4-ylm-ethyl)-1H-benzimidazol-6-yl]pyridin-2-yl}spiro[3.3]heptane-2-carboxamide;

N-{5-chloro-4-[1-(tetrahydro-2H-pyran-4-ylmethyl)-1H-benzimidazol-6-yl]pyridin-2-yl}-2-(furan-2-yl)-2-(piperazin-1-yl)acetamide;

1-amino-N-{5-chloro-4-[1-(tetrahydro-2H-pyran-4-ylm-ethyl)-1H-benzimidazol-6-yl]pyridin-2-yl}cyclopentanecarboxamide;

N-{5-chloro-4-[1-(tetrahydro-2H-pyran-4-ylmethyl)-1H-benzimidazol-6-yl]pyridin-2-yl}-5-thia-2-azaspiro[3.4]octane-8-carboxamide 5,5-dioxide;

(2S,3R)—N-{5-chloro-4-[1-(tetrahydro-2H-pyran-4-yl-methyl)-1H-benzimidazol-6-yl]pyridin-2-yl}-3-ethyl-azetidine-2-carboxamide;

N-{5-chloro-4-[1-(tetrahydro-2H-pyran-4-ylmethyl)-1H-benzimidazol-6-yl]pyridin-2-yl}-4-(4-fluorophenyl)piperidine-4-carboxamide;

N-{5-chloro-4-[1-(tetrahydro-2H-pyran-4-ylmethyl)-1H-benzimidazol-6-yl]pyridin-2-yl}-1-thia-7-azaspiro[4.4]nonane-4-carboxamide 1,1-dioxide;

(3R)—N-(5-chloro-4-{1-[2-(3-fluorophenyl)-2-oxo-ethyl]-1H-pyrrolo[3,2-b]pyridin-6-yl}pyridin-2-yl)piperidine-3-carboxamide;

N-(5-chloro-4-{1-[(5-fluoropyridin-3-yl)methyl]-1H-pyrrolo[3,2-b]pyridin-6-yl}pyridin-2-yl)-3-oxocyclobutanecarboxamide;

(3R)—N-(5-chloro-4-{1-[(1-methyl-1H-benzotriazol-6-yl)methyl]-1H-pyrrolo[3,2-b]pyridin-6-yl}pyridin-2-yl)piperidine-3-carboxamide;

(3R)—N-(5-chloro-4-{1-[2-oxo-2-(tetrahydro-2H-pyran-4-yl)ethyl]-1H-pyrrolo[3,2-b]pyridin-6-yl}pyridin-2-yl)piperidine-3-carboxamide;

(3R)—N-(5-chloro-4-{1-[2-hydroxy-2-(tetrahydro-2H-pyran-4-yl)ethyl]-1H-pyrrolo[3,2-b]pyridin-6-yl}pyridin-2-yl)piperidine-3-carboxamide;

(3R)—N-(5-chloro-4-{1-[(trans-4-hydroxy-4-methylcyclohexyl)methyl]-1H-benzotriazol-6-yl}pyridin-2-yl)piperidine-3-carboxamide;

(3R)—N-(5-chloro-4-{5-fluoro-1-[(1R)-1-(3-fluorophenyl)ethyl]-1H-benzotriazol-6-yl}pyridin-2-yl)piperidine-3-carboxamide;

methyl 4-{[6-(5-chloro-2-{[(3R)-piperidin-3-ylcarbonyl]amino}pyridin-4-yl)-1H-benzimidazol-1-yl]methyl}benzoate;

methyl 4-{[6-(5-chloro-2-{[(3R)-piperidin-3-ylcarbonyl]amino}pyridin-4-yl)-1H-benzotriazol-1-yl]methyl}benzoate;

(3R)—N-(5-chloro-4-{1-[3-(3-fluorophenyl)propyl]-1H-benzimidazol-6-yl}pyridin-2-yl)piperidine-3-carbox-amide;

(3R)—N-(5-chloro-4-{1-[3-(3-fluorophenyl)propyl]-1H-benzotriazol-6-yl}pyridin-2-yl)piperidine-3-carbox-amide;

4-{[6-(5-chloro-2-{[(3R)-piperidin-3-ylcarbonyl]amino}pyridin-4-yl)-1H-benzotriazol-1-yl]methyl}benzoic acid;

4-{[6-(2-amino-5-chloropyridin-4-yl)-1H-benzotriazol-1-yl]methyl}benzoic acid;

(3R)—N-{4-[1-(tetrahydro-2H-pyran-4-ylmethyl)-1H-benzimidazol-6-yl]pyridin-2-yl}piperidine-3-carbox-amide;

(3R)—N-(5-chloro-4-{1-[(5-fluoropyridin-3-yl)methyl]-1H-pyrrolo[3,2-b]pyridin-6-yl}pyridin-2-yl)piperidine-3-carboxamide;

(3R)—N-(5-chloro-4-{1-[1-(pyridin-3-yl)ethyl]-1H-benzotriazol-6-yl}pyridin-2-yl)piperidine-3-carboxamide;

(3R)—N-{5-chloro-4-[1-(3-fluorobenzyl)-5-methoxy-1H-benzimidazol-6-yl]pyridin-2-yl}piperidine-3-carboxamide;

4-{[6-(5-chloro-2-{[(3R)-piperidin-3-ylcarbonyl]amino}pyridin-4-yl)-1H-benzimidazol-1-yl]methyl}benzoic acid;

(3R)—N-{5-chloro-4-[1-(3-fluorobenzyl)-5-methoxy-1H-benzotriazol-6-yl]pyridin-2-yl}piperidine-3-carboxamide;

(1R,4R,6R)—N-{5-chloro-4-[1-(tetrahydro-2H-pyran-4-ylmethyl)-1H-benzimidazol-6-yl]pyridin-2-yl}-2-azabicyclo[2.2.1]heptane-6-carboxamide;

(1R,4R,6S)—N-{5-chloro-4-[1-(tetrahydro-2H-pyran-4-ylmethyl)-1H-benzimidazol-6-yl]pyridin-2-yl}-2-azabicyclo[2.2.1]heptane-6-carboxamide;

(3R)—N-{5-chloro-4-[1-(thiophen-2-ylmethyl)-1H-benzimidazol-6-yl]pyridin-2-yl}piperidine-3-carboxamide;

(3R)—N-{5-chloro-4-[1-(thiophen-2-ylmethyl)-1H-benzotriazol-6-yl]pyridin-2-yl}piperidine-3-carboxamide;

(3R)—N-(5-chloro-4-{1-[2-(dimethylamino)-2-(3-fluorophenyl)ethyl]-1H-benzotriazol-6-yl}pyridin-2-yl)piperidine-3-carboxamide;

(3R)—N-[5-chloro-4-(1-{3-[(4-methylpiperazin-1-yl)methyl]benzyl}-1H-benzotriazol-6-yl)pyridin-2-yl]piperidine-3-carboxamide;

5-chloro-4-[1-(3-fluorobenzyl)-1H-benzimidazol-6-yl]-N-{3-[(methylsulfonyl)methyl]phenyl}pyridin-2-amine;

(3R)—N-{5-chloro-4-[4-fluoro-1-(tetrahydro-2H-pyran-4-ylmethyl)-1H-benzimidazol-6-yl]pyridin-2-yl}piperidine-3-carboxamide;

ethyl {[(3R)-3-({5-chloro-4-[1-(tetrahydro-2H-pyran-4-ylmethyl)-1H-benzimidazol-6-yl]pyridin-2-yl}carbamoyl)piperidin-1-yl]sulfonyl}carbamate;

methyl (cis)-3-({5-chloro-4-[1-(tetrahydro-2H-pyran-4-ylmethyl)-1H-benzimidazol-6-yl]pyridin-2-yl}carbamoyl)cyclohexanecarboxylate;

(cis)-3-({5-chloro-4-[1-(tetrahydro-2H-pyran-4-ylm-ethyl)-1H-benzimidazol-6-yl]pyridin-2-yl}carbamoyl)cyclohexanecarboxylic acid;

(cis)-N-{5-chloro-4-[1-(tetrahydro-2H-pyran-4-ylm-ethyl)-1H-benzimidazol-6-yl]pyridin-2-yl}-3-[(3-hydroxyazetidin-1-yl)carbonyl]cyclohexanecarboxamide;

(cis)-N'-{5-chloro-4-[1-(tetrahydro-2H-pyran-4-ylm-ethyl)-1H-benzimidazol-6-yl]pyridin-2-yl}-N-(2-hydroxyethyl)-N-methylcyclohexane-1,3-dicarboxamide;

(cis)-N-{5-chloro-4-[1-(tetrahydro-2H-pyran-4-ylm-ethyl)-1H-benzimidazol-6-yl]pyridin-2-yl}-3-{[(2S)-2-(hydroxymethyl)pyrrolidin-1-yl]carbonyl}cyclohexanecarboxamide;

(3R)—N-[4-(1-methyl-1H-benzimidazol-6-yl)pyridin-2-yl]piperidine-3-carboxamide;

tert-butyl (3aR,6aS)-5-({5-chloro-4-[1-(tetrahydro-2H-pyran-4-ylmethyl)-1H-benzimidazol-6-yl]pyridin-2-yl}carbamoyl)hexahydrocyclopenta[c]pyrrole-2(1H)-carboxylate;

(3aR,6aS)—$N^5$-{5-chloro-4-[1-(tetrahydro-2H-pyran-4-ylmethyl)-1H-benzimidazol-6-yl]pyridin-2-yl}-$N^2$-methylhexahydrocyclopenta[c]pyrrole-2,5(1H)-dicarboxamide;

cis-4-({5-chloro-4-[1-(3-fluorobenzyl)-1H-benzimidazol-6-yl]pyridin-2-yl}amino)cyclohexanecarboxylic acid; and pharmaceutically acceptable salts thereof.

15. A pharmaceutical composition comprising an excipient and a therapeutically effective amount of a compound of claim 1 or a pharmaceutically acceptable salt thereof.

16. A method of treating CDK9-mediated cancer in a patient, said method comprising administering to the patient a therapeutically effective amount of a compound of claim 1, or a pharmaceutically acceptable salt thereof.

17. The method of claim 16, wherein said cancer is selected from the group consisting of acoustic neuroma, acute leukemia, acute lymphoblastic leukemia, acute myelogenous leukemia, acute t-cell leukemia, basal cell carcinoma, bile duct carcinoma, bladder cancer, brain cancer, breast cancer, bronchogenic carcinoma, Burkitt's lymphoma, cervical cancer, chondrosarcoma, chordoma, choriocarcinoma, chronic leukemia, chronic lymphocytic leukemia, chronic myelocytic leukemia, chronic myelogenous leukemia, colon cancer, colorectal cancer, craniopharyngioma, cystadenocarcinoma, dysplasias, metaplasias, embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer, lymphangioendothelio-sarcoma, lymphangiosarcoma, lymphoblastic leukemia, lymphoma, malignancies and hyperproliferative disorders of the bladder, breast, colon, lung, ovaries, pancreas, prostate, skin and uterus, lymphoid malignancies of T cell or B cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors, stomach cancer, squamous cell carcinoma, synovioma, sweat gland carcinoma, testicular cancer, thyroid cancer, Waldenström's macroglobulinemia, testicular tumors, uterine cancer, and Wilms' tumor.

18. The method of claim 17, further comprising administering to the patient a therapeutically effective amount of of at least one additional therapeutic agent.

* * * * *

UNITED STATES PATENT AND TRADEMARK OFFICE
CERTIFICATE OF CORRECTION

PATENT NO. : 9,650,358 B2
APPLICATION NO. : 14/207854
DATED : May 16, 2017
INVENTOR(S) : Mastracchio et al.

Page 1 of 1

It is certified that error appears in the above-identified patent and that said Letters Patent is hereby corrected as shown below:

In the Claims

Column No: 252, Line(s): 48, Claim: 14, "]pyridin-2-yl}-N-(2-methoxypropyl)" to read as --]pyridin-2-yl}-N'-(2-methoxypropyl)--

Column No: 252, Line(s): 54, Claim: 14, "]pyridin-2-yl}-N-[(5,5-dimethyltetrahydro-" to read as --]pyridin-2-yl)-N'-[(5,5"-dimethyltetrahydro- --

Column No: 252, Line(s): 57, Claim: 14, "]pyridin-2-yl}-N-(3-methoxypropyl)" to read as --yl)-N'-(3-methoxypropyl)--

Column No: 258, Line(s): 01, Claim: 17, "trophobalstic disease," to read as --trophoblastic disease,--

Column No: 258, Line(s): 04-05, Claim: 17, "lymphangioendothelio-sarcoma," to read as --lymphangioendothelial sarcoma,--

Column No: 258, Line(s): 24-25, Claim: 18, "amount of of at least" to read as --amount of at least--

Signed and Sealed this
Sixth Day of November, 2018

Andrei Iancu
*Director of the United States Patent and Trademark Office*